United States Patent
Zhao et al.

(10) Patent No.: US 11,453,690 B2
(45) Date of Patent: Sep. 27, 2022

(54) RECEPTOR INHIBITOR, PHARMACEUTICAL COMPOSITION COMPRISING SAME, AND USE THEREOF

(71) Applicant: BEIJING TIDE PHARMACEUTICAL CO., LTD., Beijing (CN)

(72) Inventors: Yanping Zhao, Beijing (CN); Hongjun Wang, Beijing (CN); Yeming Wang, Beijing (CN); Xiang Li, Beijing (CN); Yuanyuan Jiang, Beijing (CN); Huai Huang, Beijing (CN); Fajie Li, Beijing (CN); Liying Zhou, Beijing (CN); Ning Shao, Beijing (CN); Fengping Xiao, Beijing (CN); Zhenguang Zou, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 17/040,569

(22) PCT Filed: Mar. 22, 2019

(86) PCT No.: PCT/CN2019/079226
§ 371 (c)(1),
(2) Date: Sep. 23, 2020

(87) PCT Pub. No.: WO2019/179515
PCT Pub. Date: Sep. 26, 2019

(65) Prior Publication Data
US 2021/0054007 A1    Feb. 25, 2021

(30) Foreign Application Priority Data

Mar. 23, 2018    (CN) .......................... 201810244703.7

(51) Int. Cl.
| | | |
|---|---|---|
| C07D 241/38 | (2006.01) | |
| A61K 31/4995 | (2006.01) | |
| C07F 9/6561 | (2006.01) | |
| C07D 471/08 | (2006.01) | |
| C07D 487/08 | (2006.01) | |

(52) U.S. Cl.
CPC .......... C07F 9/6561 (2013.01); C07D 471/08 (2013.01); C07D 487/08 (2013.01)

(58) Field of Classification Search
CPC ..... C07D 241/38; A61K 31/4995; A61P 9/00; A61P 25/00; A61P 25/02
USPC .......................................... 544/349; 514/249
See application file for complete search history.

(56) References Cited

U.S. PATENT DOCUMENTS

2006/0223741 A1    10/2006  Smith et al.

FOREIGN PATENT DOCUMENTS

| CN | 101087619 | 12/2012 |
|---|---|---|
| CN | 106831787 | 6/2017 |
| EP | 3572414 | 11/2019 |
| WO | 9220661 | 11/1992 |
| WO | 9500498 | 1/1995 |
| WO | 2019183133 | 9/2019 |

OTHER PUBLICATIONS

Singh, R.K. et al.: A simple and efficient synthesis of 8-methyl-3,8-diazabicyclo[3.2.1] octane and 3-substituted azatropanes therefrom using pyroglutamic acid. Tetrahedron Letters, vol. 48, pp. 545-548, 2007.*
Jain S, Yadav A. "An Ab Initio Study of At2 Antagonists." Chemical biology & drug design. Mar. 2008;71(3):271-7.
Wu et al. "Synthesis and structure-activity relationships of a novel series of non-peptide AT2-selective angiotensin II receptor antagonists." Bioorganic & Medicinal Chemistry Letters. Oct. 1, 1993;3(10):2023-8.
Berellini et al. "Pharmacophore, drug metabolism, and pharmacokinetics models on non-peptide AT1, AT2, and AT1/AT2 angiotensin II receptor antagonists." Journal of medicinal chemistry. Jun. 30, 2005;48(13):4389-99.
Pichlmair et al. Synthesis of orthogonally protected 3, 8-diazabicyclo [3.2. 1] octane-2-carboxylic acid—a versatile building block for the synthesis of cocaine analogues. Tetrahedron letters. Feb. 9, 2004;45(7):1481-3.
Herdeis et al. Synthesis of trans-epoxy-l-proline and cis-aziridino-l-proline from S-pyroglutamic acid. Regio-and diastereoselective ring opening of its derivatives. Tetrahedron: Asymmetry. Jul. 24, 1997;8(14):2421-32.

* cited by examiner

*Primary Examiner* — Charanjit Aulakh
(74) *Attorney, Agent, or Firm* — Robin L. Teskin; Baker, Donelson, Bearman, Caldwell & Berkowitz PC

(57) ABSTRACT

The present invention discloses a receptor inhibitor of formula (I), a pharmaceutical composition comprising the same and the use thereof.

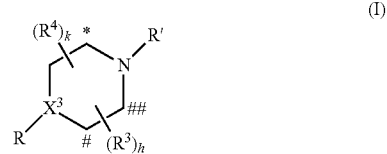

(I)

50 Claims, No Drawings

RECEPTOR INHIBITOR, PHARMACEUTICAL COMPOSITION COMPRISING SAME, AND USE THEREOF

CROSS-REFERENCE TO RELATED APPLICATIONS

This application is a U.S. National Phase application of Int'l Appl. No. PCT/CN2019/079226, filed Mar. 22, 2019, which claims priority to Int'l Appl. No. CN 201810244703.7, filed Mar. 23, 2018, each of which are incorporated herein by reference in their entireties.

FIELD OF THE INVENTION

The present invention relates to an angiotensin II type 2 ($AT_2$) receptor inhibitor, a pharmaceutical composition comprising the same, and its use for the prophylaxis or the treatment of an $AT_2$ receptor-mediated disorder or a symptom associated therewith.

BACKGROUND OF THE INVENTION

There are two known subtypes of angiotensin II (A-II) receptors, namely $AT_1$ and $AT_2$ subtypes. In rat brain, A-II receptors are mainly of $AT_2$ subtypes. $AT_2$-specific inhibitors are valuable in the treatment of various cerebrovascular, cognitive, and central nervous system (CNS) diseases. In addition, $AT_2$ receptors are found in neuronal tumor cells and transformed human nerve cells.

$AT_2$ receptors have also been implicated in the differentiation and regeneration of neuronal tissue, and the maintenance of bone mass.

In some studies, $AT_2$ receptor antagonism is associated with the treatment of pain, particularly inflammatory pain and neuropathic pain, two types of pain which are difficult to treat or relieve. Impaired nerve conduction velocity is also associated with nerve damage and has been implicated in peripheral neuropathies, Carpal Tunnel Syndrome, ulnar neuropathy, Guillain-Barre Syndrome, fascioscapulohumeral muscle dystrophy and spinal disc herniation. Impaired nerve conduction velocity may lead to diminished reflex responses and altered peripheral sensation, such as parathesia and in some cases pain. $AT_2$ receptor inhibitors have been shown to restore nerve conduction velocity.

Cell proliferation and angiogenesis are important biological functions in normal tissue. However, uncontrolled cell proliferation and angiogenesis may lead to a tumor and other proliferative disorders. $AT_2$ receptor inhibitors have been shown to have anti-proliferative activity.

Osteoporosis is a significant problem in older populations, especially in postmenopausal women. The current therapies for osteoporosis rely on calcium supplementation. However, the control the bone formation and bone resorption is complex. $AT_2$ receptor inhibitors have been shown to increase bone mass.

The role of the $AT_2$ receptors in modulating neuronal outgrowth and the associated effects of $AT_2$ receptor inhibitors on reducing neuronal outgrowth, indicates that $AT_2$ receptor inhibitors may be useful therapeutics in diseases characterized by aberrant nerve regeneration.

$AT_2$ receptors are also found in the reproductive organs of female mammals, including uterus and ovaries. The role of angiotensin II in the processes leading to ovulation has been reported.

SUMMARY OF THE INVENTION

The present invention provides a compound for use as an $AT_2$ receptor inhibitor, which exhibits excellent inhibitory activity on $AT_2$ receptors and excellent properties such as better physicochemical properties (e.g., solubility, physical and/or chemical stability), improved pharmacokinetic properties (e.g., improved bioavailability, proper half-life and duration of action), and improved safety (low toxicity and/or less side effects, wide therapeutic window). More particularly, the compound of the present invention has selective inhibitory activity on $AT_2$ receptors, compared to $AT_1$ receptors.

An aspect of the present invention provides a compound or a pharmaceutically acceptable salt, ester, stereoisomer, polymorph, solvate, N-oxide, isotopically labeled compound, metabolite or prodrug thereof, wherein the compound has a structure of formula (I) or formula (I'):

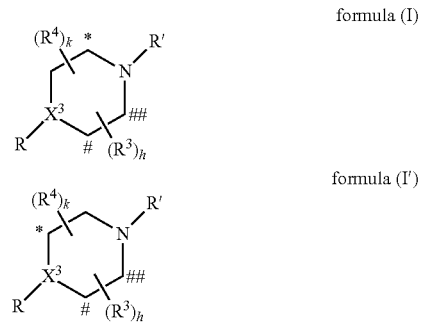

wherein:
the ring C atom at the position marked with the symbol is connected to the ring C atom at the position marked with the symbol "#" or "##" through a U group;
U is selected from the group consisting of a single bond; $NR^{10}$; $C_{1-3}$ alkylene, in which 1 or 2 $CH_2$ moieties are optionally replaced with a group independently selected from the group consisting of O, S, and $NR^{10}$; and $C_{2-3}$ alkenylene, in which any one of the CH moieties forming a C=C double bond is optionally replaced with N;
$X^3$ is $CR^{10}$ or N;
r is:

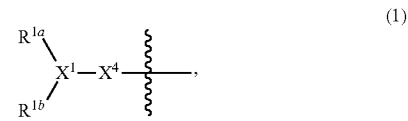

wherein
1) $R^{1a}$, $R^{1b}$ together with $X^1$ to which they are attached form a saturated or partially unsaturated $C_{3-10}$ cyclic hydrocarbyl group, a saturated or partially unsaturated 3- to 10-membered heterocyclic group, a $C_{6-10}$ aryl or a 5- to 14-membered heteroaryl; and
$X^4$ is a direct bond;
or
2) $R^{1a}$ is selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; a saturated or partially unsaturated $C_{3-10}$ cyclic hydrocarbyl group; a saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group;

—C$_{1-6}$ alkylene-saturated or partially unsaturated 3- to 10-membered heterocyclic group; —C$_{1-6}$ alkylene-C$_{6-10}$ aryl; and —C$_{1-6}$ alkylene-(5- to 14-membered heteroaryl);

R$^{1b}$ does not exist, or is selected from the group consisting of H and R$^{1a}$;

X$^1$ does not exist, or is CR$^{10}$ or N;

or

R$^{1b}$ and X$^1$ together form a saturated or partially unsaturated bivalent C$_{3-10}$ cyclic hydrocarbyl group or a saturated or partially unsaturated bivalent 3- to 10-membered heterocyclic group;

X$^4$ is selected from the group consisting of a direct bond; C(=O); S(=O)$_y$; O; S; NR$^{10}$; and —OC(=O)—, —SC(=O)—, —O—S(=O)$_y$—, —NR$^{10}$—C(=O)— and —NR$^{10}$—S(=O)$_y$—, wherein O, S, NR$^{10}$ are connected to X$^1$; preferably is a direct bond, C(=O), S(=O)$_y$, —OC(=O)—, —O—S(=O)$_y$—, —NR$^{10}$—C(=O)— or —NR$^{10}$—S(=O)$_y$—;

provided that: when X$^4$ is a direct bond, X$^1$ is CR$^{10}$ or N;

or

3) R$^{1a}$ and R$^{1b}$ are each independently C$_{3-10}$ cyclic hydrocarbyl group; 3- to 10-membered heterocyclic group, C$_{6-10}$ aryl, or 5- to 14-membered heteroaryl, and an available ring atom on R$^{1a}$ is connected to an available ring atom on R$^{1b}$ through Y group, such that R$^{1a}$ and R$^{1b}$ together with X$^1$ to which they are attached form an optionally substituted saturated or partially unsaturated fused ring system containing 3 or more rings;

X$^1$ is CR$^{10}$ or N;

X$^4$ is selected from the group consisting of C(=O); S(=O)$_y$; O; S; NR$^{10}$; and —OC(=O)—, —SC(=O)—, —O—S(=O)$_y$—, —NR$^{10}$—C(=O)— and —NR$^{10}$—S(=O)$_y$—, wherein O, S, NR$^{10}$ are connected to X$^1$; preferably is C(=O) or S(=O)$_y$; and Y is selected from the group consisting of a; NR$^{10}$; C$_{1-3}$ alkylene, in which 1 or 2 CH$_2$ moieties are optionally replaced with a group independently selected from the group consisting of O, S, and NR$^{10}$; and C$_{2-3}$ alkenylene, in which any one of the CH moieties forming a C=C double bond is optionally replaced with N;

or

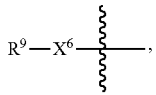 (2)

wherein

X$^6$ is selected from the group consisting of O; S; NR$^{10}$; and —C(=O)—NR$^{10}$— and —S(=O)$_y$—NR$^{10}$—, wherein C(=O) and S(=O)$_y$ are connected to R$^9$;

R$^9$ is selected from the group consisting of H, C$_{1-8}$ alkyl, C$_{2-8}$ alkenyl, C$_{2-8}$ alkynyl, C$_{3-10}$ cyclic hydrocarbyl group, 3- to 10-membered heterocyclic group, C$_{6-10}$ aryl, 5- to 14-membered heteroaryl and C$_{6-12}$ aralkyl;

R' is:

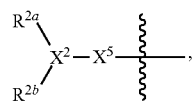

wherein (1) R$^{2a}$, R$^{2b}$ together with X$^2$ to which they are attached form a saturated or partially unsaturated C$_{3-10}$ cyclic hydrocarbyl group, a saturated or partially unsaturated 3- to 10-membered heterocyclic group, a C$_{6-10}$ aryl or a 5- to 14-membered heteroaryl; and X$^5$ is a direct bond;

or (2) R$^{2a}$ is selected from the group consisting of C$_{1-8}$ alkyl, C$_{2-8}$ alkenyl and C$_{2-8}$ alkynyl, wherein any one of the CH$_2$ moieties in the C$_{1-8}$ alkyl, C$_{2-8}$ alkenyl and C$_{2-8}$ alkynyl is optionally replaced with O or S; a saturated or partially unsaturated C$_{3-10}$ cyclic hydrocarbyl group; a saturated or partially unsaturated 3- to 10-membered heterocyclic group; C$_{6-10}$ aryl; 5- to 14-membered heteroaryl; —C$_{1-6}$ alkylene-saturated or partially unsaturated C$_{3-10}$ cyclic hydrocarbyl group; —C$_{1-6}$ alkylene-saturated or partially unsaturated 3- to 10-membered heterocyclic group; —C$_{1-6}$ alkylene-C$_{6-10}$ aryl; and —C$_{1-6}$ alkylene-(5- to 14-membered heteroaryl);

R$^{2b}$ does not exist, or is selected from the group consisting of H and R$^{2a}$;

X$^2$ does not exist, or is CR$^{10}$ or N;

or

R$^{2b}$ and X$^2$ together form a saturated or partially unsaturated bivalent C$_{3-10}$ cyclic hydrocarbyl group or a saturated or partially unsaturated bivalent 3- to 10-membered heterocyclic group;

X$^5$ is selected from the group consisting of a direct bond; C(=O); S(=O)$_y$; O; S; NR$^{10}$; and —OC(=O)—, —SC(=O)—, —O—S(=O)$_y$—, —NR$^{10}$—C(=O)— and —NR$^{10}$—S(=O)$_y$—, wherein O, S, NR$^{10}$ are connected to X$^2$; preferably is a direct bond, C(=O), S(=O)$_y$, —OC(=O)—, —O—S(=O)$_y$—, —NR$^{10}$—C(=O)— or —NR$^{10}$—S(=O)$_y$—;

provided that: when X$^5$ is a direct bond, X$^2$ is CR$^{10}$ or N;

or (3) R$^{2a}$ and R$^{2b}$ are each independently C$_{3-10}$ cyclic hydrocarbyl group; 3- to 10-membered heterocyclic group, C$_{6-10}$ aryl, or 5- to 14-membered heteroaryl, and an available ring atom on R$^{2a}$ is connected to an available ring atom on R$^{2b}$ through Z group, such that R$^{2a}$ and R$^{2b}$ together with X$^2$ to which they are attached form an optionally substituted saturated or partially unsaturated fused ring system containing 3 or more rings;

X$^2$ is CR$^{10}$ or N;

X$^5$ is selected from the group consisting of C(=O); S(=O)$_y$; O; S; NR$^{10}$; and —O—C(=O)—, —S—C(=O)—, —O—S(=O)$_y$—, —NR$^{10}$—C(=O)— and —NR$^{10}$—S(=O)$_y$—, wherein O, S, NR$^{10}$ are connected to X$^2$; preferably is C(=O) or S(=O)$_y$; and Z is selected from the group consisting of a single bond; NR$^{10}$; C$_{1-3}$ alkylene, in which 1 or 2 CH$_2$ moieties are optionally replaced with a group independently selected from the group consisting of O, S, and NR$^{10}$; and C$_{2-3}$ alkenylene, in which any one of the CH moieties forming a C=C double bond is optionally replaced with N;

R$^3$, R$^4$ and R$^{10}$ are each independently selected from the group consisting of H, halogen, cyano, nitro, C$_{1-6}$ alkyl, C$_{2-6}$ alkenyl, C$_{2-6}$ alkynyl, C$_{3-10}$ cyclic hydrocarbyl group, 3- to 10-membered heterocyclic group, C$_{6-10}$ aryl, 5- to 14-membered heteroaryl, C$_{6-12}$ aralkyl, —OR$^{11}$, —SR$^{11}$, —P(O)(OR$^{11}$)(OR$^{12}$), —OC(=O)R$^{11}$, —C(=O)R$^{11}$, —C(=O)OR$^{11}$, —C(=O)NR$^{11}$R$^{12}$, —C(=O)NR$^{11}$S(=O)$_y$NR$^{11}$R$^{12}$, —C(=O)NR$^{11}$S(=O)$_y$R$^{12}$, —S(=O)$_y$R$^{11}$, —S(=O)$_y$OR$^{11}$, —S(=O)$_y$NR$^{11}$R$^{12}$, —S(=O)$_y$NR$^{11}$S(=O)$_z$OR$^{12}$, —S(=O)$_y$NR$^{11}$C(=O)R$^{12}$, —S(=O)$_y$NR$^{11}$C(=O)OR$^{12}$, —NR$^{11}$R$^{12}$, —NR$^{11}$—C(=O)R$^{12}$, —NR$^{11}$—C(=O)OR$^{12}$, —NR$^{11}$—S(=O)$_y$—R$^{12}$, —NR$^{11}$—C(=O)—NR$^{11}$R$^{12}$, —C$_{1-6}$ alkylene-R$^{11}$, —C$_{1-6}$ alkylene-OR$^{11}$, —C$_{1-6}$ alkylene-OC(=O)R$^{11}$, —C$_{1-6}$ alkylene —C(=O)OR$^{11}$, —C$_{1-6}$ alkylene-S(=O)$_x$R$^{11}$, —C$_{1-6}$ alkylene-S(=O)$_y$OR$^{11}$, —C$_{1-6}$ alkylene-OC(=O)NR$^{11}$R$^{12}$, —C$_{1-6}$ alkylene-C(=O)NR$^{11}$R$^{12}$, —C$_{1-6}$ alkylene-C(=O)NR$^{11}$—S(=O)$_y$R$^{12}$, —C$_{1-6}$ alkylene-NR$^{11}$—C(=O)NR$^{11}$R$^{12}$, —C$_{1-6}$ alkylene-OS(=O)$_y$R$^{11}$, —C$_{1-6}$ alkylene-OS(=O)$_y$NR$^{11}$R$^{12}$, —C$_{1-6}$ alkylene-S(=O)$_y$NR$^{11}$R$^{12}$, —C$_{1-6}$ alkylene-NR$^{11}$—S(=O)$_y$NR$^{11}$R$^{12}$, —C$_{1-6}$ alkylene-NR$^{11}$R$^{12}$ and —O—C$_{1-6}$ alkylene-NR$^{11}$R$^{12}$;

R$^{11}$ and R$^{12}$, at each occurrence, are each independently selected from the group consisting of H, C$_{1-6}$ alkyl, C$_{2-6}$ alkenyl, C$_{2-6}$ alkynyl, C$_{1-6}$ alkyl-O—, C$_{1-6}$ alkyl-S—, C$_{3-10}$ cyclic hydrocarbyl group, 3- to 10-membered heterocyclic group, C$_{6-10}$ aryl, 5- to 14-membered heteroaryl and C$_{6-12}$ aralkyl;

h and k are each independently 1, 2, 3, 4, 5 or 6;

the above alkyl, alkylene, alkenyl, alkenylene, alkynyl, cyclic hydrocarbyl group, heterocyclic group, aryl, heteroaryl and aralkyl, at each occurrence, are each optionally substituted by 1, 2, 3 or more R$^{13}$, wherein the R$^{13}$, at each occurrence, is independently selected from the group consisting of halogen, cyano, nitro, C$_{1-6}$ alkyl, C$_{2-6}$ alkenyl, C$_{2-6}$ alkynyl, C$_{3-10}$ cyclic hydrocarbyl group, 3- to 10-membered heterocyclic group, C$_{6-10}$ aryl, 5- to 14-membered heteroaryl, C$_{6-12}$ aralkyl, —OR$^{11}$, —SR$^{11}$, —P(O)R$^{11}$R$^{12}$, —OC(=O)R$^{11}$, —C(=O)R$^{11}$, —C(=O)OR$^{11}$, —C(=O)NR$^{11}$R$^{12}$, —C(=O)NR$^{11}$S(=O)$_y$NR$^{11}$R$^{12}$, —C(=O)NR$^{11}$S(=O)$_y$R$^{12}$, —S(=O)$_y$R$^{11}$, —S(=O)$_y$OR$^{11}$, —S(=O)$_y$NR$^{11}$R$^{12}$, —S(=O)$_y$NR$^{11}$S(=O)$_z$OR$^{12}$, —S(=O)$_y$NR$^{11}$C(=O)R$^{12}$, —S(=O)$_y$NR$^{11}$C(=O)OR$^{12}$, —NR$^{11}$R$^{12}$, —NR$^{11}$—C(=O)R$^{12}$, —NR$^{11}$—C(=O)OR$^{12}$, —NR$^{11}$—S(=O)$_y$—R$^{12}$, —NR$^{11}$—C(=O)—NR$^{11}$R$^{12}$, —C$_{1-6}$ alkylene-R$^{11}$, —C$_{1-6}$ alkylene-OR$^{11}$, —C$_{1-6}$ alkylene-OC(=O)R$^{11}$, —C$_{1-6}$ alkylene-C(=O)OR$^{11}$, —C$_{1-6}$ alkylene-S(=O)$_x$R$^{11}$, —C$_{1-6}$ alkylene-S(=O)$_y$OR$^{11}$, —C$_{1-6}$ alkylene-OC(=O)NR$^{11}$R$^{12}$, —C$_{1-6}$ alkylene-C(=O)NR$^{11}$R$^{12}$, —C$_{1-6}$ alkylene-C(=O)NR$^{11}$—S(=O)$_y$R$^{12}$, —C$_{1-6}$ alkylene-NR$^{11}$—C(=O)NR$^{11}$R$^{12}$, —C$_{1-6}$ alkylene-OS(=O)$_y$R$^{11}$, —C$_{1-6}$ alkylene-OS(=O)$_y$NR$^{11}$R$^{12}$, —C$_{1-6}$ alkylene-S(=O)$_y$NR$^{11}$R$^{12}$, —C$_{1-6}$ alkylene-NR$^{11}$—S(=O)$_y$NR$^{11}$R$^{12}$, —C$_{1-6}$ alkylene-NR$^{11}$R$^{12}$, and —O—C$_{1-6}$ alkylene-NR$^{11}$R$^{12}$, and wherein the alkyl, alkylene, cyclic hydrocarbyl group, heterocyclic group, aryl, heteroaryl and aralkyl recited for the substituent R$^{13}$ are optionally further substituted by 1, 2, 3 or more substituents independently selected from the group consisting of halogen, OH, oxo, amino, cyano, nitro, C$_{1-6}$ alkyl, halogenated C$_{1-6}$ alkyl, hydroxy C$_{1-6}$ alkyl, C$_{3-6}$ cyclic hydrocarbyl group, 3- to 10-membered heterocyclic group, C$_{6-10}$ aryl, 5- to 14-membered heteroaryl and C$_{6-12}$ aralkyl; and wherein the heterocyclic group, aryl or heteroaryl when being a substituent is connected to the rest of the molecule through a ring C atom, or where possible, through a ring N atom;

x, at each occurrence, is independently 0, 1 or 2;

y and z, at each occurrence, are each independently 1 or 2.

Those skilled in the art understands that the above expression "X$^1$ does not exist" is intended to mean that R$^{1a}$ and R$^{1b}$ (when present) are directly connected to X$^4$, and the above expression "X$^2$ does not exist" is intended to mean that R$^{2a}$ and R$^{2b}$ (when present) are directly connected to X$^5$.

Another aspect of the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof, and one or more pharmaceutically acceptable carriers, and the pharmaceutical composition is preferably in the form of a solid, semi-solid, liquid, or gas preparation.

Another aspect of the present invention provides use of the compound of the present invention or a pharmaceutically acceptable salt, ester, stereoisomer, polymorph, solvate, N-oxide, isotopically labeled compound, metabolite or prodrug thereof, or the pharmaceutical composition of the present invention in the manufacture of a medicament for use as an AT$_2$ receptor inhibitor.

Another aspect of the present invention provides the compound of the present invention or a pharmaceutically acceptable salt, ester, stereoisomer, polymorph, solvate, N-oxide, isotopically labeled compound, metabolite or prodrug thereof, or the pharmaceutical composition of the present invention for use as an AT$_2$ receptor inhibitor.

Another aspect of the present invention provides a method for the prophylaxis or the treatment of an AT$_2$ receptor-mediated disorder or a symptom associated therewith, comprising administering to a subject in need thereof an effective amount of the compound of the present invention or a pharmaceutically acceptable salt, ester, stereoisomer, polymorph, solvate, N-oxide, isotopically labeled compound, metabolite or prodrug thereof, or the pharmaceutical composition of the present invention.

Another aspect of the present invention provides a method for regulating a reproductive function associated with AT$_2$ receptors in a female patient, comprising administering to a subject in need thereof an effective amount of the compound of the present invention or a pharmaceutically acceptable salt, ester, stereoisomer, polymorph, solvate, N-oxide, isotopically labeled compound, metabolite or prodrug thereof, or the pharmaceutical composition of the present invention.

DETAILED DESCRIPTION OF THE INVENTION

Definitions

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, particularly 1-8 ("$C_{1-8}$ alkyl") carbon atoms, e.g., 1-6 ("$C_{1-6}$ alkyl"), 1-4 ("$C_{1-4}$ alkyl") carbon atoms, more particularly, 1, 2, 3, 4, 5, 6, 7 or 8 carbon atoms. For example, as used herein, the term "$C_{1-8}$ alkyl" refers to a linear or branched group having 1-8 carbon atoms (such as methyl, ethyl, n-propyl, isopropyl, n-butyl, isobutyl, sec-butyl, tert-butyl, n-pentyl, isopentyl, neopentyl, or 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl), which is optionally substituted with one or more (e.g., 1 to 3) suitable substituents such as halogen (in which case the group may be referred to as "halogenated alkyl") (e.g., $CH_2F$, $CHF_2$, $CF_3$, $CCl_3$, $C_2F_5$, $C_2Cl_5$, $CH_2CF_3$, $CH_2Cl$ or —$CH_2CH_2CF_3$ etch. The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbyl having a double bond and 2-8 carbon atoms ("$C_{2-8}$ alkenyl", such as "$C_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, heptenyl and octenyl. When the compound of the present invention contains an alkenylene group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5, 6, 7 or 8 carbon atoms, e.g., ethynyl, 1-propynyl, 2-propynyl, 2-butynyl, 3-butynyl, 2-pentynyl, 3-pentynyl, 4-pentynyl, 2-hexynyl, 3-hexynyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6, such as 5-6 or 5-7) ring carbon atoms, including but not limited to cyclopropyl(ene) (ring), cyclobutyl(ene) (ring), cyclopentyl(ene) (ring), cyclohexyl(ene) (ring), cycloheptyl (ene) (ring), cyclooctyl(ene) (ring), cyclononyl(ene) (ring), cyclohexenyl(ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) monocyclic or bicyclic group having e.g. 3-10 (suitably having 3-8, and more suitably having 3-6; or suitably having 8-10, and more suitably having 9 or 10) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated monocyclic or bicyclic heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of monocyclic heterocyclylene, heterocyclyl and heterocycle include, but are not limited to oxiranyl(ene), aziridinyl(ene), azetidinyl(ene), oxetanyl(ene), tetrahydrofuranyl(ene), dioxolinyl(ene), pyrrolidinyl(ene), pyrrolidonyl(ene), imidazolidinyl(ene), pyrazolidinyl(ene), pyrrolinyl(ene), tetrahydropyranyl(ene), piperidinyl(ene), morpholinyl(ene), dithianyl(ene), thiomorpholinyl(ene), piperazinyl(ene) or trithianyl(ene). Other examples of monocyclic heterocycle and heterocyclyl include but are not limited to: tetrahydrofuranyl, tetrahydrothienyl, pyrrolidinyl (e.g. pyrrolidin-1-yl), oxazolidinyl, thiazolidinyl, imidazolidinyl, 1,3-dioxolanyl, 1,3-oxathiolanyl, piperidinyl, piperazinyl, morpholinyl (such as morpholine)), thiomorpholinyl, tetrahydro-2H-pyranyl, tetrahydro-2H-thiopyranyl, 1,3-oxazinanyl (1,3-oxazinane), 1,3-thiazinanyl (1,3-thiazinane), hexahydropyrimidyl, 1,3-oxathianyl (1,3-oxathiane), 1,4-oxathianyl (1,4-oxathiane), 1,3-diazepanyl (1,3-diazepane), 1,4-diazepanyl (1,4-diazepane), 1,3-oxazepanyl (1,3-oxazepane), 1,3-thiazepanyl (1,3-thiazepane). Bicyclic heterocyclylene, heterocyclyl and heterocycle include spiro ring systems, fused (e.g., benzo-fused) systems, or bridged systems. The benzo-fused heterocyclylene, heterocyclyl and heterocycle refer to the above-mentioned monocyclic heterocyclylene, heterocyclyl and heterocycle fused to benzene, for example, a benzo derivative of a saturated or partially unsaturated monocyclic group with 3-6 (suitably with 4-6, more suitably 5-6) ring atoms, in which 1, 2, 3 or 4 ring atoms are heteroatoms selected from N, O and S and the remaining ring atoms are C (i.e., "7- to 10-membered benzo fused heterocyclylene, heterocyclyl and heterocycle"), including, for example,

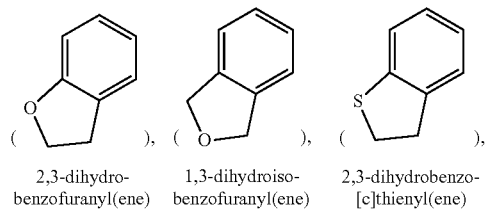

( 2,3-dihydro-benzofuranyl(ene) ), ( 1,3-dihydroiso-benzofuranyl(ene) ), ( 2,3-dihydrobenzo-[c]thienyl(ene) ),

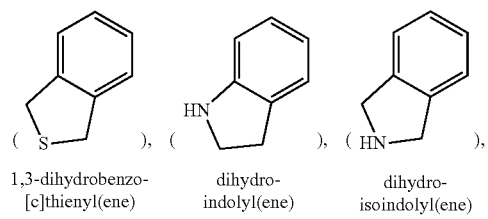

( 1,3-dihydrobenzo-[c]thienyl(ene) ), ( dihydro-indolyl(ene) ), ( dihydro-isoindolyl(ene) ),

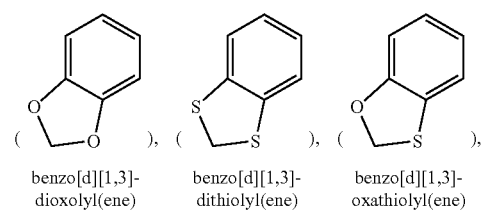

( benzo[d][1,3]-dioxolyl(ene) ), ( benzo[d][1,3]-dithiolyl(ene) ), ( benzo[d][1,3]-oxathiolyl(ene) ),

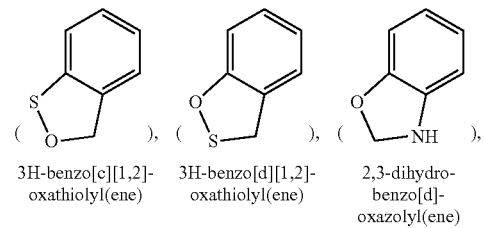

( 3H-benzo[c][1,2]-oxathiolyl(ene) ), ( 3H-benzo[d][1,2]-oxathiolyl(ene) ), ( 2,3-dihydro-benzo[d]-oxazolyl(ene) )

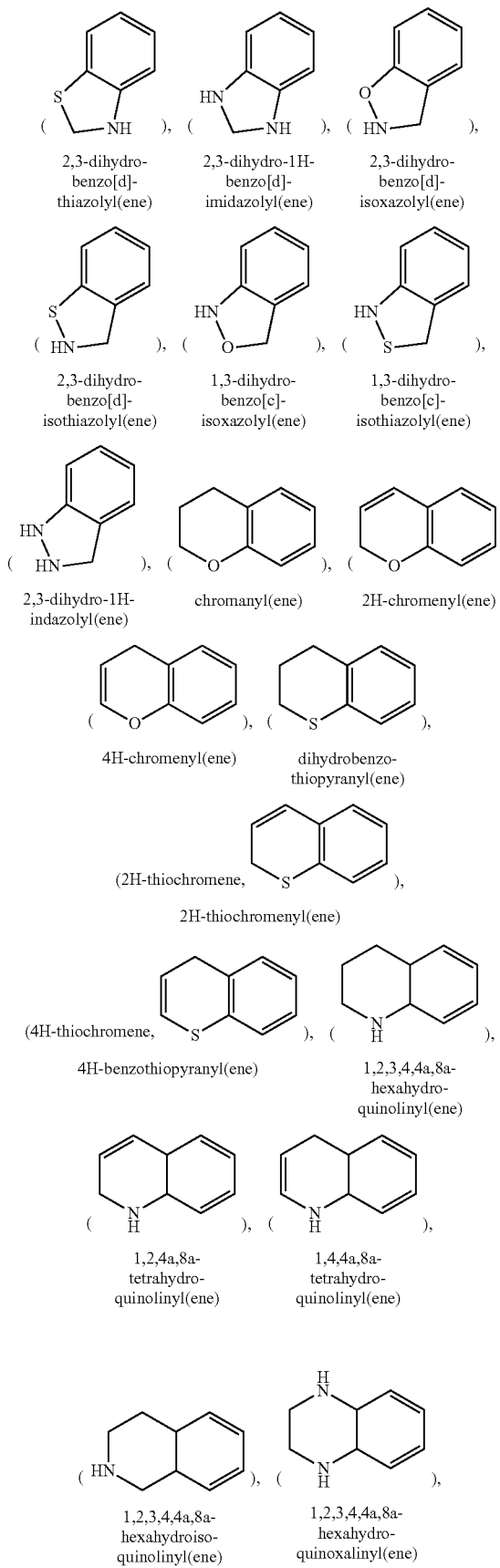
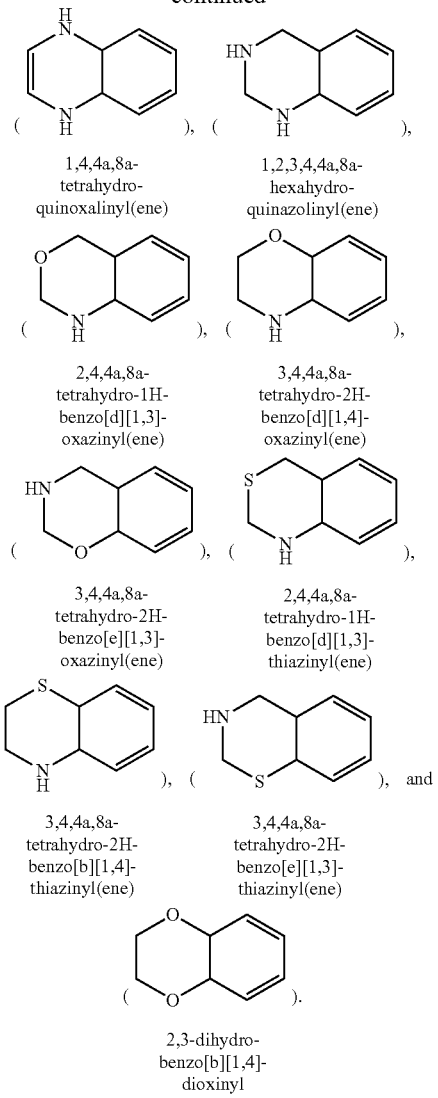

The bridged systems also include for example 8-azaspiro[4.5]decane, 3,9-diazaspiro[5.5]undecane, 2-azabicyclo[2.2.2]octane. Heterocyclylene, heterocyclyl and heterocycle may optionally be substituted with one or more (e.g. 1, 2, 3 or 4) suitable substituents.

As used herein, the terms "aryl(ene)" and "aromatic ring" refer to an all-carbon monocyclic or fused-ring polycyclic aromatic group having a conjugated π electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, —$NO_2$, and $C_{1-6}$ alkyl, etch.

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl(ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene) (e.g., 1-pyrazolyl, 3-pyrazolyl, 4-pyrazolyl and 5-pyrazolyl), isoxazolyl(ene), isothiazolyl(ene), oxadiazolyl(ene), triazolyl(ene), tetrazolyl(ene) (e.g. 1-tetrazolyl or 5-tetrazolyl), thiadiazolyl(ene) etc., and benzo derivatives thereof; or pyridinyl(ene), pyridazinyl(ene), pyrimidinyl(ene), pyrazinyl(ene), triazinyl(ene), etc., and benzo derivatives thereof. Other examples of "heteroaryl(ene)" or "heteroaromatic ring" also include pyrrolopyrimidinyl, pyrrolopyridyl, pyrazolopyrimidinyl, pyrazolopyridyl, imidazopyridyl, purinyl, and the like.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may optionally further comprise one or more (e.g., one, two, three or four) ring members selected from the group consisting of N, O, C=O, S, S=O and S(=O)$_2$. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted", the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more from a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable, including the available atoms in the bridge when the substitutable ring is a bridged ring.

The present invention also includes all pharmaceutically acceptable isotopically labeled compounds, which are identical to those of the present invention except that one or more atoms are replaced with an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically labeled compounds of the present invention, for example those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with positron-emitting isotopes, such as $^{11}$C, $^{18}$F, $^{15}$O and $^{13}$N, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., $D_2O$, acetone-d$_6$, or DMSO-d$_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The carbon-carbon bonds of the compound of the present invention may be depicted herein using a solid line ( ——— ), a solid wedge ( ◤◣ ), or a dotted wedge ( ⸳⸳⸳⸳ ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free from, or where appropriate, in a form of a pharmaceutically acceptable derivative. In the present invention, the pharmaceutically acceptable derivative includes, but is not limited to a pharmaceutically acceptable salt, ester, solvate, N-oxide, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibernate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide; a person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; A. R. Katritzky and A. J. Boulton, Eds., Academic Press; and G. W. H. Cheeseman and E. S. G. Werstiuk, *Advances in Heterocyclic Chemistry*, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems", Vol. 14, ACS Symposium Series (T. Higuchi and V. Stella). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

The term "about" refers to a range within ±10%, preferably within ±5%, and more preferably within ±2% of the specified value.

Embodiments of the Invention

Compound

In an aspect, the present invention provides a compound of formula (I) or a pharmaceutically acceptable salt, ester, stereoisomer, polymorph, solvate, N-oxide, isotopically labeled compound, metabolite or prodrug thereof as described below.

1. A compound or a pharmaceutically acceptable salt, ester, stereoisomer, polymorph, solvate, N-oxide, isotopically labeled compound, metabolite or prodrug thereof, wherein the compound has a structure of formula (I) or formula (I'):

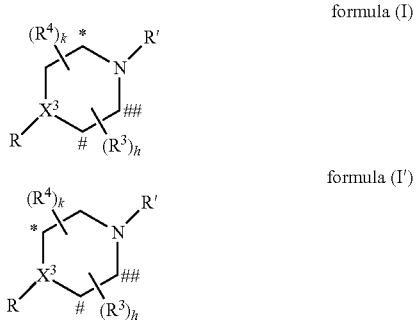

wherein:
the ring C atom at the position marked with the symbol * is connected to the ring C atom at the position marked with the symbol "#" or "##" through a U group;
U is selected from the group consisting of a single bond; $NR^{10}$; $C_{1-3}$ alkylene, in which 1 or 2 $CH_2$ moieties are optionally replaced with a group independently selected from the group consisting of O, S, and $NR^{10}$; and $C_{2-3}$ alkenylene, in which any one of the CH moieties forming a C=C double bond is optionally replaced with N;
$X^3$ is $CR^{10}$ or N;
R is:

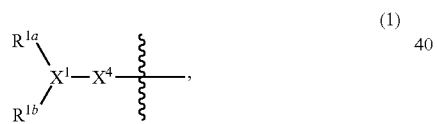

wherein
1) $R^{1a}$, $R^{1b}$ together with $X^1$ to which they are attached form a saturated or partially unsaturated $C_{3-10}$ cyclic hydrocarbyl group, a saturated or partially unsaturated 3- to 10-membered heterocyclic group, a $C_{6-10}$ aryl or a 5- to 14-membered heteroaryl; and
$X^4$ is a direct bond;
or
2) $R^{1a}$ is selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; a saturated or partially unsaturated $C_{3-10}$ cyclic hydrocarbyl group; a saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group; —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);
$R^{1b}$ does not exist, or is selected from the group consisting of H and $R^{1a}$;

$X^1$ does not exist, or is $CR^{10}$ or N;
or
$R^{1b}$ and $X^1$ together form a saturated or partially unsaturated bivalent $C_{3-10}$ cyclic hydrocarbyl group or a saturated or partially unsaturated bivalent 3- to 10-membered heterocyclic group;
$X^4$ is selected from the group consisting of a direct bond; C(=O); S(=O)$_y$; O; S; $NR^{10}$; and —OC(=O)—, —SC(=O)—, —O—S(=O)$_y$—, —$NR^{10}$—C(=O)— and —$NR^{10}$—S(=O)$_y$—, wherein O, S, $NR^{10}$ are connected to $X^1$; preferably is a direct bond, C(=O), S(=O)$_y$, —OC(=O)—, —O—S(=O)$_y$—, —$NR^{10}$—C(=O)— or —$NR^{10}$—S(=O)$_y$—;
provided that: when $X^4$ is a direct bond, $X^1$ is $CR^{10}$ or N;
or
3) $R^{1a}$ and $R^{1b}$ are each independently $C_{3-10}$ cyclic hydrocarbyl group; 3- to 10-membered heterocyclic group, $C_{6-10}$ aryl, or 5- to 14-membered heteroaryl, and an available ring atom on $R^{1a}$ is connected to an available ring atom on $R^{1b}$ through Y group, such that $R^{1a}$ and $R^{1b}$ together with $X^1$ to which they are attached form an optionally substituted saturated or partially unsaturated fused ring system containing 3 or more rings;
$X^1$ is $CR^{10}$ or N;
$X^4$ is selected from the group consisting of C(=O); S(=O)$_y$; O; S; $NR^{10}$; and —OC(=O)—, —SC(=O)—, —O—S(=O)$_y$—, —$NR^{10}$—C(=O)— and —$NR^{10}$—S(=O)$_y$—, wherein O, S, $NR^{10}$ are connected to $X^1$; preferably is C(=O) or S(=O)$_y$; and
Y is selected from the group consisting of a single bond; $NR^{10}$; $C_{1-3}$ alkylene, in which 1 or 2 $CH_2$ moieties are optionally replaced with a group independently selected from the group consisting of O, S, and $NR^{10}$; and $C_{2-3}$ alkenylene, in which any one of the CH moieties forming a C=C double bond is optionally replaced with N;
or

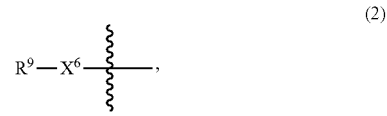

wherein
$X^6$ is selected from the group consisting of O; S; $NR^{10}$; and —C(=O)—$NR^{10}$— and —S(=O)$_y$—$NR^{10}$—, wherein C(=O) and S(=O)$_y$ are connected to $R^9$;
$R^9$ is selected from the group consisting of H, $C_{1-8}$ alkyl, $C_{2-8}$ alkenyl, $C_{2-8}$ alkynyl, $C_{3-10}$ cyclic hydrocarbyl group, 3- to 10-membered heterocyclic group, $C_{6-10}$ aryl, 5- to 14-membered heteroaryl and $C_{6-12}$ aralkyl;
R' is;

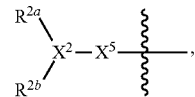

wherein
(1) $R^{2a}$, $R^{2b}$ together with $X^2$ to which they are attached form a saturated or partially unsaturated $C_{3-10}$ cyclic hydrocarbyl group, a saturated or partially unsaturated 3- to 10-membered heterocyclic group, a $C_{6-10}$ aryl or a 5- to 14-membered heteroaryl; and $X^5$ is a direct bond;

or (2) $R^{2a}$ is selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; a saturated or partially unsaturated $C_{3-10}$ cyclic hydrocarbyl group; a saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group; —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$R^{2b}$ does not exist, or is selected from the group consisting of H and $R^{2a}$;

$X^2$ does not exist, or is $CR^{10}$ or N;

or $R^{2b}$ and $X^2$ together form a saturated or partially unsaturated bivalent $C_{3-10}$ cyclic hydrocarbyl group or a saturated or partially unsaturated bivalent 3- to 10-membered heterocyclic group;

$X^5$ is selected from the group consisting of a direct bond; C(=O); S(=O)$_y$; O; S; $NR^{10}$; and —OC(=O)—, —SC(=O)—, —O—S(=O)$_y$, —$NR^{10}$—C(=O)— and —$NR^{10}$—S(=O)$_y$—, wherein O, S, $NR^{10}$ are connected to $X^2$; preferably is a direct bond, C(=O), S(=O)$_y$, —OC(=O)—, —O—S(=O)$_y$—, —$NR^{10}$—C(=O)— or —$NR^{10}$—S(=O)$_y$—;

provided that: when $X^5$ is a direct bond, $X^2$ is $CR^{10}$ or N;

or (3) $R^{2a}$ and $R^{2b}$ are each independently $C_{3-10}$ cyclic hydrocarbyl group; 3- to 10-membered heterocyclic group, $C_{6-10}$ aryl, or 5- to 14-membered heteroaryl, and an available ring atom on $R^{2a}$ is connected to an available ring atom on $R^{2b}$ through Z group, such that $R^{2a}$ and $R^{2b}$ together with $X^2$ to which they are attached form an optionally substituted saturated or partially unsaturated fused ring system containing 3 or more rings;

$X^2$ is $CR^{10}$ or N;

$X^5$ is selected from the group consisting of C(=O); S(=O)$_y$; O; S; $NR^{10}$; and —O—C(=O)—, —S—C(=O)—, —O—S(=O)$_y$—, —$NR^{10}$—C(=O)— and —$NR^{10}$—S(=O)$_y$—, wherein O, S, $NR^{10}$ are connected to $X^2$; preferably is C(=O) or S(=O)$_y$; and Z is selected from the group consisting of a single bond; $NR^{10}$; $C_{1-3}$ alkylene, in which 1 or 2 $CH_2$ moieties are optionally replaced with a group independently selected from the group consisting of O, S, and $NR^{10}$; and $C_{2-3}$ alkenylene, in which any one of the CH moieties forming a C=C double bond is optionally replaced with N;

$R^3$, $R^4$ and $R^{10}$ are each independently selected from the group consisting of H, halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —P(O)($OR^{11}$)($OR^{12}$), —OC(=O)$R^{11}$, —C(=O)$R^{11}$, —C(=O)$OR^{11}$, —C(=O)$NR^{11}R^{12}$, —C(=O)$NR^{11}$S(=O)$_y$$NR^{11}R^{12}$, —C(=O)$NR^{11}$S(=O)$_y$$R^{12}$, —S(=O)$_y$$R^{11}$, —S(=O)$_y$$OR^{11}$, —S(=O)$_y$$NR^{11}R^{12}$, —S(=O)$_y$$NR^{11}$S(=O)$_z$$OR^{12}$, —S(=O)$_y$$NR^{11}$C(=O)$R^{12}$, —S(=O)$_y$$NR^{11}$C(=O)$OR^{12}$, —$NR^{11}R^{12}$, —$NR^{11}$—C(=O)$R^{12}$, —$NR^{11}$—C(=O)$OR^{12}$, —$NR^{11}$—S(=O)$_y$—$R^{12}$, —$NR^{11}$—C(=O)—$NR^{11}R^{12}$, —$C_{1-6}$ alkylene-$R^{11}$, —$C_{1-6}$ alkylene-$OR^{11}$, —$C_{1-6}$ alkylene-OC(=O)$R^{11}$, —$C_{1-6}$ alkylene —C(=O)$OR^{11}$, —$C_{1-6}$ alkylene-S(=O)$_x$$R^{11}$, —$C_{1-6}$ alkylene-S(=O)$_y$$OR^{11}$, —$C_{1-6}$ alkylene-OC(=O)$NR^{11}R^{12}$, —$C_{1-6}$ alkylene-C(=O)$NR^{11}R^{12}$, —$C_{1-6}$ alkylene-C(=O)$NR^{11}$—S(=O)$_y$$R^{12}$, —$C_{1-6}$ alkylene-$NR^{11}$—C(=O)$NR^{11}R^{12}$, —$C_{1-6}$ alkylene-OS(=O)$_y$$R^{11}$, —$C_{1-6}$ alkylene-OS(=O)$_y$$NR^{11}R^{12}$, —$C_{1-6}$ alkylene-S(=O)$_y$$NR^{11}R^{12}$, —$C_{1-6}$ alkylene-$NR^{11}$—S(=O)$_y$$NR^{11}R^{12}$, —$C_{1-6}$ alkylene-$NR^{11}R^{12}$ and —O—$C_{1-6}$ alkylene-$NR^{11}R^{12}$;

$R^{11}$ and $R^{12}$, at each occurrence, are each independently selected from the group consisting of H, $C_{1-6}$ alkyl, $C_{2-6}$ alkenyl, $C_{2-6}$ alkynyl, $C_{1-6}$ alkyl-O—, $C_{1-6}$ alkyl-S—, $C_{3-10}$ cyclic hydrocarbyl group, 3- to 10-membered heterocyclic group, $C_{6-10}$ aryl, 5- to 14-membered heteroaryl and $C_{6-12}$ aralkyl;

h and k are each independently 1, 2, 3, 4, 5 or 6;

the above alkyl, alkylene, alkenyl, alkenylene, alkynyl, cyclic hydrocarbyl group, heterocyclic group, aryl, heteroaryl and aralkyl, at each occurrence, are each optionally substituted by 1, 2, 3 or more $R^{13}$, wherein the $R^{13}$, at each occurrence, is independently selected from the group consisting of halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —P(O)$R^{11}R^{12}$, —OC(=O)$R^{11}$, —C(=O)$R^{11}$, —C(=O)$OR^{11}$, —C(=O)$NR^{11}R^{12}$, —C(=O)$NR^{11}S(=O)_yNR^{11}R^{12}$, —C(=O)$NR^{11}S(=O)_yR^{12}$, —S(=O)$_yR^{11}$, —S(=O)$_yOR^{11}$, —S(=O)$_yNR^{11}R^{12}$, —S(=O)$_yNR^{11}S(=O)_zOR^{12}$, —S(=O)$_yNR^{11}C(=O)R^{12}$, —S(=O)$_yNR^{11}C(=O)OR^{12}$, —$NR^{11}R^{12}$, —$NR^{11}$—C(=O)$R^{12}$, —$NR^{11}$—C(=O)$OR^{12}$, —$NR^{11}$—S(=O)$_y$—$R^{12}$, —$NR^{11}$—C(=O)—$NR^{11}R^{12}$, —$C_{1-6}$ alkylene-$R^{11}$, —$C_{1-6}$ alkylene-$OR^{11}$, —$C_{1-6}$ alkylene-OC(=O)$R^{11}$, —$C_{1-6}$ alkylene-C(=O)$OR^{11}$, —$C_{1-6}$ alkylene-S(=O)$_xR^{11}$, —$C_{1-6}$ alkylene-S(=O)$_yOR^{11}$, —$C_{1-6}$ alkylene-OC(=O)$NR^{11}R^{12}$, —$C_{1-6}$ alkylene-C(=O)$NR^{11}R^{12}$, —$C_{1-6}$ alkylene-C(=O)$NR^{11}$—S(=O)$_yR^{12}$, —$C_{1-6}$ alkylene-$NR^{11}$—C(=O)$NR^{11}R^{12}$, —$C_{1-6}$ alkylene-OS(=O)$_yR^{11}$, —$C_{1-6}$ alkylene-OS(=O)$_yNR^{11}R^{12}$, —$C_{1-6}$ alkylene-S(=O)$_yNR^{11}R^{12}$, —$C_{1-6}$ alkylene-$NR^{11}$—S(=O)$_yNR^{11}R^{12}$, —$C_{1-6}$ alkylene-$NR^{11}R^{12}$, and —O—$C_{1-6}$ alkylene-$NR^{11}R^{12}$, and wherein the alkyl, alkylene, cyclic hydrocarbyl group, heterocyclic group, aryl, heteroaryl and aralkyl recited for the substituent $R^{13}$ are optionally further substituted by 1, 2, 3 or more substituents independently selected from the group consisting of halogen, OH, oxo, amino, cyano, nitro, $C_{1-6}$ alkyl, halogenated $C_{1-6}$ alkyl, hydroxy $C_{1-6}$ alkyl, $C_{3-6}$ cyclic hydrocarbyl group, 3- to 10-membered heterocyclic group, $C_{6-10}$ aryl, 5- to 14-membered heteroaryl and $C_{6-12}$ aralkyl; and wherein the heterocyclic group, aryl or heteroaryl when being a substituent is connected to the rest of the molecule through a ring C atom, or where possible, through a ring N atom;

x, at each occurrence, is independently 0, 1 or 2;

y and z, at each occurrence, are each independently 1 or 2.

2. The compound according to item 1, or a pharmaceutically acceptable salt, ester, stereoisomer, polymorph, solvate, N-oxide, isotopically labeled compound, metabolite or prodrug thereof, wherein the compound has a structure of formula (I):

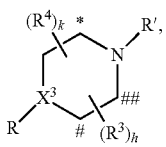

formula (I)

wherein:

R³, R⁴ and R¹⁰ are each independently selected from the group consisting of H, halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —OR¹¹, —SR¹¹, —OC(=O)R¹¹, —C(=O)R¹¹, —C(=O)OR¹¹, —C(=O)NR¹¹R¹², —C(=O)NR¹¹S(=O)$_y$NR¹¹R¹², —C(=O)NR¹¹S(=O)$_y$R¹², —S(=O)$_y$R¹¹, —S(=O)$_y$OR¹¹, —S(=O)$_y$NR¹¹R¹², —S(=O)$_y$NR¹¹S(=O)$_z$OR¹², —S(=O)$_y$NR¹¹C(=O)R¹², —S(=O)$_y$NR¹¹C(=O)OR¹², —NR¹¹R¹², —NR¹¹—C(=O)R¹², —NR¹¹—C(=O)OR¹², —NR¹¹—S(=O)$_y$—R¹², —NR¹¹—C(=O)—NR¹¹R¹², —$C_{1-6}$ alkylene-R¹¹, —$C_{1-6}$ alkylene-OR¹¹, —$C_{1-6}$ alkylene-OC(=O)R¹¹, —$C_{1-6}$ alkylene-C(=O)R¹¹, —$C_{1-6}$ alkylene-S(=O)$_x$R¹¹, —$C_{1-6}$ alkylene-S(=O)$_y$OR¹¹, —$C_{1-6}$ alkylene-OC(=O)NR¹¹R¹², —$C_{1-6}$ alkylene-C(=O)NR¹¹R¹², —$C_{1-6}$ alkylene-C(=O)NR¹¹—S(=O)$_y$R¹², —$C_{1-6}$ alkylene-NR¹¹—C(=O)NR¹¹R¹², —$C_{1-6}$ alkylene-OS(=O)$_y$R¹¹, —$C_{1-6}$ alkylene-OS(=O)$_y$NR¹¹R¹², —$C_{1-6}$ alkylene-S(=O)$_y$NR¹¹R¹², —$C_{1-6}$ alkylene NR¹¹—S(=O)$_y$NR¹¹R¹², —$C_{1-6}$ alkylene-NR¹¹R¹², and —O—$C_{1-6}$ alkylene-NR¹¹R¹²; and R¹³, at each occurrence, is independently selected from the group consisting of halogen, cyano, nitro, $C_{1-6}$ alkyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —OR¹¹, —SR¹¹, —OC(=O)R¹¹, —C(=O)R¹¹, —C(=O)OR¹¹, —C(=O)NR¹¹R¹², —C(=O)NR¹¹S(=O)$_y$ NR¹¹R¹², —C(=O)NR¹¹S(=O)$_y$R¹², —S(=O)$_y$R¹¹, —S(=O)$_y$OR¹¹, —S(=O)$_y$NR¹¹R¹², —S(=O)$_y$NR¹¹S(=O)$_z$OR¹², —S(=O)$_y$NR¹¹C(=O)R¹², —S(=O)$_y$NR¹¹C(=O)OR¹², —NR¹¹R¹², —NR¹¹—C(=O)R¹², —NR¹¹—C(=O)OR¹², —NR¹¹—S(=O)$_y$—R¹², —NR¹¹—C(=O)—NR¹¹R¹², —$C_{1-6}$ alkylene-R¹¹, —$C_{1-6}$ alkylene-OR¹¹, —$C_{1-6}$ alkylene-OC(=O)R¹¹, —$C_{1-6}$ alkylene-C(=O)R¹¹, —$C_{1-6}$ alkylene-S(=O)$_x$R¹¹, —$C_{1-6}$ alkylene-S(=O)$_y$OR¹¹, —$C_{1-6}$ alkylene-OC(=O)NR¹¹R¹², —$C_{1-6}$ alkylene-C(=O)NR¹¹R¹², —$C_{1-6}$ alkylene-C(=O)NR¹¹—S(=O)$_y$R¹², —$C_{1-6}$ alkylene-NR¹¹—C(=O)NR¹¹R¹², —$C_{1-6}$ alkylene-OS(=O)$_y$R¹¹, —$C_{1-6}$ alkylene-OS(=O)$_y$NR¹¹R¹², —$C_{1-6}$ alkylene-S(=O)$_y$NR¹¹R¹², —$C_{1-6}$ alkylene-NR¹¹—S(=O)$_y$NR¹¹R¹², —$C_{1-6}$ alkylene-NR¹¹R¹², and —O—$C_{1-6}$ alkylene-NR¹¹R¹², and wherein the alkyl, alkylene, cyclic hydrocarbyl group, heterocyclic group, aryl, heteroaryl and aralkyl recited for the substituent R¹³ are optionally further substituted by 1, 2, 3 or more substituents independently selected from the group consisting of halogen, OH, oxo, amino, cyano, nitro, $C_{1-6}$ alkyl, halogenated $C_{1-6}$ alkyl, $C_{3-6}$ cyclic hydrocarbyl group, 3- to 10-membered heterocyclic group, $C_{6-10}$ aryl, 5- to 14-membered heteroaryl and $C_{6-12}$ aralkyl; and wherein the heterocyclic group, aryl or heteroaryl when being a substituent is connected to the rest of the molecule through a ring C atom, or where possible, through a ring N atom.

3. The compound according to item 1 or 2, or a pharmaceutically acceptable salt, ester, stereoisomer, polymorph, solvate, N-oxide, isotopically labeled compound, metabolite or prodrug thereof, wherein U is a single bond, NR¹⁰, O, S, methylene, ethylene, —CH₂—O—, —O—CH₂—, —CH₂—S—, —S—CH₂—, —CH₂—NR¹⁰—, —NR¹⁰—CH₂—, —CH=CH—, —CH=N— or —N=CH—; preferably, U is a single bond, methylene or ethylene.

4. The compound according to any one of items 1 to 3, or a pharmaceutically acceptable salt, ester, stereoisomer, polymorph, solvate, N-oxide, isotopically labeled compound, metabolite or prodrug thereof, wherein R³ is F, Cl, Br, I, amino, cyano, nitro, $C_{1-4}$ alkyl, $C_{5-7}$ cyclic hydrocarbyl group, 5- to 7-membered monocyclic heterocyclic group, phenyl, 5- to 7-membered heteroaryl, —OR¹¹, —SR¹¹, —OC(=O)R¹¹, —C(=O)R¹¹, —C(=O)OR¹¹, —C(=O)NR¹¹R¹², —C(=O)NR¹¹S(=O)$_y$NR¹¹R¹², —C(=O)NR¹¹S(=O)$_y$R¹², —S(=O)$_y$OR¹¹, —S(=O)$_y$NR¹¹R¹², —S(=O)$_y$NR¹¹C(=O)R¹², —S(=O)$_y$NR¹¹C(=O)OR¹², —$C_{1-4}$ alkylene-OR¹¹, —$C_{1-4}$ alkylene-OC(=O)R¹¹, —$C_{1-4}$ alkylene-C(=O)OR¹¹, —$C_{1-4}$ alkylene-S(=O)$_y$OR¹¹, —$C_{1-4}$ alkylene-OC(=O)NR¹¹R¹², —$C_{1-4}$ alkylene-C(=O)NR¹¹R¹², —$C_{1-4}$ alkylene-OS(=O)$_y$R¹¹ or —$C_{1-4}$ alkylene-S(=O)$_y$NR¹¹R¹²; preferably is 5- to 6-membered heteroaryl, —C(=O)OR¹¹, —C(=O)NR¹¹R¹², —C(=O)NR¹¹S(=O)$_y$NR¹¹R¹², —C(=O)NR¹¹S(=O)$_y$R¹², —S(=O)$_y$OR¹¹, —S(=O)$_y$NR¹¹R¹², —S(=O)$_y$NR¹¹C(=O)R¹², —S(=O)$_y$NR¹¹C(=O)OR¹², —$C_{1-3}$ alkylene-OC(=O)R¹¹, —$C_{1-3}$ alkylene-C(=O)OR¹¹, —$C_{1-3}$ alkylene-S(=O)$_y$OR¹¹, —$C_{1-3}$ alkylene-C(=O)NR¹¹R¹² or —$C_{1-3}$ alkylene-S(=O)$_y$NR¹¹R¹²; more preferably is 5- to 6-membered heteroaryl (such as thienyl, furyl, pyrrolyl, oxazolyl, thiazolyl, imidazolyl, pyrazolyl, isoxazolyl, isothiazolyl, oxadiazolyl, triazolyl, tetrazolyl such as 1-tetrazolyl or 5-tetrazolyl, thiadiazolyl, pyridyl, pyridazinyl, pyrimidinyl, pyrazinyl or triazinyl), —C(=O)OR¹¹ (such as COOH, COOCH₃ or COOCH₂CH₃), —C(=O)NR¹¹S(=O)$_y$ NR¹¹R¹² (such as

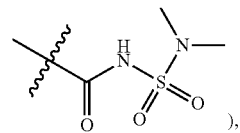 [SMILES: *C(=O)NS(=O)(=O)N(C)C]
),

—C(=O)NR¹¹S(=O)$_y$R¹² (such as

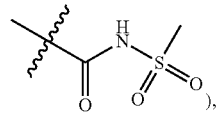
),

—C(=O)NR¹¹R¹², —S(=O)$_y$OR¹¹ or —S(=O)$_y$NR¹¹R¹², —S(=O)$_y$NR¹¹C(=O)R¹², —S(=O)$_y$NR¹¹C(=O)OR¹² (such as

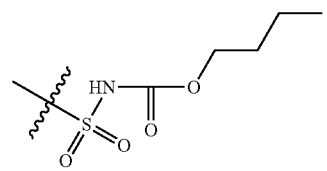

5. The compound according to any one of items 1 to 3, or a pharmaceutically acceptable salt, ester, stereoisomer, polymorph, solvate, N-oxide, isotopically labeled compound, metabolite or prodrug thereof, wherein $R^3$ is —P(O)(OR$^{11}$)(OR$^{12}$), preferably —P(O)(OH)$_2$, —P(O)(OH)(OC$_{1-6}$ alkyl) or —P(O)(OC$_{1-6}$ alkyl)$_2$, preferably —P(O)(OH)$_2$, —P(O)(OH)(OC$_{1-3}$ alkyl) or —P(O)(OC$_{1-3}$ alkyl)$_2$, more preferably —P(O)(OH)$_2$, —P(O)(OH)(OCH$_3$) or —P(O)(OH)(OCH$_2$CH$_3$).

6. The compound according to any one of items 1 to 5, or a pharmaceutically acceptable salt, ester, stereoisomer, polymorph, solvate, N-oxide, isotopically labeled compound, metabolite or prodrug thereof, wherein $R^4$ and $R^{10}$, at each occurrence, are each independently H, F, Cl, Br, I, amino, cyano, nitro, CM alkyl, $C_{5-7}$ cyclic hydrocarbyl group, 5- to 7-membered monocyclic heterocyclic group, phenyl, 5- to 6-membered heteroaryl, —OR$^{11}$, —SR$^{11}$, —OC(=O)R$^{11}$, —C(=O)OR$^{11}$, —C(=O)NR$^{11}$R$^{12}$, —C(=O)NR$^{11}$S(=O)$_y$, NR$^{11}$R$^{12}$, —C(=O)NR$^{11}$S(=O)$_y$R$^{12}$, —S(=O)$_y$OR$^{11}$, —S(=O)$_y$NR$^{11}$R$^{12}$, —S(=O)$_y$NR$^{11}$C(=O)R$^{12}$, —S(=O)$_y$NR$^{11}$C(=O)OR$^{12}$, —C$_{1-4}$ alkylene-OR$^{11}$, —C$_{1-4}$ alkylene-OC(=O)R$^{11}$, —C$_{1-4}$ alkylene-C(=O)OR$^{11}$, —C$_{1-4}$ alkylene-S(=O)$_y$OR$^{11}$, —C$_{1-4}$ alkylene-OC(=O)NR$^{11}$R$^{12}$, —C$_{1-4}$ alkylene-C(=O)NR$^{11}$R$^{12}$, —C$_{1-4}$ alkylene-OS(=O)$_y$R$^{11}$ or —C$_{1-4}$ alkylene-S(=O)$_y$NR$^{11}$R$^{12}$; preferably H, F, Cl, Br, I, OH, amino, cyano, nitro or C$_{1-4}$ alkyl (e.g. methyl).

7. The compound according to any one of items 1 to 6, or a pharmaceutically acceptable salt, ester, stereoisomer, polymorph, solvate, N-oxide, isotopically labeled compound, metabolite or prodrug thereof, wherein $R^{11}$ and $R^{12}$ at each occurrence are each independently selected from the group consisting of H, C$_{1-4}$ alkyl, C$_{5-7}$ cyclic hydrocarbyl group, 5- to 7-membered monocyclic heterocyclic group, phenyl, 5- to 6-membered heteroaryl; preferably selected from the group consisting of H and C$_{1-4}$ alkyl; the alkyl, cyclic hydrocarbyl group, heterocyclic group, phenyl and heteroaryl are each optionally substituted by 1, 2, 3 or more $R^{13}$.

8. The compound according to any one of items 1 to 7, or a pharmaceutically acceptable salt, ester, stereoisomer, polymorph, solvate, N-oxide, isotopically labeled compound, metabolite or prodrug thereof, wherein $R^{13}$, at each occurrence, is independently selected from the group consisting of F, Cl, Br, I, amino, cyano, nitro, C$_{1-4}$ alkyl, C$_{5-7}$ cyclic hydrocarbyl group, 5- to 7-membered monocyclic heterocyclic group, phenyl, 5- to 6-membered heteroaryl, C$_{6-12}$ aralkyl, —OR$^{11}$, —SR$^{11}$, —OC(=O)R$^{11}$, —C(=O)OR$^{11}$, —C(=O)NR$^{11}$R$^{12}$, —C(=O)NR$^{11}$S(=O)$_y$NR$^{11}$R$^{12}$, —C(=O)NR$^{11}$S(=O)$_y$R$^{12}$, —S(=O)$_y$OR$^{11}$, —S(=O)$_y$NR$^{11}$R$^{12}$, —S(=O)$_y$NR$^{11}$C(=O)R$^{12}$, —S(=O)$_y$NR$^{11}$C(=O)OR$^{12}$, —C$_{1-4}$ alkylene-R$^{11}$, —C$_{1-4}$ alkylene-OR$^{11}$, —C$_{1-4}$ alkylene-OC(=O)R$^{11}$, —C$_{1-4}$ alkylene-C(=O)OR$^{11}$, —C$_{1-4}$ alkylene-S(=O)$_y$OR$^{11}$, —C$_{1-4}$ alkylene-OC(=O)NR$^{11}$R$^{12}$, —C$_{1-4}$ alkylene-C(=O)NR$^{11}$R$^{12}$, —C$_{1-4}$ alkylene-OS(=O)$_y$R$^{11}$ or —C$_{1-4}$ alkylene-S(=O)$_y$NR$^{11}$R$^{12}$; preferably is F, Cl, Br, I, amino, cyano, nitro, C$_{1-4}$ alkyl, —OR$^{11}$ (preferably, $R^{11}$ is a C$_{1-6}$ alkyl optionally substituted by 1, 2, 3 or more halogens, more preferably a C$_{1-3}$ alkyl optionally substituted by 1, 2 or 3 F or Cl), —SR$^{11}$ (preferably, $R^{11}$ is C$_{1-6}$ alkyl optionally substituted by 1, 2, 3 or more halogens), more preferably C$_{1-3}$ alkyl optionally substituted by 1, 2 or 3 F or Cl), or phenyl; and preferably, wherein the alkyl, alkylene, cyclic hydrocarbyl group, heterocyclic group, phenyl and heteroaryl are optionally further substituted by 1, 2, 3 or more substitutes independently selected from the group consisting of F, Cl, Br, I, OH, oxo, amino, cyano, nitro, C$_{1-4}$ alkyl, halogenated C$_{1-4}$ alkyl, C$_{5-6}$ cyclic hydrocarbyl group, 5- to 7-membered monocyclic heterocyclic group, phenyl, 5- to 6-membered heteroaryl; preferably F, Cl, OH, amino, cyano, nitro, C$_{1-4}$ alkyl and halogenated C$_{1-4}$ alkyl.

9. The compound according to any one of items 1, and 3 to 7, or a pharmaceutically acceptable salt, ester, stereoisomer, polymorph, solvate, N-oxide, isotopically labeled compound, metabolite or prodrug thereof, wherein $R^{13}$, at each occurrence, is independently selected from the group consisting of —P(O)R$^{11}$R$^{12}$, wherein preferably, $R^{11}$ and $R^{12}$, at each occurrence, are each independently a C$_{1-6}$ alkyl optionally substituted by 1, 2, 3 or more halogens, preferably a C$_{1-3}$ alkyl optionally substituted by 1, 2 or 3 F or Cl, more preferably methyl, ethyl, propyl or isopropyl, more preferably methyl; and C$_{3-10}$ cyclic hydrocarbyl group or 3- to 10-membered heterocyclic group, which is substituted by C$_{1-6}$ alkyl, preferably C$_{3-7}$ cyclic hydrocarbyl group or 4- to 7-membered heterocyclic group, which is substituted by C$_{1-6}$ alkyl, preferably C$_{5-7}$ cyclic hydrocarbyl group or 5- to 7-membered monocyclic heterocyclic group, which is substituted by C$_{1-3}$ alkyl, wherein the alkyl is optionally substituted by 1, 2, 3 or more OH or halogens, preferably optionally substituted by 1, 2 or 3 OH, F or Cl.

10. The compound according to any one of items 1 to 9, or a pharmaceutically acceptable salt, ester, stereoisomer, polymorph, solvate, N-oxide, isotopically labeled compound, metabolite or prodrug thereof, wherein R is:

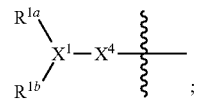

wherein $R^{1a}$, $R^{1b}$ together with $X^1$ to which they are attached form a group which is optionally substituted by 1, 2, 3 or more $R^{13}$ and is selected from the group consisting of C$_{5-7}$ cyclic hydrocarbyl group; 5- to 10-membered heterocyclic group; C$_{6-10}$ aryl; and 5- to 10-membered heteroaryl; and $X^4$ is a direct bond.

11. The compound according to item 10, or a pharmaceutically acceptable salt, ester, stereoisomer, polymorph, solvate, N-oxide, isotopically labeled compound, metabolite or prodrug thereof, wherein the compound has a structure of formula (I-1) or formula (I'-1):

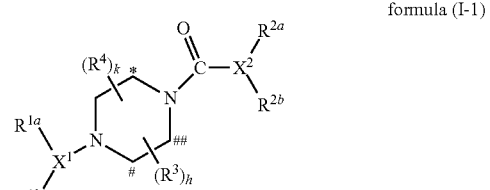

formula (I-1)

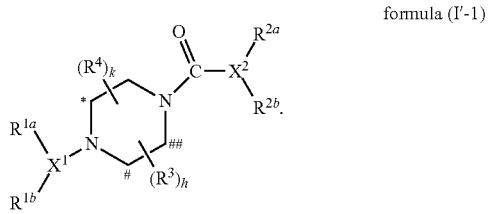

formula (I'-1)

12. The compound according to item 10 or 11, or a pharmaceutically acceptable salt, ester, stereoisomer, polymorph, solvate, N-oxide, isotopically labeled compound, metabolite or prodrug thereof, wherein $R^{1a}$, $R^{1b}$ together with $X^1$ to which they are attached form a group which is optionally substituted by 1, 2, 3 or more $R^{13}$ and is selected from the group consisting of $C_{5-7}$ cyclic hydrocarbyl group; 5-, 6- or 7-membered monocyclic heterocyclic group; and phenyl.

13. The compound according to item 10 or 11, or a pharmaceutically acceptable salt, ester, stereoisomer, polymorph, solvate, N-oxide, isotopically labeled compound, metabolite or prodrug thereof, wherein $R^{1a}$, $R^{1b}$ together with $X^1$ to which they are attached form a group which is optionally substituted by 1, 2, 3 or more $R^{13}$ and is selected from the group consisting of 5- to 10-membered heteroaryl (such as 5- to 6-membered heteroaryl);

preferably, the heteroaryl is selected from the group consisting of pyrrolyl, pyrazolyl, imidazolyl, triazolyl, pyridyl, pyrimidinyl, pyrazinyl, pyridazinyl, triazinyl, indolyl, isoindolyl, indazolyl, benzimidazolyl, benzotriazolyl, quinolinyl, isoquinolinyl, quinazolinyl, quinoxalinyl, pyrrolopyrimidinyl, pyrrolopyridyl, pyrazolopyrimidinyl, pyrazolopyridyl, imidazopyridyl, purinyl; preferably selected from the group consisting of pyrazolyl, pyrimidinyl, quinazolinyl and pyrazolopyrimidinyl; more preferably selected from the group consisting of

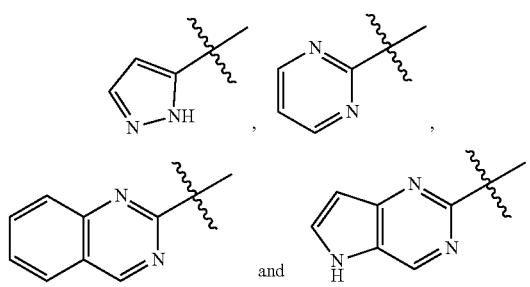

14. The compound according to any one of items 10 to 13, or a pharmaceutically acceptable salt, ester, stereoisomer, polymorph, solvate, N-oxide, isotopically labeled compound, metabolite or prodrug thereof, wherein $R^{13}$ is a $C_{1-4}$ alkyl, $C_{6-10}$ aryl or —$C_{1-4}$ alkylene-$R^{11}$, which is optionally substituted by 1, 2 or 3 substituents independently selected from the group consisting of halogen, OH, amino, cyano, $C_{1-4}$ alkyl and phenyl; and wherein $R^{11}$ is selected from the group consisting of a $C_{5-7}$ cyclic hydrocarbyl group, 5- to 7-membered monocyclic heterocyclic group, phenyl and 5- to 6-membered heteroaryl;

preferably, $R^{13}$ is a $C_{1-4}$ alkyl, phenyl or —$C_{1-4}$-alkylene-phenyl, which is optionally substituted by 1, 2 or 3 substituents independently selected from the group consisting of F, Cl, Br, $C_{1-4}$ alkyl and phenyl.

15. The compound according to item 14, or a pharmaceutically acceptable salt, ester, stereoisomer, polymorph, solvate, N-oxide, isotopically labeled compound, metabolite or prodrug thereof, wherein $R^{13}$ is a phenyl optionally substituted by 1, 2 or 3 substituents independently selected from the group consisting of F, Cl, Br and $C_{1-4}$ alkyl;

preferably, $R^{13}$ is a phenyl or fluorophenyl (preferably

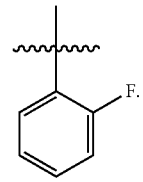 [SMILES: *c1ccccc1F]

16. The compound according to item 14, or a pharmaceutically acceptable salt, ester, stereoisomer, polymorph, solvate, N-oxide, isotopically labeled compound, metabolite or prodrug thereof, wherein $R^{13}$ is a $C_{1-4}$ alkyl or —$C_{1-4}$-alkylene-phenyl, which is optionally substituted by 1, 2 or 3 substituents independently selected from the group consisting of $C_{1-4}$ alkyl and phenyl;

preferably, $R^{13}$ is methyl or —$CH_2$-phenyl.

17. The compound according to any one of items 10 to 15, or a pharmaceutically acceptable salt, ester, stereoisomer, polymorph, solvate, N-oxide, isotopically labeled compound, metabolite or prodrug thereof, wherein $R^{1a}$, $R^{1b}$ together with $X^1$ to which they are attached form a group selected from the group consisting of phenyl,

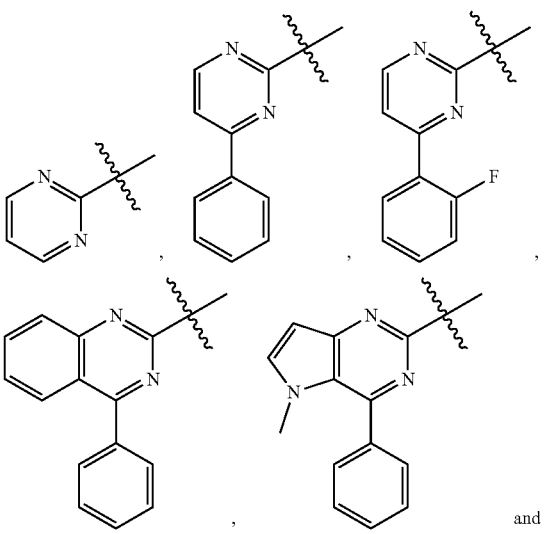

and

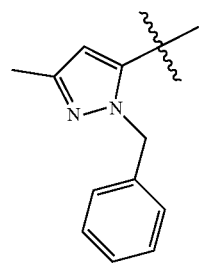

18. The compound according to any one of items 1 to 9, or a pharmaceutically acceptable salt, ester, stereoisomer, polymorph, solvate, N-oxide, isotopically labeled compound, metabolite or prodrug thereof, wherein R is:

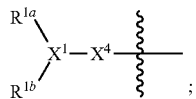

wherein $R^{1a}$ is a group which is optionally substituted by 1, 2, 3 or more $R^{13}$ and is selected from the group consisting of $C_{1-6}$ alkyl, $C_{2-6}$ alkenyl, $C_{2-6}$ alkynyl, $C_{3-7}$ cyclic hydrocarbyl group, 4- to 7-membered monocyclic heterocyclic group, 8- to 10-membered benzo-fused heterocyclic group, phenyl, 5- to 10-membered heteroaryl, —$C_{1-3}$ alkylene-$C_{3-7}$ cyclic hydrocarbyl group, —$C_{1-3}$ alkylene-(5- to 7-membered monocyclic heterocyclic group), —$C_{1-3}$ alkylene-(8- to 10-membered benzo-fused heterocyclic group), —$C_{1-3}$ alkylenephenyl and —$C_{1-3}$ alkylene-(5- to 10-membered heteroaryl); and $R^{1b}$ does not exist or is selected from the group consisting of H and $R^{1a}$.

19. The compound according to item 18, or a pharmaceutically acceptable salt, ester, stereoisomer, polymorph, solvate, N-oxide, isotopically labeled compound, metabolite or prodrug thereof, wherein $R^{1a}$ is a group which is optionally substituted by 1, 2, 3 or more $R^{13}$ and is selected from the group consisting of $C_{1-6}$ alkyl, $C_{2-6}$ alkenyl, $C_{2-6}$ alkynyl, $C_{5-7}$ cyclic hydrocarbyl group, 4- to 7-membered monocyclic heterocyclic group (including 5-, 6- or 7-membered monocyclic heterocyclic group), 8- to 10-membered benzo-fused heterocyclic group, phenyl, 5- to 10-membered heteroaryl (including 5- to 6-membered heteroaryl), —$C_{1-3}$ alkylene-$C_{3-7}$ cyclic hydrocarbyl group, —$C_{1-3}$ alkylene-(5- to 7-membered monocyclic heterocyclic group), —$C_{1-3}$ alkylenephenyl and —$C_{1-3}$ alkylene-(5- to 6-membered heteroaryl).

20. The compound according to any one of items 1 to 9 and 18-19, or a pharmaceutically acceptable salt, ester, stereoisomer, polymorph, solvate, N-oxide, isotopically labeled compound, metabolite or prodrug thereof, wherein $R^{1b}$ does not exist, and $X^1$ does not exist.

21. The compound according to item 20, or a pharmaceutically acceptable salt, ester, stereoisomer, polymorph, solvate, N-oxide, isotopically labeled compound, metabolite or prodrug thereof, wherein the compound has a structure of formula (I-2) or formula (I'-2):

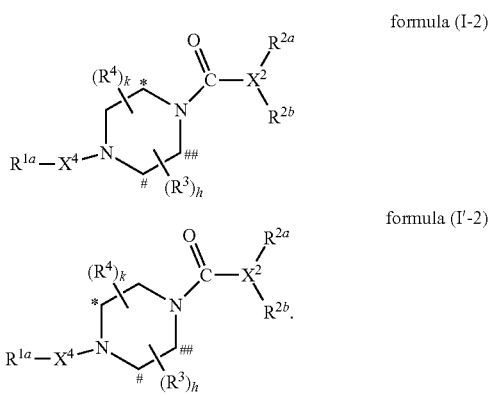

22. The compound according to item 20 or 21, or a pharmaceutically acceptable salt, ester, stereoisomer, polymorph, solvate, N-oxide, isotopically labeled compound, metabolite or prodrug thereof, wherein $X^4$ is selected from the group consisting of C(=O), S(=O)$_y$, —O—C(=O)—, —S—C(=O)—, —O—S(=O)$_y$—, —$NR^{10}$—C(=O)— and —$NR^{10}$—S(=O)$_y$—, preferably is C(=O), —O—C(=O)— or —$NR^{10}$—C(=O)—.

23. The compound according to any one of items 18 and 20-22, or a pharmaceutically acceptable salt, ester, stereoisomer, polymorph, solvate, N-oxide, isotopically labeled compound, metabolite or prodrug thereof, wherein $R^{1a}$ is a group selected from the group consisting of optionally substituted $C_{3-7}$ cyclic hydrocarbyl group, optionally substituted 4- to 7-membered monocyclic heterocyclic group, optionally substituted 8- to 10-membered benzo-fused heterocyclic group, optionally substituted phenyl, optionally substituted 5- to 10-membered heteroaryl, -optionally substituted $C_{1-3}$ alkylene-(optionally substituted $C_{3-7}$ cyclic hydrocarbyl group), -optionally substituted $C_{1-3}$ alkylene-(optionally substituted 5- to 7-membered monocyclic heterocyclic group), -optionally substituted $C_{1-3}$ alkylene-(optionally substituted 8- to 10-membered benzo-fused heterocyclic group), -optionally substituted $C_{1-3}$ alkylene-optionally substituted phenyl, and -optionally substituted $C_{1-3}$ alkylene-(optionally substituted 5- to 10-membered heteroaryl);

preferably, $R^{1a}$ is a group selected from the group consisting of optionally substituted $C_{3-7}$ cyclic hydrocarbyl group, optionally substituted 4- to 7-membered monocyclic heterocyclic group, optionally substituted 8- to 10-membered benzo-fused heterocyclic group, optionally substituted phenyl, optionally substituted 5- to 10-membered heteroaryl, —$C_{1-3}$ alkylene-(optionally substituted $C_{3-7}$ cyclic hydrocarbyl group), —$C_{1-3}$ alkylene-(optionally substituted 5- to 7-membered monocyclic heterocyclic group), —$C_{1-3}$ alkylene-(optionally substituted 8- to 10-membered benzo-fused heterocyclic group), -optionally substituted $C_{1-3}$ alkylene-optionally substituted phenyl, and —$C_{1-3}$ alkylene-(optionally substituted 5- to 10-membered heteroaryl);

wherein the term "optionally substituted" means being substituted by 1, 2, 3 or more $R^{13}$;

$R^{1b}$ does not exist;

$X^1$ does not exist; and $X^4$ is selected from the group consisting of C(=O), S(=O)$_y$, —OC(=O)— and —$NR^{10}$—C(=O)— and S(=O)$_y$, —$NR^{10}$—S(=O)$_y$—, wherein $R^{10}$ is preferably H or $C_{1-6}$ alkylene.

24. The compound according to item 23, or a pharmaceutically acceptable salt, ester, stereoisomer, polymorph, solvate, N-oxide, isotopically labeled compound, metabolite or prodrug thereof, wherein $R^{1a}$ is a group selected from the group consisting of an optionally substituted 5-, 6- or 7-membered monocyclic heterocyclic group, an optionally substituted phenyl, and -optionally substituted $C_{1-3}$ alkylene-optionally substituted phenyl;

preferably a group selected from the group consisting of an optionally substituted 5-, 6- or 7-membered monocyclic heterocyclic group, an optionally substituted phenyl, and —$C_{1-3}$ alkylene-optionally substituted phenyl; and wherein the term "optionally substituted" means being substituted by 1, 2, 3 or more $R^{13}$.

25. The compound according to item 23, or a pharmaceutically acceptable salt, ester, stereoisomer, polymorph, solvate, N-oxide, isotopically labeled compound, metabolite or prodrug thereof, wherein $R^{1a}$ is a group selected from the group consisting of an optionally substituted $C_{3-7}$ cyclic hydrocarbyl group, wherein the cyclic hydrocarbyl group is, for example, cyclopropyl, cyclobutyl, cyclopentyl, or cyclohexyl;

an optionally substituted 4- to 7-membered monocyclic heterocyclic group, wherein the heterocyclic group is, for example, an optionally substituted 8- to 10-membered benzo-fused heterocyclic group, wherein the heterocyclic group is, for example, an optionally substituted phenyl;
optionally substituted $C_{1-3}$ alkylene-optionally substituted phenyl;
an optionally substituted 5- to 10-membered heteroaryl, and —$C_{1-3}$ alkylene-(optionally substituted 5- to 10-membered heteroaryl), wherein the heteroaryl is, for example, and
wherein the term "optionally substituted" means being substituted by 1, 2, 3 or more $R^{13}$.

26. The compound according to any one of items 23 to 25, or a pharmaceutically acceptable salt, ester, stereoisomer, polymorph, solvate, N-oxide, isotopically labeled compound, metabolite or prodrug thereof, wherein $R^{13}$ is selected from the group consisting of halogen, OH, —$NR^{11}R^{12}$, cyano and $C_{1-4}$ alkyl; and phenyl, 5-, 6- or 7-membered monocyclic heterocyclic group and 5- to 6-membered heteroaryl, which are optionally substituted by 1, 2 or 3 substituents independently selected from the group consisting of halogen, OH, —$NR^{11}R^{12}$, cyano and $C_{1-4}$ alkyl, and wherein $R^{11}$ and $R^{12}$ are each independently selected from the group consisting of H and $C_{1-4}$ alkyl (preferably methyl);

preferably, $R^{13}$ is selected from the group consisting of F, Cl, Br, —N(CH$_3$)$_2$, and $C_{1-4}$ alkyl; and phenyl, 5- to 7-membered monocyclic heterocyclic group (such as

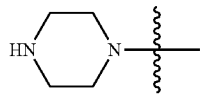

and 5- to 6-membered heteroaryl (such as

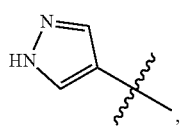 [SMILES: *c1cn[nH]c1]

which are optionally substituted by 1, 2 or 3 substituents independently selected from the group consisting of F, Cl, Br and $C_{1-4}$ alkyl.

27. The compound according to any one of items 23 to 26, or a pharmaceutically acceptable salt, ester, stereoisomer, polymorph, solvate, N-oxide, isotopically labeled compound, metabolite or prodrug thereof, wherein $R^{1a}$ is selected from the group consisting of cyclopropyl, cyclobutyl, cyclopentyl, cyclohexyl, phenyl,

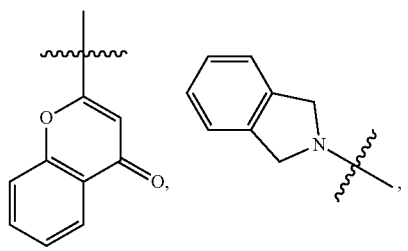

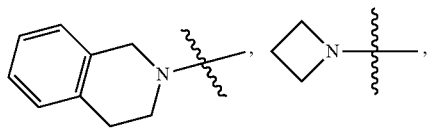

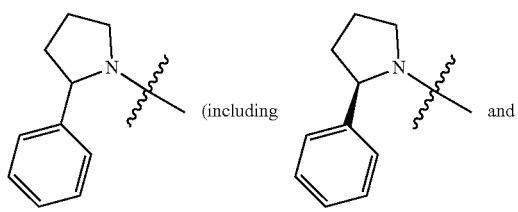 (including

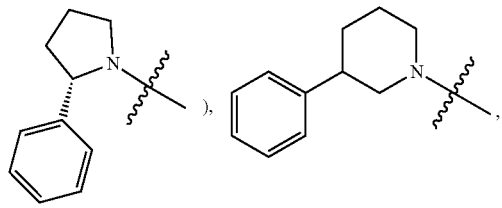

-continued

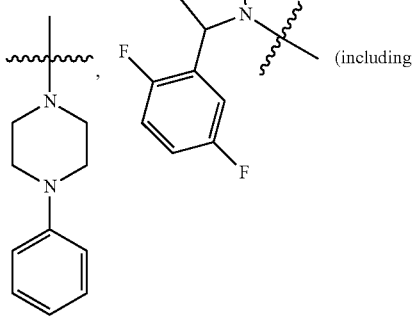 (including

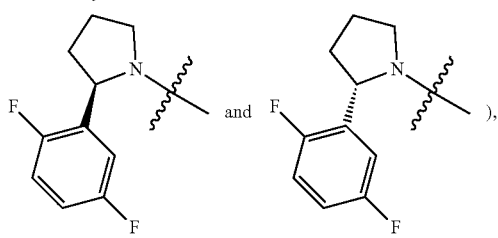 and ),

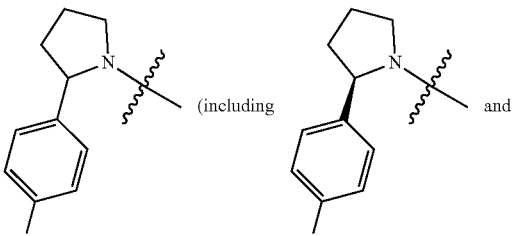 (including and

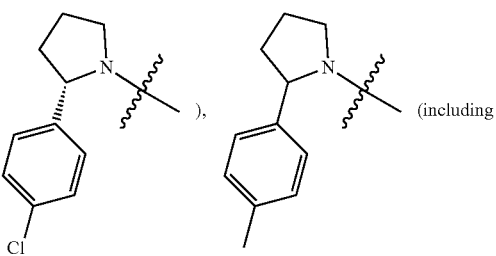 ), (including

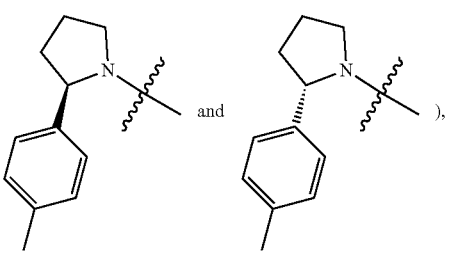 and ),

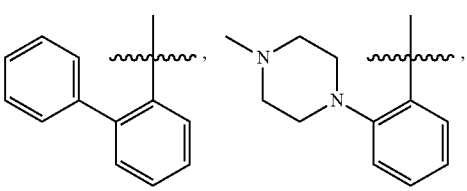

31
-continued

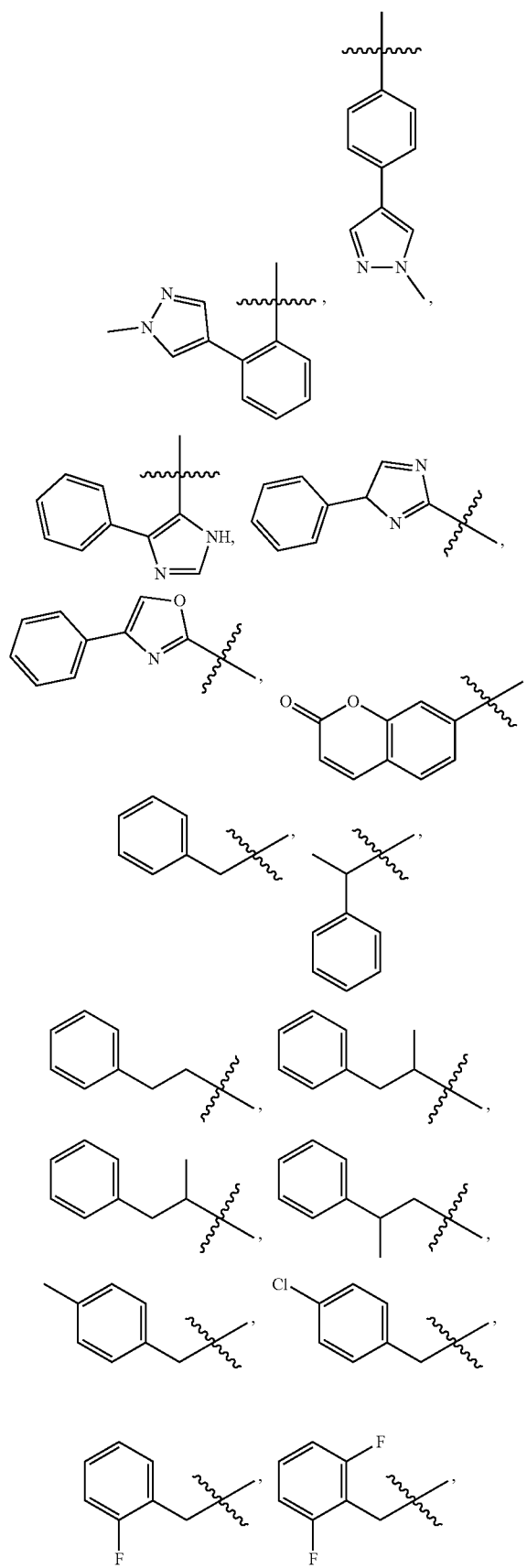

32
-continued

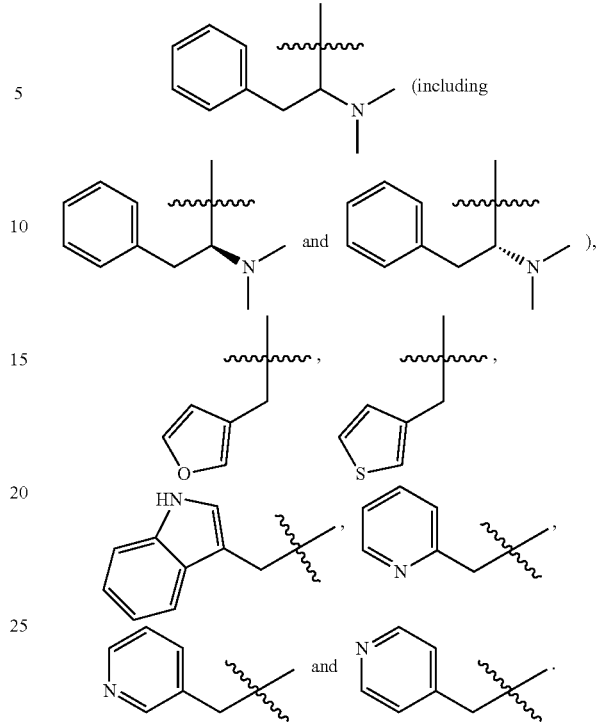

28. The compound according to any one of items 23 to 27, or a pharmaceutically acceptable salt, ester, stereoisomer, polymorph, solvate, N-oxide, isotopically labeled compound, metabolite or prodrug thereof, wherein $X^4$ is selected from the group consisting of C(=O), S(=O)$_y$, and —O—C(=O)—, and wherein y is preferably 2.

29. The compound according to any one of items 23 to 28, or a pharmaceutically acceptable salt, ester, stereoisomer, polymorph, solvate, N-oxide, isotopically labeled compound, metabolite or prodrug thereof, wherein $R^3$ is COOH,

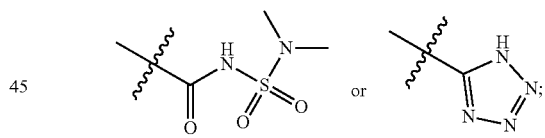

and $R^4$ is H.

30. The compound according to item 20 or 21, or a pharmaceutically acceptable salt, ester, stereoisomer, polymorph, solvate, N-oxide, isotopically labeled compound, metabolite or prodrug thereof, wherein $X^4$ is a direct bond.

31. The compound according to item 30, or a pharmaceutically acceptable salt, ester, stereoisomer, polymorph, solvate, N-oxide, isotopically labeled compound, metabolite or prodrug thereof, wherein $R^{1a}$ is —C$_{1-3}$ alkylenephenyl, preferably —CH$_2$-phenyl.

32. The compound according to item 22, or a pharmaceutically acceptable salt, ester, stereoisomer, polymorph, solvate, N-oxide, isotopically labeled compound, metabolite or prodrug thereof, wherein:
$R^{1a}$ is selected from the group consisting of C$_{2-6}$ alkenyl (preferably vinyl, 1-propenyl or 2-propenyl) and C$_{2-6}$ alkynyl (preferably ethynyl, 1-propynyl or 2-propynyl), which are optionally substituted by 1, 2, 3 or more $R^{13}$; and
$X^4$ is C(=O) or —O—C(=O)—.

33. The compound according to item 32, or a pharmaceutically acceptable salt, ester, stereoisomer, polymorph, solvate, N-oxide, isotopically labeled compound, metabolite or prodrug thereof, wherein:

$R^{13}$ is selected from the group consisting of phenyl and 5- to 6-membered heteroaryl, which are optionally substituted by 1, 2 or 3 substituents independently selected from the group consisting of halogen, OH, amino, cyano and $C_{1-4}$ alkyl;

preferably, $R^{13}$ is a phenyl or pyridyl, which is optionally substituted by 1, 2 or 3 substituents independently selected from the group consisting of F, Cl and Br.

34. The compound according to item 32 or 33, or a pharmaceutically acceptable salt, ester, stereoisomer, polymorph, solvate, N-oxide, isotopically labeled compound, metabolite or prodrug thereof, wherein $R^{1a}$ is selected from the group consisting of

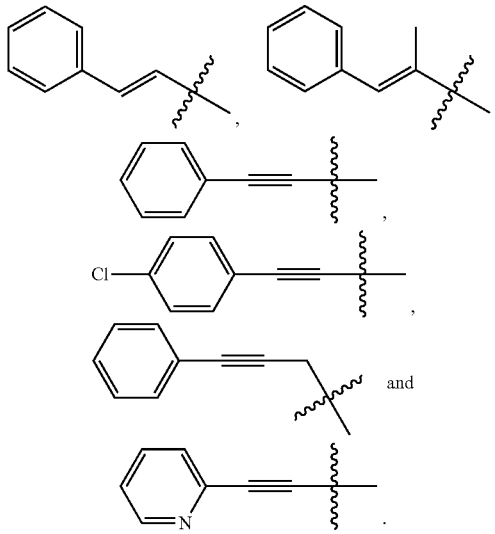

35. The compound according to any one of items 1-9 and 18-19, or a pharmaceutically acceptable salt, ester, stereoisomer, polymorph, solvate, N-oxide, isotopically labeled compound, metabolite or prodrug thereof, wherein $X^1$ is $CR^{10}$ or N.

36. The compound according to item 35, or a pharmaceutically acceptable salt, ester, stereoisomer, polymorph, solvate, N-oxide, isotopically labeled compound, metabolite or prodrug thereof, wherein $X^4$ is a direct bond.

37. The compound according to item 35, or a pharmaceutically acceptable salt, ester, stereoisomer, polymorph, solvate, N-oxide, isotopically labeled compound, metabolite or prodrug thereof, wherein $X^4$ is selected from the group consisting of C(=O), S(=O)$_y$, —O—C(=O)—, —S—C(=O)—, —O—S(=O)$_y$—, —NR$^{10}$—C(=O)— or —NR$^{10}$—S(=O)$_y$, preferably is C(=O), —O—C(=O)— or —NR$^{10}$—C(=O)—.

38. The compound according to any one of items 35 to 37, or a pharmaceutically acceptable salt, ester, stereoisomer, polymorph, solvate, N-oxide, isotopically labeled compound, metabolite or prodrug thereof, wherein $R^{1b}$ is selected from the group consisting of H and $R^{1a}$, and preferably, $X^1$ is CH.

39. The compound according to item 36, or a pharmaceutically acceptable salt, ester, stereoisomer, polymorph, solvate, N-oxide, isotopically labeled compound, metabolite or prodrug thereof, wherein:

$R^{1a}$ is selected from the group consisting of $C_{2-6}$ alkenyl (such as vinyl, 1-propenyl or 2-propenyl) and $C_{2-6}$ alkynyl (such as ethynyl, 1-propynyl or 2-propynyl) which are optionally substituted by 1, 2, 3 or more $R^{13}$; and/or $R^{1b}$ is selected from the group consisting of $C_{1-4}$ alkyl optionally substituted by 1, 2, 3 or more $R^{13}$.

40. The compound according to item 39, or a pharmaceutically acceptable salt, ester, stereoisomer, polymorph, solvate, N-oxide, isotopically labeled compound, metabolite or prodrug thereof, wherein:

$R^{13}$ is selected from the group consisting of $C_{1-4}$ alkyl, phenyl and 5- to 6-membered heteroaryl, which are optionally substituted by 1, 2 or 3 substituents independently selected from the group consisting of halogen, OH, amino, cyano and $C_{1-4}$ alkyl;

preferably, $R^{13}$ is a $C_{1-4}$ alkyl or phenyl, which is optionally substituted by 1, 2 or 3 substituents independently selected from the group consisting of F, $C_1$ and Br;

more preferably, $R^{13}$ is a $C_{1-4}$ alkyl (such as methyl, ethyl, propyl, isopropyl or tert-butyl); or a phenyl optionally substituted by 1, 2 or 3 substituents independently selected from the group consisting of F, Cl and Br.

41. The compound according to item 39 or 40, or a pharmaceutically acceptable salt, ester, stereoisomer, polymorph, solvate, N-oxide, isotopically labeled compound, metabolite or prodrug thereof, wherein:

$R^{1a}$ is

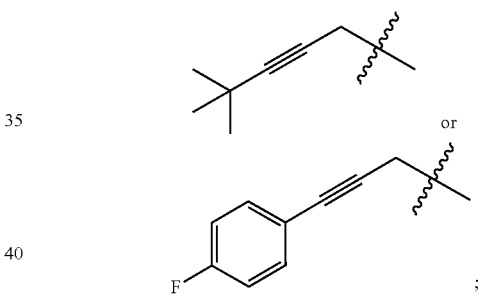

and/or $R^{1b}$ is methyl, ethyl, n-propyl or isopropyl.

42. The compound according to any one of items 39 to 41, or a pharmaceutically acceptable salt, ester, stereoisomer, polymorph, solvate, N-oxide, isotopically labeled compound, metabolite or prodrug thereof, wherein $X^1$ is CH or N, preferably CH.

43. The compound according to item 37, or a pharmaceutically acceptable salt, ester, stereoisomer, polymorph, solvate, N-oxide, isotopically labeled compound, metabolite or prodrug thereof, wherein:

$R^{1a}$ is a group selected from the group consisting of an optionally substituted $C_{3-7}$ cyclic hydrocarbyl group, an optionally substituted 4- to 7-membered monocyclic heterocyclic group, an optionally substituted 8- to 10-membered benzo-fused heterocyclic group, an optionally substituted phenyl, an optionally substituted 5- to 10-membered heteroaryl, -optionally substituted $C_{1-3}$ alkylene-(optionally substituted $C_{3-7}$ cyclic hydrocarbyl group), -optionally substituted $C_{1-3}$ alkylene-(optionally substituted 5- to 7-membered monocyclic heterocyclic group), -optionally substituted $C_{1-3}$ alkylene-(optionally substituted 8- to 10-membered benzo-fused heterocyclic group), -optionally substituted $C_{1-3}$ alkylene-optionally substituted phenyl, and -optionally substituted $C_{1-3}$ alkylene-(optionally substituted 5- to 10-membered heteroaryl);

preferably, $R^{1a}$ is a group selected from the group consisting of an optionally substituted $C_{3-7}$ cyclic hydrocarbyl group, an optionally substituted 4- to 7-membered monocyclic heterocyclic group, an optionally substituted 8- to 10-membered benzo-fused heterocyclic group, an optionally substituted phenyl, an optionally substituted 5- to 10-membered heteroaryl, —$C_{1-3}$ alkylene-(optionally substituted $C_{3-7}$ cyclic hydrocarbyl group), —$C_{1-3}$ alkylene-(optionally substituted 5- to 7-membered monocyclic heterocyclic group), —$C_{1-3}$ alkylene-(optionally substituted 8- to 10-membered benzo-fused heterocyclic group), —$C_{1-3}$ alkylene-optionally substituted phenyl, and —$C_{1-3}$ alkylene-(optionally substituted 5- to 10-membered heteroaryl); and wherein the term "optionally substituted" means being substituted by 1, 2, 3 or more $R^{13}$.

44. The compound according to item 43, or a pharmaceutically acceptable salt, ester, stereoisomer, polymorph, solvate, N-oxide, isotopically labeled compound, metabolite or prodrug thereof, wherein $R^{1a}$ is a group selected from the group consisting of an optionally substituted phenyl;

—$C_{1-3}$ alkylene-(optionally substituted $C_{3-7}$ cyclic hydrocarbyl group), the cyclic hydrocarbyl group being, for example, cyclopropyl, cyclobutyl, cyclopentyl, or cyclohexyl;

—$C_{1-3}$ alkylene-(optionally substituted 8- to 10-membered benzo-fused heterocyclic group), the heterocyclic group being, for example,

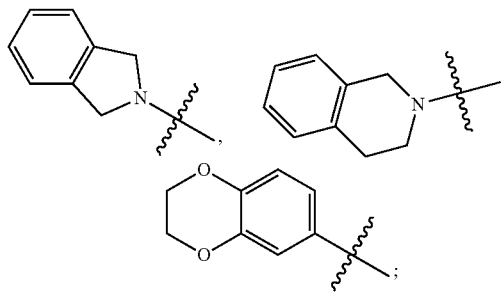

—$C_{1-3}$ alkylene-optionally substituted phenyl;

an optionally substituted 5- to 10-membered heteroaryl and —$C_{1-3}$ alkylene-(optionally substituted 5- to 10-membered heteroaryl), the heteroaryl being, for example,

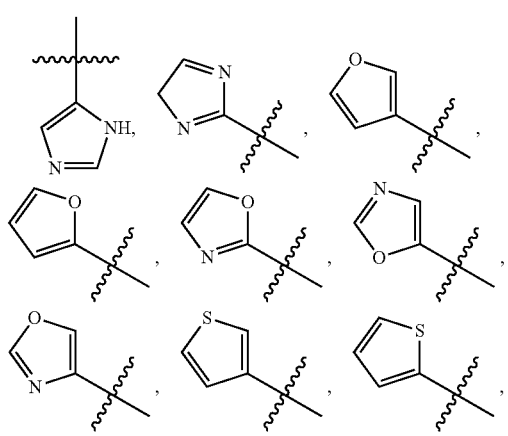

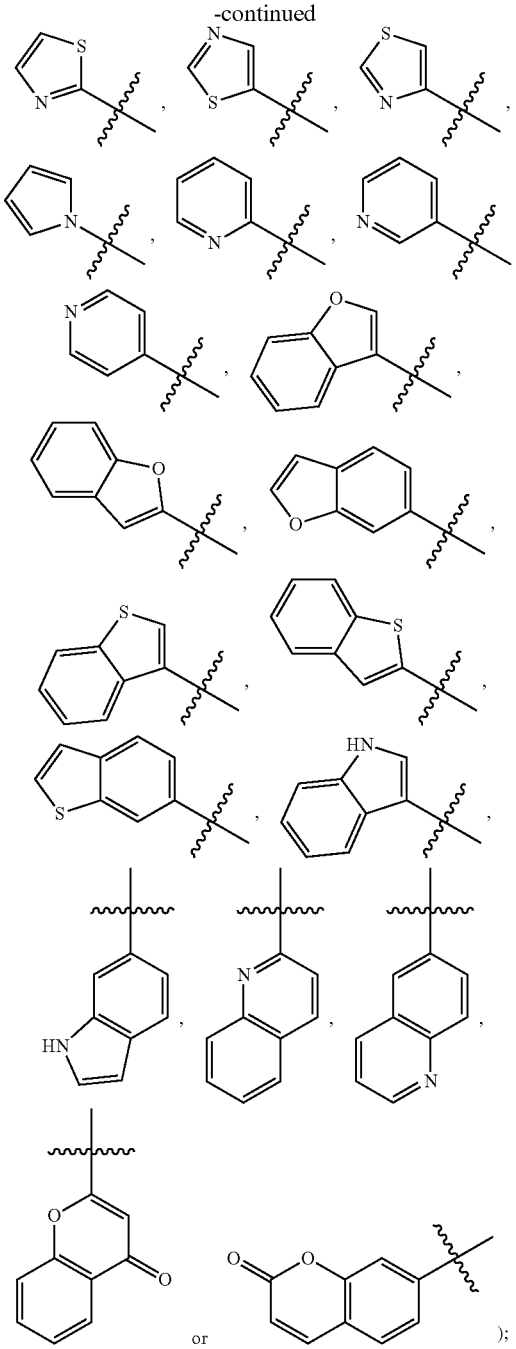

wherein the term "optionally substituted" means being substituted by 1, 2, 3 or more $R^{13}$.

45. The compound according to item 43 or 44, or a pharmaceutically acceptable salt, ester, stereoisomer, polymorph, solvate, N-oxide, isotopically labeled compound, metabolite or prodrug thereof, wherein $R^{13}$ is selected from the group consisting of halogen, —$OR^{11}$ (preferably, $R^{11}$ is $C_{1-6}$ alkyl optionally substituted by 1, 2, 3 or more halogens, more preferably $C_{1-3}$ alkyl optionally substituted by 1, 2 or 3 F or Cl), —$NR^{11}R^{12}$, cyano and $C_{3-7}$ cyclic hydrocarbyl group; and $C_{1-4}$ alkyl, $C_{2-4}$ alkenyl and $C_{2-4}$ alkynyl which are optionally substituted by 1, 2, 3 or more halogens, and wherein $R^{11}$ and $R^{12}$ are each independently selected from the group consisting of H and $C_{1-4}$ alkyl (preferably methyl);

preferably, $R^{13}$ is selected from the group consisting of F, Cl, Br, OH, —$OC_{1-4}$ alkyl, —$N(C_{1-4}$ alkyl$)_2$, cyano, $C_{3-7}$ cyclic hydrocarbyl group, $C_{2-4}$ alkenyl and $C_{2-4}$ alkynyl; and $C_{1-4}$ alkyl optionally substituted by 1, 2, 3 or more F, Cl or Br;

more preferably, $R^{13}$ is selected from the group consisting of F, Cl, Br, —$OCH_3$, —$N(CH_3)_2$, cyano, cyclopropyl, vinyl, 1-propenyl, 2-propenyl, ethynyl, 1-propenyl, 2-propynyl, methyl, ethyl, n-propyl, isopropyl, tert-butyl and $CF_3$; or $R^{13}$ is as defined in item 9.

46. The compound according to item 43 or 44, or a pharmaceutically acceptable salt, ester, stereoisomer, polymorph, solvate, N-oxide, isotopically labeled compound, metabolite or prodrug thereof, wherein $R^{1a}$ is selected from the group consisting of

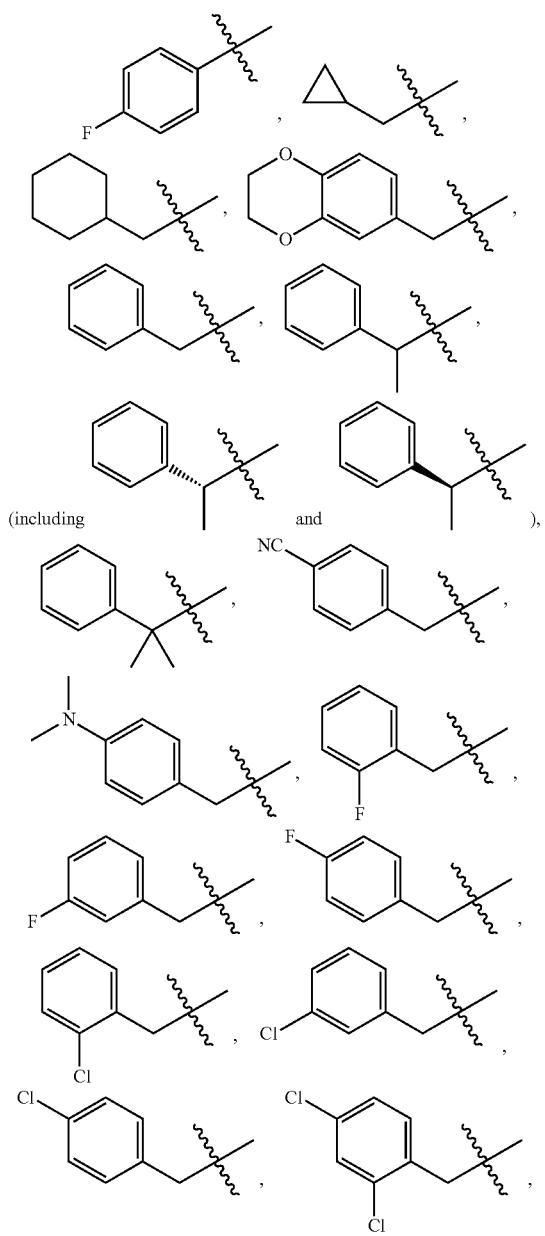

(including         and         ),

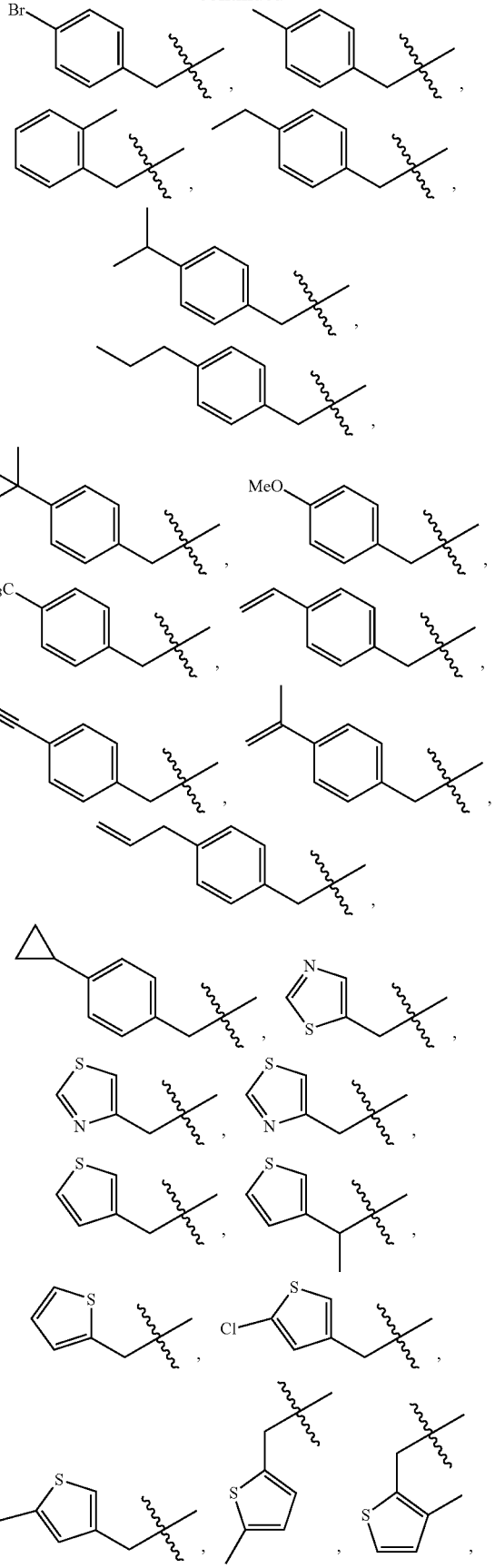

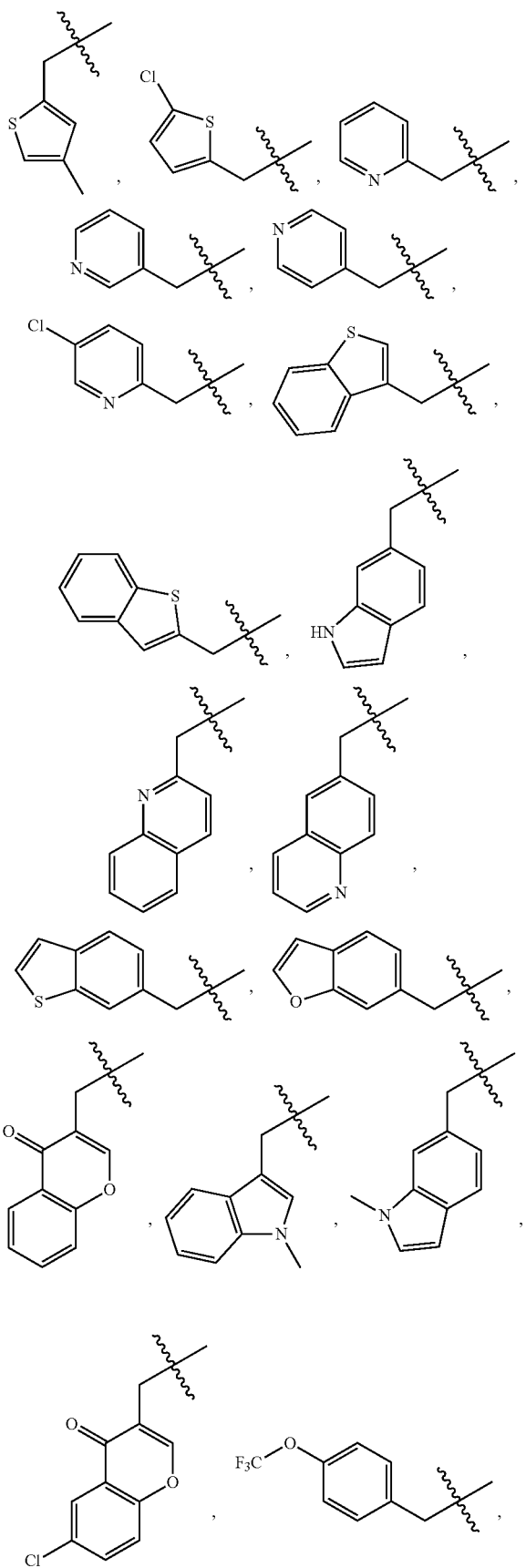

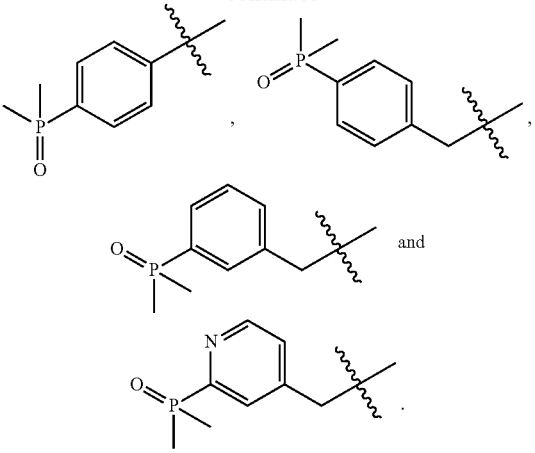

47. The compound according to any one of items 43 to 46, or a pharmaceutically acceptable salt, ester, stereoisomer, polymorph, solvate, N-oxide, isotopically labeled compound, metabolite or prodrug thereof, wherein $R^{1b}$ is a group selected from the group consisting of H, an optionally substituted $C_{1-4}$ alkyl, an optionally substituted $C_{3-7}$ cyclic hydrocarbyl group, an optionally substituted phenyl, -optionally substituted $C_{1-3}$ alkylene-(optionally substituted $C_{3-7}$ cyclic hydrocarbyl group), and -optionally substituted $C_{1-3}$ alkylene-optionally substituted phenyl;

preferably, $R^{1b}$ is a group selected from the group consisting of H, an optionally substituted $C_{1-4}$ alkyl, an optionally substituted $C_{3-7}$ cyclic hydrocarbyl group, an optionally substituted phenyl, —$C_{1-3}$ alkylene-(optionally substituted $C_{3-7}$ cyclic hydrocarbyl group), and —$C_{1-3}$ alkylene-optionally substituted phenyl;

more preferably, $R^{1b}$ is a group selected from the group consisting of

H, phenyl;

an optionally substituted $C_{1-4}$ alkyl, the alkyl being, for example, methyl, ethyl or isopropyl;

an optionally substituted $C_{3-7}$ cyclic hydrocarbyl group and —$C_{1-3}$ alkylene-($C_{3-7}$ cyclic hydrocarbyl group), the cyclic hydrocarbyl group being, for example, cyclopropyl, cyclobutyl, cyclopentyl, or cyclohexyl; and —$C_{1-3}$ alkylene-phenyl; and wherein the term "optionally substituted" means being substituted by 1, 2, 3 or more $R^{13}$;

wherein $R^{13}$ is preferably selected from the group consisting of halogen and $C_{1-4}$ alkyl, more preferably selected from the group consisting of F, Cl, Br and methyl.

48. The compound according to item 47, or a pharmaceutically acceptable salt, ester, stereoisomer, polymorph, solvate, N-oxide, isotopically labeled compound, metabolite or prodrug thereof, wherein $R^{1b}$ is selected from the group consisting of H, methyl, ethyl, isopropyl, $CF_3CH_2$, cyclopropyl, phenyl,

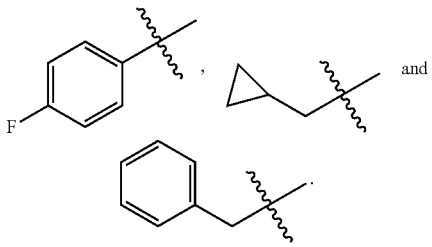

49. The compound according to any one of items 43 to 48, or a pharmaceutically acceptable salt, ester, stereoisomer, polymorph, solvate, N-oxide, isotopically labeled compound, metabolite or prodrug thereof, wherein $X^1$ is CFI or N, preferably N.

50. The compound according to any one of items 43 to 49, or a pharmaceutically acceptable salt, ester, stereoisomer, polymorph, solvate, N-oxide, isotopically labeled compound, metabolite or prodrug thereof, wherein $X^4$ is selected from the group consisting of C(=O) and S(=O)$_y$, and wherein y is preferably 2.

51. The compound according to any one of items 43 to 50, or a pharmaceutically acceptable salt, ester, stereoisomer, polymorph, solvate, N-oxide, isotopically labeled compound, metabolite or prodrug thereof, wherein $R^3$ is COOH or

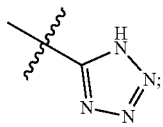

and $R^4$ is H.

52. The compound according to any one of items 1 to 51, or a pharmaceutically acceptable salt, ester, stereoisomer, polymorph, solvate, N-oxide, isotopically labeled compound, metabolite or prodrug thereof, wherein:

$R^{2a}$ is selected from the group consisting of an optionally substituted phenyl, and -optionally substituted $C_{1-3}$ alkylene-optionally substituted phenyl;

preferably, $R^{2a}$ is selected from the group consisting of an optionally substituted phenyl, and —$C_{1-3}$ alkylene-optionally substituted phenyl; and/or $R^{2b}$ is selected from the group consisting of an optionally substituted $C_{1-4}$ alkyl, an optionally substituted phenyl, and -optionally substituted $C_{1-3}$ alkylene-optionally substituted phenyl;

preferably, $R^{2b}$ is selected from the group consisting of $C_{1-4}$ alkyl, an optionally substituted phenyl, and —$C_{1-3}$ alkylene-optionally substituted phenyl;

wherein the term "optionally substituted" means being substituted by 1, 2, 3 or more $R^{13}$.

53. The compound according to item 52, or a pharmaceutically acceptable salt, ester, stereoisomer, polymorph, solvate, N-oxide, isotopically labeled compound, metabolite or prodrug thereof, wherein $R^{13}$ is selected from the group consisting of halogen and —$OR^{11}$, and wherein $R^{11}$ is selected from $C_{1-4}$ alkyl (preferably methyl);

preferably, $R^{13}$ is selected from the group consisting of F, Cl, Br and —$OCH_3$.

54. The compound according to item 52 or 53, or a pharmaceutically acceptable salt, ester, stereoisomer, polymorph, solvate, N-oxide, isotopically labeled compound, metabolite or prodrug thereof, wherein:

$R^{2a}$ is selected from the group consisting of phenyl,

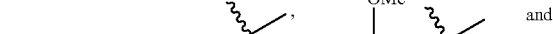
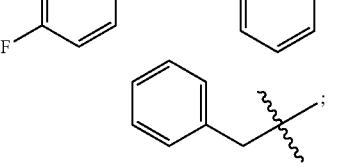

and/or $R^{2b}$ is selected from the group consisting of methyl, phenyl,

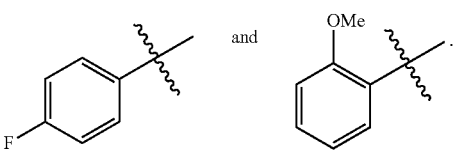 [SMILES: *c1ccc(F)cc1 ; *c1ccccc1OC]

55. The compound according to any one of items 43 to 54, or a pharmaceutically acceptable salt, ester, stereoisomer, polymorph, solvate, N-oxide, isotopically labeled compound, metabolite or prodrug thereof, wherein the compound has a structure of formula (II) or formula (III):

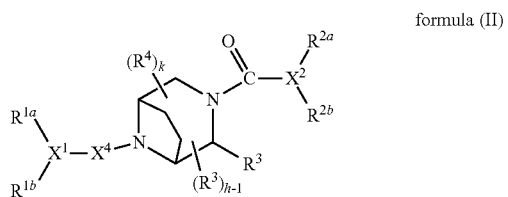

formula (II)

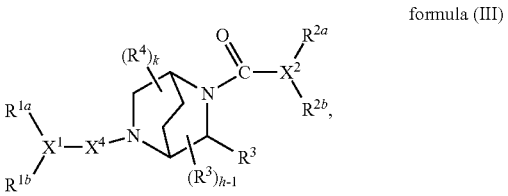

formula (III)

wherein $R^{1a}$, $R^{1b}$, $X^1$, $X^4$, $R^{2a}$, $R^{2b}$, $X^2$, $R^3$, $R^4$, h and k are as defined in any one of items 43 to 54.

56. The compound according to any one of items 1 to 9, or a pharmaceutically acceptable salt, ester, stereoisomer, polymorph, solvate, N-oxide, isotopically labeled compound, metabolite or prodrug thereof, wherein R is:

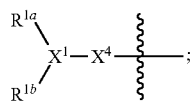

wherein $R^{1a}$ is a group which is optionally substituted by 1, 2, 3 or more $R^{13}$ and is selected from the group consisting of $C_{1-6}$ alkyl, $C_{2-6}$ alkenyl, $C_{2-6}$ alkynyl, $C_{5-7}$ cyclic hydrocarbyl group, 5-, 6- or 7-membered monocyclic heterocyclic group, 8- to 10-membered benzo-fused heterocyclic group, phenyl, 5- to 6-membered heteroaryl, —$C_{1-3}$ alkylene-$C_{3-7}$ cyclic hydrocarbyl group, —$C_{1-3}$ alkylene-(5- to 7-membered monocyclic heterocyclic group), —$C_{1-3}$ alkylenephenyl and —$C_{1-3}$ alkylene-(5- to 6-membered heteroaryl);

$R^{1b}$ and $X^1$ together form a bivalent $C_{5-7}$ cyclic hydrocarbyl group or a bivalent 5-, 6- or 7-membered monocyclic heterocyclic group; and $X^4$ is selected from the group consisting of C(=O) and S(=O)$_y$.

57. The compound according to item 56, or a pharmaceutically acceptable salt, ester, stereoisomer, polymorph, solvate, N-oxide, isotopically labeled compound, metabolite or prodrug thereof, wherein:

$R^{1a}$ is phenyl; and
$R^{1b}$ and $X^1$ together form

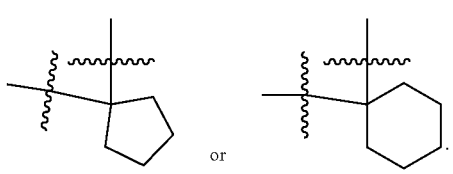 [SMILES: *C1(*)CCCC1 ; *C1(*)CCCCC1]

58. The compound according to any one of items 18 to 22, 35 to 38, and 56 to 57, or a pharmaceutically acceptable salt, ester, stereoisomer, polymorph, solvate, N-oxide, isotopically labeled compound, metabolite or prodrug thereof, wherein $R^{13}$ is selected from the group consisting of $C_{1-4}$ alkyl-O—; halogen (including F, Cl, Br and I); and $C_{1-4}$ alkyl or phenyl, which is optionally substituted by 1, 2 or 3 substituents independently selected from halogen.

59. The compound according to any one of items 10 to 12, 14 to 16, 18 to 24, 26, 31 to 33, 39 to 40, 43, 45, 47, 52 to 53, 56 and 58, or a pharmaceutically acceptable salt, ester, stereoisomer, polymorph, solvate, N-oxide, isotopically labeled compound, metabolite or prodrug thereof, wherein:

the alkyl is selected from the group consisting of methyl, ethyl, n-propyl, isopropyl, n-butyl, isobutyl, sec-butyl, tert-butyl, n-pentyl, isopentyl, neopentyl, 1-hexyl, 1-heptyl, 1-octyl;

the alkenyl is selected from the group consisting of vinyl, 1-propenyl, 2-propenyl, 2-butenyl, 3-butenyl, 2-pentenyl, 3-pentenyl, 4-pentenyl and 2-hexenyl;

the alkynyl is selected from the group consisting of ethynyl, 1-propynyl, 2-propynyl, 2-butynyl, 3-butynyl, 2-pentynyl, 3-pentynyl, 4-pentynyl, 2-hexynyl and 3-hexynyl;

the —$C_{1-3}$ alkylenephenyl is selected from the group consisting of benzyl and phenethyl;

the cyclic hydrocarbyl group is selected from the group consisting of cyclopropyl, cyclobutyl, cyclopentyl, cyclohexyl or cycloheptyl;

the monocyclic heterocyclic group is selected from the group consisting of tetrahydrofuranyl, tetrahydro thienyl, pyrrolidinyl (e.g. pyrrolidin-1-yl), oxazolidinyl, thiazolidinyl, imidazolidinyl, 1,3-dioxolanyl, 1,3-oxathiolanyl, piperidinyl, piperazinyl, morpholinyl (such as morpholino)), thiomorpholinyl, tetrahydro-2H-pyranyl, tetrahydro-2H-thiopyranyl, 1,3-oxazinanyl (1,3-oxazinane), 1,3-thiazi-nanyl (1,3-thiazinane), hexahydropyrimidyl, 1,3-oxathianyl (1,3-oxathiane), 1,4-oxathianyl (1,4-oxathiane), 1,3-diazepanyl (1,3-diazepane), 1,4-diazepanyl (1,4-diazepane), 1,3-oxazepanyl (1,3-oxazepane), 1,3-thiazepanyl (1,3-thiazepane);

the heteroaryl is selected from the group consisting of thienyl, furyl, pyrrolyl, oxazolyl, thiazolyl, imidazolyl, pyrazolyl (such as 1-pyrazolyl, 3-pyrazolyl, 4-pyrazolyl, 5-pryazolyl), isoxazolyl, isothiazolyl, oxadiazolyl, triazolyl, thiadiazolyl, pyridyl, pyridazinyl, pyrimidinyl, pyrazinyl and triazinyl; and/or the benzo-fused heterocyclic group is selected from the group consisting of

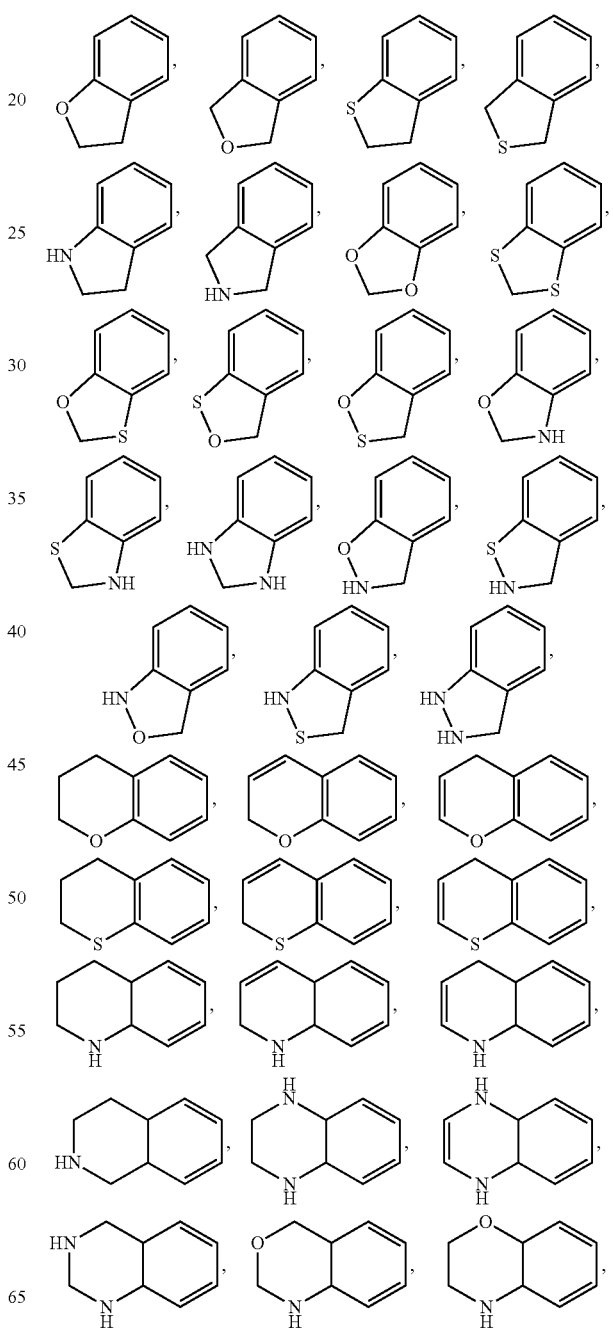

-continued
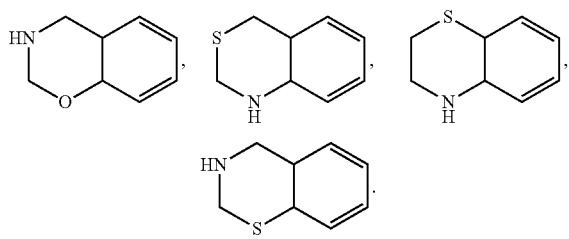
60. The compound according to any one of items 1 to 59, or a pharmaceutically acceptable salt, ester, stereoisomer, polymorph, solvate, N-oxide, isotopically labeled compound, metabolite or prodrug thereof, wherein R is:
-continued
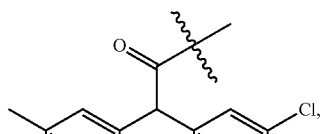
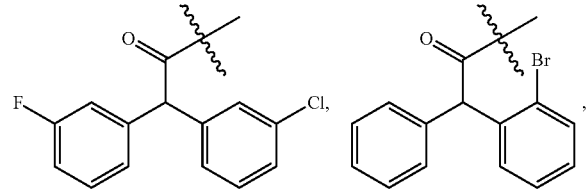
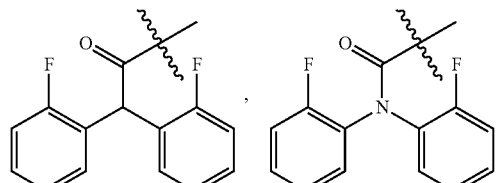
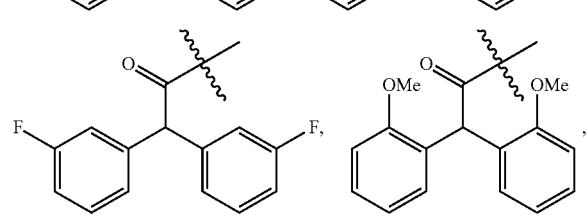
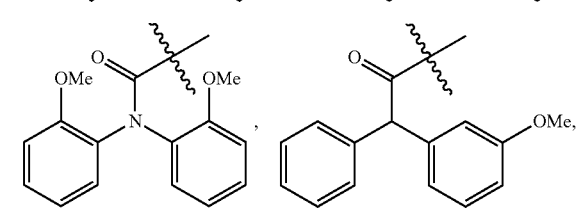
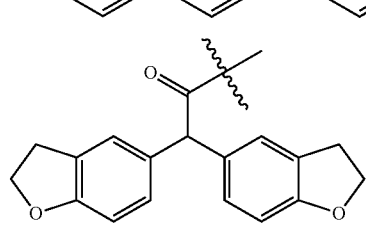
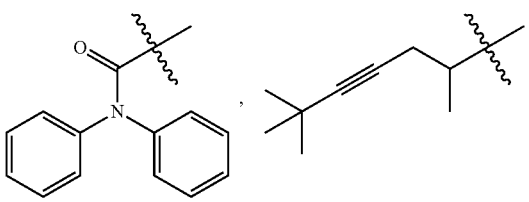
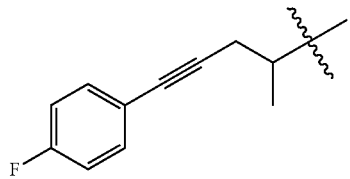

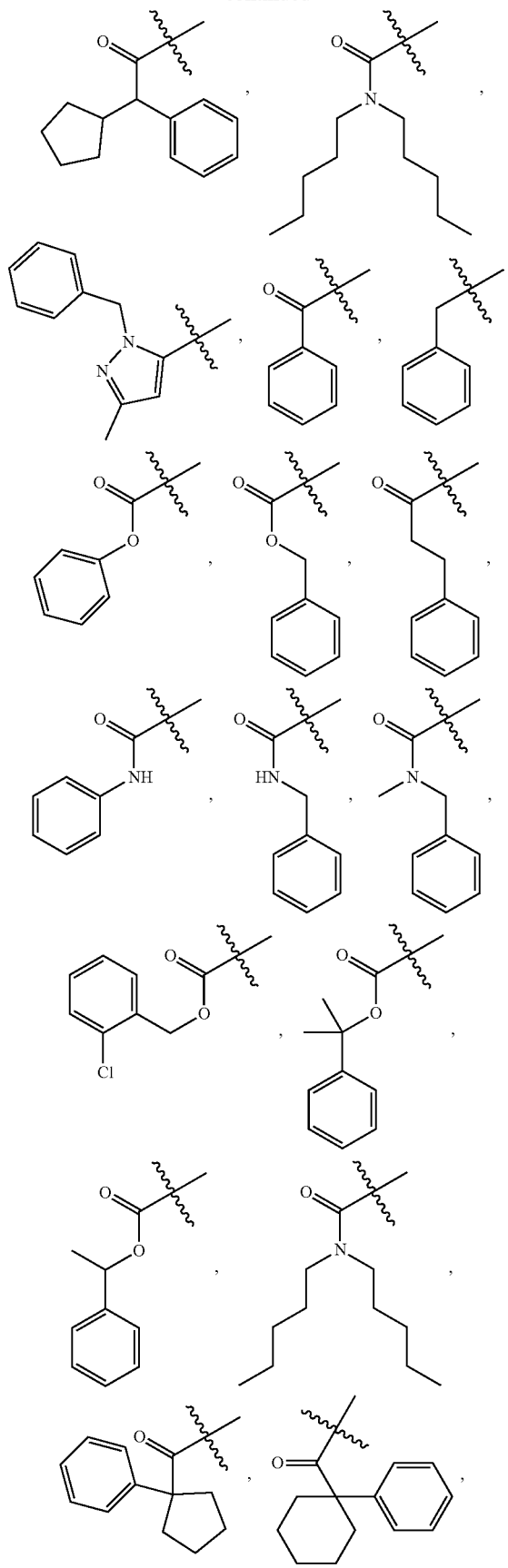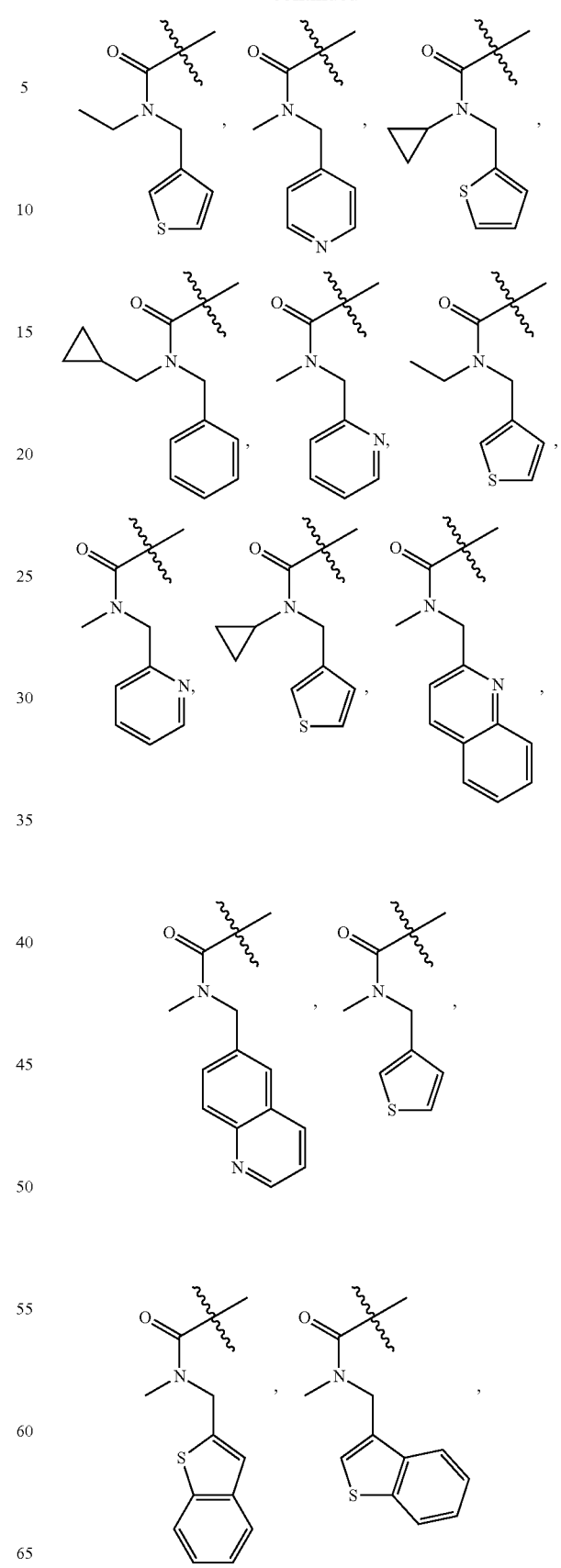

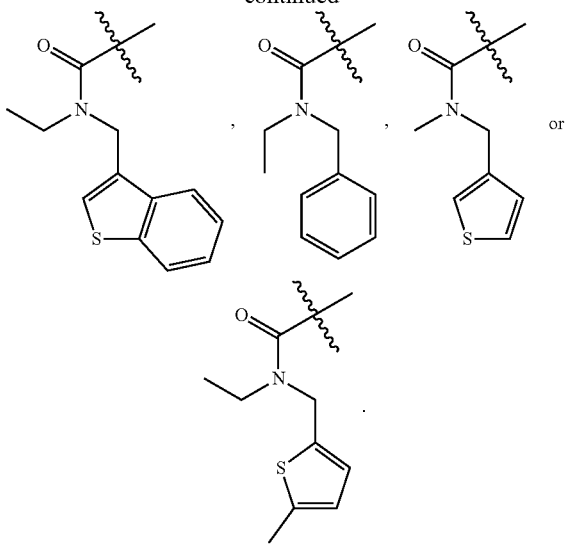

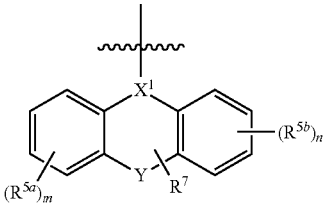

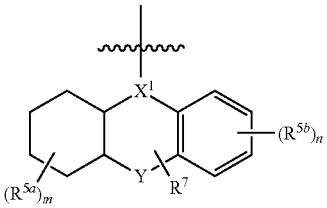

61. The compound according to any one of items 1 to 9, or a pharmaceutically acceptable salt, ester, stereoisomer, polymorph, solvate, N-oxide, isotopically labeled compound, metabolite or prodrug thereof, wherein Y is a single bond, $NR^{10}$, O, S, methylene, ethylene, —$CH_2$—O—, —O—$CH_2$—, —$CH_2$—S—, —S—$CH_2$—, —$CH_2$—$NR^{10}$—, —$NR^{10}$—$CH_2$—, —CH=CH—, —CH=N— or —N=CH—.

62. The compound according to any one of items 1 to 9 and 61, or a pharmaceutically acceptable salt, ester, stereoisomer, polymorph, solvate, N-oxide, isotopically labeled compound, metabolite or prodrug thereof, wherein
R is

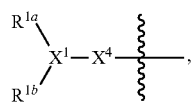

and
the optionally substituted saturated or partially unsaturated fused ring system comprising 3 or more rings which is formed by $R^{1a}$ and $R^{1b}$ together with $X^1$ to which they are attached has a structure of formula (a):

formula (a)

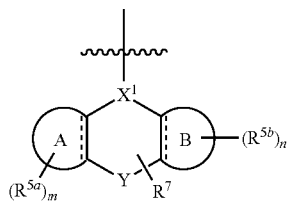

wherein:
ring A and ring B are each independently $C_{3-10}$ cyclic hydrocarbyl group, 3- to 10-membered heterocyclic group, $C_{6-10}$ aryl, or 5- to 14-membered heteroaryl, preferably $C_{5-7}$ cyclic hydrocarbyl group (such as, cyclopentyl or cyclohexyl), 5- to 7-membered monocyclic heterocyclic group, phenyl, or 5- to 6-membered heteroaryl;

═══ represents a single bond or a double bond;
preferably the fused ring system has a structure of formula (1) or formula (2):

formula (1)

formula (2)

wherein $R^{5a}$ and $R^{5b}$, at each occurrence, are each independently $R^{10}$;

$R^7$ does not exist or is $R^{10}$; and m and n, at each occurrence, are each independently 0, 1, 2 or 3.

63. The compound according to any one of items 1 to 9 and 61 to 62, or a pharmaceutically acceptable salt, ester, stereoisomer, polymorph, solvate, N-oxide, isotopically labeled compound, metabolite or prodrug thereof, wherein $X^1$ is CH or N.

64. The compound according to item 62 or 63, or a pharmaceutically acceptable salt, ester, stereoisomer, polymorph, solvate, N-oxide, isotopically labeled compound, metabolite or prodrug thereof, wherein:

the group of formula (1) has a structure selected from the group consisting of formula (1a-1)

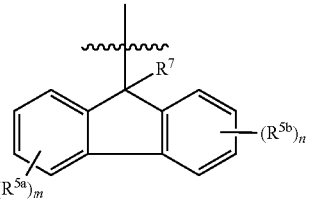

formula (1a-2)

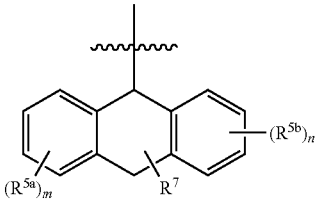

formula (1a-3)
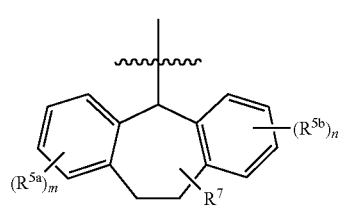
formula (1a-4)
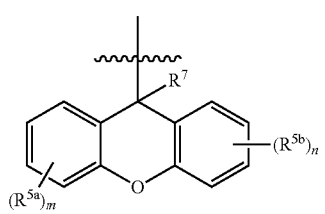
formula (1a-5)
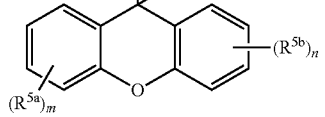
formula (1a-6)
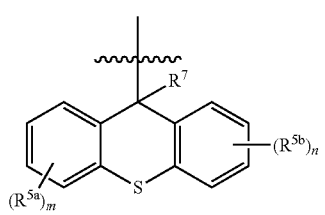
formula (1a-7)
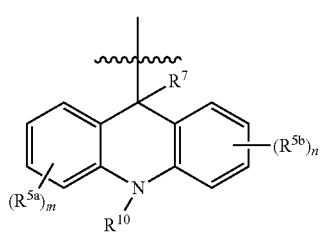
formula (1a-8)
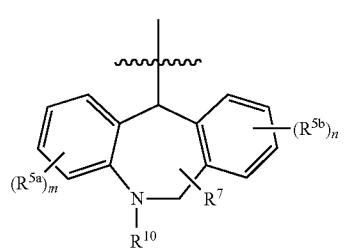
formula (1a-9)
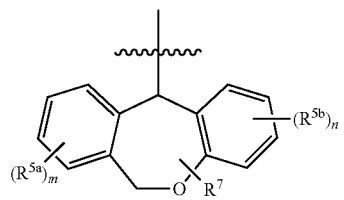
formula (1a-10)
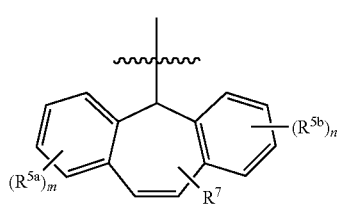
formula (1a-11)
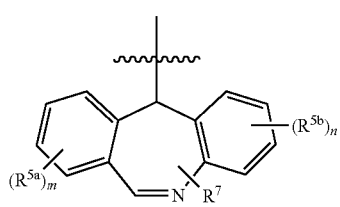
formula (1b-1)
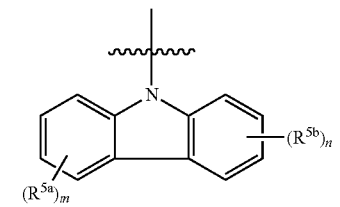
formula (1b-2)
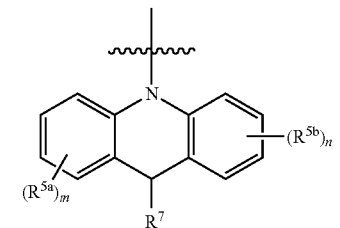
formula (1b-3)
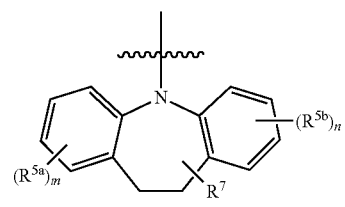
formula (1b-4)
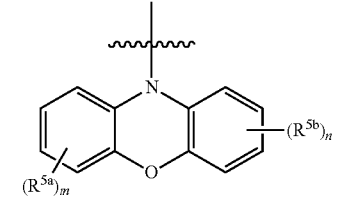
formula (1b-5)
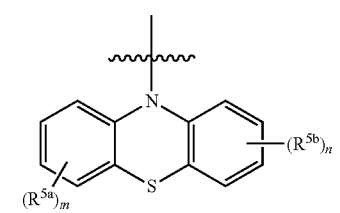

formula (1b-6)
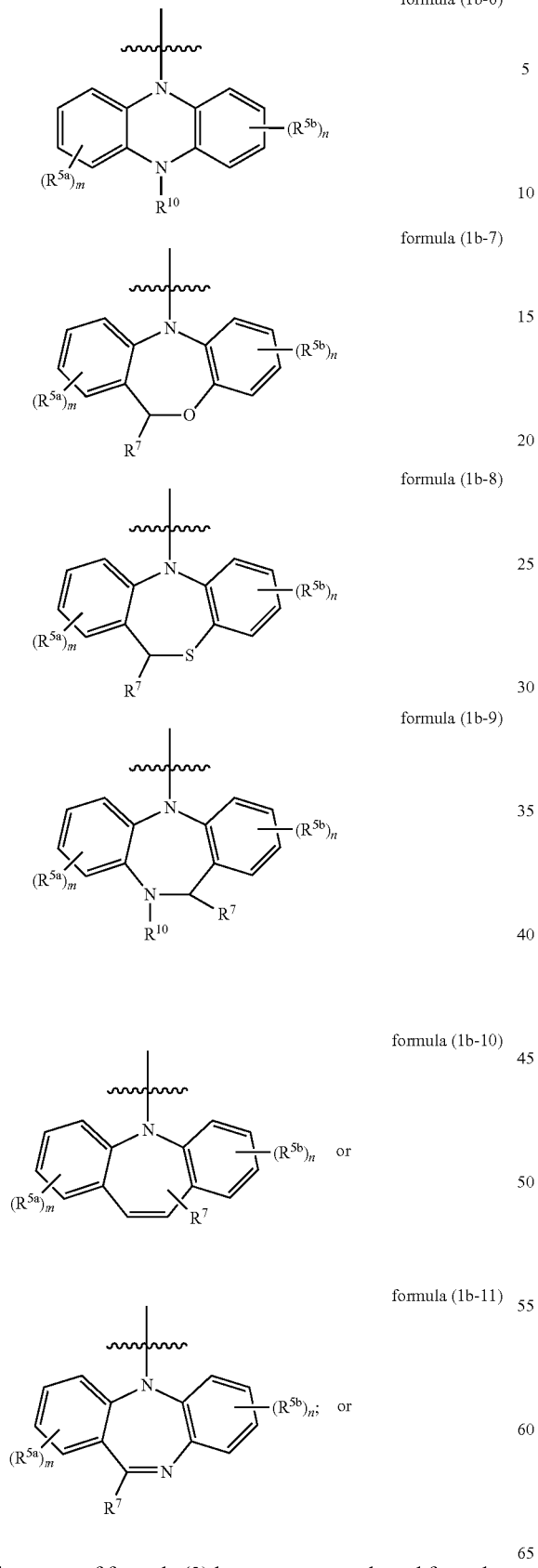
formula (1b-7)
formula (1b-8)
formula (1b-9)
formula (1b-10) or
formula (1b-11); or
the group of formula (2) has a structure selected from the group consisting of
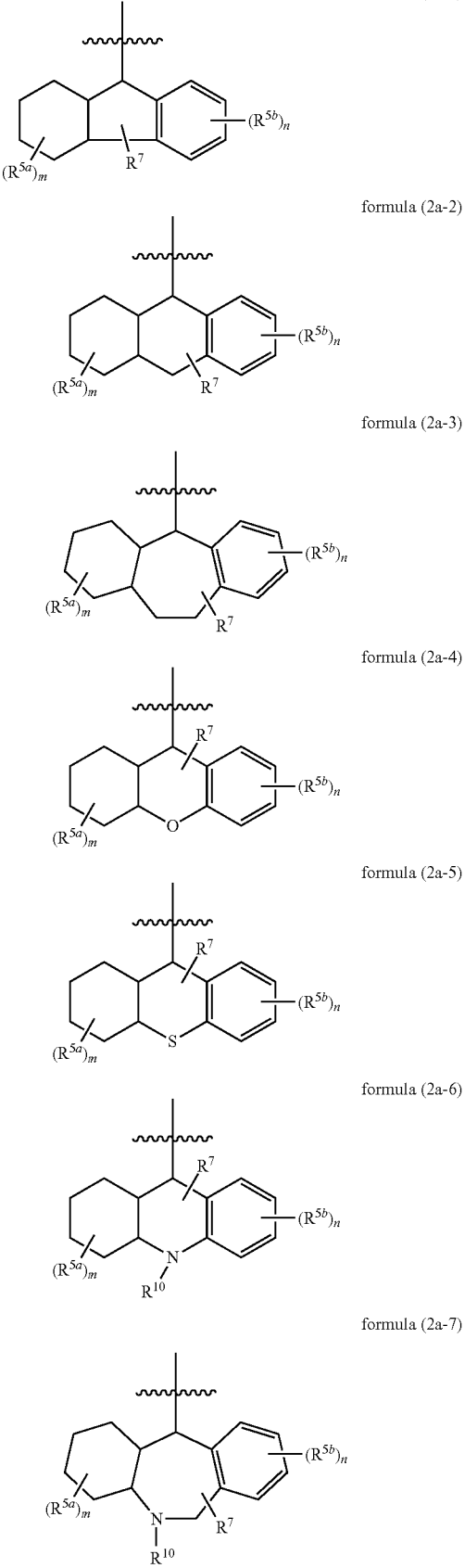
formula (2a-1)
formula (2a-2)
formula (2a-3)
formula (2a-4)
formula (2a-5)
formula (2a-6)
formula (2a-7)

formula (2a-8)
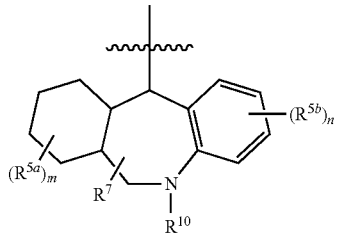
formula (2a-9)
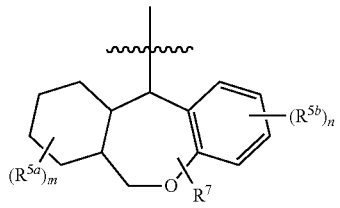
formula (2a-10)
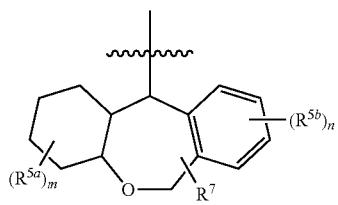
formula (2a-11)
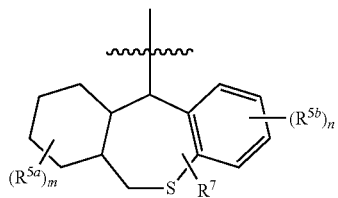
formula (2a-12)
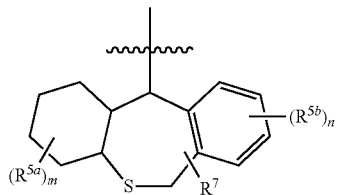
formula (2a-13)
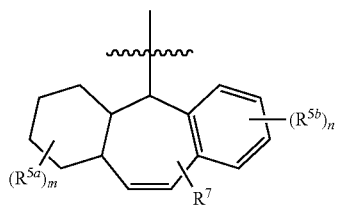
formula (2a-14)
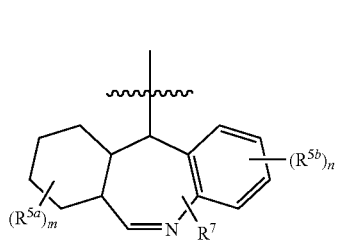
formula (2a-15)
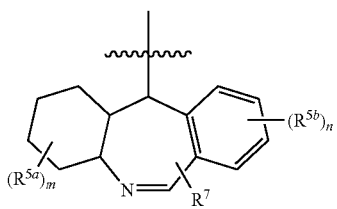
formula (2b-1)
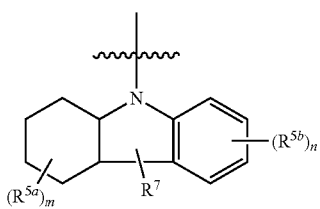
formula (2b-2)
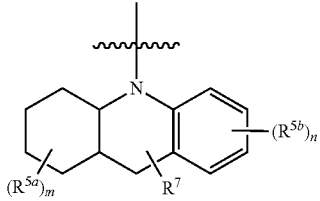
formula (2b-3)
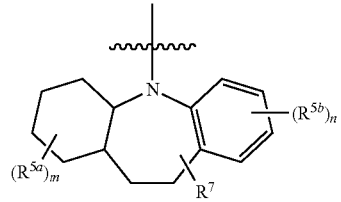
formula (2b-4)
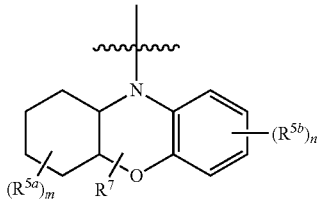
formula (2b-5)
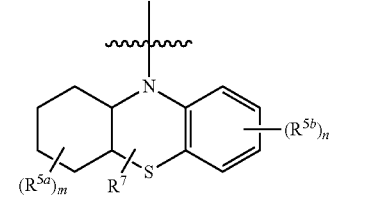
formula (2b-6)
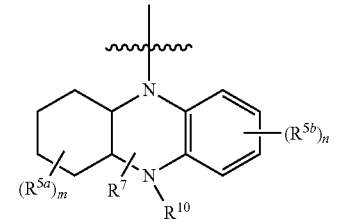

formula (2b-7)
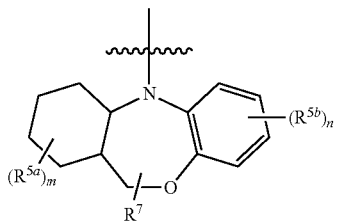

formula (2b-8)
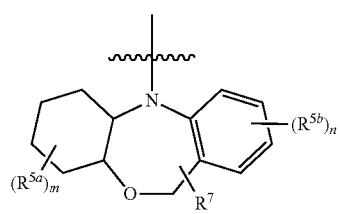

formula (2b-9)
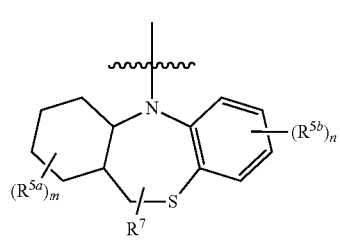

formula (2b-10)
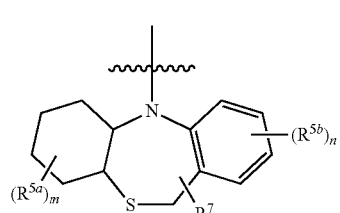

formula (2b-11)
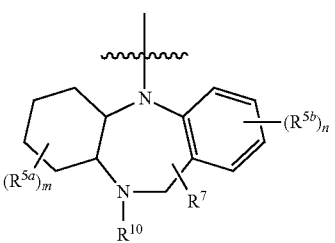

formula (2b-12)
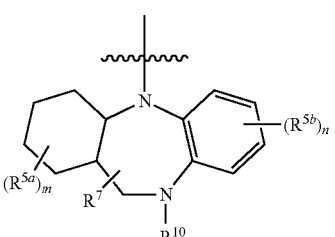

formula (2b-13)
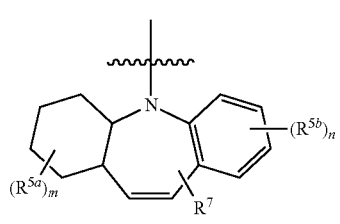

formula (2b-14)
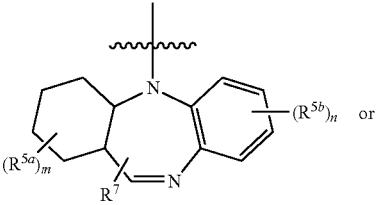

or formula (2b-15)
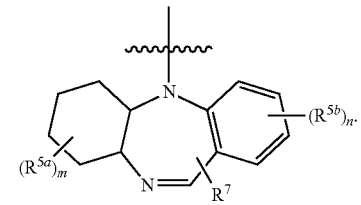

65. The compound according to any one of items 1 to 9, or a pharmaceutically acceptable salt, ester, stereoisomer, polymorph, solvate, N-oxide, isotopically labeled compound, metabolite or prodrug thereof, wherein
R is:

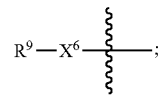

and $X^6$ is selected from the group consisting of O, S, $NR^{10}$, —C(=O)—$NR^{10}$— and —S(=O)$_y$—$NR^{10}$—, preferably selected from the group consisting of O, S, NH, N($C_{1-6}$ alkyl), —C(=O)—NH—, —C(=O)—N($C_{1-6}$ alkyl)-, —S(=O)$_y$—NH— and —S(=O)$_y$—N($C_{1-6}$ alkyl)-, more preferably selected from the group consisting of O, S, NH, N($C_{1-4}$ alkyl) and —C(=O)—NH—, even more preferably selected from the group consisting of O, S, NH, N(CH$_3$) and —C(=O)—NH—; and/or $R^9$ is selected from the group consisting of H, $C_{1-6}$ alkyl, $C_{2-6}$ alkenyl, $C_{2-6}$ alkynyl, $C_{5-7}$ cyclic hydrocarbyl group, 5- to 7-membered monocyclic heterocyclic group, phenyl, 5- to 6-membered heteroaryl and phenyl-$C_{1-6}$ alkylene-, preferably selected from the group consisting of H, $C_{1-4}$ alkyl (including methyl, ethyl, n-propyl, isopropyl, n-butyl, isobutyl, sec-butyl and tert-butyl), $C_{2-4}$ alkenyl (including vinyl, 1-propenyl, 2-propenyl, 2-butenyl and 3-butenyl), $C_{2-4}$ alkynyl (including ethynyl, 1-propynyl, 2-propynyl, 2-butynyl, 3-butynyl), phenyl and phenyl-$C_{1-4}$ alkylene- (including phenyl-methylene- and phenyl-ethylene-);

the above alkyl, alkylene, alkenyl, alkynyl, cyclic hydrocarbyl group, heterocyclic group, aryl and heteroaryl are each optionally substituted by 1, 2, 3 or more $R^{13}$;

$R^{13}$ is as defined in any one of items 1 to 9;

preferably, $R^{13}$, at each occurrence, is independently selected from the group consisting of halogen (including F, Cl, Br, and I); OH; amino; cyano; nitro; and $C_{1-6}$ alkyl (including $C_{1-4}$ alkyl, such as methyl, ethyl, n-propyl, isopropyl, n-butyl, isobutyl, sec-butyl and tert-butyl) and $C_{6-10}$ aryl (such as phenyl), which are optionally substituted by 1, 2, 3 or more substituents independently selected from the group consisting of halogen (including F, Cl, Br, and I), OH, amino, cyano, nitro and phenyl.

66. The compound according to item 65, or a pharmaceutically acceptable salt, ester, stereoisomer, polymorph, solvate, N-oxide, isotopically labeled compound, metabolite or prodrug thereof, wherein $R^9$ is phenyl-$C_{1-4}$ alkylene-.

67. The compound according to item 65, or a pharmaceutically acceptable salt, ester, stereoisomer, polymorph, solvate, N-oxide, isotopically labeled compound, metabolite or prodrug thereof, wherein R is selected from the group consisting of:

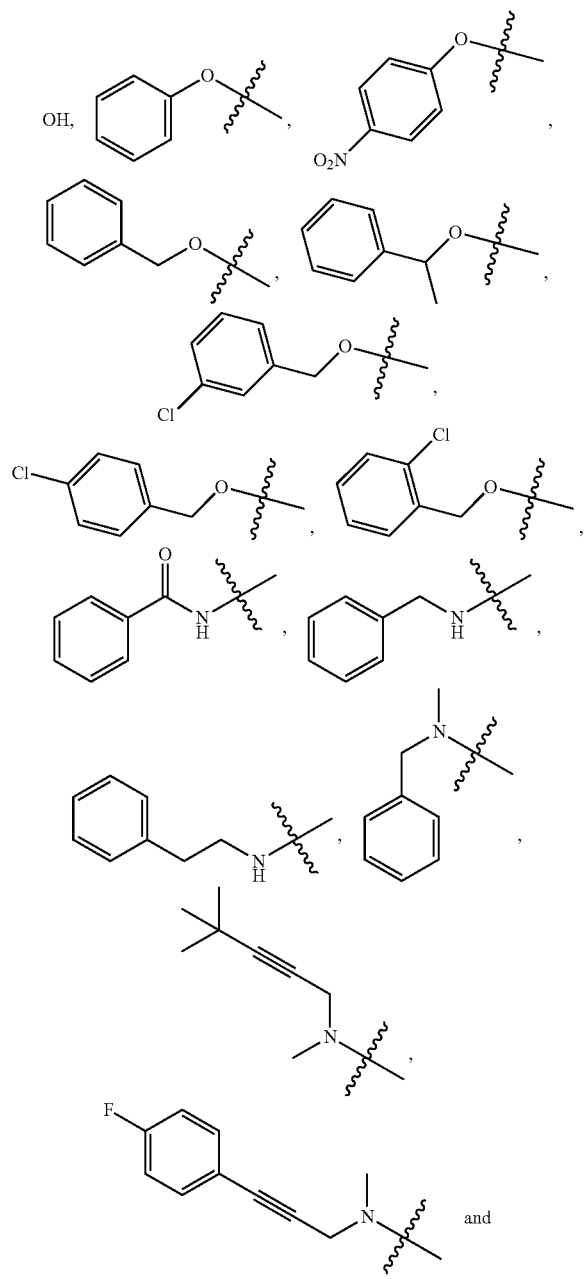

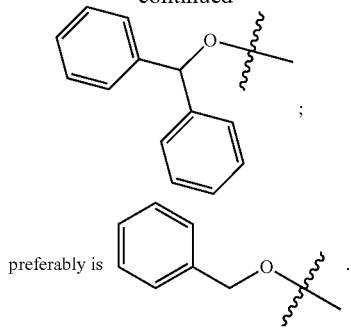

preferably is

68. The compound according to any one of items 65 to 67, or a pharmaceutically acceptable salt, ester, stereoisomer, polymorph, solvate, N-oxide, isotopically labeled compound, metabolite or prodrug thereof, wherein $X^6$ is selected from the group consisting of O and S, preferably is O.

69. The compound according to any one of items 65 to 68, or a pharmaceutically acceptable salt, ester, stereoisomer, polymorph, solvate, N-oxide, isotopically labeled compound, metabolite or prodrug thereof, wherein $X^3$ is CH.

70. The compound according to any one of items 1 to 51 and 56 to 69, or a pharmaceutically acceptable salt, ester, stereoisomer, polymorph, solvate, N-oxide, isotopically labeled compound, metabolite or prodrug thereof, wherein
$R^{2a}$, $R^{2b}$ together with $X^2$ to which they are attached form a group which is optionally substituted by 1, 2, 3 or more $R^{13}$ and is selected from the group consisting of $C_{5-7}$ cyclic hydrocarbyl group; 5-, 6- or 7-membered monocyclic heterocyclic group; phenyl; and 5- to 6-membered heteroaryl; and
$X^5$ is a direct bond.

71. The compound according to item 70, or a pharmaceutically acceptable salt, ester, stereoisomer, polymorph, solvate, N-oxide, isotopically labeled compound, metabolite or prodrug thereof, wherein $R^{13}$ is $C_{1-4}$ alkyl or phenyl-$C_{1-4}$-alkyl-, which is optionally substituted by 1, 2 or 3 substituents independently selected from the group consisting of $C_{1-4}$ alkyl and phenyl.

72. The compound according to any one of items 1 to 51 and 56 to 69, or a pharmaceutically acceptable salt, ester, stereoisomer, polymorph, solvate, N-oxide, isotopically labeled compound, metabolite or prodrug thereof, wherein
$R^{2a}$ is a group which is optionally substituted by 1, 2, 3 or more $R^{13}$ and is selected from the group consisting of $C_{1-6}$ alkyl, $C_{2-6}$ alkenyl, $C_{2-6}$ alkynyl, $C_{5-7}$ cyclic hydrocarbyl group, 5-, 6- or 7-membered monocyclic heterocyclic group, 8- to 10-membered benzo-fused heterocyclic group, phenyl, 5- to 6-membered heteroaryl, —$C_{1-3}$ alkylene-$C_{3-7}$ cyclic hydrocarbyl group, —$C_{1-3}$ alkylene-(5- to 7-membered monocyclic heterocyclic group), —$C_{1-3}$ alkylenephenyl and —$C_{1-3}$ alkylene-(5- to 6-membered heteroaryl); and
$R^{2b}$ does not exist or is selected from the group consisting of H and $R^{2a}$.

73. The compound according to any one of items 1 to 51, 56 to 69 and 72, or a pharmaceutically acceptable salt, ester, stereoisomer, polymorph, solvate, N-oxide, isotopically labeled compound, metabolite or prodrug thereof, wherein $R^{2b}$ does not exist, and $X^2$ does not exist.

74. The compound according to item 73, or a pharmaceutically acceptable salt, ester, stereoisomer, polymorph, solvate, N-oxide, isotopically labeled compound, metabolite or prodrug thereof, wherein $X^5$ is selected from the group consisting of C(=O), S(=O)$_y$, —O—C(=O)—, —S—C (=O)—, —O—S(=O)$_y$—, —NR$^{10}$—C(=O)— and —NR$^{10}$—S(=O)$_y$—, preferably is C(=O), —O—C(=O)— or —NR$^{10}$—C(=O)—.

75. The compound according to any one of items 70 to 74, or a pharmaceutically acceptable salt, ester, stereoisomer, polymorph, solvate, N-oxide, isotopically labeled compound, metabolite or prodrug thereof, wherein R$^{2a}$ is a group selected from the group consisting of an optionally substituted 5-, 6- or 7-membered monocyclic heterocyclic group, an optionally substituted phenyl, and -optionally substituted C$_{1-3}$ alkylene-optionally substituted phenyl, wherein the term "optionally substituted" means being substituted by 1, 2, 3 or more R$^{13}$;

R$^{2b}$ does not exist;

X$^2$ does not exist; and

X$^5$ is selected from the group consisting of C(=O), S(=O)$_y$, —OC(=O)— and —NR$^{10}$—C(=O)— and —NR$^{10}$—S(=O)$_y$—, wherein R$^{10}$ is preferably H or C$_{1-6}$ alkylene.

76. The compound according to any one of items 1 to 69 and 72, or a pharmaceutically acceptable salt, ester, stereoisomer, polymorph, solvate, N-oxide, isotopically labeled compound, metabolite or prodrug thereof, wherein X$^2$ is CR$^{10}$ or N, and wherein R$^{10}$ is preferably H, OH or C$_{1-4}$ alkyl (such as methyl).

77. The compound according to item 76, or a pharmaceutically acceptable salt, ester, stereoisomer, polymorph, solvate, N-oxide, isotopically labeled compound, metabolite or prodrug thereof, wherein X$^5$ is a direct bond.

78. The compound according to item 76, or a pharmaceutically acceptable salt, ester, stereoisomer, polymorph, solvate, N-oxide, isotopically labeled compound, metabolite or prodrug thereof, wherein X$^5$ is selected from the group consisting of C(=O), S(=O)$_y$, —O—C(=O)—, —S—C(=O)—, —O—S(=O)$_y$—, —NR$^{10}$—C(=O)— or —NR$^{10}$—S(=O)$_y$, preferably is C(=O), —O—C(=O)— or —NR$^{10}$—C(=O)—.

79. The compound according to any one of items 76 to 78, or a pharmaceutically acceptable salt, ester, stereoisomer, polymorph, solvate, N-oxide, isotopically labeled compound, metabolite or prodrug thereof, wherein R$^{2b}$ is selected from the group consisting of H and R$^{2a}$, and preferably, X$^2$ is CH.

80. The compound according to any one of items 1 to 51 and 56 to 69, or a pharmaceutically acceptable salt, ester, stereoisomer, polymorph, solvate, N-oxide, isotopically labeled compound, metabolite or prodrug thereof, wherein R$^{2a}$ is a group which is optionally substituted by 1, 2, 3 or more R$^{13}$ and is selected from the group consisting of C$_{1-6}$ alkyl, C$_{2-6}$ alkenyl, C$_{2-6}$ alkynyl, C$_{5-7}$ cyclic hydrocarbyl group, 5-, 6- or 7-membered monocyclic heterocyclic group, 8- to 10-membered benzo-fused heterocyclic group, phenyl, 5- to 6-membered heteroaryl, —C$_{1-3}$ alkylene-C$_{3-7}$ cyclic hydrocarbyl group, —C$_{1-3}$ alkylene-(5- to 7-membered monocyclic heterocyclic group), —C$_{1-3}$ alkylenephenyl and —C$_{1-3}$ alkylene-(5- to 6-membered heteroaryl);

R$^{2b}$ and X$^2$ together form a bivalent C$_{5-7}$ cyclic hydrocarbyl group or a bivalent 5-, 6- or 7-membered monocyclic heterocyclic group; and X$^5$ is selected from the group consisting of C(=O) and S(=O)$_y$.

81. The compound according to any one of items 72 to 80, or a pharmaceutically acceptable salt, ester, stereoisomer, polymorph, solvate, N-oxide, isotopically labeled compound, metabolite or prodrug thereof, wherein R$^{13}$ is selected from the group consisting of C$_{1-4}$ alkyl-O—; halogen (including F, Cl, Br, and I); and C$_{1-4}$ alkyl or phenyl, which is optionally substituted by 1, 2 or 3 substituents independently selected from halogen.

82. The compound according to any one of items 70 to 81, or a pharmaceutically acceptable salt, ester, stereoisomer, polymorph, solvate, N-oxide, isotopically labeled compound, metabolite or prodrug thereof, wherein:

the alkyl is selected from the group consisting of methyl, ethyl, n-propyl, isopropyl, n-butyl, isobutyl, sec-butyl, tert-butyl, n-pentyl, isopentyl, neopentyl, 1-hexyl, 1-heptyl, 1-octyl;

the alkenyl is selected from the group consisting of vinyl, 1-propenyl, 2-propenyl, 2-butenyl, 3-butenyl, 2-pentenyl, 3-pentenyl, 4-pentenyl and 2-hexenyl;

the alkynyl is selected from the group consisting of ethynyl, 1-propynyl, 2-propynyl, 2-butynyl, 3-butynyl, 2-pentynyl, 3-pentynyl, 4-pentynyl, 2-hexynyl and 3-hexynyl;

the cyclic hydrocarbyl group is selected from the group consisting of cyclopropyl, cyclobutyl, cyclopentyl, cyclohexyl or cycloheptyl;

the monocyclic heterocyclic group is selected from the group consisting of tetrahydrofuranyl, tetrahydro thienyl, pyrrolidinyl (e.g. pyrrolidin-1-yl), oxazolidinyl, thiazolidinyl, imidazolidinyl, 1,3-dioxolanyl, 1,3-oxathiolanyl, piperidinyl, piperazinyl, morpholinyl (such as morpholine)), thiomorpholinyl, tetrahydro-2H-pyranyl, tetrahydro-2H-thiopyranyl, 1,3-oxazinanyl (1,3-oxazinane), 1,3-thiazinanyl (1,3-thiazinane), hexahydropyrimidyl, 1,3-oxathianyl (1,3-oxathiane), 1,4-oxathianyl (1,4-oxathiane), 1,3-diazepanyl (1,3-diazepane), 1,4-diazepanyl (1,4-diazepane), 1,3-oxazepanyl (1,3-oxazepane), 1,3-thiazepanyl (1,3-thiazepane);

the heteroaryl is selected from the group consisting of thienyl, furyl, pyrrolyl, oxazolyl, thiazolyl, imidazolyl, pyrazolyl (such as 1-pyrazolyl, 3-pyrazolyl, 4-pyrazolyl, 5-pryazolyl), isoxazolyl, isothiazolyl, oxadiazolyl, triazolyl, thiadiazolyl, pyridyl, pyridazinyl, pyrimidinyl, pyrazinyl and triazinyl;

the benzo-fused heterocyclic group is selected from the group consisting of

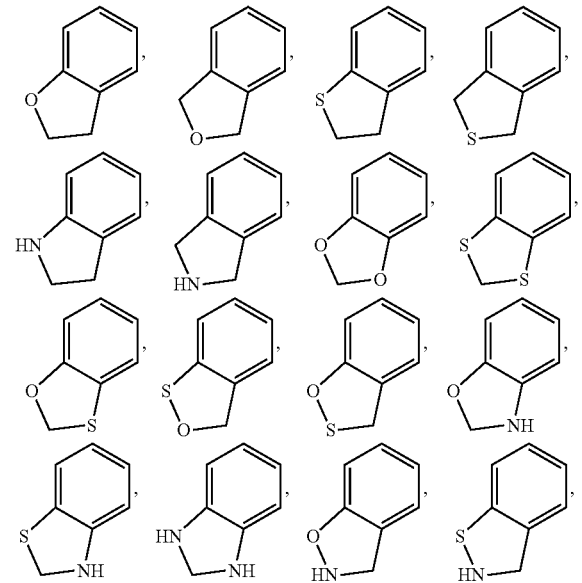

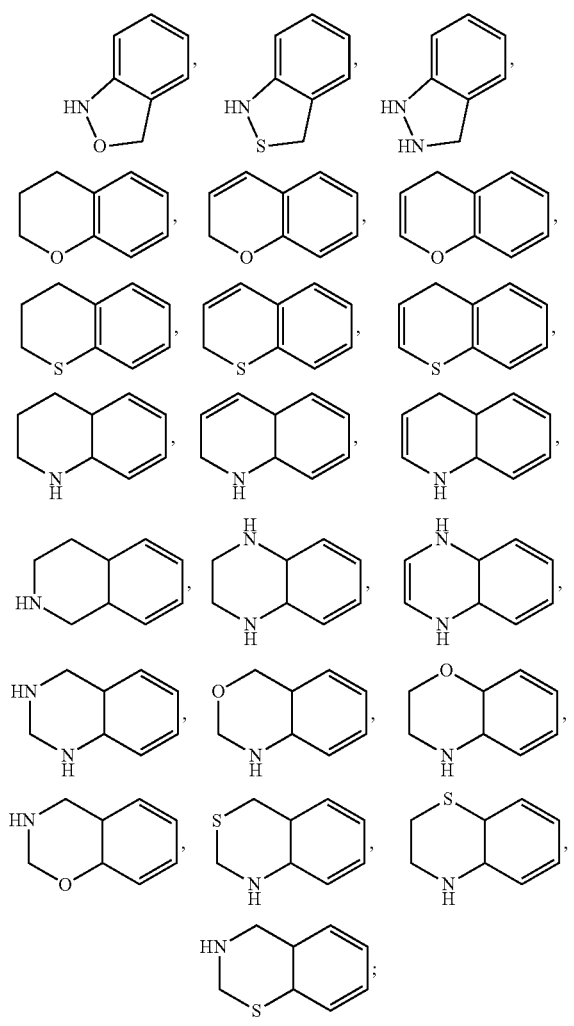
the —$C_{1-3}$ alkylenephenyl is selected from the group consisting of benzyl and phenethyl.
83. The compound according to any one of items 1 to 51 and 56 to 82, or the pharmaceutically acceptable salt, ester, stereoisomer, polymorph, solvate, N-oxide, isotopically labeled compound, metabolite or prodrug thereof, wherein R' is:
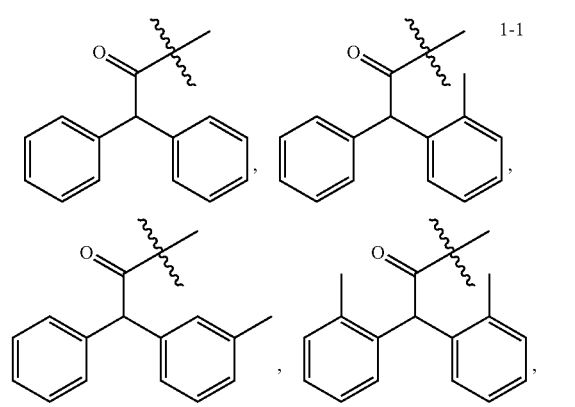
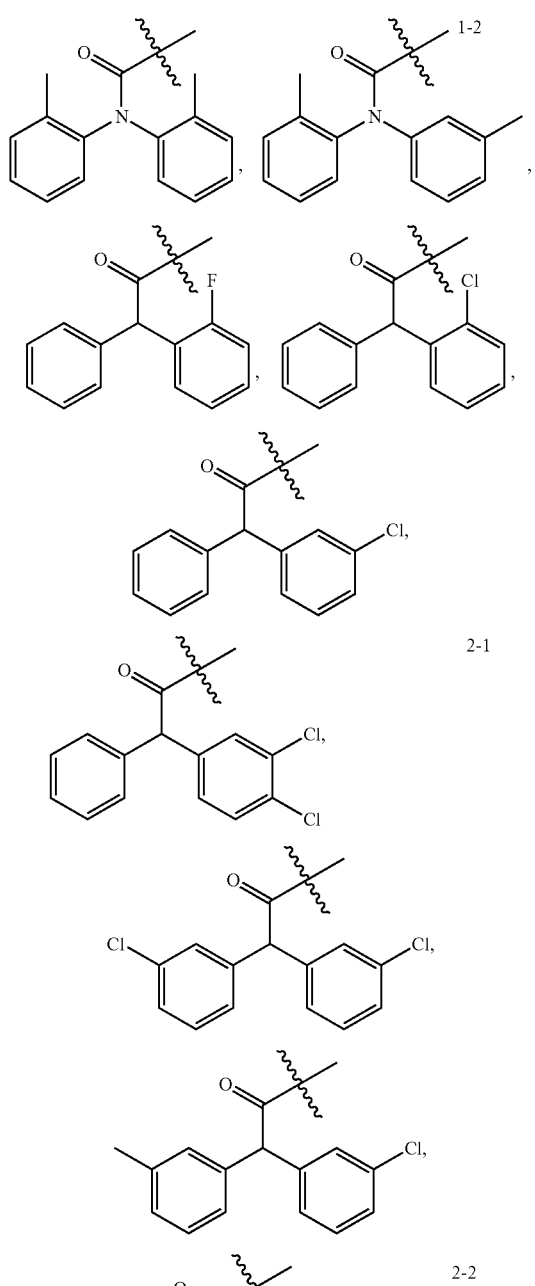
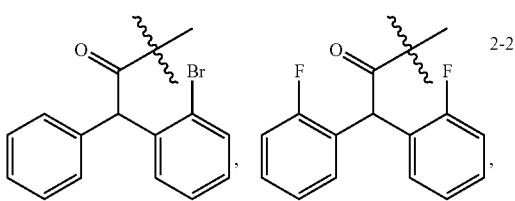

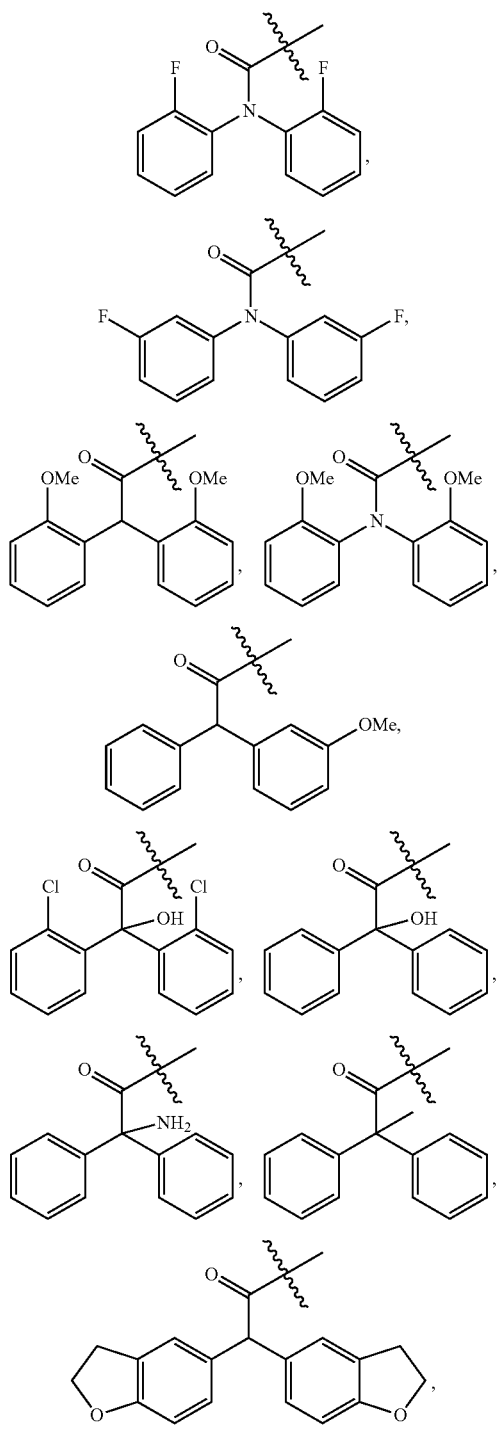

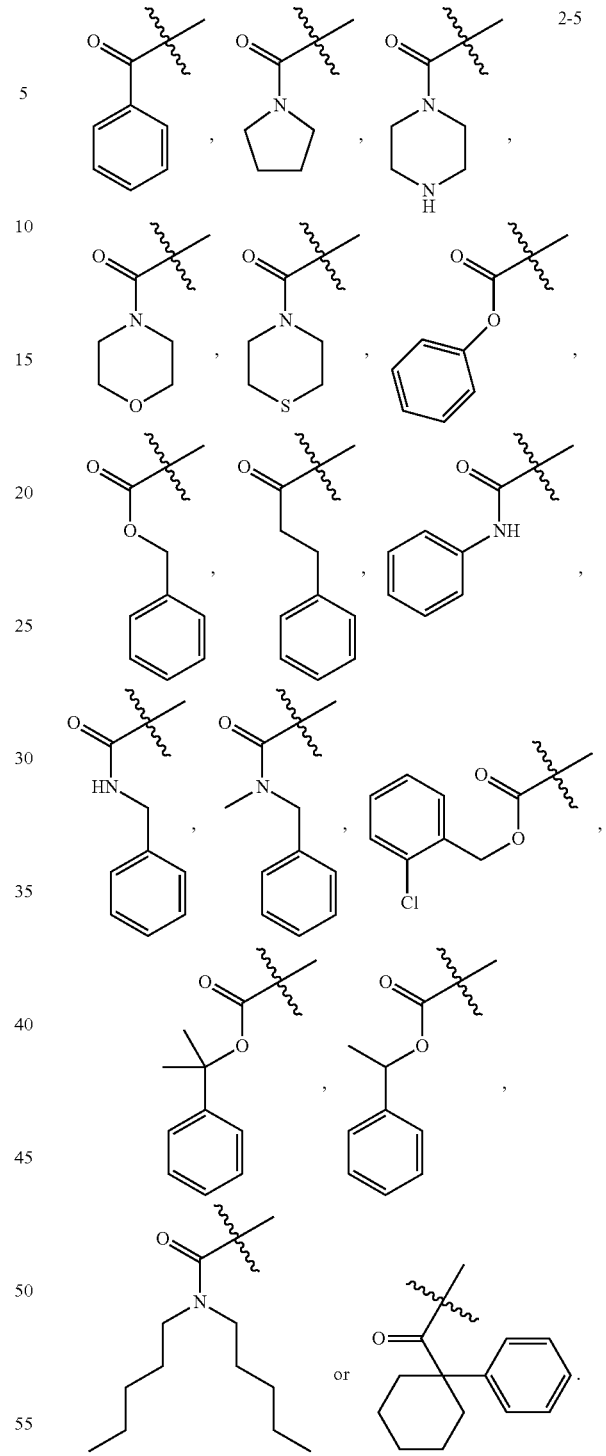

84. The compound according to any one of items 1 to 51 and items 56 to 69, or the pharmaceutically acceptable salt, ester, stereoisomer, polymorph, solvate, N-oxide, isotopically labeled compound, metabolite or prodrug thereof, wherein Z is a single bond, $NR^{10}$, O, S, methylene, ethylene, —$CH_2$—O—, —O—$CH_2$—, —$CH_2$—S—, —S—$CH_2$—, —$CH_2$—$NR^{10}$—, —$NR^{10}$—$CH_2$—, —CH=CH—, —CH=N— or —N=CH—.

85. The compound according to any one of items 1 to 51, 56 to 69 and 84, or a pharmaceutically acceptable salt, ester, stereoisomer, polymorph, solvate, N-oxide, isotopically labeled compound, metabolite or prodrug thereof, wherein the optionally substituted saturated or partially unsaturated fused ring system comprising 3 or more rings which is formed by $R^{2a}$ and $R^{2b}$ together with $X^2$ to which they are attached has a structure of formula (b):

formula (b)

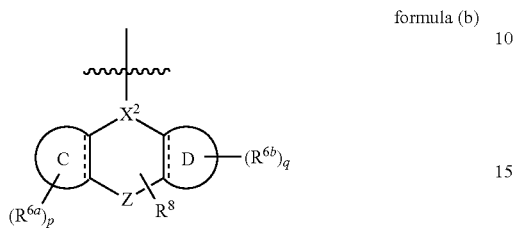

wherein:

ring C and ring D are each independently $C_{3-10}$ cyclic hydrocarbyl group, 3- to 10-membered heterocyclic group, $C_{6-10}$ aryl or 5- to 14-membered heteroaryl, preferably $C_{5-7}$ cyclic hydrocarbyl group, 5- to 7-membered monocyclic heterocyclic group, phenyl or 5- to 6-membered heteroaryl;

" ===== " represents a single bond or a double bond;

preferably, the fused ring system has a structure of formula (3) or formula (4):

formula (3)

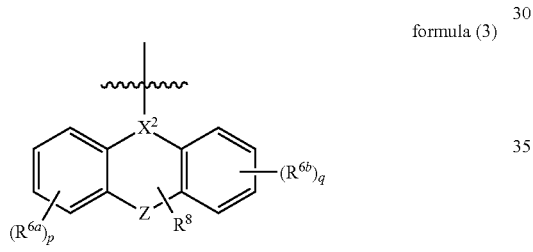

formula (4)

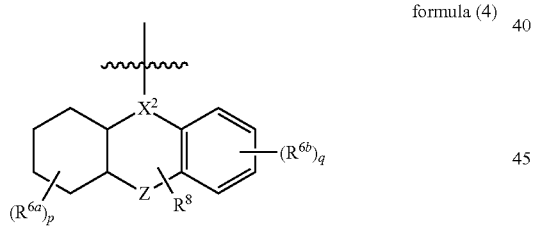

wherein $R^{6a}$ and $R^{6b}$, at each occurrence, are each independently $R^{10}$;

$R^8$ does not exist or is $R^{10}$; and p and q, at each occurrence, are each independently 0, 1, 2 or 3.

86. The compound according to any one of items 1 to 69 and 84 to 85, or a pharmaceutically acceptable salt, ester, stereoisomer, polymorph, solvate, N-oxide, isotopically labeled compound, metabolite or prodrug thereof, wherein $X^2$, at each occurrence, is independently $CR^{10}$ or N, and wherein $R^{10}$ is H, OH, amino or $C_{1-4}$ alkyl (such as methyl).

87. The compound according to item 85 or 86, or a pharmaceutically acceptable salt, ester, stereoisomer, polymorph, solvate, N-oxide, isotopically labeled compound, metabolite or prodrug thereof, wherein:

the group of formula (3) has a structure selected from the group consisting of formula (3a-1)

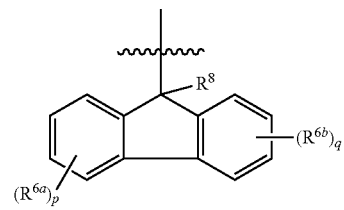

formula (3a-2)

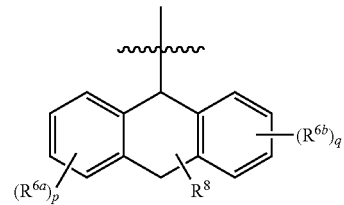

formula (3a-3)

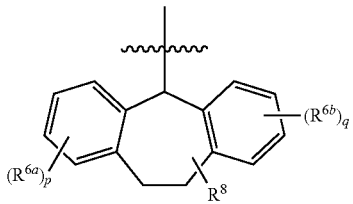

formula (3a-4)

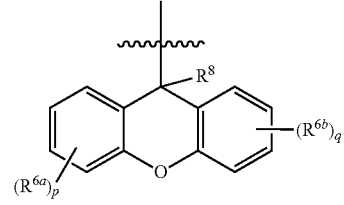

formula (3a-5)

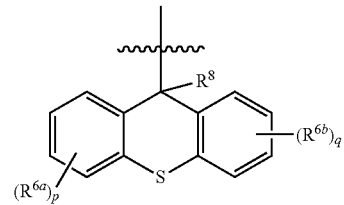

formula (3a-6)

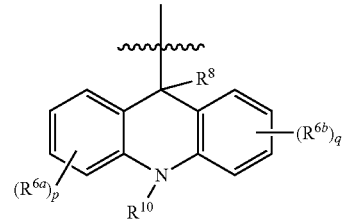

-continued
formula (3a-7)
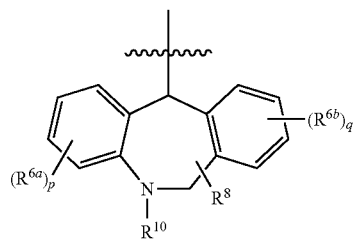
formula (3a-8)
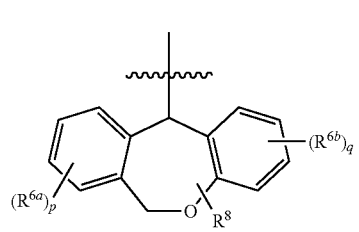
formula (3a-9)
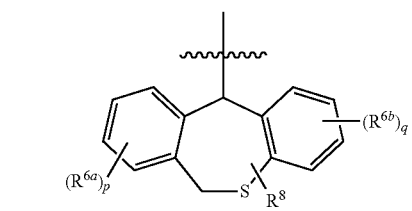
formula (3a-10)
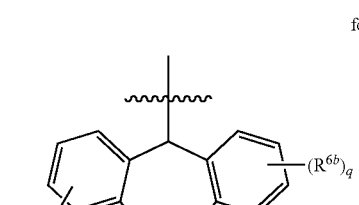
formula (3a-11)
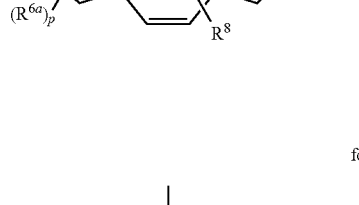
formula (3b-1)
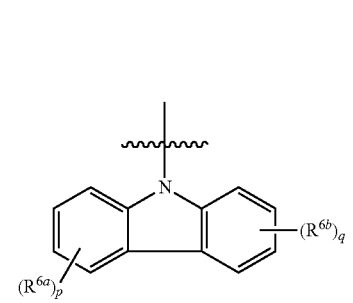
formula (3b-2)
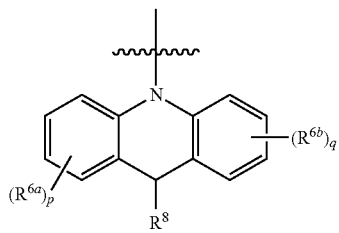
formula (3b-3)
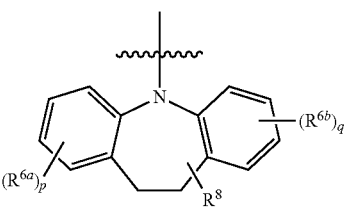
formula (3b-4)
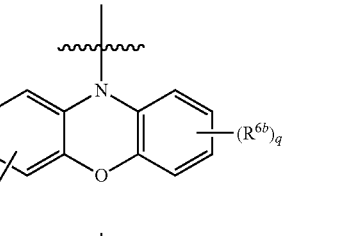
formula (3b-5)
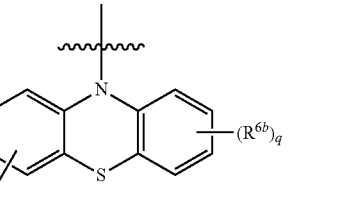
formula (3b-6)
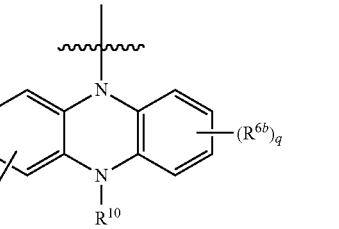
formula (3b-7)
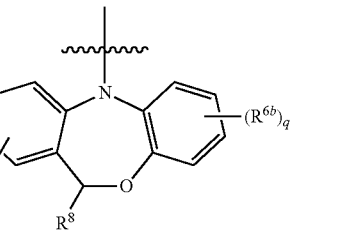
formula (3b-8)
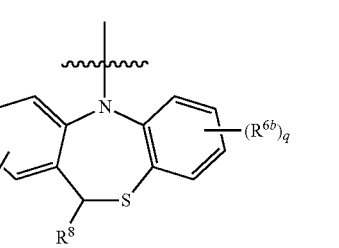

formula (3b-9)

formula (3b-10)

formula (3b-11)

or the group of formula (4) has a structure selected from the group consisting of formula (4a-1)

formula (4a-2)

formula (4a-3)

formula (4a-4)

formula (4a-5)

formula (4a-6)

formula (4a-7)

formula (4a-8)

formula (4a-9)

formula (4a-10)

-continued
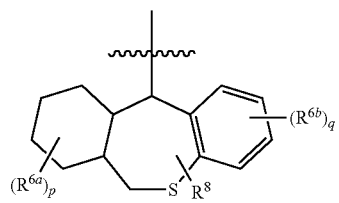
formula (4a-11)
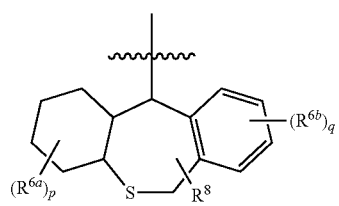
formula (4a-12)
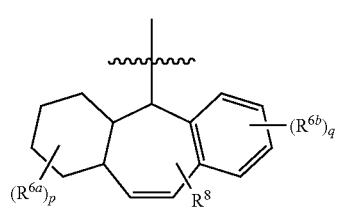
formula (4a-13)
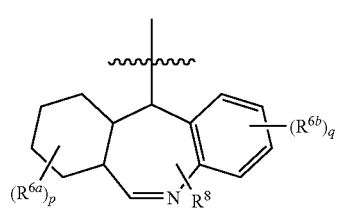
formula (4a-14)
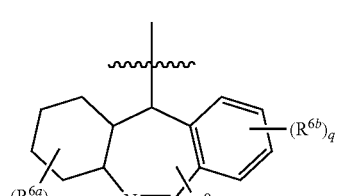
formula (4a-15)
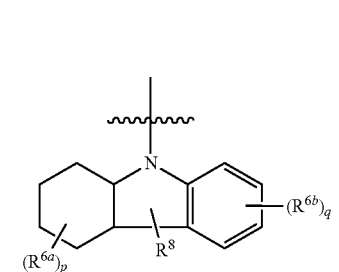
formula (4b-1)
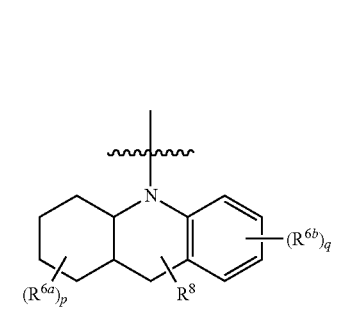
formula (4b-2)
-continued
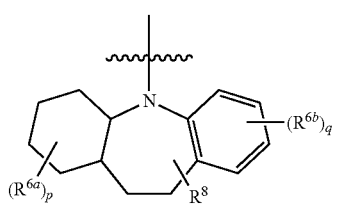
formula (4b-3)
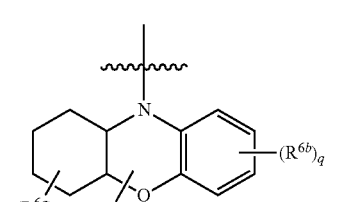
formula (4b-4)
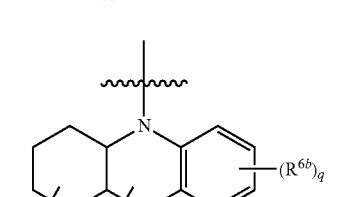
formula (4b-5)
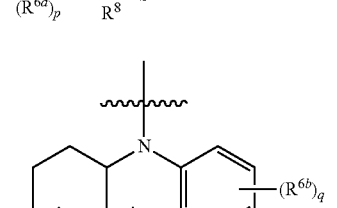
formula (4b-6)
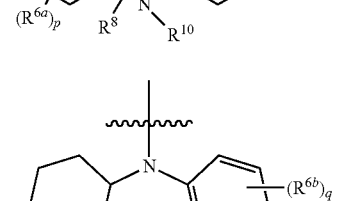
formula (4b-7)
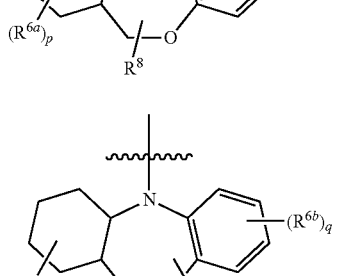
formula (4b-8)
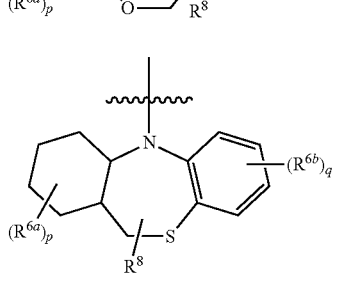
formula (4b-9)

-continued formula (4b-10)
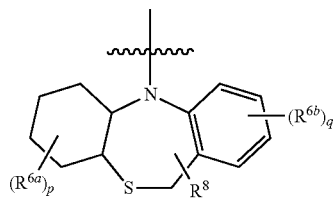

formula (4b-11)
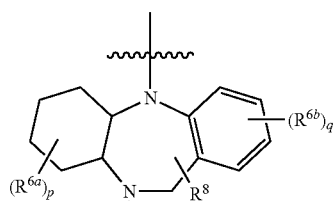

formula (4b-12)
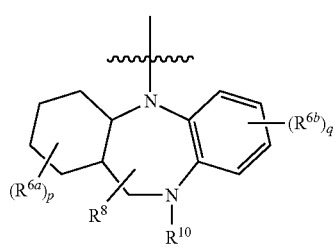

formula (4b-13)
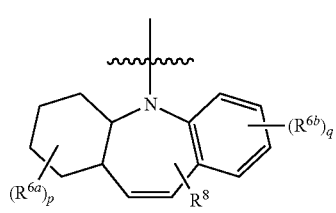

formula (4b-14)
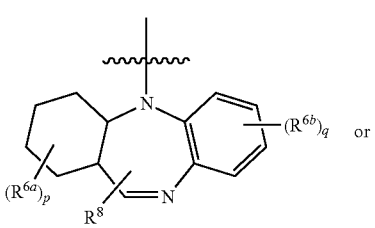

or formula (4b-15)
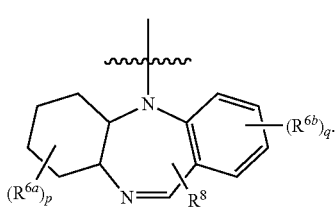

88. The compound according to any one of items 1 to 10, 12 to 20, 22 to 54 and 56 to 87, or a pharmaceutically acceptable salt, ester, stereoisomer, polymorph, solvate, N-oxide, isotopically labeled compound, metabolite or prodrug thereof, wherein:

the compound has a structure of formula (I-a) or formula (I'-a):

formula (I-a)
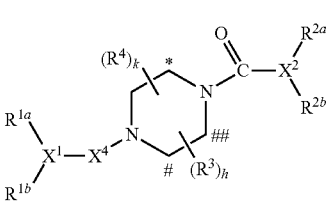

formula (I'-a)
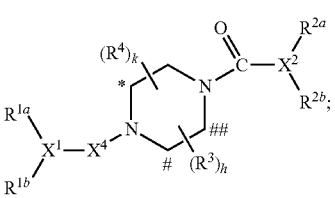

particularly, the structure of formula (IV) or formula (V):

formula (IV)
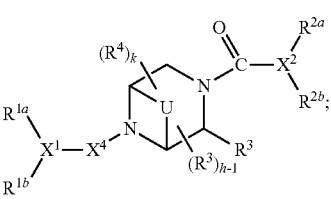

formula (V)
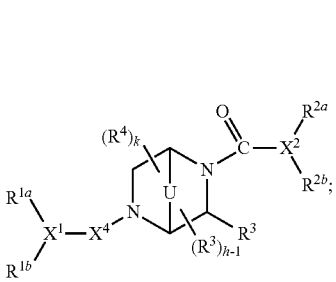

or the structure of formula (a-1), (a-2), (a-3), (a-4), (a-5), (a-6), (a-7) or (a-8):

formula (a-1)
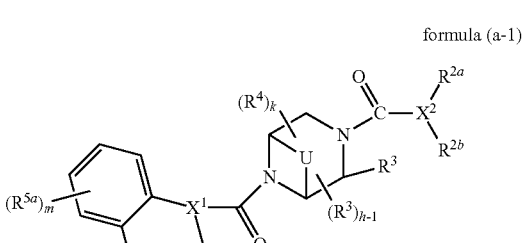

formula (a-2)
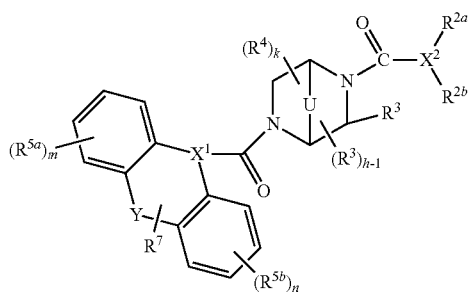
formula (a-3)
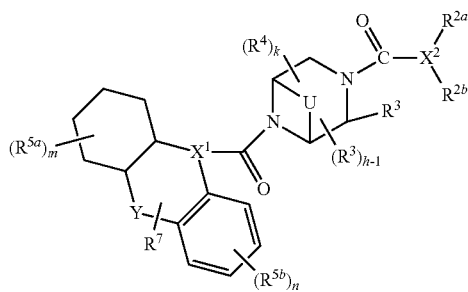
formula (a-4)
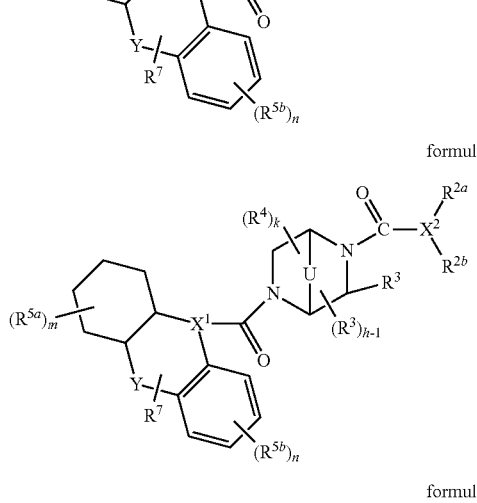
formula (a-5)
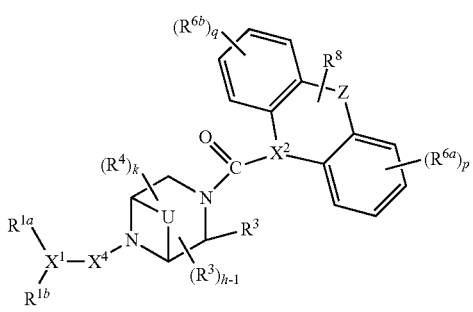
formula (a-6)
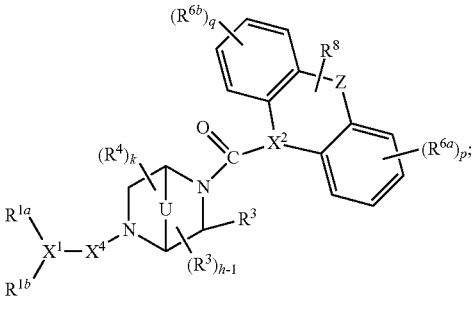
formula (a-7)
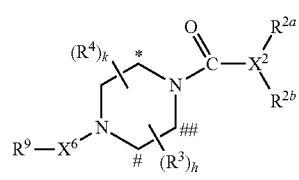
formula (a-8)
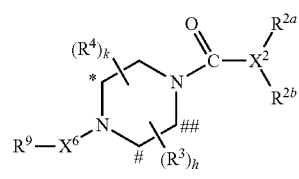
or
the compound has a structure of formula (I-b) or formula (I'-b):
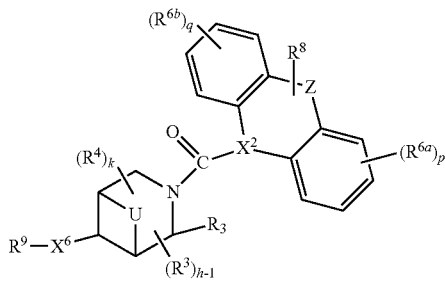
formula (I-b)
formula (I'b)
particularly, the structure of formula (b-1), (b-2), (b-3) or (b-4):
formula (b-1)

| | formula (b-2) |
|---|---|
| 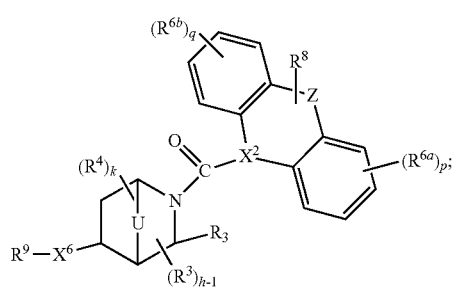 | |
| | formula (b-3) |
|---|---|
| 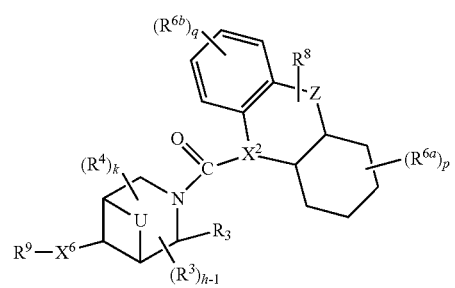 | |
| | formula (b-4) |
|---|---|
| 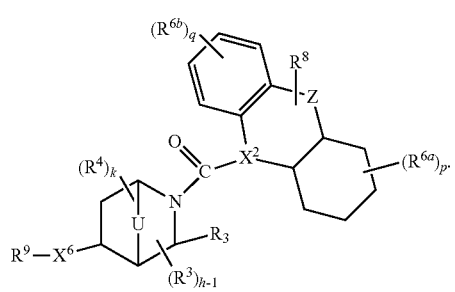 | |
89. The compound according to item 1, or a pharmaceutically acceptable salt, ester, stereoisomer, polymorph, solvate, N-oxide, isotopically labeled compound, metabolite or prodrug thereof, wherein the compound has a structure of
| No. | Structure |
|---|---|
| C1 | 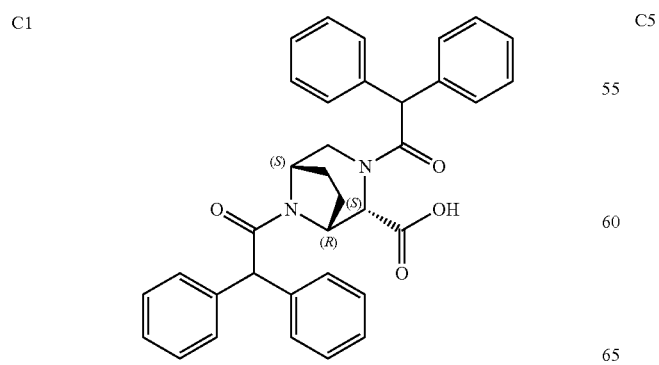 |
| C2 | 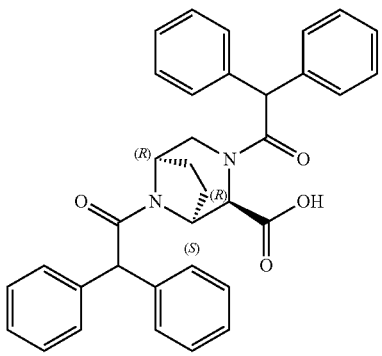 |
| C3 | 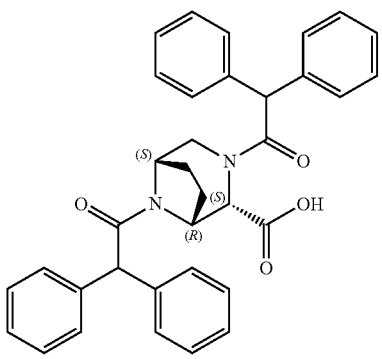 |
| C4 | 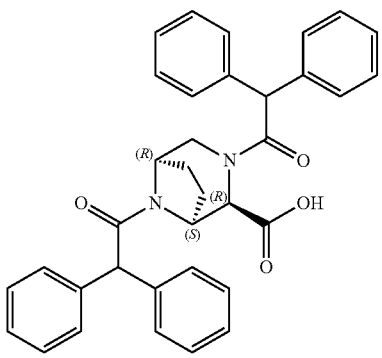 |
| C5 | 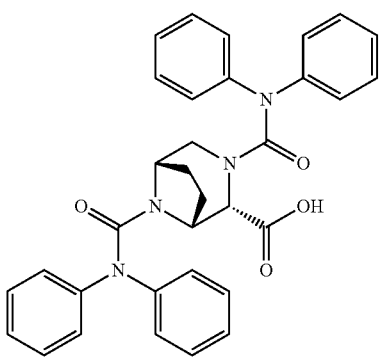 [SMILES: O=C(O)[C@@H]1[C@H]2CC[C@@H](CN1C(=O)N(c1ccccc1)c1ccccc1)N2C(=O)N(c1ccccc1)c1ccccc1] |

| No. | Structure |
|---|---|
| C6 | 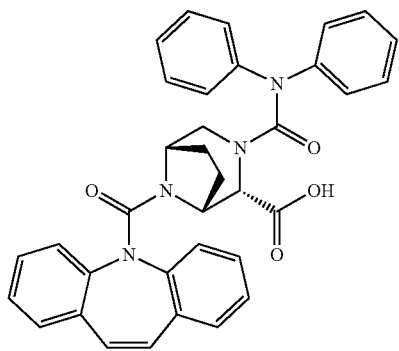 [SMILES: O=C(O)[C@@H]1[C@H]2CC[C@@H](CN1C(=O)N(c1ccccc1)c1ccccc1)N2C(=O)N1c2ccccc2C=Cc2ccccc21] |
| C7 | 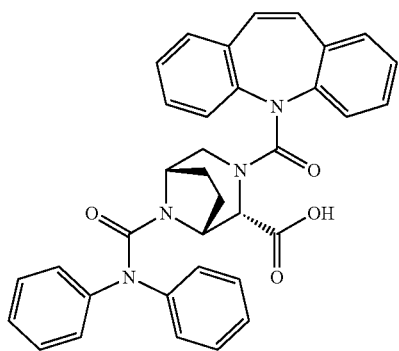 [SMILES: O=C(O)[C@@H]1[C@H]2CC[C@@H](CN1C(=O)N1c3ccccc3C=Cc3ccccc31)N2C(=O)N(c1ccccc1)c1ccccc1] |
| C8 | 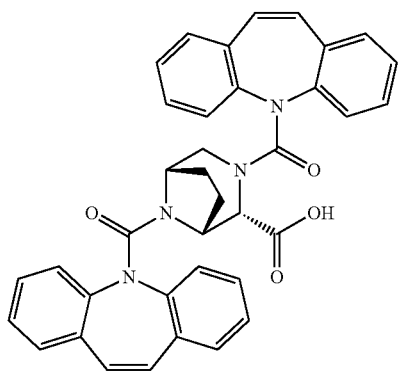 [SMILES: O=C(O)[C@@H]1[C@H]2CC[C@@H](CN1C(=O)N1c3ccccc3C=Cc3ccccc31)N2C(=O)N1c2ccccc2C=Cc2ccccc21] |
| C9 | 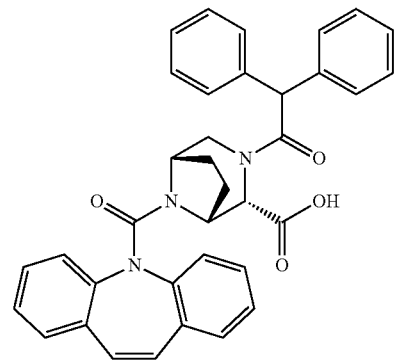 |
| No. | Structure |
|---|---|
| C10 | 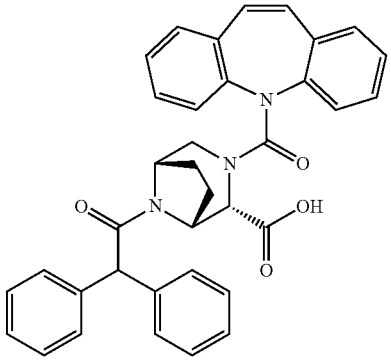 [SMILES: O=C(O)[C@@H]1[C@H]2CC[C@@H](CN1C(=O)N1c3ccccc3C=Cc3ccccc31)N2C(=O)C(c1ccccc1)c1ccccc1] |
| C11 | 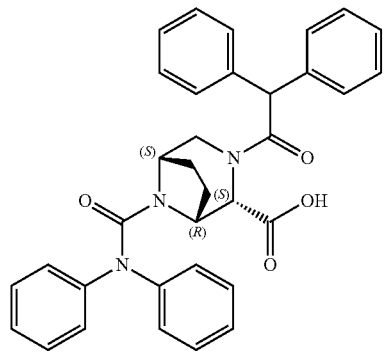 |
| C12 | 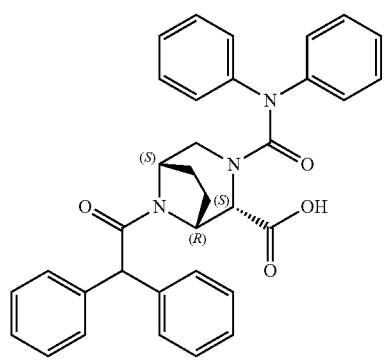 |
| C13 | 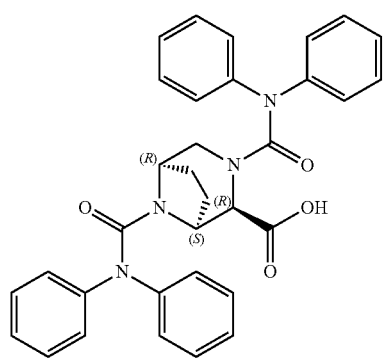 |

| No. | Structure |
|---|---|
| C14 | 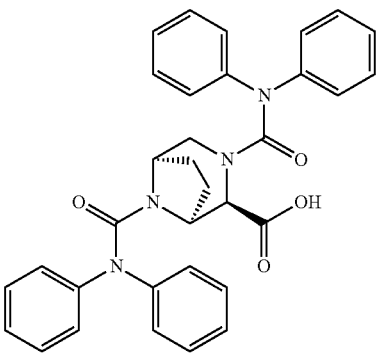 [SMILES: O=C(O)[C@H]1[C@@H]2CC[C@H](CN1C(=O)N(c1ccccc1)c1ccccc1)N2C(=O)N(c1ccccc1)c1ccccc1] |
| C15 | 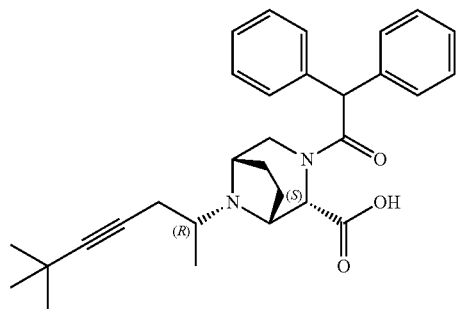 |
| C16 | 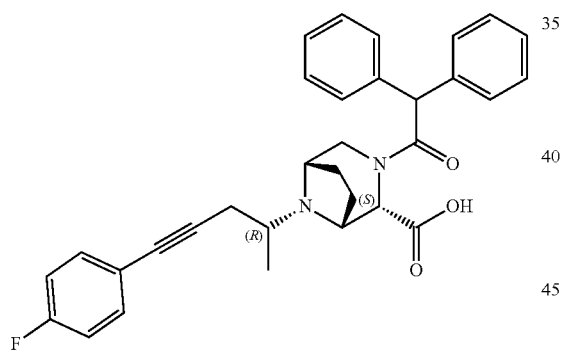 |
| C17 | 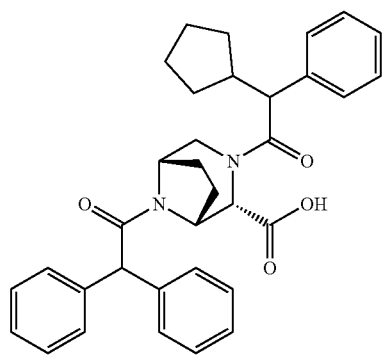 [SMILES: O=C(O)[C@@H]1[C@H]2CC[C@@H](CN1C(=O)C(c1ccccc1)C1CCCC1)N2C(=O)C(c1ccccc1)c1ccccc1] |
| No. | Structure |
|---|---|
| C18 | 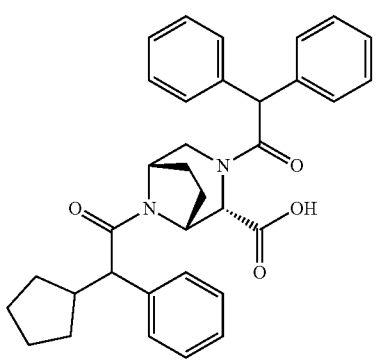 [SMILES: O=C(O)[C@@H]1[C@H]2CC[C@@H](CN1C(=O)C(c1ccccc1)c1ccccc1)N2C(=O)C(c1ccccc1)C1CCCC1] |
| C19 | 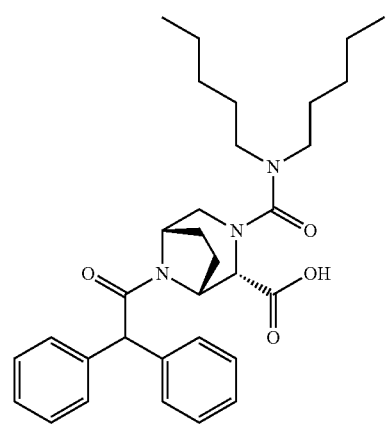 [SMILES: CCCCCN(CCCCC)C(=O)N1C[C@@H]2CC[C@H]([C@H]1C(=O)O)N2C(=O)C(c1ccccc1)c1ccccc1] |
| C20 | 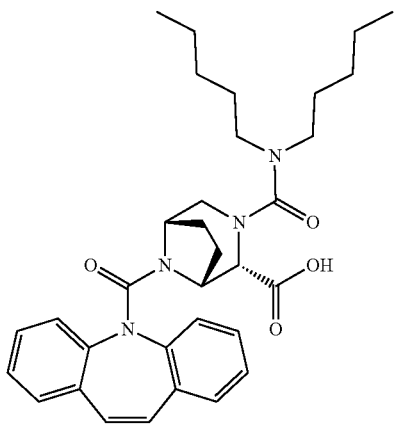 [SMILES: CCCCCN(CCCCC)C(=O)N1C[C@@H]2CC[C@H]([C@H]1C(=O)O)N2C(=O)N1c2ccccc2C=Cc2ccccc21] |

| No. | Structure |
|---|---|
| C21 | 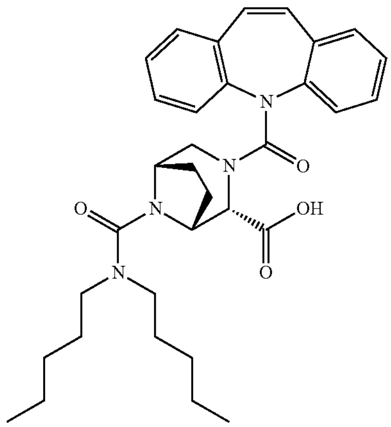 [SMILES: CCCCCN(CCCCC)C(=O)N1[C@H]2CC[C@@H]1[C@@H](C(=O)O)N(C(=O)N1c3ccccc3C=Cc3ccccc31)C2] |
| C22 | 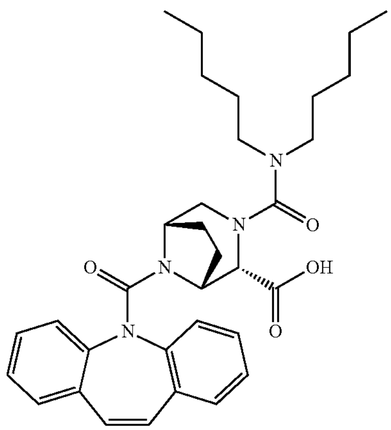 [SMILES: CCCCCN(CCCCC)C(=O)N1C[C@@H]2CC[C@H]([C@H]1C(=O)O)N2C(=O)N1c2ccccc2C=Cc2ccccc21] |
| C23 | 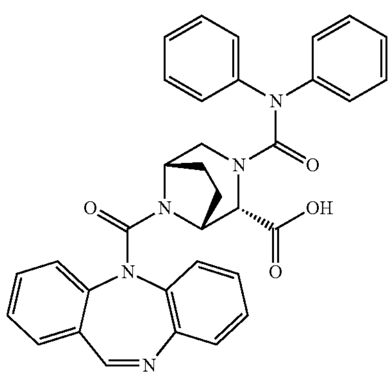 [SMILES: O=C(O)[C@@H]1[C@H]2CC[C@@H](CN1C(=O)N(c1ccccc1)c1ccccc1)N2C(=O)N1c2ccccc2C=Nc2ccccc21] |
| C24 | 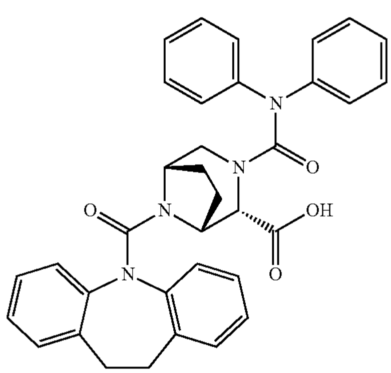 [SMILES: O=C(O)[C@@H]1[C@H]2CC[C@@H](CN1C(=O)N(c1ccccc1)c1ccccc1)N2C(=O)N1c2ccccc2CCc2ccccc21] |
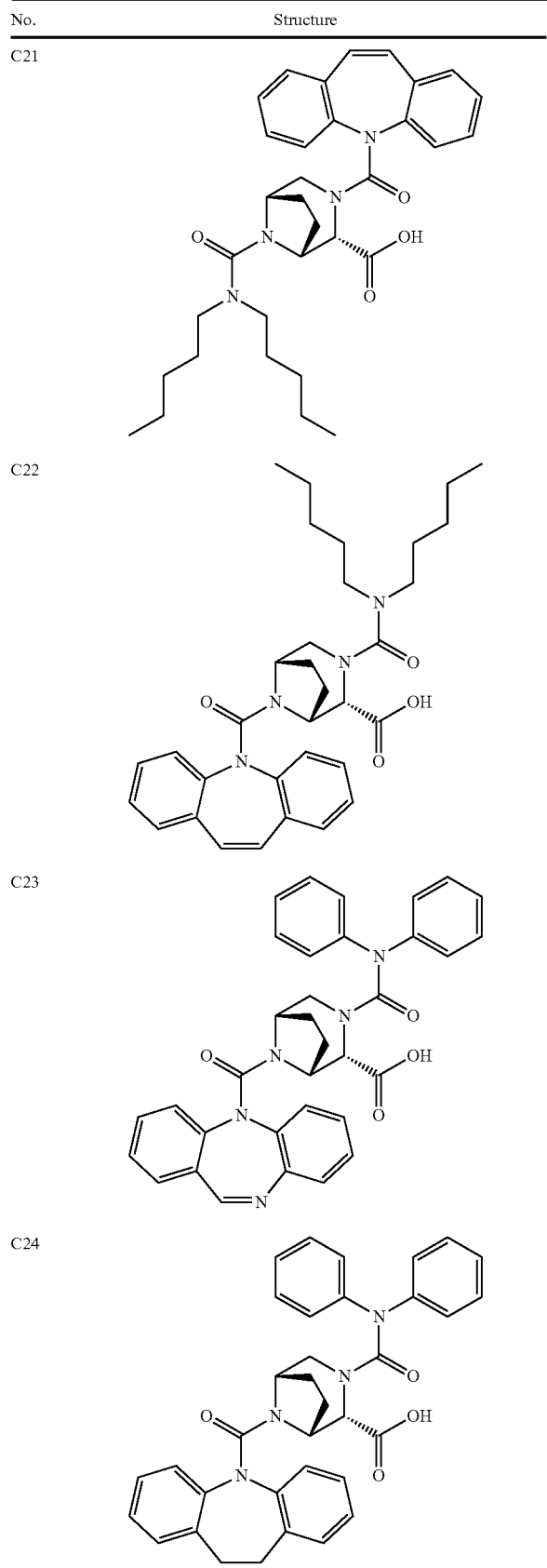
| No. | Structure |
|---|---|
| C25 | 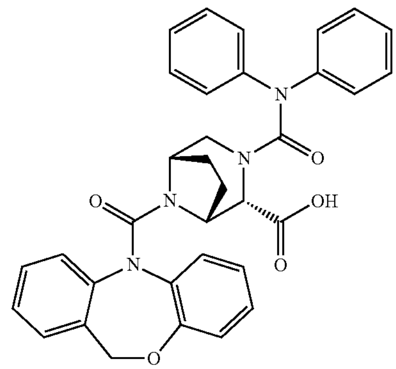 [SMILES: O=C(O)[C@@H]1[C@H]2CC[C@@H](CN1C(=O)N(c1ccccc1)c1ccccc1)N2C(=O)N1c2ccccc2COc2ccccc21] |
| C26 | 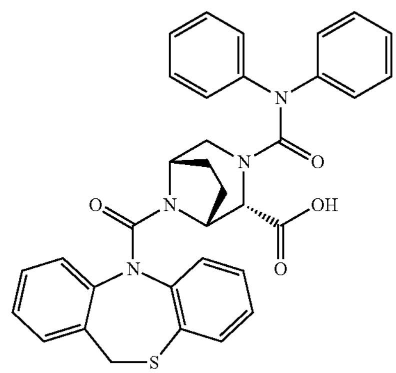 [SMILES: O=C(O)[C@@H]1[C@H]2CC[C@@H](CN1C(=O)N(c1ccccc1)c1ccccc1)N2C(=O)N1c2ccccc2CSc2ccccc21] |
| C27 | 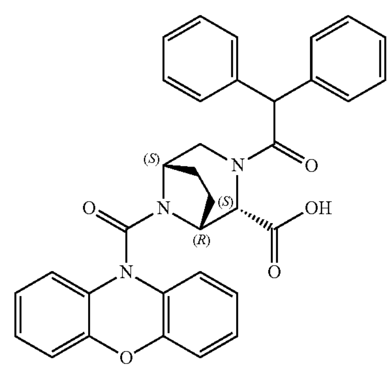 |
| C28 | 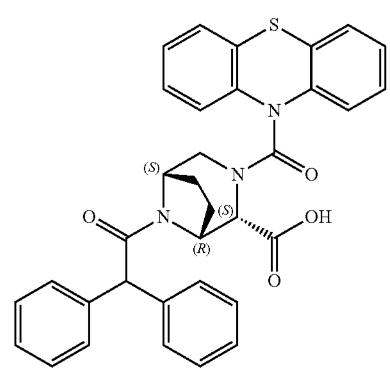 |
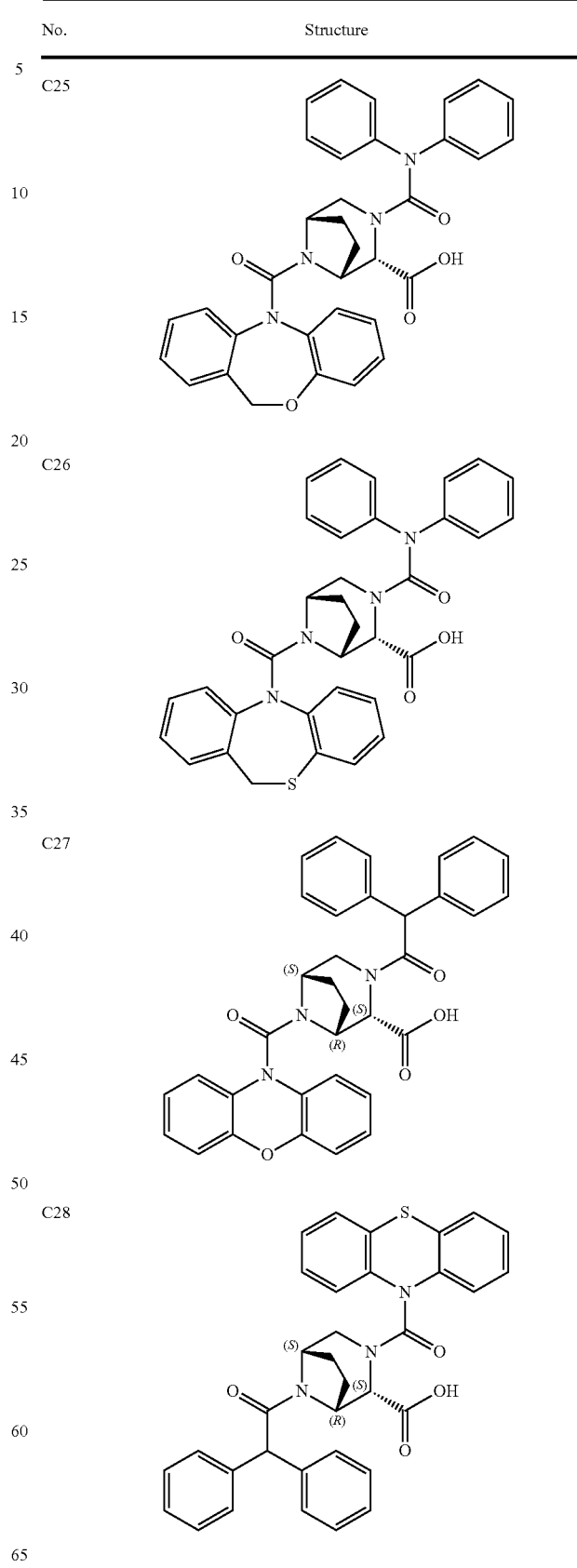

| No. | Structure |
|---|---|
| C29 | 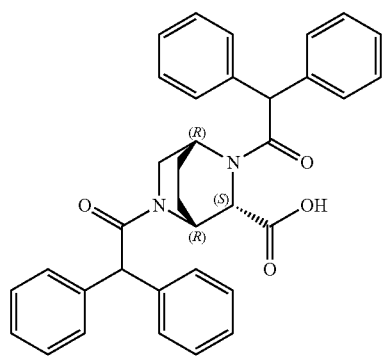 |
| C30 | 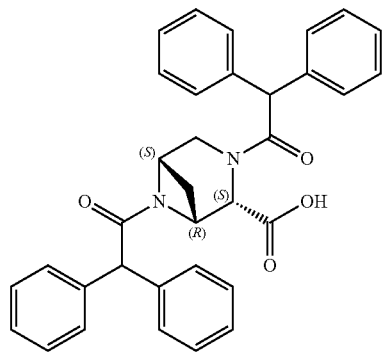 |
| C31 | 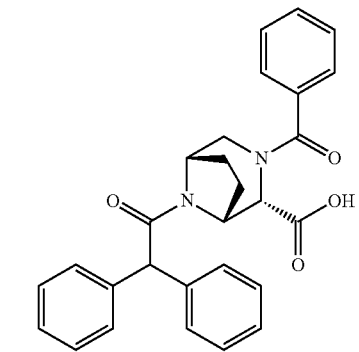 [SMILES: O=C(O)[C@@H]1[C@H]2CC[C@@H](CN1C(=O)c1ccccc1)N2C(=O)C(c1ccccc1)c1ccccc1] |
| C32 | 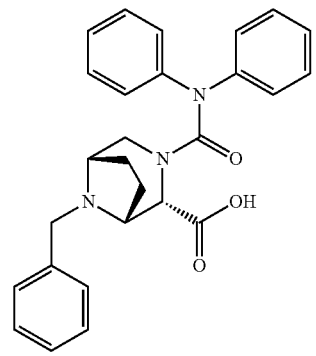 [SMILES: O=C(O)[C@@H]1[C@H]2CC[C@@H](CN1C(=O)N(c1ccccc1)c1ccccc1)N2Cc1ccccc1] |
| No. | Structure |
|---|---|
| C33 | 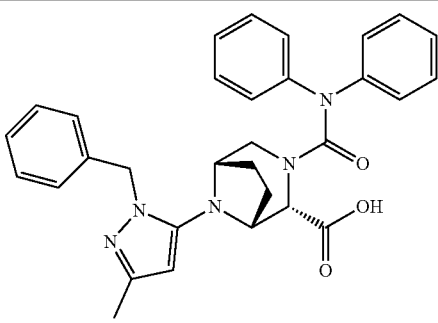 [SMILES: Cc1cc(N2[C@H]3CC[C@@H]2[C@@H](C(=O)O)N(C(=O)N(c2ccccc2)c2ccccc2)C3)n(Cc2ccccc2)n1] |
| C34 | 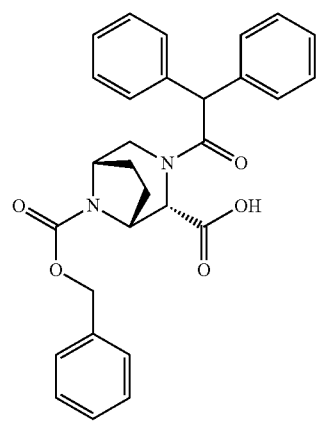 [SMILES: O=C(O)[C@@H]1[C@H]2CC[C@@H](CN1C(=O)C(c1ccccc1)c1ccccc1)N2C(=O)OCc1ccccc1] |
| C35 | 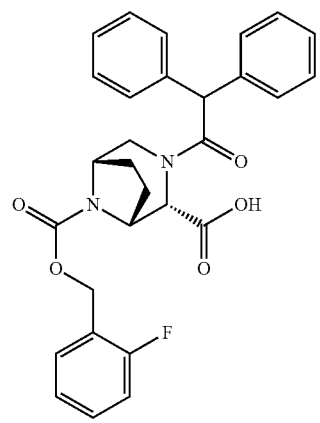 [SMILES: O=C(O)[C@@H]1[C@H]2CC[C@@H](CN1C(=O)C(c1ccccc1)c1ccccc1)N2C(=O)OCc1ccccc1F] |
| C36 | 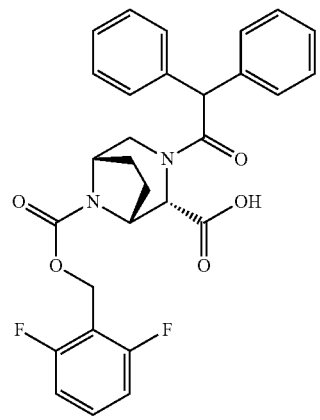 [SMILES: O=C(O)[C@@H]1[C@H]2CC[C@@H](CN1C(=O)C(c1ccccc1)c1ccccc1)N2C(=O)OCc1c(F)cccc1F] |

| No. | Structure |
|---|---|
| C37 | 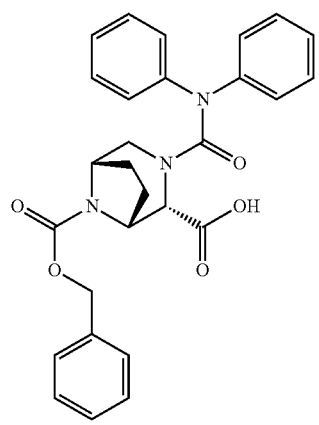 [SMILES: O=C(O)[C@@H]1[C@H]2CC[C@@H](CN1C(=O)N(c1ccccc1)c1ccccc1)N2C(=O)OCc1ccccc1] |
| C38 | 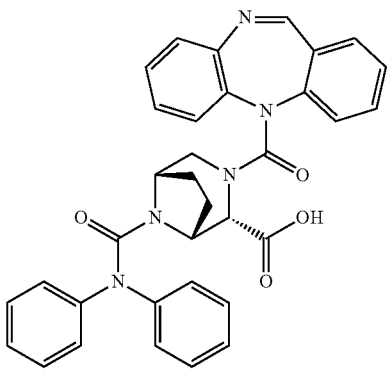 [SMILES: O=C(O)[C@@H]1[C@H]2CC[C@@H](CN1C(=O)N1c3ccccc3C=Nc3ccccc31)N2C(=O)N(c1ccccc1)c1ccccc1] |
| C39 | 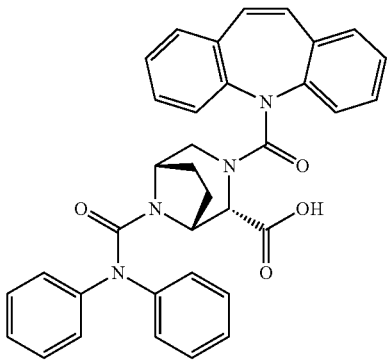 [SMILES: O=C(O)[C@@H]1[C@H]2CC[C@@H](CN1C(=O)N1c3ccccc3C=Cc3ccccc31)N2C(=O)N(c1ccccc1)c1ccccc1] |
| C40 | 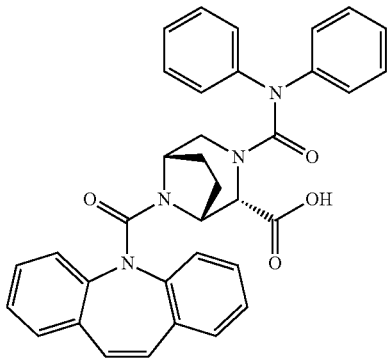 [SMILES: O=C(O)[C@@H]1[C@H]2CC[C@@H](CN1C(=O)N(c1ccccc1)c1ccccc1)N2C(=O)N1c2ccccc2C=Cc2ccccc21] |
| No. | Structure |
|---|---|
| C41 | 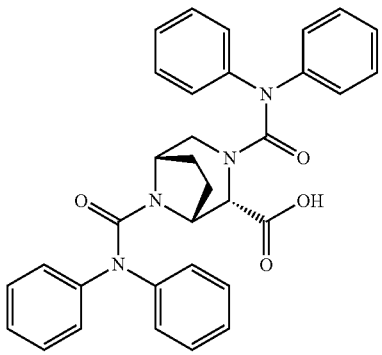 [SMILES: O=C(O)[C@@H]1[C@H]2CC[C@@H](CN1C(=O)N(c1ccccc1)c1ccccc1)N2C(=O)N(c1ccccc1)c1ccccc1] |
| C42 | 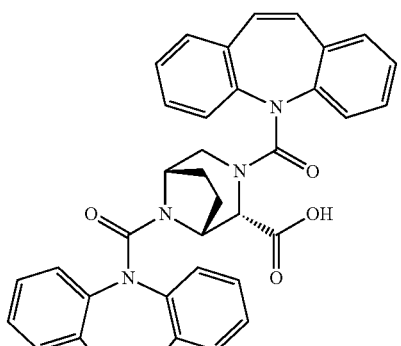 |
| C43 | 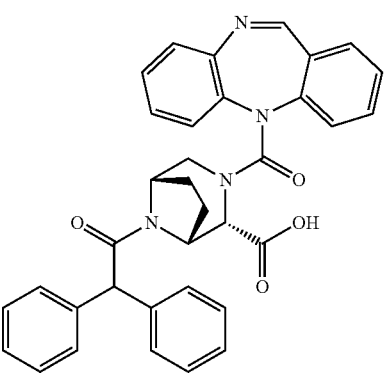 [SMILES: O=C(O)[C@@H]1[C@H]2CC[C@@H](CN1C(=O)N1c3ccccc3C=Nc3ccccc31)N2C(=O)C(c1ccccc1)c1ccccc1] |
| C44 | 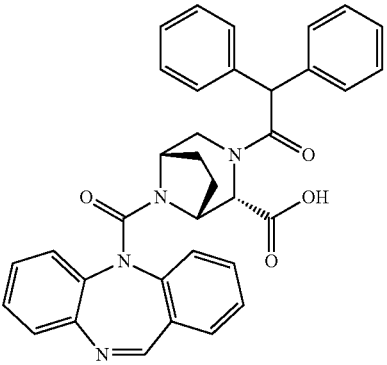 |

| No. | Structure |
|---|---|
| C45 | 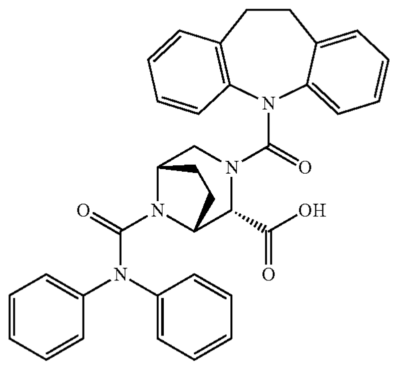 |
| C46 | 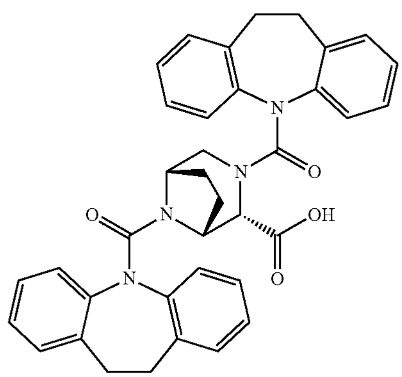 [SMILES: O=C(O)[C@@H]1[C@H]2CC[C@@H](CN1C(=O)N1c3ccccc3CCc3ccccc31)N2C(=O)N1c2ccccc2CCc2ccccc21] |
| C47 | 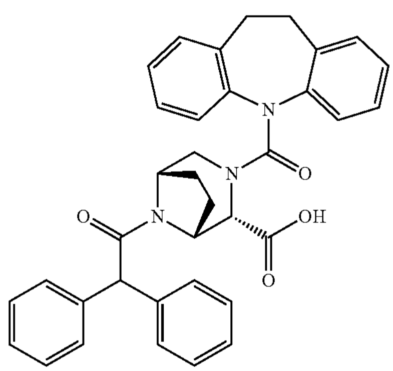 [SMILES: O=C(O)[C@@H]1[C@H]2CC[C@@H](CN1C(=O)N1c3ccccc3CCc3ccccc31)N2C(=O)C(c1ccccc1)c1ccccc1] |
| C48 | 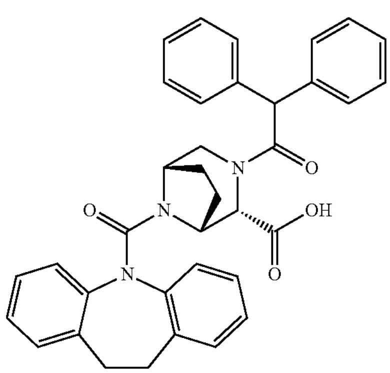 [SMILES: O=C(O)[C@@H]1[C@H]2CC[C@@H](CN1C(=O)C(c1ccccc1)c1ccccc1)N2C(=O)N1c2ccccc2CCc2ccccc21] |
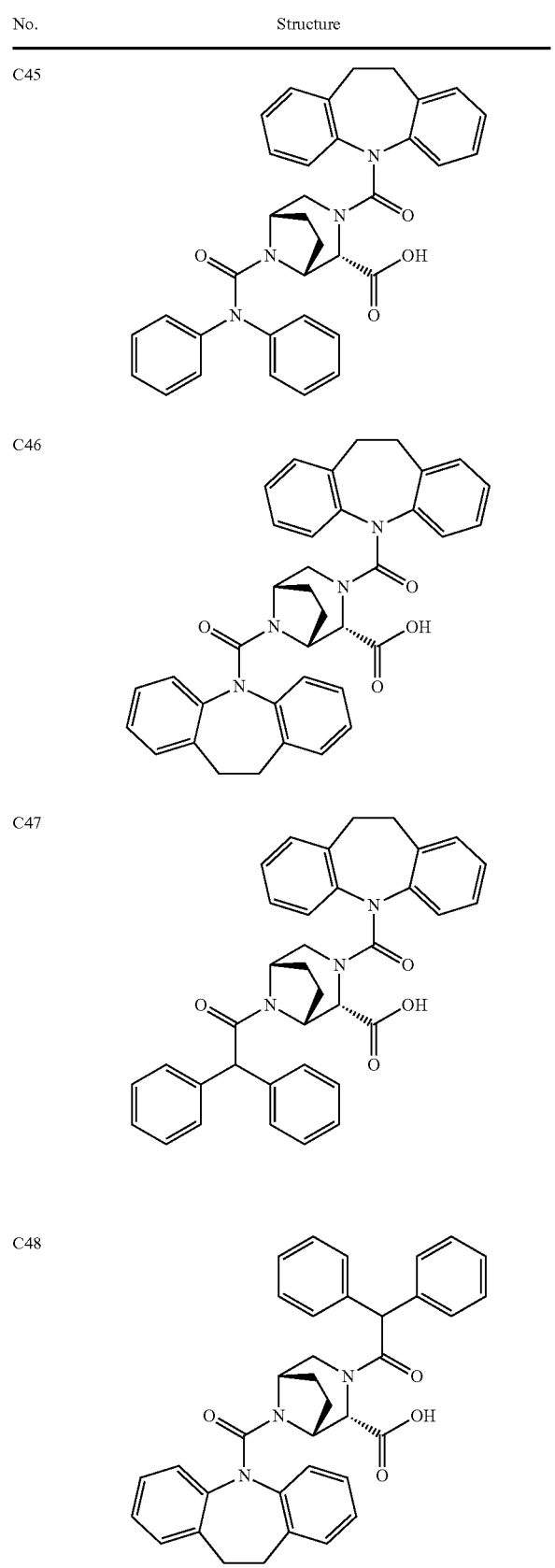
| No. | Structure |
|---|---|
| C49 | 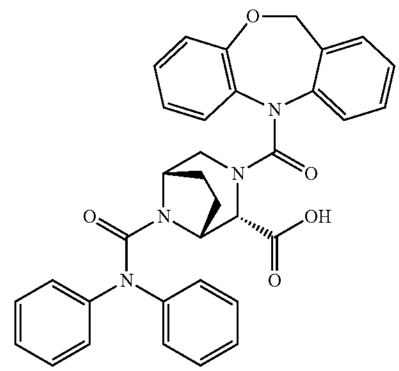 [SMILES: O=C(O)[C@@H]1[C@H]2CC[C@@H](CN1C(=O)N1c3ccccc3COc3ccccc31)N2C(=O)N(c1ccccc1)c1ccccc1] |
| C50 | 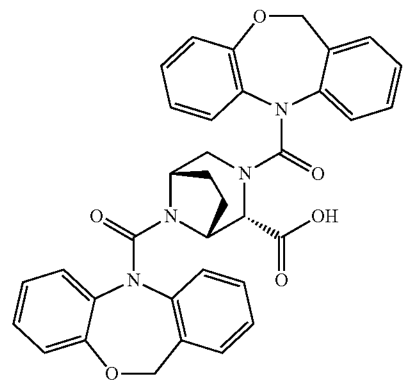 |
| C51 | 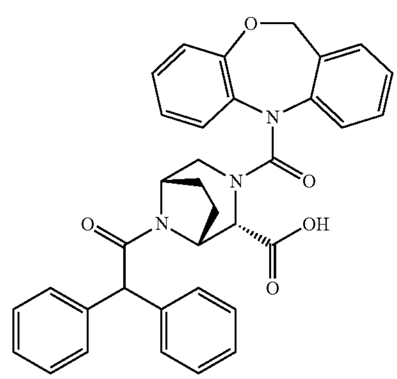 [SMILES: O=C(O)[C@@H]1[C@H]2CC[C@@H](CN1C(=O)N1c3ccccc3COc3ccccc31)N2C(=O)C(c1ccccc1)c1ccccc1] |
| C52 | 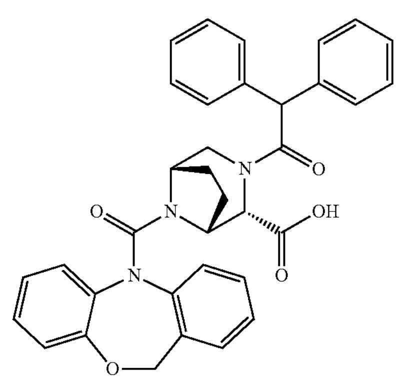 |
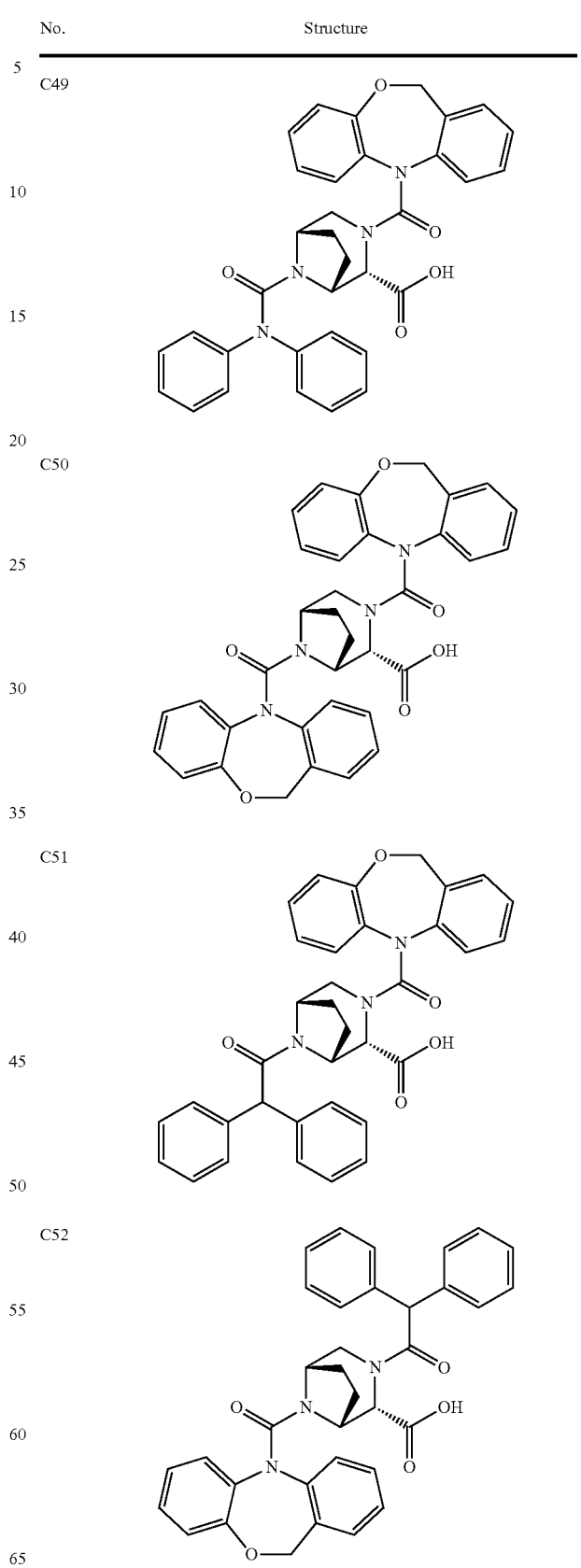

| No. | Structure |
|---|---|
| C53 | 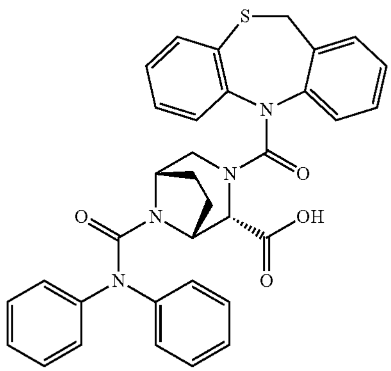 |
| C54 | 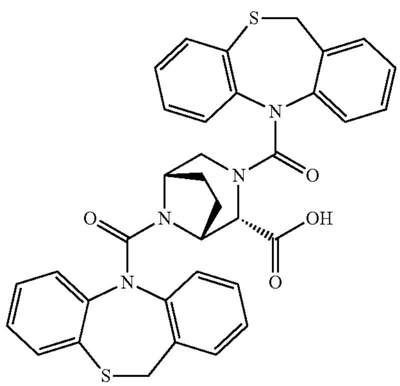 [SMILES: O=C(O)[C@@H]1[C@H]2CC[C@@H](CN1C(=O)N1c3ccccc3CSc3ccccc31)N2C(=O)N1c2ccccc2CSc2ccccc21] |
| C55 | 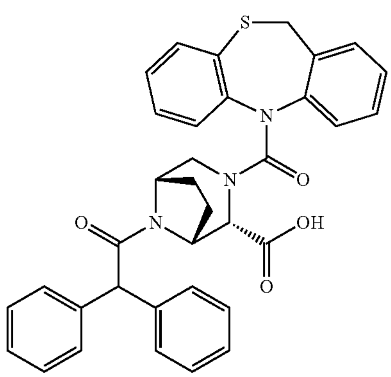 |
| C56 | 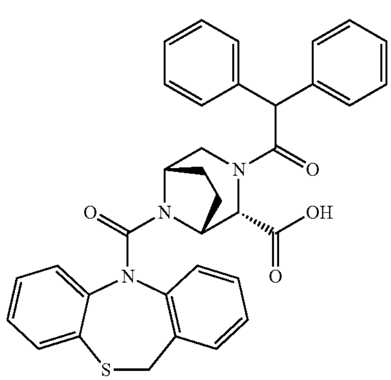 [SMILES: O=C(O)[C@@H]1[C@H]2CC[C@@H](CN1C(=O)C(c1ccccc1)c1ccccc1)N2C(=O)N1c2ccccc2CSc2ccccc21] |
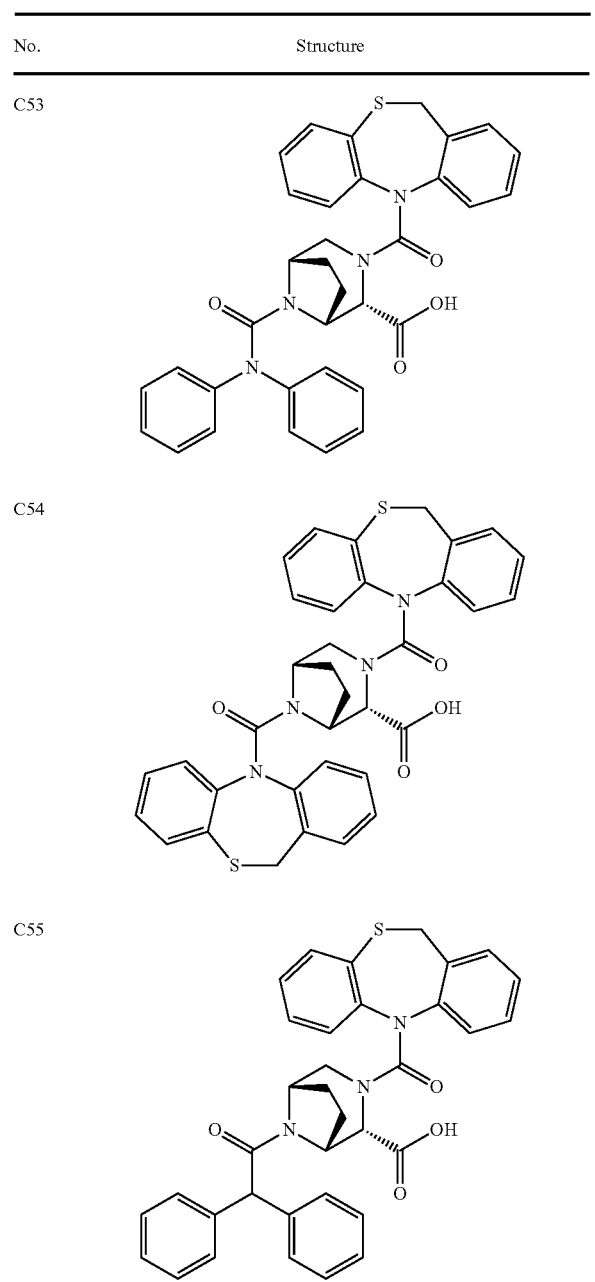
| No. | Structure |
|---|---|
| C57 | 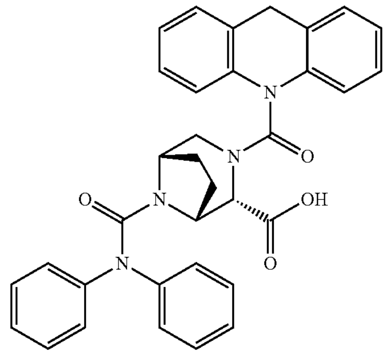 [SMILES: O=C(O)[C@@H]1[C@H]2CC[C@@H](CN1C(=O)N1c3ccccc3Cc3ccccc31)N2C(=O)N(c1ccccc1)c1ccccc1] |
| C58 | 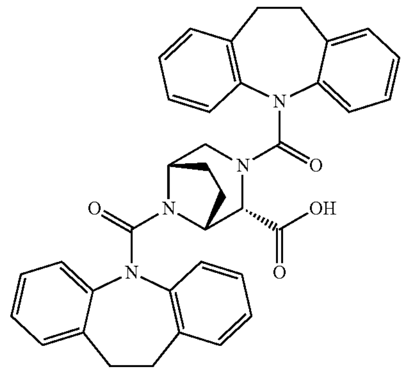 [SMILES: O=C(O)[C@@H]1[C@H]2CC[C@@H](CN1C(=O)N1c3ccccc3CCc3ccccc31)N2C(=O)N1c2ccccc2CCc2ccccc21] |
| C59 | 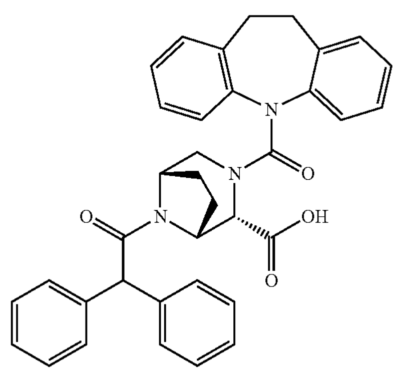 [SMILES: O=C(O)[C@@H]1[C@H]2CC[C@@H](CN1C(=O)N1c3ccccc3CCc3ccccc31)N2C(=O)C(c1ccccc1)c1ccccc1] |
| C60 | 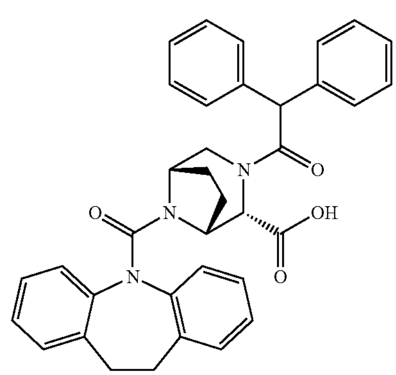 [SMILES: O=C(O)[C@@H]1[C@H]2CC[C@@H](CN1C(=O)C(c1ccccc1)c1ccccc1)N2C(=O)N1c2ccccc2CCc2ccccc21] |
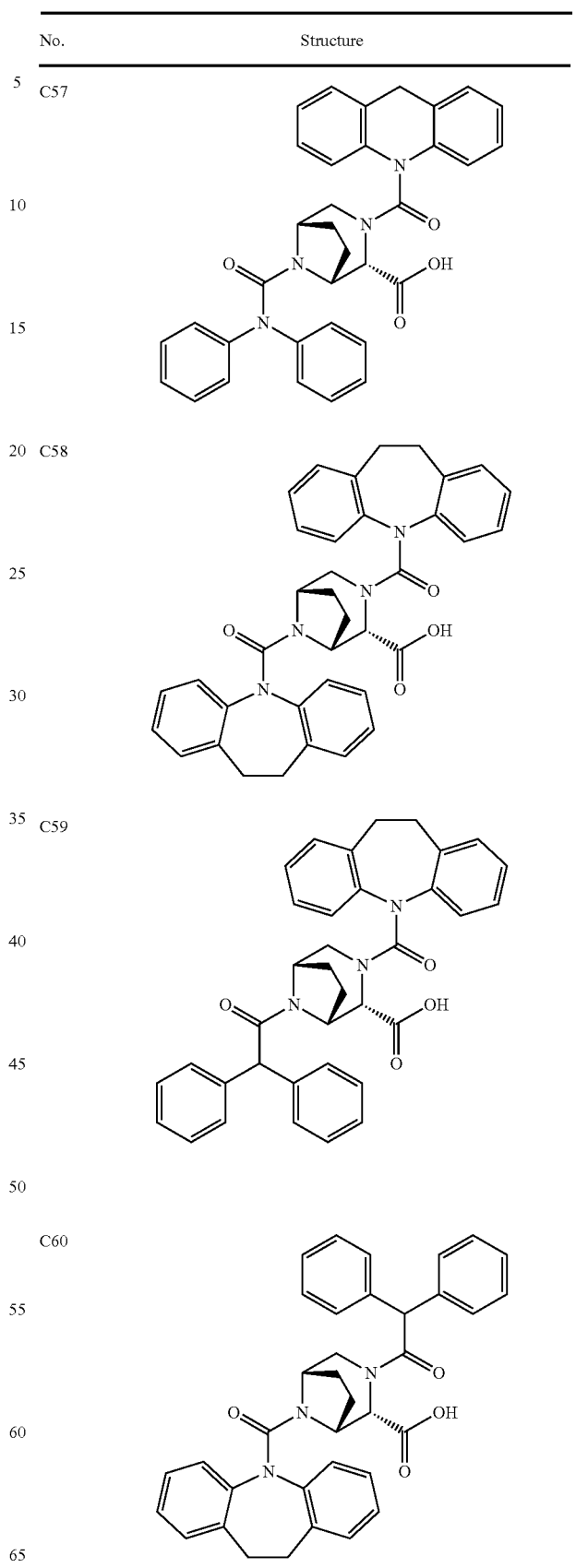

-continued
| No. | Structure |
|---|---|
| C61 | 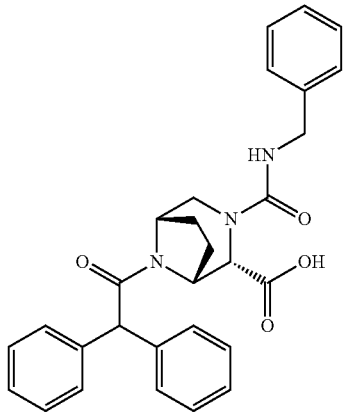 [SMILES: O=C(O)[C@@H]1[C@H]2CC[C@@H](CN1C(=O)NCc1ccccc1)N2C(=O)C(c1ccccc1)c1ccccc1] |
| C62 | 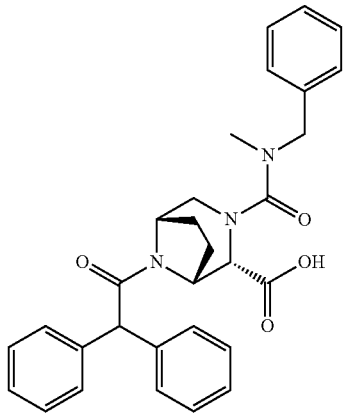 [SMILES: CN(Cc1ccccc1)C(=O)N1C[C@@H]2CC[C@H]([C@H]1C(=O)O)N2C(=O)C(c1ccccc1)c1ccccc1] |
| C63 | 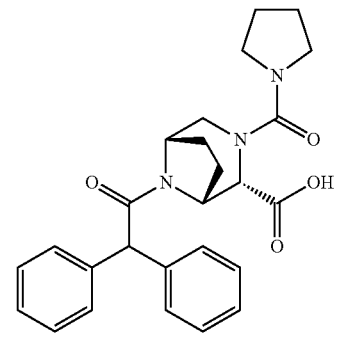 [SMILES: O=C(O)[C@@H]1[C@H]2CC[C@@H](CN1C(=O)N1CCCC1)N2C(=O)C(c1ccccc1)c1ccccc1] |
| C64 | 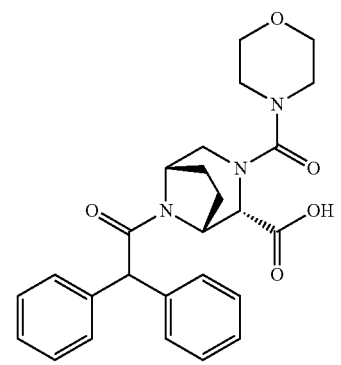 [SMILES: O=C(O)[C@@H]1[C@H]2CC[C@@H](CN1C(=O)N1CCOCC1)N2C(=O)C(c1ccccc1)c1ccccc1] |
-continued
| No. | Structure |
|---|---|
| C65 | 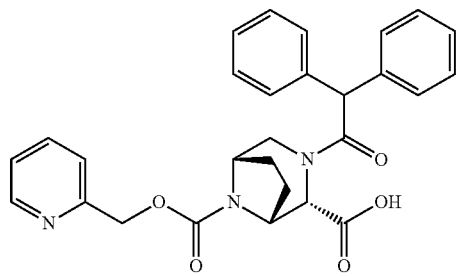 [SMILES: O=C(O)[C@@H]1[C@H]2CC[C@@H](CN1C(=O)C(c1ccccc1)c1ccccc1)N2C(=O)OCc1ccccn1] |
| C66 | 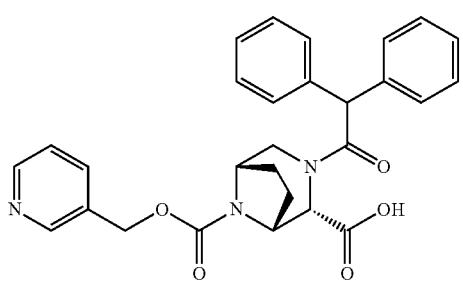 [SMILES: O=C(O)[C@@H]1[C@H]2CC[C@@H](CN1C(=O)C(c1ccccc1)c1ccccc1)N2C(=O)OCc1cccnc1] |
| C67 | 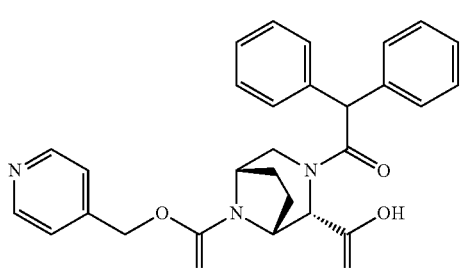 |
| C68 | 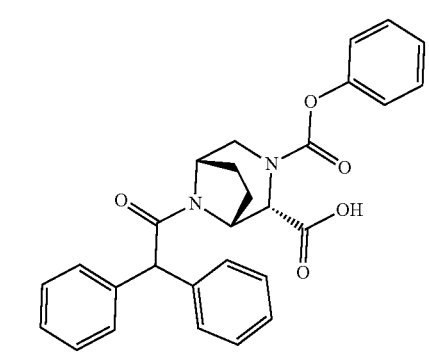 [SMILES: O=C(O)[C@@H]1[C@H]2CC[C@@H](CN1C(=O)Oc1ccccc1)N2C(=O)N(c1ccccc1)c1ccccc1] |
| C69 | 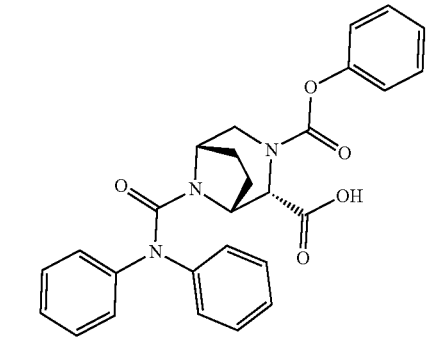 |

| No. | Structure |
|---|---|
| C70 | 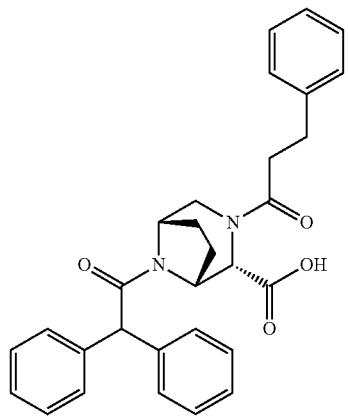 |
| C71 | 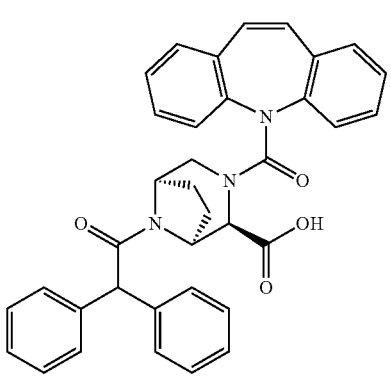 [SMILES: O=C(O)[C@H]1[C@@H]2CC[C@H](CN1C(=O)N1c3ccccc3C=Cc3ccccc31)N2C(=O)C(c1ccccc1)c1ccccc1] |
| C72 | 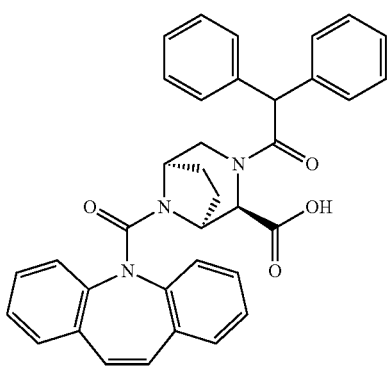 [SMILES: O=C(O)[C@H]1[C@@H]2CC[C@H](CN1C(=O)C(c1ccccc1)c1ccccc1)N2C(=O)N1c2ccccc2C=Cc2ccccc21] |
| C73 | 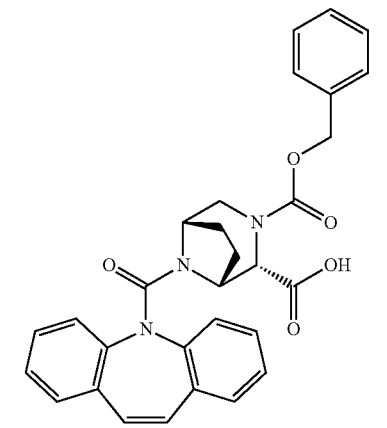 [SMILES: O=C(O)[C@@H]1[C@H]2CC[C@@H](CN1C(=O)OCc1ccccc1)N2C(=O)N1c2ccccc2C=Cc2ccccc21] |
| No. | Structure |
|---|---|
| C74 | 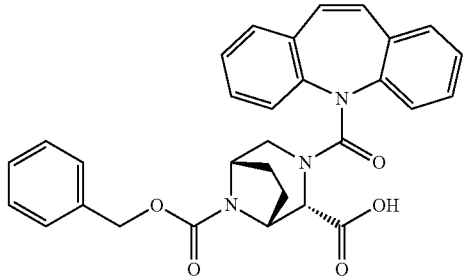 [SMILES: O=C(O)[C@@H]1[C@H]2CC[C@@H](CN1C(=O)N1c3ccccc3C=Cc3ccccc31)N2C(=O)OCc1ccccc1] |
| C75 | 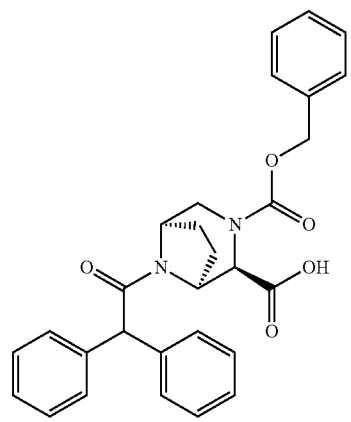 [SMILES: O=C(O)[C@H]1[C@@H]2CC[C@H](CN1C(=O)OCc1ccccc1)N2C(=O)C(c1ccccc1)c1ccccc1] |
| C76 | 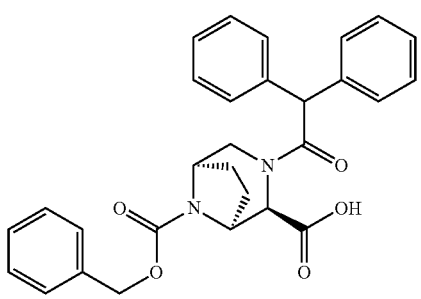 [SMILES: O=C(O)[C@H]1[C@@H]2CC[C@H](CN1C(=O)C(c1ccccc1)c1ccccc1)N2C(=O)OCc1ccccc1] |
| C77 | 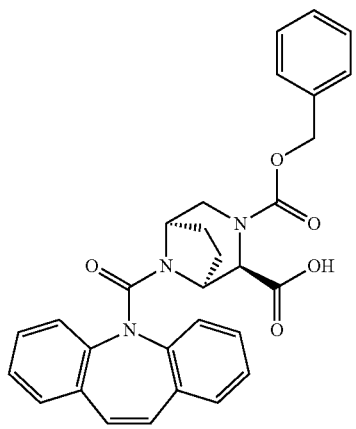 [SMILES: O=C(O)[C@H]1[C@@H]2CC[C@H](CN1C(=O)OCc1ccccc1)N2C(=O)N1c2ccccc2C=Cc2ccccc21] |

-continued
| No. | Structure |
|---|---|
| C78 | 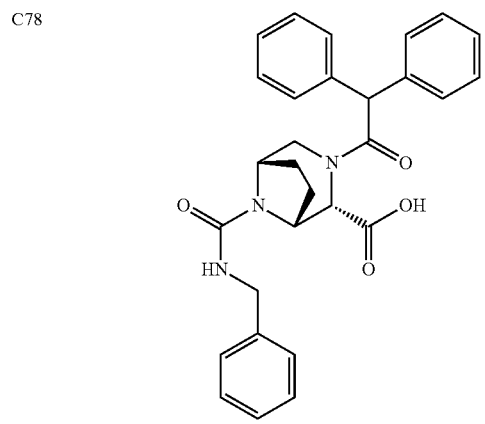 |
| C79 | 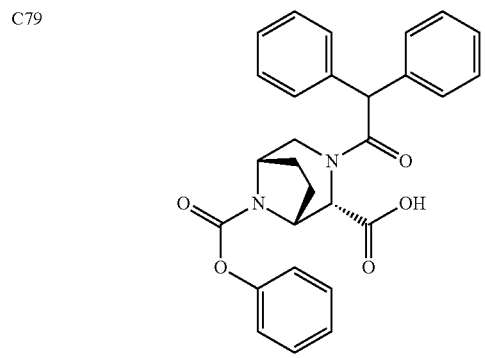 |
| C80 | 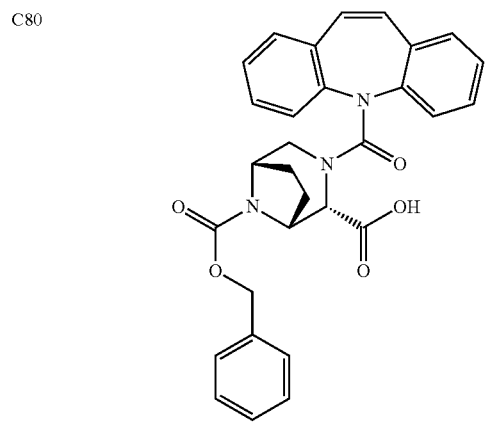 |
| C81 | 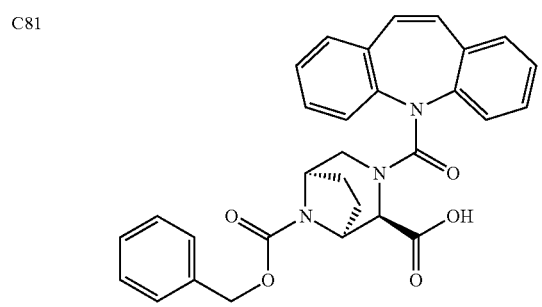 |
-continued
| No. | Structure |
|---|---|
| C82 | 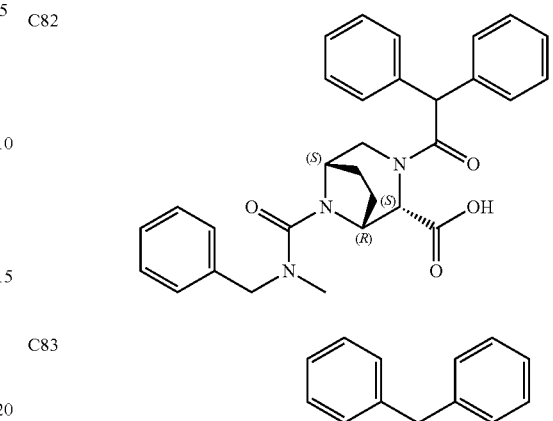 |
| C83 | 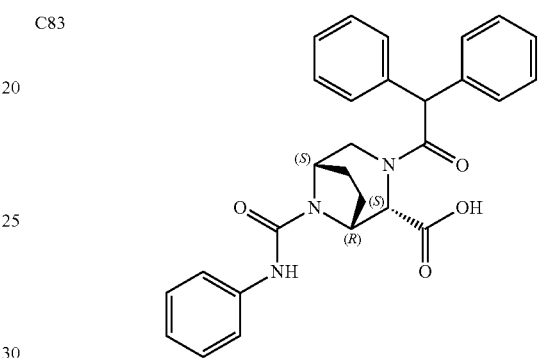 |
| C84 | 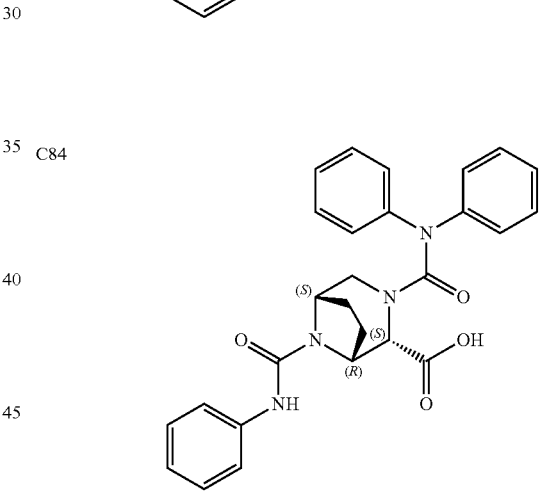 |
| C85 | 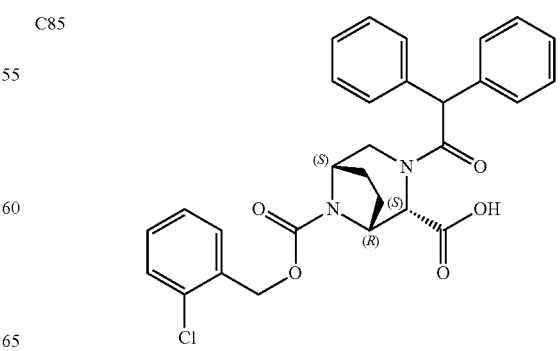 |

| No. | Structure |
|---|---|
| C86 | 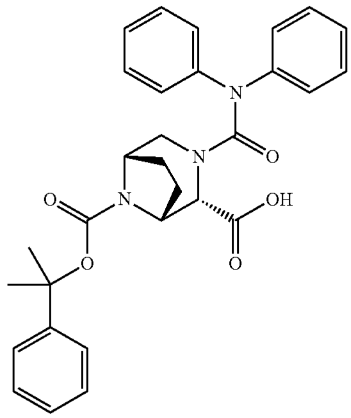 [SMILES: CC(C)(OC(=O)N1[C@H]2CC[C@@H]1[C@@H](C(=O)O)N(C(=O)N(c1ccccc1)c1ccccc1)C2)c1ccccc1] |
| C87 | 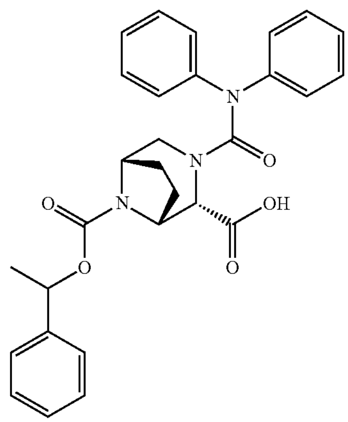 [SMILES: CC(OC(=O)N1[C@H]2CC[C@@H]1[C@@H](C(=O)O)N(C(=O)N(c1ccccc1)c1ccccc1)C2)c1ccccc1] |
| C88 | 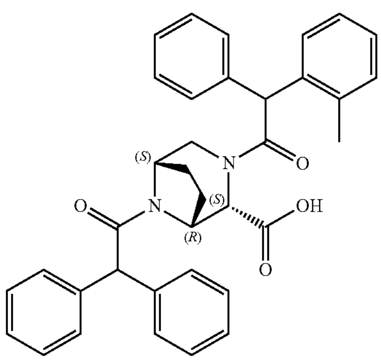 |
| C89 | 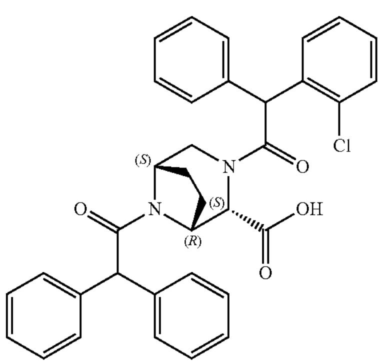 |

| No. | Structure |
|---|---|
| C90 | 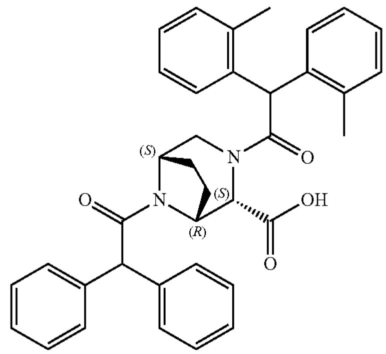 |
| C91 | 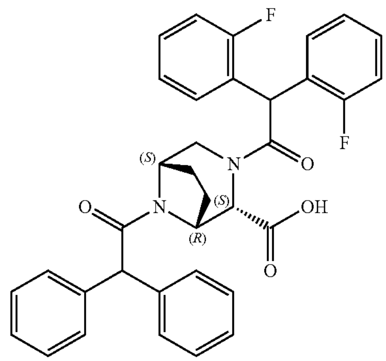 |
| C92 | 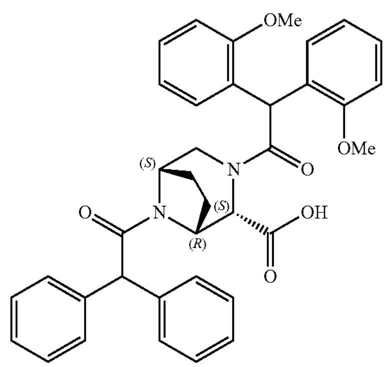 |
| C93 | 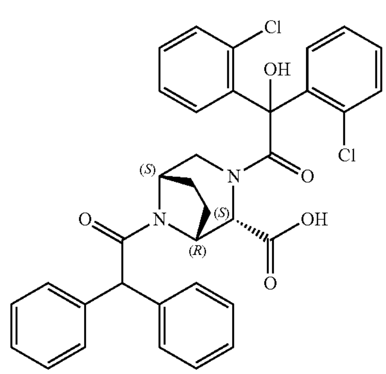 |

| No. | Structure |
|---|---|
| C94 | 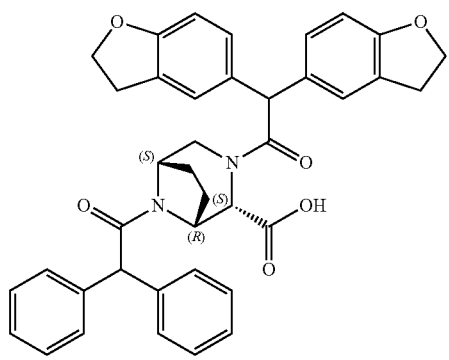 |
| C95 | 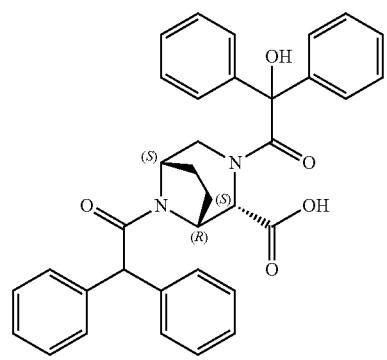 |
| C96 | 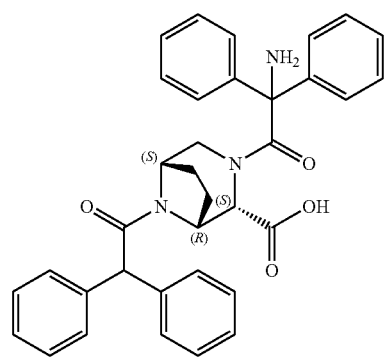 |
| C97 | 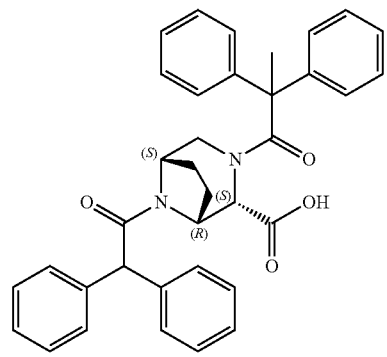 |
| No. | Structure |
|---|---|
| C98 | 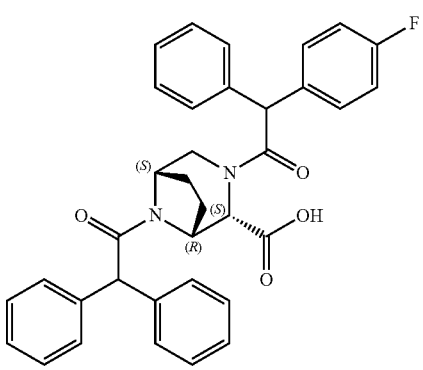 |
| C99 | 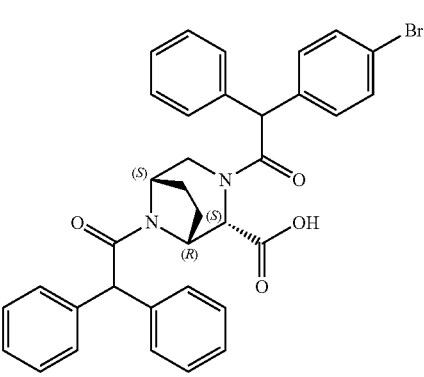 |
| C100 | 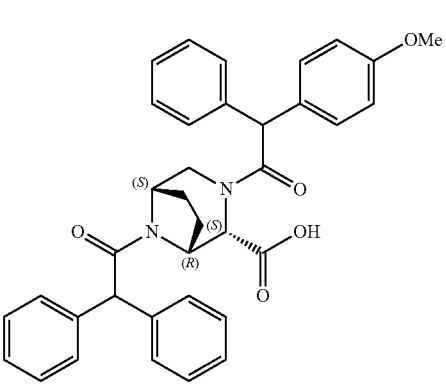 |
| C101 | 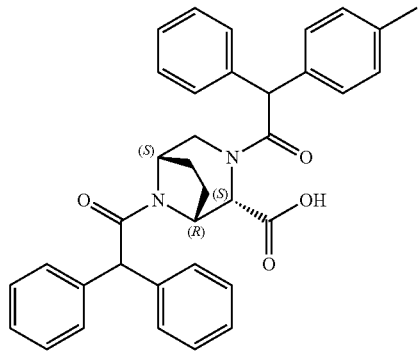 |

| No. | Structure |
|---|---|
| C102 | 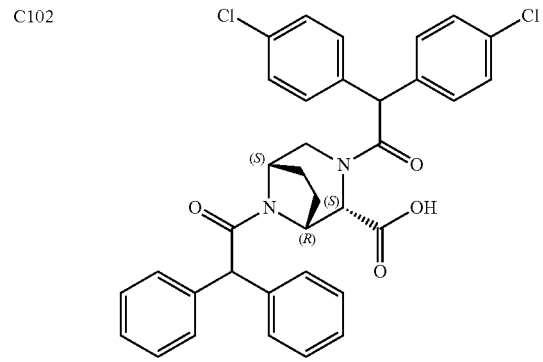 |
| C103 | 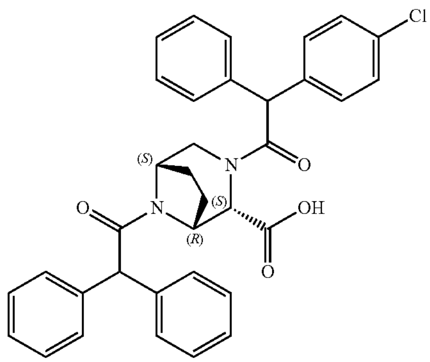 |
| C104 | 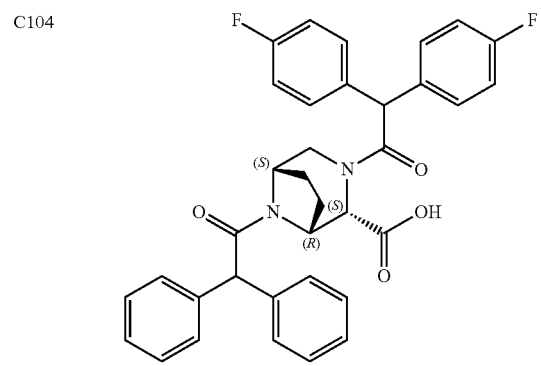 |
| C105 | 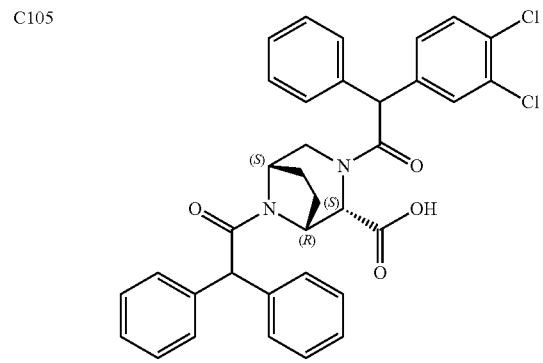 |
| C106 | 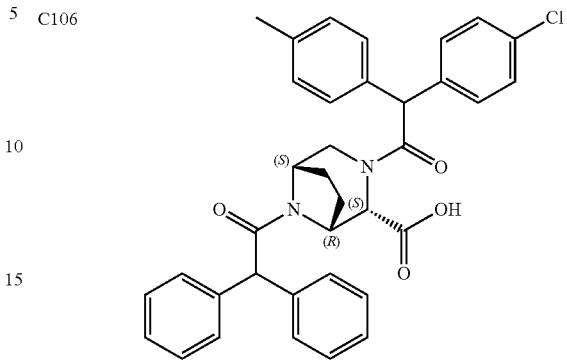 |
| C107 | 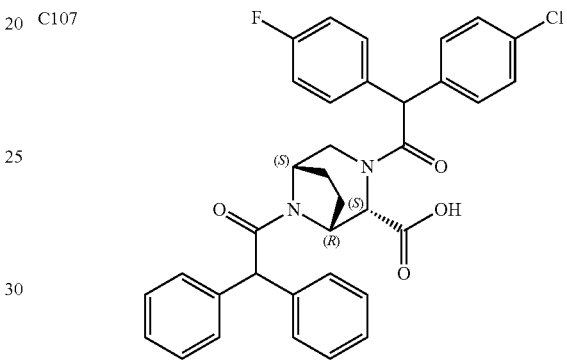 |
| C108 | 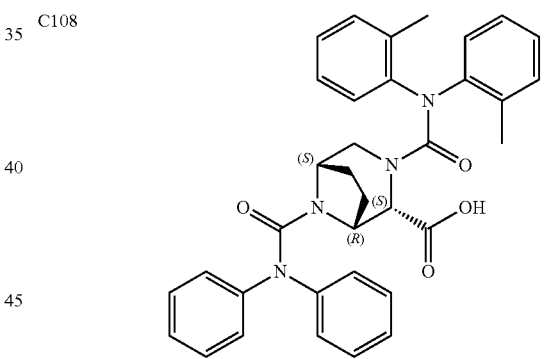 |
| C109 | 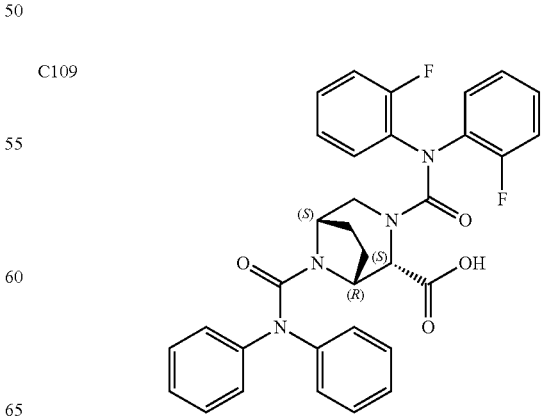 |

-continued

| No. | Structure |
|---|---|
| C110 | 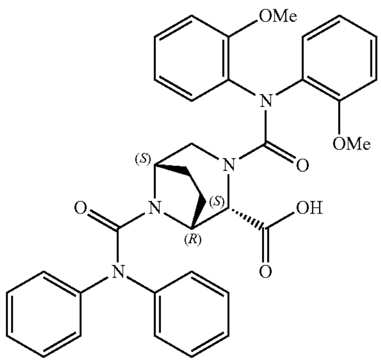 |
| C111 | 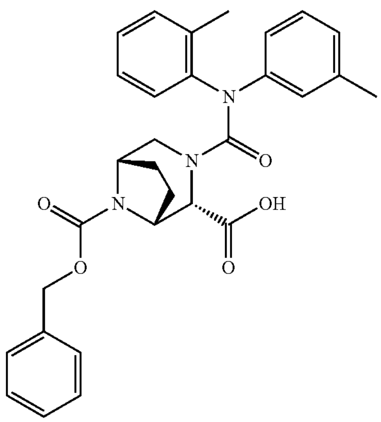 [SMILES: Cc1cccc(N(C(=O)N2C[C@@H]3CC[C@H]([C@H]2C(=O)O)N3C(=O)OCc2ccccc2)c2ccccc2C)c1] |
| C112 | 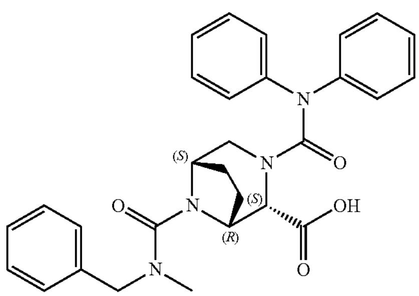 |
| C113 | 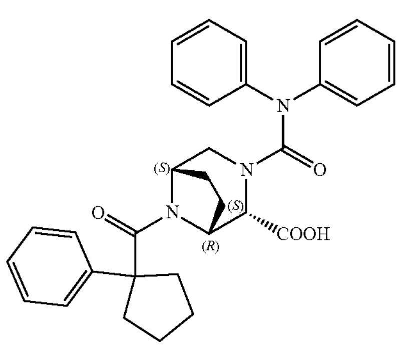 |

-continued

| No. | Structure |
|---|---|
| C114 | 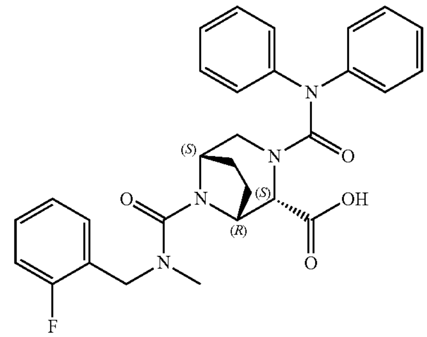 |
| C115 | 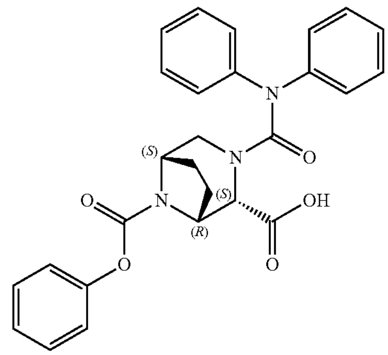 |
| C116 | 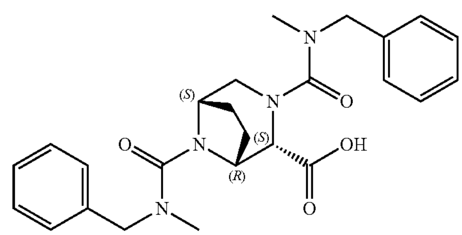 |
| C117 | 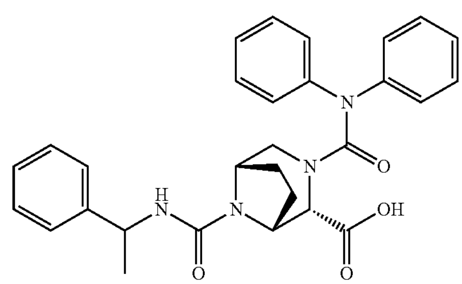 |
| C118 | 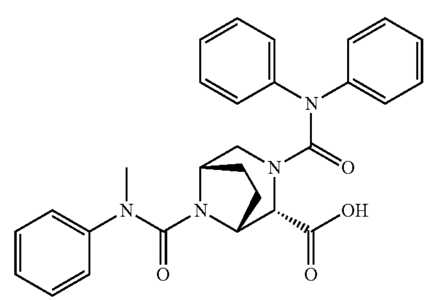 [SMILES: CN(C(=O)N1[C@H]2CC[C@@H]1[C@@H](C(=O)O)N(C(=O)N(c1ccccc1)c1ccccc1)C2)c1ccccc1] |

| No. | Structure |
|---|---|
| C119 | 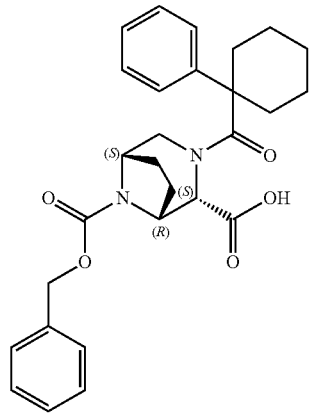 |
| C120 | 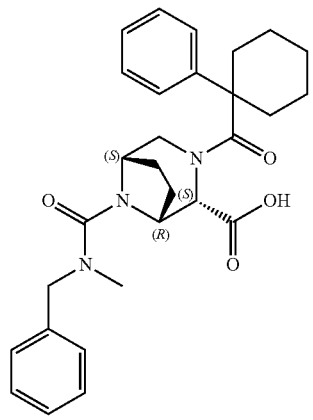 |
| C121 | 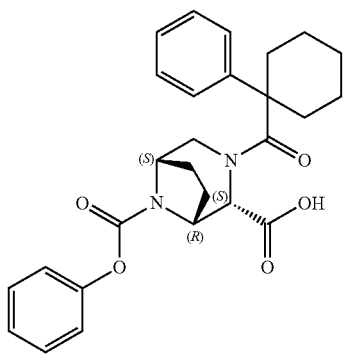 |
| C122 | 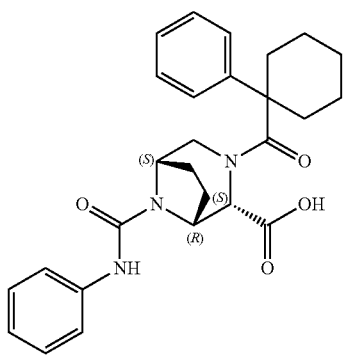 |
| No. | Structure |
|---|---|
| C123 | 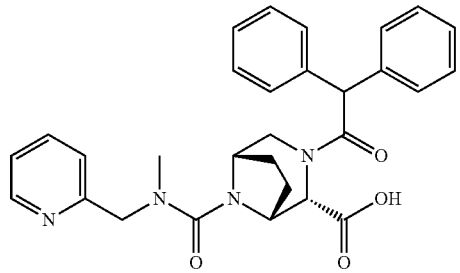 [SMILES: CN(Cc1ccccn1)C(=O)N1[C@H]2CC[C@@H]1[C@@H](C(=O)O)N(C(=O)C(c1ccccc1)c1ccccc1)C2] |
| C124 | 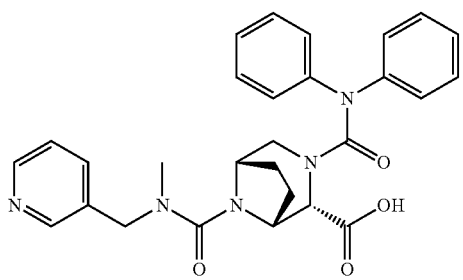 [SMILES: CN(Cc1cccnc1)C(=O)N1[C@H]2CC[C@@H]1[C@@H](C(=O)O)N(C(=O)N(c1ccccc1)c1ccccc1)C2] |
| C125 | 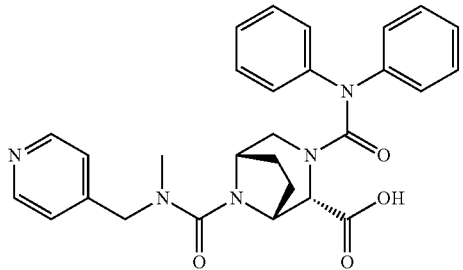 [SMILES: CN(Cc1ccncc1)C(=O)N1[C@H]2CC[C@@H]1[C@@H](C(=O)O)N(C(=O)N(c1ccccc1)c1ccccc1)C2] |
| C126 | 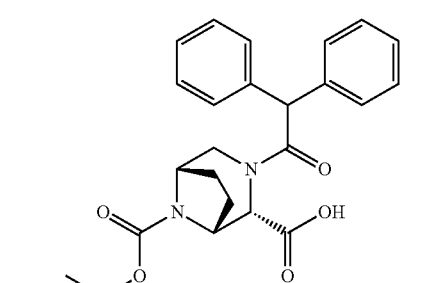 |
| C127 | 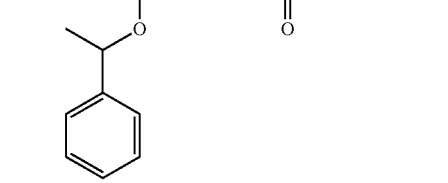 |

| No. | Structure |
|---|---|
| C128 | 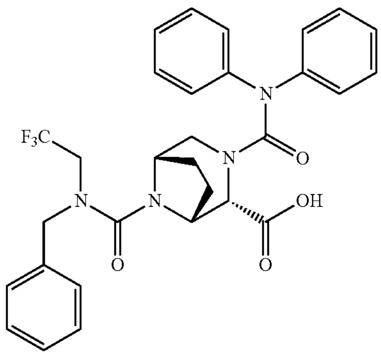 [SMILES: O=C(O)[C@@H]1[C@H]2CC[C@@H](CN1C(=O)N(c1ccccc1)c1ccccc1)N2C(=O)N(Cc1ccccc1)CC(F)(F)F] |
| C129 | 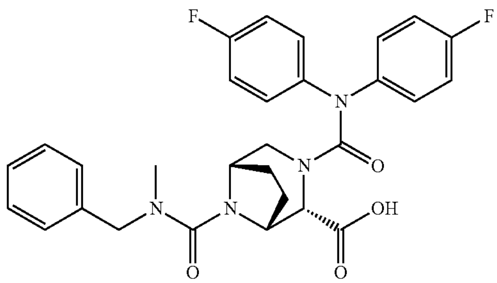 [SMILES: CN(Cc1ccccc1)C(=O)N1[C@H]2CC[C@@H]1[C@@H](C(=O)O)N(C(=O)N(c1ccc(F)cc1)c1ccc(F)cc1)C2] |
| C130 | 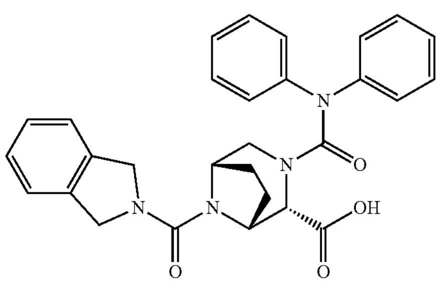 [SMILES: O=C(O)[C@@H]1[C@H]2CC[C@@H](CN1C(=O)N(c1ccccc1)c1ccccc1)N2C(=O)N1Cc2ccccc2C1] |
| C131 | 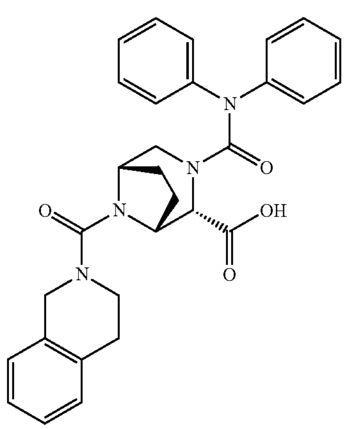 [SMILES: O=C(O)[C@@H]1[C@H]2CC[C@@H](CN1C(=O)N(c1ccccc1)c1ccccc1)N2C(=O)N1CCc2ccccc2C1] |

| No. | Structure |
|---|---|
| C132 | 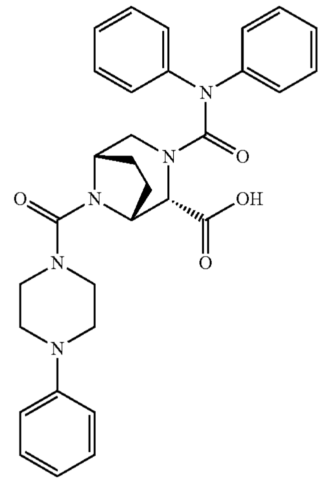 [SMILES: O=C(O)[C@@H]1[C@H]2CC[C@@H](CN1C(=O)N(c1ccccc1)c1ccccc1)N2C(=O)N1CCN(c2ccccc2)CC1] |
| C133 | 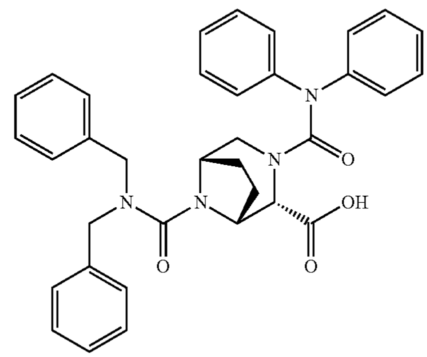 [SMILES: O=C(O)[C@@H]1[C@H]2CC[C@@H](CN1C(=O)N(c1ccccc1)c1ccccc1)N2C(=O)N(Cc1ccccc1)Cc1ccccc1] |
| C134 | 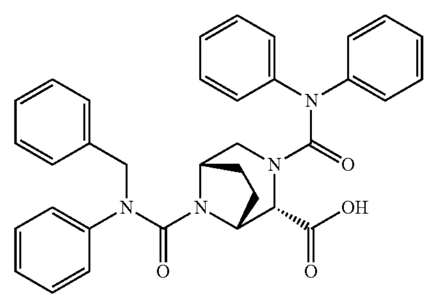 [SMILES: O=C(O)[C@@H]1[C@H]2CC[C@@H](CN1C(=O)N(c1ccccc1)c1ccccc1)N2C(=O)N(Cc1ccccc1)c1ccccc1] |
| C135 | 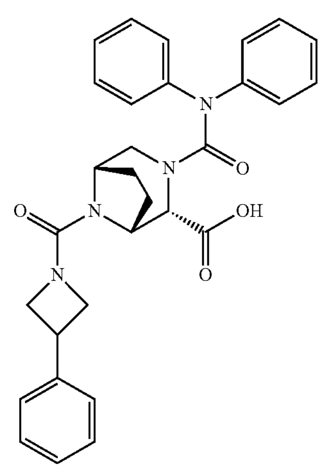 [SMILES: O=C(O)[C@@H]1[C@H]2CC[C@@H](CN1C(=O)N(c1ccccc1)c1ccccc1)N2C(=O)N1CC(c2ccccc2)C1] |

| No. | Structure |
|---|---|
| C136 | 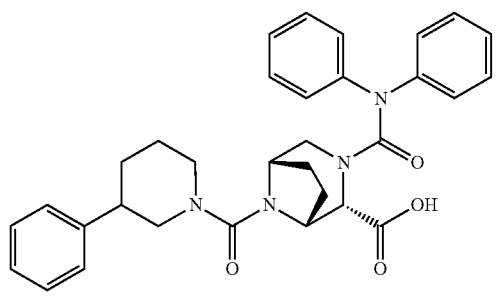 [SMILES: O=C(O)[C@@H]1[C@H]2CC[C@@H](CN1C(=O)N(c1ccccc1)c1ccccc1)N2C(=O)N1CCCC(c2ccccc2)C1] |
| C137 | 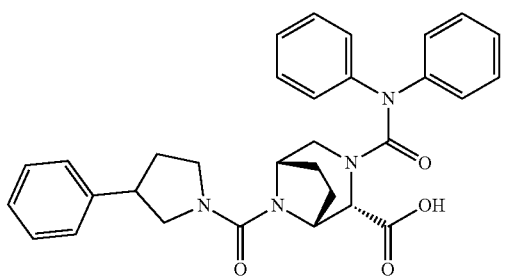 [SMILES: O=C(O)[C@@H]1[C@H]2CC[C@@H](CN1C(=O)N(c1ccccc1)c1ccccc1)N2C(=O)N1CCC(c2ccccc2)C1] |
| C138 | 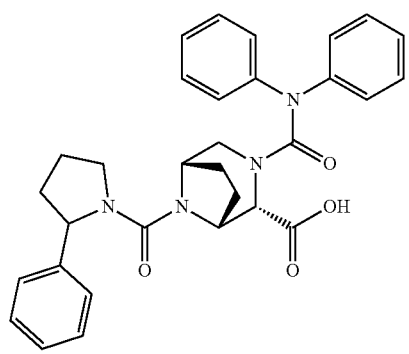 [SMILES: O=C(O)[C@@H]1[C@H]2CC[C@@H](CN1C(=O)N(c1ccccc1)c1ccccc1)N2C(=O)N1CCCC1c1ccccc1] |
| C139 | 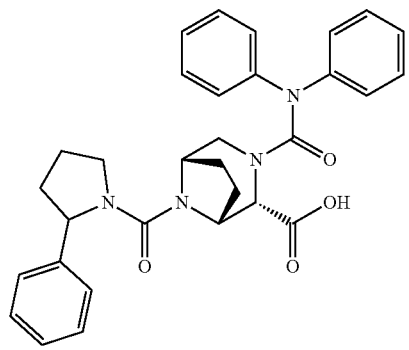 [SMILES: O=C(O)[C@@H]1[C@H]2CC[C@@H](CN1C(=O)N(c1ccccc1)c1ccccc1)N2C(=O)N1CCCC1c1ccccc1] |
| No. | Structure |
|---|---|
| C140 | 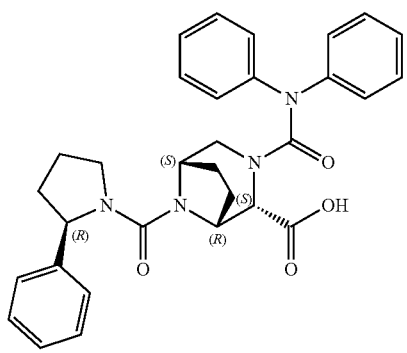 |
| C141 | 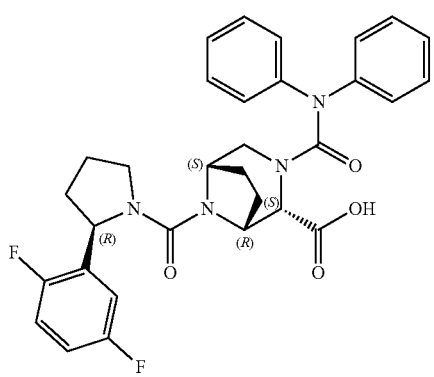 |
| C142 | 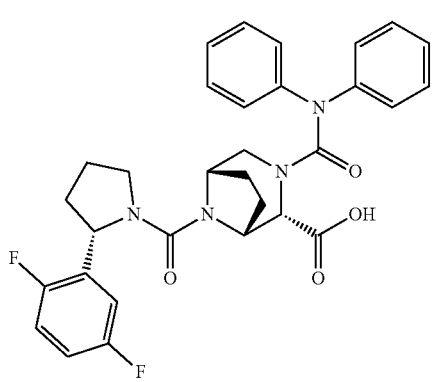 [SMILES: O=C(O)[C@@H]1[C@H]2CC[C@@H](CN1C(=O)N(c1ccccc1)c1ccccc1)N2C(=O)N1CCC[C@H]1c1cc(F)ccc1F] |
| C143 | 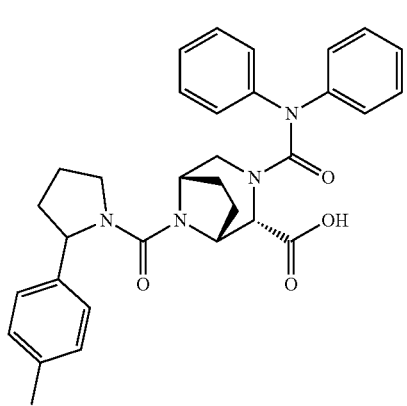 [SMILES: Cc1ccc(C2CCCN2C(=O)N2[C@H]3CC[C@@H]2[C@@H](C(=O)O)N(C(=O)N(c2ccccc2)c2ccccc2)C3)cc1] |

| No. | Structure |
|---|---|
| C144 | 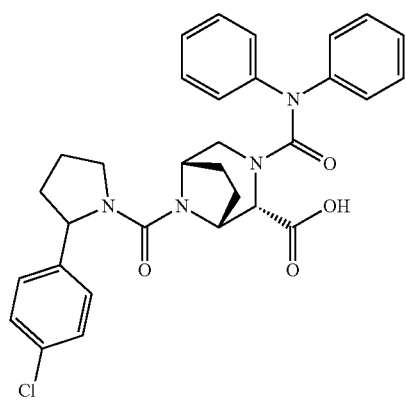 [SMILES: O=C(O)[C@@H]1[C@H]2CC[C@@H](CN1C(=O)N(c1ccccc1)c1ccccc1)N2C(=O)N1CCCC1c1ccc(Cl)cc1] |
| C145 | 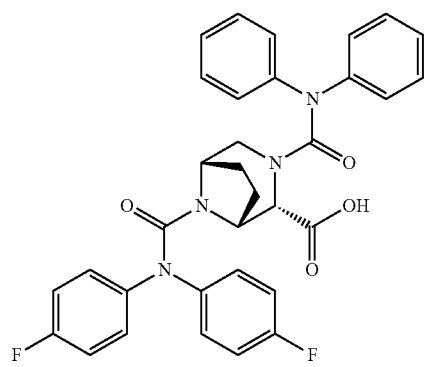 [SMILES: O=C(O)[C@@H]1[C@H]2CC[C@@H](CN1C(=O)N(c1ccccc1)c1ccccc1)N2C(=O)N(c1ccc(F)cc1)c1ccc(F)cc1] |
| C146 | 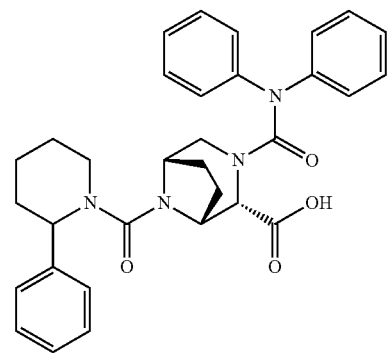 [SMILES: O=C(O)[C@@H]1[C@H]2CC[C@@H](CN1C(=O)N(c1ccccc1)c1ccccc1)N2C(=O)N1CCCCC1c1ccccc1] |
| C147 | 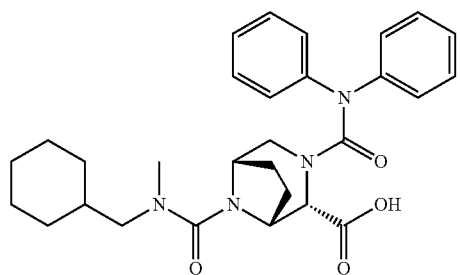 [SMILES: CN(CC1CCCCC1)C(=O)N1[C@H]2CC[C@@H]1[C@@H](C(=O)O)N(C(=O)N(c1ccccc1)c1ccccc1)C2] |
| No. | Structure |
|---|---|
| C148 | 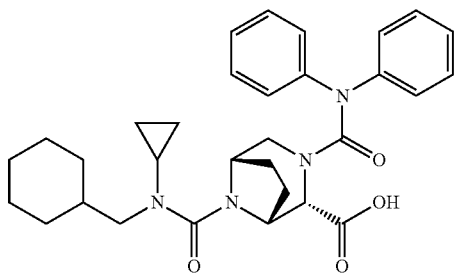 [SMILES: O=C(O)[C@@H]1[C@H]2CC[C@@H](CN1C(=O)N(c1ccccc1)c1ccccc1)N2C(=O)N(CC1CCCCC1)C1CC1] |
| C149 | 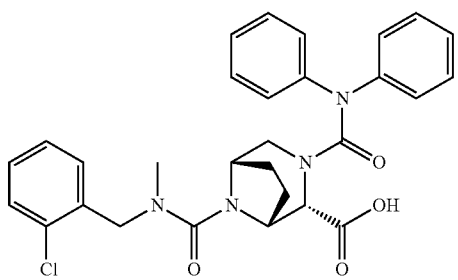 [SMILES: CN(Cc1ccccc1Cl)C(=O)N1[C@H]2CC[C@@H]1[C@@H](C(=O)O)N(C(=O)N(c1ccccc1)c1ccccc1)C2] |
| C150 | 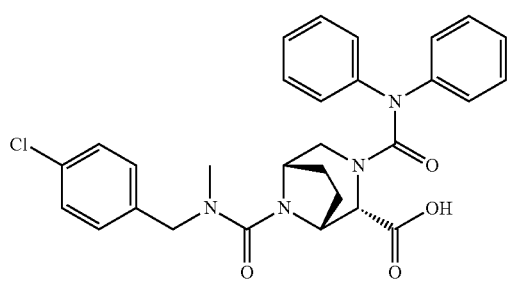 |
| C151 | 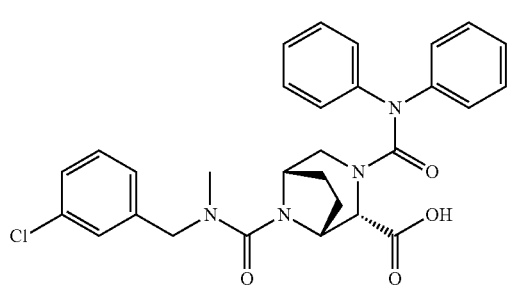 [SMILES: CN(Cc1cccc(Cl)c1)C(=O)N1[C@H]2CC[C@@H]1[C@@H](C(=O)O)N(C(=O)N(c1ccccc1)c1ccccc1)C2] |
| C152 | 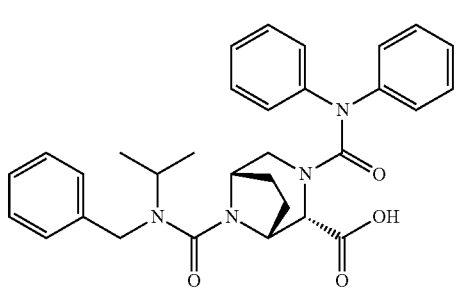 [SMILES: CC(C)N(Cc1ccccc1)C(=O)N1[C@H]2CC[C@@H]1[C@@H](C(=O)O)N(C(=O)N(c1ccccc1)c1ccccc1)C2] |

-continued
| No. | Structure |
|---|---|
| C153 | 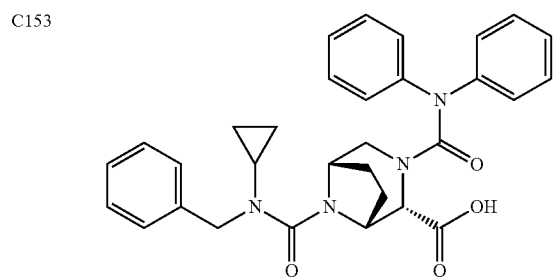 |
| C154 | 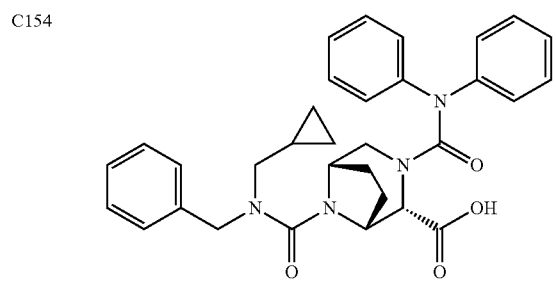 |
| C155 | 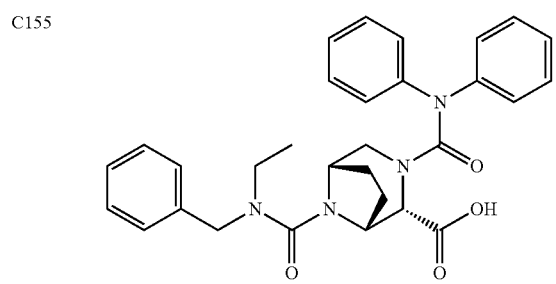 |
| C156 | 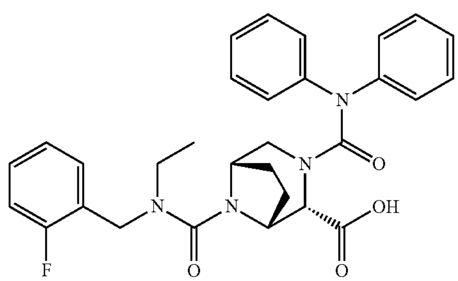 [SMILES: CCN(Cc1ccccc1F)C(=O)N1[C@H]2CC[C@@H]1[C@@H](C(=O)O)N(C(=O)N(c1ccccc1)c1ccccc1)C2] |
| C157 | 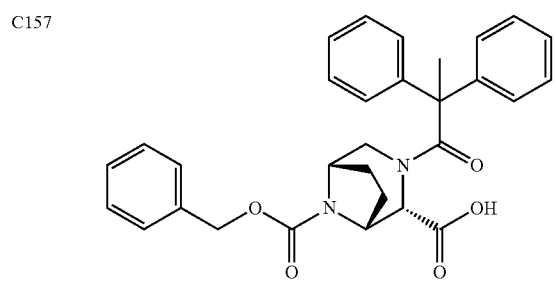 |
-continued
| No. | Structure |
|---|---|
| C158 | 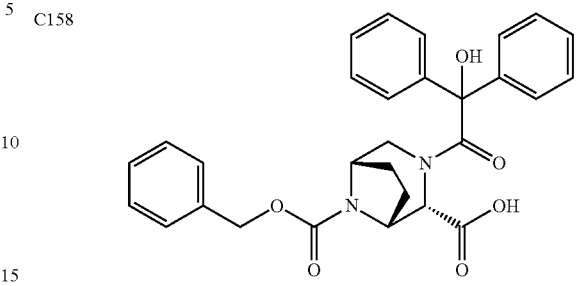 |
| C159 | 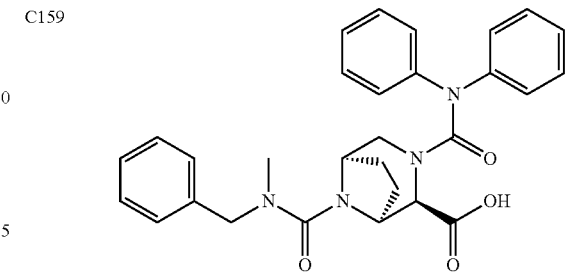 |
| C160 | 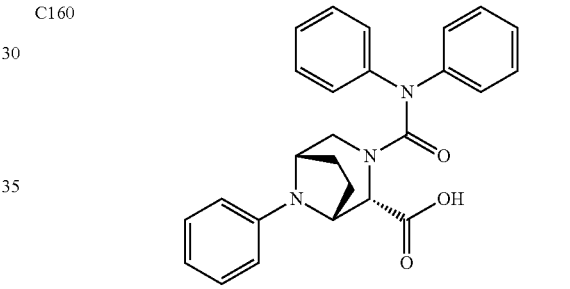 |
| C161 | 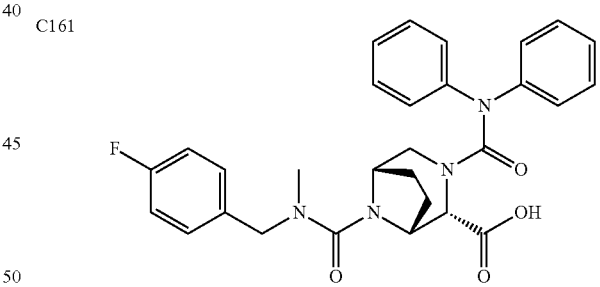 |
| C162 | 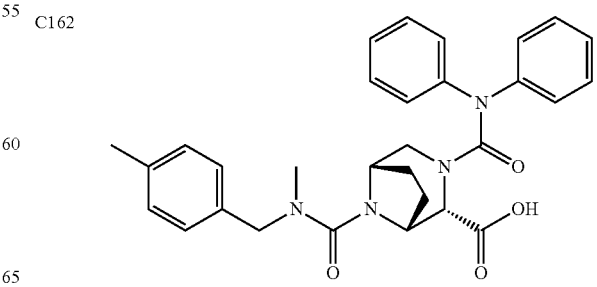 |

| No. | Structure |
|---|---|
| C163 | (2-methylbenzyl-N-methyl urea bridged bicyclic with N,N-diphenyl carbamoyl, carboxylic acid) |
| C164 | (4-ethylbenzyl-N-methyl urea bridged bicyclic with N,N-diphenyl carbamoyl, carboxylic acid) |
| C165 | (4-bromobenzyl-N-methyl urea bridged bicyclic with N,N-diphenyl carbamoyl, carboxylic acid) |
| C166 | (4-methoxybenzyl-N-methyl urea bridged bicyclic with N,N-diphenyl carbamoyl, carboxylic acid) |
| C167 | (4-cyanobenzyl-N-methyl urea bridged bicyclic with N,N-diphenyl carbamoyl, carboxylic acid) |

| No. | Structure |
|---|---|
| C168 | (4-dimethylaminobenzyl-N-methyl urea bridged bicyclic with N,N-diphenyl carbamoyl, carboxylic acid) |
| C169 | (4-trifluoromethylbenzyl-N-methyl urea bridged bicyclic with N,N-diphenyl carbamoyl, carboxylic acid) |
| C170 | (4-vinylbenzyl-N-methyl urea bridged bicyclic with N,N-diphenyl carbamoyl, carboxylic acid) |
| C171 | (4-ethynylbenzyl-N-methyl urea bridged bicyclic with N,N-diphenyl carbamoyl, carboxylic acid) |
| C172 | (2-(4-methylphenyl)pyrrolidine-1-carbonyl bridged bicyclic with N,N-diphenyl carbamoyl, carboxylic acid) |

| No. | Structure |
|---|---|
| C173 | 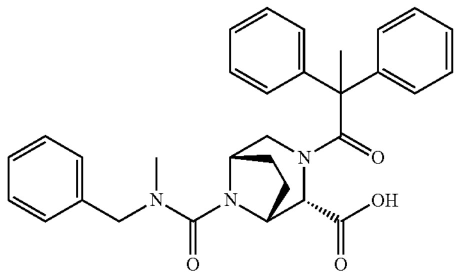 [SMILES: CN(Cc1ccccc1)C(=O)N1[C@H]2CC[C@@H]1[C@@H](C(=O)O)N(C(=O)C(C)(c1ccccc1)c1ccccc1)C2] |
| C174 | 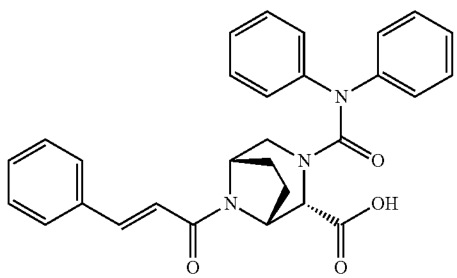 [SMILES: O=C(O)[C@@H]1[C@H]2CC[C@@H](CN1C(=O)N(c1ccccc1)c1ccccc1)N2C(=O)/C=C/c1ccccc1] |
| C177 | 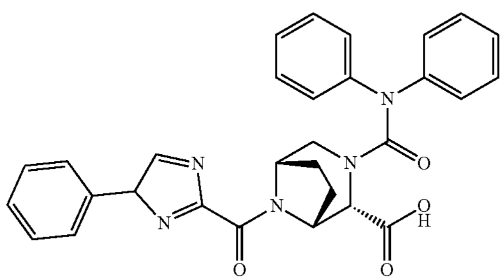 [SMILES: O=C(O)[C@@H]1[C@H]2CC[C@@H](CN1C(=O)N(c1ccccc1)c1ccccc1)N2C(=O)C1=NC(c2ccccc2)C=N1] |
| C178 | 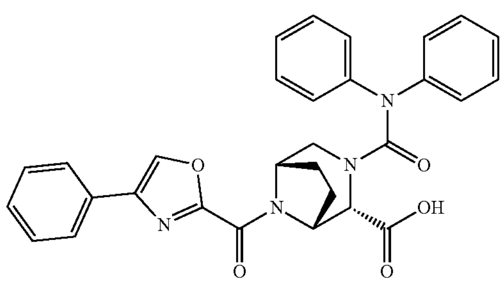 [SMILES: O=C(O)[C@@H]1[C@H]2CC[C@@H](CN1C(=O)N(c1ccccc1)c1ccccc1)N2C(=O)c1nc(-c2ccccc2)co1] |
| C179 | 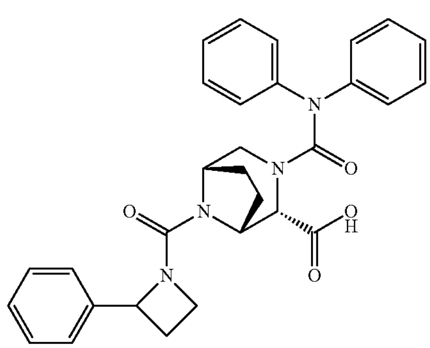 [SMILES: O=C(O)[C@@H]1[C@H]2CC[C@@H](CN1C(=O)N(c1ccccc1)c1ccccc1)N2C(=O)N1CCC1c1ccccc1] |

| No. | Structure |
|---|---|
| C180 | 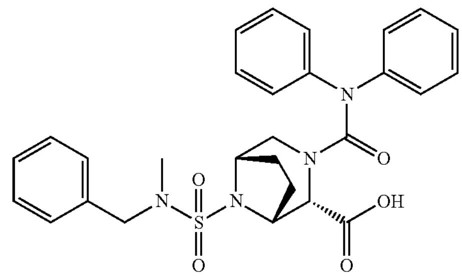 [SMILES: CN(Cc1ccccc1)S(=O)(=O)N1[C@H]2CC[C@@H]1[C@@H](C(=O)O)N(C(=O)N(c1ccccc1)c1ccccc1)C2] |
| C181 | 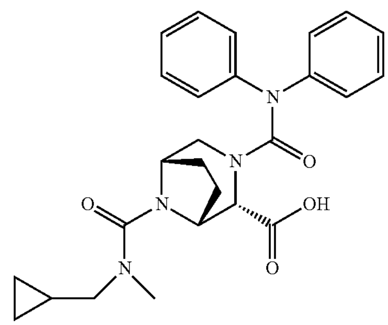 [SMILES: CN(CC1CC1)C(=O)N1[C@H]2CC[C@@H]1[C@@H](C(=O)O)N(C(=O)N(c1ccccc1)c1ccccc1)C2] |
| C182 | 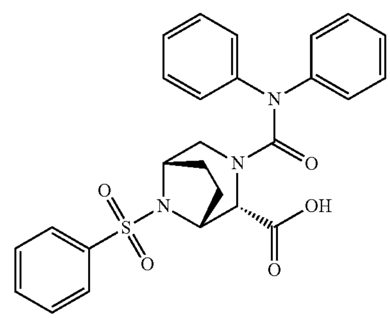 [SMILES: O=C(O)[C@@H]1[C@H]2CC[C@@H](CN1C(=O)N(c1ccccc1)c1ccccc1)N2S(=O)(=O)c1ccccc1] |
| C183 | 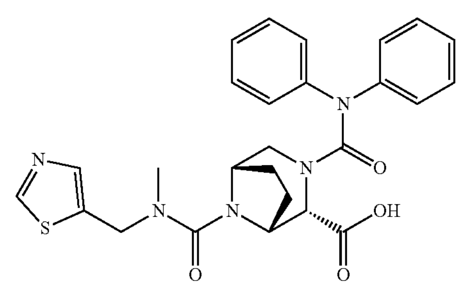 [SMILES: CN(Cc1cncs1)C(=O)N1[C@H]2CC[C@@H]1[C@@H](C(=O)O)N(C(=O)N(c1ccccc1)c1ccccc1)C2] |
| C184 | 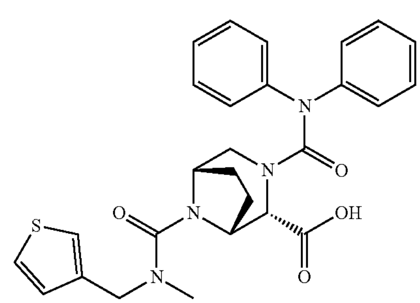 |

| No. | Structure |
|---|---|
| C185 | 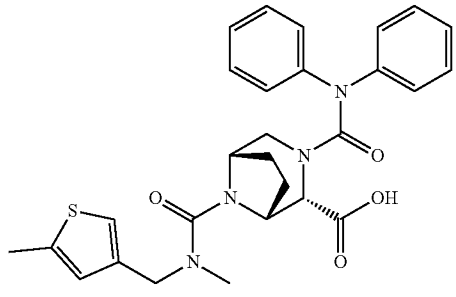 [SMILES: Cc1cc(CN(C)C(=O)N2[C@H]3CC[C@@H]2[C@@H](C(=O)O)N(C(=O)N(c2ccccc2)c2ccccc2)C3)cs1] |
| C186 | 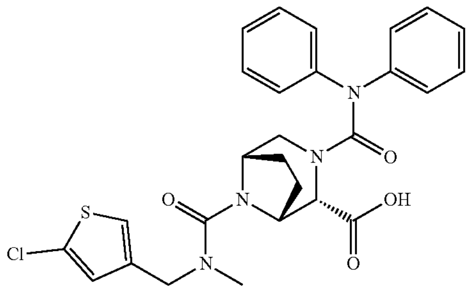 [SMILES: CN(Cc1csc(Cl)c1)C(=O)N1[C@H]2CC[C@@H]1[C@@H](C(=O)O)N(C(=O)N(c1ccccc1)c1ccccc1)C2] |
| C187 | 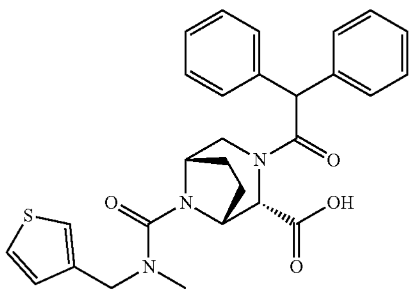 [SMILES: CN(Cc1ccsc1)C(=O)N1[C@H]2CC[C@@H]1[C@@H](C(=O)O)N(C(=O)C(c1ccccc1)c1ccccc1)C2] |
| C188 | 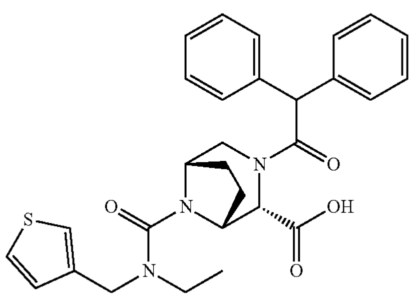 [SMILES: CCN(Cc1ccsc1)C(=O)N1[C@H]2CC[C@@H]1[C@@H](C(=O)O)N(C(=O)C(c1ccccc1)c1ccccc1)C2] |
| C189 | 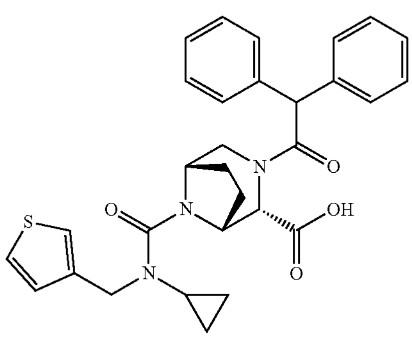 [SMILES: O=C(O)[C@@H]1[C@H]2CC[C@@H](CN1C(=O)C(c1ccccc1)c1ccccc1)N2C(=O)N(Cc1ccsc1)C1CC1] |

| No. | Structure |
|---|---|
| C190 | 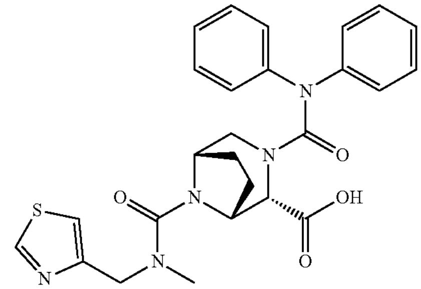 [SMILES: CN(Cc1cscn1)C(=O)N1[C@H]2CC[C@@H]1[C@@H](C(=O)O)N(C(=O)N(c1ccccc1)c1ccccc1)C2] |
| C191 | 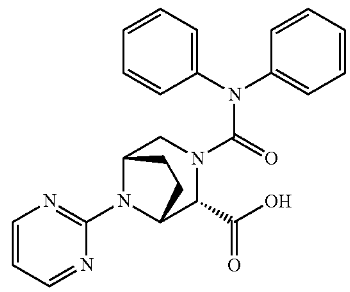 [SMILES: O=C(O)[C@@H]1[C@H]2CC[C@@H](CN1C(=O)N(c1ccccc1)c1ccccc1)N2c1ncccn1] |
| C192 | 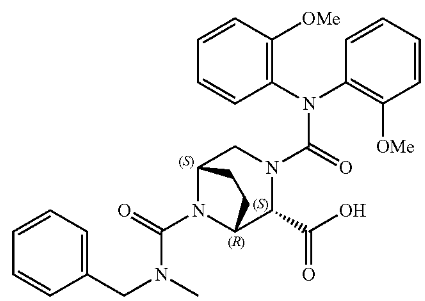 |
| C193 | 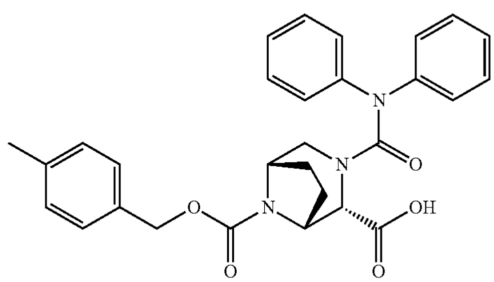 |
| C194 | 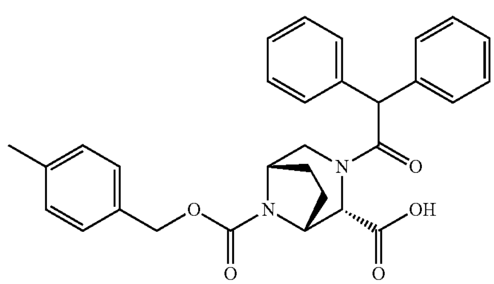 [SMILES: Cc1ccc(COC(=O)N2[C@H]3CC[C@@H]2[C@@H](C(=O)O)N(C(=O)C(c2ccccc2)c2ccccc2)C3)cc1] |

TABLE-continued
| No. | Structure |
|---|---|
| C195 | 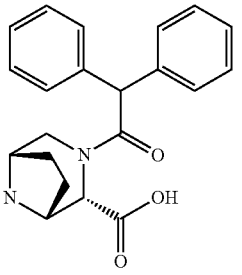 |
| C196 | 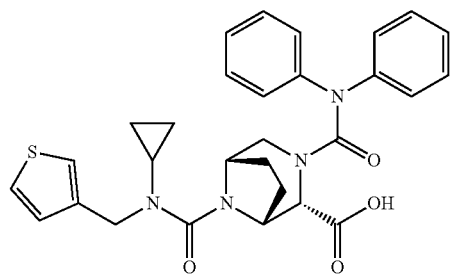 |
| C197 | 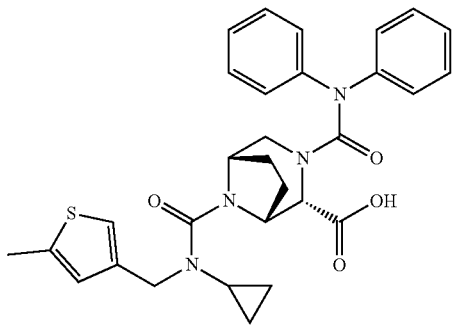 [SMILES: Cc1cc(CN(C(=O)N2[C@H]3CC[C@@H]2[C@@H](C(=O)O)N(C(=O)N(c2ccccc2)c2ccccc2)C3)C2CC2)cs1] |
| C198 | 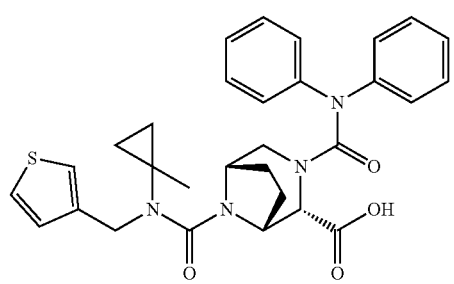 [SMILES: CC1(N(Cc2ccsc2)C(=O)N2[C@H]3CC[C@@H]2[C@@H](C(=O)O)N(C(=O)N(c2ccccc2)c2ccccc2)C3)CC1] |
| C199 | 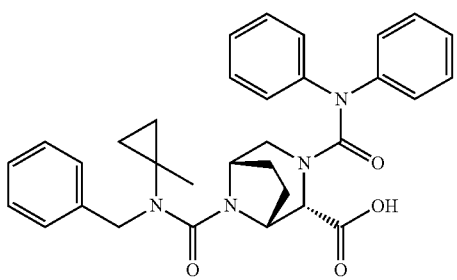 [SMILES: CC1(N(Cc2ccccc2)C(=O)N2[C@H]3CC[C@@H]2[C@@H](C(=O)O)N(C(=O)N(c2ccccc2)c2ccccc2)C3)CC1] |
TABLE-continued
| No. | Structure |
|---|---|
| C200 | 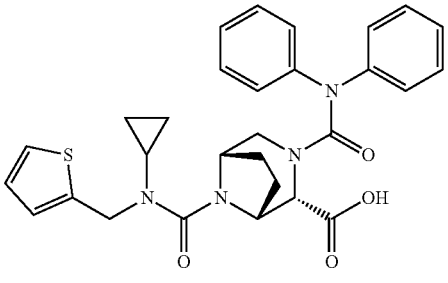 [SMILES: O=C(O)[C@@H]1[C@H]2CC[C@@H](CN1C(=O)N(c1ccccc1)c1ccccc1)N2C(=O)N(Cc1cccs1)C1CC1] |
| C201 | 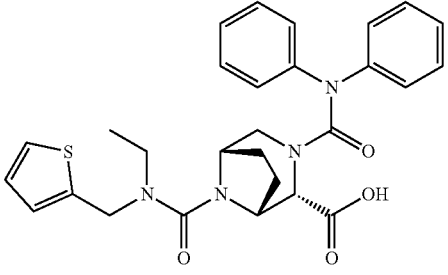 [SMILES: CCN(Cc1cccs1)C(=O)N1[C@H]2CC[C@@H]1[C@@H](C(=O)O)N(C(=O)N(c1ccccc1)c1ccccc1)C2] |
| C202 | 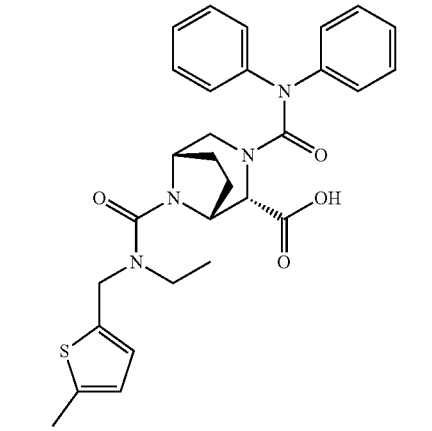 [SMILES: CCN(Cc1ccc(C)s1)C(=O)N1[C@H]2CC[C@@H]1[C@@H](C(=O)O)N(C(=O)N(c1ccccc1)c1ccccc1)C2] |
| C203 | 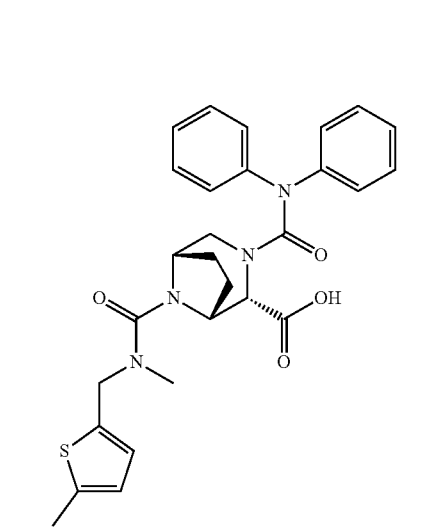 |

-continued

| No. | Structure |
|---|---|
| C204 | 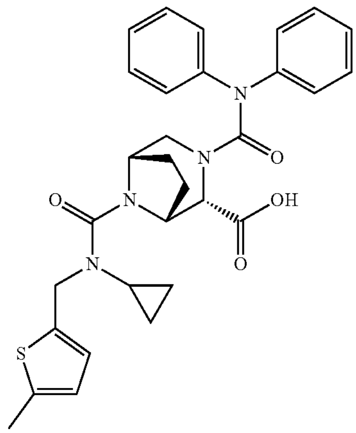 [SMILES: Cc1ccc(CN(C(=O)N2[C@H]3CC[C@@H]2[C@@H](C(=O)O)N(C(=O)N(c2ccccc2)c2ccccc2)C3)C2CC2)s1] |
| C205 | 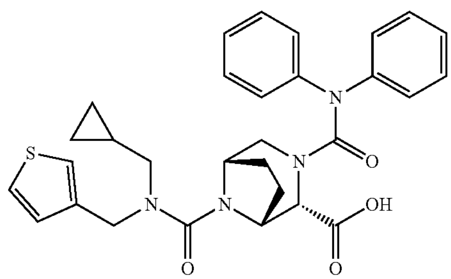 [SMILES: O=C(O)[C@@H]1[C@H]2CC[C@@H](CN1C(=O)N(c1ccccc1)c1ccccc1)N2C(=O)N(Cc1ccsc1)CC1CC1] |
| C206 | 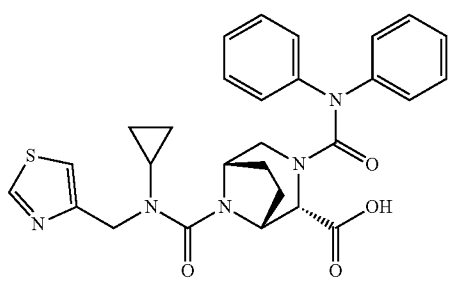 [SMILES: O=C(O)[C@@H]1[C@H]2CC[C@@H](CN1C(=O)N(c1ccccc1)c1ccccc1)N2C(=O)N(Cc1cscn1)C1CC1] |
| C207 | 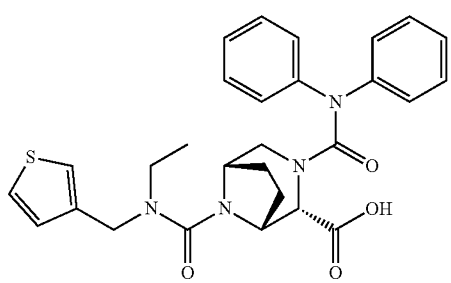 [SMILES: CCN(Cc1ccsc1)C(=O)N1[C@H]2CC[C@@H]1[C@@H](C(=O)O)N(C(=O)N(c1ccccc1)c1ccccc1)C2] |
| C208 | 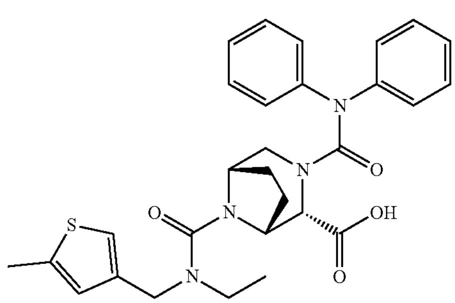 [SMILES: CCN(Cc1csc(C)c1)C(=O)N1[C@H]2CC[C@@H]1[C@@H](C(=O)O)N(C(=O)N(c1ccccc1)c1ccccc1)C2] |

-continued

| No. | Structure |
|---|---|
| C209 | 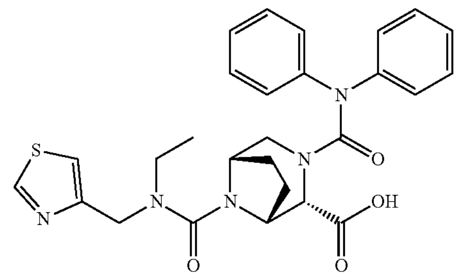 [SMILES: CCN(Cc1cscn1)C(=O)N1[C@H]2CC[C@@H]1[C@@H](C(=O)O)N(C(=O)N(c1ccccc1)c1ccccc1)C2] |
| C210 | 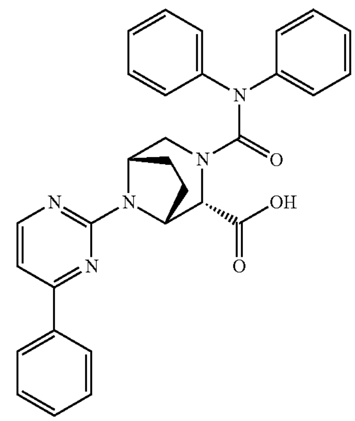 [SMILES: O=C(O)[C@@H]1[C@H]2CC[C@@H](CN1C(=O)N(c1ccccc1)c1ccccc1)N2c1nccc(-c2ccccc2)n1] |
| C211 | 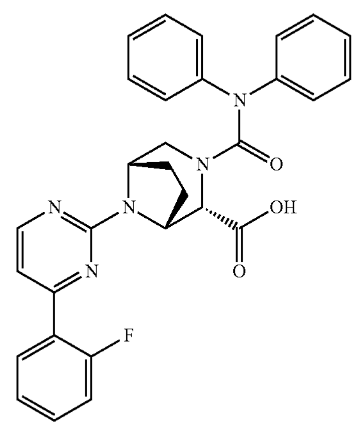 [SMILES: O=C(O)[C@@H]1[C@H]2CC[C@@H](CN1C(=O)N(c1ccccc1)c1ccccc1)N2c1nccc(-c2ccccc2F)n1] |
| C212 | 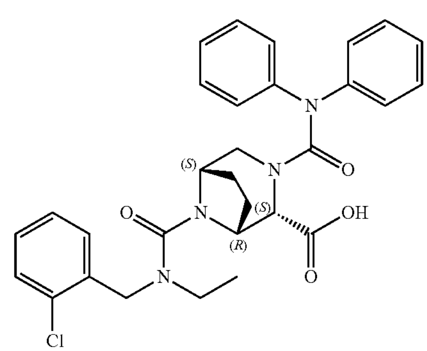 |

| No. | Structure |
|---|---|
| C213 | 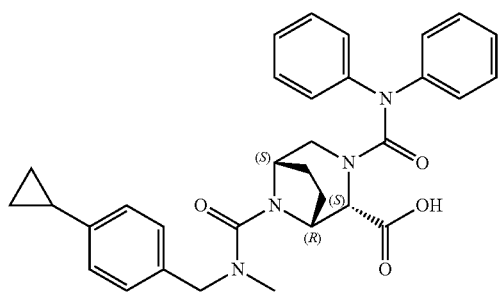 |
| C214 | 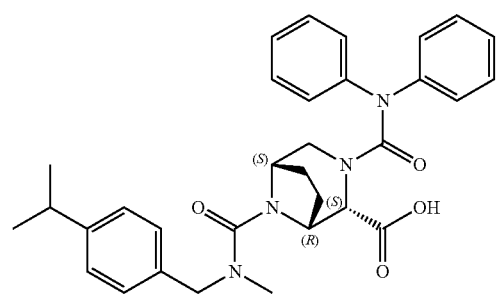 |
| C215 | 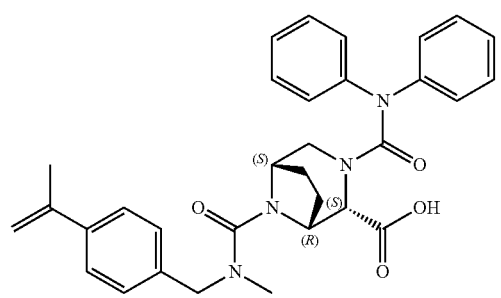 |
| C216 | 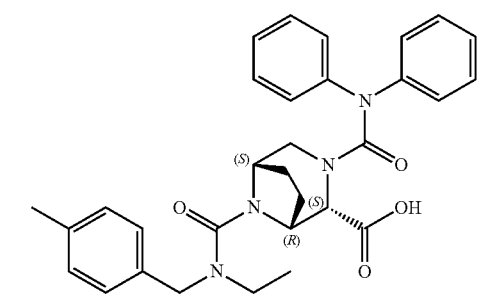 |
| C217 | 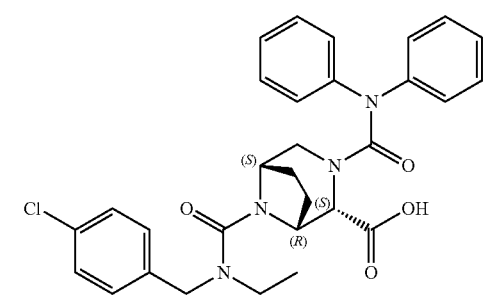 |
| No. | Structure |
|---|---|
| C218 | 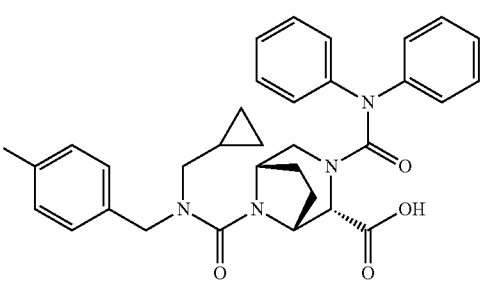 |
| C219 | 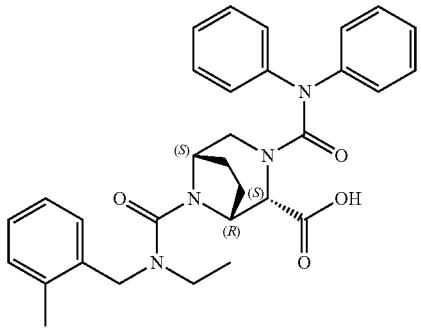 |
| C220 | 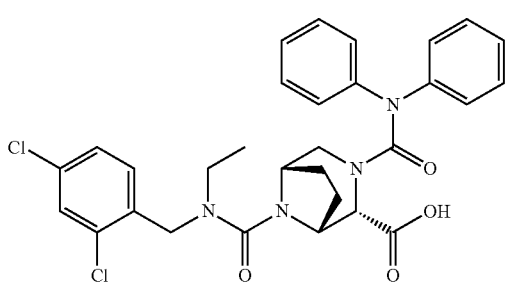 [SMILES: CCN(Cc1ccc(Cl)cc1Cl)C(=O)N1[C@H]2CC[C@@H]1[C@@H](C(=O)O)N(C(=O)N(c1ccccc1)c1ccccc1)C2] |
| C221 | 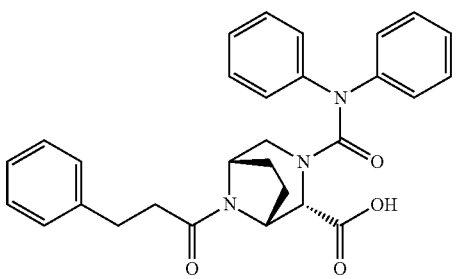 |
| C222 | 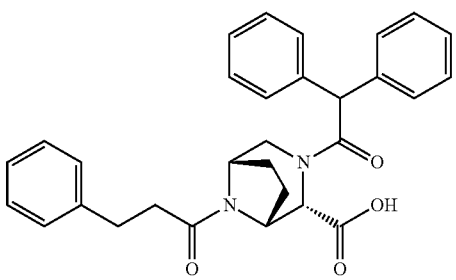 |

| No. | Structure |
|---|---|
| C223 | 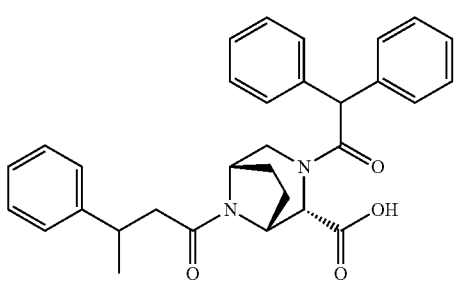 [SMILES: CC(CC(=O)N1[C@H]2CC[C@@H]1[C@@H](C(=O)O)N(C(=O)C(c1ccccc1)c1ccccc1)C2)c1ccccc1] |
| C224 | 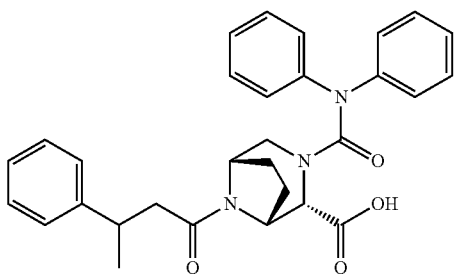 |
| C225 | 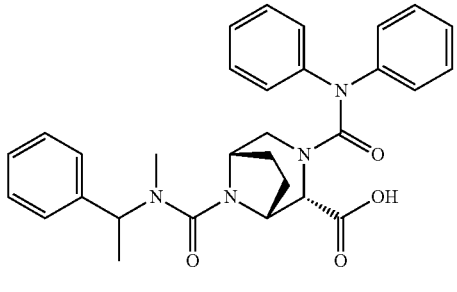 |
| C226 | 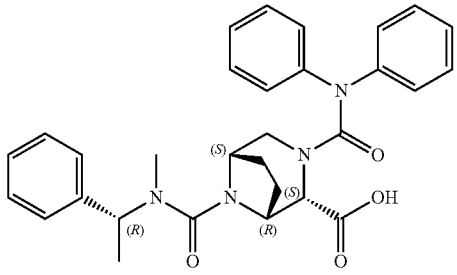 |
| C227 | 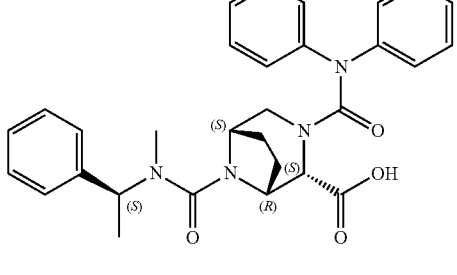 |
| No. | Structure |
|---|---|
| C228 | 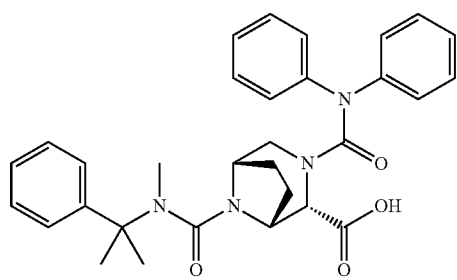 [SMILES: CN(C(=O)N1[C@H]2CC[C@@H]1[C@@H](C(=O)O)N(C(=O)N(c1ccccc1)c1ccccc1)C2)C(C)(C)c1ccccc1] |
| C229 | 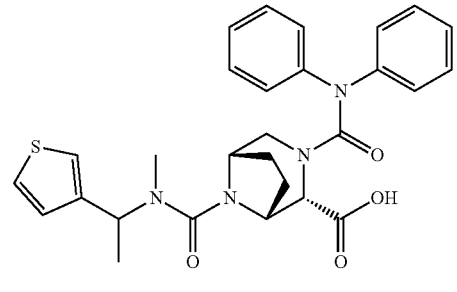 [SMILES: CC(c1ccsc1)N(C)C(=O)N1[C@H]2CC[C@@H]1[C@@H](C(=O)O)N(C(=O)N(c1ccccc1)c1ccccc1)C2] |
| C230 | 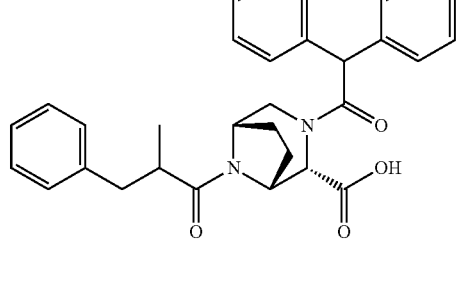 |
| C231 | 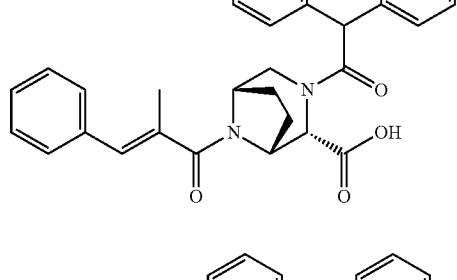 |
| C232 | 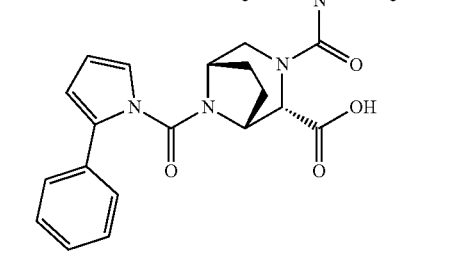 |

| No. | Structure |
|---|---|
| C233 | 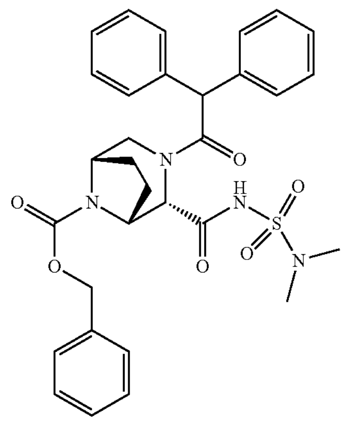 [SMILES: CN(C)S(=O)(=O)NC(=O)[C@@H]1[C@H]2CC[C@@H](CN1C(=O)C(c1ccccc1)c1ccccc1)N2C(=O)OCc1ccccc1] |
| C234 | 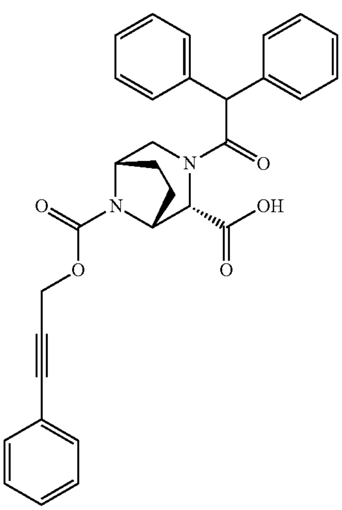 [SMILES: O=C(O)[C@@H]1[C@H]2CC[C@@H](CN1C(=O)C(c1ccccc1)c1ccccc1)N2C(=O)OCC#Cc1ccccc1] |
| C235 | 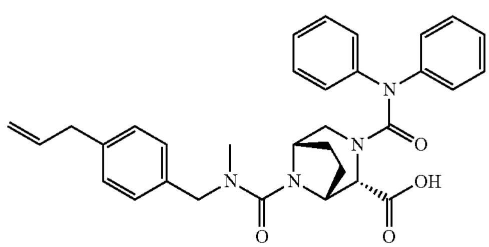 [SMILES: C=CCc1ccc(CN(C)C(=O)N2[C@H]3CC[C@@H]2[C@@H](C(=O)O)N(C(=O)N(c2ccccc2)c2ccccc2)C3)cc1] |
| C236 | 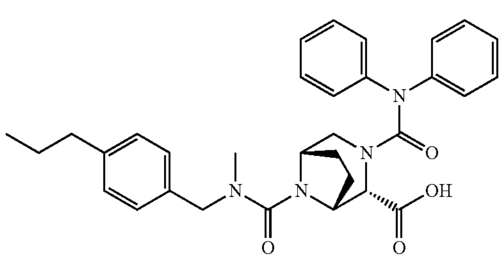 [SMILES: CCCc1ccc(CN(C)C(=O)N2[C@H]3CC[C@@H]2[C@@H](C(=O)O)N(C(=O)N(c2ccccc2)c2ccccc2)C3)cc1] |

| No. | Structure |
|---|---|
| C237 | 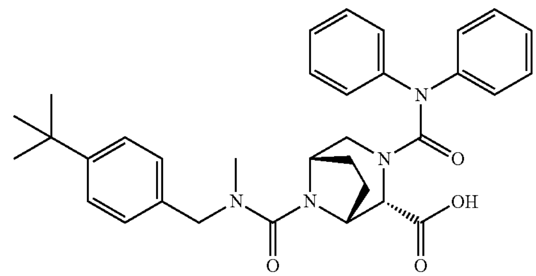 [SMILES: CN(Cc1ccc(C(C)(C)C)cc1)C(=O)N1[C@H]2CC[C@@H]1[C@@H](C(=O)O)N(C(=O)N(c1ccccc1)c1ccccc1)C2] |
| C238 | 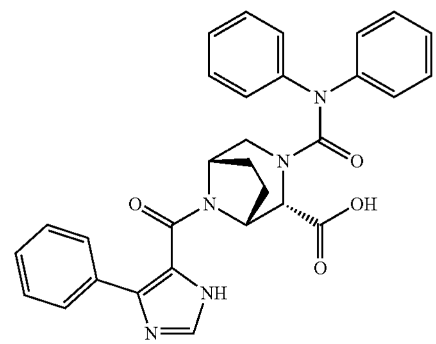 [SMILES: O=C(O)[C@@H]1[C@H]2CC[C@@H](CN1C(=O)N(c1ccccc1)c1ccccc1)N2C(=O)c1[nH]cnc1-c1ccccc1] |
| C239 | 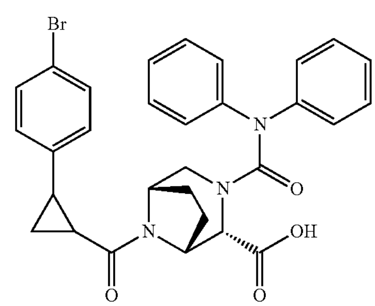 [SMILES: O=C(O)[C@@H]1[C@H]2CC[C@@H](CN1C(=O)N(c1ccccc1)c1ccccc1)N2C(=O)C1CC1c1ccc(Br)cc1] |
| C240 | 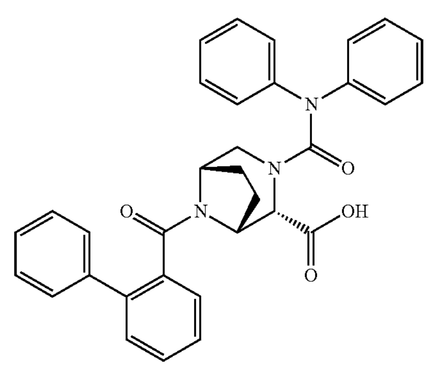 [SMILES: O=C(O)[C@@H]1[C@H]2CC[C@@H](CN1C(=O)N(c1ccccc1)c1ccccc1)N2C(=O)c1ccccc1-c1ccccc1] |

| No. | Structure |
|-----|-----------|
| C241 | 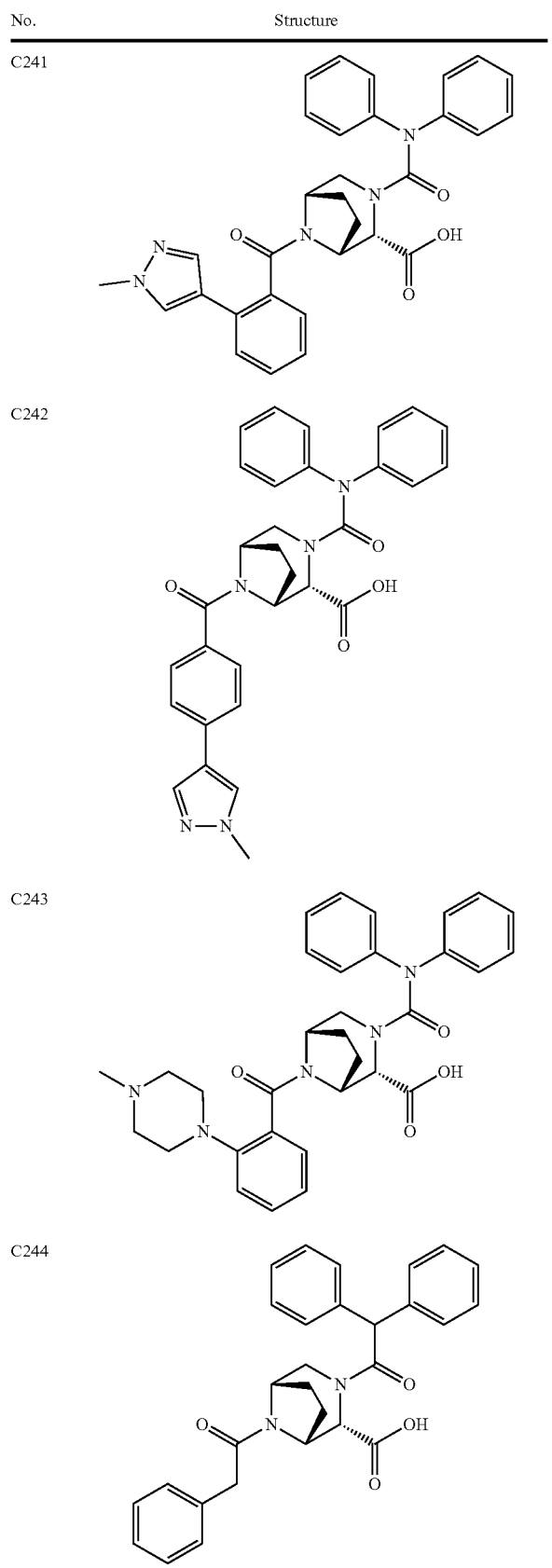 |
| C242 | |
| C243 | |
| C244 | |
| No. | Structure |
|-----|-----------|
| C245 | 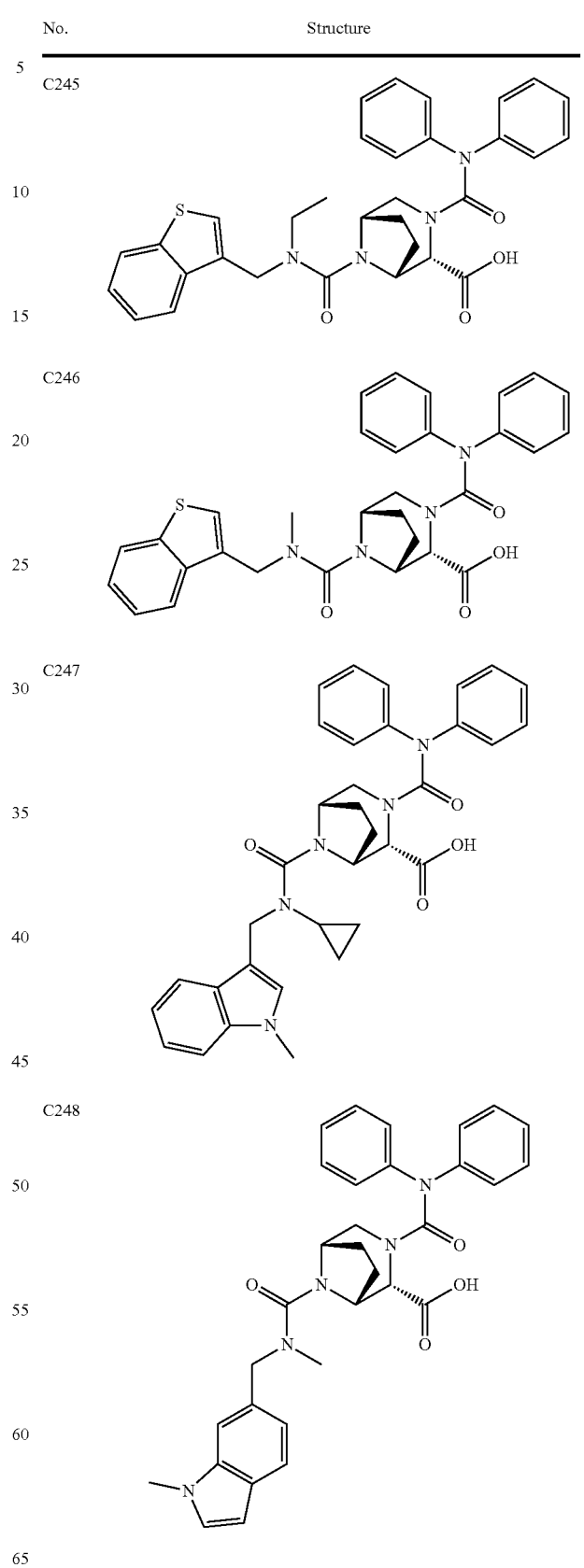 |
| C246 | |
| C247 | |
| C248 | |

US 11,453,690 B2
137
-continued
| No. | Structure |
|---|---|
| C249 | 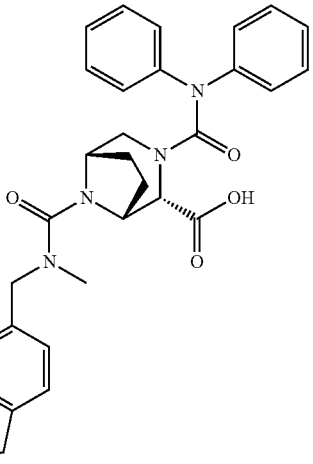 |
| C250 | 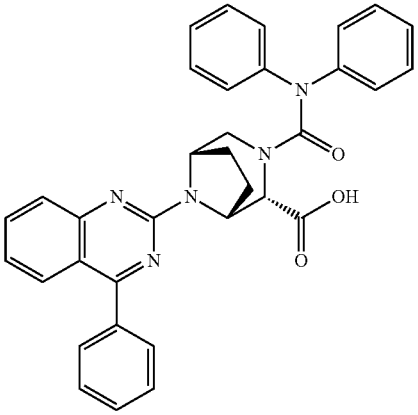 [SMILES: O=C(O)[C@@H]1[C@H]2CC[C@@H](CN1C(=O)N(c1ccccc1)c1ccccc1)N2c1nc(-c2ccccc2)c2ccccc2n1] |
| C251 | 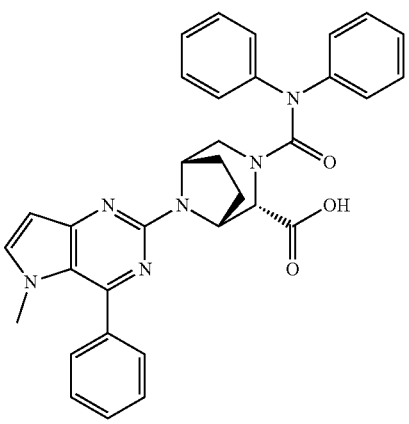 [SMILES: Cn1ccc2nc(N3[C@H]4CC[C@@H]3[C@@H](C(=O)O)N(C(=O)N(c3ccccc3)c3ccccc3)C4)nc(-c3ccccc3)c21] |
| C252 | 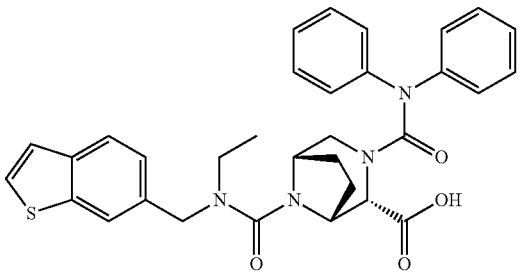 |
138
-continued
| No. | Structure |
|---|---|
| C253 | 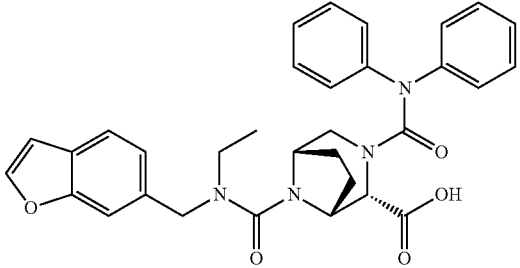 |
| C254 | 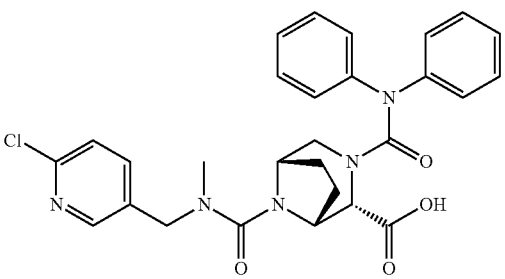 [SMILES: CN(Cc1ccc(Cl)nc1)C(=O)N1[C@H]2CC[C@@H]1[C@@H](C(=O)O)N(C(=O)N(c1ccccc1)c1ccccc1)C2] |
| C255 | 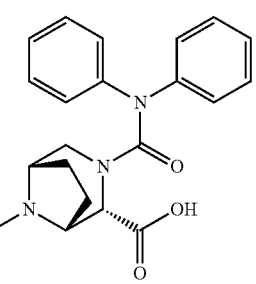 |
| C256 | 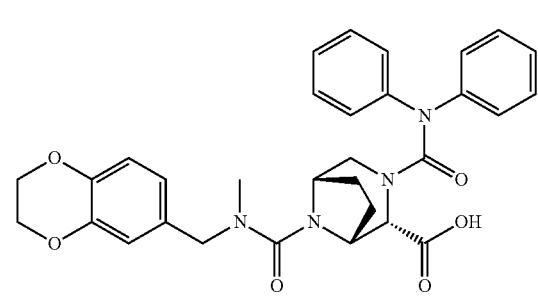 |

| No. | Structure |
|---|---|
| C257 | 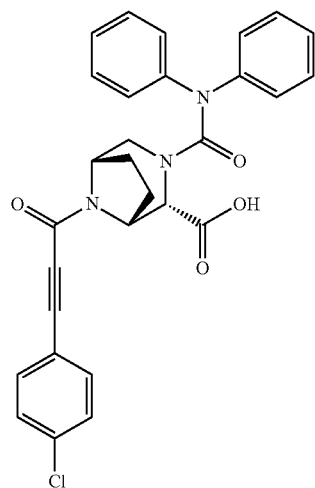 |
| C258 | 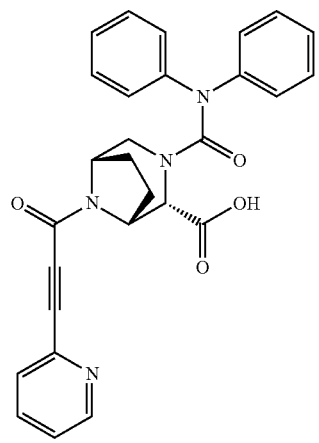 [SMILES: O=C(O)[C@@H]1[C@H]2CC[C@@H](CN1C(=O)N(c1ccccc1)c1ccccc1)N2C(=O)C#Cc1ccccc1] |
| C259 | 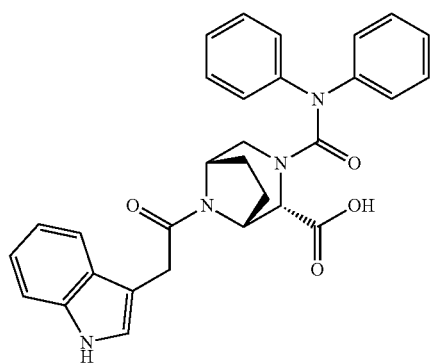 [SMILES: O=C(O)[C@@H]1[C@H]2CC[C@@H](CN1C(=O)N(c1ccccc1)c1ccccc1)N2C(=O)Cc1c[nH]c2ccccc12] |
| No. | Structure |
|---|---|
| C260 | 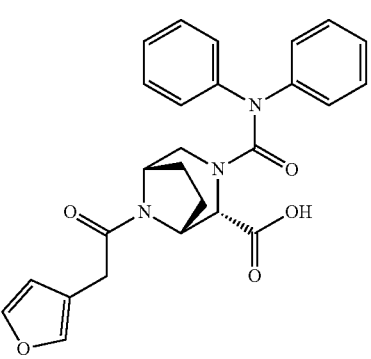 [SMILES: O=C(O)[C@@H]1[C@H]2CC[C@@H](CN1C(=O)N(c1ccccc1)c1ccccc1)N2C(=O)Cc1ccoc1] |
| C261 | 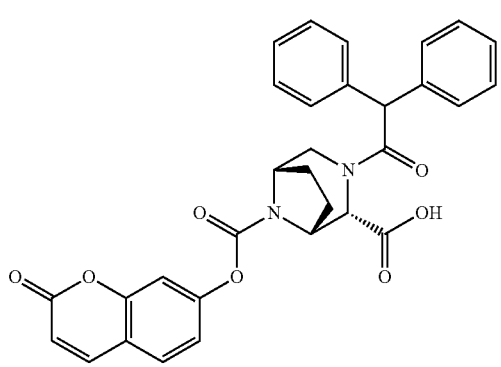 [SMILES: O=C(O)[C@@H]1[C@H]2CC[C@@H](CN1C(=O)C(c1ccccc1)c1ccccc1)N2C(=O)Oc1ccc2ccc(=O)oc2c1] |
| C262 | |

| No. | Structure |
|---|---|
| C263 | 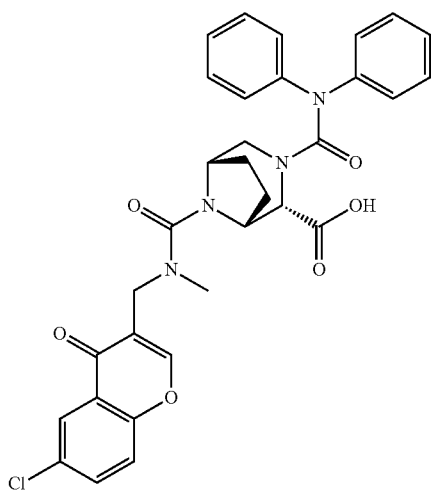 [SMILES: CN(Cc1coc2ccc(Cl)cc2c1=O)C(=O)N1[C@H]2CC[C@@H]1[C@@H](C(=O)O)N(C(=O)N(c1ccccc1)c1ccccc1)C2] |
| C264 | 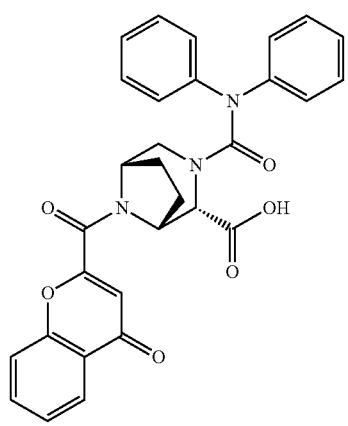 [SMILES: O=C(O)[C@@H]1[C@H]2CC[C@@H](CN1C(=O)N(c1ccccc1)c1ccccc1)N2C(=O)c1cc(=O)c2ccccc2o1] |
| C265 | 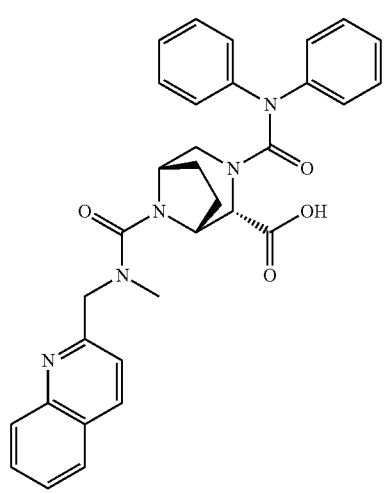 [SMILES: CN(Cc1ccc2ccccc2n1)C(=O)N1[C@H]2CC[C@@H]1[C@@H](C(=O)O)N(C(=O)N(c1ccccc1)c1ccccc1)C2] |
| No. | Structure |
|---|---|
| C266 | 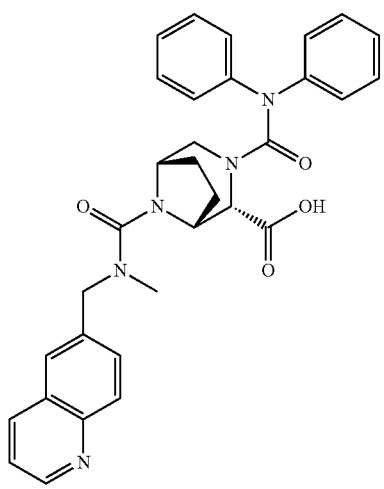 [SMILES: CN(Cc1ccc2ncccc2c1)C(=O)N1[C@H]2CC[C@@H]1[C@@H](C(=O)O)N(C(=O)N(c1ccccc1)c1ccccc1)C2] |
| C267 | 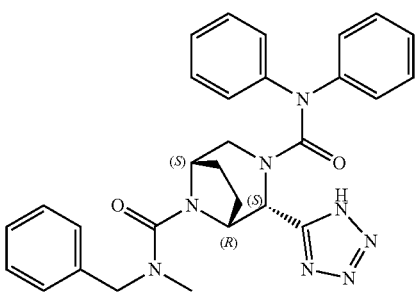 |
| C268 | 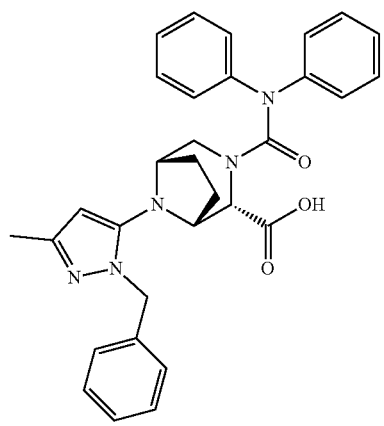 [SMILES: Cc1cc(N2[C@H]3CC[C@@H]2[C@@H](C(=O)O)N(C(=O)N(c2ccccc2)c2ccccc2)C3)n(Cc2ccccc2)n1] |
| C269 | 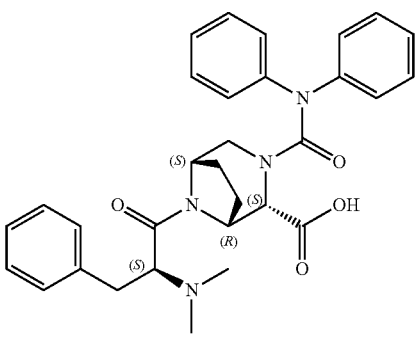 |

| No. | Structure |
|---|---|
| C270 | 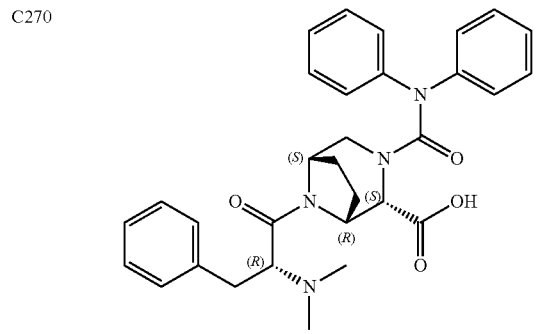 |
| C271 | 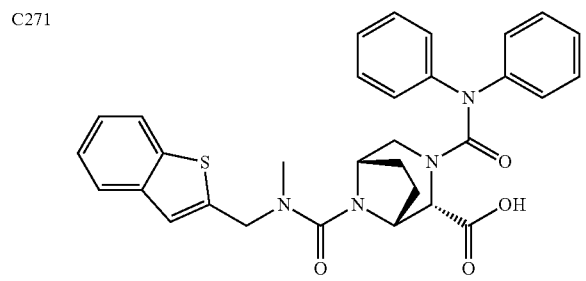 |
| C272 | 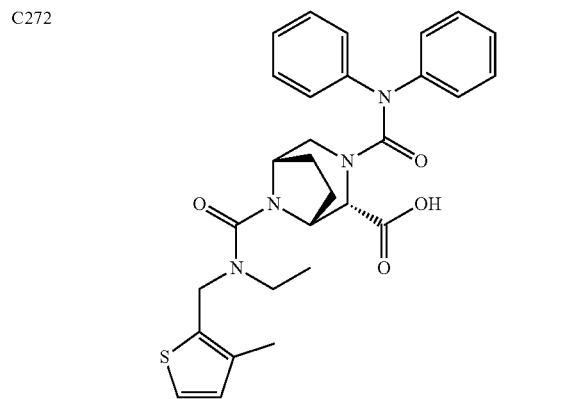 |
| C273 | 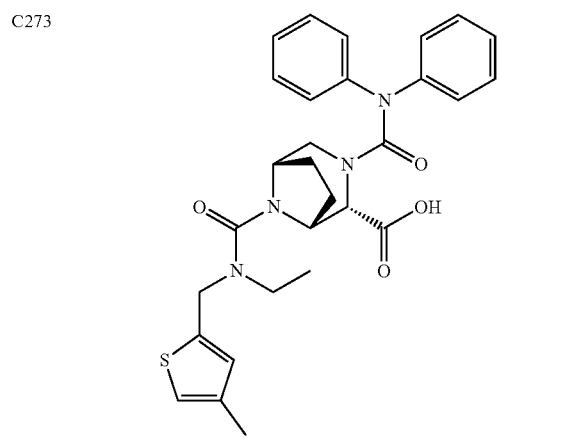 |
| C274 | 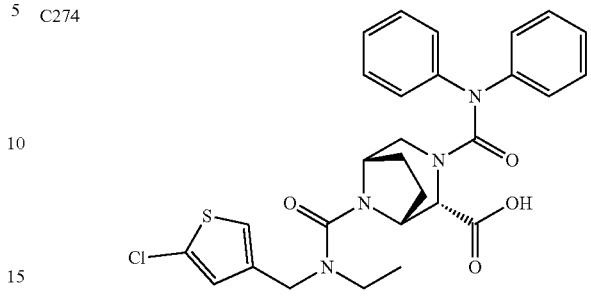 |
| C275 | 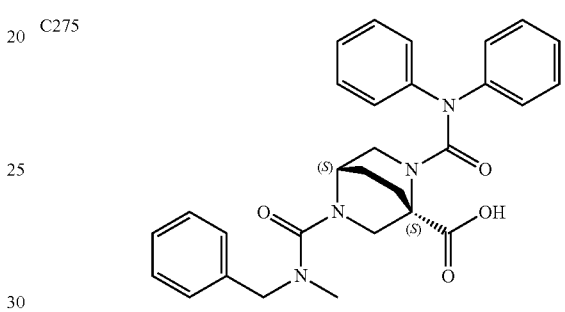 |
| C276 | 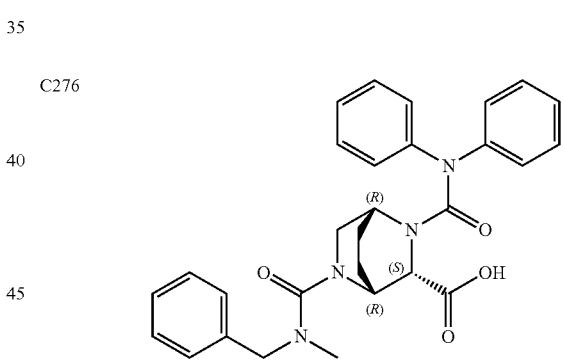 |
| C277 | 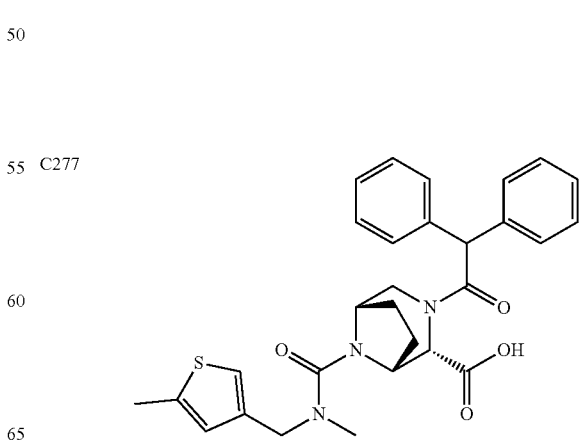 |

| No. | Structure |
|---|---|
| C278 | 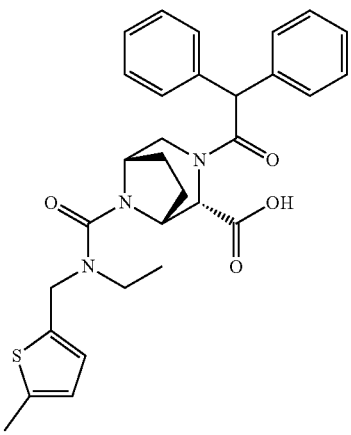 [SMILES: CCN(Cc1ccc(C)s1)C(=O)N1[C@H]2CC[C@@H]1[C@@H](C(=O)O)N(C(=O)C(c1ccccc1)c1ccccc1)C2] |
| C279 | 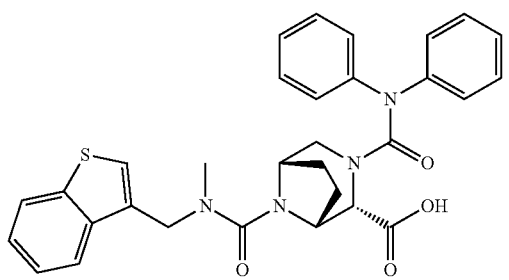 |
| C280 | 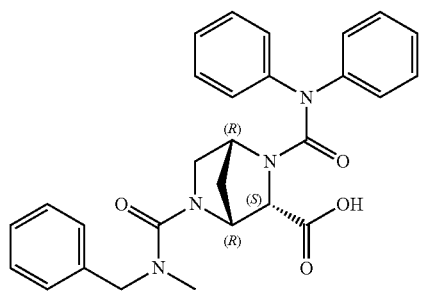 |
| C281 | 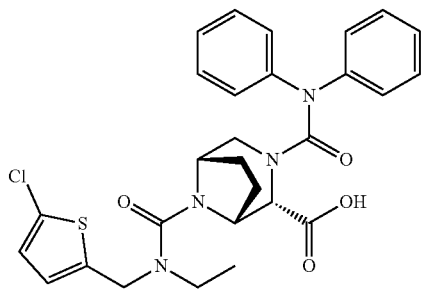 |
| No. | Structure |
|---|---|
| C282 | 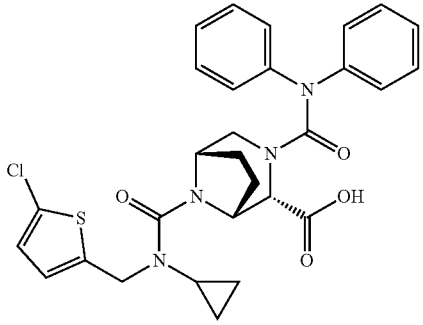 |
| C283 | 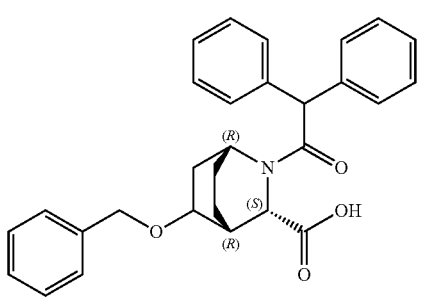 |
| C284 | 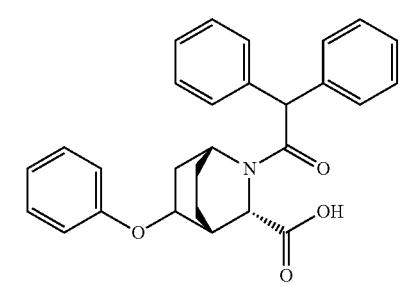 [SMILES: O=C(O)[C@@H]1[C@H]2CC[C@H](CC2Oc2ccccc2)N1C(=O)C(c1ccccc1)c1ccccc1] |
| C285 | 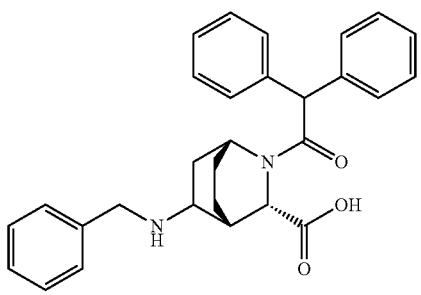 [SMILES: O=C(O)[C@@H]1[C@H]2CC[C@H](CC2NCc2ccccc2)N1C(=O)C(c1ccccc1)c1ccccc1] |
| C286 | 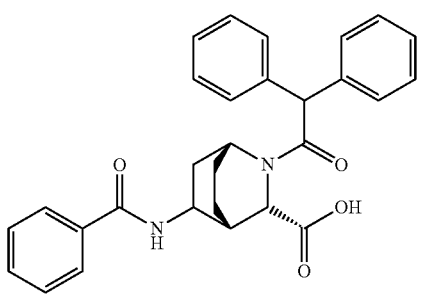 |

| No. | Structure |
|---|---|
| C287 | 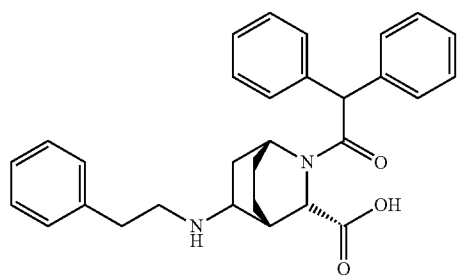 |
| C288 | 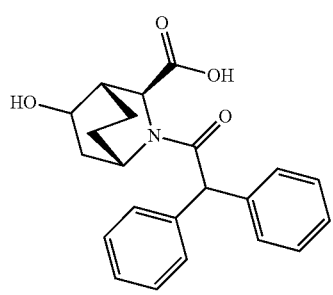 [SMILES: O=C(O)[C@@H]1[C@@H]2CC[C@@H](CC2O)N1C(=O)C(c1ccccc1)c1ccccc1] |
| C289 | 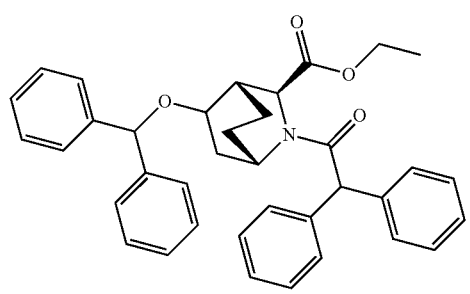 [SMILES: CCOC(=O)[C@@H]1[C@@H]2CC[C@@H](CC2OC(c2ccccc2)c2ccccc2)N1C(=O)C(c1ccccc1)c1ccccc1] |
| C290 | 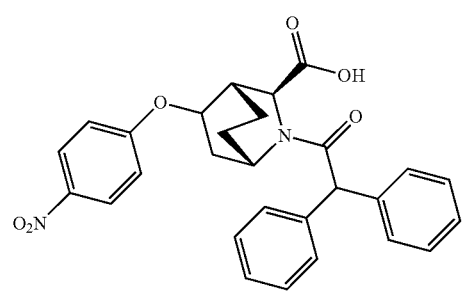 [SMILES: O=C(O)[C@@H]1[C@@H]2CC[C@@H](CC2Oc2ccc([N+](=O)[O-])cc2)N1C(=O)C(c1ccccc1)c1ccccc1] |
| C291 | 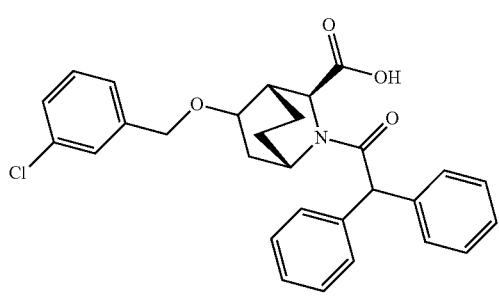 [SMILES: O=C(O)[C@@H]1[C@@H]2CC[C@@H](CC2OCc2cccc(Cl)c2)N1C(=O)C(c1ccccc1)c1ccccc1] |
| No. | Structure |
|---|---|
| C292 | 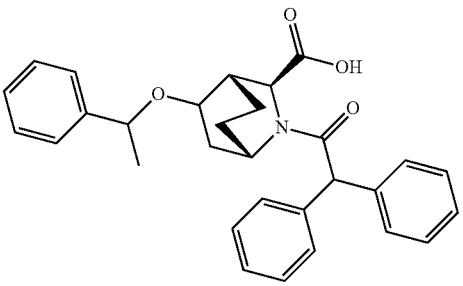 [SMILES: CC(OC1C[C@@H]2CC[C@H]1[C@@H](C(=O)O)N2C(=O)C(c1ccccc1)c1ccccc1)c1ccccc1] |
| C293 | 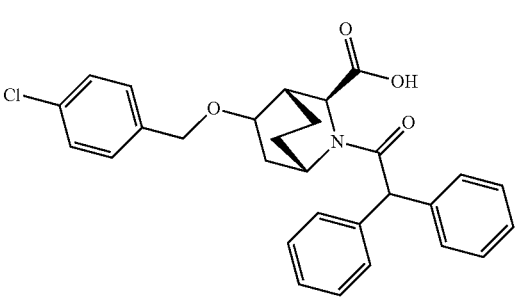 [SMILES: O=C(O)[C@@H]1[C@@H]2CC[C@@H](CC2OCc2ccc(Cl)cc2)N1C(=O)C(c1ccccc1)c1ccccc1] |
| C294 | 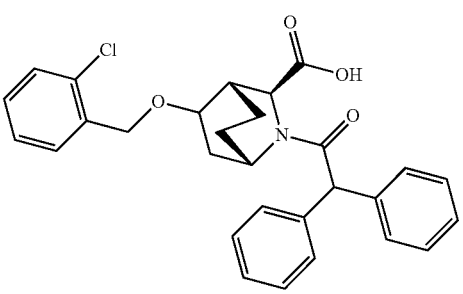 [SMILES: O=C(O)[C@@H]1[C@@H]2CC[C@@H](CC2OCc2ccccc2Cl)N1C(=O)C(c1ccccc1)c1ccccc1] |
| C295 | 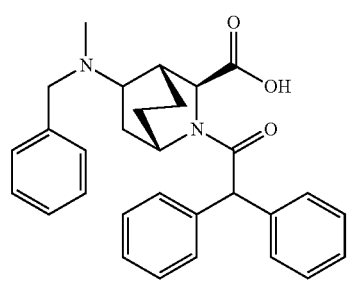 [SMILES: CN(Cc1ccccc1)C1C[C@@H]2CC[C@H]1[C@@H](C(=O)O)N2C(=O)C(c1ccccc1)c1ccccc1] |
| C296 | 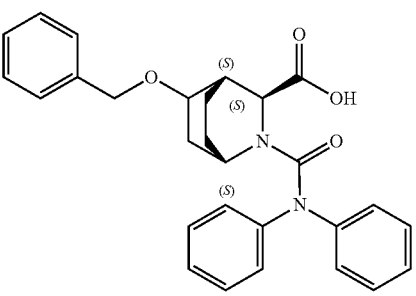 |

| No. | Structure |
|---|---|
| C297 | 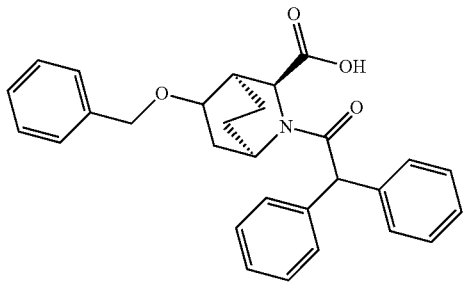 [SMILES: O=C(O)[C@@H]1[C@H]2CC[C@H](CC2OCc2ccccc2)N1C(=O)C(c1ccccc1)c1ccccc1] |
| C298 | 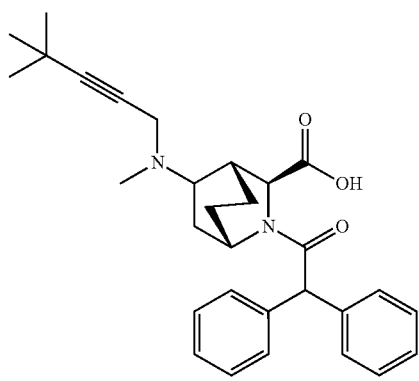 [SMILES: CN(CC#CC(C)(C)C)C1C[C@@H]2CC[C@H]1[C@@H](C(=O)O)N2C(=O)C(c1ccccc1)c1ccccc1] |
| C299 | 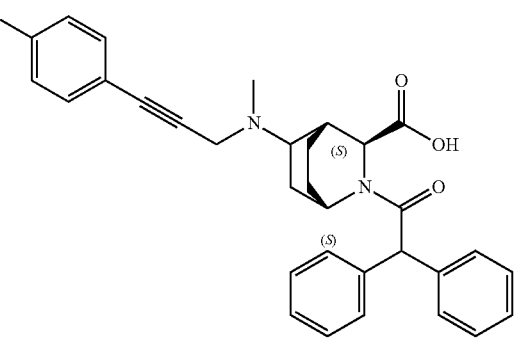 |
| C300 | 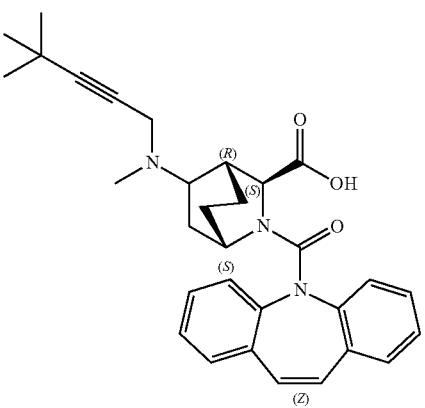 |
| C301 | 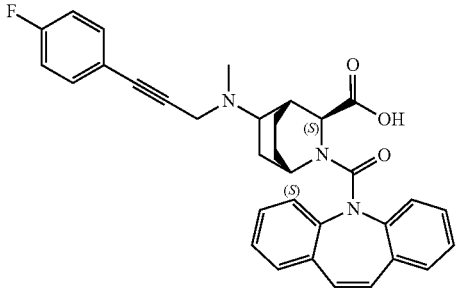 |
| C302 | 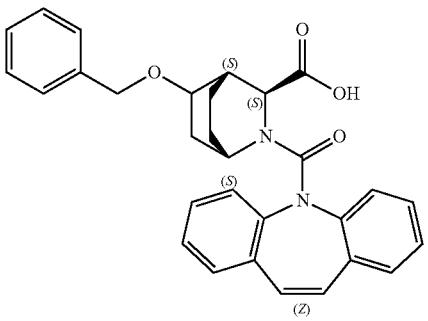 |
| C303 | 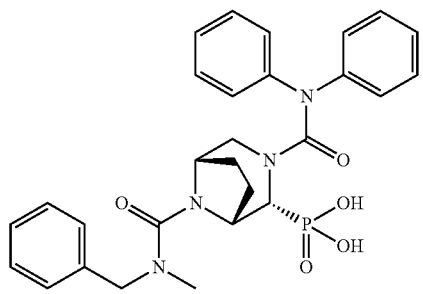 [SMILES: CN(Cc1ccccc1)C(=O)N1[C@H]2CC[C@@H]1[C@@H](P(=O)(O)O)N(C(=O)N(c1ccccc1)c1ccccc1)C2] |
| C304 | 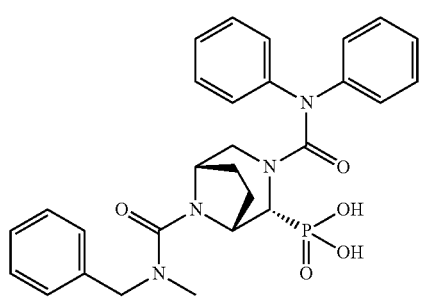 [SMILES: CN(Cc1ccccc1)C(=O)N1[C@H]2CC[C@@H]1[C@@H](P(=O)(O)O)N(C(=O)N(c1ccccc1)c1ccccc1)C2] |
| C305 | 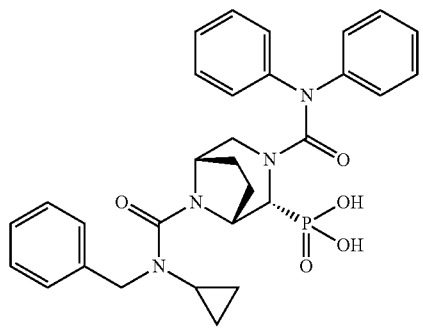 [SMILES: O=C(N(c1ccccc1)c1ccccc1)N1C[C@@H]2CC[C@H]([C@H]1P(=O)(O)O)N2C(=O)N(Cc1ccccc1)C1CC1] |

| No. | Structure |
|-----|-----------|
| C306 | 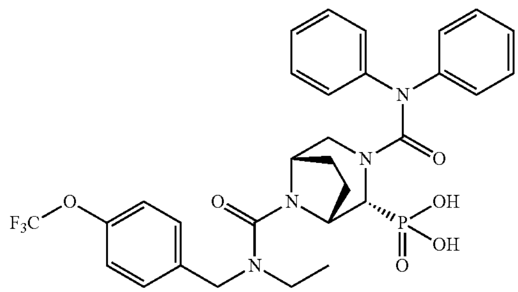 [SMILES: CCN(Cc1ccc(OC(F)(F)F)cc1)C(=O)N1[C@H]2CC[C@@H]1[C@@H](P(=O)(O)O)N(C(=O)N(c1ccccc1)c1ccccc1)C2] |
| C307 | 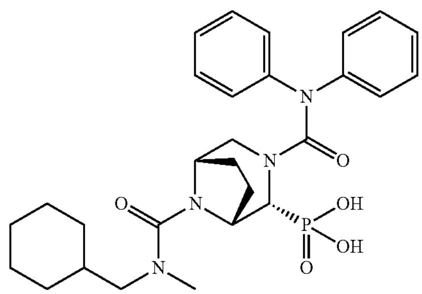 [SMILES: CN(CC1CCCCC1)C(=O)N1[C@H]2CC[C@@H]1[C@@H](P(=O)(O)O)N(C(=O)N(c1ccccc1)c1ccccc1)C2] |
| C308 | 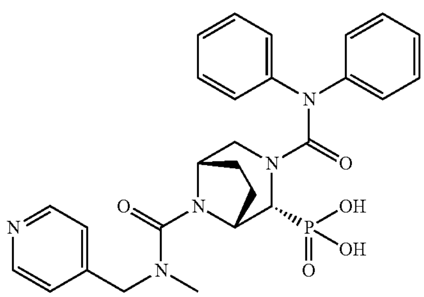 [SMILES: CN(Cc1ccncc1)C(=O)N1[C@H]2CC[C@@H]1[C@@H](P(=O)(O)O)N(C(=O)N(c1ccccc1)c1ccccc1)C2] |
| C309 | 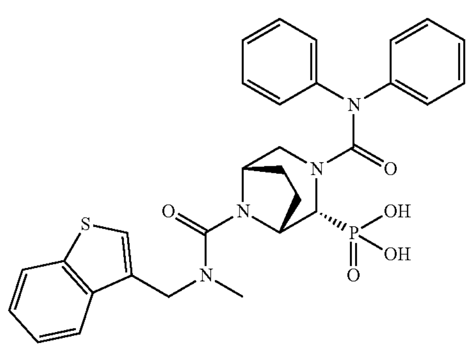 [SMILES: CN(Cc1csc2ccccc12)C(=O)N1[C@H]2CC[C@@H]1[C@@H](P(=O)(O)O)N(C(=O)N(c1ccccc1)c1ccccc1)C2] |
| C310 | 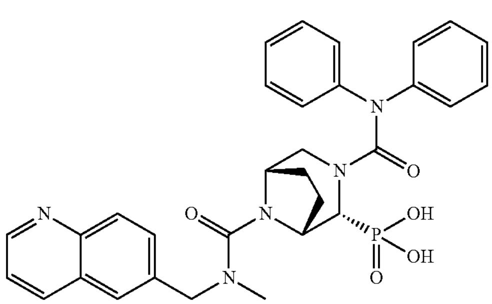 [SMILES: CN(Cc1ccc2ncccc2c1)C(=O)N1[C@H]2CC[C@@H]1[C@@H](P(=O)(O)O)N(C(=O)N(c1ccccc1)c1ccccc1)C2] |

| No. | Structure |
|-----|-----------|
| C311 | 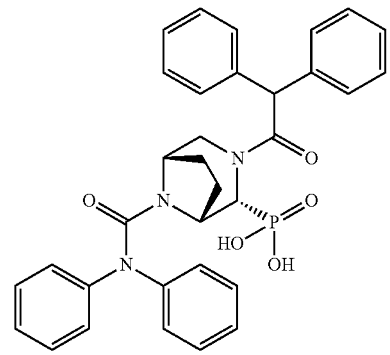 [SMILES: O=C(C(c1ccccc1)c1ccccc1)N1C[C@@H]2CC[C@H]([C@H]1P(=O)(O)O)N2C(=O)N(c1ccccc1)c1ccccc1] |
| C312 | 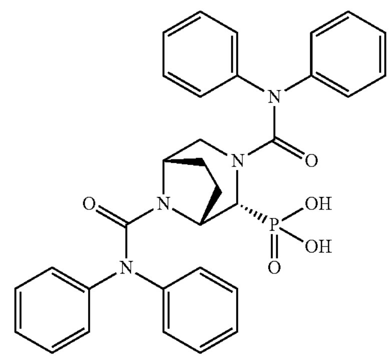 [SMILES: O=C(N(c1ccccc1)c1ccccc1)N1C[C@@H]2CC[C@H]([C@H]1P(=O)(O)O)N2C(=O)N(c1ccccc1)c1ccccc1] |
| C313 | 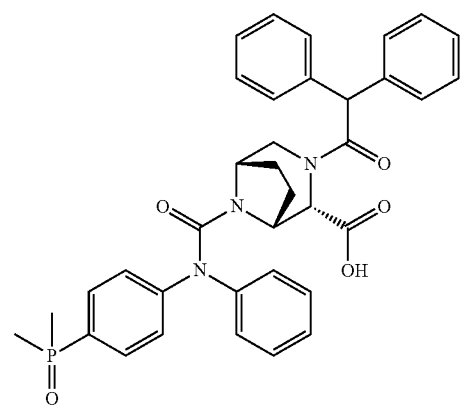 |
| C314 | 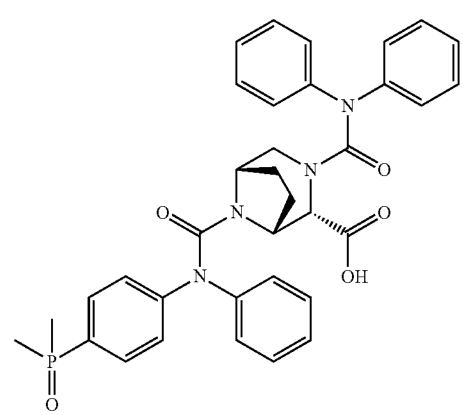 [SMILES: CP(C)(=O)c1ccc(N(C(=O)N2[C@H]3CC[C@@H]2[C@@H](C(=O)O)N(C(=O)N(c2ccccc2)c2ccccc2)C3)c2ccccc2)cc1] |

| No. | Structure |
|---|---|
| C315 | 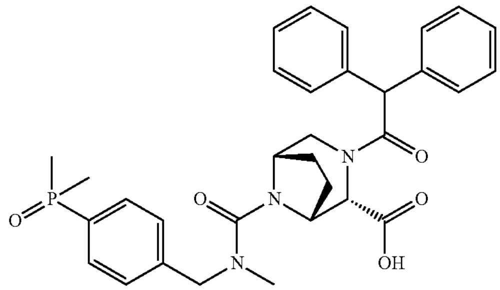 [SMILES: CN(Cc1ccc(P(C)(C)=O)cc1)C(=O)N1[C@H]2CC[C@@H]1[C@@H](C(=O)O)N(C(=O)C(c1ccccc1)c1ccccc1)C2] |
| C316 | 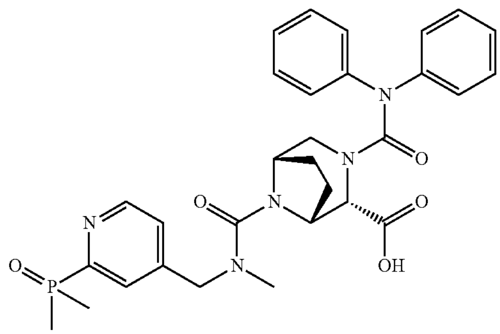 [SMILES: CN(Cc1ccnc(P(C)(C)=O)c1)C(=O)N1[C@H]2CC[C@@H]1[C@@H](C(=O)O)N(C(=O)N(c1ccccc1)c1ccccc1)C2] |
| C317 | 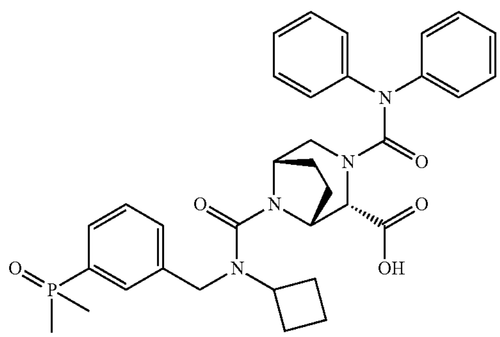 [SMILES: CP(C)(=O)c1cccc(CN(C(=O)N2[C@H]3CC[C@@H]2[C@@H](C(=O)O)N(C(=O)N(c2ccccc2)c2ccccc2)C3)C2CCC2)c1] |
| C318 | 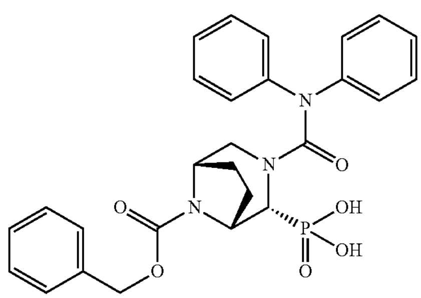 [SMILES: O=C(N(c1ccccc1)c1ccccc1)N1C[C@@H]2CC[C@H]([C@H]1P(=O)(O)O)N2C(=O)OCc1ccccc1] |
| C319 | 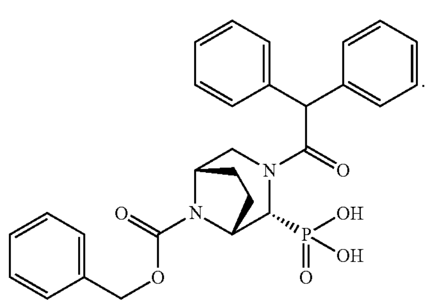 [SMILES: O=C(C(c1ccccc1)c1ccccc1)N1C[C@@H]2CC[C@H]([C@H]1P(=O)(O)O)N2C(=O)OCc1ccccc1] |

In some embodiments, the compound of the present invention has selective inhibitory activity on $AT_2$ receptors, compared to $AT_1$ receptors.

Pharmaceutical Composition and Therapeutic Method

In some embodiments, the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof and one or more pharmaceutically acceptable carriers, and the pharmaceutical composition is preferably in the form of a solid, semi-solid, liquid, or gas preparation. In some embodiments, the pharmaceutical composition can further comprise one or more additional therapeutic agents.

In some embodiments, the present invention provides use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the manufacture of a medicament for use as an angiotensin II type 2 ($AT_2$) receptor inhibitor.

In some embodiments, the present invention provides the compound of the present invention or a pharmaceutically acceptable salt, ester, stereoisomer, polymorph, solvate, N-oxide, isotopically labeled compound, metabolite or prodrug thereof or the pharmaceutical composition of the present invention for use as an angiotensin II type 2 ($AT_2$) receptor inhibitor.

In some embodiments, the present invention provides a method for the prophylaxis or the treatment of an $AT_2$ receptor-mediated disorder or a symptom associated therewith, comprising administering to a subject in need thereof an effective amount of the compound of the present invention or a pharmaceutically acceptable salt, ester, stereoisomer, polymorph, solvate, N-oxide, isotopically labeled compound, metabolite or prodrug thereof, or the pharmaceutical composition of the present invention.

In some embodiments, the AT2 receptor-mediated disorder is selected from cerebrovascular disorders (including cerebrovascular spasm and cerebral ischemia); cognitive disorders (including amnesia, senile dementia, AIDS related dementia and Down's syndrome); central nervous system diseases or disorders (including addiction such as alcoholism, anxiety, depression or dysthymic disorders, epilepsy, hyperactivity, pain, Parkinson's disease, psychosis, sleep disorders, irregular autonomic function, and tardive dyskinesia, schizophrenia, demyelinating diseases such as multiple sclerosis and amyotrophic lateral sclerosis); respiratory diseases (including bronchospasm, asthma, chronic obstructive airways disease), neural tumors; inflammatory diseases (including inflammatory bowel disease and osteoarthritis); gastrointestinal (GI) diseases or disorders (including ulcerative colitis, Crohn's disease and incontinence); disorders of blood flow caused by vasodilation; hypersensitivity disorders (including allergies such as eczema, rhinitis and contact dermatitis); vasospastic diseases (including angina, migraine and Reynaud's disease); fibrosing and collagen diseases (including scleroderma and eosinophilic fascioliasis); reflex sympathetic dystrophy (including shoulder/hand syndrome); stress related somatic disorders; peripheral neuropathy; neuralgia; autoimmune disease (including systemic lupus erythematosus, rheumatoid arthritis, psoriasis and graft versus host disease); and rheumatic diseases (including fibrositis).

In some embodiments, the AT2 receptor-mediated disorder is selected from neuropathic conditions (including primary neuropathy and secondary neuropathy, such as peripheral neuropathy) or symptoms associated with the same (including hyperesthesia, hyperalgesia, allodynia, spontaneous burning pain, numbness, weakness, burning pain, shooting pain, and loss of reflexes), preferably neuropathic pain; wherein the secondary neuropathy includes diabetic neuropathy; Herpes Zoster-related neuropathy; uremia-associated neuropathy; amyloidosis neuropathy; HIV sensory neuropathies; hereditary motor and sensory neuropathies; hereditary sensory neuropathies; hereditary sensory and autonomic neuropathies; hereditary neuropathies with ulcero-mutilation; nitrofurantoin neuropathy; tomaculous neuropathy; neuropathy caused by nutritional deficiency; neuropathy caused by kidney failure and complex regional pain syndrome; neuropathes caused by repetitive activities (such as typing or working on an assembly line); peripheral neuropathies caused by antiretroviral drags (such as zalcitabine and didanosine), antibiotics (such metronidazole and isoniazid), gold compounds, chemotherapy drugs (such as vincristine), alcohol, lead, arsenic, mercury and organophosphate pesticides; peripheral neuropathies associated with infectious processes (such as Guillian-Barre syndrome);

a condition characterized by neuronal hypersensitivity, including a hyperalgesic condition such as fibromyalgia and irritable bowel syndrome;

a disorder associated with aberrant nerve regeneration, including neuronal hypersensitivity, breast pain, interstitial cystitis, vulvodynia, a cancer chemotherapy-induced neuropathy;

inflammatory pain that can be due to conditions that are characterized by inflammation (including burns such as chemical, frictional or thermal burns; autoimmune diseases such as rheumatoid arthritis; inflammatory bowel disease such as Crohn's disease and colitis; osteoarthritis, carditis, dermatitis, myositis, neuritis and collagen vascular diseases);

impaired nerve conduction velocity which may be associated with a neuropathic condition as described above (such as a peripheral neuropathy) as well as Carpel Tunnel Syndrome, ulnar neuropathy, Guillian-Barre Syndrome, fascioscapulohumeral muscular dystrophy and spinal disc herniation;

a cell proliferative disorder, including a cancer (including leukaemia, melanoma, prostate cancer, breast cancer, ovarian cancer, basal cell carcinoma, squamous cell carcinoma, sarcoma, fibrosarcoma, colon cancer, lung cancer); and a non-cancerous proliferative disorder (including dermatological disorders such as warts, keloids, psoriasis, proud flesh disorder and also the reduction in scar tissue and cosmetic remodelling);

a disorder associated with an imbalance between bone resorption and bone formation, including osteoporosis.

In some embodiments, the present invention provides a method for regulating a reproductive function associated with $AT_2$ receptors in a female patient, comprising administering to a subject in need thereof an effective amount of the compound of the present invention or a pharmaceutically acceptable salt, ester, stereoisomer, polymorph, solvate, N-oxide, isotopically labeled compound, metabolite or prodrug thereof, or the pharmaceutical composition of the present invention. In some embodiments, the reproductive function is selected from the menstrual cycle, fertility, and hormonal balances of the estrus cycle.

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The pharmaceutical composition of the present invention can act systemically and/or topically. To this end, it can be administered through a suitable route, such as through injection, (intravenous, intraarterial, subcutaneous, intraperitoneal, intramuscular injection, including dripping), or transdermal administration, or administered via oral, buccal, nasal, transmucosal, topical, as an ophthalmic formulation, or via inhalation.

For these routes of administration, the pharmaceutical composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

As used herein, the term "effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

In some embodiments, the pharmaceutical composition of the present invention can further comprise one or more additional therapeutic agents or prophylactic agents.

EXAMPLES

The present invention is further described with reference to the following examples, which are not provided to limit the scope of the present invention.

The structure of the compound was confirmed by nuclear magnetic resonance spectrum ($^1$H NMR) or mass spectrum (MS).

Chemical shifts (δ) are expressed in parts per million (ppm). $^1$H NMR was recorded on a Broker 400 spectrometer, the test solvent was deuterated methanol (CD$_3$OD), deuterated chloroform (CDCl$_3$) or hexadeuterated dimethyl sulfoxide (DMSO-d$_6$), and the internal standard was tetramethylsilane (TMS).

The LC-MS assay was conducted on Agilent LC-MS—1110 liquid chromatography-mass spectrometer, Agilent LC-MS—6110 liquid chromatography-mass spectrometer, Agilent LC-MS—6120 liquid chromatography-mass spectrometer (Manufacturer: Agilent) or Shimadzu LC-MS—2020.

Preparative high-performance liquid chromatography was conducted on MS induced AutoPurification system (Waters), Gilson GX-281 (Gilson), or semi-preparative liquid chromatograph (Tong Heng Innovation Technology Co., Ltd., LC3000 (Ddlsogel, C18, 30 mm×250 mm 10 μm).

Thin layer chromatography (TLC) was performed with Huanghai HSGF 254 (5×20 cm) silica gel plates, and preparative thin layer chromatography was performed with GF 254 (0.4~0.5 nm) silica gel plates produced in Yantai.

The reaction was monitored by thin layer chromatography (TLC) or LC-MS, the developing solvent system included dichloromethane and methanol system, n-hexane and ethyl acetate system, as well as petroleum ether and ethyl acetate system, and was adjusted (by adjusting the volume ratio of the solvents, or by adding triethylamine, etc.) according to the polarity of the compound to be separated.

The microwave reaction was conducted by CEM Discovery Sp (400 W, RT~300° C.) microwave reactor.

Silica gel (200-300 mesh) produced by Yucheng Chemical Co., Ltd was normally employed as a stationary phase in column chromatography. The eluent system included dichloromethane and methanol system, as well as n-hexane and ethyl acetate system, and was adjusted (by adjusting the volume ratio of the solvents, or by adding triethylamine, etc.) according to the polarity of the compound to be separated.

In the following examples, unless otherwise specified, the reaction temperature was room temperature (20° C.~30° C.).

The reagents employed in the Examples were purchased from companies such as Aldrich Chemical Company, Shanghai Bide Pharmatech Co. Ltd., Beijing Greenchem Co. Ltd., Shanghai Shaoyuan Co. Ltd. or Ables Technology Co. Ltd. etc.

The abbreviations as used in the present invention have the following meanings:

| Abbreviation | Meaning |
|---|---|
| CH$_3$CN | acetonitrile |
| (Boc)$_2$O | di-tert-butyl dicarbonate |
| BTC | triphosgene |
| DCM | dichloromethane |
| DMSO | dimethyl sulfoxide |
| TEA | triethylamine |
| HCl | hydrochloric acid |
| H$_2$O | water |
| AcOH | acetic acid |
| MeOH | methanol |
| EtOH | ethanol |
| Na$_2$CO$_3$ | sodium carbonate |
| NaOH | sodium hydroxide |
| SOCl$_2$ | thionyl chloride |
| TFA | trifluoroacetic acid |
| THF | tetrahydrofuran |
| Me$_3$O$^+$ BF$_4^-$ | trimethyloxonium tetrafluoroborate |
| BF$_3$E$_{t2}$O | boron trifluoride etherate |
| PdCl$_2$(PPh$_3$)$_2$ | bis(triphenylphosphine)dichloropalladium |
| Pd/C | Palladium on carbon |

Preparation of Intermediate Compound CL Intermediate Preparation Example 1: preparation of (1R, 2R,5S)-ethyl 4-oxo-3,8-diazabicyclo[3.2.1]octane-2-carboxylate (Compound 5) and (1R,2S,5S)-ethyl 4-oxo-3,8-diazabicyclo[3.2.1]octane-2-carboxylate (Compound 5')

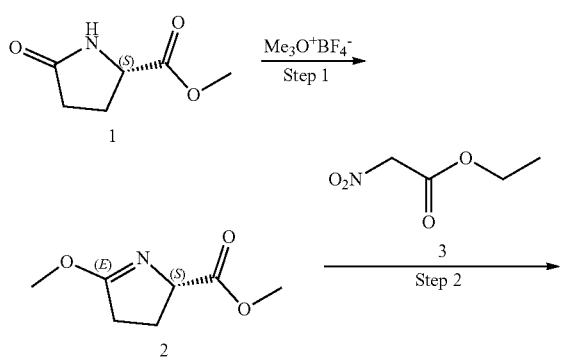

-continued

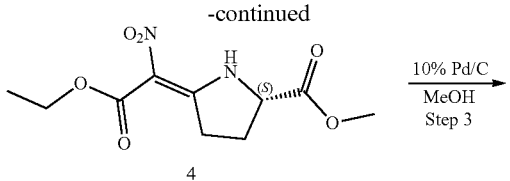

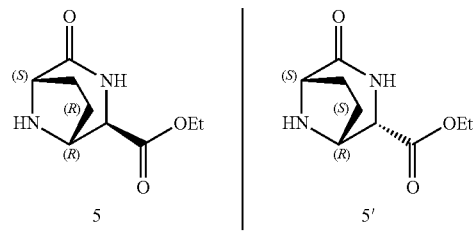

Step 1:
Compound 1 (14.3 g, 0.1 mol) was dissolved in dichloromethane (150 mL). The starting material, trimethyloxonium tetrafluoroborate (16.3 g, 0.11 mol), was added in portions, and the reaction solution was reacted at room temperature for 16 hours. The reaction solution was cooled in an ice-water bath, adjusted to pH 8.0 with saturated sodium bicarbonate solution, and extracted with dichloromethane (200 mL×2). The combined organic phase was dried with anhydrous sodium sulfate (100 g) for 30 min, and then filtered and concentrated under reduced pressure. The resulting crude product was separated and purified by column chromatography (dichloromethane:methanol=9:1) to obtain Compound 2 (8.5 g, a yellow oily matter, yield: 54%).
MS m/z (ESI): 158.0 [M+H]$^+$.

Step 2:
A mixture of Compound 2 (8.5 g, 0.054 mol) and Compound 3 (21.6 g, 0.162 mmol) was reacted at 60° C. for 16 horns. LC-MS indicated that the reaction of the starting materials was complete. To the reaction solution, 50 g of silica gel was added, and it was separated and purified by column chromatography (petroleum ether:ethyl acetate=3:2) to obtain Compound 4 (4 g, a yellow oily matter, yield: 29%).
$^1$H NMR (400 MHz, DMSO-d$_6$): δ 10.21 (brs, 1H), 4.64 (dd, J=3.6 Hz, J=8.8 Hz, 1H), 4.20 (q, J=6.8 Hz, 2H), 3.72 (s, 3H), 3.20-2.90 (m, 2H), 2.50-2.30 (m, 1H), 2.10-2.00 (m, 1H), 1.23 (t, J=6.8 Hz, 3H).
MS m/z (ESI): 259.0 [M+H]$^+$.

Step 3:
Compound 4 (12 g, 46.47 mmol) was dissolved in ethanol (1.2 L), and 12 g 10% wet palladium on carbon was added. The reaction solution was purged with hydrogen 5 times in an enclosed tank, and then reacted under the hydrogen atmosphere (0.4 MPa) at room temperature for 72 hours. After completing reaction, it was filtered, and concentrated. The resulting crude product was separated and purified by column chromatography (dichloromethane:methanol=10:1) to obtain two isomers: Compound 5 (3 g, a yellow solid, yield: 32.6%) and Compound 5' (1.5 g, a brown yellow solid, 16.3%).

Compound 5:
$^1$H NMR (400 MHz, DMSO-d$_6$): δ 7.25 (s, 1H), 4.25 (d, J=4.4 Hz, 1H), 4.20-4.10 (m, 2H), 3.75-3.7 (m, 1H), 3.39 (d, J=6.4 Hz, 1H), 1.80-1.60 (m, 3H), 1.50-1.40 (m, 1H), 1.21 (t, J=9.2 Hz, 3H).
MS m/z (ESI): 199.0 [M+H]$^+$.

Compound 5':
$^1$H NMR (400 MHz, DMSO-d$_6$): δ 7.38 (s, 1H), 4.20-4.05 (m, 2H), 3.84 (d, J=6.8 Hz, 1H), 3.68 (s, 1H), 3.42 (d, J=6.0 Hz, 1H), 1.95-1.65 (m, 4H), 1.20 (t, J=6.4 Hz, 3H).
MS m/z (ESI): 199.0 [M+H]$^+$.

The intermediate compounds in Table 1 were prepared by methods similar to that described in the Intermediate Preparation Example 1.

TABLE 1

| Compound Structure | Compound Name | Starting material or reaction condition different from that in Intermediate Preparation Example 1 | Characterization data |
|---|---|---|---|
| 5* | (1S,2R,5R)-ethyl 4-oxo-3,8-diazabicyclo[3.2.1]octane-2-carboxylate; | Compound 1 in step 1 of Intermediate Preparation Example 1 was replaced with | $^1$H NMR (400 MHz, DMSO-d$_6$): δ 7.38 (s, 1H), 4.20-4.05 (m, 2H), 3.84 (d, J = 6.8 Hz, 1H), 3.68 (s, 1H), 3.42 (d, J = 6.0 Hz, 1H), 1.95-1.65 (m, 4H), 1.20 (t, J = 6.4 Hz, 3H). MS m/z (ESI): 199.0 [M + H]$^+$. |
| 5# | (1S,2S,5R)-ethyl 4-oxo-3,8-diazabicyclo[3.2.1]octane-2-carboxylate | Compound 1 in step 1 of Intermediate Preparation Example 1 was replaced with | $^1$H NMR (400 MHz, DMSO-d$_6$): δ 7.25 (s, 1H), 4.25 (d, J = 4.4 Hz, 1H), 4.20-4.10 (m, 2H), 3.75-3.70 (m, 1H), 3.39 (d, J = 6.4 Hz, 1H), 1.80-1.60 (m, 3H), 1.50-1.40 (m, 1 H), 1.21 (t, J = 9.2 Hz, 3H). MS m/z (ESI): 199.0 [M + H]$^+$. |

Intermediate Preparation Example 2: preparation of (1R,2R,5S)-ethyl 3,8-diazabicyclo[3.2.1]octane-2-carboxylate (Compound 6)

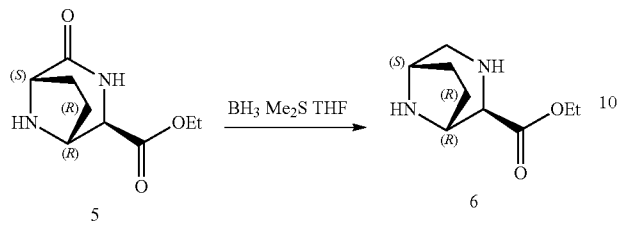

Compound 5 (3 g, 15.13 mmol) obtained from Intermediate Preparation Example 1 was dissolved in a solution of borane dimethylsulfide in tetrahydrofuran (2M, 20 mL), purged with nitrogen for 5 times, and reacted at room temperature in a nitrogen atmosphere for 16 horns. After the reaction was complete, the reaction solution was slowly poured into methanol and stirred at 50° C. for 16 hours, and then the reaction was quenched. The resulting crude product was separated and purified by column chromatography (dichloromethane:methanol=20:1) to obtain Compound 6 (1.5 g, a brown yellow oily matter, yield: 54%).

$^1$H NMR (400 MHz, DMSO-$d_6$): δ 6.42 (s, 1H), 4.10 (q, J=7.2 Hz, 2H), 3.78 (s, 1H), 3.30 (d, J=5.2 Hz, 1H), 3.13 (d, J=6.4 Hz, 1H), 2.90 (d, J=12.4 Hz, 1H), 2.70-2.50 (m, 2H), 2.05-1.85 (m, 2H), 1.80-1.60 (m, 1H), 1.50-1.40 (m, 1H), 1.19 (t, J=7.2 Hz, 3H).

MS m/z (ESI): 185.0 [M+H]$^+$.

The intermediates in Table 2 were prepared by methods similar to that described in the Intermediate Preparation Example 2.

Intermediate Preparation Example 3: preparation of (1R,2S,5S)-ethyl 3,8-diazabicyclo[3.2.1]octane-2-carboxylate (Compound 6')

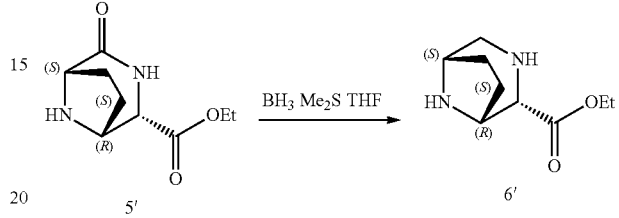

By a method similar to Intermediate Preparation Example 2, Compound 6' (0.16 g, a brown yellow oily liquid, 11%) was obtained from Compound 5' (1.5 g, 7.57 mmol) obtained in Intermediate Preparation Example 1.

$^1$H NMR (400 MHz, DMSO-$d_6$): δ 5.65 (s, 1H), 4.10 (q, J=9.6 Hz, 2H), 3.50 (d, J=7.2 Hz, 1H), 3.34 (s, 1H), 3.28 (s, 1H), 3.11 (d, J=8.4 Hz, 1H), 2.99 (d, J=16.4 Hz, 1H), 2.22-1.60 (m, 4H), 1.19 (t, J=9.2 Hz, 3H).

MS m/z (ESI): 185.0 [M+H]$^+$.

TABLE 2

| Compound Structure | Compound Name | Starting material or reaction condition different from that in Intermediate Preparation Example 2 | Characterization data |
| --- | --- | --- | --- |
| 6* | (1S,2R,5R)-ethyl 3,8-diazabicyclo[3.2.1]octane-2-carboxylate | Compound 5 of Intermediate Preparation Example 2 was replaced with Compound 5*. | $^1$H NMR (400 MHz, DMSO-$d_6$): δ 5.65 (s, 1H), 4.10 (q, J = 9.6 Hz, 2H), 3.50 (d, J = 7.2 Hz, 1H), 3.34 (s, 1H), 3.28 (s, 1H), 3.11 (d, J = 8.4 Hz, 1H) , 2.99 (d, J = 16.4 Hz, 1H), 2.22-1.60 (m, 4H), 1.19 (t, J = 9.2 Hz, 3H). MS m/z (ESI): 185.0 [M + H]$^+$. |
| 6# | (1S,2S,5R)-ethyl 3,8-diazabicyclo[3.2.1]octane-2-carboxylate | Compound 5 of Intermediate Preparation Example 2 was replaced with compound 5#. | $^1$H NMR (400 MHz, DMSO-$d_6$): δ 6.42 (s, 1H), 4.10 (q, J = 7.2 Hz, 2H), 3.78 (s, 1H), 3.30 (d, J = 5.2 Hz, 1H), 3.13 (d, J = 6.4 Hz, 1H), 2.90 (d, J = 12.4 Hz, 1H), 2.70-2.50 (m, 2H), 2.05-1.85 (m, 2H), 1.80-1.60 (m, 1H), 1.50-1.40 (m, 1 H), 1.19 (t, J = 7.2 Hz, 3H). MS m/z (ESI): 185.0 [M + H]$^+$. |

Preparation of Compounds of the Invention

Example 1: preparation of (1R,2S,5S)-3,8-bis(2,2-diphenylacetyl)-3,8-diazabicyclo[3.2.1]octane-2-carboxylic acid (C1)

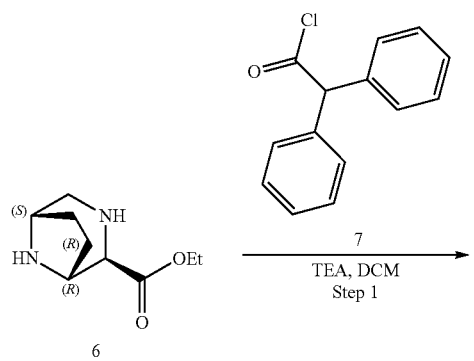

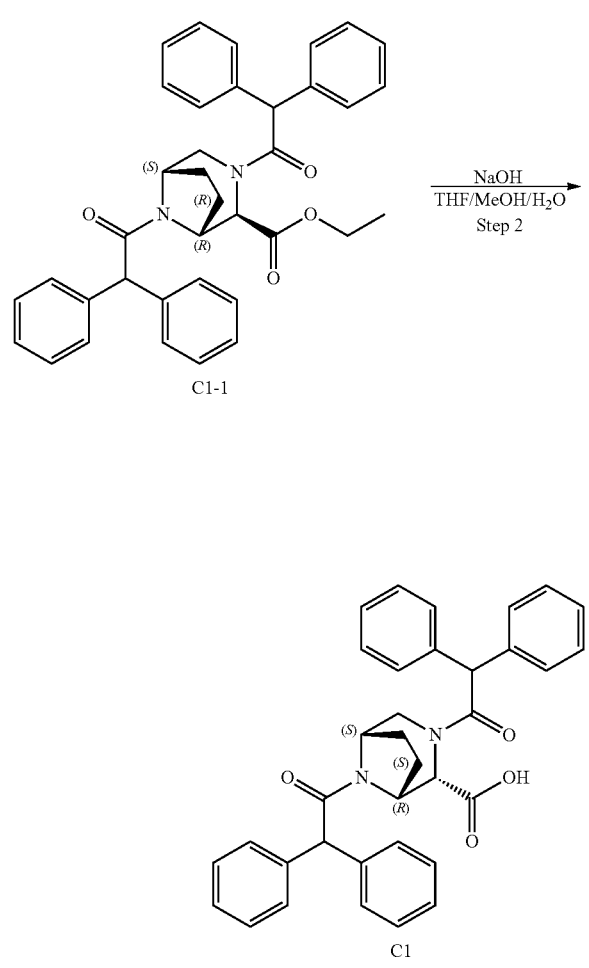

Step 1:

Compound 6 (0.15 g, 0.81 mmol) obtained from Intermediate Preparation Example 2 was dissolved in dichloromethane (30 mL). triethylamine (0.267 g, 2.64 mmol) and Compound 7 (0.203 g, 0.81 mmol) were added and reacted at room temperature for 4 hours. LC-MS indicated that the reaction of the starting materials was complete. The solution was then quenched by adding water (30 mL), and extracted with ethyl acetate (20 mL/3). The combined organic phases were washed with saturated brine (50 mL×3). After that, the organic phases were dried by adding anhydrous sodium sulfate for 30 min, and then filtered. The filtrate was concentrated under reduced pressure. The resulting crude product was subjected to separation by column chromatography (petroleum ether:methyl tert-butyl ether=3:7) to obtain Compound C1-1 (50 mg, a dark yellow solid, yield: 11%).

MS m/z (ESI): 573.0 [M+H]$^+$.

Step 2:

Compound C1-1 (50 mg, 0.087 mmol) was dissolved in a mixed solution of tetrahydrofuran, methanol and water (5 mL/5 mL/5 mL). Sodium hydroxide (35 mg, 0.87 mmol) was added and stirred at room temperature for 3 hours. After concentrated, a crude product was obtained. The crude product was adjusted to pH 5.0 with 3N hydrochloric acid solution, and then extracted with ethyl acetate (20 mL×3). The combined organic phases were washed with saturated brine (50 mL×3). After that, the organic phases were dried by adding anhydrous sodium sulfate for 30 min and then filtered. The filtrate was concentrated under reduced pressure, and the crude product was subjected to separation by reversed phase chromatography (acetonitrile/water (0.1% trifluoroacetic acid solution) 60/40-70/30) to obtain the target compound C1 (15 mg, a light yellow solid, yield: 31%).

$^1$H NMR (400 MHz, DMSO-d$_6$): δ 7.50-7.00 (m, 20H), 5.50-5.30 (m, 2H), 5.02 (s, 1H), 4.90-4.60 (m, 2H), 3.90-3.40 (m, 2H), 1.70-1.00 (m, 4H).

MS m/z (ESI): 545.0 [M+H]$^+$.

The compounds in Table 3 were prepared by methods similar to that described in Example 1.

TABLE 3

| No. | Compound Structure | Compound Name | Starting material or reaction condition different from that in Example 1 | Characterization data |
|---|---|---|---|---|
| C3 | 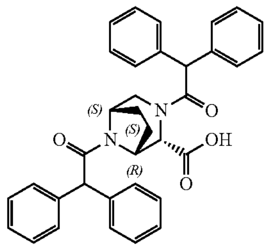 | (1R,2S,5S)-3,8-bis(2,2-diphenylacetyl)-3,8-diazabicyclo[3.2.1]octane-2-carboxylic acid | Compound 6 in step 1 of Example 1 was replaced with compound 6'. | $^1$H NMR (400 MHz, DMSO-d$_6$): δ 7.35-7.00 (m, 20 H), 5.49 (s, 1H), 5.37 (s, 1H), 5.14 (s, 1H), 4.73 (s, 1H), 4.57 (s, 1H), 3.75-3.45 (m, 2H), 2.25-2.00 (m, 1H), 1.95-1.50 (m, 3H). MS m/z (ESI): 544.9 [M + H]$^+$. |
| C5 | 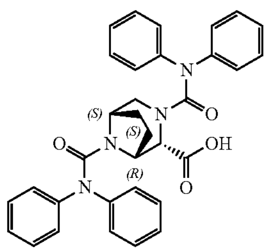 | (1R,2S,5S)-3,8-bis(diphenylcarbamoyl)-3,8-diazabicyclo[3.2.1]octane-2-carboxylic acid | Compound 7 in step 1 of Example 1 was replaced with | $^1$H NMR (400 MHz, DMSO-d$_6$): δ 7.40-7.30 (m, 8H), 7.25-7.15 (m, 4H), 7.10-7.00 (m, 8H), 4.44 (s, 2H), 4.11 (s, 1H), 3.25-3.05 (m, 2H), 1.85-1.60 (m, 2H), 1.55-1.45 (m, 1H), 1.35-1.30 (m, 1H). MS m/z (ESI): 547.0 [M + H]$^+$. |
| C4 | 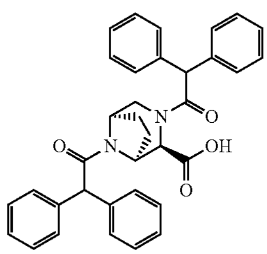 [SMILES: O=C(O)[C@H]1[C@@H]2CC[C@H](CN1C(=O)C(c1ccccc1)c1ccccc1)N2C(=O)C(c1ccccc1)c1ccccc1] | (1S,2R,5R)-3,8-bis(2,2-diphenylacetyl)-3,8-diazabicyclo[3.2.1]octane-2-carboxylic acid | Compound 6 in step 1 of Example 1 was replaced with compound 6$^\#$. | $^1$H NMR (400 MHz, CD$_3$OD): δ 7.57-7.03 (m, 20H), 5.50 (d, J = 6.5 Hz, 1H), 5.35 (d, J = 8.5 Hz, 1H), 4.67 (s, 1H), 4.33 (d, J = 20.2 Hz, 1H), 3.86 (d, J = 14.7 Hz, 1H), 3.65 (d, J = 21.2 Hz, 1H), 3.48 (d, J = 13.3 Hz, 1H), 1.62 (m, 2H), 1.50 (m, 1H), 1.11 (m, 1H). MS m/z (ESI): 544.9 [M + H]$^+$. |
| C14 | 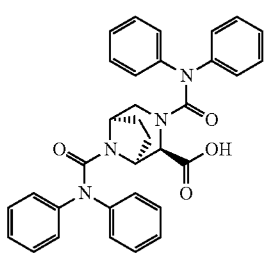 [SMILES: O=C(O)[C@H]1[C@@H]2CC[C@H](CN1C(=O)N(c1ccccc1)c1ccccc1)N2C(=O)N(c1ccccc1)c1ccccc1] | (1S,2R,5R)-3,8-bis(diphenylcarbamoyl)-3,8-diazabicyclo[3.2.1]octane-2-carboxylic acid | Compound 6 in step 1 of Example 1 was replaced with compound 6$^\#$, and Compound 7 was replaced with | $^1$H NMR (400 MHz, DMSO-d$_6$): δ 13.19 (s, 1H), 7.33 (dd, J = 15.9, 8.1 Hz, 8H), 7.16 (t, J = 7.3 Hz, 4H), 7.09-6.86 (m, 8H), 4.27 (m, 2H), 3.96 (m, 1H), 3.16 (d, J = 13.5 Hz, 1H), 2.99-2.87 (m, 1H), 1.64 (m, 1H), 1.53 (m, 1H), 1.29 (d, J = 37.9 Hz, 1H), 1.14 (m, 1H). MS m/z (ESI): 546.8 [M + H]$^+$. |
| C8 | 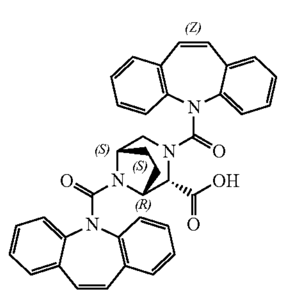 | (1R,2S,5S)-3,8-bis(5H-dibenzo[b,f]azepine-5-carbonyl)-3,8-diazabicyclo[3.2.1]octane-2-carboxylic acid | Compound 7 in step 1 of Example 1 was replaced with and reacted at 50° C. | $^1$H NMR (400 MHz, DMSO-d$_6$): δ 12.76 (s, 1H), 7.56-6.99 (m, 20H), 4.38 (m, 1H), 3.92 (s, 1H), 3.18 (s, 1H), 2.02 (m, 1H), 1.46 (s, 1H), 1.24 (s, 2H), 1.12-0.96 (m, 2H). MS m/z (ESI): 595.0 [M + H]$^+$. |

TABLE 3-continued

| No. | Compound Structure | Compound Name | Starting material or reaction condition different from that in Example 1 | Characterization data |
|---|---|---|---|---|
| C41 | 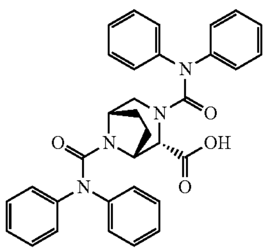 [SMILES: O=C(O)[C@@H]1[C@H]2CC[C@@H](CN1C(=O)N(c1ccccc1)c1ccccc1)N2C(=O)N(c1ccccc1)c1ccccc1] | (1R,2S,5S)-3,8-bis(diphenylcarbamoyl)-3,8-diazabicyclo[3.2.1]octane-2-carboxylic acid | Compound 6 in step 1 of Example 1 was replaced with compound 6', and Compound 7 was replaced with [structure shown] and reacted at 50° C. | $^1$H NMR (400 MHz, CD$_3$OD): δ 7.40-7.30 (m, 8H), 7.25-7.15 (m, 4H), 7.10-7.00 (m, 8H), 4.48 (s, 2H), 4.1 (s, 1H), 3.30-3.10 (m, 2H), 1.85-1.40 (m, 4H). MS m/z (ESI): 547.0 [M + H]$^+$. |
| C2 | 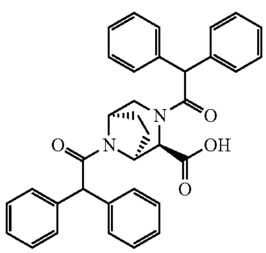 [SMILES: O=C(O)[C@H]1[C@@H]2CC[C@H](CN1C(=O)C(c1ccccc1)c1ccccc1)N2C(=O)C(c1ccccc1)c1ccccc1] | (1S,2R,5R)-3,8-bis(2,2-diphenylacetyl)-3,8-diazabicyclo[3.2.1]octane-2-carboxylic acid | Compound 6 in step 1 of Example 1 was replaced with compound 6* and reacted at room temperature for 16 hours. The reaction time in step 2 was 16 hours, and the condition of the reverse phase chromatography was acetonitrile/water = 55/75. | $^1$H NMR (400 MHz, DMSO-d$_6$): δ 7.41-7.03 (m, 20H), 5.46 (dd, J = 29.9, 16.6 Hz, 2H), 5.16 (dd, J = 97.5, 9.8 Hz, 1H), 4.75-4.64 (m, 1H), 4.56 (s, 1H), 4.39 (s, 1H), 3.22-3.11 (m, 1H), 1.39 (d, J = 6.7 Hz, 2H), 1.07 (s, 1H), 0.87 (t, J = 7.3 Hz, 1H). MS m/z (ESI): 544.8 [M + H]$^+$. |
| C13 | 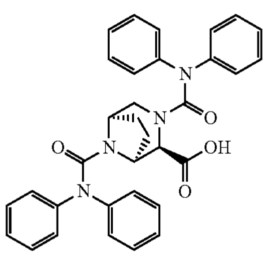 [SMILES: O=C(O)[C@H]1[C@@H]2CC[C@H](CN1C(=O)N(c1ccccc1)c1ccccc1)N2C(=O)N(c1ccccc1)c1ccccc1] | (1S,2R,5R)-3,8-bis(diphenylcarbamoyl)-3,8-diazabicyclo[3.2.1]octane-2-carboxylic acid | Compound 6 in step 1 of Example 1 was replaced with compound 6*, and Compound 7 was replaced with [structure shown] and reacted at 45° C. for 48 hours. The reaction time in step 2 was 16 hours, and the condition of the reverse phase chromatography was acetonitrile/water = 50/80. | $^1$H NMR (400 MHz, DMSO-d$_6$): δ 13.23 (s, 1H), 7.32 (dd, J = 15.8 Hz, J = 8.0 Hz, 8H), 7.15 (t, J = 7.2 Hz, 4H), 7.05-6.89 (m, 8H), 4.27 (s, 2H), 3.96 (s, 1H), 3.15 (d, J = 12.8 Hz, 1H), 2.96 (s, 1H), 1.64 (s, 1H), 1.51 (s, 1H), 1.29 (d, J = 40.5 Hz, 2H). MS m/z (ESI): 546.8 [M + H]$^+$. |

Example 2: preparation of (1R,2S,5S)-3-benzoyl-8-(2,2-diphenylacetyl)-3,8-diazabicyclo[3.2.1]octane-2-carboxylic acid (C31)

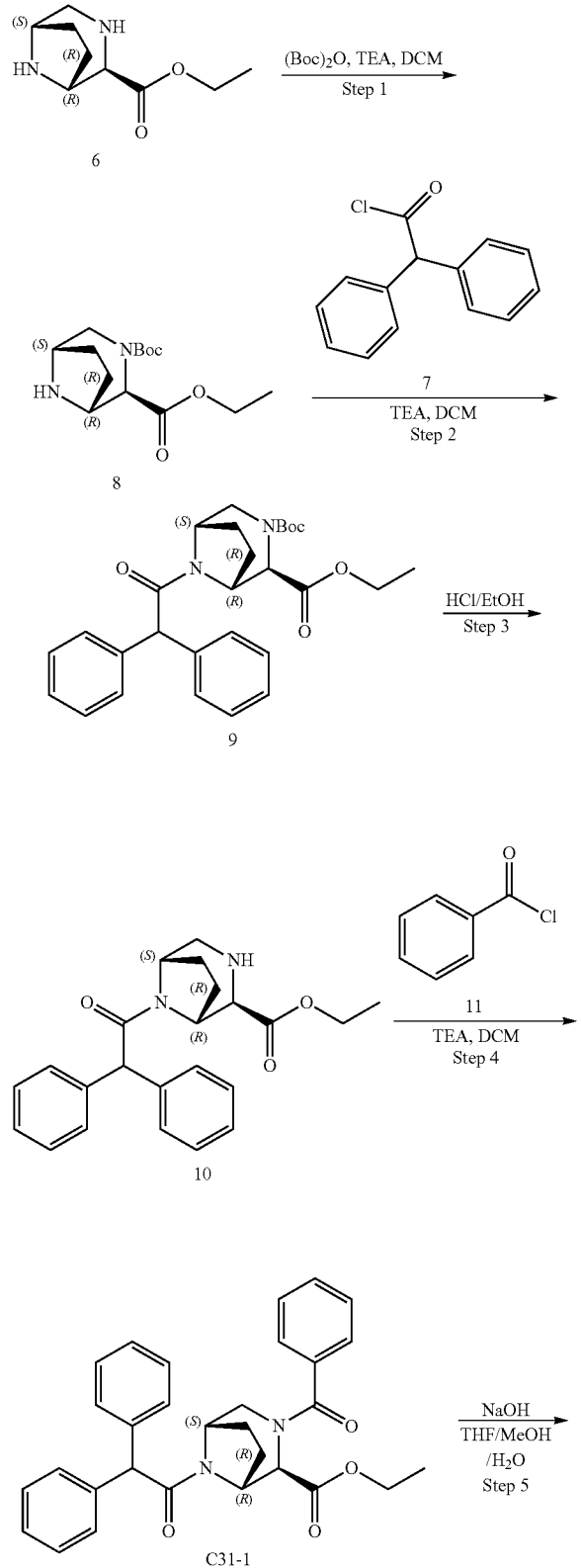

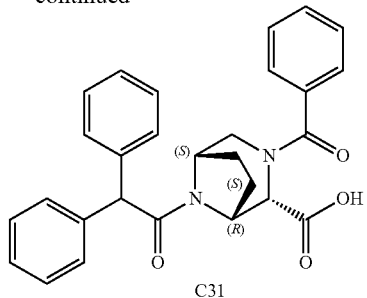

Step 1:

Compound 6 (2.3 g, 12.48 mmol) obtained from Intermediate Preparation Example 2 was dissolved in a dichloromethane solution (50 mL), cooled with an ice-water bath, followed by sequential addition of di-tert-butyl dicarbonate (2.7 g, 12.48 mmol) and triethylamine (3.78 g, 37.45 mmol) and reaction at room temperature for 16 hours. After the reaction was complete, 50 mL water was added to the reaction solution and extracted with dichloromethane (50 mL×2). The combined organic phases were dried over anhydrous sodium sulfate (100 g) for 30 min and then filtered. The filtrate was concentrated under reduced pressure. The resulting crude product was separated and purified by column chromatography (petroleum ether:ethyl acetate=3:7) to obtain Compound 8 (1.4 g, a yellow oily matter, crude product).

$^1$H NMR (400 MHz, DMSO-$d_6$): δ 6.80 (s, 1H), 4.20-4.00 (m, 3H), 3.45-3.40 (m, 2H), 3.30-3.20 (m, 2H), 2.20-2.10 (m, 1H), 2.00-1.85 (m, 2H), 1.65-1.55 (m, 1H), 1.38 (s, 9H), 1.20 (t, J=7.2 Hz, 3H).

MS m/z (ESI): 307.0 [M+Na]+.

Step 2:

Compound 8 (1.4 g, 4.92 mmol) was dissolved in dichloromethane (20 mL). To the resulting solution, triethylamine (1.49 g, 14.77 mmol) and then a solution of Compound 7 (1.14 g, 4.92 mmol) in dichloromethane (10 mL) were added. After reacting at room temperature for 3 hours, LC-MS indicated that the reaction of the starting materials was complete. The solution was quenched by adding water (30 mL) and extracted with dichloromethane (20 mL×3). The combined organic phases were washed with saturated brine (50 mL×3). After that, the organic phases were dried by adding anhydrous sodium sulfate for 30 min, and then filtered and concentrated under reduced pressure. The resulting crude product was subjected to separation by column chromatography (petroleum ether:methyl tert-butyl ether=3:2) to obtain Compound 9 (0.8 g, a dark yellow solid, crude product).

MS m/z (ESI): 479.0 [M+H]+.

Step 3:

Compound 9 (0.8 g, 1.67 mmol) was dissolved in a hydrochloric acid solution in ethanol (8M, 10 mL), and reacted at room temperature for 2 hours. After the reaction was complete, a crude product of compound 10 was obtained by concentration (0.5 g, a dark yellow solid, crude product).

MS m/z (ESI): 379.0 [M+H]+.

Step 4:

Compound 10 (0.25 g, 0.6 mmol) was dissolved in dichloromethane (20 mL), followed by sequential addition of Compound 11 (85 mg, 0.6 mmol) and triethylamine (0.183 g, 1.8 mmol) and reaction at room temperature for 16 horns. After the reaction was complete, 50 mL water was added to the reaction solution and extracted with dichloromethane (50 mL×2). The combined organic phases were dried with anhydrous sodium sulfate (100 g) for 30 min, then filtered and concentrated under reduced pressure. The resulting crude product was separated and purified by column chromatography (petroleum ether:ethyl acetate=3:2) to obtain Compound C31-1 (0.2 g, a yellow oily matter, 69%).

MS m/z (ESI): 483.0 [M+H]$^+$.

Step 5:

Compound C31-1 (0.2 g, 0.41 mmol) was dissolved in a mixed solution of tetrahydrofuran, methanol and water (5 mL/5 mL/5 mL), followed by adding sodium hydroxide (83 mg, 2.07 mmol) and stirring at room temperature for 3 horns. After concentration, the obtained crude product was adjusted to pH 5.0 with 3N hydrochloric acid solution. A solid was filtered and washed with 10 mL water, and then dried to obtain Compound C31 (130 mg, a light yellow solid, yield: 70%)

$^1$H NMR (400 MHz, DMSO-d$_6$): δ 7.50-7.00 (m, 15H), 5.50-5.30 (m, 1H), 5.20-4.90 (m, 1H), 4.70-4.40 (m, 2H), 4.25-3.80 (m, 1H), 3.25-3.00 (m, 1H), 1.8-1.25 (m, 4H).

MS m/z (ESI): 455.0 [M+H]$^+$.

The compounds in Table 4 were prepared by methods similar to that described in Example 2.

TABLE 4

| Compound No. | Compound Structure | Compound Name | Starting material or reaction condition different from that in Example 2 | Characterization data |
|---|---|---|---|---|
| C7 | 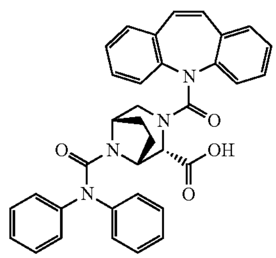 [SMILES: O=C(O)[C@@H]1[C@H]2CC[C@@H](CN1C(=O)N1c3ccccc3C=Cc3ccccc31)N2C(=O)N(c1ccccc1)c1ccccc1] | (1R,2S,5S)-3-(5H-dibenzo[b,f]azepine-5-carbonyl)-8-(diphenylcarbamoyl)-3,8-diazabicyclo[3.2.1]octane-2-carboxylic acid | Compound 7 in step 2 of Example 2 was replaced with [diphenylcarbamoyl chloride structure] Compound 11 in step 4 of Example 2 was replaced with [dibenzazepine carbonyl chloride structure] And the reactions in step 2 and step 4 were performed at 50° C. | $^1$H NMR (400 MHz, CD$_3$OD): δ 7.70-6.90 (m, 20H), 4.32 (s, 1H), 4.20 (s, 1H), 3.98 (d, J = 5.6 Hz, 1H), 2.93 (s, 2H), 1.80-1.50 (m, 2H), 1.425-1.40 (m, 2H). MS m/z (ESI): 571.0 [M + H]$^+$. |
| C6 | 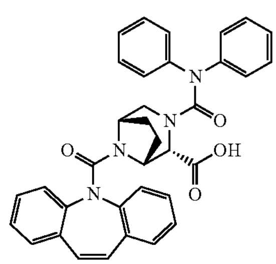 [SMILES: O=C(O)[C@@H]1[C@H]2CC[C@@H](CN1C(=O)N(c1ccccc1)c1ccccc1)N2C(=O)N1c2ccccc2C=Cc2ccccc21] | (1R,2S,5S)-8-(5H-dibenzo[b,f]azepine-5-carbonyl)-3-(diphenylcarbamoyl)-3,8-diazabicyclo[3.2.1]octane-2-carboxylic acid | Compound 7 in step 2 of Example 2 was replaced with [dibenzazepine carbonyl chloride structure] Compound 11 in step 4 of the Example was replaced with [diphenylcarbamoyl chloride structure] And, the reactions in step 2 and step 4 were performed at 50° C. | $^1$H NMR (400 MHz, CD$_3$OD): δ 7.59-6.96 (m, 20H), 4.90 (s, 1H), 4.41 (s, 1H), 3.50-3.33 (m, 1H), 3.15 (s, 1H), 2.88 (d, J = 12.8 Hz, 1H), 2.37 (s, 2H), 2.00-1.96 (m, 2H), 1.70-1.31 (m, 3H). MS m/z (ESI): 571.0 [M + H]$^+$. |

TABLE 4-continued

| No. | Compound Structure | Compound Name | Starting material or reaction condition different from that in Example 2 | Characterization data |
|---|---|---|---|---|
| C9 | 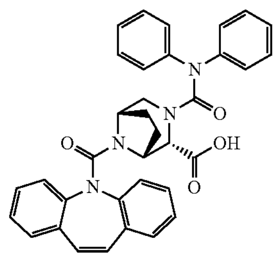 [SMILES: O=C(O)[C@@H]1[C@H]2CC[C@@H](CN1C(=O)N(c1ccccc1)c1ccccc1)N2C(=O)N1c2ccccc2C=Cc2ccccc21] | (1R,2S,5S)-8-(5H-dibenzo[b,f]azepine-5-carbonyl)-3-(2,2-diphenylacetyl)-3,8-diazabicyclo[3.2.1]octane-2-carboxylic acid | Compound 7 in step 2 of Example 2 was replaced with [structure] Compound 11 in step 4 was replaced with Compound 7. | $^1$H NMR (400 MHz, CD$_3$OD): δ 7.27-6.96 (m, 20H), 5.19 (d, J = 20.0 Hz, 1H), 4.90-4.77 (m, 2H), 4.40 (s, 1H), 3.53 (d, J = 16 Hz, 1H), 3.41 (d, J = 4.0 Hz, 1H), 3.18 (d, J = 12.0 Hz, 1H), 2.60 (d, J = 12.0 Hz, 1H), 2.20 (d, J = 12.0 Hz, 1H), 1.84-1.81 (m, 1H), 1.49-1.31 (m, 2H). MS m/z (ESI): 570.0 [M + H]$^+$. |
| C10 | 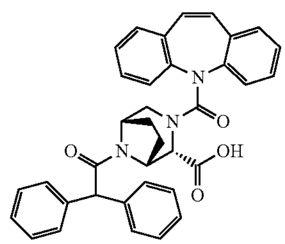 [SMILES: O=C(O)[C@@H]1[C@H]2CC[C@@H](CN1C(=O)N1c3ccccc3C=Cc3ccccc31)N2C(=O)C(c1ccccc1)c1ccccc1] | (1R,2S,5S)-3-(5H-dibenzo[b,f]azepine-5-carbonyl)-8-(2,2-diphenylacetyl)-3,8-diazabicyclo[3.2.1]octane-2-carboxylic acid | Compound 11 in step 4 of Example 2 was replaced with [structure], and the reaction in step 4 was performed at 50° C. | $^1$H NMR (400 MHz, DMSO-d$_6$): δ 7.70-6.90 (m, 20H), 5.34-5.21 (m, 1H), 4.83-4.43 (m, 1H), 4.23-4.16 (m, 1H), 3.97-3.31 (m, 1H), 3.10-2.70 (m, 2H), 1.60-0.80 (m, 4H). MS m/z (ESI): 570.0 [M + H]$^+$. |
| C12 | 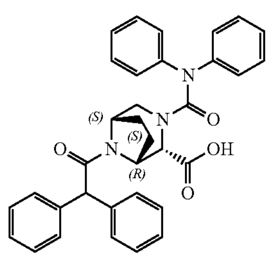 | (1R,2S,5S)-8-(2,2-diphenylacetyl)-3-(diphenylcarbamoyl)-3,8-diazabicyclo[3.2.1]octane-2-carboxylic acid | Compound 11 in step 4 of Example 2 was replaced with [structure], and the reaction in step 4 was performed at 50° C. | $^1$H NMR (400 MHz, CD$_3$OD) δ 7.50-7.00 (m, 20H), 5.49-5.34 (m, 1H), 5.14-4.67 (m, 2H), 4.37 (s, 1H), 3.65-3.35 (m, 2H), 1.60-0.80 (m, 4H). MS m/z (ESI): 546.0 [M + H]$^+$. |
| C28 | 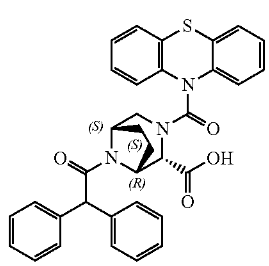 | (1R,2S,5S)-8-(2,2-diphenylacetyl)-3-(10H-phenothiazine-10-carbonyl)-3,8-diazabicyclo[3.2.1]octane-2-carboxylic acid | Compound 11 in step 4 of Example 2 was replaced with [structure] | $^1$H NMR (400 MHz, DMSO-d$_6$): δ 7.60-7.00 (m, 18H), 5.39-5.28 (s, 1H), 4.97 (s, 1H), 4.60 (s, 1H), 4.39 (s, 1H), 3.20-2.80 (m, 2H), 1.70-1.10 (m, 4H). MS m/z (ESI): 575.9 [M + H]$^+$. |
| C63 | 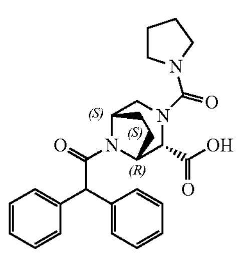 | (1R,2S,5S)-8-(2,2-diphenylacetyl)-3-(pyrrolidine-1-carbonyl)-3,8-diazabicyclo[3.2.1]octane-2-carboxylic acid | Compound 11 in step 4 of Example 2 was replaced with [structure] | $^1$H NMR (400 MHz, DMSO-d$_6$): δ 7.50-6.90 (m, 10H), 5.52-5.43 (m, 1H), 5.10-4.20 (m, 3H), 3.50-3.10 (m, 6H), 1.78 (m, 4H), 1.75-1.00 (m, 4H). MS m/z (ESI): 448.0 [M + H]$^+$. |

TABLE 4-continued

| No. | Compound Structure | Compound Name | Starting material or reaction condition different from that in Example 2 | Characterization data |
| --- | --- | --- | --- | --- |
| C68 | 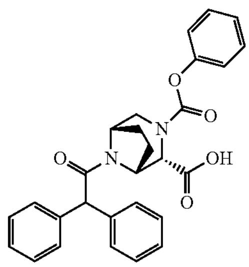 [SMILES: O=C(O)[C@@H]1[C@H]2CC[C@@H](CN1C(=O)Oc1ccccc1)N2C(=O)C(c1ccccc1)c1ccccc1] | (1R,2S,5S)-8-(2,2-diphenylacetyl)-3-(phenoxycarbonyl)-3,8-diazabicyclo[3.2.1]octane-2-carboxylic acid | Compound 11 in step 4 of Example 2 was replaced with phenyl chloroformate. | $^1$H NMR (400 MHz, DMSO-d$_6$): δ 7.70-6.90 (m, 15H), 5.50-5.30 (m, 1H), 5.10-4.50 (m, 3H), 4.00-3.00 (m, 2H), 1.90-1.50 (m, 4H). MS m/z (ESI): 570.9 [M + H]$^+$. |
| C70 | 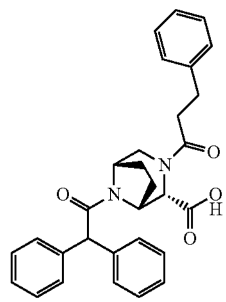 [SMILES: O=C(O)[C@@H]1[C@H]2CC[C@@H](CN1C(=O)CCc1ccccc1)N2C(=O)C(c1ccccc1)c1ccccc1] | (1R,2S,5S)-8-(2,2-diphenylacetyl)-3-(3-phenylpropionyl)-3,8-diazabicyclo[3.2.1]octane-2-carboxylic acid | Compound 11 in step 4 of Example 2 was replaced with | $^1$H NMR (400 MHz, DMSO-d$_6$): δ 7.50-6.90 (m, 15H), 5.50-5.20 (m, 1H), 5.10-4.50 (m, 4H), 3.60-3.20 (m, 2H), 2.80-2.50 (m, 3H), 1.80-1.20 (m, 4H). MS m/z (ESI): 483.0 [M + H]$^+$. |
| C71 | 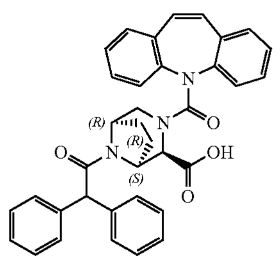 | (1S,2R,5R)-3-(5H-dibenzo[bf]azepine-5-carbonyl)-8-(2,2-diphenylacetyl)-3,8-diazabicyclo[3.2.1]octane-2-carboxylic acid | Compound 6 in step 1 of Example 2 was replaced with compound 6$^#$. The reaction time in step 2 was 16 hours. In step 4, Compound 11 was replaced with [structure], the reaction temperature was 50° C. and the reaction time was 48 hours. The reaction time in step 5 was 16 hours. | $^1$H NMR (300 MHz, CD$_3$OD): δ 7.60-6.94 (m, 20H), 5.31 (d, J = 42.0 Hz, 1H), 4.99 (s, 1H), 4.62-4.50 (m, 1H), 4.30 (d, J = 37.8 Hz, 1H), 3.16-2.85 (m, 2H), 1.71-0.93 (m, 4H). MS m/z (ESI): 569.8 [M + H]$^+$. |
| C72 | 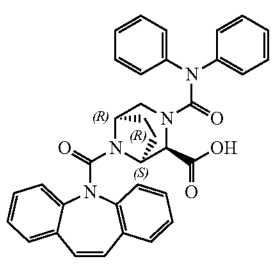 | (1S,2R,5R)-8-(5H-dibenzo[bf]azepine-5-carbonyl)-3-(2,2-diphenylacetyl)-3,8-diazabicyclo[3.2.1]octane-2-carboxylic acid | Compound 6 in step 1 of Example 2 was replaced with compound 6$^#$. In step 2, Compound 7 was replaced with [structure], the reaction time was 48 hours and the reaction temperature was 40° C. Compound 11 in step 4 was replaced with compound 7. The reaction time in step 5 was 16 hours, and the | $^1$H NMR (400 MHz, CD$_3$OD): δ 7.61 (d, J = 8.3 Hz, 1H), 7.47-6.90 (m, 19H), 5.22 (d, J = 7.9 Hz, 1H), 4.80 (d, J = 7.4 Hz, 1H), 3.57 (d, J = 11.3 Hz, 1H), 3.51-3.43 (m, 1H), 3.25-3.12 (m, 1H), 2.53 (d, J = 11.1 Hz, 1H), 1.88-1.77 (m, 1H), 1.52-1.34 (m, 2H), 0.99 (d, J = 9.2 Hz, 1H). MS m/z (ESI): 569.9 [M + H]$^+$. |

TABLE 4-continued

| No. | Compound Structure | Compound Name | Starting material or reaction condition different from that in Example 2 | Characterization data |
|---|---|---|---|---|
| | | | reaction temperature was 50° C. | |
| C73 | (structure) | (1R,2S,5S)-3-((benzyloxy)carbonyl)-8-(5H-dibenzo[bf]azepine-5-carbonyl)-3,8-diazabicyclo[3.2.1]octane-2-carboxylic acid | In step 2, Compound 7 of Example 2 was replaced with (structure), the reaction time was 48 hours, and the reaction temperature was 40° C. Compound 11 in step 4 was replaced with benzyl chloroformate. | $^1$H NMR (300 MHz, CD$_3$OD) δ 7.70-7.18 (m, 13H), 7.01 (s, 2H), 5.21-4.99 (m, 2H), 4.77 (s, 1H), 4.44 (s, 1H), 4.20-3.76 (m, 1H), 3.59 (s, 1H), 3.21-3.04 (m, 1H), 2.35 (dd, J = 22.2, 11.7 Hz, 1H), 1.85 (s, 1H), 1.59 (s, 3H), 1.28 (s, 1H). MS m/z (ESI): 510.0 [M + H]$^+$. |
| C77 | (structure) | (1S,2R,5R)-3-((benzyloxy)carbonyl)-8-(5H-dibenzo[b,f]azepine-5-carbonyl)-3,8-diazabicyclo[3.2.1]octane-2-carboxylic acid | Compound 6 in step 1 of Example 2 was replaced with compound 6$^#$. In step 2, 4-Dimethylaminopyridine was added and Compound 7 was replaced with (structure), and the reaction time was 48 hours and the reaction temperature was 40° C. In step 4, Compound 11 was replaced with benzyl chloroformate, and the reaction tempearture was 45° C. The reaction time in step 5 was 16 hours, and the reaction temperature was 45° C. | $^1$H NMR (400 MHz, DMSO-d$_6$): δ 13.04 (s, 1H), 7.66-7.00 (m, 15H), 5.01 (dt, J = 12.9 Hz, J = 10.9 Hz, 2H), 4.63 (t, J = 7.7 Hz, 1H), 4.34 (dd, J = 17.1, J = 2.5 Hz, 1H), 3.48 (s, 1H), 3.06 (dd, J = 25.2, J = 9.8 Hz, 1H), 2.18 (dd, J = 47.4 Hz, J = 10.4 Hz, 1H), 1.73 (s, 1H), 1.64-1.36 (m, 3H). MS m/z (ESI): 509.9 [M + H]$^+$. |
| C75 | (structure) | (1S,2R,5R)-3-((benzyloxy)carbonyl)-8-(2,2-diphenylacetyl)-3,8-diazabicyclo[3.2.1]octane-2-carboxylic acid | Compound 6 in step 1 of Example 2 was replaced with compound 6$^#$. The reaction time in step 2 was 16 hours. In step 4, Compound 11 was replaced with benzyl chloroformate, 4-dimethylaminopyridine was added, and the reaction temperature was 40° C., and the reaction time was 48 hours. The reaction time in step 5 was 16 hours. | $^1$H NMR (400 MHz, DMSO-d$_6$): δ 13.30 (dd, J = 286.6, 29.9 Hz, 1H), 7.50-7.03 (m, 15H), 5.50-5.26 (m, 1H), 5.19-4.98 (m, 2H), 4.78-4.63 (m, 1H), 4.52 (t, J = 27.1 Hz, 1H), 4.35 (dd, J = 23.9 Hz, J = 1.9 Hz, 1H), 3.80-3.45 (m, 1H), 3.22-2.93 (m, 1H), 1.83-1.43 (m, 4H). MS m/z (ESI): 484.9 [M + H]$^+$. |

TABLE 4-continued

| Compound No. | Compound Structure | Compound Name | Starting material or reaction condition different from that in Example 2 | Characterization data |
|---|---|---|---|---|
| C20 | 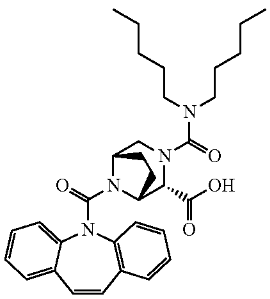 [SMILES: CCCCCN(CCCCC)C(=O)N1C[C@@H]2CC[C@H]([C@H]1C(=O)O)N2C(=O)N1c2ccccc2C=Cc2ccccc21] | (1R,2S,5S)-8-(5H-dibenzo[b,f]azepine-5-carbonyl)-3-(diphenylcarbamoyl)-3,8-diazabicyclo[3.2.1]octane-2-carboxylic acid | In step 2 of Example 2, 4-dimethylaminopyridine was added, Compound 7 was replaced with <br><br> and the reaction time was 48 hours and the reaction temperature was 40° C. Compound 11 in step 4 was replaced with Di-pentyl amine. | $^1$H NMR (400 MHz, CD$_3$OD): δ 7.64 (d, J = 8.0 Hz, 1H), 7.46-7.42 (m, 3H), 7.35-7.29 (m, 3H), 7.09-7.02 (m, 2H), 4.84 (s, 1H), 4.48 (s, 1H), 3.52 (s, 2H), 3.15-3.03 (s, 2H), 3.01-2.78 (m, 4H), 2.69-2.64 (m, 2H), 1.88-1.84 (m, 1H), 1.80-1.66 (m, 1H), 1.66-1.57 (m, 2H), 1.56-1.44 (m, 2H), 1.40-1.29 (m, 3H), 1.27-1.15 (m, 2H), 0.94-0.86 (m, 6H), 0.82-0.78 (m, 2H). <br> MS m/z (ESI): 559.1 [M + H]$^+$. |
| C45 | 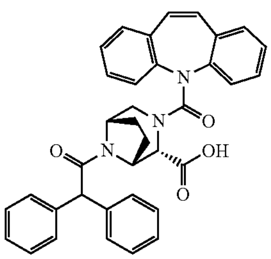 [SMILES: O=C(O)[C@@H]1[C@H]2CC[C@@H](CN1C(=O)N1c3ccccc3C=Cc3ccccc31)N2C(=O)C(c1ccccc1)c1ccccc1] | (1R,2S,5S)-3-(10,11-dihydro-5H-dibenzo[bf]azepine-5-carbonyl)-8-(diphenylcarbamoyl)-3,8-diazabicyclo[3.2.1]octane-2-carboxylic acid | Compound 7 in step 2 of Example 2 was replaced with <br><br> Compound 11 in step 4 was replaced with | $^1$H NMR (400 MHz, CD$_3$OD) δ 7.43 (d, J = 5.6 Hz, 2H), 7.32 (d, J = 7.6 Hz, 4H), 7.24-7.15 (m, 8H), 7.06 (d, J = 7.6 Hz, 4H), 4.42-4.30 (m, 3H), 4.12-4.05 (m, 1H), 3.25-3.05 (m, 6H), 1.80-1.30 (m, 4H). <br> MS m/z (ESI): 572.8 [M + H]$^+$. |
| C69 | 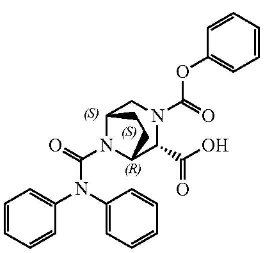 | (1R,2S,5S)-8-(diphenylcarbamoyl)-3-(phenoxycarbonyl)-3,8-diazabicyclo[3.2.1]octane-2-carboxylic acid | Compound 7 in step 2 Example 2 was replaced with <br><br> Compound 11 in step 4 was replaced with phenyl chloroformate. | $^1$H NMR (400 MHz, DMSO-d$_6$) δ 7.42-7.31 (m, 6H), 7.25-7.15 (m, 3H), 7.12-7.01 (m, 6H), 4.60-4.35 (m, 2H), 4.17-4.10 (m, 1H), 3.60-3.50 (m, 2H), 1.90-1.60 (m, 4H). <br> MS m/z (ESI): 472.1 [M + H]$^+$. |

Example 3: Preparation of (1S,2R,5R)-8-((benzyloxy)carbonyl)-3-(5H-dibenzo[b,f]azepine-5-carbonyl)-3,8-diazabicyclo[3.2.1]octane-2-carboxylic acid (C81)

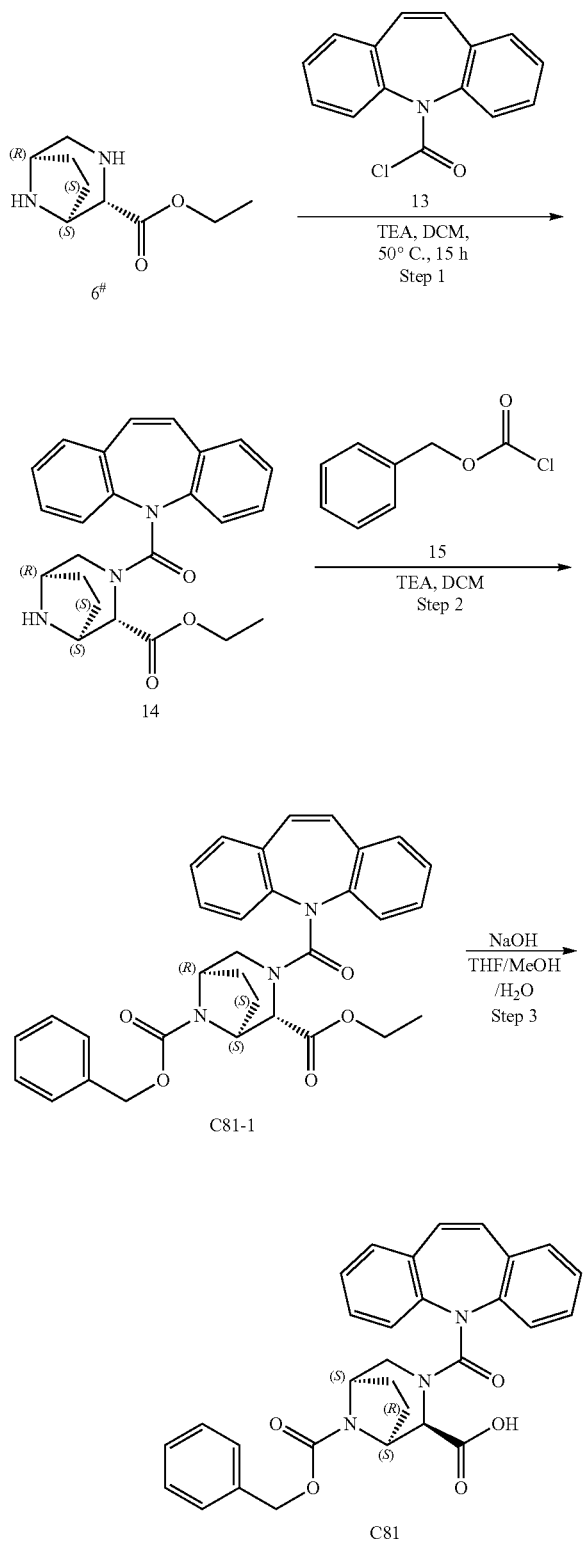

Step 1:

Compound 6# (36.8 mg, 0.2 mmol) was dissolved in dichloromethane (20 mL), and Compound 13 (51.2 mg, 0.2 mmol) and triethylamine (60.6 mg, 0.6 mmol) were then added sequentially. The mixture was reacted in a sealed tube at 50° C. for 16 hours. After the reaction was complete, 20 mL water was added to the reaction solution and extracted with dichloromethane (20 mL×3). The combined organic phases were washed with saturated brine (20 mL×2) and dried by adding anhydrous sodium sulfate for 30 min, then filtered and concentrated under reduced pressure to obtain a crude product. The resulting crude product was separated and purified by column chromatography (petroleum ether: ethyl acetate=1:1) to obtain Compound 14 (40.3 mg, a yellow solid, 50%).

$^1$H NMR (400 MHz, DMSO-$d_6$): δ 7.65-7.25 (m, 8H), 7.05 (d, J=7.5 Hz, 2H), 4.15 (m, 2H), 4.03 (dd, J=14.2, 7.1 Hz, 2H), 3.76 (d, J=4.6 Hz, 1H), 3.55 (d, J=6.3 Hz, 1H), 3.02 (dd, J=14.1, 6.8 Hz, 1H), 1.82 (m, 1H), 1.60 (m, 1H), 1.53-1.34 (m, 2H), 1.24-1.14 (t, J=7.1 Hz, 3H).

MS m/z (ESI): 404.0 [M+H]$^+$.

Step 2:

Compound 14 (40.3 mg, 0.1 mmol) was dissolved in dichloromethane (5 mL), and Compound 15 (51 mg, 0.3 mmol) and triethylamine (0.05 g, 0.5 mmol) was added sequentially. The reaction was carried out at 50° C. for 16 horns. After the reaction was complete, 20 mL water was added to the reaction solution and extracted with dichloromethane (20 mL×2). The combined organic phases were dried with anhydrous sodium sulfate (50 g) for 30 min, then filtered and concentrated under reduced pressure. The resulting crude product was separated and purified by column chromatography (petroleum ether:ethyl acetate=10:1) to obtain Compound C81-1 (25 mg, a yellow solid, 46%).

$^1$H NMR (400 MHz, CD$_3$OD): δ 7.55 (d, J=8.0 Hz, 1H), 7.49-7.39 (m, 4H), 7.34 (ddd, J=14.1, 10.6, 4.3 Hz, 8H), 7.06 (d, J=1.6 Hz, 2H), 5.04 (s, 2H), 4.12 (q, J=7.1 Hz, 2H), 3.91 (s, 1H), 3.86-3.76 (m, 1H), 3.37 (m, 1H), 3.26 (s, 2H), 1.94-1.74 (m, 1H), 1.70-1.57 (m, 1H), 1.34 (dd, J=7.4, 2.6 Hz, 2H), 1.26 (t, J=7.1 Hz, 3H).

MS m/z (ESI): 538.0 [M+H]$^+$.

Step 3:

Compound C81-1 (25 mg, 0.0466 mmol) was dissolved in a mixed solution of tetrahydrofuran, methanol and water (5 mL/5 mL/5 mL), followed by adding sodium hydroxide (5.6 mg, 0.14 mmol) and stirring at room temperature for 16 hours. After concentration, the obtained crude product was adjusted to pH 5.0 with 3N hydrochloric acid solution, and filtered. The obtained solid was washed with 10 mL water, and then dried. The obtained crude product of the compound was subjected to separation by reversed phase chromatography (acetonitrile/water (0.1% trifluoroacetic acid solution) 55/45-85/15) to obtain the target compound C81 (3.41 mg, a white solid, yield: 14.4%).

$^1$H NMR (300 MHz, DMSO-$d_6$): δ 7.29 (dd, J=40.7, 31.1 Hz, 15H), 5.01 (dd, J=15.4, 9.5 Hz, 2H), 4.60 (s, 1H), 4.32 (d, J=11.5 Hz, 1H), 3.45 (s, 1H), 3.08-2.92 (m, 2H), 1.57 (d, J=79.4 Hz, 3H), 1.22-1.17 (m, 1H).

MS m/z (ESI): 510.1 [M+H]$^+$.

The compounds in Table 5 were prepared by methods similar to that described in Example 3.

TABLE 5

| No. | Compound Structure | Compound Name | Starting material or reaction condition different from that in Example 3 | Characterization data |
|---|---|---|---|---|
| C80 | 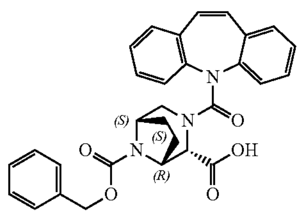 | (1R,2S,5S)-8-((benzyloxy)carbonyl)-3-(5H-dibenzo[b,f]azepine-5-carbonyl)-3,8-diazabicyclo[3.2.1]octane-2-carboxylic acid | Compound 6# in step 1 of Example 3 was replaced with compound 5. | $^1$H NMR (400 MHz, DMSO-d$_6$) δ 7.59 (s, 2H), 7.47-7.24 (m, 10H), 7.05 (s, 2H), 5.07-5.00 (m, 1H), 4.92 (s, 1H), 4.48 (d, J = 6.8 Hz, 1H), 4.06 (s, 1H), 4.01 (d, J = 2.4 Hz, 1H), 3.15-2.97 (m, 2H), 1.75-1.62 (m, 1H), 1.60-1.47 (m, 1H), 1.33-1.20 (m, 1H), 1.15-1.05 (m, 1H). MS m/z (ESI): 510.2 [M + H]$^+$. |

Example 4: preparation of (1R,2S,5S)-3-(benzyl(methyl)carbamoyl)-8-(2,2-diphenylacetyl)-3,8-diazabicyclo[3.2.1]octane-2-carboxylic acid (C62)

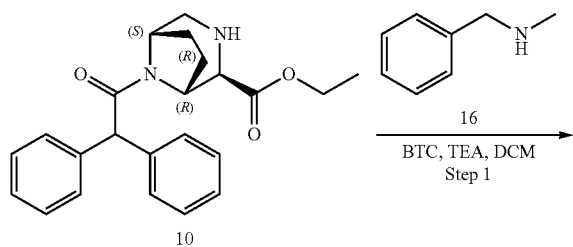

Step 1:

Compound 10 (0.1 g, 0.264 mmol) was dissolved in a dichloromethane solution (15 mL), cooled to 0° C. with an ice-water bath. Triphosgene (118 mg, 0.396 mmol) and triethylamine (82 mg, 0.792 mmol) were added to the solution and reacted at 0° C. for 2 hours. Compound 16 (48 mg, 0.396 mmol) was then added to the reaction solution, and was slowly heated up to room temperature and reacted at room temperature for 16 horns. After the reaction was complete, 50 mL water was added to the reaction solution and extracted with dichloromethane (50 mL/2). The combined organic phases were then dried by adding anhydrous sodium sulfate (30 g) for 30 min, then filtered and concentrated under reduced pressure. The resulting crude product was separated and purified by column chromatography (petroleum ether:ethyl acetate=2:3) to obtain Compound C62-1 (50 mg, a yellow oily matter, 36%).

MS m/z (ESI): 526 [M+H]$^+$.

Step 2:

Compound C62-1 (50 mg, 0.095 mmol) was dissolved in a mixed solution of tetrahydrofuran, methanol and water (5 mL/5 mL/5 mL), followed by adding sodium hydroxide (38 mg, 0.95 mmol) and stirring at room temperature for 2 hours. After concentration, the obtained crude product was adjusted to pH 5.0 with 3N hydrochloric acid solution, and extracted with ethyl acetate (20 mL/3). The combined organic phases were washed with saturated brine (20 mL×3). After that, the organic phases were dried by adding anhydrous sodium sulfate for 30 min, and then filtered. The filtrate was concentrated under reduced pressure. The resulting crude product was subjected to separation by reversed phase preparative chromatography (acetonitrile/water (0.1% trifluoroacetic acid solution) 25/75-50/50) to obtain Compound C$_{62}$ (12 mg, light yellow solid, yield: 25%).

$^1$H NMR (400 MHz, CD$_3$OD): δ 7.50-6.90 (m, 15H), 5.58-5.40 (m, 1H), 5.00-4.20 (m, 5H), 3.60-3.30 (m, 2H), 2.80-2.70 (m, 3H), 2.00-1.10 (m, 4H).

MS m/z (ESI): 498.0 [M+H]$^+$.

The compounds in Table 6 were prepared by methods similar to that described in Example 4.

TABLE 6

| No. | Compound Structure | Compound Name | Starting material or reaction condition different from that in Example 4 | Characterization data |
|---|---|---|---|---|
| C64 | 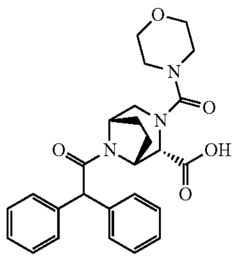 [SMILES: O=C(O)[C@@H]1[C@H]2CC[C@@H](CN1C(=O)N1CCOCC1)N2C(=O)C(c1ccccc1)c1ccccc1] | (1R,2S,5S)-8-(2,2-diphenylacetyl)-3-(morpholine-4-carbonyl)-3,8-diazabicyclo[3.2.1]octane-2-carboxylic acid | Compound 16 in step 1 of Example 4 was replaced with morpholine. | $^1$H NMR (400 MHz, DMSO-d$_6$): δ 7.50-7.00 (m, 10H), 5.43-4.84 (m, 1H), 5.00-4.20 (m, 3H), 3.60-2.80 (m, 10H), 2.00-1.10 (m, 4H). MS m/z (ESI): 464.1 [M + H]$^+$. |
| C19 | 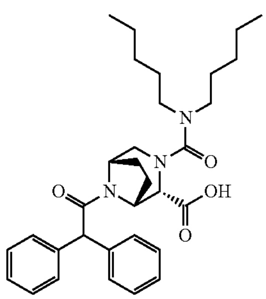 [SMILES: CCCCCN(CCCCC)C(=O)N1C[C@@H]2CC[C@H]([C@H]1C(=O)O)N2C(=O)C(c1ccccc1)c1ccccc1] | (1R,2S,5S)-3-(dipentylcarbamoyl)-8-(2,2-diphenylacetyl)-3,8-diazabicyclo[3.2.1]octane-2-carboxylic acid | Compound 16 in step 1 of Example 4 was replaced with Di-pentyl amine. | $^1$H NMR (400 MHz, CD$_3$OD): δ 7.42-7.12 (m, 10H), 5.57-5.41 (m, 1H), 4.83 (s, 1H), 4.76-4.73 (m, 1H), 4.58-4.46 (m, 1H), 3.62-3.49 (m, 3H), 3.31-3.14 (m, 2H), 3.09-3.00 (m, 2H), 2.79-2.72 (m, 1H), 1.96-1.89 (m, 1H), 1.80-1.70 (m, 3H), 1.53-1.49 (m, 4H), 1.43-1.23 (m, 8H), 0.96-0.90 (m, 8H). MS m/z (ESI): 534.1 [M + H]$^+$. |
| C61 | 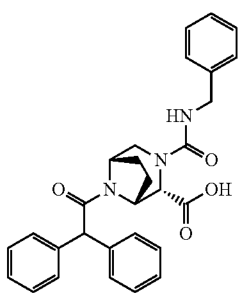 [SMILES: O=C(O)[C@@H]1[C@H]2CC[C@@H](CN1C(=O)NCc1ccccc1)N2C(=O)C(c1ccccc1)c1ccccc1] | (1R,2S,5S)-3-(benzylcarbamoyl)-8-(2,2-diphenylacetyl)-3,8-diazabicyclo[3.2.1]octane-2-carboxylic acid | Compound 16 in step 1 of Example 4 was replaced with benzylamine. | $^1$H NMR (400 MHz, CD$_3$OD) δ 7.45-7.11 (m, 16H), 5.62 (s, 1H), 5.47 (d, J = 46.9 Hz, 1H), 4.83 (s, 2H), 4.45-4.33 (m, 2H), 4.31-4.25 (m, 1H), 3.60 (s, 1H), 1.95-1.82 (m, 1H), 1.79-1.62 (m, 2H), 1.38-1.26 (m, 1H). MS m/z (ESI): 484.0 [M + H]$^+$. |
| C116 | 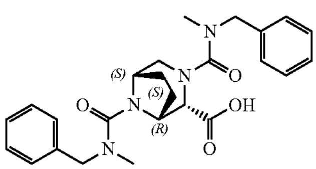 | (1R,2S,5S)-3,8-bis(benzyl(methyl)carbamoyl)-3,8-diazabicyclo[3.2.1]octane-2-carboxylic acid | Compound 10 in step 1 of Example 4 was replaced with compound 6. The amount of compound 16 was increased from 1.5 times in Example 4 to 2.5 times higher than compound 6. | $^1$H NMR (400 MHz, CD$_3$OD) δ 7.38-7.32 (m, 4H), 7.31-7.23 (m, 6H), 4.73-4.66 (m, 2H), 4.59 (d, J = 14.8 Hz, 1H), 4.51 (d, J = 15.2 Hz, 1H), 4.40 (d, J = 15.2 Hz, 1H), 4.29 (d, J = 15.2 Hz, 1H), 4.06 (d, J = 6.0 Hz, 1H), 3.77 (d, J = 10.4 Hz, 1H), 3.49 (dd, J = 12.4, 2.0 Hz, 1H), 2.84 (s, 3H), 2.76 (s, 3H), 2.10-2.00 (m, 1H), 1.96-1.70 (m, 3H). MS m/z (ESI): 451.0 [M + H]$^+$. |

Example 5: preparation of (1R,2S,5S)-3-(2,2-diphenylacetyl)-8-(phenoxycarbonyl)-3,8-diazabicyclo[3.2.1]octane-2-carboxylic acid (C79) and (1R,2S,5S)-8-(benzyl(methyl)carbamoyl)-3-(2,2-diphenylacetyl)-3,8-diazabicyclo[3.2.1]octane-2-carboxylic acid (C82)

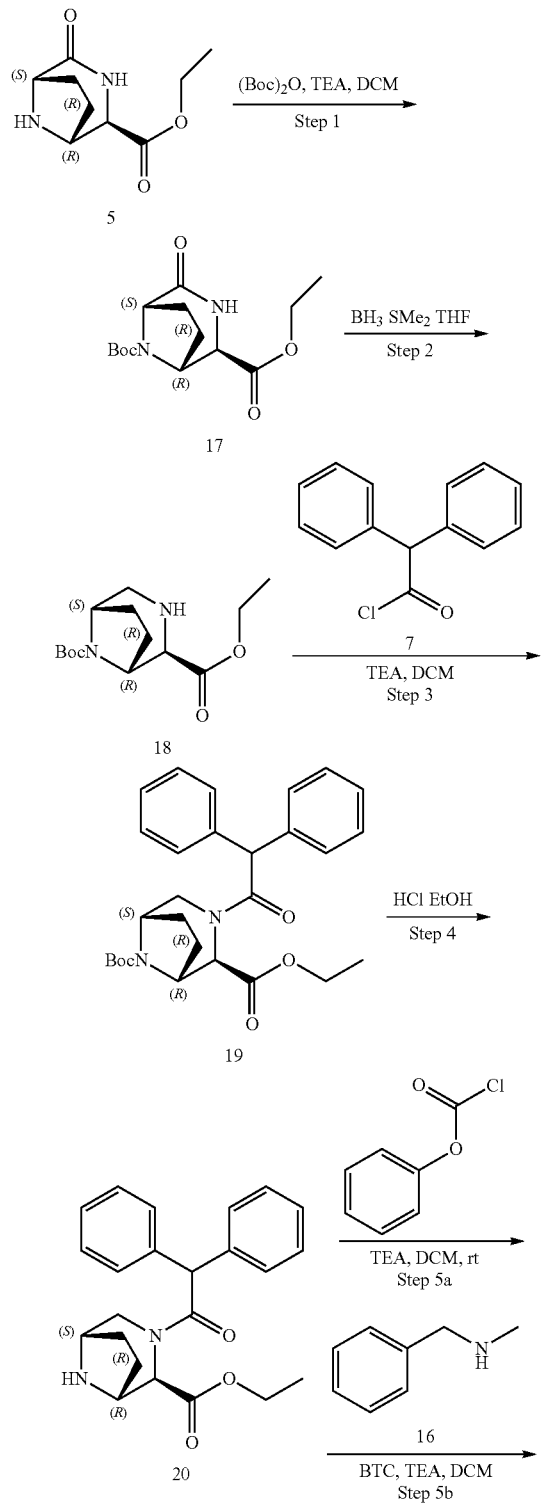

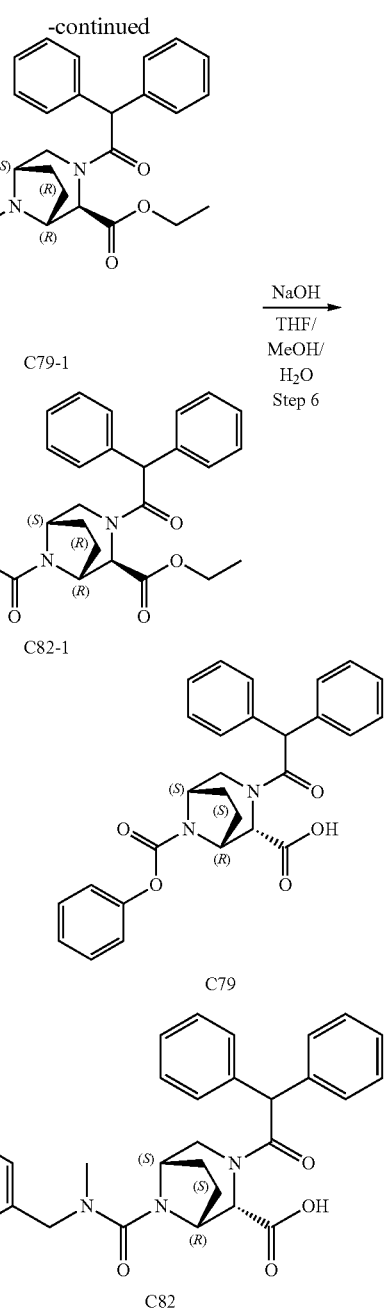

Step 1:

Compound 5 (1.98 g, 10 mmol) was dissolved in a dichloromethane solution (40 mL) and cooled in an ice-water bath. Di-tert-butyl dicarbonate (2.18 g, 10 mmol) and triethylamine (3.03 g, 30 mmol) were sequentially added and reacted at room temperature for 16 hours. After the reaction was complete, 50 mL water was added to the reaction solution and extracted with dichloromethane (50 mL/2). The combined organic phases were then dried by adding anhydrous sodium sulfate (100 g) for 30 min, then filtered and concentrated under reduced pressure. The resulting crude product was separated and purified by column chromatography (petroleum ether:ethyl acetate=1:1) to obtain Compound 17 (2.3 g, a yellow oily matter, 77%).

¹H NMR (400 MHz, CD₃OD): δ 7.65 (brs, 1H), 4.50-4.40 (m, 2H), 4.25-4.15 (m, 2H), 4.15-4.05 (m, 1H), 2.10-1.90 (m, 2H), 1.85-1.75 (m, 1H), 1.60-1.50 (m, 1H), 1.42 (s, 9H), 1.23 (t, J=7.2 Hz, 3H).

MS m/z (ESI): 321.0 [M+Na]+.

Step 2:

Compound 17 (2.3 g, 7.71 mmol) was dissolved in a solution of borane dimethylsulfide in tetrahydrofuran (2M, 20 mL), purged with nitrogen for 5 times, and reacted at room temperature in a nitrogen atmosphere for 16 horns. After the reaction was complete, the reaction was slowly quenched with methanol and stirred at 50° C. for 16 hours. A crude product of compound 18 was obtained by concentration, and was separated and purified by column chromatography (petroleum ether:ethyl acetate=3:7) to obtain Compound 18 (1.1 g, a yellow oily matter, crude product).

¹H NMR (400 MHz, DMSO-d₆): δ 4.2-4.15 (m, 1H), 4.11 (q, J=7.2 Hz, 2H), 3.93 (s, 1H), 3.52 (s, 1H), 2.80-2.55 (m, 2H), 1.80-1.55 (m, 4H), 1.42 (s, 9H), 1.20 (t, J=7.2 Hz, 3H).

MS m/z (ESI): 285.1 [M+Na]+.

Step 3:

Compound 18 (0.55 g, 1.934 mmol) was dissolved in dichloromethane (20 mL). To the solution, Compound 7 (0.446 g, 1.934 mmol) and triethylamine (0.586 g, 5.80 mmol) was then added sequentially and reacted at room temperature for 48 hours. LC-MS indicated that the reaction of the starting materials was complete. The solution was then quenched by adding water (30 mL), and extracted with dichloromethane (20 mL/3). The combined organic phases were washed with saturated brine (50 mL×3). The organic phases were dried by adding anhydrous sodium sulfate for 30 min, and then filtered. The filtrate was concentrated under reduced pressure. The resulting crude product was subjected to separation by column chromatography (petroleum ether: methyl tert-butyl ether=2:3) to obtain Compound 19 (0.55 g, a dark yellow solid, crude product).

¹H NMR (400 MHz, CD₃OD): δ 7.35-7.10 (m, 10H), 5.43 (s, 1H), 4.20-4.00 (m, 5H), 3.60-3.40 (m, 2H), 2.00-1.50 (m, 4H), 1.34 (s, 9H), 1.19 (t, J=7.2 Hz, 3H).

MS m/z (ESI): 479.0 [M+H]⁺.

Step 4:

Compound 19 (0.55 g, 1.15 mmol) was dissolved in a solution of hydrochloric acid in ethanol (8M, 10 mL), and reacted at room temperature for 2 hours. After the reaction was complete, a crude product of compound 20 was obtained by concentration (0.35 g, a yellow solid, 81%).

MS m/z (ESI): 379.0 [M+H]⁺.

Step 5a:

Compound 20 (50 mg, 0.132 mmol) was dissolved in a dichloromethane solution (20 mL). Phenyl chloroformate (42 mg, 0.264 mmol) and triethylamine (0.133 g, 1.32 mmol) were added sequentially, and reacted at room temperature for 16 horns. After the reaction was complete, 50 mL water was added to the reaction solution and extracted with dichloromethane (50 mL×2). The combined organic phases were dried with anhydrous sodium sulfate (100 g) for 30 min, then filtered and concentrated under reduced pressure. The resulting crude product was separated and purified by column chromatography (petroleum ether:ethyl acetate=3:2) to obtain Compound C79-1 (50 g, a yellow solid, 76%).

MS m/z (ESI): 499.0 [M+H]⁺.

Step 5b:

Compound 20 (50 mg, 0.132 mmol) was dissolved in dichloromethane (15 mL), cooled to 0° C. in an ice-water bath. To the solution, triphosgene (59 mg, 0.198 mmol) and triethylamine (41 mg, 0.396 mmol) were added and reacted at 0° C. for 2 horns. Compound 16 (24 mg, 0.198 mmol) was then added to the reaction solution, and was slowly heated up to room temperature for further reaction at room temperature for 16 hours. After the reaction was complete, 50 mL water was added to the reaction solution and extracted with dichloromethane (50 mL/2). The combined organic phases were then dried by adding anhydrous sodium sulfate (30 g) for 30 min, then filtered and concentrated under reduced pressure. The resulting crude product was separated and purified by column chromatography (petroleum ether: ethyl acetate=2:3) to obtain Compound C82-1 (50 mg, a yellow oily matter, 72%).

MS m/z (ESI): 526.0 [M+H]⁺.

Step 6:

Compound C79-1 (50 mg, 0.1 mmol) was dissolved in a mixed solution of tetrahydrofuran, methanol and water (5 mL/5 mL/5 mL). Sodium hydroxide (40 mg, 1 mmol) was added, stirred at room temperature for 3 hours and then concentrated. The obtained crude product was adjusted to pH 5.0 with 3N hydrochloric acid solution, and extracted with ethyl acetate (20 mL/3). The combined organic phases were washed with saturated brine (50 mL×3). The organic phases were dried by adding anhydrous sodium sulfate for 30 min, and then filtered The filtrate was concentrated under reduced pressure. The resulting crude product was subjected to separation by reversed phase preparative chromatography (acetonitrile/water (0.1% trifluoroacetic acid solution) 40/60-20/80) to obtain Compound C79 (25 mg, a light yellow solid, yield: 53%).

¹H NMR (400 MHz, CD₃OD): δ 12.995 (brs, 1H), 7.50-6.90 (m, 15H), 5.60-5.30 (m, 1H), 4.80-4.60 (m, 2H), 4.20-4.10 (m, 1H), 3.70-3.40 (m, 2H), 2.10-1.40 (m, 4H).

MS m/z (ESI): 471.0 [M+H]⁺.

Compound C82-1 (50 mg, 0.095 mmol) was dissolved in a mixed solution of tetrahydrofuran, methanol and water (5 mL/5 mL/5 mL). Sodium hydroxide (38 mg, 0.95 mmol) was added, stirred at room temperature for 2 hours, and then concentrated. The obtained crude product was adjusted to pH 5.0 with 3N hydrochloric acid solution, and extracted with ethyl acetate (20 mL/3). The combined organic phases were washed with saturated brine (20 mL×3). The organic phases were dried by adding anhydrous sodium sulfate for 30 min and then filtered. The filtrate was concentrated under reduced pressure. The resulting crude product was subjected to separation by reversed phase preparative chromatography (acetonitrile/water (0.1% trifluoroacetic acid solution) 25/75-50/50) to obtain Compound C82 (30 mg, a light yellow solid, yield: 63%).

¹H NMR (400 MHz, CD₃OD): δ 7.50-6.90 (m, 15H), 5.46-5.38 (m, 1H), 4.70-4.20 (m, 4H), 4.20-4.05 (m, 1H), 3.80-3.60 (m, 2H), 2.85-2.75 (m, 3H), 2.05-1.45 (m, 4H).

MS m/z (ESI): 498.1 [M+H]⁺.

The compounds in Table 7 were prepared by methods similar to that described in Example 5,

TABLE 7

| No. | Compound Structure | Compound Name | Starting material or reagent different from that in Example 5 | Characterization data |
|---|---|---|---|---|
| C78 | 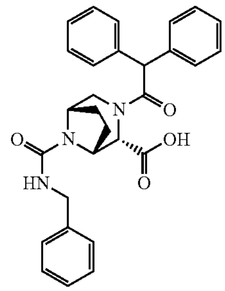 [SMILES: O=C(O)[C@@H]1[C@H]2CC[C@@H](CN1C(=O)C(c1ccccc1)c1ccccc1)N2C(=O)NCc1ccccc1] | (1R,2S,5S)-8-(benzylcarbamoyl)-3-(2,2-diphenylacetyl)-3,8-diazabicyclo[3.2.1]octane-2-carboxylic acid | Compound 16 in step 5b of Example 5 was replaced with benzylamine. The reaction in step 5a did not take place. | $^1$H NMR (400 Hz, CD$_3$OD) δ 7.44-7.08 (m, 15H), 5.46 (s, 1H), 5.23 (s, 1H), 4.52-4.49 (m, 1H), 4.45-4.21 (m, 3H), 4.17 (s, 1H), 3.75 (s, 1H), 3.58-3.55 (m, 1H), 2.23-2.19 (m, 1H), 2.05 (s, 1H), 1.95-1.91 (m, 2H). MS m/z (ESI): 484.0 [M + H]$^+$. |
| C76 | 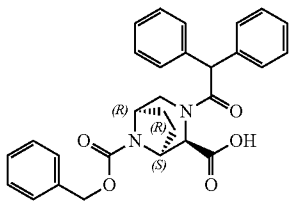 | (1S,2R,5R)-8-((benzyloxy)carbonyl)-3-(2,2-diphenylacetyl)-3,8-diazabicyclo[3.2.1]octane-2-carboxylic acid | Compound 5 in step 1 of Example 5 was replaced with compound 5$^\#$. In step 5a, the phenyl chloroformate was replaced with benzyl chloroformate; the reaction temperature was 50° C. and the reaction time was 48 hours. The reaction time in step 6 was 16 hours. The reaction in step 5b did not take place. | $^1$H NMR (400 MHz, DMSO-d$_6$): δ 12.88 (s, 1H), 7.43-7.07 (m, 15H), 5.51 (s, 1H), 5.14-4.90 (m, 3H), 4.69 (d, J = 6.0 Hz, 2H), 4.20 (s, 1H), 3.73 (d, J = 11.2 Hz, 1H), 1.85 (s, 1H), 1.70-1.52 (m, 2H), 1.12 (s, 1H). MS m/z (ESI): 485.1 [M + H]$^+$. |
| C157 | 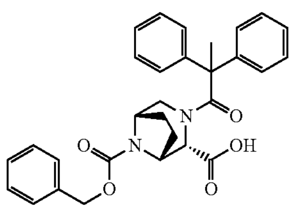 [SMILES: CC(C(=O)N1C[C@@H]2CC[C@H]([C@H]1C(=O)O)N2C(=O)OCc1ccccc1)(c1ccccc1)c1ccccc1] | (1R,2S,5S)-8-((benzyloxy)carbonyl)-3-(2,2-diphenylacetyl)-3,8-diazabicyclo[3.2.1]octane-2-carboxylic acid | Compound 7 in step 3 of Example 5 was replaced with [structure shown]. The phenyl chloroformate in step 5a was replaced with benzyl chloroformate. The reaction in step 5b did not take place. | $^1$H NMR (400 MHz, CD$_3$OD) δ 7.60-7.50 (m, 4H), 7.47-7.19 (m, 11H), 5.11 (d, J = 12.4 Hz, 1H), 4.98 (d, J = 12.8 Hz, 1H), 4.84 (s, 1H), 4.80 (d, J = 6.8 Hz, 1H), 3.85 (s, 1H), 3.40-3.35 (m, 1H), 3.19 (d, J = 12.4 Hz, 1H), 1.90-1.75 (m, 4H), 1.50-1.35 (m, 1H), 1.32-1.16 (m, 2H). MS m/z (ESI): 498.8 [M + H]$^+$. |
| C222 | 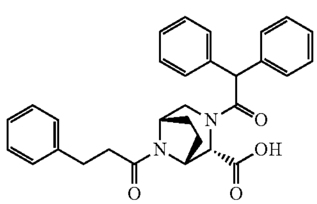 [SMILES: O=C(O)[C@@H]1[C@H]2CC[C@@H](CN1C(=O)C(c1ccccc1)c1ccccc1)N2C(=O)CCc1ccccc1] | (1R,2S,5S)-3-(2,2-diphenylacetyl)-8-(3-phenylpropionyl)-3,8-diazabicyclo[3.2.1]octane-2-carboxylic acid | The phenyl chloroformate in step 5a of Example 5 was replaced with [structure shown] and the reaction was performed at room temperature for 12 hours. The reaction in step 5b did not take place. | 1H NMR (400 MHz, DMSO-d$_6$) δ 7.50-7.00 (m, 15H), 5.55-5.40 (m, 1H), 4.90-4.25 (m, 3H), 3.75-3.55 (m, 1H), 3.40-3.00 (m, 1H), 2.85-2.40 (m, 4H), 1.75-1.00 (m, 6H). MS m/z (ESI): 483.0 [M + H]$^+$. |
| C223 | 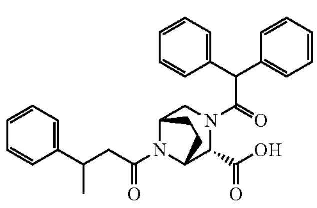 [SMILES: CC(CC(=O)N1[C@H]2CC[C@@H]1[C@@H](C(=O)O)N(C(=O)C(c1ccccc1)c1ccccc1)C2)c1ccccc1] | (1R,2S,5S)-3-(2,2-diphenylacetyl)-8-(3-phenylbutyryl)-3,8-diazabicyclo[3.2.1]octane-2-carboxylic acid | The phenyl chloroformate in step 5a of Example 5 was replaced with [structure shown], | $^1$H NMR (400 MHz, DMSO-d$_6$) δ 7.50-7.00 (m, 15H), 5.55-5.40 (m, 1H), 4.87-4.25 (m, 3H), 3.75-3.60 (m, 1H), 3.30-3.00 (m, 2H), 2.75-2.51 (m, 1H), 2.49-2.25 (m, 1H), 1.75-1.00 (m, 7H). MS m/z (ESI): 497.1 [M + H]$^+$. |

TABLE 7-continued

| No. | Compound Structure | Compound Name | Starting material or reagent different from that in Example 5 | Characterization data |
|---|---|---|---|---|
| | | | and the reaction was performed at room temperature for 6 hours. The reaction in step 5b did not take place. | |
| C230 | 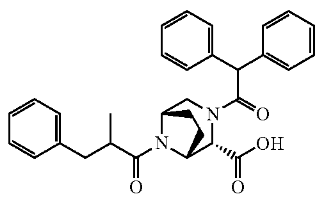 [SMILES: CC(Cc1ccccc1)C(=O)N1[C@H]2CC[C@@H]1[C@@H](C(=O)O)N(C(=O)C(c1ccccc1)c1ccccc1)C2] | (1R,2S,5S)-3-(2,2-diphenylacetyl)-8-(2-methyl-3-phenylpropionyl)-3,8-diazabicyclo[3.2.1]octane-2-carboxylic acid | The phenyl chloroformate in step 5a of Example 5 was replaced with <br><br> and the reaction was performed at room temperature for 6 hours. The reaction in step 5b did not take place. | $^1$HNMR (400 MHz, DMSO-d6) δ 7.41-7.02 (m, 15H), 5.56-5.40 (m, 1H), 4.96-4.78 (m, 1H), 4.61 (d, J = 20.7 Hz, 1H), 4.50 (s, 1H), 4.42-4.28 (m, 1H), 4.25 (s, 1H), 4.12-3.97 (m, 1H), 3.63 (dd, J = 26.0, 11.9 Hz, 1H), 3.03-2.86 (m, 2H), 2.61 (s, 1H), 1.36 (s, 1H), 1.26-1.15 (m, 1H), 1.09-0.95 (m, 3H), 0.92-0.85 (m, 1H), 0.80 (s, 1H). MS m/z (ESI): 496.8 [M + H]$^+$. |
| C231 | 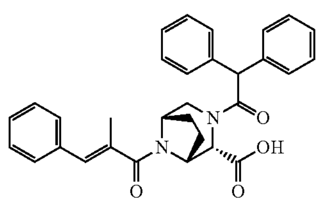 [SMILES: C/C(=C\c1ccccc1)C(=O)N1[C@H]2CC[C@@H]1[C@@H](C(=O)O)N(C(=O)C(c1ccccc1)c1ccccc1)C2] | (1R,2S,5S)-3-(2,2-diphenylacetyl)-8-((E)-2-methyl-3-phenylacryloyl)-3,8-diazabicyclo[3.2.1]octane-2-carboxylic acid | The phenyl chloroformate in step 5a of Example 5 was replaced with <br><br> and the reaction was performed at room temperature for 6 hours. The reaction in step 5b did not take place. | $^1$H NMR (400 MHz, DMSO-d$_6$) δ 7.50-7.00 (m, 15H), 6.54 (s, 1H), 5.55-5.30 (m, 1H), 4.87-4.25 (m, 3H), 3.77 (d, J = 10.8 Hz, 1H), 3.50 (d, J = 10.8 Hz, 1H), 1.93 (s, 3H), 1.75-1.00 (m, 4H). MS m/z (ESI): 495.0 [M + H]$^+$. |
| C194 | 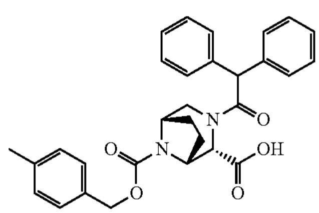 [SMILES: Cc1ccc(COC(=O)N2[C@H]3CC[C@@H]2[C@@H](C(=O)O)N(C(=O)C(c2ccccc2)c2ccccc2)C3)cc1] | (1R,2S,5S)-3-(2,2-diphenylacetyl)-8-(((4-methylbenzyl)oxy)carbonyl)-3,8-diazabicyclo[3.2.1]octane-2-carboxylic acid | The phenyl chloroformate in step 5a of Example 5 was replaced with <br><br> The reaction in step 5b did not take place. | $^1$H NMR (400 MHz, DMSO-d$_6$) δ 7.42-7.07 (m, 14H), 5.70-5.30 (m, 1H), 5.10-5.01 (m, 1H), 4.70-4.55 (m, 2H), 4.32-4.07 (m, 2H), 3.72 (d, J = 10.4 Hz, 1H), 3.55-3.30 (m, 1H), 2.30 (s, 3H), 1.85-1.30 (m, 4H). MS m/z (ESI): 499.1 [M + H]$^+$. |
| C83 | 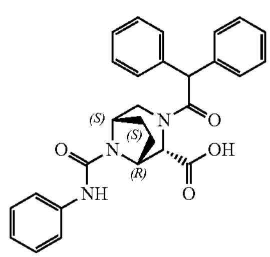 | (1R,2S,5S)-3-(2,2-diphenylacetyl)-8-(phenylcarbamoyl)-3,8-diazabicyclo[3.2.1]octane-2-carboxylic acid | Compound 16 in step 5b of Example 5 was replaced with phenylamine. The reaction in step 5a did not take place. | $^1$H NMR (400 MHz, CD$_3$OD): δ 7.50-6.90 (m, 15H), 5.49-5.27 (s, 1H), 5.08 (d, J = 7.2 Hz, 1H), 4.97 (s, 1H), 4.60-4.50 (m, 1H), 4.40-4.20 (m, 1H), 3.81 (d, J = 12.4 Hz, 1H), 3.66 (d, J = 12.4 Hz, 1H), 2.10-1.50 (m, 4H). MS m/z (ESI): 470.1 [M + H]$^+$. |

TABLE 7-continued

| No. | Compound Structure | Compound Name | Starting material or reagent different from that in Example 5 | Characterization data |
|---|---|---|---|---|
| C123 | 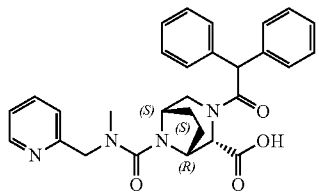 | (1R,2S,5S)-3-(2,2-diphenylacetyl)-8-(methyl(pyridine-2-ylmethyl)carbamoyl)-3,8-diazabicyclo[3.2.1]octane-2-carboxylic acid | Compound 16 in step 5b of Example 5 was replaced with <br><br> The reaction in step 5a did not take place. | $^1$H NMR (400 MHz, DMSO-d$_6$) δ 8.62 (d, J = 4.4 Hz 1H), 8.03 (s, 1H), 7.55-7.07 (m, 13H), 5.55-5.30 (m, 1H), 4.80-4.40 (m, 3H), 4.25-3.95 (m, 2H), 3.75-3.45 (m, 2H), 2.95-2.85 (m, 3H), 1.85-1.30 (m, 4H). <br> MS m/z (ESI): 499.1 [M + H]$^+$. |
| C188 | 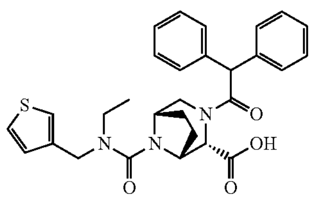 [SMILES: CCN(Cc1ccsc1)C(=O)N1[C@H]2CC[C@@H]1[C@@H](C(=O)O)N(C(=O)C(c1ccccc1)c1ccccc1)C2] | (1R,2S,5S)-3-(2,2-diphenylacetyl)-8-(ethyl(thiophene-3-ylmethyl)carbamoyl)-3,8-diazabicyclo[3.2.1]octane-2-carboxylic acid | Compound 16 in step 5b of Example 5 was replaced with <br><br> The reaction in step 5a did not take place. | $^1$H NMR (400 MHz, DMSO-d$_6$) δ 7.54-6.91 (m, 13H), 5.56-5.30 (m, 1H), 4.83-4.55 (m, 1H), 4.48-4.32 (m, 2H), 4.29-4.19 (m, 1H), 4.15-3.96 (m, 1H), 3.87 (d, J = 5.7 Hz, 1H), 3.70 (d, J = 11.3 Hz, 1H), 3.49 (d, J = 11.9 Hz, 1H), 3.28-2.95 (m, 2H), 1.86-1.73 (m, 1H), 1.59 (s, 1H), 1.52-1.40 (m, 1H), 1.35 (s, 1H), 1.00 (dt, J = 13.8, 7.1 Hz, 3H). <br> MS m/z (ESI): 518.1 [M + H ]$^+$. |
| C189 | 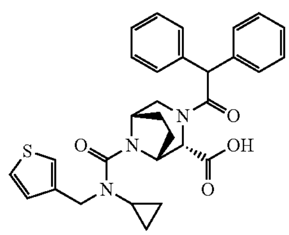 [SMILES: O=C(O)[C@@H]1[C@H]2CC[C@@H](CN1C(=O)C(c1ccccc1)c1ccccc1)N2C(=O)N(Cc1ccsc1)C1CC1] | (1R,2S,5S)-8-(cyclopropyl(thiophene-3-yl-methyl)carbamoyl)-3-(2,2-diphenylacetyl)-3,8-diazabicyclo[3.2.1]octane-2-carboxylic acid | Compound 16 in step 5b of Example 5 was replaced with <br><br> The reaction in step 5a did not take place. | $^1$H NMR (400 MHz, DMSO-d$_6$) δ 7.50-7.45 (m, 1H), 7.40-7.10 (m, 11H), 6.93-6.89 (m, 1H), 5.45-5.35 (m, 1H), 4.60 (d, J = 14.7 Hz, 1H), 4.37 (s, 1H), 4.31 (s, 1H), 4.21 (s, 1H), 4.10 (s, 1H), 3.48-3.38 (m, 2H), 2.46-2.40 (m, 1H), 2.00 (s, 1H), 1.76 (s, 1H), 1.60 (s, 1H), 1.39 (s, 2H), 0.84 (d, J = 92.5 Hz, 2H), 0.58 (s, 2H). <br> MS m/z (ESI): 529.6 [M + H]$^+$. |
| C277 | 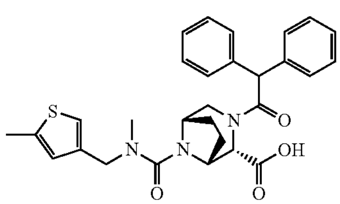 [SMILES: Cc1cc(CN(C)C(=O)N2[C@H]3CC[C@@H]2[C@@H](C(=O)O)N(C(=O)C(c2ccccc2)c2ccccc2)C3)cs1] | (1R,2S,5S)-3-(2,2-diphenylacetyl)-8-(methyl((5-methylthiophen-3-yl)methyl)carbamoyl)-3,8-diazabicyclo[3.2.1]octane-2-carboxylic acid | Compound 16 in step 5b of Example 5 was replaced with <br><br> The reaction in step 5a did not take place. | $^1$H NMR (400 MHz, DMSO-d$_6$) δ 12.87 (s, 1H), 7.40-7.23 (m, 6H), 7.23-7.10 (m, 3H), 7.01 (d, J = 16.0 Hz, 1H), 6.64 (s, 1H), 5.45 (s, 1H), 4.60-4.40 (m, 2H), 4.31-4.11 (m, 3H), 3.71 (s, 1H), 3.50 (d, J = 12.4 Hz, 1H), 2.77-2.66 (m, 3H), 2.40 (s, 3H), 2.09-1.74 (m, 1H), 1.66-1.40 (m, 2H). <br> MS m/z (ESI): 518.1 [M + H ]$^+$. |
| C278 | 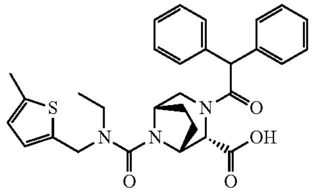 [SMILES: CCN(Cc1ccc(C)s1)C(=O)N1[C@H]2CC[C@@H]1[C@@H](C(=O)O)N(C(=O)C(c1ccccc1)c1ccccc1)C2] | (1R,2S,5S)-3-(2,2-diphenylacetyl)-8-(ethyl((5-methylthiophen-2-yl)methyl)carbamoyl)-3,8-diazabicyclo[3.2.1]octane-2-carboxylic acid | Compound 16 in step 5b of Example 5 was replaced with <br><br> The reaction in step 5a did not take place. | $^1$HNMR (400 MHz, DMSO-d$_6$) δ 7.40-7.05 (m, 10H), 6.78-6.73 (m, 1H), 6.63-6.59 (m, 1H), 5.51-5.37 (m, 1H), 4.75-4.32 (m, 4H), 4.13-3.84 (m, 2H), 3.74-3.44 (m, 2H), 3.16-3.02 (m, 2H), 2.37 (s, 3H), 1.85-1.25 (m, 4H), 1.02 (t, J = 7.2 Hz, 3H). <br> MS m/z (ESI): 554.1 [M + Na]$^+$. |

TABLE 7-continued

| No. | Compound Structure | Compound Name | Starting material or reagent different from that in Example 5 | Characterization data |
|---|---|---|---|---|
| C279 | 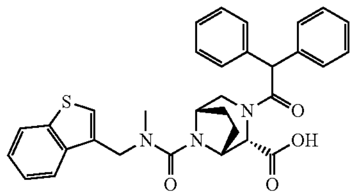 [SMILES: CN(Cc1csc2ccccc12)C(=O)N1[C@H]2CC[C@@H]1[C@@H](C(=O)O)N(C(=O)C(c1ccccc1)c1ccccc1)C2] | (1R,2S,5S)-8-(benzo[b]thiophene-3-ylmethyl)(methyl)carbamoyl)-3-(2,2-diphenylacetyl)-3,8-diazabicyclo[3.2.1]octane-2-carboxylic acid | Compound 16 in step 6 5b of Example 5 was replaced with <br><br> The reaction in step 5a did not take place. | ¹HNMR (400 MHz, DMSO-d₆) 8.02-7.97 (m, 1H), 7.76-7.68 (m, 1H), 7.61-7.54 (m, 1H), 7.44-7.07 (m, 12H), 5.48-5.32 (m, 1H), 4.90-4.75 (m, 1H), 4.64-4.47 (m, 2H), 4.25-3.90 (m, 2H), 3.86-3.45 (m, 2H), 2.80-2.70 (m, 3H), 1.90-1.10 (m, 4H). MS m/z (ESI): 554.1 [M + H]⁺. |
| 23 | 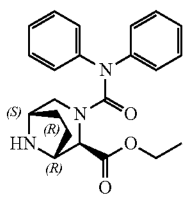 | (1R,2R,5S)-3-(diphenylcarbamoyl)-3,8-diazabicyclo[3.2.1]octane-2-carboxylic acid | Compound 7 in step 3 of Example 5 was replaced with <br><br> The reactions in the steps 5a, 5b and 6 did not take place. | ¹H NMR (400 MHz DMSO-d₆) δ 7.39 (t, J = 8.0 Hz, 4H), 7.21 (t, J = 7.6 Hz, 2H), 7.07 (dd, J = 8.8, 0.8 Hz, 4H), 4.80 (s, 1H), 4.33-4.15 (m, 4H), 3.90 (s, 1H), 3.57 (d, J = 12.4 Hz, 1H), 3.14 (d, J = 13.2 Hz, 1H), 2.13-1.87 (m, 3H), 1.70-1.45 (m, 1H), 1.29 (t, J = 7.2 Hz, 3H). m/z (ESI): 380.1 [M + H]⁺. |
| C115 | 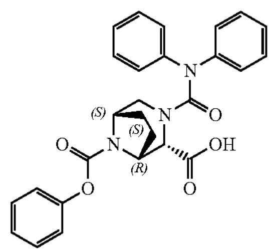 | (1R,2S,5S)-3-(diphenylcarbamoyl)-8-(phenoxycarbonyl)-3,8-diazabicyclo[3.2.1]octane-2-carboxylic acid | Compound 20 in step 5a of Example 5 was replaced with Compound 23. The reaction in step 5b did not take place. | ¹H NMR (400 MHz, DMSO-d₆) δ 7.45-7.32 (m, 6H), 7.31-7.15 (m, 4H), 7.12-7.05 (m, 2H), 7.05-6.96 (m, 3H), 4.80-4.10 (m, 3H), 3.50-3.30 (m, 2H), 2.0-1.70 (m, 3H), 1.50-MS m/z (ESI): 472.2 [M + H]⁺. |
| C112 | 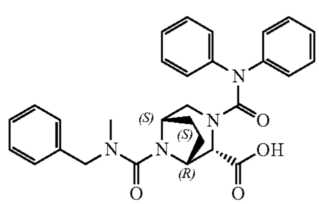 | (1R,2S,5S)-8-(benzyl(methyl)carbamoyl)-3-(diphenylcarbamoyl)-3,8-diazabicyclo[3.2.1]octane-2-carboxylic acid | Compound 20 in step 5b of Example 5 was replaced with Compound 23. The reaction in step 5a did not take place. | ¹H NMR (400 MHz, DMSO-d₆) δ 7.50-6.89 (m, 15H), 4.51-4.13 (m, 4H), 3.91 (s, 1H), 3.45-3.25 (m, 2H), 2.70 (s, 3H), 1.75-1.20 (m, 4H). MS m/z (ESI): 499.1 [M + H]⁺. |
| C84 | 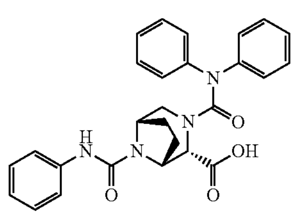 [SMILES: O=C(O)[C@@H]1[C@H]2CC[C@@H](CN1C(=O)N(c1ccccc1)c1ccccc1)N2C(=O)Nc1ccccc1] | (1R,2S,5S)-3-(diphenylcarbamoyl)-8-(phenylcarbamoyl)-3,8-diazabicyclo[3.2.1]octane-2-carboxylic acid | Compound 20 in step 5b of Example 5 was replaced with Compound 23. Compound 16 was replaced with phenylamine. The reaction in step 5a did not take place. | ¹H NMR (400 MHz, DMSO-d₆) δ 8.57 (s, 1H), 7.55-7.30 (m, 7H), 7.25-7.15 (m, 2H), 7.03 (d, J = 7.6 Hz, 3H), 6.93 (t, J = 7.6 Hz, 1H), 4.85 (s, 1H), 4.37 (s, 2H), 3.43 (d, J = 12.0 Hz, 1H), 3.30 (d, J = 13.2 Hz, 1H), 1.85-1.30 (m, 4H). MS m/z (ESI): 471.2 [M + H]⁺. |
| C117 | 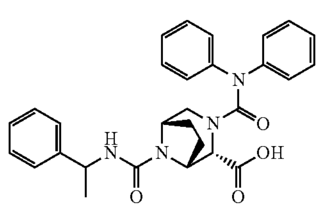 [SMILES: CC(NC(=O)N1[C@H]2CC[C@@H]1[C@@H](C(=O)O)N(C(=O)N(c1ccccc1)c1ccccc1)C2)c1ccccc1] | (1R,2S,5S)-3-(diphenylcarbamoyl)-8-((1-phenylethyl)carbamoyl)-3,8-diazabicyclo[3.2.1]octane-2-carboxylic acid | Compound 20 in step 5b of Example 5 was replaced with Compound 23. Compound 16 was replaced with <br><br> | ¹H NMR (400 MHz, CD₃OD) δ 7.37 (t, J = 8.0 Hz, 4H), 7.33-7.25 (m, 5H), 7.24-7.17 (m, 3H), 7.13-7.08 (m, 3H), 4.87-4.80 (m, 2H), 4.60-4.50 (m, 1H), 4.35-4.25 (m, 1H), 3.60-3.45 (m, 2H), 1.85-1.50 (m, 4H), 1.42 (d, J = 6.8 Hz, 3H). MS m/z (ESI): 499.1 [M + H]⁺. |

TABLE 7-continued

| No. | Compound Structure | Compound Name | Starting material or reagent different from that in Example 5 | Characterization data |
|---|---|---|---|---|
| C118 | 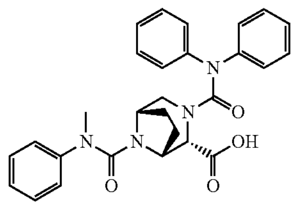 [SMILES: CN(C(=O)N1[C@H]2CC[C@@H]1[C@@H](C(=O)O)N(C(=O)N(c1ccccc1)c1ccccc1)C2)c1ccccc1] | (1R,2S,5S)-3-(diphenylcarbamoyl)-8-(methyl(phenyl)carbamoyl)-3,8-diazabicyclo[3.2.1]octane-2-carboxylic acid | The reaction in step 5a did not take place. Compound 20 in step 5b of Example 5 was replaced with Compound 23. Compound 16 was replaced with aniline (PhNH-). | ¹H NMR (400 MHz, DMSO-d₆) δ 7.4-7.25 (m, 6H), 7.20-7.10 (m, 5H), 7.0-6.90 (m, 4H), 4.35-4.10 (m, 2H), 3.69 (s, 1H), 3.08 (s, 3H), 3.01 (d, J = 11.2 Hz, 1H), 2.8 (d, J = 11.6 Hz, 1H), 1.60-1.10 (m, 4H). MS m/z (ESI): 484.8 [M + H]⁺. |
| C124 | 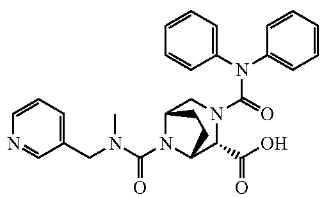 [SMILES: CN(Cc1cccnc1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(methyl(pyridine-3-ylmethyl)carbamoyl)-3,8-diazabicyclo[3.2.1]octane-2-carboxylic acid | The reaction in step 5a did not take place. Compound 20 in step 5b of Example 5 was replaced with Compound 23. Compound 16 was replaced with (pyridin-3-yl)methanamine. | 1H NMR (400 MHz, DMSO-d₆) δ 8.80 (d, J = 5.2 Hz, 1H), 8.74 (s, 1H), 8.30 (d, J = 8.0 Hz, 1H), 8.00-7.90 (m, 1H), 7.36 (t, J = 8.0 Hz, 4H), 7.17 (t, J = 7.2 Hz, 2H), 7.01 (d, J = 7.6 Hz, 4H), 4.56 (d, J = 15.6 Hz, 1H), 4.45-4.20 (m, 3H), 3.99 (s, 1H), 3.45-3.30 (m, 2H), 2.84 (s, 3H), 1.80-1.20 (m, 4H). MS m/z (ESI): 500.1 [M + H]⁺. |
| C125 | 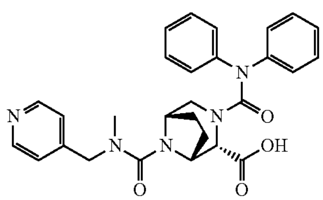 [SMILES: CN(Cc1ccncc1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(methyl(pyridine-4-ylmethyl)carbamoyl)-3,8-diazabicyclo[3.2.1]octane-2-carboxylic acid | The reaction in step 5a did not take place. Compound 20 in step 5b of Example 5 was replaced with Compound 23. Compound 16 was replaced with (pyridin-4-yl)methanamine. | ¹H NMR (400 MHz, DMSO-d₆) δ 8.76 (d, J = 6.0 Hz, 2H), 7.65 (d, J = 5.6 Hz, 2H), 7.36 (t, J = 7.6 Hz, 4H), 7.16 (t, J = 7.6 Hz, 2H), 7.02 (d, J = 8.0 Hz, 4H), 4.64 (d, J = 17.2 Hz, 1H), 4.49 (d, J = 16.8 Hz, 1H), 4.45-4.20 (m, 2H), 4.01 (s, 1H), 3.50-3.30 (m, 2H), 2.87 (s, 3H), 1.80-1.20 (m, 4H). MS m/z (ESI): 500.1 [M + H]⁺. |
| C126 | 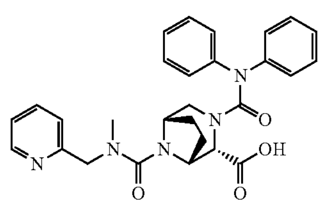 [SMILES: CN(Cc1ccccn1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(methyl(pyridine-2-ylmethyl)carbamoyl)-3,8-diazabicyclo[3.2.1]octane-2-carboxylic acid | The reaction in step 5a did not take place. Compound 20 in step 5b of Example 5 was replaced with Compound 23. Compound 16 was replaced with (pyridin-2-yl)methanamine. | ¹HNMR (400 MHz, DMSO-d₆) δ 7.2 Hz, 1H), 7.36 (t, J = 7.6 Hz, 4H), 7.17 (t, J = 7.4 Hz, 2H), 7.01 (d, J = 7.9 Hz, 4H), 4.65 (d, J = 16.3 Hz, 1H), 4.48 (d, J = 16.2 Hz, 2H), 4.38 (s, 2H), 4.03 (s, 2H), 3.47-3.33 (m, 2H), 2.90 (s, 3H), 1.67 (s, 1H), 1.55 (s, 1H), 1.37 (s, 1H), 1.27-1.10 (m, 1H). MS m/z (ESI): 500.1 [M + H]⁺. |
| C128 | 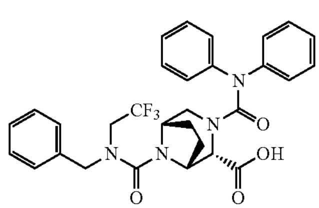 [SMILES: O=C(O)[C@@H]1[C@H]2CC[C@@H](CN1C(=O)N(c1ccccc1)c1ccccc1)N2C(=O)N(Cc1ccccc1)CC(F)(F)F] | (1R,2S,5S)-8-(benzyl(2,2,2-trifluoroethyl)carbamoyl)-3-(diphenylcarbamoyl)-3,8-diazabicyclo[3.2.1]octane-2-carboxylic acid | The reaction in step 5a did not take place. Compound 20 in step 5b of Example 5 was replaced with Compound 23. Compound 16 was replaced with N-benzyl-2,2,2-trifluoroethan-1-amine. | ¹HNMR (400 MHz, DMSO-d₆) δ 13.13 (s, 1H), 7.50-6.93 (m, 15H), 4.70 (d, J = 15.3 Hz, 1H), 4.42 (s, 1H), 4.29 (d, J = 15.2 Hz, 1H), 4.13 (dd, J = 15.7, 9.9 Hz, 1H), 4.04 (s, 1H), 3.58-3.44 (m, 2H), 3.40 (s, 1H), 1.68 (s, 1H), 1.47 (s, 2H), 1.34-1.11 (m, 1H). MS m/z (ESI): 567.2 [M + H]⁺. |

TABLE 7-continued

| No. | Compound Structure | Compound Name | Starting material or reagent different from that in Example 5 | Characterization data |
|---|---|---|---|---|
| C129 | 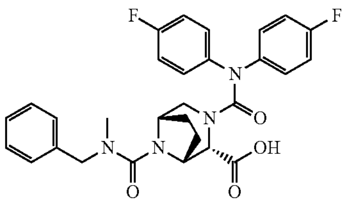 [SMILES: CN(Cc1ccccc1)C(=O)N1[C@H]2CC[C@@H]1[C@@H](C(=O)O)N(C(=O)N(c1ccc(F)cc1)c1ccc(F)cc1)C2] | (1R,2S,5S)-8-(benzyl(methyl)carbamoyl)-3-(bis(4-fluorophenyl)carbamoyl)-3,8-diazabicyclo[3.2.1]octane-2-carboxylic acid | Compound 7 in step 3 of Example 5 was replaced with [structure]. The reaction in step 5a did not take place. | $^1$HNMR (400 MHz, DMSO-d$_6$) δ 12.97 (s, 1H), 7.62-6.95 (m, 13H), 4.45 (d, J = 15.4 Hz, 1H), 4.42-4.30 (m, 2H), 4.26 (d, J = 15.2 Hz, 1H), 3.93 (s, 1H), 3.42 (d, J = 12.1 Hz, 2H), 2.70 (s, 3H), 1.76 (s, 1H), 1.66-1.53 (m, 1H), 1.46 (s, 1H), 1.37-1.22 (m, 1H). MS m/z (ESI): 535.0 [M + H]$^+$. |
| C130 | 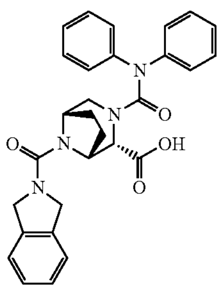 [SMILES: O=C(O)[C@@H]1[C@H]2CC[C@@H](CN1C(=O)N(c1ccccc1)c1ccccc1)N2C(=O)N1Cc2ccccc2C1] | (1R,2S,5S)-3-(diphenylcarbamoyl)-8-(isoindoline-2-carbonyl)-3,8-diazabicyclo[3.2.1]octane-2-carboxylic acid | Compound 20 in step 5b of Example 5 was replaced with Compound 23. Compound 16 was replaced with isoindoline. The reaction in step 5a did not take place. | $^1$HNMR (400 MHz, DMSO-d$_6$) δ 12.97 (s, 1H), 7.46-6.98 (m, 14H), 4.87-4.76 (m, 2H), 4.54 (d, J = 14.2 Hz, 3H), 4.34 (s, 1H), 4.15 (s, 1H), 3.47 (s, 2H), 1.74 (s, 1H), 1.67-1.51 (m, 1H), 1.41 (s, 1H), 1.33-1.21 (m, 1H). MS m/z (ESI): 497.2 [M + H]$^+$. |
| C131 | 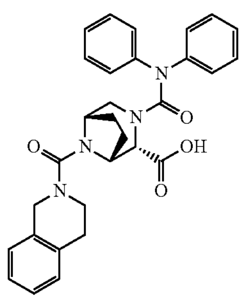 [SMILES: O=C(O)[C@@H]1[C@H]2CC[C@@H](CN1C(=O)N(c1ccccc1)c1ccccc1)N2C(=O)N1CCc2ccccc2C1] | (1R,2S,5S)-3-(diphenylcarbamoyl)-8-(1,2,3,4-tetrahydroisoquinoline-2-carbonyl)-3,8-diazabicyclo[3.2.1]octane-2-carboxylic acid | Compound 20 in step 5b of Example 5 was replaced with Compound 23. Compound 16 was replaced with tetrahydroisoquinoline. The reaction in step 5a did not take place. | $^1$HNMR (400 MHz, DMSO-d$_6$) δ 13.02 (s, 1H), 7.50-6.91 (m, 14H), 4.51-4.25 (m, 4H), 3.95 (s, 1H), 3.61-3.51 (m, 1H), 3.51-3.35 (m, 3H), 2.88-2.65 (m, 2H), 1.68 (s, 1H), 1.56 (s, 1H), 1.37 (s, 1H), 1.27-1.10 (m, 1H). MS m/z (ESI): 511.1 [M + H]$^+$. |
| C132 | 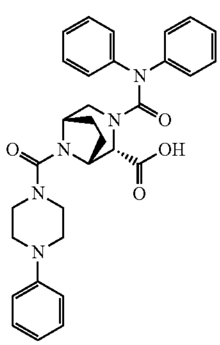 [SMILES: O=C(O)[C@@H]1[C@H]2CC[C@@H](CN1C(=O)N(c1ccccc1)c1ccccc1)N2C(=O)N1CCN(c2ccccc2)CC1] | (1R,2S,5S)-3-(diphenylcarbamoyl)-8-(4-phenylpiperazine-1-carbonyl)-3,8-diazabicyclo[3.2.1]octane-2-carboxylic acid | Compound 20 in step 5b of Example 5 was replaced with Compound 23. Compound 16 was replaced with 1-phenylpiperazine. The reaction in step 5a did not take place. | $^1$HNMR (400 MHz, DMSO-d$_6$) δ 7.36 (t, J = 7.7 Hz, 4H), 7.20 (dt, J = 14.7, 7.7 Hz, 4H), 6.98 (dd, J = 27.6, 8.0 Hz, 6H), 6.82 (t, J = 7.2 Hz, 1H), 4.46-4.23 (m, 2H), 3.91 (s, 1H), 3.56-3.28 (m, 6H), 3.22-3.00 (m, 4H), 1.70 (s, 1H), 1.55 (s, 1H), 1.46-1.09 (m, 2H). MS m/z (ESI): 540.1 [M + H]$^+$. |

TABLE 7-continued

| No. | Compound Structure | Compound Name | Starting material or reagent different from that in Example 5 | Characterization data |
|---|---|---|---|---|
| C133 | 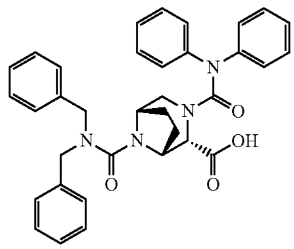 [SMILES: O=C(O)[C@@H]1[C@H]2CC[C@@H](CN1C(=O)N(c1ccccc1)c1ccccc1)N2C(=O)N(Cc1ccccc1)Cc1ccccc1] | (1R,2S,5S)-8-(dibenzylcarbamoyl)-3-(diphenylcarbamoyl)-3,8-diazabicyclo[3.2.1]octane-2-carboxylic acid | Compound 20 in step 5b of Example 5 was replaced with Compound 23; Compound 16 was replaced with dibenzylamine; and the reaction condition was changed to reacting in a sealed tube at 50° C. for 50 hours. The reaction in step 5a did not take place. | $^1$HNMR (400 MHz, DMSO-d$_6$) δ 13.1 (s, 1H), 7.45-7.25 (m, 10H), 7.20-7.10 (m, 6H), 7.05-6.95 (m, 4H), 4.55-4.30 (m, 4H), 4.10-3.95 (m, 3H), 3.45-3.35 (m, 2H), 1.80-1.20 (m, 4H). MS m/z (ESI): 575.0 [M + H]$^+$. |
| C134 | 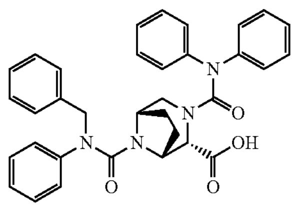 [SMILES: O=C(O)[C@@H]1[C@H]2CC[C@@H](CN1C(=O)N(c1ccccc1)c1ccccc1)N2C(=O)N(Cc1ccccc1)c1ccccc1] | (1R,2S,5S)-8-(benzyl(phenyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [benzyl(phenyl)amine structure]. The reaction in step 5a did not take place. | $^1$H NMR (400 MHz, DMSO-d$_6$) δ 7.35-7.28 (m, 5H), 7.27-7.20 (m, 4H), 7.20-7.10 (m, 4H), 7.11-7.02 (m, 3H), 7.00-6.90 (m, 4H), 4.85-4.70 (m, 2H), 4.40 (s, 1H), 4.20 (s, 1H), 3.71 (s, 1H), 2.98 (d, J = 12.8 1Hz, 1H), 2.75 (d, J = 12.0 Hz, H), 1.70-1.20 (m, 4H). MS m/z (ESI): 561.0 [M + H]$^+$. |
| C135 | 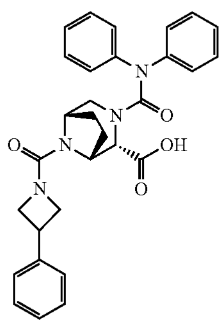 [SMILES: O=C(O)[C@@H]1[C@H]2CC[C@@H](CN1C(=O)N(c1ccccc1)c1ccccc1)N2C(=O)N1CC(c2ccccc2)C1] | (1R,2S,5S)-3-(diphenylcarbamoyl)-8-(3-phenylazetidine-1-carbonyl)-3,8-diazabicyclo[3.2.1]octane-2-carboxylic acid | Compound 20 in step 5b of Example 5 was replaced with Compound 23. Compound 16 was replaced with [3-phenylazetidine structure]. The reaction in step 5a did not take place. | $^1$HNMR (400 MHz, DMSO-d$_6$) δ 12.97 (s, 1H), 7.43-6.95 (m, 15H), 4.46 (s, 1H), 4.36-4.20 (m, 3H), 4.10 (s, 1H), 3.95-3.72 (m, 4H), 3.42 (d, J = 11.9 Hz, 1H), 1.68-1.50 (m, 2H), 1.41-1.20 (m, 2H). MS m/z (ESI): 510.6 [M + H]$^+$. |
| C136 | 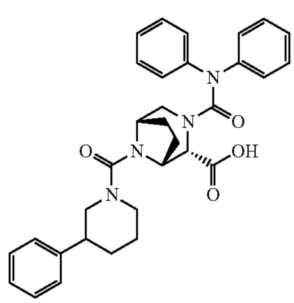 [SMILES: O=C(O)[C@@H]1[C@H]2CC[C@@H](CN1C(=O)N(c1ccccc1)c1ccccc1)N2C(=O)N1CCCC(c2ccccc2)C1] | (1R,2S,5S)-3-(diphenylcarbamoyl)-8-(3-phenylpiperidine-1-carbonyl)-3,8-diazabicyclo[3.2.1]octane-2-carboxylic acid | Compound 20 in step 5b of Example 5 was replaced with Compound 23. Compound 16 was replaced with [3-phenylpiperidine structure]. The reaction in step 5a did not take place. | $^1$HNMR (400 MHz DMSO-d$_6$) δ 12.95 (s, 1H), 7.50-6.93 (m, 15H), 4.34 (s, 2H), 3.91-3.68 (m, 3H), 3.50-3.27 (m, 2H), 2.90-2.77 (m, 1H), 2.76-2.64 (m, 2H), 1.88 (d, J = 11.1 Hz, 1H), 1.75-1.62 (m, 3H), 1.59-1.47 (m, 2H), 1.46-1.31 (m, 2H). MS m/z (ESI): 539.1 [M + H]$^+$. |

TABLE 7-continued

| No. | Compound Structure | Compound Name | Starting material or reagent different from that in Example 5 | Characterization data |
|---|---|---|---|---|
| C137 | 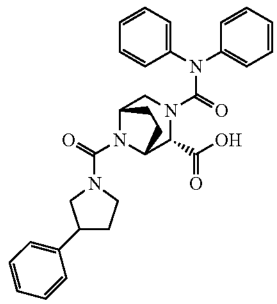 [SMILES: O=C(O)[C@@H]1[C@H]2CC[C@@H](CN1C(=O)N(c1ccccc1)c1ccccc1)N2C(=O)N1CCC(c2ccccc2)C1] | (1R,2S,5S)-3-(diphenylcarbamoyl)-8-(3-phenylpyrrolidine-1-carbonyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | 1HNMR (400 MHz, DMSO-d$_6$) δ 13.00 (s, 1H), 7.62-6.87 (m, 15H), 4.44 (d, J = 18.7 Hz, 1H), 4.30 (s, 1H), 4.11-3.96 (m, 1H), 3.80-3.67 (m, 1H), 3.60-3.52 (m, 1H), 3.52-3.42 (m, 2H), 3.41-3.32 (m, 2H), 3.29-3.21 (m, 1H), 2.22-2.12 (m, 1H), 1.96-1.79 (m, 1H), 1.71 (s, 1H), 1.62 (s, 1H), 1.57-1.46 (m, 1H), 1.36 (s, 1H). MS m/z (ESI): 524.6 [M + H]$^+$. |
| C138 | 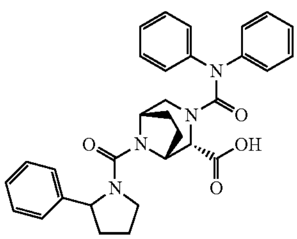 [SMILES: O=C(O)[C@@H]1[C@H]2CC[C@@H](CN1C(=O)N(c1ccccc1)c1ccccc1)N2C(=O)N1CCCC1c1ccccc1] | (1R,2S,5S)-3-(diphenylcarbamoyl)-8-(2-phenylpyrrolidine-1-carbonyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$HNMR (400 MHz, DMSO-d$_6$) δ 13.08 (s, 1H), 7.59-6.96 (m, 15H), 4.88-4.78 (m, 1H), 4.51-4.11 (m, 2H), 3.95 (s, 1H), 3.71-3.52 (m, 2H), 3.51-3.44 (m, 1H), 3.43-3.36 (m, 2H), 2.31-2.18 (m, 1H), 1.98-1.64 (m, 3H), 1.59-1.49 (m, 2H), 1.47-1.07 (m, 3H). MS m/z (ESI): 525.1 [M + H]$^+$. |
| C145 | 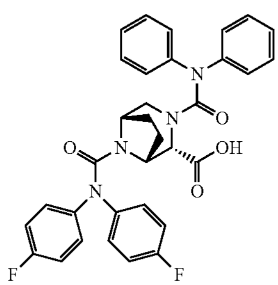 [SMILES: O=C(O)[C@@H]1[C@H]2CC[C@@H](CN1C(=O)N(c1ccccc1)c1ccccc1)N2C(=O)N(c1ccc(F)cc1)c1ccc(F)cc1] | (1R,2S,5S)-8-(bis(4-fluorophenyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$HNMR (400 MHz, DMSO-d$_6$) δ 13.22 (s, 1H), 7.64-6.89 (m, 18H), 4.35-4.15 (m, 2H), 3.97 (s, 1H), 3.56 (s, 2H), 3.19 (d, J = 9.1 Hz, 1H), 2.94 (d, J = 12.0 Hz, 1H), 1.72-1.61 (m, 1H), 1.54 (s, 1H), 1.35 (s, 1H), 1.26-1.06 (m, 1H). MS m/z (ESI): 583.1 [M + H]$^+$. |
| C147 | 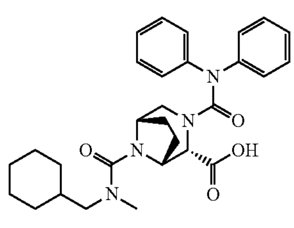 [SMILES: CN(CC1CCCCC1)C(=O)N1[C@H]2CC[C@@H]1[C@@H](C(=O)O)N(C(=O)N(c1ccccc1)c1ccccc1)C2] | (1R,2S,5S)-8-((cyclohexylmethyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$H NMR (400 MHz, DMSO-d$_6$) δ 7.36 (t, J = 7.6 Hz, 4H), 7.17 (t, J = 7.2 Hz, 2H), 7.01 (t, J = 7.6 Hz, 4H), 4.35-4.15 (m, 2H), 3.85 (s, 1H), 3.45-3.30 (m, 2H), 3.29-3.15 (m, 1H), 2.85-2.70 (m, 4H), 1.70-1.35 (m, 9H), 1.25-1.05 (m, 4H), 0.85-0.7 (m, 2H). MS m/z (ESI): 505.2 [M + H]$^+$. |

TABLE 7-continued

| No. | Compound Structure | Compound Name | Starting material or reagent different from that in Example 5 | Characterization data |
|---|---|---|---|---|
| C149 | 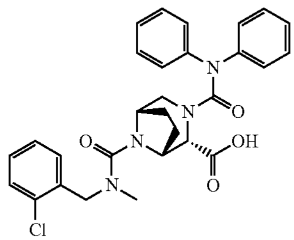 [SMILES: CN(Cc1ccccc1Cl)C(=O)N1[C@H]2CC[C@@H]1[C@@H](C(=O)O)N(C(=O)N(c1ccccc1)c1ccccc1)C2] | (1R,2S,5S)-8-((2-chlorobenzyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with (2-chlorobenzyl)methylamine. The reaction in step 5a did not take place. | $^1$H NMR (400 MHz, DMSO-d$_6$) δ 8.10-7.95 (m, 1H), 7.70-7.29 (m, 6H), 7.27-7.12 (m, 3H), 7.07-6.95 (m, 3H), 6.80-6.65 (m, 2H), 4.80-4.20 (m, 4H), 3.91 (s, 1H), 3.50-3.30 (m, 2H), 2.76 (s, 3H), 1.80-1.20 (m, 4H). MS m/z (ESI): 533.0 [M + H]$^+$. |
| C151 | 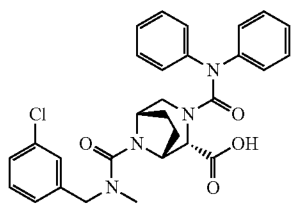 [SMILES: CN(Cc1cccc(Cl)c1)C(=O)N1[C@H]2CC[C@@H]1[C@@H](C(=O)O)N(C(=O)N(c1ccccc1)c1ccccc1)C2] | (1R,2S,5S)-8-((3-chlorobenzyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with (3-chlorobenzyl)methylamine. The reaction in step 5a did not take place. | $^1$HNMR (400 MHz, DMSO-d$_6$) δ 12.99 (s, 1H), 7.42-6.98 (m, 14H), 4.42 (d, J = 15.3 Hz, 2H), 4.37 (s, 1H), 4.27 (d, J = 15.4 Hz, 1H), 3.94 (s, 1H), 3.48-3.36 (m, 2H), 2.74 (s, 3H), 1.72 (s, 1H), 1.56 (s, 1H), 1.46-1.33 (m, 1H), 1.32-1.13 (m, 1H). MS m/z (ESI): 533.1 [M + H]$^+$. |
| C150 | 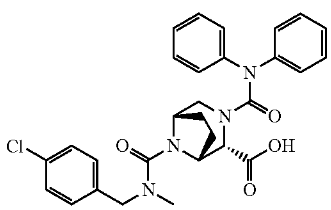 [SMILES: CN(Cc1ccc(Cl)cc1)C(=O)N1[C@H]2CC[C@@H]1[C@@H](C(=O)O)N(C(=O)N(c1ccccc1)c1ccccc1)C2] | (1R,2S,5S)-8-((4-chlorobenzyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with (4-chlorobenzyl)methylamine. The reaction in step 5a did not take place. | 1HNMR (400 MHz, DMSO-d$_6$) δ 13.38 (s, 1H), 7.45-6.94 (m, 14H), 4.47-4.32 (m, 2H), 4.29-4.07 (m, 2H), 3.92 (s, 1H), 3.42 (d, J = 12.0 Hz, 2H), 2.71 (s, 3H), 1.67 (s, 1H), 1.56 (s, 1H), 1.39 (s, 1H), 1.29-1.14 (m, 1H). MS m/z (ESI): 532.8 [M + H]$^+$. |
| C179 | 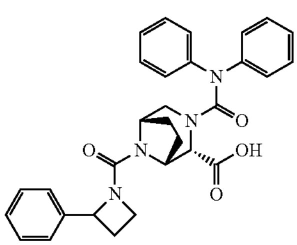 [SMILES: O=C(O)[C@@H]1[C@H]2CC[C@@H](CN1C(=O)N(c1ccccc1)c1ccccc1)N2C(=O)N1CCC1c1ccccc1] | (1R,2S,5S)-3-(diphenylcarbamoyl)-8-(2-phenylazetidine-1-carbonyl)-3,8-diazabicyclo[3.2.1]octane-2-carboxylic acid | Compound 20 in step 5b of Example 5 was replaced with Compound 23. Compound 16 was replaced with 2-phenylazetidine. The reaction in step 5a did not take place. | $^1$H NMR (400 MHz, DMSO-d$_6$) δ 7.35-7.20 (m, 10H), 7.15-7.00 (m, 5H), 5.25-5.05 (m, 1H), 4.50-4.35 (m, 1H), 4.15-3.95 (m, 3H), 3.85-3.75 (m, 1H), 3.30-3.15 (m, 2H), 2.05-1.85 (m, 2H), 1.60-1.15 (m, 4H). MS m/z (ESI): 511.1 [M + H]$^+$. |
| C152 | 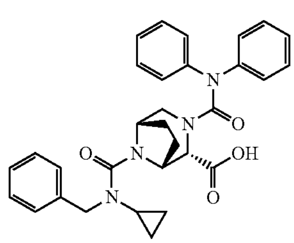 [SMILES: O=C(O)[C@@H]1[C@H]2CC[C@@H](CN1C(=O)N(c1ccccc1)c1ccccc1)N2C(=O)N(Cc1ccccc1)C1CC1] | (1R,2S,5S)-8-(benzyl(isopropyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with N-benzylisopropylamine. | $^1$HNMR (400 MHz, DMSO-d$_6$) δ 13.03 (s, 1H), 7.45-6.89 (m, 15H), 4.40 (d, J = 15.9 Hz, 1H), 4.35-4.20 (m, 2H), 4.14 (d, J = 16.0 Hz 1H), 4.09-4.01 (m, 1H), 3.91 (s, 1H), 3.56-3.45 (m, 2H), 1.57 (s, 1H), 1.44 (s, 1H), 1.38-1.28 (m, 1H), 1.27-1.16 (m, 1H), 1.07 (dd, J = 14.6, 6.5 Hz, 6H). MS m/z (ESI): 526.8 [M + H]$^+$. |

TABLE 7-continued

| No. | Compound Structure | Compound Name | Starting material or reagent different from that in Example 5 | Characterization data |
|---|---|---|---|---|
| C153 | 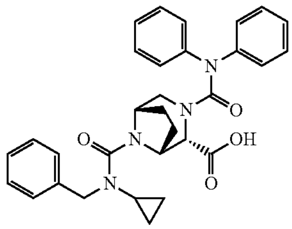 [SMILES: O=C(O)[C@@H]1[C@H]2CC[C@@H](CN1C(=O)N(c1ccccc1)c1ccccc1)N2C(=O)N(Cc1ccccc1)C1CC1] | (1R,2S,5S)-8-(benzyl (cyclopropyl) carbamoyl)-3-(diphenylcarbamoyl)-3,8-diazabicyclo [3.2.1]octane-2-carboxylic acid | The reaction in step 5a did not take place. Compound 20 in step 5b of Example 5 was replaced with Compound 23. Compound 16 was replaced with [benzyl-cyclopropyl amine structure]. | $^1$H NMR (400 MHz, DMSO-d$_6$) δ 13.00 (s, 1H), 7.45-6.93 (m, 15H), 4.68 (d, J = 15.0 Hz, 1H), 4.48 (s, 1H), 4.41-4.26 (m, 1H), 4.15 (s, 1H), 4.04 (d, J = 15.1 Hz, 1H), 3.51-3.42 (m, 2H), 2.45-2.32 (m, 1H), 1.69 (s, 1H), 1.57-1.28 (m, 3H), 0.79-0.68 (m, 1H), 0.67-0.58 (m, 1H), 0.57-0.46 (m, 2H). MS m/z (ESI): 524.8 [M + H]$^+$. |
| C154 | 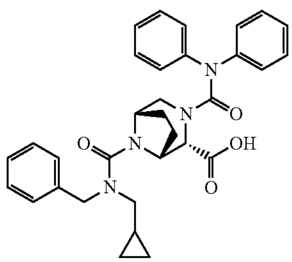 [SMILES: O=C(O)[C@@H]1[C@H]2CC[C@@H](CN1C(=O)N(c1ccccc1)c1ccccc1)N2C(=O)N(Cc1ccccc1)CC1CC1] | (1R,2S,5S)-8-(benzyl (cyclopropylmethyl) carbamoyl)-3-(diphenylcarbamoyl)-3,8-diazabicyclo [3.2.1]octane-2-carboxylic acid | The reaction in step 5a did not take place. Compound 20 in step 5b of Example 5 was replaced with Compound 23. Compound 16 was replaced with [benzyl-cyclopropylmethyl amine structure]. | $^1$H NMR (400 MHz, DMSO-d$_6$) δ 13.04 (s, 1H), 7.41-6.96 (m, 15H), 4.65 (d, J = 15.5 Hz, 1H), 4.38-4.12 (m, 3H), 3.90 (s, 1H), 3.43 (d, J = 12.1 Hz, 2H), 1.53 (s, 1H), 1.41-1.31 (m, 1H), 1.28-1.15 (m, 1H), 0.99-0.87 (m, 1H), 0.47-0.30 (m, 2H), 0.06 (d, J = 4.7 Hz, 2H). MS m/z (ESI): 538.9 [M + H]$^+$. |
| C155 | 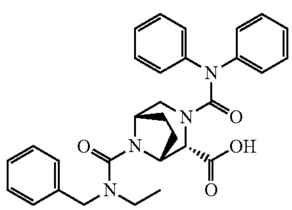 [SMILES: CCN(Cc1ccccc1)C(=O)N1[C@H]2CC[C@@H]1[C@@H](C(=O)O)N(C(=O)N(c1ccccc1)c1ccccc1)C2] | (1R,2S,5S)-8-(benzyl (ethyl)carbamoyl)-3-(diphenylcarbamoyl)-3,8-diazabicyclo [3.2.1]octane-2-carboxylic acid | The reaction in step 5a did not take place. Compound 20 in step 5b of Example 5 was replaced with Compound 23. Compound 16 was replaced with [benzyl-ethyl amine structure]. | $^1$H NMR (400 MHz, DMSO-d$_6$) δ 13.17 (s, 1H), 7.43-6.89 (m, 15H), 4.51 (d, J = 15.6 Hz, 1H), 4.36-4.20 (m, 2H), 3.90 (s, 1H), 3.39 (dd, J = 32.0, 11.7 Hz, 3H), 3.24-3.13 (m, 1H), 3.05-2.93 (m, 1H), 1.68 (s, 1H), 1.62-1.49 (m, 1H), 1.47-1.32 (m, 1H), 1.29-1.10 (m, 1H), 0.98 (t, J = 7.0 Hz, 3H). MS m/z (ESI): 512.8 [M + H]$^+$. |
| C182 | 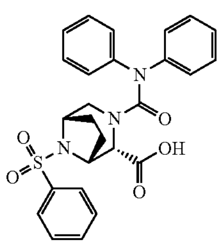 [SMILES: O=C(O)[C@@H]1[C@H]2CC[C@@H](CN1C(=O)N(c1ccccc1)c1ccccc1)N2S(=O)(=O)c1ccccc1] | (1R,2S,5S)-3-(diphenylcarbamoyl)-8-(phenylsulfulyl)-3,8-diazabicyclo [3.2.1]octane-2-carboxylic acid | The reaction in step 5a did not take place. Compound 20 in step 5a of Example 5 was replaced with Compound 23. [phenyl chloroformate structure] was replaced with benzene sulfonyl chloride. TEA was replaced with DIPEA. DCM was replaced with DCE. The reaction in step 5b did not take place. | $^1$H NMR (400 MHz, DMSO-d$_6$) δ 7.82 (d, J = 7.6 Hz, 2H), 7.68 (t, J = 6.4 Hz, 1H), 7.57 (t, J = 7.2 Hz, 2H), 7.33 (t, J = 7.6 Hz, 4H), 7.15 (t, J = 7.2 Hz, 2H), 6.99 (d, J = 8.0 Hz, 4H), 4.52 (s, 1H), 4.37-4.27 (m, 1H), 4.14 (s, 1H), 3.39-3.34 (m, 1H), 3.16 (d, J = 12.0 Hz, 1H), 1.35-1.00 (m, 4H). MS m/z (ESI): 492.0 [M + H]$^+$. |

TABLE 7-continued

| No. | Compound Name | Starting material or reagent different from that in Example 5 | Characterization data |
|---|---|---|---|
| C159 | (1S,2R,5R)-8-(benzyl (methyl)carbamoyl)-3-(diphenylcarbamoyl)-3,8-diazabicyclo[3.2.1]octane-2-carboxylic acid | Compound 5 in step 1 of Example 5 was replaced with compound 6*. Compound 7 in step 3 was replaced with diphenylcarbamoyl chloride. The reaction in step 5a did not take place. | $^1$H NMR (400 MHz, DMSO-$d_6$) δ 7.45-7.30 (m, 6H), 7.29-7.12 (m, 5H), 7.05-6.95 (m, 4H), 4.45 (d, J = 15.6 Hz, 1H), 4.40-4.30 (m, 2H), 4.26 (d, J = 15.6 Hz, 1H), 3.93 (s, 1H), 3.50-3.42 (m, 2H), 2.70 (s, 3H), 1.80-1.20 (m, 4H). MS m/z (ESI): 498.9 [M + H]$^+$. |
| C139 | (1R,2S,5S)-3-(diphenylcarbamoyl)-8-((S)-2-phenylpyrrolidine-1-carbonyl)-3,8-diazabicyclo[3.2.1]octane-2-carboxylic acid | Compound 20 in step 5b of Example 5 was replaced with Compound 23. Compound 16 was replaced with (S)-2-phenylpyrrolidine. The reaction in step 5a did not take place. | $^1$H NMR (300 MHz, DMSO-$d_6$) δ 13.11 (s, 1H), 7.45-6.84 (m, 15H), 4.82 (t, J = 7.2 Hz, 1H), 4.44 (s, 1H), 4.22 (s, 1H), 3.92 (s, 1H), 3.61-3.48 (m, 2H), 3.20 (d, J = 11.9 Hz, 1H), 2.27-2.13 (m, 1H), 1.85-1.67 (m, 2H), 1.58-1.46 (m, 1H), 1.45-1.34 (m, 2H), 1.28-1.06 (m, 2H). MS m/z (ESI): 525.1 [M + H]$^+$. |
| C140 | (1R,2S,5S)-3-(diphenylcarbamoyl)-8-((R)-2-phenylpyrrolidine-1-carbonyl)-3,8-diazabicyclo[3.2.1]octane-2-carboxylic acid | Compound 20 in step 5b of Example 5 was replaced with Compound 23. Compound 16 was replaced with (R)-2-phenylpyrrolidine. The reaction in step 5a did not take place. | $^1$H NMR (400 MHz, DMSO-$d_6$) δ 12.89 (s, 1H), 7.56-6.93 (m, 15H), 4.85 (t, J = 7.6 Hz, 1H), 4.42-4.22 (m, 2H), 4.18 (s, 1H), 3.72-3.60 (m, 1H), 3.54-3.46 (m, 2H), 2.39-2.21 (m, 2H), 1.84 (s, 1H), 1.79-1.67 (m, 1H), 1.62-1.45 (m, 2H), 1.42-1.26 (m, 2H). MS m/z (ESI): 525.2 [M + H]$^+$. |
| C161 | (1R,2S,5S)-3-(diphenylcarbamoyl)-8-((4-fluorobenzyl)(methyl)carbamoyl)-3,8-thazabicyclo[3.2.1]octane-2-carboxylic acid | Compound 20 in step 5b of Example 5 was replaced with Compound 23. Compound 16 was replaced with 4-fluoro-N-methylbenzylamine. The reaction in step 5a did not take place. | $^1$H NMR (400 MHz, DMSO-$d_6$) δ 13.01 (s, 1H), 7.41-6.96 (m, 14H), 4.43-4.22 (m, 4H), 3.92 (s, 1H), 3.47-3.33 (m, 2H), 2.70 (s, 3H), 1.77-1.35 (m, 4H). MS m/z (ESI): 517.1 [M + H]$^+$. |
| C162 | (1R,2S,5S)-3-(diphenylcarbamoyl)-8-(methyl(4-methylbenzyl)carbamoyl)-3,8-diazabicyclo[3.2.1]octane-2-carboxylic acid | Compound 20 in step 5b of Example 5 was replaced with Compound 23. Compound 16 was replaced with N-methyl-4-methylbenzylamine. | $^1$H NMR (400 MHz, DMSO-$d_6$) δ 7.35 (t, J = 8.0 Hz, 4H), 7.20-7.10 (m, 4H), 7.07 (d, J = 8.0 Hz, 2H), 7.02 (d, J = 7.6 Hz, 4H), 4.45-4.25 (m, 3H), 4.21 (d, J = 15.2 Hz, 1H), 3.91 (s, 1H), 3.45-3.35 (m, 2H), 2.68 (s, 3H), 2.28 (s, 3H), 1.75-1.30 (m, 4H). MS m/z (ESI): 513.1 [M + H]$^+$. |

TABLE 7-continued

| No. | Compound Structure | Compound Name | Starting material or reagent different from that in Example 5 | Characterization data |
|---|---|---|---|---|
| C165 | 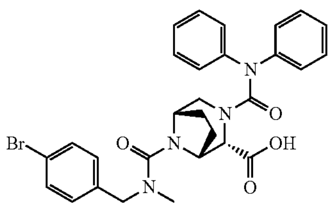 | (1R,2S,5S)-8-((4-bromobenzyl)(methyl)carbamoyl)-3-(diphenylcarbamoyl)-3,8-diazabicyclo[3.2.1]octane-2-carboxylic acid | The reaction in step 5a did not take place. Compound 20 in step 5b of Example 5 was replaced with Compound 23. Compound 16 was replaced with [4-bromobenzyl methylamine]. | $^1$H NMR (400 Hz, DMSO-d$_6$) δ 12.97 (s, 1H), 7.57-6.97 (m, 14H), 4.45-4.19 (m, 4H), 3.93 (s, 1H), 3.48-3.36 (m, 2H), 2.71 (s, 3H), 1.77-1.32 (m, 4H). MS m/z (ESI): 576.7 [M + H]$^+$. |
| C165-1 | 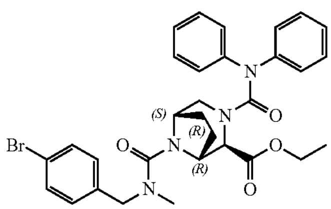 | (1R,2R,5S)-ethyl 8-((4-bromobenzyl)(methyl)carbamoyl)-3-(diphenylcarbamoyl)-3,8-diazabicyclo[3.2.1]octane-2-carboxylate | The reaction in step 5a did not take place. Compound 20 in step 5b of Example 5 was replaced with Compound 23. Compound 16 was replaced with [4-bromobenzyl methylamine]. | MS m/z (ESI): 604.6 [M + H]+. |
| C166 | 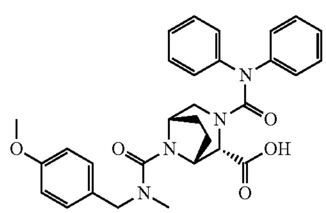 [SMILES: COc1ccc(CN(C)C(=O)N2[C@H]3CC[C@@H]2[C@@H](C(=O)O)N(C(=O)N(c2ccccc2)c2ccccc2)C3)cc1] | (1R,2S,5S)-3-(diphenylcarbamoyl)-8-(4-methoxybenzyl)(methyl)carbamoyl)-3,8-diazabicyclo[3.2.1]octane-2-carboxylic acid | The reactions in the steps 5a and 6 were not performed. Compound 20 in step 5b of Example 5 was replaced with Compound 23. Compound 16 was replaced with [4-methoxybenzyl methylamine]. | $^1$H NMR (400 MHz, DMSO-d$_6$) δ 12.99 (s, 1H), 7.41-6.85 (m, 14H), 4.36 (d, J = 14.6 Hz, 2H), 4.18 (d, J = 14.8 Hz, 1H), 3.90 (s, 1H), 3.73 (s, 3H), 3.62-3.47 (m, 3H), 2.66 (s, 3H), 1.72 (s, 1H), 1.62-1.46 (m, 1H), 1.45-1.12 (m, 2H). MS m/z (ESI): 528.8 [M + H]$^+$. |
| C191 | 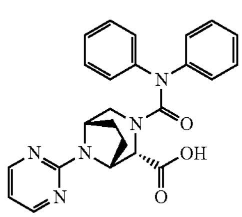 [SMILES: O=C(O)[C@@H]1[C@H]2CC[C@@H](CN1C(=O)N(c1ccccc1)c1ccccc1)N2c1ncccn1] | (1R,2S,5S)-3-(diphenylcarbamoyl)-8-(pyrimidine-2-yl)-3,8-diazabicyclo[3.2.1]octane-2-carboxylic acid | The reaction in step 5a did not take place. In step 5a of Example 5, Compound 20 was replaced with Compound 23, phenyl chloroformate was replaced with 2-chloropyrimidine, TEA was replaced with DIPEA, and DCM was replaced with NMP; and the reaction condition was changed to reacting at 130° C. for 16 hours. The reaction in step 5b did not take place. | $^1$H NMR (400 MHz, CD$_3$OD) δ 8.58 (s, 2H), 7.39 (t, J = 7.2 Hz, 4H), 7.24 (t, J = 7.2 Hz, 2H), 7.13 (d, J = 8.0 Hz, 4H), 7.00 (s, 1H), 5.34 (s, 1H), 4.8-4.7 (m, 2H), 3.72 (d, J = 12.4 Hz, 1H), 3.39 (d, J = 12.4 Hz, 1H), 2.15-1.95 (m, 2H), 1.90-1.70 (m, 2H). MS m/z (ESI): 430.0 [M + H]$^+$. |

TABLE 7-continued

| No. | Compound Structure | Compound Name | Starting material or reagent different from that in Example 5 | Characterization data |
|---|---|---|---|---|
| C184 | 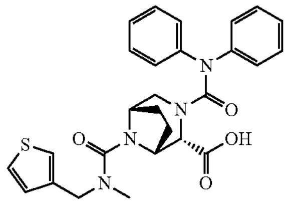 [SMILES: CN(Cc1ccsc1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(methyl(thiophene-3-ylmethyl)carbamoyl)-3,8-diazabicyclo[3.2.1]octane-2-carboxylic acid | Compound 20 in step 5b of Example 5 was replaced with Compound 23. Compound 16 was replaced with [thiophen-3-ylmethyl(methyl)amine]. The reaction in step 5a did not take place. | $^1$H NMR (400 MHz, DMSO-$d_6$) δ 12.99 (s, 1H), 7.49 (dd, J = 4.9, 2.9 Hz, 1H), 7.41-7.28 (m, 5H), 7.17 (t, J = 7.4 Hz, 2H), 7.05-6.92 (m, 5H), 4.42-4.20 (m, 4H), 3.92 (s, 1H), 3.39 (dd, J = 24.8, 11.6 Hz, 2H), 2.70 (d, J = 3.0 Hz, 3H), 1.77-1.63 (m, 1H), 1.60-1.47 (m, 1H), 1.44-1.15 (m, 2H). MS m/z (ESI): 504.6 [M + H]$^+$. |
| C169 | 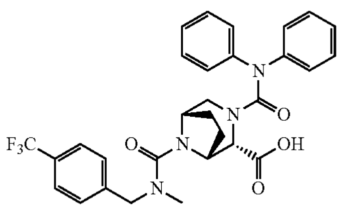 [SMILES: CN(Cc1ccc(C(F)(F)F)cc1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(methyl(4-trifluoromethyl)benzyl)carbamoyl)-3,8-diazabicyclo[3.2.1]octane-2-carboxylic acid | Compound 20 in step 5b of Example 5 was replaced with Compound 23. Compound 16 was replaced with [4-(trifluoromethyl)benzyl(methyl)amine]. The reaction in step 5a did not take place. | $^1$H NMR (400 MHz, DMSO-$d_6$) δ 7.70 (d, J = 8.0 Hz, 2H), 7.41 (d, J = 8.0 Hz, 2H), 7.36 (t, J = 8.0 Hz, 4H), 7.17 (t, J = 7.6 Hz, 2H), 7.01 (d, J = 7.6 Hz, 4H), 4.51 (d, J = 16.0 Hz, 1H), 4.45-4.30 (m, 3H), 3.95 (s, 1H), 3.45-3.20 (m, 2H), 2.75 (s, 3H), 1.80-1.30 (m, 4H). MS m/z (ESI): 566.8 [M + H]$^+$. |
| C146 | 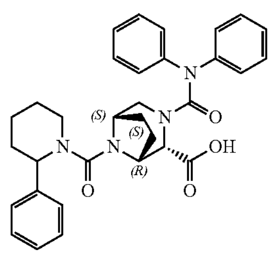 | (1R,2S,5S)-3-(diphenylcarbamoyl)-8-(2-phenylpiperidine-1-carbonyl)-3,8-diazabicyclo[3.2.1]octane-2-carboxylic acid | Compound 20 in step 5b of Example 5 was replaced with Compound 23. Compound 16 was replaced with [2-phenylpiperidine]. The reaction in step 5a did not take place. | $^1$H NMR (400 MHz, DMSO-$d_6$) δ 13.05 (s, 1H), 7.54-6.90 (m, 12H), 5.13 (d, J = 32.5 Hz, 1H), 4.44-4.17 (m, 2H), 3.98 (s, 1H), 3.80 (s, 1H), 3.71-3.58 (m, 1H), 3.41-3.53 (m, 2H), 2.90-2.69 (m, 1H), 2.36-2.21 (m, 1H), 1.85-1.66 (m, 2H), 1.63-1.41 (m, 3H), 1.39-1.14 (m, 3H). MS m/z (ESI): 538.8 [M + H]$^+$. |
| C143 | 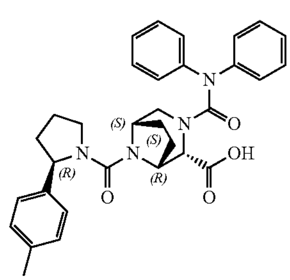 | (1R,2S,5S)-3-(diphenylcarbamoyl)-8-((R)-2-(p-tolyl)pyrrolidine-1-carbonyl)-3,8-diazabicyclo[3.2.1]octane-2-carboxylic acid | Compound 20 in step 5b of Example 5 was replaced with Compound 23. Compound 16 was replaced with [(R)-2-(p-tolyl)pyrrolidine]. The reaction in step 5a did not take place. | $^1$H NMR (400 MHz, DMSO-$d_6$) δ 7.40-7.32 (m, 4H), 7.20-7.12 (m, 2H), 7.10-6.95 (m, 8H), 4.85-4.75 (m, 1H), 4.47-4.32 (m, 1H), 4.27-4.02 (m, 1H), 3.92 (s, 1H), 3.65-3.52 (m, 2H), 3.40-3.15 (m, 2H), 2.27-2.12 (m, 4H), 1.87-1.65 (m, 3H), 1.60-1.20 (m, 4H). MS m/z (ESI): 538.6 [M + H]$^+$. |

TABLE 7-continued

| No. | Compound Structure | Compound Name | Starting material or reagent different from that in Example 5 | Characterization data |
|---|---|---|---|---|
| C213 | 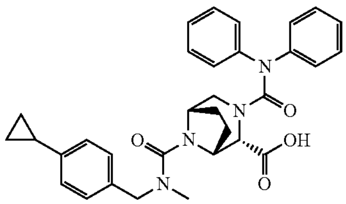 [SMILES: CN(Cc1ccc(C2CC2)cc1)C(=O)N1[C@H]2CC[C@@H]1[C@@H](C(=O)O)N(C(=O)N(c1ccccc1)c1ccccc1)C2] | (1R,2S,5S)-8-((4-cyclopropylbenzyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [4-cyclopropylbenzyl methylamine]. The reaction in step 5a did not take place. | $^1$H NMR (400 MHz, DMSO-$d_6$) δ 13.40-12.85 (m, 1H), 7.34 (t, J = 7.8 Hz, 4H), 7.15 (t, J = 7.4 Hz, 2H), 7.06-6.97 (m, 8H), 4.37 (d, J = 15.1 Hz, 2H), 4.20 (d, J = 15.1 Hz, 1H), 3.90 (s, 1H), 3.50-3.37 (m, 2H), 2.67 (s, 3H), 1.95-1.83 (m, 1H), 1.68 (s, 1H), 1.55 (s, 1H), 1.46-1.32 (m, 1.27-1.09 (m, 2H), 0.95-0.89 (m, 2H), 0.67-0.58 (m, 2H). MS m/z (ESI): 538.7 [M + H]$^+$. |
| C214 | 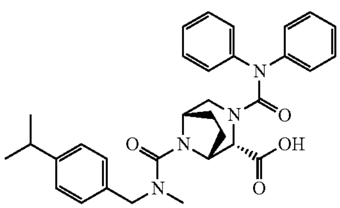 [SMILES: CC(C)c1ccc(CN(C)C(=O)N2[C@H]3CC[C@@H]2[C@@H](C(=O)O)N(C(=O)N(c2ccccc2)c2ccccc2)C3)cc1] | (1R,2S,5S)-3-(diphenylcarbamoyl)-8-((4-isopropylbenzyl)(methyl)carbamoyl)-3,8-diazabicyclo[3.2.1]octane-2-carboxylic acid | Compound 20 in step 5b of Example 5 was replaced with Compound 23. Compound 16 was replaced with [4-isopropylbenzyl methylamine]. The reaction in step 5a did not take place. | $^1$H NMR (400 MHz, DMSO-$d_6$) δ 7.33 (t, J = 7.6 Hz, 4H), 7.19 (d, J = 8.0 Hz, 2H), 7.17-7.06 (m, 4H), 7.03 (d, J = 7.6 Hz, 4H), 4.39 (d, J = 14.8 Hz, 2H), 4.25 (d, J = 15.2 Hz, 2H), 3.92 (s, 1H), 3.37 (s, 2H), 2.90-2.80 (m, 1H), 2.70 (s, 3H), 1.57 (s, 2H), 1.42 (s, 2H), 1.18 (d, J = 6.9 Hz, 6H). MS m/z (ESI): 541.3 [M + H]$^+$. |
| C144 | 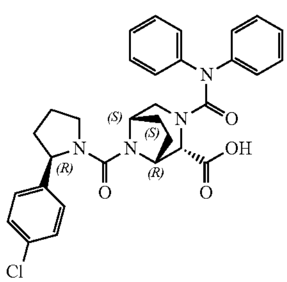 | (1R,2S,5S)-8-((R)-2-(4-chlorphenyl)pyrrolidine-1-carbonyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [(R)-2-(4-chlorophenyl)pyrrolidine]. The reaction in step 5a did not take place. | $^1$H NMR (400 MHz, DMSO-$d_6$) δ 7.42-7.26 (m, 6H), 7.23-7.12 (m, 4H), 7.05-6.95 (m, 4H), 4.82 (t, J = 7.2 Hz, 1H), 4.50-3.90 (m, 3H), 3.70-3.53 (m, 2H), 3.45-3.35 (m, 1H), 3.23 (d, J = 10.8 Hz, 1H), 2.30-2.15 (m, 1H), 1.90-1.65 (m, 2H), 1.55-1.20 (m, 5H). MS m/z (ESI): 559.1 [M + H]$^+$. |
| C216 | 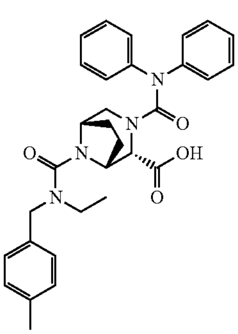 [SMILES: CCN(Cc1ccc(C)cc1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(ethyl(4-methylbenzyl)carbamoyl)-3,8-diazabicyclo[3.2.1]octane-2-carboxylic acid | Compound 20 in step 5b of Example 5 was replaced with Compound 23. Compound 16 was replaced with [N-ethyl-4-methylbenzylamine]. The reaction in step 5a did not take place. | $^1$H NMR (400 MHz, DMSO-$d_6$) δ 12.996 (brs, 1H), 7.35 (t, J = 8.0 Hz, 4H), 7.17 (t, 8.0 Hz, 2H), 7.08 (d, J = 8.0 Hz, 2H), 7.01 (d, J = 7.6 Hz, 4H), 4.46 (d, J = 15.2 Hz, 1H), 4.41-4.22 (m, 2H), 4.19 (d, J = 15.2 Hz, 1H), 3.88 (s, 1H), (m, 1H), 3.01-2.90 (m, 1H), 2.28 (s, 3H), 1.75-1.25 (m, 4H), 0.97 (t, J = 6.8 Hz, 3H). MS m/z (ESI): 526.7 [M + H]$^+$. |

TABLE 7-continued

| No. | Compound Structure | Compound Name | Starting material or reagent different from that in Example 5 | Characterization data |
|---|---|---|---|---|
| C217 | 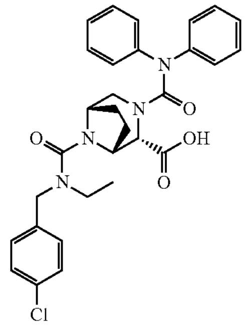 [SMILES: CCN(Cc1ccc(Cl)cc1)C(=O)N1[C@H]2CC[C@@H]1[C@@H](C(=O)O)N(C(=O)N(c1ccccc1)c1ccccc1)C2] | (1R,2S,5S)-8-((4-chlorobenzyl)(ethyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [4-chlorobenzyl ethylamine]. The reaction in step 5a did not take place. | $^1$H NMR (400 MHz, DMSO-d$_6$) δ 7.42-7.30 (m, 6H), 7.22 (d, J = 8.4 Hz, 2H), 7.16 (t, J = 7.2 Hz, 2H), 7.01 (d, J = 7.6 Hz, 4H), 4.48 (d, J = 16.0 Hz, 1H), 4.41-4.26 (m, 2H), 4.25 (d, J = 15.6 Hz, 1H), 3.90 (s, 1H), 3.42 (d, J = 12.0 Hz, 1H), 3.30-3.15 (m, 2H), 3.05-2.90 (m, 1H), 1.70-1.28 (m, 4H), 0.98 (t, J = 7.2 Hz, 3H). MS m/z (ESI): 546.8 [M + H]$^+$. |
| C219 | 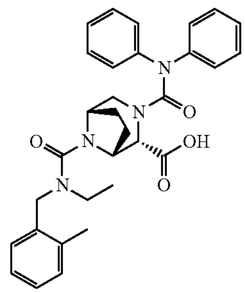 [SMILES: CCN(Cc1ccccc1C)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(ethyl(2-methylbenzyl)carbamoyl)-3,8-diazabicyclo[3.2.1]octane-2-carboxylic acid | Compound 20 in step 5b of Example 5 was replaced with Compound 23. Compound 16 was replaced with [2-methylbenzyl ethylamine]. The reaction in step 5a did not take place. | $^1$H NMR (400 MHz, DMSO-d$_6$) δ 13.02 (s, 1H), 7.35 (t, J = 7.9 Hz, 4H), 7.21-7.06 (m, 6H), 7.01 (d, J = 7.5 Hz, 4H), 4.55 (d, J = 15.6 Hz, 1H), 4.33 (s, 1H), 4.18 (d, J = 15.6 Hz, 1H), 3.89 (s, 1H), 3.41-3.28 (m, 3H), 3.25 3.14 (m, 1H), 2.96-2.85 (m, 1H), 2.17 (s, 3H), 1.77-1.64 (m, 1H), 1.58-1.46 (s, 1H), 1.45-1.33 (m, 1H), 1.29-1.22 (m, 1H), 0.94 (t, J = 7.0 Hz, 3H). MS m/z (ESI): 526.7 [M + H]$^+$. |
| C212 | 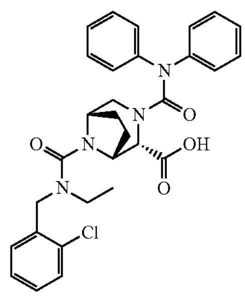 [SMILES: CCN(Cc1ccccc1Cl)C(=O)N1[C@H]2CC[C@@H]1[C@@H](C(=O)O)N(C(=O)N(c1ccccc1)c1ccccc1)C2] | (1R,2S,SS)-8-((2-chlorobenzyl)(ethyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [2-chlorobenzyl ethylamine]. The reaction in step 5a did not take place. | $^1$H NMR (400 MHz, DMSO-d$_6$) δ 13.03 (s, 1H), 7.46-7.14 (m, 10H), 7.04-6.98 (m, 4H), 4.61 (d, J = 16.0 Hz, 1H), 4.33 (s, 1H), 4.26 (d, J = 16.0 Hz, 2H), 3.90 (s, 1H), 3.42 (d, J = 12.9 Hz, 2H), 3.26 (dd, J = 14.1, 7.1 Hz, 1H), 3.02 (dd, J = 14.2, 7.0 Hz, 1H), 1.74-1.61 (m, 1H), 1.59-1.47 (m, 1H), 1.44-1.32 (m, 1H), 1.28-1.16 (m, 1H), 0.99 (t, J = 7.0 Hz, 3H). MS m/z (ESI): 546.7 [M + H]$^+$. |
| C210 | 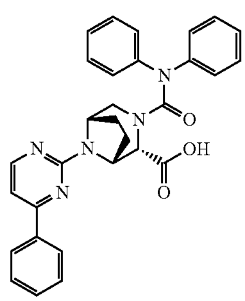 [SMILES: O=C(O)[C@@H]1[C@H]2CC[C@@H](CN1C(=O)N(c1ccccc1)c1ccccc1)N2c1nccc(-c2ccccc2)n1] | (1R,2S,5S)-3-(diphenylcarbamoyl)-8-(4-phenylpyrimidine-2-yl)-3,8-diazabicyclo[3.2.1]octane-2-carboxylic acid | In step 5a of Example 5, Compound 20 was replaced with Compound 23, phenyl chloroformate was replaced with [2-chloro-4-phenylpyrimidine]. TEA was replaced with DIPEA and DCM was replaced with NMP; and the reaction condition was changed to reacting at 130° C. for 16 hours. The reaction in step 5b did not take place. | $^1$H NMR (400 MHz, DMSO-d$_6$) δ 8.42 (d, J = 5.2 Hz, 1H), 8.17-8.10 (m, 2H), 7.55-7.45 (m, 3H), 7.37 (t, J = 8.0 Hz, 4H), 7.28 (d, J = 5.2 Hz, 1H), 7.18 (t, J = 7.2 Hz, 2H), 7.07-7.00 (m, 4H), 5.33 (s, 1H), 4.88 (s, 1H), 4.38 (s, 1H), 3.56 (d, J = 12.0 Hz, 1H), 3.41 (d, J = 11.6 Hz, 1H), 1.81-1.61 (m, 2H), 1.50-1.30 (m, 2H). MS m/z (ESI): 505.8 [M + H]$^+$. |

TABLE 7-continued

| No. | Compound Structure | Compound Name | Starting material or reagent different from that in Example 5 | Characterization data |
|---|---|---|---|---|
| C253 | 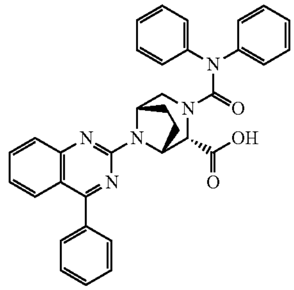 [SMILES: O=C(O)[C@@H]1[C@H]2CC[C@@H](CN1C(=O)N(c1ccccc1)c1ccccc1)N2c1nc(-c2ccccc2)c2ccccc2n1] | (1R,2S,5S)-3-(diphenylcarbamoyl)-8-(4-phenylquinazoline-2-yl)-3,8-diazabicyclo[3.2.1]octane-2-carboxylic acid | In step 5a of Example 5, Compound 20 was replaced with Compound 23, phenyl chloroformate was replaced with [2-chloro-4-phenylquinazoline structure]. TEA was replaced with DIPEA, and DCM was replaced with NMP; and the reaction condition was changed to reacting at 130° C. for 16 hours. The reaction in step 5b did not take place. | $^1$H NMR (400 MHz, DMSO-d$_6$) δ 7.86-7.74 (m, 4H), 7.66-7.56 (m, 4H), 7.40-7.30 (m, 5H), 7.19 (t, J = 7.2 Hz, 2H), 7.03 (d, J = 7.2 Hz, 4H), 5.42 (s, 1H), 4.97 (s, 1H), 4.42 (s, 1H), 3.60 (d, J = 13.2 Hz, 1H), 3.50-3.40 (m, 1H), 1.86-1.65 (m, 2H), 1.61-1.40 (m, 2H). MS m/z (ESI): 556.1 [M + H]$^+$. |
| C173 | 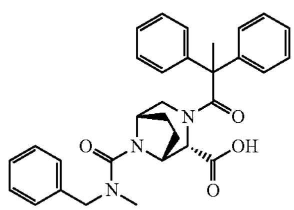 | (1R,2S,5S)-8-(benzyl(methyl)carbamoyl)-3-(2,2-diphenylpropionyl)-3,8-diazabicyclo[3.2.1]octane-2-carboxylic acid | Compound 7 in step 3 of Example 5 was replaced with [2,2-diphenylpropionyl chloride structure]. The reaction in step 5a did not take place. | $^1$H NMR (400 MHz, DMSO-d$_6$) δ 7.52 (d, J = 7.26 Hz, 2H), 7.45-7.10 (m, 13H), 4.77 (d, J = 2.8 Hz, 1H), 4.45-4.05 (m, 3H), 3.52 (d, J = 5.6 Hz, 1H), 3.20-3.05 (m, 2H), 2.72-2.57 (m, 3H), 1.85-1.51 (m, 4H), 1.30-1.00 (m, 3H). MS m/z (ESI): 511.8 [M + H]$^+$. |
| C192 | 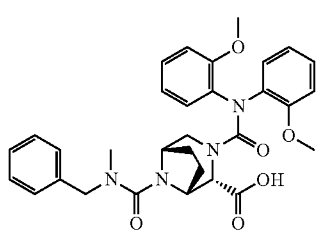 [SMILES: COc1ccccc1N(C(=O)N1C[C@@H]2CC[C@H]([C@H]1C(=O)O)N2C(=O)N(C)Cc1ccccc1)c1ccccc1OC] | (1R,2S,5S)-8-(benzyl(methyl)carbamoyl)-3-(bis(2-methoxylphenyl)carbamoyl)-3,8-diazabicyclo[3.2.1]octane-2-carboxylic acid | Compound 7 in step 3 of Example 5 was replaced with [bis(2-methoxyphenyl)carbamoyl chloride structure]. The reaction in step 5a did not take place. | $^1$H NMR (400 MHz, DMSO-d$_6$) δ 12.53 (brs, 1H), 7.33 (t, J = 7.2 Hz, 2H), 7.28-7.22 (m, 1H), 7.21-7.11 (m, 4H), 7.07-7.00 (m, 2H), 6.85 (t, J = 7.6 Hz, 2H), 6.82-6.75 (m, 2H), 4.49-4.38 (m, 2H), 4.37-4.31 (m, 1H), 4.23 (d, J = 15.2 Hz, 1H), 3.87 (s, 1H), 3.70 (s, 6H), 3.41 (d, J = 11.6 Hz, 1H), 3.25 (d, J = 11.2 Hz, 1H), 2.68 (s, 3H), 1.85-1.71 (m, 1H), 1.61-1.31 (m, 3H). MS m/z (ESI): 558.7 [M + H]$^+$. |
| C171 | 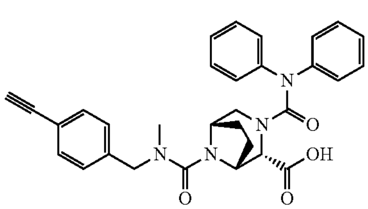 [SMILES: C#Cc1ccc(CN(C)C(=O)N2[C@H]3CC[C@@H]2[C@@H](C(=O)O)N(C(=O)N(c2ccccc2)c2ccccc2)C3)cc1] | (1R,2S,5S)-3-(diphenylcarbamoyl)-8-((4-ethynylbenzyl)(methyl)carbamoyl)-3,8-diazabicyclo[3.2.1]octane-2-carboxylic acid | Compound 20 in step 5b of Example 5 was replaced with Compound 23. Compound 16 was replaced with [4-ethynylbenzyl(methyl)amine structure]. The reaction in step 5a did not take place. | 1H NMR (400 MHz, DMSO-d$_6$) δ 7.44 (d, J = 8.0 Hz, 2H), 7.35 (t, J = 8.0 Hz, 4H), 7.25-7.05 (m, 4H), 7.01 (d, J = 7.6 Hz, 4H), 4.45 (d, J = 15.6 Hz, 1H), 4.38-4.30 (m, 2H), 4.27 (d, J = 15.6 Hz, 1H), 4.17 (s, 1H), 3.93 (s, 1H), 3.45-3.34 (m, 2H), 2.71 (s, 3H), 1.77-1.65 (m, 1H), 1.60-1.46 (m, 1H), 1.45-1.20 (m, 1H). MS m/z (ESI): 523.0 [M + H]$^+$. |

TABLE 7-continued

| No. | Compound Structure | Compound Name | Starting material or reagent different from that in Example 5 | Characterization data |
|---|---|---|---|---|
| C220 | 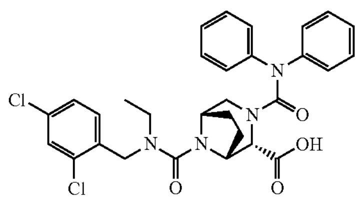 | (1R,2S,5S)-8-((2,4-dichlorobenzyl)(ethyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$H NMR (400 MHz, DMSO-d$_6$) δ 7.35-7.0 (m, 20H), 5.49 (s, 1H), 5.37 (s, 1H), 5.14 (s, 1H), 4.73 (s, 1H), 4.57 (s, 1H), 3.75-3.45 (m, 2H), 2.25-2.0 (m, 1H), 1.95-1.50 (m, 3H). MS m/z (ESI): 544.9 [M + H]$^+$. |
| C196 | 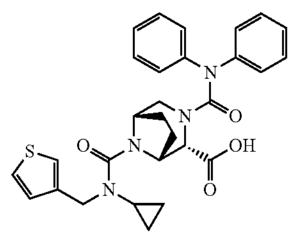 [SMILES: O=C(O)[C@@H]1[C@H]2CC[C@@H](CN1C(=O)N(c1ccccc1)c1ccccc1)N2C(=O)N(Cc1ccsc1)C1CC1] | (1R,2S,5S)-8-(cyclopropyl(thiophene-3-yl-methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$H NMR (400 MHz, DMSO-d$_6$) δ 12.99 (s, 1H), 7.60-6.89 (m, 13H), 4.61 (d, J = 15.1 Hz, 1H), 4.46 (s, 1H), 4.31 (s, 1H), 4.18-4.04 (m, 2H), 3.43 (s, 2H), 2.43 (s, 1H), 1.68 (s, 1H), 1.54-1.33 (m, 2H), 1.26-1.14 (m, 1H), 0.78-0.66 (m, 1H), 0.64-0.42 MS m/z (ESI): 531.0 [M + H]$^+$. |
| C205 | 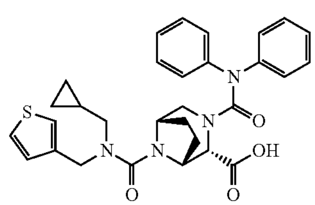 [SMILES: O=C(O)[C@@H]1[C@H]2CC[C@@H](CN1C(=O)N(c1ccccc1)c1ccccc1)N2C(=O)N(Cc1ccsc1)CC1CC1] | (1R,2S,5S)-8-((cyclopropylmethyl)(thiophene-3-ylmethyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$H NMR (400 MHz, DMSO-d$_6$) δ 13.04 (s, 1H), 7.48 (dd, J = 4.9, 2.9 Hz, 1H), 7.41-7.27 (m, 5H), 7.17 (t, J = 7.4 Hz, 2H), 7.01 (d, J = 7.6 Hz, 4H), 6.94 (d, J = 4.9 Hz, 1H), 4.58 (d, J = 15.4 Hz, 1H), 4.33 (d, J = 15.3 Hz, 3H), 3.89 (s, 1H), 3.48-3.27 (m, 2H), 3.04-2.87 (m, 2H), 1.69 (s, 1H), 1.53 (s, 1H), 1.43-1.31 (m, 1H), 1.27-1.15 (m, 1H), 0.95 (s, 1H), 0.45-0.30 (m, 2H), 0.09 (d, J = 4.6 Hz, 2H). MS m/z (ESI): 544.6 [M + H]$^+$. |
| C255 | 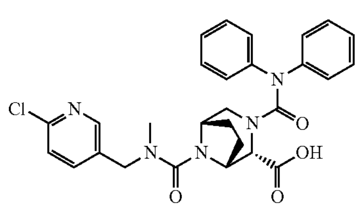 [SMILES: CN(Cc1ccc(Cl)nc1)C(=O)N1[C@H]2CC[C@@H]1[C@@H](C(=O)O)N(C(=O)N(c1ccccc1)c1ccccc1)C2] | (1R,2S,5S)-8-((6-chloropyridine-3-yl)methyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$H NMR (400 MHz, DMSO-d$_6$) δ 13.00 (s, 1H), 8.26 (s, 1H), 7.68 (d, J = 7.6 Hz, 1H), 7.48 (d, J = 8.0 Hz, 1H), 7.35 (t, J = 7.6 Hz, 4H), 7.16 (t, J = 7.2 Hz, 2H), 7.01 (d, J = 7.6 Hz, 4H), 4.42 (d, J = 15.6 Hz, 1H), 4.35 (s, 1H), 4.28 (d, J = 15.2 Hz, 1H), 3.94 (s, 2H), 3.44-3.34 (m, 3H), 2.74 (s, 3H), 1.69 (s, 1H), 1.54 (s, 1H), 1.37 (s, 1H), 1.24 (s, 1H). MS m/z (ESI): 534.1 [M + H]$^+$. |

TABLE 7-continued

| No. | Compound Structure | Compound Name | Starting material or reagent different from that in Example 5 | Characterization data |
|---|---|---|---|---|
| C206 | 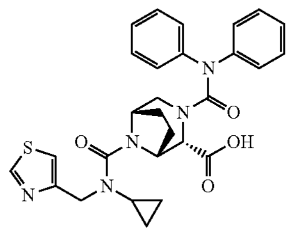 [SMILES: O=C(O)[C@@H]1[C@H]2CC[C@@H](CN1C(=O)N(c1ccccc1)c1ccccc1)N2C(=O)N(Cc1cscn1)C1CC1] | (1R,2S,5S)-8-(cyclopropyl(thiazole-4-ylmethyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [structure]. The reaction in step 5a did not take place. | $^1$H NMR (400 MHz, DMSO-d$_6$) δ 9.03 (d, J = 2.0 Hz, 1H), 7.45-7.31 (m, 5H), 7.17 (t, J = 7.2 Hz, 2H), 7.01 (d, J = 7.6 Hz, 4H), 4.80 (d, J = 15.6 Hz, 1H), 4.50-4.25 (m, 2H), 4.22 (d, J = 15.6 Hz, 1H), 3.50-3.30 (m, 2H), 2.6-2.51 (m, 1H), 1.75-1.20 (m, 4H), 0.75-0.50 (m, 4H). MS m/z (ESI): 520.0 [M + H]$^+$. |
| C207 | 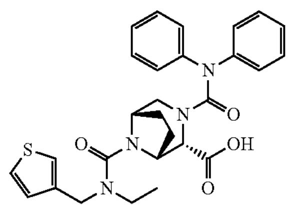 | (1R,2S,5S)-3-(diphenylcarbamoyl)-8-(ethyl(thiophene-3-ylmethyl)carbamoyl)-3,8-diazabicyclo[3.2.1]octane-2-carboxylic acid | Compound 20 in step 5b of Example 5 was replaced with Compound 23. Compound 16 was replaced with [structure]. The reaction in step 5a did not take place. | $^1$H NMR (400 MHz, DMSO-d$_6$) δ 13.05 (s, 1H), 7.48 (dd, J = 4.8 Hz, 2.8 Hz, 1H), 7.35 (t, J = 8.0 Hz, 4H), 7.30 (d, J = 1.6 Hz, 1H), 7.16 (t, J = 7.2 Hz, 2H), 7.01 (d, J = 7.6 Hz, 4H), 6.95 (dd, J = 4.8, 1.2 Hz, 1H), 4.43 (d, J = 15.2 Hz, 1H), 4.40-4.26 (m, 2H), 4.23 (d, J = 15.2 Hz, 1H), 3.89 (s, 1H), 3.49-3.34 (m, 2H), 3.25-3.12 (m, 1H), 3.05-2.94 (m, 1H), 1.75-1.19 (m, 4H), 0.98 (t, J = 6.8 Hz, 3H). MS m/z (ESI): 519.0 [M + H]$^+$. |
| C218 | 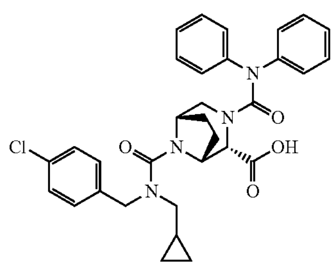 [SMILES: O=C(O)[C@@H]1[C@H]2CC[C@@H](CN1C(=O)N(c1ccccc1)c1ccccc1)N2C(=O)N(Cc1ccc(Cl)cc1)CC1CC1] | (1R,2S,5S)-8-((4-chlorobenzyl)(cyclopropylmethyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [structure]. The reaction in step 5a did not take place. | $^1$H NMR (400 MHz, DMSO-d$_6$) δ 13.04 (s, 1H), 7.41-7.30 (m, 6H), 7.25-7.11 (m, 4H), 7.05-6.98 (m, 4H), 4.61 (d, J = 15.7 Hz, 1H), 4.38-4.22 (m, 3H), 3.91 (s, 1H), 3.39 (dd, J = 39.5, 11.8 Hz, 2H), 3.07-2.89 (m, 2H), 1.69 (s, 1H), 1.52 (s, 1H), 1.37 (s, 1H), 1.24 (s, 1H), 0.92 (s, 1H), 0.44-0.31 (m, 2H), 0.12-0.04 (m, 2H). MS m/z (ESI): 573.1 [M + H]$^+$. |
| C209 | 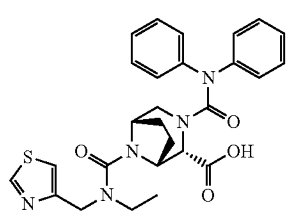 | (1R,2S,5S)-3-(diphenylcarbamoyl)-8-(ethyl(thiazole-4-ylmethyl)carbamoyl)-3,8-diazabicyclo[3.2.1]octane-2-carboxylic acid | Compound 20 in step 5b of Example 5 was replaced with Compound 23. Compound 16 was replaced with [structure]. The reaction in step 5a did not take place. | $^1$H NMR (400 MHz, DMSO-d$_6$) δ 9.06 (d, J = 2.0 Hz, 1H), 7.46 (d, J = 2.0 Hz, 1H), 7.35 (t, J = 8.0 Hz, 4H), 7.17 (t, J = 7.2 Hz, 2H), 7.01 (d, J = 7.2 Hz, 4H), 4.57 (d, J = 15.6 Hz, 1H), 4.41 (d, J = 15.6 Hz, 1H), 4.39-4.20 (m, 2H), 4.04 (s, 1H), 3.45-3.30 (m, 2H), 3.25-3.16 (m, 1H), 3.13-3.04 (m, 1H), 1.80-1.20 (m, 4H), 0.99 (t, J = 7.2 Hz, 3H). MS m/z (ESI): 520.1 [M + H]$^+$. |
| C180 | 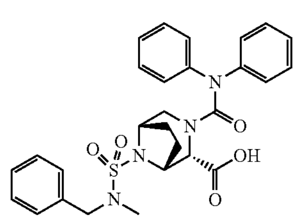 [SMILES: CN(Cc1ccccc1)S(=O)(=O)N1[C@H]2CC[C@@H]1[C@@H](C(=O)O)N(C(=O)N(c1ccccc1)c1ccccc1)C2] | (1R,2S,5S)-8-(N-benzyl-N-methylsulphamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [structure]. | $^1$H NMR (400 MHz, DMSO-d$_6$) δ 7.45-7.25 (m, 9H), 7.24-7.12 (m, 2H), 7.08-6.92 (m, 4H), 4.37 (s, 1H), 4.22 (s, 2H), 4.05-3.95 (m, 2H), 3.50 (d, J = 11.2 Hz, 1H), 3.26 (d, J = 12.8 Hz, 1H), 2.59 (s, 3H), 1.90-1.70 (m, 2H), 1.55-1.25 (m, 2H). MS m/z (ESI): 534.6 [M + H]$^+$. |

TABLE 7-continued

| No. | Compound Structure | Compound Name | Starting material or reagent different from that in Example 5 | Characterization data |
|---|---|---|---|---|
| C260 | 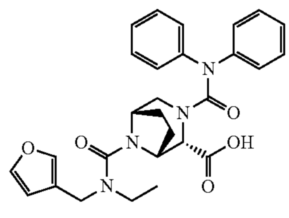 [SMILES: CCN(Cc1ccoc1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(ethyl (furan-3-ylmethyl) carbamoyl)-3,8-diazabicyclo [3.2.1]octane-2-carboxylic acid | The reaction in step 5a did not take place.<br><br>Compound 20 in step 5b of Example 5 was replaced with Compound 23. Compound 16 was replaced with<br><br>[furan-3-ylmethyl ethylamine structure]<br><br>The reaction in step 5a did not take place. | 1H NMR (400 MHz, DMSO-d$_6$) δ 13.02 (s, 1H), 7.60-7.56 (m, 2H), 7.35 (t, J = 7.9 Hz, 4H), 7.17 (t, J = 7.4 Hz, 2H), 7.01 (d, J = 7.6 Hz, 4H), 6.35 (s, 1H), 4.35-4.20 (m, 3H), 4.07 (d, J = 15.4 Hz, 1H), 3.88 (s, 1H), 3.42 (s, 1H), 3.36 (s, 1H), 3.22-3.14 (m, 1H), 3.05-2.95 (m, 1H), 1.68 (s, 1H), 1.53 (s, 1H), 1.30 (d, J = 42.4 Hz, 2H), 0.99 (t, J = 7.0 Hz, 3H).<br>MS m/z (ESI): 503.1 [M + H]$^+$. |
| C225 | 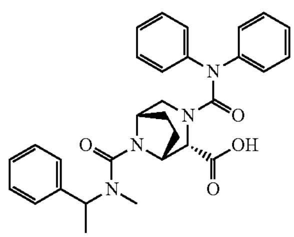 [SMILES: CC(c1ccccc1)N(C)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(methyl (1-phenylethyl) carbamoyl)-3,8-diazabicyclo [3.2.1]octane-2-carboxylic acid | Compound 20 in step 5b of Example 5 was replaced with Compound 23. Compound 16 was replaced with<br><br>[1-phenylethyl methylamine structure]<br><br>The reaction in step 5a did not take place. | $^1$H NMR (400 MHz, DMSO-d$_6$) δ 13.02 (s, 1H), 7.48-7.30 (m, 6H), 7.30-7.20 (m, 3H), 7.17 (t, J = 8.0 Hz, 2H), 7.01 (d, J = 8.0 Hz, 4H), 5.24-5.16 (m, 1H), 4.41-4.28 (m, 2H), 3.40-3.80 (m, 1H), 3.50-3.39 (m, 2H), 2.53 (s, 1H), 2.43 (s, 1H), 1.76 (s, 1H), 1.58 (s, 1H), 1.49-1.39 (m, 3H), 1.33-1.16 (m, 2H).<br>MS m/z (ESI): 513.1 [M + H]$^+$. |
| C229 | 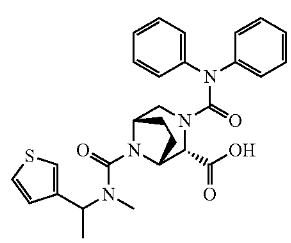 [SMILES: CC(c1ccsc1)N(C)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(methyl (1-(thiophene-3-yl)ethyl) carbamoyl)-3,8-diazabicyclo[3.2.1] octane-2-carboxylic acid | Compound 20 in step 5b of Example 5 was replaced with Compound 23. Compound 16 was replaced with<br><br>[1-(thiophen-3-yl)ethyl methylamine structure]<br><br>The reaction in step 5a did not take place. | $^1$H NMR (400 MHz, DMSO-d$_6$) δ 13.03 (s, 1H), 7.53-7.47 (m, 1H), 7.45-7.28 (m, 5H), 7.25-7.15 (m, 2H), 7.10-6.98 (m, 4H), 6.97-6.88 (m, 1H), 5.20-5.05 (m, 1H), 4.40-4.15 (m, 2H), 3.89 (d, J = 22.4 Hz, 1H), 3.45-3.35 (m, 2H), 2.50-2.40 (m, 3H), 1.80-1.48 (m, 2H), 1.48-1.27 (m, 5H).<br>MS m/z (ESI): 541.0 [M + Na]$^+$. |
| C215 | 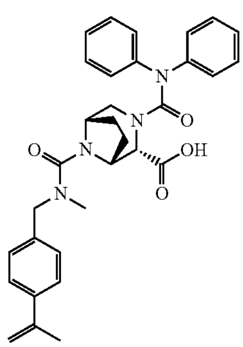 [SMILES: C=C(C)c1ccc(CN(C)C(=O)N2[C@H]3CC[C@@H]2[C@@H](C(=O)O)N(C(=O)N(c2ccccc2)c2ccccc2)C3)cc1] | (1R,2S,5S)-3-(diphenylcarbamoyl)-8-(Methyl(4-(prop-1-ene-2-yl)benzyl)) carbamoyl)-3,8-diazabicyclo[3.2.1] octane-2-carboxylic acid | Compound 20 in step 5b of Example 5 was replaced with Compound 23. Compound 16 was replaced with<br><br>[4-(prop-1-en-2-yl)benzyl methylamine structure]<br><br>The reaction in step 5a did not take place. | $^1$H NMR (400 MHz, DMSO-d$_6$) δ 7.47 (d, J = 8.4 Hz, 2H), 7.36 (t, J = 8.0 Hz, 4H), 7.20-7.10 (m, 4H), 7.01 (d, J = 7.6 Hz, 4H), 5.42 (s, 1H), 5.08 (s, 1H), 4.42 (d, J = 15.2 Hz, 1H), 4.40-4.28 (m, 2H), 4.27 (d, J = 15.6 Hz, 1H), 3.93 (s, 1H), 3.45-3.34 (m, 2H), 2.70 (s, 3H), 2.10 (s, 3H), 1.80-1.65 (m, 1H), 1.62-1.50 (m, 1H), 1.45-1.20 (m, 1H).<br>MS m/z (ESI): 539.0 [M + H]$^+$. |

TABLE 7-continued

| No. | Compound Name | Starting material or reagent different from that in Example 5 | Characterization data |
|---|---|---|---|
| C200 | (1R,2S,5S)-8-(cyclopropyl (thiophene-2-ylmethyl) carbamoyl)-3-(diphenylcarbamoyl)-3,8-diazabicyclo [3.2.1]octane-2-carboxylic acid | Compound 20 in step 5b of Example 5 was replaced with Compound 23. Compound 16 was replaced with [structure]. The reaction in step 5a did not take place. | $^1$H NMR (400 MHz, DMSO-d$_6$) δ 12.76 (s, 1H), 7.47-7.34 (m, 3H), 7.22 (d, J = 8.4 Hz, 3H), 7.03-6.95 (m, 1H), 4.59 (s, 1H), 4.27 (s, 1H), 4.15-4.05 (m, 1H), 3.20-3.09 (m, 1H), 2.55 (s, 1H), 1.92-1.80 (m, 1H), 1.52 (s, 2H), 0.76-0.64 (m, 2H). MS m/z (ESI): 531.1 [M + H]$^+$. |
| C265 | (1R,2S,5S)-3-(diphenylcarbamoyl)-8-(methyl (quinoline-2-ylmethyl)carbamoyl)-3,8-diazabicyclo [3.2.1]octane-2-carboxylic acid | Compound 20 in step 5b of Example 5 was replaced with Compound 23. Compound 16 was replaced with [structure]. The reaction in step 5a did not take place. | $^1$H NMR (400 MHz, DMSO-d$_6$) δ 8.72 (s, 1H), 8.15 (d, J = 7.6 Hz, 2H), 7.94 (d, J = 7.6 Hz, 1H), 7.76 (t, J = 7.2 Hz, 1H), 7.61 (d, J = 7.6 Hz, 1H), 7.36 (t, J = 8.0 Hz, 4H), 7.17 (t, J = 7.6 Hz, 2H), 7.02 (d, J = 7.2 Hz, 4H), 4.86 (d, J = 16.4 Hz, 1H), 4.66 (d, J = 16.4 Hz, 1H), 4.44-4.20 (m, 2H), 4.09 (s, 1H), 3.50-3.30 (m, 2H), 2.97 (s, 3H), 1.75-1.20 (m, 4H). MS m/z (ESI): 549.8 [M + H]$^+$. |
| C266 | (1R,2S,5S)-3-(diphenylcarbamoyl)-8-(methyl (quinoline-6-ylmethyl)carbamoyl)-3,8-diazabicyclo [3.2.1]octane-2-carboxylic acid | Compound 20 in step 5b of Example 5 was replaced with Compound 23. Compound 16 was replaced with [structure]. The reaction in step 5a did not take place. | $^1$H NMR (400 MHz, DMSO-d$_6$) δ 9.03 (s, 1H), 8.64 (s, 1H), 8.10 (d, J = 8.8 Hz, 1H), 7.90 (s, 1H), 7.72 (d, J = 8.0 Hz, 2H), 7.36 (t, J = 8.0 Hz, 4H), 7.17 (t, J = 7.2 Hz, 2H), 7.01 (d, J = 7.2 Hz, 4H), 4.68 (d, J = 16.0 Hz, 1H), 4.48 (d, J = 16.0 Hz, 1H), 4.44-4.25 (m, 2H), 3.99 (s, 1H), 3.48-3.32 (m, 2H), 2.79 (s, 3H), 1.79-1.20 (m, 4H). MS m/z (ESI): 549.8 [M + H]$^+$. |
| C187 | (1R,2S,5S)-3-(2,2-diphenylacetyl)-8-(methyl(thiophene-3-ylmethyl) carbamoyl)-3,8-diazabicyclo [3.2.1]octane-2-carboxylic acid | Compound 16 in step 5b of Example 5 was replaced with [structure]. The reaction in step 5a did not take place. | $^1$H NMR (400 MHz, DMSO-d$_6$) δ 7.50-6.95 (m, 13H), 5.50-5.35 (m, 1H), 4.80-4.00 (m, 5H), 4.00-3.50 (m, 2H), 2.80-2.60 (m, 3H), 1.80-1.00 (m, 4H). MS m/z (ESI): 504.1 [M + H]$^+$. |
| C237 | (1R,2S,5S)-8-((4-(tert-butyl)benzyl) (methyl)carbamoyl)-3-(diphenylcarbamoyl)-3,8-diazabicyclo [3.2.1]octane-2-carboxylic acid | Compound 20 in step 5b of Example 5 was replaced with Compound 23. Compound 16 was replaced with [structure]. | $^1$H NMR (400 MHz, DMSO-d$_6$) δ 13.12 (s, 1H), 7.45-6.89 (m, 14H), 4.40 (d, J = 15.2 Hz, 2H), 4.22 (d, J = 15.2 Hz, 1H), 3.94 (s, 1H), 3.42 (d, J = 12.5 Hz, 2H), 2.71 (s, 3H), 1.69 (s, 1H), 1.57 (s, 1H), 1.41 (d, J = 6.1 Hz, 1H), 1.25 (s, 9H), 1.21-1.07 (m, 1H). MS m/z (ESI): 554.7 [M + H]$^+$. |

TABLE 7-continued

| No. | Compound Structure | Compound Name | Starting material or reagent different from that in Example 5 | Characterization data |
|---|---|---|---|---|
| | | | The reaction in step 5a did not take place. | |
| C148 | 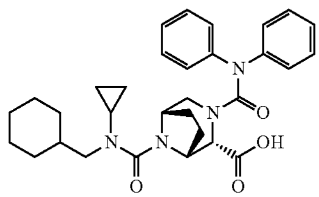 [SMILES: O=C(O)[C@@H]1[C@H]2CC[C@@H](CN1C(=O)N(c1ccccc1)c1ccccc1)N2C(=O)N(CC1CCCCC1)C1CC1] | (1R,2S,5S)-8-((cyclohexylmethyl)(cyclopropyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br>The reaction in step 5a did not take place. | $^1$H NMR (400 MHz, DMSO-d$_6$) δ 12.93 (s, 1H), 7.36 (t, J = 7.9 Hz, 4H), 7.17 (t, J = 7.4 Hz, 2H), 7.02 (d, J = 7.6 Hz, 4H), 4.48-4.18 (m, 2H), 4.08 (s, 1H), 3.34 (dd, J = 13.4, 8.7 Hz, 1H), 2.68 (dd, J = 13.4, 5.5 Hz, 1H), 2.58 (s, 1H), 1.73-1.48 (m, 7H), 1.42 (s, 2H), 1.29-1.05 (m, 4H), 0.92-0.67 (m, 3H), 0.65-0.57 (m, 1H), 0.55-0.40 (m, 2H). <br>MS m/z (ESI): 530.7 [M + H]$^+$. |
| C201 | 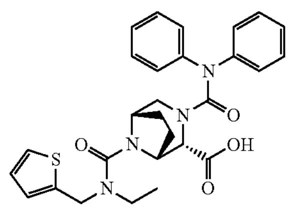 [SMILES: CCN(Cc1cccs1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(ethyl(thiophene-2-ylmethyl)carbamoyl)-3,8-diazabicyclo[3.2.1]octane-2-carboxylic acid | Compound 20 in step 5b of Example 5 was replaced with Compound 23. Compound 16 was replaced with <br><br>The reaction in step 5a did not take place. | $^1$H NMR (400 MHz, CD$_3$OD) δ 7.40-7.33 (m, 4H), 7.30 (dd, J = 5.2, 1.2 Hz, 1H), 7.24-7.18 (m, 2H), 7.15-7.05 (m, 4H), 7.00-6.92 (m, 2H), 4.70 (d, J = 15.6 Hz, 1H), 4.58-4.45 (m, 3H), 3.99 (s, 1H), 3.58-3.45 (m, 2H), 3.40-3.34 (m, 1H), 3.23-3.14 (m, 1H), 1.95-1.53 (m, 4H), 1.11 (t, J = 7.2 Hz, 3H). <br>MS m/z (ESI): 518.8 [M + H]$^+$. |
| C245 | 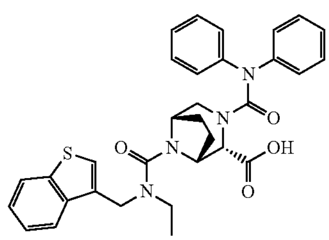 [SMILES: CCN(Cc1csc2ccccc12)C(=O)N1[C@H]2CC[C@@H]1[C@@H](C(=O)O)N(C(=O)N(c1ccccc1)c1ccccc1)C2] | (1R,2S,5S)-8-((benzo[b]thiophene-3-ylmethyl)(ethyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br>The reaction in step 5a did not take place. | $^1$H NMR (400 MHz, DMSO-d$_6$) δ 13.04 (s, 1H), 8.02-7.95 (m, 1H), 7.69 (dd, J = 6.1, 2.8 Hz, 1H), 7.60 (s, 1H), 7.44-7.31 (m, 6H), 7.16 (t, J = 7.4 Hz, 2H), 7.01 (d, J = 7.5 Hz, 4H), 4.82 (d, J = 15.4 Hz, 1H), 4.44 (d, J = 15.4 Hz, 1H), 4.41-4.27 (m, 2H), 3.88 (s, 1H), 3.38 (dd, J = 29.8, 12.4 Hz, 2H), 3.29-3.18 (m, 1H), 3.03-2.91 (m, 1H), 1.83-1.68 (m, 1H), 1.63-1.50 (m, 1H), 1.46-1.31 (m, 1H), 1.24 (s, 1H), 0.98 (t, J = 7.0 Hz, 3H). <br>MS m/z (ESI): 569.1 [M + H]$^+$. |
| C246 | 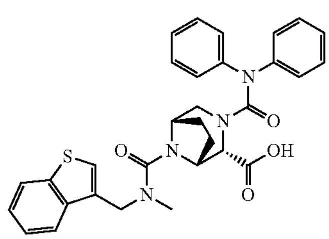 [SMILES: CN(Cc1csc2ccccc12)C(=O)N1[C@H]2CC[C@@H]1[C@@H](C(=O)O)N(C(=O)N(c1ccccc1)c1ccccc1)C2] | (1R,2S,5S)-8-(benzo[b]thiophene-3-ylmethyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br>The reaction in step 5a did not take place. | $^1$H NMR (400 MHz, DMSO-d$_6$) δ 8.00-7.97 (m, 1H), 7.72-7.65 (m, 1H), 7.60 (s, 1H), 7.40-7.30 (m, 6H), 7.16 (t, J = 7.2 Hz, 2H), 7.00 (d, J = 6.0 Hz, 4H), 4.82 (d, J = 15.0 Hz, 1H), 4.44 (d, J = 15.1 Hz, 1H), 4.39 (s, 1H), 3.84 (s, 1H), 3.43-3.35 (m, 2H), 2.72 (s, 3H), 1.77 (s, 1H), 1.54 (s, 1H), 1.33 (d, J = 14.4 Hz, 1H), 1.31-1.24 (m, 1H). <br>MS m/z (ESI): 555.0 [M + H]$^+$. |

TABLE 7-continued

| No. | Compound Structure | Compound Name | Starting material or reagent different from that in Example 5 | Characterization data |
|---|---|---|---|---|
| C156 | 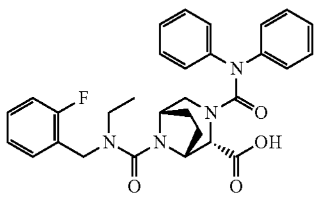 [SMILES: CCN(Cc1ccccc1F)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(ethyl(2-fluorobenzyl)carbamoyl)-3,8-diazabicyclo[3.2.1]octane-2-carboxylic acid | Compound 20 in step 5b of Example 5 was replaced with Compound 23. Compound 16 was replaced with <br><br>The reaction in step 5a did not take place. | $^1$H NMR (400 MHz, DMSO-$d_6$) δ 13.04 (s, 1H), 7.43-7.32 (m, 4H), 7.31-7.2 (m, 2H), 7.21-7.11 (m, 4H), 7.01 (d, J = 7.6 Hz, 4H), 4.57 (d, J = 15.6 Hz, 1H), 4.31 (s, 1H), 4.25 (d, J = 15.6 Hz, 1H), 3.89 (s, 1H), 3.43 (d, J = 12.0 Hz, 1H), 3.35 (d, J = 12.2 Hz, 1H), 3.29-3.21 (m, 1H), 3.05-2.96 (m, 1H), 2.49-2.44 (m, 1H), 1.66 (s, 1H), 1.52 (s, 1H), 1.44-1.17 (m, 2H), 1.00 (t, J = 6.8 Hz, 3H). MS m/z (ESI): 531.1 [M + H]$^+$. |
| C198 | 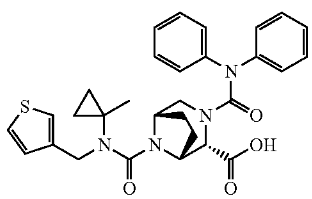 [SMILES: CC1(N(Cc2ccsc2)C(=O)N2[C@H]3CC[C@@H]2[C@@H](C(=O)O)N(C(=O)N(c2ccccc2)c2ccccc2)C3)CC1] | (1R,2S,5S)-3-(diphenylcarbamoyl)-8-((1-methylcyclopropyl(thiophene-3-ylmethyl)carbamoyl)-3,8-diazabicyclo[3.2.1]octane-2-carboxylic acid | Compound 20 in step 5b of Example 5 was replaced with Compound 23. Compound 16 was replaced with <br><br>The reaction in step 5a did not take place. | $^1$H NMR (400 MHz, DMSO-$d_6$) δ 13.05 (s, 1H), 7.50-7.44 (m, 1H), 7.35 (t, J = 8.0 Hz, 4H), 7.28 (d, J = 2.0 Hz, 1H), 7.23-7.13 (m, 2H), 7.01 (d, J = 7.6 Hz, 4H), 6.96 (d, J = 4.6 Hz, 1H), 4.55 (d, J = 15.2 Hz, 1H), 4.44-4.25 (m, 2H), 4.19 (d, J = 15.2 Hz, 1H), 3.94 (s, 1H), 3.42-3.36 (m, 2H), 1.70-1.20 (m, 4H), 0.97 (s, 3H), 0.75-0.65 (m, 2H), 0.59-0.56 (m, 1H), 0.48-0.44 (m, 1H). MS m/z (ESI): 545.1 [M + H]$^+$. |
| C114 | 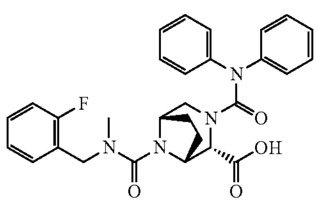 [SMILES: CN(Cc1ccccc1F)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-((2-fluorobenzyl)(methyl)carbamoyl)-3,8-diazabicyclo[3.2.1]octane-2-carboxylic acid | Compound 20 in step 5b of Example 5 was replaced with Compound 23. Compound 16 was replaced with <br><br>The reaction in step 5a did not take place. | 1H NMR (400 MHz, DMSO-$d_6$) δ 12.96 (s, 1H), 7.37-7.33 (m, 4H), 7.33-7.21 (m, 2H), 7.21-7.19 (m, 4H), 7.01 (d, J = 7.6 Hz, 4H), 4.56 (d, J = 15.6 Hz, 1H), 4.34 (s, 1H), 4.27 (d, J = 15.6 Hz, 1H), 3.90 (s, 1H), 3.46-3.35 (m, 2H), 3.33-3.27 (m, 1H), 2.75 (s, 3H), 1.69 (s, 1H), 1.53 (s, 1H), 1.30 (d, J = 47.7 Hz, 2H). MS m/z (ESI): 517.2 [M + H]$^+$. |
| C142 | 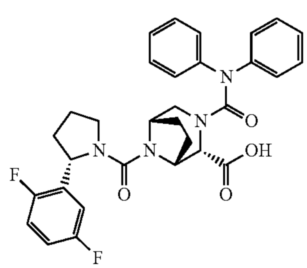 [SMILES: O=C(O)[C@@H]1[C@H]2CC[C@@H](CN1C(=O)N(c1ccccc1)c1ccccc1)N2C(=O)N1CCC[C@H]1c1cc(F)ccc1F] | (1R,2S,5S)-8-((S)-2-(2,5-difluorophenyl)pyrrolidine-1-carbonyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br>The reaction in step 5a did not take place. | $^1$H NMR (400 MHz, DMSO-$d_6$) δ 13.23 (s, 1H), 7.43-6.94 (m, 13H), 5.01 (t, J = 7.8 Hz, 1H), 4.56 (s, 1H), 4.32-4.06 (m, 1H), 4.00 (s, 1H), 3.72-3.60 (m, 1H), 3.52 (t, J = 7.2 Hz, 1H), 3.41 (d, J = 11.4 Hz, 1H), 3.24 (d, J = 11.7 Hz, 1H), 2.33-2.19 (m, 1H), 1.91-1.71 (m, 2H), 1.59-1.16 (m, 5H). MS m/z (ESI): 560.7 [M + H]$^+$. |

TABLE 7-continued

| No. | Compound Structure | Compound Name | Starting material or reagent different from that in Example 5 | Characterization data |
|---|---|---|---|---|
| C141 | 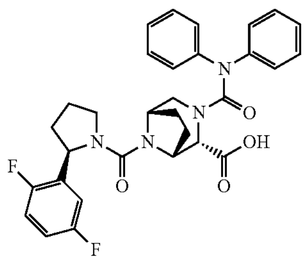 [SMILES: O=C(O)[C@@H]1[C@H]2CC[C@@H](CN1C(=O)N(c1ccccc1)c1ccccc1)N2C(=O)N1CCC[C@@H]1c1cc(F)ccc1F] | (1R,2S,5S)-8-((R)-2-(2,5-difluorophenyl)pyrrolidine-1-carbonyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [structure]. The reaction in step 5a did not take place. | ¹H NMR (400 MHz, DMSO-d₆) δ 13.23 (s, 1H), 7.44-6.95 (m, 13H), 5.01 (t, J = 7.8 Hz, 1H), 4.56 (s, 1H), 4.32-4.09 (m, 1H), 4.00 (s, 1H), 3.71-3.58 (m, 1H), 3.57-3.48 (m, 1H), 3.41 (d, J = 11.4 Hz, 1H), 3.24 (d, J = 11.7 Hz, 1H), 2.35-2.21 (m, 1H), 1.91-1.72 (m, 2H), 1.62-1.11 (m, 5H). MS m/z (ESI): 560.7 [M + H]⁺. |
| C202 | 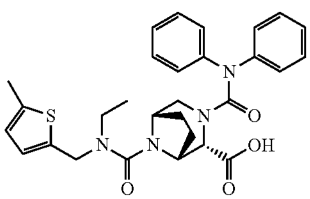 [SMILES: CCN(Cc1ccc(C)s1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(ethyl((5-methylthiophen-2-yl)methyl)carbamoyl)-3,8-diazabicyclo[3.2.1]octane-2-carboxylic acid | Compound 20 in step 5b of Example 5 was replaced with Compound 23. Compound 16 was replaced with [structure]. The reaction in step 5a did not take place. | ¹H NMR (400 MHz, DMSO-d₆) δ 7.35 (t, J = 7.6 Hz, 4H), 7.16 (t, J = 7.2 Hz, 2H), 7.01 (d, J = 8.0 Hz, 4H), 6.75 (s, 1H), 6.60 (s, 1H), 4.51-4.42 (m, 1H), 4.37-4.10 (m, 3H), 3.88 (s, 1H), 3.44 (d, J = 12.0 Hz, 1H), 3.34 (d, J = 12.0 Hz, 1H), 3.29-3.13 (m, 1H), 3.09-2.98 (m, 1H), 2.37 (s, 3H), 1.74-1.21 (m, 4H), 1.01 (t, J = 6.8 Hz, 3H). MS m/z (ESI): 533.1 [M + H]⁺. |
| C249 | 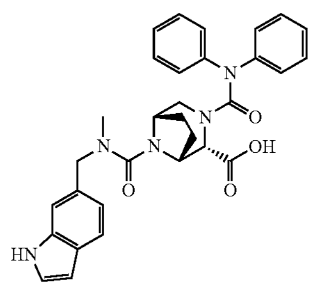 [SMILES: CN(Cc1ccc2cc[nH]c2c1)C(=O)N1[C@H]2CC[C@@H]1[C@@H](C(=O)O)N(C(=O)N(c1ccccc1)c1ccccc1)C2] | (1R,2S,5S)-8-(((1H-indole-6-yl)methyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [structure]. The reaction in step 5a did not take place. | ¹H NMR (400 MHz, DMSO-d₆) δ 11.02 (s, 1H), 7.48 (d, J = 8.4 Hz, 1H), 7.41-7.28 (m, 5H), 7.23 (s, 1H), 7.17 (t, J = 7.2 Hz, 2H), 7.01 (d, J = 7.6 Hz, 4H), 6.83 (d, J = 8.0 Hz, 1H), 6.39 (s, 1H), 4.51 (d, J = 14.8 Hz, 1H), 4.35 (d, J = 14.8 Hz, 3H), 3.91 (s, 1H), 2.72-2.66 (m, 3H), 1.76 (s, 1H), 1.57 (s, 2H), 1.39 (s, 1H). MS m/z (ESI): 537.7 [M + H]⁺. |
| C204 | 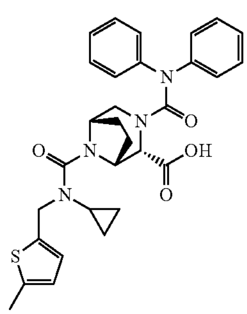 [SMILES: Cc1ccc(CN(C(=O)N2[C@H]3CC[C@@H]2[C@@H](C(=O)O)N(C(=O)N(c2ccccc2)c2ccccc2)C3)C2CC2)s1] | (1R,2S,5S)-8-(cyclopropyl(5-methylthiophen-2-yl)methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [structure]. The reaction in step 5a did not take place. | 1H NMR (400 MHz, DMSO-d₆) δ 13.00 (s, 1H), 7.36 (t, J = 7.6 Hz, 4H), 7.21-7.11 (m, 2H), 7.02 (d, J = 8.0 Hz, 4H), 6.79-6.69 (m, 1H), 6.62 (s, 1H), 4.72 (d, J = 15.2 Hz, 1H), 4.52-4.22 (s, 2H), 4.19-4.04 (m, 2H), 3.93-3.59 (m, 2H), 2.38 (s, 4H), 1.69 (s, 1H), 1.49 (s, 3H), 0.74 (s, 1H), 0.61 (d, J = 5.2 Hz, 2H), 0.53 (s, 1H). MS m/z (ESI): 545.1 [M + H]⁺. |

TABLE 7-continued

| No. | Compound Structure | Compound Name | Starting material or reagent different from that in Example 5 | Characterization data |
| --- | --- | --- | --- | --- |
| C252 | 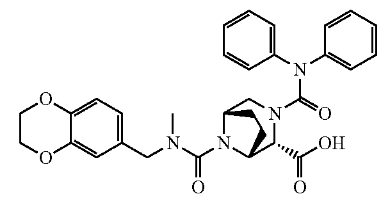 [SMILES: CN(Cc1ccc2c(c1)OCCO2)C(=O)N1[C@H]2CC[C@@H]1[C@@H](C(=O)O)N(C(=O)N(c1ccccc1)c1ccccc1)C2] | (1R,2S,5S)-8-(((2,3-dihydrobenzo[b][1,4]dioxin-6-yl)methyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$H NMR (400 MHz, DMSO-d$_6$) δ 13.06 (s, 1H), (t, J = 7.4 Hz, 2H), 7.01 (d, J = 7.9 Hz, 4H), 6.79 (d, J = 8.1 Hz, 1H), 6.72-6.57 (m, 2H), 4.35 (s, 1H), 4.28 (d, J = 15.0 Hz, 2H), 4.21 (s, 4H), 4.15 (d, J = 14.9 Hz, 1H), 3.90 (s, 1H), 3.39 (dd, J = 30.2, 12.1 Hz, 2H), 2.67 (s, 3H), 1.73 (s, 1H), 1.54 (s, 1H), 1.40 (s, 1H), 1.28-1.16 (m, 1H). MS m/z (ESI): 556.6 [M + H]$^+$. |
| C226 | 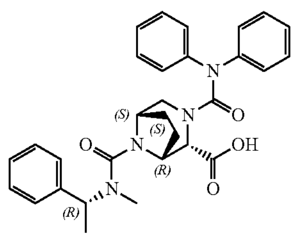 | (1R,2S,5S)-3-(diphenylcarbamoyl)-8-(methyl((R)-1-phenylethyl)carbamoyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$H NMR (400 MHz, DMSO-d$_6$) δ 7.39-7.31 (m, 6H), 7.29-7.21 (m, 3H), 7.20-7.14 (m, 2H), 7.03-7.00 (m, 4H), 5.21-5.15 (m, 1H), 4.37-4.25 (m, 2H), 3.86 (s, 1H), 3.46-3.36 (m, 2H), 2.43 (s, 3H), 1.80-1.51 (m, 3H), 1.46 (d, J = 7.2 Hz, 3H), 1.40-1.30 (m, 1H). MS m/z (ESI): 513.2 [M + H]$^+$. |
| C227 | 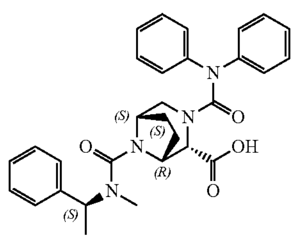 | (1R,2S,5S)-3-(diphenylcarbamoyl)-8-(methyl((S)-1-phenylethyl)carbamoyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$H NMR (400 MHz, DMSO-d$_6$) δ 13.00 (s, 1H), 7.39-7.32 (m, 6H), 7.29-7.23 (m, 3H), 7.20-7.14 (m, 2H), 7.01 (d, J = 7.6 Hz, 4H), 5.27-5.19 (m, 1H), 4.32 (s, 2H), 3.93 (s, 1H), 3.46-3.36 (m, 2H), 2.55 (d, J = 14.2 Hz, 3H), 1.71 (s, 1H), 1.65-1.53 (m, 1H), 1.53-1.26 (m, 5H). MS m/z (ESI): 513.1 [M + H]$^+$. |
| C203 | 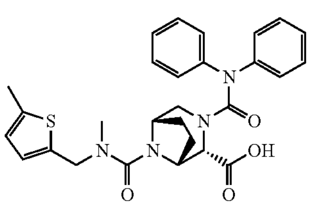 [SMILES: Cc1ccc(CN(C)C(=O)N2[C@H]3CC[C@@H]2[C@@H](C(=O)O)N(C(=O)N(c2ccccc2)c2ccccc2)C3)s1] | (1R,2S,5S)-3-(diphenylcarbamoyl)-8-(methyl((5-methylthiophen-2-yl)methyl)carbamoyl)-3,8-diazabicyclo[3.2.1]octane-2-carboxylic acid | Compound 20 in step 5b of Example 5 was replaced with Compound 23. Compound 16 was replaced with <br><br> The reaction in step 5a did not take place. | $^1$H NMR (400 MHz, DMSO-d$_6$) δ 7.36 (t, J = 7.6 Hz, 4H), 7.17 (t, J = 7.6 Hz, 2H), 7.01 (d, J = 7.6 Hz, 4H), 6.76 (d, J = 3.2 Hz, 1H), 6.63-6.15 (m, 1H), 4.43-4.31 (m, 4H), 3.89 (s, 1H), 3.44-3.32 (m, 2H), 2.73 (s, 3H), 2.38 (s, 3H), 1.75-1.30 (m, 4H). MS m/z (ESI): 518.8 [M + H]$^+$. |

TABLE 7-continued

| No. | Compound Structure | Compound Name | Starting material or reagent different from that in Example 5 | Characterization data |
|---|---|---|---|---|
| C185 | 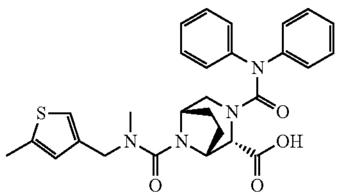 [SMILES: Cc1cc(CN(C)C(=O)N2[C@H]3CC[C@@H]2[C@@H](C(=O)O)N(C(=O)N(c2ccccc2)c2ccccc2)C3)cs1] | (1R,2S,5S)-3-(diphenylcarbamoyl)-8-(methyl(5-methylthiophen-3-yl)methyl)carbamoyl)-3,8-diazabicyclo[3.2.1]octane-2-carboxylic acid | Compound 20 in step 5b of Example 5 was replaced with Compound 23. Compound 16 was replaced with [5-methylthiophen-3-yl-CH2-NHMe structure]. The reaction in step 5a did not take place. | ¹H NMR (400 MHz, DMSO-d₆) δ 7.36 (t, J = 8.0 Hz, 4H), 7.17 (t, J = 7.2 Hz, 2H), 7.05-6.96 (m, 5H), 6.64 (s, 1H), 4.39-4.23 (m, 3H), 4.15 (d, J = 14.8 Hz, 1H), 3.91 (s, 1H), 3.45-3.35 (m, 2H), 2.70 (s, 3H), 2.40 (s, 3H), 1.80-1.45 (m, 4H). MS m/z (ESI): 519.1 [M + H]⁺. |
| C186 | 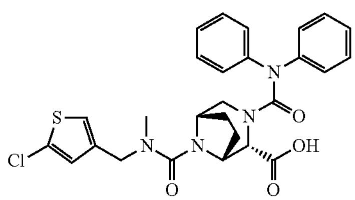 [SMILES: CN(Cc1csc(Cl)c1)C(=O)N1[C@H]2CC[C@@H]1[C@@H](C(=O)O)N(C(=O)N(c1ccccc1)c1ccccc1)C2] | (1R,2S,5S)-8-(((5-chlorothiophene-3-yl)methyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [5-chlorothiophen-3-yl-CH2-NHMe structure]. The reaction in step 5a did not take place. | ¹H NMR (400 MHz, DMSO-d₆) δ 13.15 (s, 1H), 7.35 (t, J = 7.6 Hz, 4H), 7.22 (s, 1H), 7.16 (t, J = 7.2 Hz, 2H), 7.02 (d, J = 7.6 Hz, 4H), 6.95 (d, J = 1.6 Hz, 1H), 4.36 (s, 1H) 4.28 (d, J = 15.2 Hz, 2H), 4.22-4.11 (m, 1H), 3.93 (s, 1H), 3.50-3.36 (m, 2H), 2.73 (s, 3H), 1.67 (s, 1H), 1.60-1.50 (m, 1H), 1.46-1.23 (m, 2H). MS m/z (ESI): 539.0 [M + H]⁺. |
| C208 | 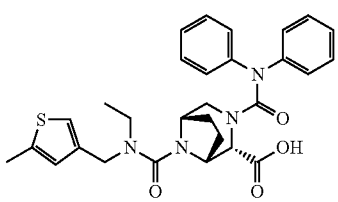 [SMILES: CCN(Cc1csc(C)c1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(ethyl((5-methylthiophen-3-yl)methyl)carbamoyl)-3,8-diazabicyclo[3.2.1]octane-2-carboxylic acid | Compound 20 in step 5b of Example 5 was replaced with Compound 23. Compound 16 was replaced with [5-methylthiophen-3-yl-CH2-NHEt structure]. The reaction in step 5a did not take place. | ¹H NMR (400 MHz, DMSO-d₆) δ 7.36 (t, J = 7.2 Hz, 4H), 7.17 (t, J = 7.2 Hz, 2H), 7.03-7.00 (m, 5H), 6.63 (s, 1H), 4.36-4.20 (m, 3H), 4.13 (d, J = 15.6 Hz, 1H), 3.88 (s, 1H), 3.45-3.30 (m, 2H), 3.21-3.15 (m, 1H), 3.02-2.96 (m, 1H), 2.40 (s, 3H), 1.70-1.49 (m, 2H), 1.45-1.24 (m, 2H), 0.98 (t, J = 7.2 Hz, 3H). MS m/z (ESI): 532.8 [M + H]⁺. |
| C274 | 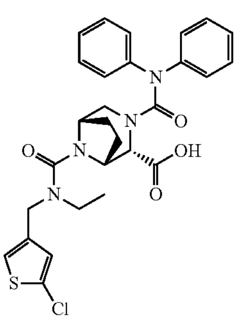 [SMILES: CCN(Cc1csc(Cl)c1)C(=O)N1[C@H]2CC[C@@H]1[C@@H](C(=O)O)N(C(=O)N(c1ccccc1)c1ccccc1)C2] | (1R,2S,5S)-8-(((5-chlorothiophene-3-yl)methyl)(ethyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [5-chlorothiophen-3-yl-CH2-NHEt structure]. The reaction in step 5a did not take place. | ¹H NMR (400 MHz DMSO-d₆) δ 13.10 (s, 1H), 7.35 (t, J = 8.0 Hz, 4H), 7.21 (d, J = 1.2 Hz, 1H), 7.16 (t, J = 7.2 Hz, 2H), 7.02 (d, J = 7.6 Hz, 4H), 6.94 (d, J = 1.6 Hz, 1H), 4.34 (d, J = 15.6 Hz, 2H), 4.16 (d, J = 15.6 Hz, 1H), 3.90 (s, 1H), 3.45-3.35 (m, 2H), 3.25-3.15 (m, 1H), 3.07-2.98 (m, 1H), 1.66 (s, 1H), 1.55 (s, 1H), 1.45-1.19 (m, 2H), 0.99 (t, J = 7.0 Hz, 3H). MS m/z (ESI): 552.7 [M + H]⁺. |

TABLE 7-continued

| No. | Compound Structure | Compound Name | Starting material or reagent different from that in Example 5 | Characterization data |
|---|---|---|---|---|
| C271 | 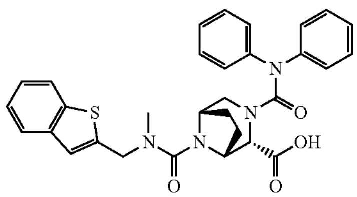 [SMILES: CN(Cc1cc2ccccc2s1)C(=O)N1[C@H]2CC[C@@H]1[C@@H](C(=O)O)N(C(=O)N(c1ccccc1)c1ccccc1)C2] | (1R,2S,5S)-8-(benzo[b]thiophene-2-ylmethyl)(methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [structure shown]. The reaction in step 5a did not take place. | $^1$H NMR (400 MHz, DMSO-d$_6$) δ 13.01 (s, 1 H), 7.90 (d, J = 7.6 Hz, 1H), 7.81-7.75 (m, 1H), 7.39-7.29 (m, 7H), 7.17 (t, J = 7.2 Hz, 2H), 7.02 (d, J = 7.2 Hz, 4H), 4.65 (d, J = 15.6 Hz, 1H), 4.54 (d, J = 15.6 Hz, 1H), 4.45-4.20 (m, 2H), 3.96 (s, 1H), 3.50-3.33 (m, 2H), 2.83 (s, 3H), 1.80-1.30 (m, 4H). MS m/z (ESI): 555.1 [M + H]$^+$. |
| C273 | 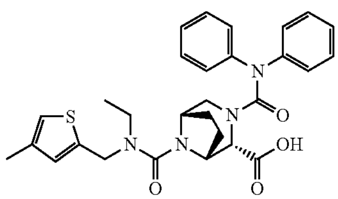 [SMILES: CCN(Cc1cc(C)cs1)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(ethyl((4-methylthiophen-2-yl)methyl)carbamoyl)-3,8-diazabicyclo[3.2.1]octane-2-carboxylic acid | Compound 20 in step 5b of Example 5 was replaced with Compound 23. Compound 16 was replaced with [structure shown]. The reaction in step 5a did not take place. | $^1$H NMR (400 MHz, DMSO-d$_6$) δ 7.35 (t, J = 8.0 Hz, 4H), 7.16 (t, J = 7.2 Hz, 2H), 7.07-6.90 (m, 5H), 6.79 (s, 1H), 4.52 (d, J = 15.6 Hz, 1H), 4.35 (d, J = 15.6 Hz, 2H), 3.88 (s, 1H), 3.44 (d, J = 12.8 Hz, 1H), 3.34 (d, J = 12.0 Hz, 2H), 3.25-3.16 (m, 1H), 3.11-3.02 (m, 1H), 2.18-2.11 (m, 3H), 1.67 (s, 1H), 1.55 (s, 1H), 1.49-1.24 (m, 2H), 1.02 (t, J = 7.0 Hz, 3H). MS m/z (ESI): 532.9 [M + H]$^+$. |
| C272 | 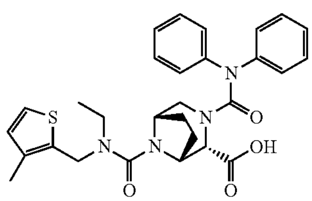 [SMILES: CCN(Cc1sccc1C)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(ethyl((3-methylthiophen-2-yl)methyl)carbamoyl)-3,8-diazabicyclo[3.2.1]octane-2-carboxylic acid | Compound 20 in step 5b of Example 5 was replaced with Compound 23. Compound 16 was replaced with [structure shown]. The reaction in step 5a did not take place. | $^1$H NMR (400 MHz, DMSO-d$_6$) δ 13.02 (s, 1H), 7.36 (t, J = 7.6 Hz, 4H), 7.28 (d, J = 5.2 Hz, 1H), 7.17 (t, J = 7.2 Hz, 2H), 6.99 (d, J = 7.6 Hz, 4H), 6.81 (t, J = 8.0 Hz, 1H), 4.57 (d, J = 15.6 Hz, 1H), 4.42-4.16 (m, 3H), 3.88 (s, 1H), 3.45 (d, J = 12.0 Hz, 1H), 3.36 (s, 1H), 3.27-3.16 (m, 1H), 3.07-2.96 (m, 1H), 2.16-2.08 (m, 3H), 1.70 (s, 1H), 1.54 (s, 1H), 1.45-1.20 (m, 2H), 1.04-0.96 (m, 3H). MS m/z (ESI): 533.2 [M + H]$^+$. |
| C197 | 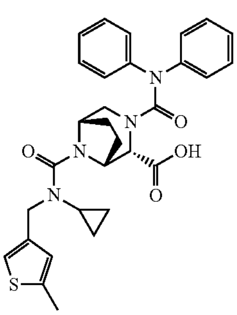 [SMILES: Cc1cc(CN(C(=O)N2[C@H]3CC[C@@H]2[C@@H](C(=O)O)N(C(=O)N(c2ccccc2)c2ccccc2)C3)C2CC2)cs1] | (1R,2S,5S)-8-(cyclopropyl(5-methylthiophen-3-yl)methyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with [structure shown]. The reaction in step 5a did not take place. | $^1$H NMR (400 MHz, DMSO-d$_6$) δ 12.96 (s, 1H), 7.36 (t, J = 8.0 Hz, 4H), 7.17 (t, J = 7.2 Hz, 2H), 7.02 (d, J = 7.6 Hz, 4H), 6.98 (s, 1H), 6.62 (s, 1H), 4.52 (d, J = 15.2 Hz, 1H), 4.46 (s, 1H), 4.38-4.21 (m, 1H), 4.17-4.05 (m, 1H), 3.96 (d, J = 14.8 Hz, 1H), 3.45-3.35 (m, 2H), 2.45-2.35 (m, 4H), 1.75-1.20 (m, 4H), 0.75-0.40 (m, 4H). MS m/z (ESI): 544.6 [M + H]$^+$. |

TABLE 7-continued

| No. | Compound Structure | Compound Name | Starting material or reagent different from that in Example 5 | Characterization data |
|---|---|---|---|---|
| C281 | 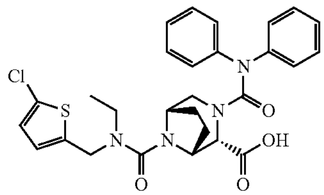 [SMILES: CCN(Cc1ccc(Cl)s1)C(=O)N1[C@H]2CC[C@@H]1[C@@H](C(=O)O)N(C(=O)N(c1ccccc1)c1ccccc1)C2] | (1R,2S,5S)-8-(((5-chlorothiophene-2-yl)methyl)(ethyl)carbamoyl)-3-(diphenylcarbamoyl)-3,8-diazabicyclo[3.2.1]octane-2-carboxylic acid | Compound 20 in step 5b of Example 5 was replaced with Compound 23. Compound 16 was replaced with <br><br>The reaction in step 5a did not take place. | $^1$H NMR (400 MHz, DMSO-d$_6$) δ 13.07 (s, 1H), 7.35 (t, J = 7.6 Hz, 4H), 7.17 (t, J = 7.6 Hz, 2H), 7.02 (d, J = 7.6 Hz, 4H), 6.93 (d, J = 4.0 Hz, 1H), 6.90 (d, J = 4.0 Hz, 1H), 4.43 (d, J = 15.6 Hz, 1H), 4.37-4.20 (m, 3H), 3.90 (s, 1H), 3.45 (d, J = 11.6 Hz, 1H), 3.36 (s, 1H), 3.25-3.15 (m, 6.7 Hz, 1H), 3.12-3.04 (m, 1H), 1.65 (s, 1H), 1.55 (s, 1H), 1.41 (s, 2H), 1.03 (t, J 7.0 Hz, 3H). <br>MS m/z (ESI): 553.2 [M + H]$^+$. |
| C163 | 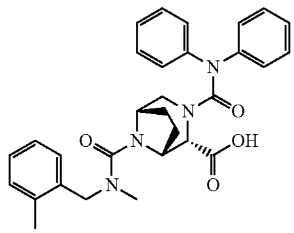 [SMILES: Cc1ccccc1CN(C)C(=O)N1[C@H]2CC[C@@H]1[C@@H](C(=O)O)N(C(=O)N(c1ccccc1)c1ccccc1)C2] | (1R,2S,5S)-3-(diphenylcarbamoyl)-8-(methyl(2-methylbenzyl)carbamoyl)-3,8-diazabicyclo[3.2.1]octane-2-carboxylic acid | Compound 20 in step 5b of Example 5 was replaced with Compound 23. Compound 16 was replaced with <br><br>The reaction in step 5a did not take place. | $^1$H NMR (400 MHz, DMSO-d$_6$) δ 7.51-6.86 (m, 14H), 4.50-4.20 (m, 4H), 3.91 (s, 1H), 3.51-3.45 (m, 1H), 2.71 (s, 3H), 2.16 (s, 3H), 1.70-1.10 (m, 4H). <br>MS m/z (ESI): 513.1 [M + H]$^+$. |
| C119 | 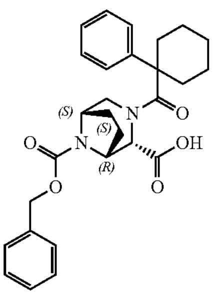 | (1R,2S,5S)-8-((benzyloxy)carbonyl)-3-(1-phenylcyclohexane-1-carbonyl)-3,8-diazabicyclo[3.2.1]octane-2-carboxylic acid | Compound 7 in step 3 of Example 5 was replaced with <br><br>Phenyl chloroformate in step 5a was replaced with benzyl chloroformate. The reaction in step 5b did not take place. | $^1$H NMR (400 Hz, DMSO-d$_6$) δ 7.40-7.24 (m, 10H), 5.03 (d, J = 13.2 Hz, 1H), 5.00-4.80 (m, 1H), 4.72 (s, 1H), 4.64 (d, J = 6.0 Hz, 1H), 3.92 (s, 1H), 3.19 (d, J = 12.0 Hz, 1H), 3.03 (d, J = 12.0 Hz, 1H), 2.36-2.25 (m, 2H), 1.86-1.29 (m, 12H). <br>MS m/z (ESI): 477.2 [M + H]$^+$. |
| C120 | 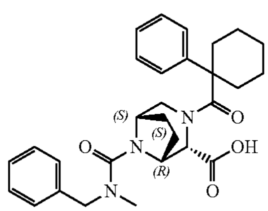 | (1R,2S,5S)-8-(benzyl(methyl)carbamoyl)-3-(1-phenylcyclohexane-1-carbonyl)-3,8-diazabicyclo[3.2.1]octane-2-carboxylic acid | Compound 7 in step 3 of Example 5 was replaced with <br><br>The reaction in step 5a did not take place. | $^1$H NMR (400 MHz, DMSO-d$_6$) δ 7.39-7.23 (m, 8H), 7.14 (d, J = 7.2 Hz, 2H), 4.84 (s, 1H), 4.45-4.36 (m, 2H), 4.25-4.15 (m, 1H), 3.62 (s, 1H), 3.30-3.10 (m, 2H), 2.64 (s, 3H), 2.35-2.20 (m, 2H), 1.85-1.70 (m, 3H), 1.69-1.47 (m, 5H), 1.40-1.20 (m, 4H). <br>MS m/z (ESI): 490.1 [M + H]$^+$. |
| C122 | 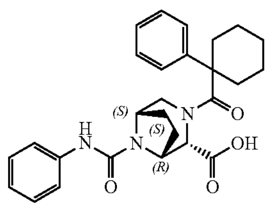 | (1R,2S,5S)-8-(phenylcarbamoyl)-3-(1-phenylcyclohexane-1-carbonyl)-3,8-diazabicyclo[3.2.1]octane-2-carboxylic acid | Compound 7 in step 3 of Example 5 was replaced with <br><br>Compound 16 in step 5b was replaced with | $^1$H NMR (400 MHz, DMSO-d$_6$) δ 8.49 (brs, 1H), 7.46-7.14 (m, 9H), 6.95-6.85 (s, 1H), 4.89 (d, J = 6.4 Hz, 1H), 4.74 (s, 1H), 4.06 (s, 1H), 3.2-3.05 (m, 2H), 2.35-2.20 (m, 2H), 1.90-1.50 (m, 8H), 1.50-1.33 (m, 2H), 1.3-1.15 (m, 2H). <br>MS m/z (ESI): 462.1 [M + H]$^+$. |

TABLE 7-continued

| No. | Compound Structure | Compound Name | Starting material or reagent different from that in Example 5 | Characterization data |
|---|---|---|---|---|
| | | | phenylamine. The reaction in step 5a did not take place. | |
| C37 | 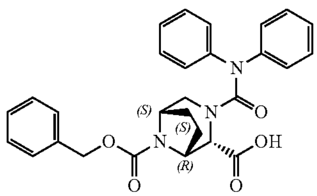 | (1R,2S,5S)-8-((benzyloxy)carbonyl)-3-(diphenylcarbamoyl)-3,8-diazabicyclo[3.2.1]octane-2-carboxylic acid | Compound 20 in step 5a of Example 5 was replaced with Compound 23. The phenyl chloroformate was replaced with benzyl chloroformate. The reaction in step 5b did not take place. | $^1$H NMR (400 MHz, DMSO-$d_6$) δ 13.03 (s, 1H), 7.40-7.26 (m, 8H), 7.17 (t, J = 7.4 Hz, 2H), 7.01 (d, J = 7.5 Hz, 4H), 5.08 (d, J = 12.8 Hz, 1H), 4.98 (s, 1H), 4.58 (s, 1H), 4.25 (d, J = 22.0 Hz, 2H), 3.44 (d, J = 12.1 Hz, 1H), 3.27 (d, J = 10.9 Hz, 1H), 1.77-1.62 (m, 2H), 1.45-1.23 (m, 2H). MS m/z (ESI): 486.0 [M + H]$^+$. |
| C174 | 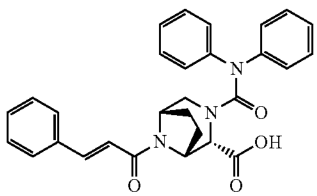 [SMILES: O=C(O)[C@@H]1[C@H]2CC[C@@H](CN1C(=O)N(c1ccccc1)c1ccccc1)N2C(=O)/C=C/c1ccccc1] | (1R,2S,5S)-8-cinnamoyl-3-(diphenylcarbamoyl)-3,8-diazabicyclo[3.2.1]octane-2-carboxylic acid | Compound 20 in step 5a of Example 5 was replaced with Compound 23. The phenyl chloroformate was replaced with cinnamoyl chloride. The reaction in step 5b did not take place. | $^1$H NMR (400 MHz, DMSO-$d_6$) δ 13.27 (s, 1H), 7.67 (d, J = 16.8 Hz, 2H), 7.52-7.29 (m, 7H) 7.18 (t, J = 7.4 Hz, 2H), 7.02, (d, J = 7.6 Hz, 4H), 5.03 (d, J = 28.3 Hz, 1H), 4.66 (d, J = 47.4 Hz, 1H), 4.35 (s, 1H), 3.47 (s, 1H), 3.19 (s, 1H), 1.93-1.62 (m, 2H), 1.58-1.35 (m, 2H). MS m/z (ESI): 481.8 [M + H]$^+$. |
| C193 | 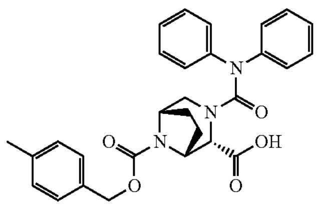 [SMILES: Cc1ccc(COC(=O)N2[C@H]3CC[C@@H]2[C@@H](C(=O)O)N(C(=O)N(c2ccccc2)c2ccccc2)C3)cc1] | (1R,2S,5S)-3-(diphenylcarbamoyl)-8-(((4-methylbenzyl)oxy)carbonyl)-3,8-diazabicyclo[3.2.1]octane-2-carboxylic acid | Compound 20 in step 5a of Example 5 was replaced with Compound 23, phenyl chloroformate was replaced with <br><br>And the reaction condition was changed to reacting at room temperature for 16 hours. The reaction in step 5b did not take place. | $^1$H NMR (400 MHz, DMSO-$d_6$) δ 13.01 (brs, 1H), 7.36 (t, J = 8.0 Hz, 4H), 7.24-7.12 (m, 6H), 7.00 (d, J = 7.6 Hz, 4H), 5.05-4.85 (m, 2H), 4.57 (d, J = 5.6 Hz, 1H), 4.25 (s, 1H), 4.20 (s, 1H), 3.43 (d, J = 11.6 Hz, 1H), 3.26 (d, J = 11.2 Hz, 1H), 2.29 (s, 3H), 1.80-1.58 (m, 2H), 1.45-1.25 (m, 2H). MS m/z (ESI): 499.8 [M + H]$^+$. |
| C221 | 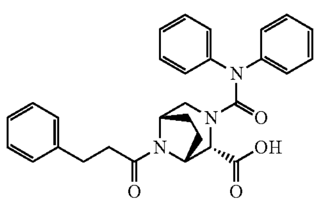 [SMILES: O=C(O)[C@@H]1[C@H]2CC[C@@H](CN1C(=O)N(c1ccccc1)c1ccccc1)N2C(=O)CCc1ccccc1] | (1R,2S,5S)-3-(diphenylcarbamoyl)-8-(3-phenylpropionyl)-3,8-diazabicyclo[3.2.1]octane-2-carboxylic acid | Compound 20 in step 5a of Example 5 was replaced with Compound 23. The phenyl chloroformate was replaced with phenyl propionyl chloride. The reaction in step 5b did not take place. | 1H NMR (400 MHz, DMSO-$d_6$) δ 7.35 (t, J = 8.0 Hz, 4H), 7.30-7.14 (m, 7H), 7.00 (t, J = 7.2 Hz, 4H), 4.90-4.30 (m, 2H), 4.25 (s, 1H), 3.45-3.25 (m, 2H), 3.05 (d, J = 12 Hz, 1H), 2.75 (t, J = 8.0 Hz, 2H), 2.65-2.30 (m, 2H), 1.60-1.40 (m, 2H), 1.39-1.20 (m, 2H). MS m/z (ESI): 484.1 [M + H]$^+$. |
| C238 | 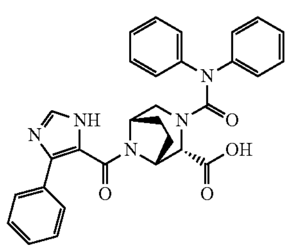 [SMILES: O=C(O)[C@@H]1[C@H]2CC[C@@H](CN1C(=O)N(c1ccccc1)c1ccccc1)N2C(=O)c1[nH]cnc1-c1ccccc1] | (1R,2S,5S)-3-(diphenylcarbamoyl)-8-(4-phenyl-1H-iminazole-5-carbonyl)-3,8-diazabicyclo[3.2.1]octane-2-carboxylic acid | Compound 20 in step 5a of Example 5 was replaced with Compound 23. The phenyl chloroformate was replaced with <br><br>The reaction in step 5b did not take place. | $^1$H NMR (400 MHz, CDCl$_3$) δ 7.74-6.82 (m, 15H), 4.64 (s, 1H), 4.27 (s, 1H), 4.05 (s, 1H), 3.66 (s, 1H), 3.50 (d, J = 9.1 Hz, 1H), 1.71 (s, 1H), 1.45 (s, 1H), 1.22 (s, 1H), 0.95-0.75 (m, 1H). MS m/z (ESI): 522.0 [M + H]$^+$. |

TABLE 7-continued

| No. | Compound Structure | Compound Name | Starting material or reagent different from that in Example 5 | Characterization data |
|---|---|---|---|---|
| C240 | 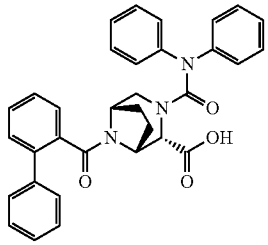 [SMILES: O=C(O)[C@@H]1[C@H]2CC[C@@H](CN1C(=O)N(c1ccccc1)c1ccccc1)N2C(=O)c1ccccc1-c1ccccc1] | (1R,2S,5S)-8-([1,1'-biphenyl]-2-carbonyl)-3-(diphenylcarbamoyl)-3,8-diazabicyclo[3.2.1]octane-2-carboxylic acid | Compound 20 in step 5a of Example 5 was replaced with Compound 23. The phenyl chloroformate was replaced with <br><br> The reaction in step 5b did not take place. | $^1$H NMR (400 MHz, DMSO-$d_6$) δ 13.01 (s, 1H), 7.60-7.05 (m, 15H), 6.92 (d, J = 7.7 Hz, 4H), 4.81 (s, 1H), 4.46 (s, 1H), 4.21 (s, 1H), 3.96 (s, 1H), 3.58 (s, 1H), 1.24 (m, 2H), 0.89 (m, 2H).<br>MS m/z (ESI): 531.8 [M + H]$^+$. |
| C239 | 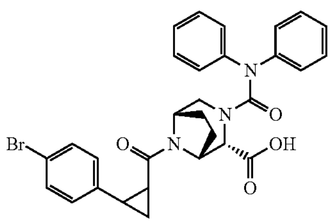 [SMILES: O=C(O)[C@@H]1[C@H]2CC[C@@H](CN1C(=O)N(c1ccccc1)c1ccccc1)N2C(=O)C1CC1c1ccc(Br)cc1] | (1R,2S,5S)-8-(2-(4-bromophenyl)cyclopropane-1-carbonyl)-3-(diphenylcarbamoyl)-3,8-diazabicyclo[3.2.1]octane-2-carboxylic acid | Compound 20 in step 5a of Example 5 was replaced with Compound 23, the phenyl chloroformate was replaced with <br><br> and the reaction condition was changed to reacting at room temperature for 12 hours. | $^1$H NMR (400 MHz DMSO-$d_6$) δ 7.50-7.00 (m, 14H), 5.00-4.75 (m, 1H), 4.70-4.20 (m, 2H), 3.40-3.00 (m, 2H), 2.30-2.00 (m, 2H), 1.75-1.50 (m, 2H), 1.49-1.00 (m, 4H).<br>MS m/z (ESI): 575.7 [M + H]$^+$. |
| C259 | 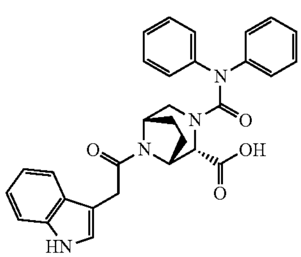 [SMILES: O=C(O)[C@@H]1[C@H]2CC[C@@H](CN1C(=O)N(c1ccccc1)c1ccccc1)N2C(=O)Cc1c[nH]c2ccccc12] | (1R,2S,5S)-8-(2-(1H-indol-3-yl)acetyl)-3-(diphenylcarbamoyl)-3,8-diazabicyclo[3.2.1]octane-2-carboxylic acid | Compound 20 in step 5a of Example 5 was replaced with Compound 23. The phenyl chloroformate was replaced with <br><br> The reaction in step 5b did not take place. | $^1$H NMR (400 MHz, DMSO-$d_6$) δ 10.87 (s, 1H), 7.58-7.25 (m, 6H), 7.26-7.11 (m, 3H), 7.11-6.84 (m, 6H), 4.83 (d, J = 39.7 Hz, 1H), 4.45 (d, J = 38.5 Hz, 1H), 4.23 (s, 1H), 3.77 (d, J = 49.0 Hz, 1H), 3.64 (s, 1H), 3.53-3.42 (m, 1H), 3.11 (d, J = 12.9 Hz, 1H), 1.50 (s, 2H), 1.35 (s, 2H).<br>MS m/z (ESI): 509.1 [M + H]$^+$. |

TABLE 7-continued

| No. | Compound Structure | Compound Name | Starting material or reagent different from that in Example 5 | Characterization data |
|---|---|---|---|---|
| C224 | 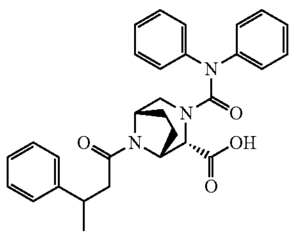 [SMILES: CC(CC(=O)N1[C@H]2CC[C@@H]1[C@@H](C(=O)O)N(C(=O)N(c1ccccc1)c1ccccc1)C2)c1ccccc1] | (1R,2S,5S)-3-(diphenylcarbamoyl)-8-(3-phenylbutylyl)-3,8-diazabicyclo[3.2.1]octane-2-carboxylic acid | Compound 20 in step 5a of Example 5 was replaced with Compound 23. The phenyl chloroformate was replaced with [structure]. The reaction in step 5b did not take place. | $^1$H NMR (400 MHz, DMSO-$d_6$) δ 7.39-7.30 (m, 4H), 7.29-7.21 (m, 3H), 7.20-7.11 (m, 4H), 7.01 (dd, J = 7.8, 7.6 Hz, 4H), 4.83 (s, 1H), 4.53-4.09 (m, 2H), 3.39 (s, 1H), 3.15-2.99 (m, 2H), 2.72-2.56 (m, 1H), 2.42-2.30 (m, 1H), 1.61 (s, 1H), 1.39 (s, 1H), 1.31-1.21 (m, 2H), 1.21-1.13 (m, 3H). MS m/z (ESI): 498.1 [M + H]$^+$. |
| C264 | 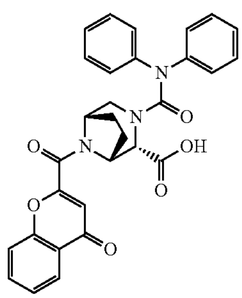 [SMILES: O=C(O)[C@@H]1[C@H]2CC[C@@H](CN1C(=O)N(c1ccccc1)c1ccccc1)N2C(=O)c1cc(=O)c2ccccc2o1] | (1R,2S,5S)-3-(diphenylcarbamoyl)-8-(4-oxo-4H-benzopyran-2-carbonyl)-3,8-diazabicyclo[3.2.1]octane-2-carboxylic acid | Compound 20 in step 5a of Example 5 was replaced with Compound 23. The phenyl chloroformate was replaced with [structure]. The reaction in step 5b did not take place. | $^1$H NMR (400 MHz, CD$_3$OD) δ 8.17 (d, J = 6.8 Hz, 1H), 7.90-7.77 (m, 1H), 7.61-7.51 (m, 1H), 7.50-7.30 (m, 5H), 7.28-7.18 (m, 2H), 7.11 (t, J = 8.4, 8.8 Hz, 4H), 5.21 (s, 1H), 4.57 (d, J = 48.4 Hz, 2H), 3.62 (dd, J = 47.1, 27.4 Hz, 3H), 1.97 (s, 1H), 1.72 (s, 3H). MS m/z (ESI): 524.0 [M + H]$^+$. |
| C256 | 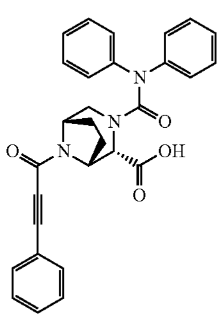 [SMILES: O=C(O)[C@@H]1[C@H]2CC[C@@H](CN1C(=O)N(c1ccccc1)c1ccccc1)N2C(=O)C#Cc1ccccc1] | (1R,2S,5S)-3-(diphenylcarbamoyl)-8-(3-phenylpropioloyl)-3,8-diazabicyclo[3.2.1]octane-2-carboxylic acid | Compound 20 in step 5a of Example 5 was replaced with Compound 23. The phenyl chloroformate was replaced with [structure]. The reaction in step 5b did not take place. | $^1$H NMR (400 MHz, DMSO-$d_6$) δ 13.26 (s, 1H), 7.70-6.98 (m, 15H), 4.93-4.85 (m, 1H), 4.63-4.49 (m, 1H), 4.38 (d, J = 35.6 Hz, 1H), 3.41 (d, J = 10.4 Hz, 1H), 3.28-3.16 (m, 1H), 1.96-1.85 (m, 1H), 1.84-1.75 (m, MS m/z (ESI): 480.1 [M + H]$^+$. |

TABLE 7-continued

| No. | Compound Structure | Compound Name | Starting material or reagent different from that in Example 5 | Characterization data |
|---|---|---|---|---|
| C257 | 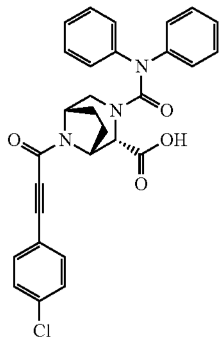 [SMILES: O=C(O)[C@@H]1[C@H]2CC[C@@H](CN1C(=O)N(c1ccccc1)c1ccccc1)N2C(=O)C#Cc1ccc(Cl)cc1] | (1R,2S,5S)-8-(3-(4-chlorophenyl)propioloyl)-3-(diphenylcarbamoyl)-3,8-diazabicyclo[3.2.1]octane-2-carboxylic acid | Compound 20 in step 5a of Example 5 was replaced with Compound 23. The phenyl chloroformate was replaced with [4-chlorophenyl propioloyl chloride structure]. The reaction in step 5b did not take place. | $^1$H NMR (400 MHz, DMSO-d$_6$) δ 13.15 (s, 1H), 7.72-7.50 (m, 4H), 7.35 (t, J = 7.6, 8.0 Hz, 4H), 7.21 (t, J = 7.6, 7.2 Hz, 4H), 7.01 (d, J = 8.0 Hz, 4H), 4.92-4.85 (m, 1H), 4.60-4.50 (m, 1H), 4.45-4.30 (m, 1H), 3.45-3.32 (m, 1H), 3.23 (d, J = 24.0 Hz, 1H), 1.90-1.62 (m, 2H), 1.44 (s, 2H). MS m/z (ESI): 514.0 [M + H]$^+$. |
| C35 | 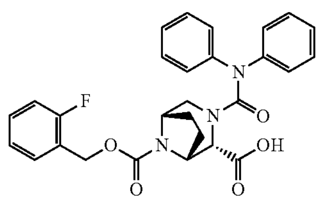 [SMILES: O=C(O)[C@@H]1[C@H]2CC[C@@H](CN1C(=O)N(c1ccccc1)c1ccccc1)N2C(=O)OCc1ccccc1F] | (1R,2S,5S)-3-(2,2-diphenylacetyl)-8-(((2-fluorobenzyl)oxy)carbonyl)-3,8-diazabicyclo[3.2.1]octane-2-carboxylic acid | Compound 20 in step 5a of Example 5 was replaced with Compound 23. The phenyl chloroformate was replaced with [2-fluorobenzyl chloroformate structure]. The reaction in step 5b did not take place. | $^1$H NMR (400 MHz, DMSO-d$_6$) δ 7.45-7.05 (m, 14H), 5.55-5.30 (m, 1H), 5.20-4.60 (m, 2H), 4.30-4.00 (m, 2H), 3.71-3.50 (m, 1H), 3.45-3.37 (m, 2H), 1.90-1.00 (m, 4H). MS m/z (ESI): 502.8 [M + H]$^+$. |
| C241 | 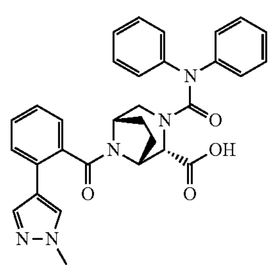 [SMILES: Cn1cc(-c2ccccc2C(=O)N2[C@H]3CC[C@@H]2[C@@H](C(=O)O)N(C(=O)N(c2ccccc2)c2ccccc2)C3)cn1] | (1R,2S,5S)-3-(diphenylcarbamoyl)-8-(2-(1-methyl-1H-pyrazole-4-yl)benzoyl)-3,8-diazabicyclo[3.2.1]octane-2-carboxylic acid | Compound 20 in step 5a of Example 5 was replaced with Compound 23. The phenyl chloroformate was replaced with [2-(1-methyl-1H-pyrazol-4-yl)benzoyl chloride structure]. The reaction in step 5b did not take place. | $^1$H NMR (400 MHz, DMSO-d$_6$) δ 7.75-7.65 (m, 1H), 7.55-7.45 (m, 2H), 7.44-7.36 (m, 1H), 7.35-7.22 (m, 5H), 7.19-7.08 (m, 3H), 6.95 (d, J = 8.0 Hz, 4H), 4.99 (s, 1H), 4.63 (s, 1H), 4.27 (s, 1H), 3.83 (s, 3H), 3.30-3.14 (m, 2H), 1.65-0.95 (m, 4H). MS m/z (ESI): 536.1 [M + H]$^+$. |
| C36 | 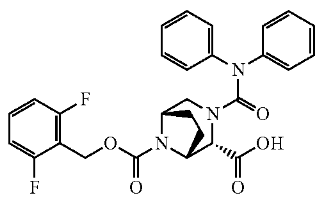 [SMILES: O=C(O)[C@@H]1[C@H]2CC[C@@H](CN1C(=O)N(c1ccccc1)c1ccccc1)N2C(=O)OCc1c(F)cccc1F] | (1R,2S,5S)-8-(((2,6-difluorbenzyl)oxy)carbonyl)-3-(2,2-diphenylacetyl)-3,8-diazabicyclo[3.2.1]octane-2-carboxylic acid | Compound 20 in step 5a of Example 5 was replaced with Compound 23. The phenyl chloroformate was replaced with [2,6-difluorobenzyl chloroformate structure]. | $^1$H NMR (400 MHz, DMSO-d$_6$) δ 13.00-12.50 (m, 1H), 7.55-7.41 (m, 1H), 7.40-7.06 (m, 12H), 5.51-5.29 (m, 1H), 5.20-5.00 (m, 2H), 4.65-4.50 (m, 1H), 4.27-4.00 (m, 2H), 3.73-3.30 (m, 2H), 2.10-1.30 (m, 4H). MS m/z (ESI): 521.0 [M + H]$^+$. |

TABLE 7-continued

| No. | Compound Structure | Compound Name | Starting material or reagent different from that in Example 5 | Characterization data |
|---|---|---|---|---|
| C113 | 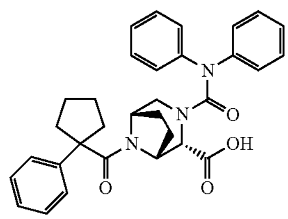 [SMILES: O=C(O)[C@@H]1[C@H]2CC[C@@H](CN1C(=O)N(c1ccccc1)c1ccccc1)N2C(=O)C1(c2ccccc2)CCCC1] | (1R,2S,5S)-3-(diphenylcarbamoyl)-8-(1-phenylcyclopentane-1-carbonyl)-3,8-diazabicyclo[3.2.1]octane-2-carboxylic acid | The reaction in step 5b did not take place. Compound 20 in step 5a of Example 5 was replaced with Compound 23. The phenyl chloroformate was replaced with (1-phenylcyclopentane-1-carbonyl chloride). | $^1$H NMR (400 MHz, DMSO-d$_6$) δ 12.97 (s, 1H), 7.39-7.22 (m, 6H), 7.21-7.09 (m, 5H), 6.92 (d, J = 7.6 Hz, 4H), 4.94 (s, 1H), 4.18 (s, 1H), 3.72 (s, 1H), 3.03 (s, 1H), 2.87 (s, 1H), 2.20 (s, 2H), 1.99 (s, 2H), 1.79-1.41 (m, 6H), 1.30-1.11 (m, 2H). MS m/z (ESI): 524.1 [M + H]$^+$. |
| C243 | 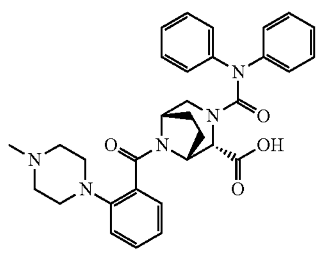 [SMILES: CN1CCN(c2ccccc2C(=O)N2[C@H]3CC[C@@H]2[C@@H](C(=O)O)N(C(=O)N(c2ccccc2)c2ccccc2)C3)CC1] | (1R,2S,5S)-3-(diphenylcarbamoyl)-8-(2-(4-methylpiperazine-1-yl)benzoyl)-3,8-diazabicyclo[3.2.1]octane-2-carboxylic acid | The reaction in step 5b did not take place. Compound 20 in step 5a of Example 5 was replaced with Compound 23. The phenyl chloroformate was replaced with (2-(4-methylpiperazin-1-yl)benzoyl chloride). | $^1$H NMR (400 MHz, DMSO-d$_6$) δ 7.45 (t, J = 7.2 Hz, 1H), 7.36 (t, J = 7.2 Hz, 4H), 7.30-7.12 (m, 5H), 7.07 (d, J = 7.6 Hz, 4H), 5.22 (s, 1H), 4.80-4.25 (m, 2H), 3.62-3.36 (m, 5H), 3.28-3.06 (m, 3H), 3.05-2.97 (s, 3H), 2.96-2.75 (m, 2H), 2.05-1.50 (m, 4H). MS m/z (ESI): 554.2 [M + H]$^+$. |
| C242 | 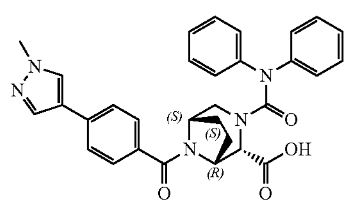 | (1R,2S,5S)-3-(diphenylcarbamoyl)-8-(4-(1-methyl-1H-pyrazole-4-yl)benzoyl)-3,8-diazabicyclo[3.2.1]octane-2-carboxylic acid | The reaction in step 5b did not take place. Compound 20 in step 5a of Example 5 was replaced with Compound 23. The phenyl chloroformate was replaced with (4-(1-methyl-1H-pyrazol-4-yl)benzoyl chloride). | $^1$H NMR (400 MHz, CD$_3$OD) δ 8.04 (s, 1H), 7.89 (s, 1H), 7.63 (d, J = 8.0 Hz, 2H), 7.48-7.34 (m, 6H), 7.22 (t, J = 7.2 Hz, 2H), 7.10 (d, J = 7.6 Hz, 4H), 4.54 (s, 2H), 3.95 (s, 3H), 3.60 (s, 2H), 2.00 (d, J = 33.5 Hz, 1H), 1.89 (s, 1H), 1.62 (s, 2H). MS m/z (ESI): 535.7 [M + H]$^+$. |
| C270 | 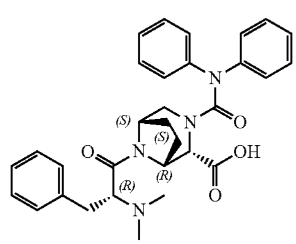 | (1R,2S,5S)-8-((R)-2-(dimethylamino)-3-phenylpropionyl)-3-(diphenylcarbamoyl)-3,8-diazabicyclo[3.2.1]octane-2-carboxylic acid | The reaction in step 5b did not take place. C79-1 in step 6 of Example 5 was replaced with C270-1. | $^1$H NMR (400 MHz, CD$_3$OD) δ 7.41-7.25 (m, 9H), 7.24-7.16 (m, 2H), 7.05 (d, J = 7.6 Hz, 4H), 4.60-4.41 (m, 3H), 4.14 (s, 1H), 3.59-3.48 (m, 2H), 3.10-2.83 (m, 8H), 1.43-1.29 (m, 2H), 1.29-1.15 (m, 1H), 1.02 (s, 2H). MS m/z (ESI): 526.9 [M + H]$^+$. |

TABLE 7-continued

| No. | Compound Structure | Compound Name | Starting material or reagent different from that in Example 5 | Characterization data |
|---|---|---|---|---|
| C269 | 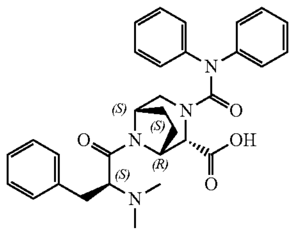 | (1R,2S,5S)-8-((S)-2-(dimethylamino)-3-phenylpropionyl)-3-(diphenylcarbamoyl)-3,8-diazabicyclo[3.2.1]octane-2-carboxylic acid | C79-1 in step 6 of Example 5 was replaced with C269-1. | $^1$H NMR (400 MHz, DMSO-d$_6$) δ 7.39-7.30 (m, 4H), 7.27-7.18 (m, 3H), 7.17-7.10 (m, 4H), 7.03 (d, J = 7.6 Hz, 1H), 6.96 (d, J = 7.6 Hz, 3H), 4.90-4.75 (m, 1H), 4.55-4.35 (m, 1H), 4.20-4.00 (m, 2H), 3.75-3.55 (m, 1H), 3.35-3.25 (m, 2H), 2.90-2.70 (m, 2H), 2.27-2.19 (m, 6H), 1.75-0.90 (m, 4H). MS m/z (ESI): 527.1 [M + H]$^+$. |
| C167 | 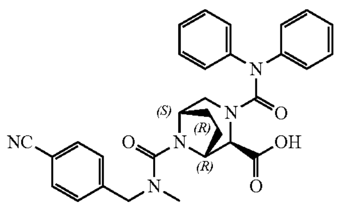 | (1R,2R,5S)-8-((4-cyanobenzyl)(methyl)carbamoyl)-3-(diphenylcarbamoyl)-3,8-diazabicyclo[3.2.1]octane-2-carboxylic acid | Compound C82-1 in step 6 of Example 5 was replaced with C167-1. | $^1$H NMR (400 MHz, DMSO-d$_6$) δ 13.06 (s, 1H), 7.81-6.95 (m, 14H), 4.51 (s, 1H), 4.43-4.28 (m, 3H), 3.95 (s, 1H), 3.46-3.36 (m, 2H), 2.75 (s, 3H), 1.75-1.40 (m, 4H). MS m/z (ESI): 523.8 [M + H]$^+$. |

Example 6: preparation of (1R,2R,5S)-ethyl 8-((4-cyanobenzyl)(methyl)carbamoyl)-3-(diphenyl-carbamoyl)-3,8-diazabicyclo[3.2.1]octane-2-carboxylate (C167-1)

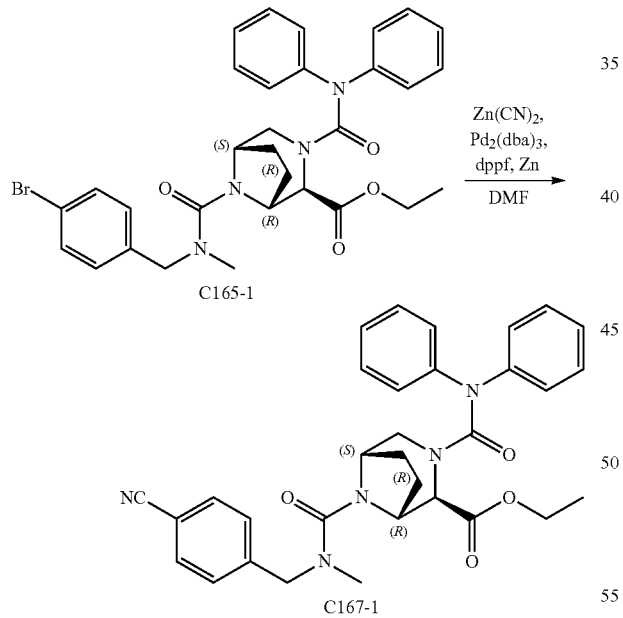

Compound C165-1 (60 mg, 0.1 mmol) was dissolved in N,N-dimethylformamide (20 mL), and Zn(CN)$_2$ (24 mg, 0.2 mmol), Pd$_2$(dba)$_3$ (92 mg, 0.1 mmol), dppf (56 mg, 0.1 mmol), and Zn (7 mg, 0.1 mmol) were added sequentially. The reaction solution was allowed to react for 16 hours at 100° C. under nitrogen protection. LC-MS indicated that the reaction of the starting materials was substantially complete. The reaction solution was concentrated under reduced pressure to evaporate off N,N-dimethylformamide. Saturated sodium chloride solution (10 mL) was then added and extracted with ethyl acetate (20 mL/2), and dried by adding anhydrous sodium sulfate (5 g) for 30 min, filtered and concentrated under reduced pressure. The resulting crude product was subjected to separation by preparative plate chromatography to obtain Compound C167-1 (50 mg, white solid, yield: 90%).

MS m/z (ESI): 551.8 [M+H]$^+$.

Example 7: preparation of (1R,2R,5S)-ethyl 8-((R)-2-(dimethylamino)-3-phenylpropanoyl)-3-(di-phenylcarbamoyl)-3,8-diazabicyclo[3.2.1]octane-2-carboxylate (C270-1) and (1R,2R,5S)-ethyl 8-((S)-2-(dimethylamino)-3-phenylpropanoyl)-3-(diphenylcarbamoyl)-3,8-diazabicyclo[3.2.1]octane-2-carboxylate (C269-1)

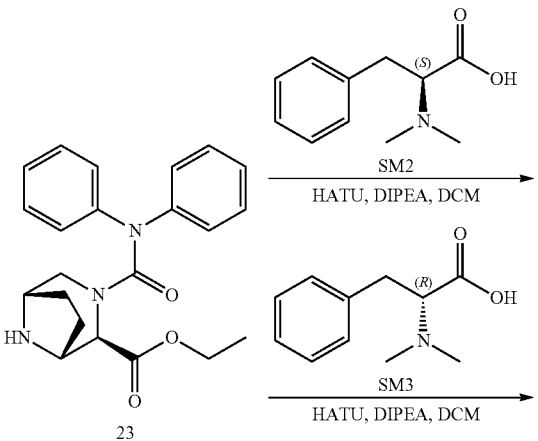

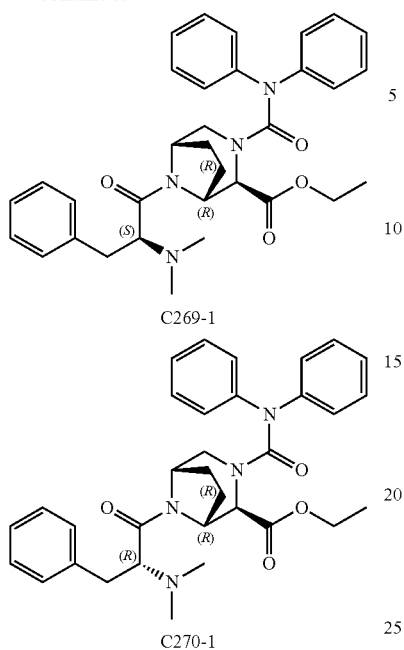

Compound 23 (90 mg, 0.466 mmol) was dissolved in a dichloromethane solution (20 mL), followed by sequential addition of HATU (265 mg, 0.699 mmol) and diisopropylethylamine (0.3 g, 2.33 mmol), and reaction at room temperature for 1 hour. Compound SM2 (88 mg, 0.233 mmol) was then added to the reaction solution, and was reacted at 50° C. for 16 hours. After the reaction was complete, 50 mL water was added to the reaction solution, followed by extraction with dichloromethane (20 mL×2). The combined organic phases were dried by adding anhydrous sodium sulfate (20 g) for 30 min, filtered and concentrated under reduced pressure to obtain a crude product. The crude product was separated and purified by column chromatography (petroleum ether:ethyl acetate=3:7) to obtain Compound C269-1 (90 mg, a yellow solid, crude product).

MS m/z (ESI): 555.2 [M+H]$^+$.

Except replacing SM2 with SM3, by the above reaction process, Compound C270-1 was prepared.

MS m/z (ESI): 555.2 [M+H]$^+$.

Example 8: preparation of (1R,2S,5S)-8-((benzyloxy)carbonyl)-3-(2,2-diphenylacetyl)-3,8-diazabicyclo[3.2.1]octane-2-carboxylic acid (C34)

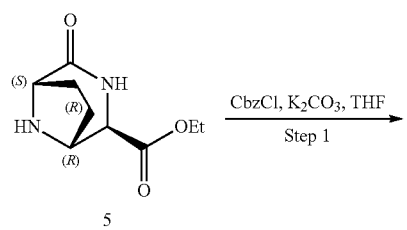

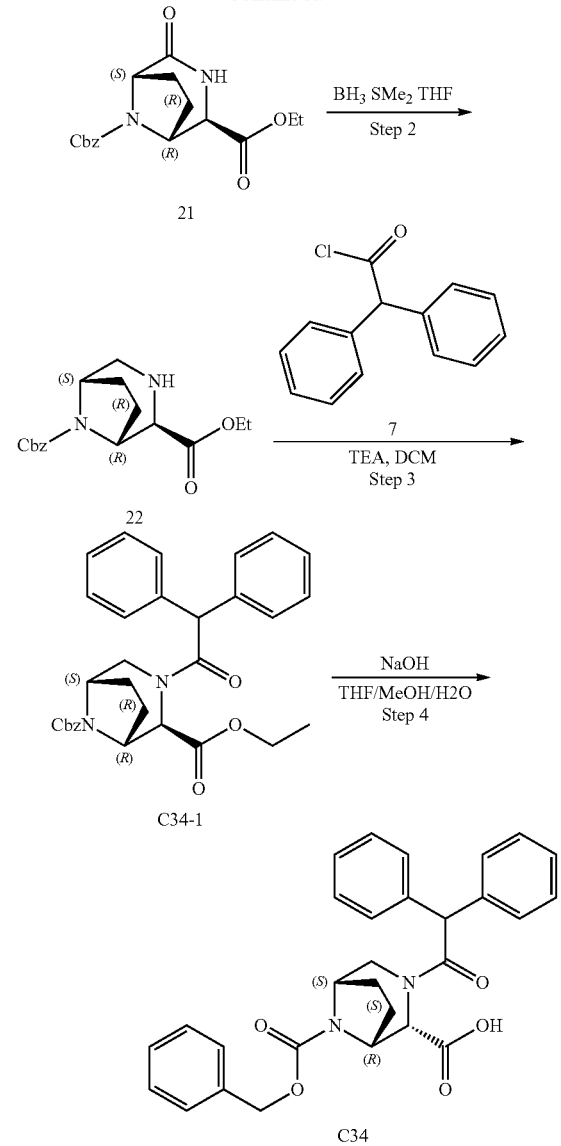

Step 1:

Compound 5 (1 g, 5.04 mmol) was dissolved in a tetrahydrofuran solution (30 mL). Phenyl chloroformate (0.86 g, 5.04 mmol) and potassium carbonate (2.1 g, 15.13 mmol) were added sequentially, and reacted at room temperature for 16 hours. After the reaction was complete, 50 mL water was added to the reaction solution and extracted with ethyl acetate (50 mL×2). The combined organic phases were dried by adding anhydrous sodium sulfate (100 g) for 30 min., filtered and concentrated under reduced pressure to obtain a crude product. The crude product was separated and purified by column chromatography on silica gel (petroleum ether: ethyl acetate=3:2) to obtain Compound 21 (1 g, a yellow oily matter, crude product).

MS m/z (ESI): 333.1 [M+H]$^+$.

Step 2:

Compound 21 (1 g, 3 mmol) was dissolved in a solution of borane dimethylsulfide in tetrahydrofuran (2M, 10 mL), purged with nitrogen for 5 times, and reacted at room temperature in a nitrogen atmosphere for 3 hours. After the reaction was complete, the reaction was quenched with methanol slowly and then concentrated to obtain a crude product of compound 22 (0.35 g, a brownish-yellow oily liquid, crude product).

MS m/z (ESI): 319.0 [M+H]+.

Step 3:

Compound 22 (0.35 g, 1.1 mmol) was dissolved in dichloromethane (20 mL). To the solution, triethylamine (0.33 g, 3.3 mmol) was then added. Compound 7 (0.25 g, 1.1 mmol) was dissolved in 10 mL dichloromethane, and added dropwise to the above reaction solution and allowed to react at room temperature for 4 horns. LC-MS indicated that the reaction of the starting materials was complete. It was then quenched by adding water (30 mL), and extracted with ethyl acetate (20 mL/3). The combined organic phases were washed with saturated brine (20 mL×3). The organic phases were dried by adding anhydrous sodium sulfate for half an hour, and filtered. The filtrate was concentrated under reduced pressure. The resulting crude product was subjected to separation by column chromatography on silica gel (petroleum ether:methyl tert-butyl ether=1.5:1) to obtain Compound C34-1 (0.12 g, a dark yellow solid, crude product).

MS m/z (ESI): 513.0 [M+H]+.

Step 4:

Compound C34-1 (0.12 g, 0.234 mmol) was dissolved in a mixed solution of tetrahydrofuran, methanol and water (5 mL/5 mL/5 mL). After adding sodium hydroxide (47 mg, 1.17 mmol) and stirring at room temperature for 5 horns, it was concentrated to obtain a crude product. Then, it was adjusted to pH 5.0 with 3N hydrochloric acid solution, and extracted with ethyl acetate (50 mL/3). The combined organic phases were washed with saturated brine (50 mL/3). The organic phases were dried by adding anhydrous sodium sulfate for half an hour, and filtered. The filtrate was concentrated under reduced pressure, and the resulting crude product was purified by preparative high-performance liquid chromatography (acetonitrile/water (0.1% trifluoroacetic acid solution) 40/60-20/80) to obtain Compound C34 (30 mg, a light yellow solid, yield: 26%).

$^1$H NMR (400 MHz, DMSO-$d_6$) δ 7.50-7.00 (m, 15H), 5.50-5.30 (m, 1H), 5.15-5.00 (m, 1H), 4.60 (s, 1H), 4.45-4.00 (m, 3H), 3.75-3.25 (m, 2H), 2.10-1.75 (m, 2H), 1.65-1.25 (m, 2H).

MS m/z (ESI): 485.0 [M+H]+.

Example 9: preparation of (1S,3S,4S)-5-(benzyloxy)-2-(2,2-diphenylacetyl)-2-azabicyclo[2.2.2]octane-3-carboxylic acid (C283)

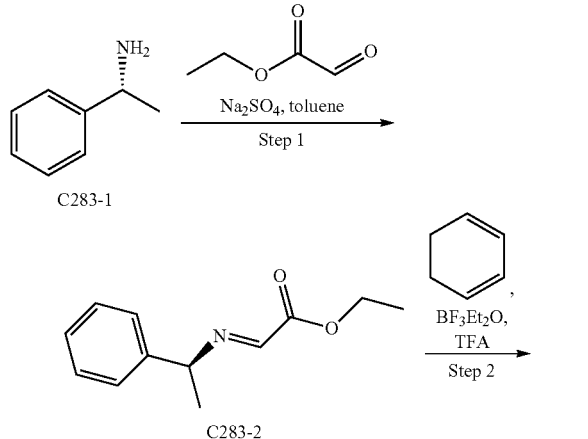

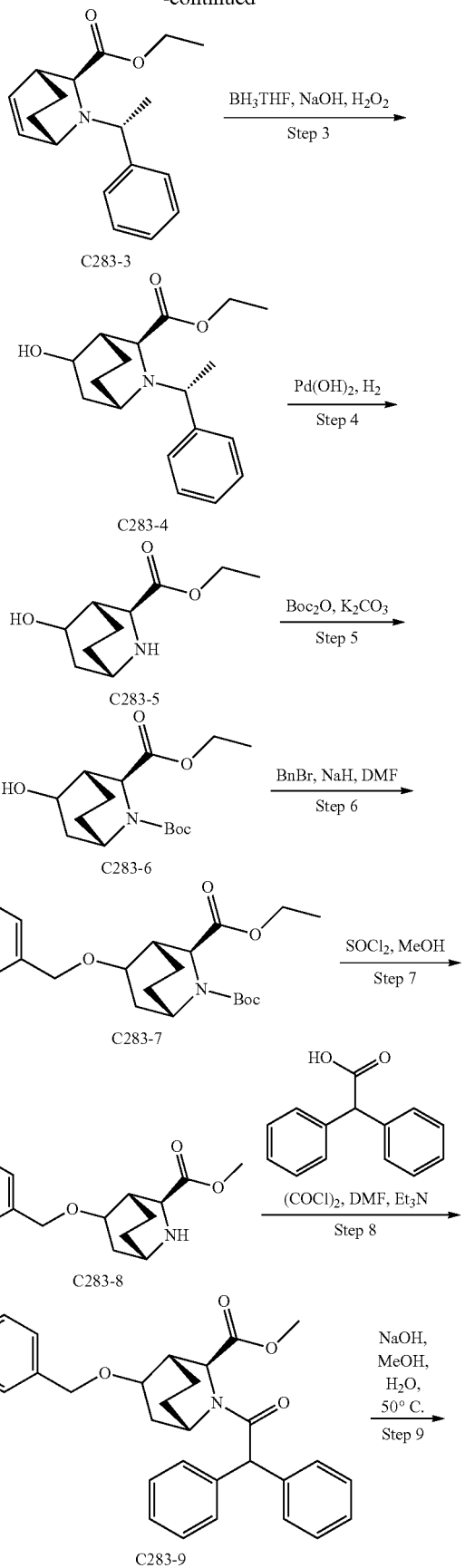

-continued

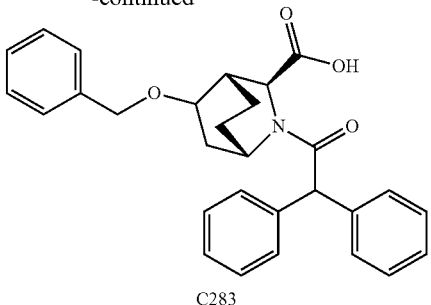

C283

Step 1:

Compound C283-1 (10 g, 82.6 mmol) was dissolved in toluene (100 mL). Anhydrous sodium sulfate (35 g, 0.25 mol) and a 50% solution of ethyl glyoxylate in toluene (16.8 g, 82.6 mmol) were added sequentially, and the reaction solution was allowed to react at room temperature for 18 hours. After filtration, the filter cake was washed with toluene (100 mL), and the filtrate was concentrated under reduced pressure to remove toluene, obtaining Compound C283-2 (16 g, a colorless oily liquid, yield: 94%).

$^1$H NMR (400 MHz, CDCl$_3$): δ 7.72 (s, 1H), 7.36-7.24 (m, 5H), 4.61 (q, J=6.8 Hz, 1H), 4.35 (q, J=7.2 Hz, 2H), 1.62 (d, J=6.8 Hz, 3H), 1.34 (t, J=7.2 Hz, 3H).

Step 2:

Compound C283-2 (16 g, 78 mmol) was dissolved in dry dichloromethane (100 mL). Under nitrogen protection, it was cooled to −15° C. to −20° C., and trifluoroacetic acid (8.3 g, 86 mmol), boron trifluoride etherate (12.2 g, 86 mmol) and 1,3-cyclohexadiene (6.9 g, 86 mmol) were added sequentially. The reaction solution was allowed to react at −10° C. for 2 horns. LC-MS indicated that the reaction of the starting materials was complete. It was then quenched by adding a saturated NaHCO$_3$ solution, and extracted with dichloromethane (100 mL×3). The combined organic phases were washed once with saturated brine (300 mL), and then dried over anhydrous sodium sulfate for 30 min, filtered and concentrated to obtain a crude product. The crude product was subjected to separation by column chromatography (petroleum ether:ethyl acetate=50:1 to 30:1) to obtain Compound C283-3 (7.4 g, a light yellow oily liquid, yield: 33.6%).

$^1$H NMR (400 MHz, CDCl$_3$): δ 7.42-7.31 (m, 2H), 7.27-7.16 (m, 3H), 6.41-6.37 (m, 1H), 6.27-6.24 (m, 1H), 3.97 (q, J=7.2 Hz, 2H), 3.64-3.60 (m, 1H), 3.43 (q, J=6.8 Hz, 1H), 2.89 (brs, 1H), 2.76-2.71 (m, 1H), 2.06-2.00 (m, 1H), 1.62-1.54 (m, 1H), 1.30 (d, J=6.8 Hz, 3H), 1.31-1.24 (m, 1H), 1.12 (t, J=7.2 Hz, 3H,), 1.05-0.99 (m, 1H).

MS m/z (ESI): 304.1 [M+H]$^+$.

Step 3:

Compound C283-3 (4 g, 14 mmol) was dissolved in tetrahydrofuran (50 mL) and cooled to 0° C. under nitrogen protection. 1 M/L BH$_3$THF (15.4 mL, 15.4 mmol) was slowly added dropwise. After the addition was complete, the reaction solution was stirred at room temperature for 3 hours, and then 3N NaOH (10 mL, 30 mmol) and 30% H$_2$O$_2$ solution (20 mL) were slowly added dropwise at 0° C. After the addition was completed, the reaction solution was stirred at room temperature for 0.5 horn, followed by addition of saturated brine (100 mL) and extraction with tetrahydrofuran (50 mL×3). The combined organic phases were dried with anhydrous sodium sulfate for 30 min, then filtered and concentrated to obtain a crude product. The crude product was subjected to separation by column chromatography (petroleum ether:ethyl acetate=8:1) to obtain Compound C283-4 (1.3 g, a colorless oily liquid, yield: 30%).

$^1$H NMR (400 MHz, CDCl$_3$): δ 7.41-7.36 (m, 2H), 7.31-7.19 (m, 3H), 4.11-4.05 (m, 1H), 3.89 (q, J=7.2 Hz 2H), 3.59-3.54 (m, 1H), 3.17 (brs, 1H), 3.10 (brs, 1H), 2.45-2.38 (m, 1H), 1.33 (d, J=6.4 Hz, 3H), 2.05-1.18 (m, 6H), 1.06 (t, J=7.2 Hz, 3H).

MS m/z (ESI): 229.9 [M+H]$^+$.

Step 4:

Compound C283-4 (800 mg, 2.64 mmol) and 10% wet Pd/C (80 mg) were dissolved in absolute ethanol (20 mL), reacted at room temperature in hydrogen atmosphere for 18 horns, and filtered. The filter cake was washed twice with ethanol (10 mL), and the filtrate was concentrated under reduced pressure to obtain Compound C283-5 (500 mg, a colorless oily liquid, yield: 95%).

MS m/z (ESI): 200.1 [M+H]$^+$.

Step 5:

Compound C283-5 (200 mg, 1 mmol) and potassium carbonate (276 mg, 2 mmol) were dissolved in tetrahydrofuran (5 mL) and water (5 mL), and di-tert-butyl dicarbonate (327 mg, 1.5 mmol) was added while stirring, and was stirred at room temperature for 16 hours. LC-MS indicated that the reaction of the starting materials was complete. Ethyl acetate (50 mL) was added and washed with saturated brine (40 mL×3). The organic phase was dried with anhydrous sodium sulfate for 30 min, and filtered. The filtrate was concentrated under reduced pressure to obtain a crude product of Compound C283-6 (300 mg, a colorless oily liquid, yield: 100%).

MS m/z (ESI): 322.2 [M+Na]+.

Step 6:

Compound C283-6 (120 mg, 0.4 mmol) was dissolved in DMF (5 mL). Under nitrogen protection, after added NaH (60%, 24 mg, 0.4 mmol) and stirring for 1 h, benzyl bromide (82 mg, 0.48 mmol) was added and then stirred at room temperature for 16 hours. It was quenched by adding water (10 mL), adjusted to pH 5 with 1N acetic acid solution, and then extracted with ethyl acetate (20 mL×3). The combined organic phases were washed with saturated brine (50 mL×3), dried with anhydrous sodium sulfate for 30 min and filtered. The filtrate was concentrated under reduced pressure to obtain a crude product of Compound C283-7 (60 mg, a light yellow oily liquid, yield: 38%).

MS m/z (ESI): 411.9 [M+Na]+.

Step 7:

Compound C283-7 (60 mg, 0.17 mmol) was dissolved in methanol (5 mL). After cooling to 0° C., thionyl chloride (1 mL) was added, and heated up to 40° C., and stirred for 16 horns. LC-MS indicated that the reaction of the starting materials was complete. The reaction solution was cooled to room temperature and concentrated under reduced pressure to obtain a crude product. The crude product was subjected to separation by preparative high-performance liquid chromatography (CH$_3$CN:H$_2$O (0.1% TFA)=20%-50%) to obtain Compound C283-8 (40 mg, a colorless oily liquid, yield: 87%).

$^1$H NMR (400 MHz, CDCl$_3$): δ 7.38-7.31 (m, 6H), 4.53 (s, 2H), 4.37-4.35 (m, 3H), 4.06 (brs, 1H), 3.77-3.73 (m, 1H), 2.58 (brs, 1H), 2.16-2.10 (m, 1H), 1.97-1.90 (m, 1H), 1.83-1.67 (m, 2H), 1.36-1.33 (m, 2H).

MS m/z (ESI): 275.9 [M+H]$^+$.

Step 8:

2,2-diphenylacetic acid (37 mg, 0.17 mmol) and DMF (1 drop) were added to dry dichloromethane (10 mL). After cooling to 0° C., oxalyl chloride (27 mg, 0.21 mmol) was added, stirred at room temperature for 1 horn, and then concentrated under reduced pressure. The residue was dissolved in dichloromethane (2 mL) to obtain a 2,2-diphenylacetyl chloride solution. C283-8 (40 mg, 0.14 mmol) and triethylamine (28 mg, 0.28 mmol) were dissolved in dichloromethane (5 mL) and cooled to 0° C. The previous 2,2-diphenylacetyl chloride solution was then slowly added. The reaction solution was allowed to react at room temperature for 5 hours. LC-MS indicated that the reaction of the starting materials was complete. Dichloromethane (30 mL) was added, washed with saturated brine (20 mL×3), dried over anhydrous sodium sulfate for 30 min and then filtered. The filtrate was concentrated under reduced pressure to obtain a crude compound. The crude product was subjected to separation by thin layer chromatography (petroleum ether:ethyl acetate=2:1) to obtain Compound C283-9 (30 mg, a colorless oily liquid, yield: 44%).

MS m/z (ESI): 470.0 [M+H]⁺.

Step 9:

C283-9 (30 mg, 0.06 mmol) was dissolved in tetrahydrofuran (1 mL) and water (1 mL). Sodium hydroxide (13 mg, 0.32 mmol) was added at room temperature, stirred at room temperature for 16 hours, and then concentrated under reduced pressure. The residue was dissolved in water (10 mL), adjusted to pH 5 with 1N dilute hydrochloric acid, and then extracted with ethyl acetate (20 mL×3). The combined organic phases were washed with saturated brine (30 mL×2), dried over anhydrous sodium sulfate for 30 min, and then filtered. The filtrate was concentrated under reduced pressure to obtain a crude product. The crude product was subjected to separation by preparative high-performance liquid chromatography (CH$_3$CN:H$_2$O (0.1% TFA)=20%-70%) to obtain Compound C283 (12 mg, a white solid, yield: 41%).

$^1$H NMR (400 MHz, DMSO-d$_6$): δ 12.51 (brs, 1H), 7.33-7.19 (m, 15H), 5.47-5.43 (m, 1H), 4.48-4.37 (m, 2H), 4.10-4.02 (m, 2H), 3.75-3.73 (m, 1H), 3.11-3.07 (m, 1H), 1.80-1.74 (m, 1H), 1.63 (m, 1H), 1.51-1.23 (m, 4H).

MS m/z (ESI): 455.8 [M+H]⁺.

The compounds in Table 8 were prepared by methods similar to that described in Example 9.

TABLE 8

| No. | Compound Structure | Compound Name | Starting material or reagent different from that in Example 9 | Characterization data |
|---|---|---|---|---|
| C291 | 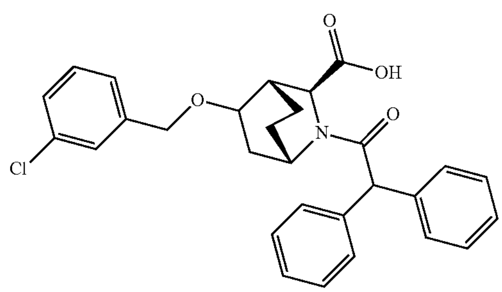 [SMILES: O=C(O)[C@@H]1[C@@H]2CC[C@@H](CC2OCc2cccc(Cl)c2)N1C(=O)C(c1ccccc1)c1ccccc1] | (1S,3S,4S)-5-((3-chlorobenzyl)oxy)-2-(2,2-diphenylacetyl)-2-azabicyclo[2.2.2]octane-3-carboxylic acid | The benzyl bromide in step 6 of Example 9 was replaced with 3-chlorobenzyl bromide. | $^1$H NMR (400 MHz, CD$_3$OD): δ 7.35-7.23 (m, 14H), 5.41 (s, 1H), 4.56-4.45 (m, 2H), 4.29-4.23 (m, 1H), 4.15-4.04 (m, 1H), 3.79 (s, 1H), 2.63-2.49 (m, 1H), 2.15-1.80 (m, 3H), 1.69-1.41 (m, 4H). MS m/z (ESI): 490.2 [M + H]⁺. |
| C293 | 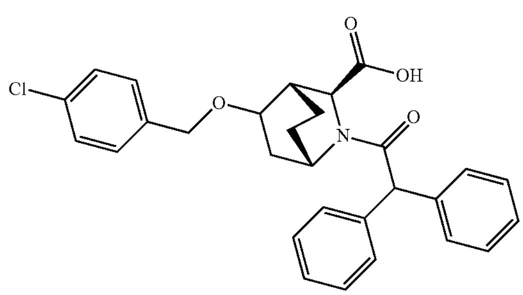 [SMILES: O=C(O)[C@@H]1[C@@H]2CC[C@@H](CC2OCc2ccc(Cl)cc2)N1C(=O)C(c1ccccc1)c1ccccc1] | (1S,3S,4S)-5-((4-chlorobenzyl)oxy)-2-(2,2-diphenylacetyl)-2-azabicyclo[2.2.2]octane-3-carboxylic acid | The benzyl bromide in step 6 of Example 9 was replaced with 4-chlorobenzyl bromide | $^1$H NMR (400 MHz, CD$_3$OD): δ 7.45-7.16 (m, 14H), 5.40 (d, J = 7.1 Hz, 1H), 4.56-4.45 (m, 2H), 4.31-4.16 (m, 1H), 4.12-4.01 (m, 1H), 3.79 (d, J = 9.4 Hz, 1H), 2.51 (s, 1H), 2.06-1.78 (m, 3H), 1.68-1.38 (m, 4H). MS m/z (ESI): 489.8 [M + H]⁺. |
| C294 | 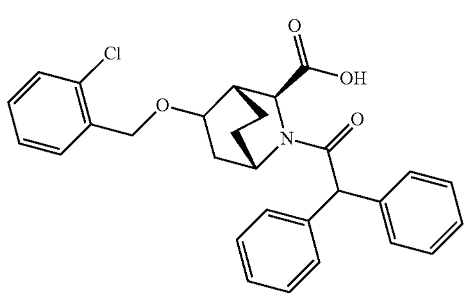 [SMILES: O=C(O)[C@@H]1[C@@H]2CC[C@@H](CC2OCc2ccccc2Cl)N1C(=O)C(c1ccccc1)c1ccccc1] | (1S,3S,4S)-5-((2-chlorobenzyl)oxy)-2-(2,2-diphenylacetyl)-2-azabicyclo[2.2.2]octane-3-carboxylic acid | The benzyl bromide in step 6 of Example 9 was replaced with 2-chlorobenzyl bromide. | $^1$H NMR (400 MHz, CD$_3$OD): δ 7.50-7.10 (m, 14H), 5.44 (d, J = 16.8 Hz, 1H), 4.68-4.48 (m, 2H), 4.32-4.16 (m, 1H), 4.12 (d, J = 12.4 Hz, 1H), 3.85 (d, J = 9.3 Hz, 1H), 2.54 (s, 1H), 2.06-1.78 (m, 3H), 1.62-1.44 (m, 4H). MS m/z (ESI): 489.8 [M + H]⁺. |

TABLE 8-continued

| No. | Compound Structure | Compound Name | Starting material or reagent different from that in Example 9 | Characterization data |
|---|---|---|---|---|
| C290 | 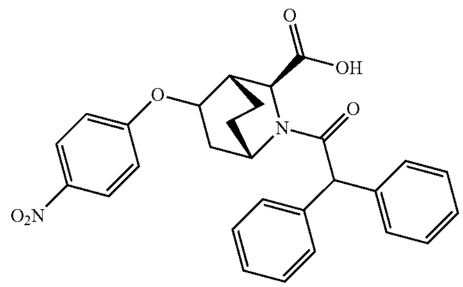 [SMILES: O=C(O)[C@@H]1[C@@H]2CC[C@@H](CC2Oc2ccc([N+](=O)[O-])cc2)N1C(=O)C(c1ccccc1)c1ccccc1] | (1S,3S,4S)-2-(2,2-diphenyl-acetyl)-5-(4-nitrophenoxy)-2-azabicyclo[2.2.2]octane-3-carboxylic acid | The benzyl bromide in step 6 of Example 9 was replaced with 4-fluoronitrobenzene, and DMF was replaced with tetrahydrofuran. | $^1$H NMR (400 MHz, CD$_3$OD): δ 8.22 (d, J = 9.6 Hz, 2H). 7.50-7.20 (m, 10H), 7.0 (d, J = 6.8 Hz, 2H), 5.46 (s, 1H), 4.72 (d, J = 9.6 Hz, 1H), 4.52 (d, J = 2.8 Hz, 1H), 4.24 (s, 1H). 2.70 (s, 1H), 2.50-2.40 (m, 1H), 2.30-2.20 (m, 1H), 1.70-1.50 (m, 4H). MS m/z (ESI): 486.9 [M + H]$^+$. |
| C296 | 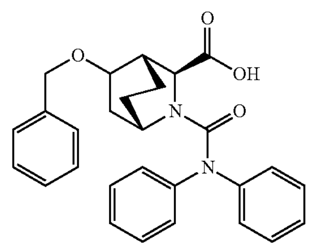 [SMILES: O=C(O)[C@@H]1[C@@H]2CC[C@@H](CC2OCc2ccccc2)N1C(=O)N(c1ccccc1)c1ccccc1] | (1S,3S,4S)-5-(benzyloxy)-2-(diphenyl-carbamoyl)-2-azabicyclo[2.2.2]octane-3-carboxylic acid | The process of preparing 2,2-diphenylacetyl chloride in step 8 of Example 9 was completely replaced with | $^1$H NMR (400 MHz, DMSO-d$_6$): δ 12.79 (brs, 1H), 7.36-7.05 (m, 15H), 4.55-4.31 (m, 3H), 3.80 (brs, 2H), 3.61-3.59 (m, 1H), 2.13 (brs, 1H), 1.75-1.70 (m, 1H), 1.46-1.24 (m, 4H). MS m/z (ESI): 456.9 [M + H]$^+$. |
| C297 | 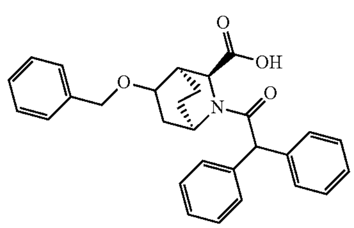 [SMILES: O=C(O)[C@@H]1[C@H]2CC[C@H](CC2OCc2ccccc2)N1C(=O)C(c1ccccc1)c1ccccc1] | (1R,3S,4R)-5-(benzyloxy)-2-(2,2-diphenylacetyl)-2-azabicyclo[2.2.2]octane-3-carboxylic acid | It was prepared from the isomer separated in step 2 of Example 9. | $^1$H NMR (400 MHz, DMSO-d$_6$): δ 12.52 (brs, 1H), 7.33-7.19 (m, 15H), 5.47-5.44 (m, 1H), 4.49-4.35 (m, 2H), 4.24-4.21 (m, 1H), 4.10-4.00 (m, 2H), 3.75-3.62 (m, 1H), 1.80-1.60 (m, 2H), 1.43-1.24 (m, 4H). MS m/z (ESI): 455.9 [M + H]$^+$. |
| C302 | 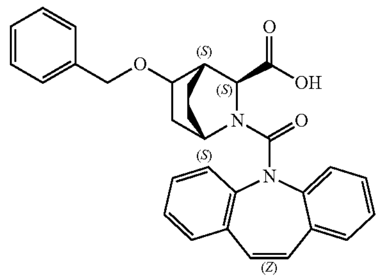 | (1S,3S,4S)-5-(benzyloxy)-2-(5H-dibenzo[b,f]azepine-5-carbonyl)-2-azabicyclo[2.2.2]octane-3-carboxylic acid | The process of preparing 2,2-diphenylacetyl chloride in step 8 of Example 9 was completely replaced with | $^1$H NMR (400 MHz, CD$_3$OD): δ 7.71 (d, J = 6.8 Hz, 1H), 7.39-7.25 (m, 11H), 6.99 (d, J = 12.4 Hz, 2H), 4.44 (t, J = 12.0 Hz, 2H), 4.36-4.30 (m, 1H), 4.13 (s, 1H), 3.76-3.73 (m, 1H), 2.44 (s, 1H), 2.73-2.03 (m, 2H), 1.51-1.29 (m, 2H), 1.05 (s, 1H). MS m/z (ESI): 480.8 [M + H]$^+$. |

TABLE 8-continued

| No. | Compound Structure | Compound Name | Starting material or reagent different from that in Example 9 | Characterization data |
|-----|--------------------|---------------|---------------------------------------------------------------|------------------------|
|     |                    |               | (Z) dibenzazepine-N-carbonyl chloride |                        |

Example 10: preparation of (1S,3S,4R)-5-(benzylamino)-2-(2,2-diphenylacetyl)-2-azabicyclo[2.2.2]octane-3-carboxylic acid (C285) and (1S,3S,4R)-5-(benzyl(methyl)amino)-2-(2,2-diphenylacetyl)-2-azabicyclo[2.2.2]octane-3-carboxylic acid (C295)

Step 1:

2,2-diphenylacetic acid (383 mg, 1.8 mmol) and DMF (1 drop) were added to dry dichloromethane (10 mL). After cooling to 0° C., oxalyl chloride (286 mg, 2.2 mmol) was added, stirred at room temperature for 1 horn, and then concentrated under reduced pressure. The residue was dissolved in ethyl acetate (2 mL) to obtain a 2,2-diphenylacetyl chloride solution. C283-5 (40 mg, 0.14 mmol) and potassium carbonate (414 mg, 3 mmol) were dissolved in ethyl acetate (10 mL) and water (10 mL), and cooled to 0° C. The previous 2,2-diphenylacetyl chloride solution was then slowly added. The reaction solution was allowed to react at room temperature for 16 hours. LC-MS indicated that the reaction of the starting materials was complete. Ethyl acetate (30 mL) was added, washed with saturated brine (20 mL×2), dried over anhydrous sodium sulfate for 30 min, and then filtered. The filtrate was concentrated under reduced pressure to obtain a crude compound. The crude product was subjected to separation by column chromatography (petroleum ether:ethyl acetate=2:1) to obtain Compound C295-1 (350 mg, a white solid, yield: 59%).

$^1$H NMR (400 MHz, CDCl$_3$): δ 7.32-7.18 (m, 10H), 5.10 (s, 1H), 4.36 (s, 1H), 4.27-4.20 (m, 2H), 4.12 (q, J=7.2 Hz, 2H), 3.92 (brs, 1H), 2.24 (s, 1H), 1.99-1.91 (m, 1H), 1.85-1.76 (m, 1H), 1.55-1.50 (m, 1H), 1.46-1.39 (m, 1H), 1.29-1.24 (m, 2H), 1.26 (t, J=7.2 Hz, 3H).

MS m/z (ESI): 394.0 [M+H]$^+$.

Step 2:

Compound C295-1 (320 mg, 0.81 mmol) was dissolved in dry dichloromethane (20 mL) and Dess-Martin periodinane (690 mg, 1.62 mmol) was added. The reaction solution was allowed to react at room temperature for 16 hours. LC-MS indicated that the reaction of the starting materials was complete. It was then filtered. Dichloromethane (30 mL) was added to the filtrate, washed with a saturated NaHCO$_3$ solution (50 mL×2) and then saturated brine (50 mL×1). After that, it was dried over anhydrous sodium sulfate for 30 min, filtered, and concentrated under reduced pressure to obtain a crude compound. The crude product was subjected to separation by column chromatography (petroleum ether:ethyl acetate=50:1 to 30:1) to obtain Compound C295-2 (300 mg, a white solid, yield: 93%).

$^1$H-NMR (400 MHz, CDCl3): δ 7.37-7.17 (m, 10H), 5.16 (s, 1H), 4.63 (s, 1H), 4.38 (s, 1H), 4.24 (q, J=6.4 Hz, 2H), 2.82 (s, 1H), 2.22-2.15 (m, 2H), 2.10-2.05 (m, 1H), 1.97-1.91 (m, 1H), 1.77-1.63 (m, 2H), 1.28 (t, J=6.4 Hz, 3H).

MS m/z (ESI): 391.8 [M+H]$^+$.

Step 3:

Compound C295-2 (30 mg, 0.077 mmol) was dissolved in methanol (10 mL), and benzylamine (10 mg, 0.092 mmol) and acetic acid (0.1 mL) were sequentially added. After stirring at room temperature for 1 hour, sodium cyanoborohydride (10 mg, 0.154 mmol) was added, stirred at room temperature for 16 horns and then concentrated to obtain Compound C295-3 (30 mg, a light yellow oily liquid, yield 83%).

MS m/z (ESI): 483.0 [M+H]$^+$.

Step 4:

C295-3 (100 mg, 0.2 mmol) was dissolved in methanol (10 mL) and water (3 mL). Sodium hydroxide (20 mg, 0.5 mmol) was added at room temperature and stirred at 50° C. for 16 hours while heating, and then concentrated under reduced pressure. The residue was dissolved in water (10 mL), and adjusted to pH 5 with 1N diluted hydrochloric acid, followed by extraction with ethyl acetate (20 mL×3). The organic phases were washed with saturated brine (30 mL×2), dried over anhydrous sodium sulfate for 30 min, and then filtered. The filtrate was concentrated under reduced pressure to obtain a crude product. The crude product was subjected to separation by preparative high-performance liquid chromatography (CH$_3$CN:H$_2$O (0.1% TFA)=20%-50%) to obtain Compound C285 (70 mg, a white solid, yield: 74%).

$^1$H NMR (400 MHz, DMSO-d$_6$): δ 12.64 (brs, 1H), 7.52-7.45 (m, 5H), 7.35-7.19 (m, 10H), 5.44 (s, 1H), 4.44 (s, 1H), 4.14-4.11 (m, 3H), 2.10 (t, J=12.0 Hz, 1H), 1.66-1.58 (m, 2H), 1.53-1.35 (m, 4H).

MS m/z (ESI): 455.0 [M+H]$^+$.

Step 5:

Compound C285 (30 mg, 0.07 mmol) and 30% aqueous formaldehyde solution (12 mg, 0.7 mmol) were dissolved in methanol (3 mL). Acetic acid (0.1 mL) and 2N hydrochloric acid (0.2 mL) were then sequentially added and stirred at room temperature for 1 hour. Sodium cyanoborohydride (9 mg, 0.14 mmol) was added, and then stirred at room temperature for 16 hour. LC-MS indicated that the reaction of the starting materials was complete. After concentration under reduced pressure, a crude product was obtained. The crude product was subjected to separation by preparative high-performance liquid chromatography (CH$_3$CN:H$_2$O (0.1% TFA)=20%-50%) to obtain Compound C295 (10 mg, a white solid, yield: 32%).

$^1$H NMR (400 MHz, DMSO-d$_6$): δ 12.78 (brs, 1H), 7.52-7.26 (m, 15H), 5.50 (s, 1H), 4.58-4.51 (m, 1H), 4.44-4.39 (m, 2H), 4.19 (brs, 1H), 4.08-4.03 (m, 1H), 2.70-2.63 (m, 3H), 2.38-2.33 (m, 1H), 1.80-1.41 (m, 6H).

MS m/z (ESI): 468.8 [M+H]$^+$.

The compound in Table 9 was prepared by a method similar to that described in Example 10.

TABLE 9

| No. | Compound Structure | Compound Name | Starting material or reagent different from that in Example 10 | Characterization data |
| --- | --- | --- | --- | --- |
| C287 | 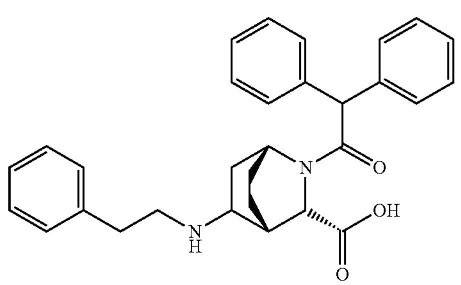 | (3S)-2-(2,2-diphenylacetyl)-5-(phenoxyamino)-2-azabicyclo[2.2.2]octane-3-carboxylic acid | Benzylamine in step 3 of Example 10 was replaced with phenethylamine | $^1$H NMR (400 MHz, DMSO-d$_6$): δ 7.35-7.21 (m, 15H), 5.45 (d, J = 6.0 Hz, 1H), 4.44 (s, 1H). 4.26 (s, 1H), 4.13 (s, 1H), 4.10 (s, 1H), 3.51 (brs, 1H), 3.13 (s, 1H), 2.94-2.88 (m, 2H), 2.14-2.06 (m, 1H), 1.91-1.34 (m, 5H). MS m/z (ESI): 468.8 [M + H]$^+$. |

Example 11: preparation of (1S,3S,4S)-2-(2,2-diphenylacetyl)-5-hydroxyl-2-azabicyclo[2.2.2]octane-3-carboxylic acid (C288)

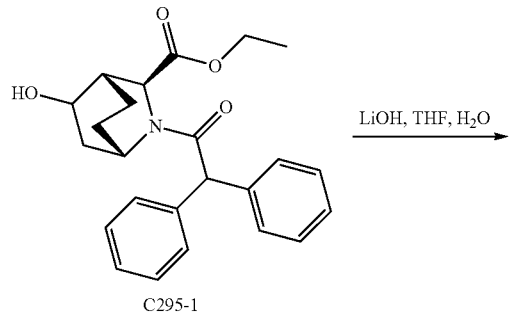

Example 12: preparation of (1S,3S,4R)-5-benzamido-2-(2,2-diphenylacetyl)-2-azabicyclo[2.2.2]octane-3-carboxylic acid (C286)

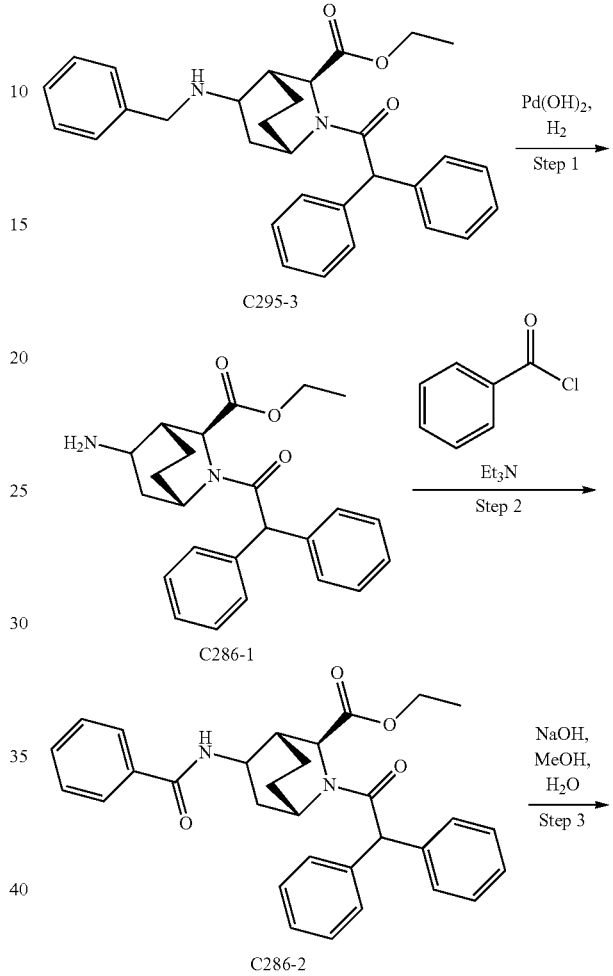

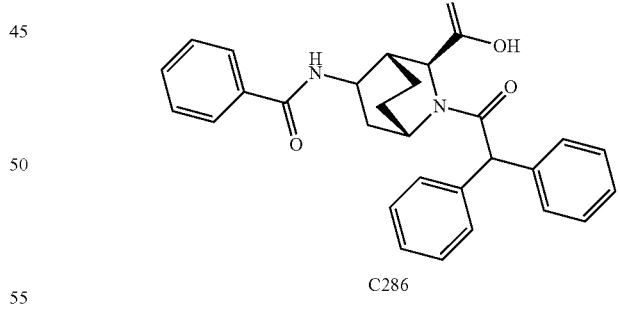

C295-1 (30 mg, 0.08 mmol) was dissolved in tetrahydrofuran (3 mL) and water (2 mL). Lithium hydroxide (10 mg, 0.38 mmol) was added at room temperature, stirred at room temperature for 16 hours, and then concentrated under reduced pressure. The residue was dissolved in water (10 mL), adjusted to pH 5 with 1N diluted hydrochloric acid, and then extracted with ethyl acetate (10 mL×3). The organic phases were washed with saturated brine (20 mL×2), and then dried over anhydrous sodium sulfate for 30 min and filtered. The filtrate was concentrated under reduced pressure to obtain a crude product. The crude product was subjected to separation by preparative high-performance liquid chromatography (CH$_3$CN:H$_2$O (0.1% TFA)=20%-60%) to obtain Compound C288 (16 mg, a white solid, yield: 57%).

$^1$H NMR (400 MHz, DMSO-d$_6$): δ 12.38 (brs, 1H), 7.28-7.20 (m, 10H), 5.41 (s, 1H), 4.09 (s, 1H), 3.96 (s, 1H), 3.81-4.77 (m, 1H), 2.10 (s, 1H), 1.87-1.79 (m, 1H), 1.87-1.79 (m, 1H), 1.73-1.58 (m, 2H), 1.47-1.41 (m, 1H), 1.27-1.21 (m, 1H), 1.13-1.08 (m, 1H).

MS m/z (ESI): 365.9 [M+H]$^+$.

Step 1:

C295-3 (60 mg, 0.12 mmol) and Pd(OH)$_2$ (20%, 12 mg) were added to ethanol (10 mL), hydrogenated in a hydrogen atmosphere for 16 horns, and then filtered. The filtrate was concentrated under reduced pressure to obtain a crude Compound C286-1 (40 mg, a white solid, yield: 83%).

$^1$H NMR (400 MHz, DMSO-d$_6$): δ 7.97 (brs, 2H), 7.34-7.20 (m, 10H), 5.47 (s, 1H), 4.40 (s, 1H), 4.17-4.08 (m, 3H), 2.94 (s, 1H), 1.92-1.86 (m, 1H), 1.73 (m, 1H), 1.62-1.45 (m, 2H), 1.35-1.28 (m, 2H), 1.20 (t, J=7.2 Hz, 3H).

MS m/z (ESI): 393.2 [M+H]$^+$.

Step 2:

Compound C286-1 (25 mg, 0.064 mmol) and triethylamine (19 mg, 0.192 mmol) were dissolved in dry dichloromethane (5 mL) and then benzoyl chloride (10 mg, 0.07 mmol) was added. The reaction solution was reacted at room temperature for 16 hours. LC-MS indicated that the reaction of the starting materials was complete. After that, dichloromethane (20 mL) was added, washed with saturated brine (20 mL×2), and then dried over anhydrous sodium sulfate for 30 min. It was then filtered, and concentrated to obtain a crude product. The crude product was subjected to separation by preparative thin layer chromatography (petroleum ether:ethyl acetate=2:1) to obtain Compound C286-2 (25 mg, a colorless solid, yield: 80%).

MS m/z (ESI): 496.7 [M+H]$^+$.

Step 3:

C286-2 (25 mg, 0.05 mmol) was dissolved in methanol (10 mL) and water (3 mL). Sodium hydroxide (20 mg, 0.5 mmol) was added at room temperature and stirred at 50° C. for 16 hours while heating, and then concentrated under reduced pressure. The residue was dissolved in water (10 mL), adjusted to pH 5 with 1N diluted hydrochloric acid, and then extracted with ethyl acetate (10 mL×3). The organic phases were washed with saturated brine (30 mL×2), dried over anhydrous sodium sulfate for 30 min and then filtered. The filtrate was concentrated under reduced pressure to obtain a crude product. The crude product was subjected to separation by preparative high-performance liquid chromatography (CH$_3$CN:H$_2$O (0.1% TFA)=30%-60%) to obtain Compound C286 (6 mg, a white solid, yield: 25%).

$^1$H NMR (400 MHz, CD$_3$OD): δ 8.39 (d, J=6.0 Hz, 1H), 7.83-7.79 (m, 2H), 7.57-7.53 (m, 1H), 7.49-7.45 (m, 2H), 7.37-7.25 (m, 10H), 5.45 (s, 1H), 4.53 (s, 1H), 4.20-4.15 (m, 2H), 2.50 (s, 1H), 1.99-1.50 (m, 6H).

MS m/z (ESI): 468.8 [M+H]$^+$.

Example 13: preparation of (1S,3S,4R)-5-((4,4-dimethylpenta-2-alkyne-1-yl)(methyl)amino)-2-(2,2-diphenyl)-2-azabicyclo[2.2.2]octane-3-carboxylic acid (C298)

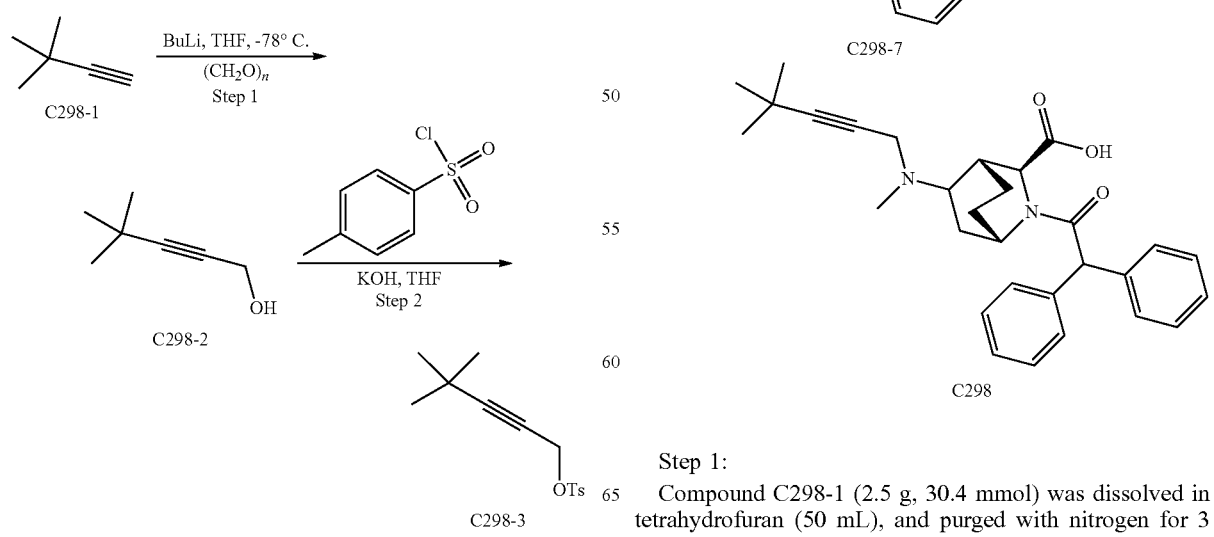

Step 1:

Compound C298-1 (2.5 g, 30.4 mmol) was dissolved in tetrahydrofuran (50 mL), and purged with nitrogen for 3 times. After that, the reaction solution was cooled to −78° C.

under nitrogen protection, n-butyllithium was added dropwise (18 ml, 30.4 mmol) and reacted for 2 hours at a temperature not higher than −30° C. After cooling to −78° C. again, paraformaldehyde (1.1 g, 36.7 mmol) was added. After 16 hours of reaction, the reaction was quenched with saturated aqueous ammonium chloride solution (50 ml) and extracted with ethyl acetate (100 mL×3). The combined organic phases were dried with anhydrous sodium sulfate (100 g) for 30 min, then filtered and concentrated under reduced pressure to obtain Compound C298-2 (2.4 g, a yellow oily liquid, yield: 70.59%).

$^1$H NMR (400 MHz, DMSO-$d_6$): δ 5.02 (t, J=6.0 Hz, 1H), 4.01 (d, J=4.0 Hz, 2H), 1.18 (s, 9H).

Step 2:

Compound C298-2 (2.0 g, 17.8 mmol) was dissolved in tetrahydrofuran (50 mL). Tosyl chloride (6.8 g, 35.6 mmol) and potassium hydroxide (3.0 g, 53.4 mmol) were added and allowed to react at room temperature for 16 hours, and then filtered. The filtrate was concentrated under reduced pressure to obtain a crude product. The crude product was dissolved in ethyl acetate (100 ml), and washed with saturated brine (100 ml×2). The combined organic phases were dried with anhydrous sodium sulfate (50 g) for 30 min, and then filtered. The filtrate was concentrated under reduced pressure to obtain Compound C298-3 (1 g, an orange oily liquid, yield: 43.5%).

MS m/z (ESI): 267.1 [M+H]$^+$.

Step 3:

Compound C298-4 (400 mg, 0.83 mmol) was dissolved in dry dichloromethane (40 mL). An aqueous formaldehyde solution (2 ml) and acetic acid (1 mL) were added, and stirred at room temperature for 4 hours. After that, sodium triacetoxyborohydride (703.6 mg, 3.32 mmol) was added, and stirring was continued for 16 hours. LC-MS indicated that the reaction of the starting materials was complete. It was then washed with saturated brine (20 ml×3), dried over anhydrous sodium sulfate (10 g) for 30 min, filtered and then concentrated to obtain a crude product. The crude product was subjected to separation by column chromatography (petroleum ether:ethyl acetate=1:1) to obtain Compound C298-5 (200 mg, a light yellow oily liquid, yield: 48.66%).

MS m/z (ESI): 497.1[M+H]$^+$.

Step 4:

Compound C298-5 (200 mg, 0.4 mmol) was dissolved in isopropyl alcohol (50 mL), and palladium hydroxide/carbon (50 mg) was added. It was purged with hydrogen for 3 times, and stirred at room temperature for 4 hours. LC-MS indicated that the reaction of starting materials was complete. It was then filtered, and the filtrate was concentrated to obtain Compound C298-6 (60 mg, a light yellow oily liquid, yield 36.8%).

MS m/z (ESI): 407.2 [M+H]$^+$.

Step 5:

Compound C298-6 (60 mg, 0.15 mmol) was dissolved in tetrahydrofuran (20 mL), and anhydrous potassium carbonate (61.2 mg, 0.44 mmol) and C298-3 (80 mg, 0.3 mmol) were added. After stirring for 8 hours at room temperature, LC-MS indicated that a product was produced. It was filtered, and the filtrate was concentrated. The residue was subjected to separation by preparative high performance liquid chromatography, and lyophilized to obtain Compound C298-7 (8 mg, a white solid, yield: 11.0%).

MS m/z (ESI): 501.1 [M+H]$^+$.

Step 6:

Compound C298-7 (8 mg, 0.016 mmol) was dissolved in methanol (10 mL), and water (3 mL), sodium hydroxide (5.12 mg, 0.13 mmol) were added and stirred at 50° C. for 16 hours. The reaction solution was concentrated, subjected to separation by preparative high performance liquid chromatography (water:acetonitrile=60:40), and lyophilized to obtain Compound C298 (4.4 mg, a white solid, yield: 58.3%).

$^1$H NMR (400 MHz, CD$_3$OD): δ 7.29 (m, 10H), 5.40 (s, 1H), 4.41 (s, 1H), 4.10 (s, 1H), 3.80 (d, J=16.8 Hz, 1H), 3.59 (d, J=17.1 Hz, 1H), 2.90 (s, 1H), 2.50 (s, 3H), 2.07-2.01 (m, 2H), 1.86-1.83 (m, 2H), 1.43 (m, 2H), 1.30-1.18 (m, 9H).

MS m/z (ESI): 473.1 [M+H]$^+$.

Example 14: preparation of (1S,3S,4R)-2-(2,2-diphenylacetyl)-5-((3-(4-fluorophenyl)prop-2-yn-1-yl)(methyl)amino)-2-azabicyclo[2.2.2]octane-3-carboxylic acid (C299)

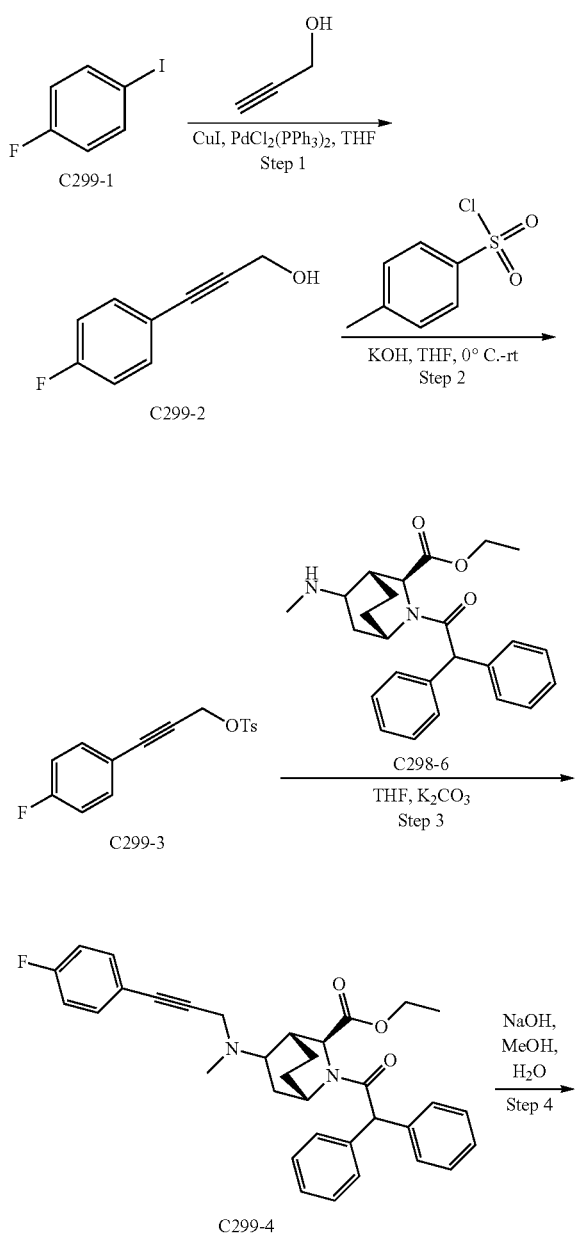

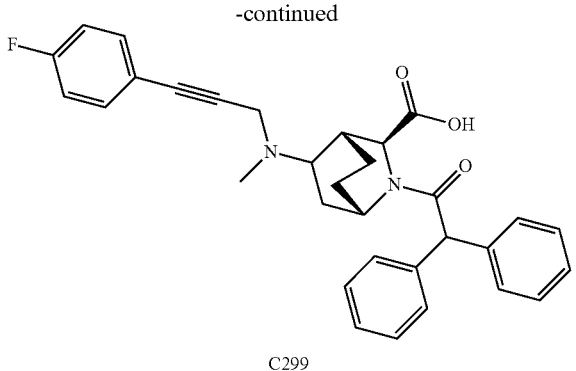

C299

Step 1:

Compound C299-1 (1.0 g, 4.5 mmol) was dissolved in tetrahydrofuran (50 mL), and Copper iodide (85.7 mg, 0.45 mmol), bis(triphenylphosphine)palladium dichloride (315.9 mg, 0.45 mmol) and propynol (378.4 mg, 6.75 mmol) were added, purged with nitrogen for 3 times, and stirred at room temperature for 16 hours under nitrogen protection. Water (50 mL) was added and extracted with ethyl acetate (50 mL×3). The combined organic phases were washed with saturated brine (20 mL×2), dried with anhydrous sodium sulfate (30 g) for 30 min and then filtered. The filtrate was concentrated under reduced pressure, and subjected to separation by column chromatography (petroleum ether:ethyl acetate=70:30) to obtain Compound C299-2 (642 mg, a yellow oily liquid, yield: 95.0%).

$^1$H NMR (400 MHz, CDCl$_3$): δ 7.43 (dd, J=5.6, 8.4 Hz, 2H), 7.05-6.95 (m, 2H), 4.51 (s, 2H).

Step 2:

Compound C299-2 (642 mg, 4.27 mmol) was dissolved in tetrahydrofuran (50 mL), and tosyl chloride (1.63 g, 8.55 mmol) and potassium hydroxide (956.5 mg, 17.8 mmol) were added. The reaction was carried out at room temperature for 16 hours, and then filtered. The filtrate was concentrated under reduced pressure to obtain a crude product. The crude product was dissolved in ethyl acetate (100 ml). The organic phase was washed with saturated brine (100 ml×2), dried with anhydrous sodium sulfate (50 g) for 30 min and then filtered. The filtrate was concentrated under reduced pressure to obtain Compound C299-3 (360 mg, an orange oily liquid, yield: 27.7%).

MS m/z (ESI): 305.3 [M+H]$^+$.

Step 3:

Compound C298-6 (100 mg, 0.25 mmol) prepared according to Step 3 and Step 4 of Example 10 was dissolved in tetrahydrofuran (20 mL), and anhydrous potassium carbonate (101.8 mg, 0.74 mmol) and C299-3 (115 mg, 0.37 mmol) were added and stirred for 8 hours at room temperature. LC-MS indicated that a product is produced. After filtration, the filtrate was concentrated and subjected to separation by column chromatography (petroleum ether:ethyl acetate=60:40) to obtain Compound C299-4 (28 mg, a transparency liquid, yield: 21.2%).

MS m/z (ESI): 538.9 [M+H]$^+$.

Step 4:

Compound C299-4 (28 mg, 0.052 mmol) was dissolved in methanol (10 mL), and water (3 mL) and sodium hydroxide (5.12 mg, 0.13 mmol) were added and stirred at 50° C. for 16 hours. The reaction solution was concentrated and subjected to separation by preparative high performance liquid chromatography (water:acetonitrile=60:40), and then lyophilized to obtain Compound C299 (6.5 mg, a white solid, yield: 25.0%).

$^1$H NMR (400 MHz, CD$_3$OD): δ 8.00 (s, 1H), 7.63-7.54 (m, 2H), 7.36-7.14 (m, 12H), 5.46 (s, 1H), 4.50 (s, 1H), 4.30-4.24 (m, 1H), 3.51 (s, 1H), 3.01 (s, 2H), 2.95 (s, 2H), 2.88 (s, 2H), 2.23-2.21 (m, 1H), 1.96-1.87 (m, 2H), 1.77-1.71 (m, 2H), 1.60-1.46 (m, 2H).

MS m/z (ESI): 510.9 [M+H]$^+$.

Example 15: preparation of (1R,2S,5S)-2-((N,N-dimethylsulphamoyl)carbamoyl)-3-(2,2-diphenyl acetyl)-3,8-diazabicyclo[3.2.1]octane-8-carboxylic acid (C233)

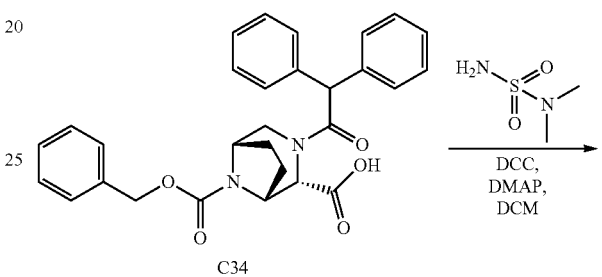

C34 lp;1p

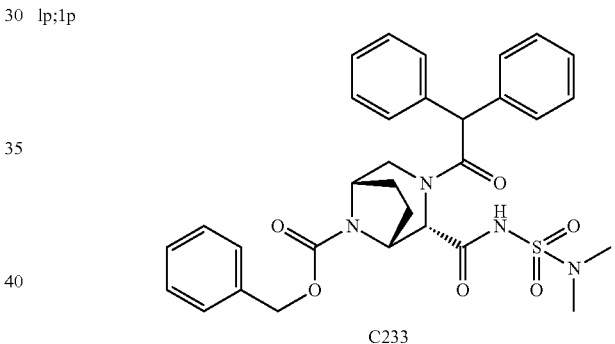

C233

Compound C34 (130 mg, 0.26 mmol) was dissolved in a dichloromethane solution (20 mL). N,N-dimethylsulfamoylamide (49 mg, 0.4 mmol), DCC (82 mg, 0.4 mmol) and DMAP (15 mg, 0.13 mmol) were added to the solution sequentially, and reacted at room temperature for 16 hours. After the reaction was complete, 20 mL water was added to the reaction solution and extracted with dichloromethane (20 mL×2). The organic phases were combined, dried with anhydrous sodium sulfate (10 g) for 30 min, filtered, and concentrated under reduced pressure to obtain a crude product. The crude product was purified by preparative high-performance liquid chromatography (acetonitrile/water (0.1% trifluoroacetic acid solution), 50/50 to 90/10) to obtain Compound C233 (50 mg, a light yellow solid, yield: 32%).

$^1$H NMR (400 MHz, DMSO-d$_6$) δ 11.71 (brs, 1H), 7.49-7.11 (m, 15H), 5.52 (s, 1H), 5.20-5.05 (m, 1H), 5.02-4.80 (m, 1H), 4.66 (s, 2H), 4.23 (s, 1H), 3.80-3.65 (m, 1H), 3.47-3.42 (m, 1H), 2.75 (s, 6H), 1.95-1.80 (m, 1H), 1.72-1.60 (m, 1H), 1.55-1.40 (m, 1H), 1.25-1.05 (m, 1H).

MS m/z (ESI): 591.0 [M+H]$^+$.

Example 16: preparation of (1R,2S,5S)-8-((4-allyl-benzyl)(methyl)carbamoyl)-3-(diphenylcarbamoyl)-3,8-diazabicyclo[3.2.1]octane-2-carboxylic acid (C235) and (1R,2S,5S)-3-(diphenylcarbamoyl)-8-(methyl(4-propylbenzyl)carbamoyl)-3,8-diazabicyclo[3.2.1]octane-2-carboxylic acid (C236)

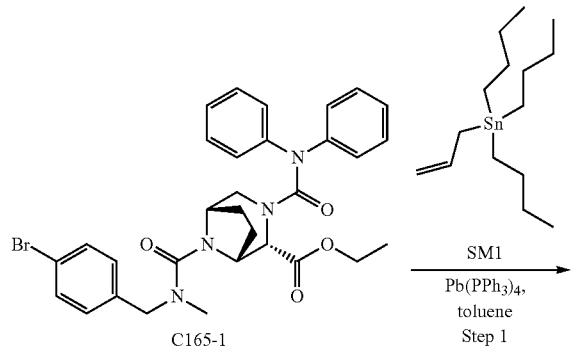

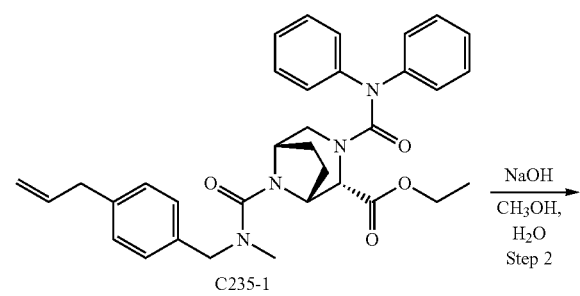

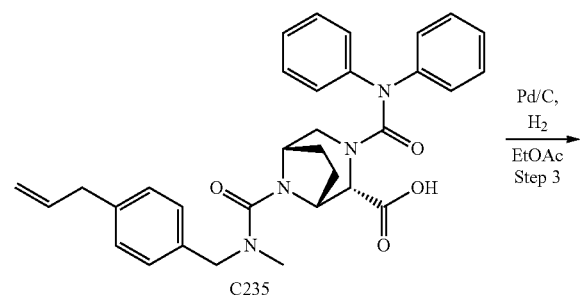

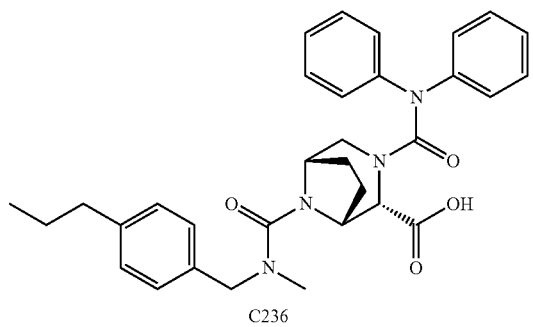

Step 1:

Compound C165-1 (121 mg, 0.13 mmol) was dissolved in dry toluene (20 mL). SM1 (100 mg, 0.3 mmol) and tetrakis(triphenylphosphine)palladium (26 mg, 0.02 mmol) were sequentially added and allowed to react at 100° C. for 16 horns under nitrogen protection. LC-MS indicated that the reaction of the starting materials was complete. The reaction solution was concentrated under reduced pressure to evaporate off toluene, then dissolved in ethyl acetate (30 mL) and washed once with saturated brine (30 mL). After that, the organic phase was dried over anhydrous sodium sulfate (20 g) for half an horn, filtered, and concentrated. The resulting crude product was subjected to separation by preparative plate chromatography (ethyl acetate:petroleum ether=1:2) to obtain Compound C235-1 (70 mg, a white solid, yield: 61%).

MS m/z (ESI): 566.8 [M+H]$^+$.

Step 2:

Compound C235-1 (70 mg, 0.13 mmol) was dissolved in dry methanol (30 mL) and water (10 mL), and sodium hydroxide (21 mg, 0.52 mmol) was added. The reaction solution was allowed to react at 40° C. for 16 horns. LC-MS indicated that the reaction of starting materials was complete. The reaction solution was concentrated under reduced pressure to remove the solvent, dissolved in water (30 mL) and adjusted to pH=4 to 5 with 2N HCl solution, leading to a white precipitate. The reaction solution was filtered, and the white solid was rinsed with water (10 mL). After that, it was concentrated under reduced pressure, and the white solid was dried by rotary vaporization to remove water therein, obtaining compound C235 (60 mg, a white solid, yield: 90%).

$^1$H NMR (400 MHz, DMSO-d$_6$) δ 12.98 (s, 1H), 7.38-7.32 (m, 4H), 7.19-7.11 (m, 6H), 7.04-6.96 (m, 4H), 5.95 (s, 1H), 5.12-4.98 (m, 2H), 4.43-4.19 (m, 4H), 3.91 (s, 1H), 3.46-3.34 (m, 4H), 2.68 (s, 3H), 1.78-1.22 (m, 4H).

MS m/z (ESI): 538.8 [M+H]$^+$.

Step 3:

Compound C235 (53 mg, 0.1 mmol) was dissolved in ethyl acetate (20 mL). Pd/C catalyst (10 mg) was added, and the reaction was carried out at room temperature under the protection of H$_2$ for 0.5 hour. LC-MS indicated that the reaction of the starting materials was complete. The reaction solution was filtered, concentrated to obtain Compound C236 (30 mg, a white solid, yield: 57%).

$^1$H NMR (400 MHz, DMSO-cfc) δ 13.02 (s, 1H), 7.37-7.31 (m, 4H), 7.18-7.12 (m, 6H), 7.04-6.96 (m, 4H), 4.40-4.20 (m, 3H), 3.91 (s, 1H), 3.46-3.34 (m, 3H), 2.68 (s, 3H), 2.56-2.52 (m, 2H), 1.78-1.22 (m, 6H), 0.88 (t, J=7.2 Hz, 3H).

MS m/z (ESI): 540.8 [M+H]$^+$.

The compounds in Table 10 were prepared by methods similar to that described in Example 16.

TABLE 10

| No. | Compound Structure | Compound Name | Starting material or reagent different from that in Example 16 | Characterization data |
|---|---|---|---|---|
| C170 | 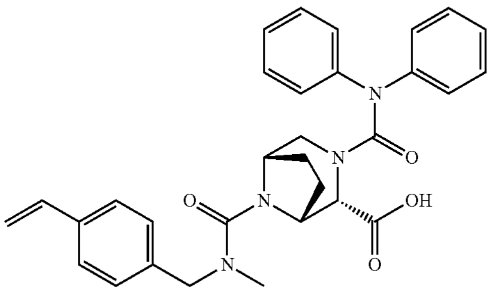 [SMILES: C=Cc1ccc(CN(C)C(=O)N2[C@H]3CC[C@@H]2[C@@H](C(=O)O)N(C(=O)N(c2ccccc2)c2ccccc2)C3)cc1] | (1R,2S,5S)-3-(diphenylcarbamoyl)-8-(methyl(4-vinylbenzyl)carbamoyl)-3,8-diazabicyclo[3.2.1]octane-2-carboxylic acid | SMI in step 1 was replaced with tributyl(vinyl)stannane. The reaction in step 3 did not take place. | $^1$H NMR (400 MHz, DMSO-$d_6$) δ 12.98 (s, 1H), 7.45-7.32 (m, 6H), 7.22-7.14 (m, 4H), 7.06-6.98 (m, 4H), 6.72 (dd, J = 17.6, 11.0 Hz, 1H), 5.81 (d, J = 17.6 Hz, 1H), 5.24 (d, J = 10.8 Hz, 1H), 4.46-4.20 (m 4H), 3.92 (s, 1H), 3.39 (dd, J = 26.1, 11.8 Hz, 2H), 2.70 (s, 3H), 1.77-1.27 (m, 4H).<br>MS m/z (ESI): 524.8 [M + H]$^+$. |
| C164 | 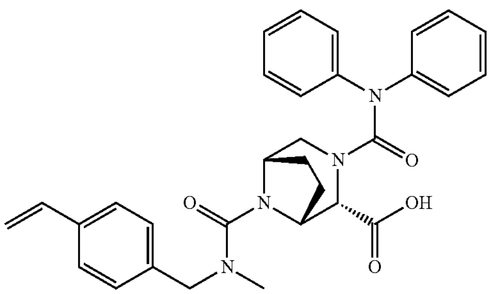 [SMILES: C=Cc1ccc(CN(C)C(=O)N2[C@H]3CC[C@@H]2[C@@H](C(=O)O)N(C(=O)N(c2ccccc2)c2ccccc2)C3)cc1] | (1R,2S,5S)-3-(diphenylcarbamoyl)-8-((4-ethylbenzyl)(methyl)carbamoyl)-3,8-diazabicyclo[3.2.1]octane-2-carboxylic acid | SMI in step 1 was replaced with tributyl(vinyl)stannane. | $^1$H NMR (400 MHz, DMSO-$d_6$) δ 13.00 (s, 1H), 7.38-7.34 (m, 4H), 7.18-7.08 (m, 6H), 7.04-6.96 (m, 4H), 4.44-4.18 (m, 4H), 3.91 (s, 1H), 3.49-3.36 (m, 2H), 2.68 (s, 3H), 2.58 (dd, J = 15.0, 7.5 Hz, 2H), 1.74-1.24 (m, 4H), 1.17 (t, J = 7.5 Hz, 3H).<br>MS m/z (ESI): 526.8 [M + H]$^+$. |

Biological Assay

Measurement of Inhibitory Activity on $AT_1$ Receptor ($AT_1R$)/$AT_2$ Receptor ($AT_2R$)

Through the following steps, the inhibitory activity of the compound on $AT_1R$/$AT_2R$ ($IC_{50}$ value) was determined:

1) An appropriate amount of 1×TLB (Tag-lite Buffer) was prepared and well mixed for use.

2) The compound was diluted by 10 times with ddH$_2$O or DMSO. The compound was then dilute to 4 times of the working concentration with 1×TLB and mixed well for use.

3) 8600 nM Tag-lite angiotensin receptor red agonist was diluted to 12 nM (4×Kd) with 1×TLB.

4) 5 ml 1×TLB was taken into a 15 ml centrifuge tube.

5) After thawing 1 tube of Tb-labeled $AT_1R$/$AT_2R$ cells in a 37° C. water bath, the cells were quickly transferred to the 1×TLB in step 4), mixed gently, and centrifuged at 1200 g for 5 minutes at room temperature.

6) The supernatant was aspirated gently, and the cells were resuspended and mixed in 2.7 ml 1×TLB, and then placed at room temperature until use.

7) 10 μl cells were added to all test wells, and 5 μl 4× working solution of the compound from step 2) was added to the corresponding test wells. 5 μl 4× Tag-lite angiotensin receptor red agonist well diluted in step 3) was added to all test wells.

8) After leaving the reaction plate at room temperature for 1 h, data were measured and analyzed using Envision HTRF Reader, and the half inhibitory concentration ($IC_{50}$) of the compound on $AT_1R$/$AT_2R$ was calculated with the GraphPad Prism four-parameter equation.

The measured $IC_{50}$ values of the compounds are shown in Table 11 below.

TABLE 11

| No. | $AT_2R$ $IC_{50}$ (nM) | $AT_1R$ $IC_{50}$ (nM) |
|---|---|---|
| C1 | 6.67 | >10000 |
| C2 | 9.11 | NA |
| C3 | 13.86 | NA |
| C4 | 9.82 | NA |
| C5 | 15.26 | >10000 |
| C7 | 82.71 | NA |
| C9 | 107.4 | NA |
| C10 | 58.77 | >10000 |
| C12 | 17.11 | >10000 |
| C13 | 22.25 | NA |
| C14 | 29.39 | >10000 |
| C28 | 473.30 | NA |
| C34 | 35.19 | >10000 |
| C35 | 36.60 | NA |
| C36 | 20.66 | NA |
| C37 | 55.33 | >10000 |
| C41 | 9.765 | NA |
| C45 | 84.69 | NA |
| C62 | 104.00 | NA |
| C68 | 58.12 | >10000 |
| C69 | 169.80 | NA |
| C71 | 50.44 | >10000 |
| C72 | 19.07 | NA |
| C75 | 54.03 | NA |
| C76 | 69.65 | NA |
| C78 | 55.01 | >10000 |
| C79 | 24.63 | >10000 |
| C82 | 3.98 | >10000 |
| C83 | 18.10 | >10000 |
| C112 | 21.51 | >10000 |
| C113 | 12.1 | NA |
| C114 | 26.39 | NA |
| C115 | 431.1 | NA |
| C117 | 61.26 | NA |
| C120 | 349.90 | NA |
| C123 | 11.73 | >10000 |
| C124 | 37.83 | NA |
| C125 | 19.00 | NA |
| C126 | 78.03 | NA |
| C128 | 21.46 | NA |

TABLE 11-continued

| No. | AT$_2$R IC$_{50}$ (nM) | AT$_1$R IC$_{50}$ (nM) |
|---|---|---|
| C129 | 147.80 | NA |
| C131 | 495.10 | NA |
| C132 | 481.50 | NA |
| C133 | 243.2 | NA |
| C134 | 322.10 | NA |
| C138 | 11.66 | NA |
| C140 | 5.49 | NA |
| C141 | 7.99 | NA |
| C142 | 653.5 | NA |
| C143 | 9.97 | NA |
| C144 | 21.57 | NA |
| C145 | 110.00 | NA |
| C146 | 14.04 | NA |
| C147 | 111.10 | NA |
| C148 | 7.26 | NA |
| C149 | 16.58 | >10000 |
| C150 | 9.82 | >10000 |
| C151 | 74.32 | NA |
| C152 | 47.37 | NA |
| C153 | 2.78 | NA |
| C154 | 19.83 | NA |
| C155 | 9.03 | >10000 |
| C156 | 10.14 | NA |
| C157 | 27.06 | >10000 |
| C161 | 30.49 | NA |
| C162 | 4.04 | >10000 |
| C163 | 65.60 | NA |
| C164 | 4.35 | NA |
| C165 | 14.00 | NA |
| C166 | 4.42 | >10000 |
| C167 | 18.9 | >10000 |
| C169 | 7.26 | NA |
| C170 | 3.87 | NA |
| C171 | 19.16 | NA |
| C173 | 5.57 | NA |
| C174 | 225.7 | NA |
| C182 | 431.9 | NA |
| C184 | 41.67 | NA |
| C185 | 38.75 | NA |
| C186 | 64.56 | NA |
| C187 | 3.75 | NA |
| C188 | 7.11 | NA |
| C189 | 4.04 | NA |
| C194 | 129.20 | NA |
| C196 | 1.63 | NA |
| C197 | 5.52 | NA |
| C198 | 10.19 | NA |
| C200 | 3.25 | NA |
| C201 | 18.43 | NA |
| C202 | 3.866 | NA |
| C203 | 13.68 | NA |
| C204 | 4.931 | NA |
| C205 | 42.84 | NA |
| C206 | 10.08 | NA |
| C207 | 10.36 | NA |
| C208 | 11.84 | NA |
| C209 | 81.39 | NA |
| C210 | 49.55 | NA |
| C212 | 9.038 | NA |
| C213 | 5.92 | NA |
| C214 | 11.33 | NA |
| C215 | 26.47 | NA |
| C216 | 3.22 | NA |
| C217 | 9.13 | NA |
| C218 | 11.48 | NA |
| C219 | 19.79 | NA |
| C220 | 12.49 | NA |
| C221 | 76.67 | NA |
| C222 | 11.67 | NA |
| C223 | 7.87 | NA |
| C224 | 23.84 | NA |
| C225 | 11.68 | NA |
| C226 | 12.67 | NA |
| C227 | 18.27 | NA |
| C229 | 10.07 | NA |
| C230 | 50.24 | NA |
| C231 | 103.2 | NA |
| C233 | 102.50 | NA |
| C235 | 6.78 | NA |
| C236 | 6.13 | NA |
| C237 | 37.60 | NA |
| C239 | 160.8 | NA |
| C240 | 113.30 | NA |
| C241 | 155.50 | NA |
| C245 | 10.52 | NA |
| C246 | 10.05 | NA |
| C249 | 10.88 | NA |
| C252 | 16.18 | NA |
| C255 | 13.77 | NA |
| C256 | 39.97 | NA |
| C259 | 244.80 | NA |
| C260 | 29.59 | NA |
| C265 | 27.25 | NA |
| C266 | 1.63 | NA |
| C269 | 68.22 | NA |
| C271 | 14.53 | NA |
| C272 | 16.60 | NA |
| C273 | 20.93 | NA |
| C274 | 19.77 | NA |
| C277 | 10.46 | NA |
| C278 | 10.56 | NA |
| C279 | 24.19 | NA |
| C281 | 20.29 | NA |
| C283 | 46.30 | >10000 |
| C286 | 760.20 | NA |
| C290 | 560.90 | NA |
| C291 | 765.20 | NA |
| C294 | 665.90 | NA |

Note:
NA means Not Assayed.

Various modifications of the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A compound or a pharmaceutically acceptable salt, stereoisomer, or N-oxide thereof, wherein the compound has a structure of formula (IV):

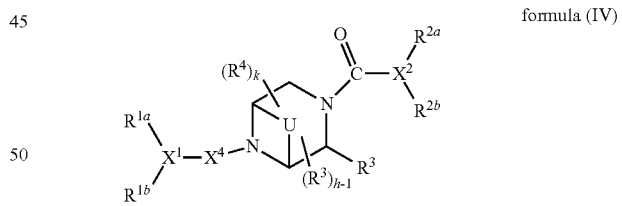

formula (IV)

wherein:
U is $C_{1-3}$ alkylene;
$R^{1a}$ is selected from the group consisting of $C_{2-8}$ alkenyl and $C_{2-8}$ alkynyl, each of which is substituted by one $C_{6-10}$ aryl or 5- to 14-membered heteroaryl; $C_{6-10}$ aryl; —$C_{1-6}$ alkylene-saturated or partially unsaturated $C_{3-10}$ cyclic hydrocarbyl group; —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);
$R^{1b}$ does not exist, or is selected from the group consisting of H, $C_{1-8}$ alkyl optionally substituted by 1, 2, 3 or more $R^{13}$; a saturated or partially unsaturated $C_{3-10}$ cyclic hydrocarbyl group; $C_{6-10}$ aryl; —$C_{1-6}$ alkylene-saturated or partially unsaturated $C_{3-10}$ cyclic hydrocarbyl group; and —$C_{1-6}$ alkylene-$C_{6-10}$ aryl;

$X^1$ does not exist, or is $CR^{10}$ or N;

$X^4$ is selected from the group consisting of C(=O); and —OC(=O)— and —SC(=O)—, wherein O and S are connected to $X^1$;

$R^{2a}$ is $C_{6-10}$ aryl;

$R^{2b}$ is $C_{6-10}$ aryl;

$X^2$ is $CR^{10}$ or N;

$R^3$ is —C(=O)$R^{11}$;

$R^4$ is H;

$R^{10}$, at each occurrence, is selected from the group consisting of H, —$OR^{11}$, —$SR^{11}$, and $C_{1-6}$ alkyl;

$R^{11}$ and $R^{12}$, at each occurrence, are each independently H, or $C_{1-6}$ alkyl;

h and k are each independently 1;

the above alkylene, cyclic hydrocarbyl group, heterocyclic group, aryl, and heteroaryl, at each occurrence, are each optionally substituted by 1, 2, 3 or more $R^{13}$;

wherein the $R^{13}$, at each occurrence, is independently selected from the group consisting of halogen, cyano, nitro, $C_{1-6}$ alkyl, $C_{2-6}$ alkenyl, $C_{2-6}$ alkynyl, $C_{3-10}$ cyclic hydrocarbyl group, $C_{6-10}$ aryl, 5- to 14-membered heteroaryl, —$OR^1$, —$SR^{11}$, —$P(O)R^{11}R^{12}$, and —$NR^{11}R^{12}$, and wherein the alkyl, alkylene, aryl, and heteroaryl recited for the substituent $R^{13}$ are optionally further substituted by 1, 2, 3 or more substituents independently selected from halogen and $C_{1-6}$ alkyl.

2. The compound according to claim 1, or a pharmaceutically acceptable salt, stereoisomer, or N-oxide thereof, wherein:

$R^{13}$, at each occurrence, is independently selected from the group consisting of halogen, cyano, nitro, $C_{1-6}$ alkyl, $C_{3-7}$ cyclic hydrocarbyl group, $C_{6-10}$ aryl, 5- to 14-membered heteroaryl, —$OR^1$, —$SR^{11}$, and —$NR^{11}R^{12}$, and wherein the alkyl, aryl, and heteroaryl recited for the substituent $R^{13}$ are optionally further substituted by 1, 2, 3 or more substituents independently selected from halogen and $C_{1-6}$ alkyl.

3. The compound according to claim 1, or a pharmaceutically acceptable salt, stereoisomer, or N-oxide thereof, wherein U is methylene or ethylene.

4. The compound according to claim 1, or a pharmaceutically acceptable salt, stereoisomer, or N-oxide thereof, wherein $R^3$ is —C(=O)OH.

5. The compound according to claim 1, or a pharmaceutically acceptable salt, stereoisomer, or N-oxide thereof, wherein $R^{10}$, at each occurrence, is each independently H, $C_{1-4}$ alkyl, —OH, or —SH.

6. The compound according to claim 1, or a pharmaceutically acceptable salt, stereoisomer, or N-oxide thereof, wherein $R^{11}$ and $R^{12}$ at each occurrence are each independently selected from the group consisting of H, and $C_{1-4}$ alkyl.

7. The compound according to claim 1, or a pharmaceutically acceptable salt, stereoisomer, or N-oxide thereof, wherein $R^{13}$, at each occurrence, is independently selected from the group consisting of F, Cl, Br, I, amino, cyano, nitro; $C_{1-4}$ alkyl optionally further substituted by 1, 2, 3 or more substituents independently selected from halogen; $C_{5-7}$ cyclic hydrocarbyl group; phenyl, 5- to 6-membered heteroaryl and 9- to 10-membered heteroaryl, each optionally further substituted by 1, 2, 3 or more substitutes independently selected from the group consisting of halogen, OH, amino, cyano, and $C_{1-4}$ alkyl; —$OR^{11}$ wherein $R^{11}$ is a $C_{1-6}$ alkyl optionally substituted by 1, 2, 3 or more halogens; —$SR^{11}$ wherein $R^{11}$ is $C_{1-6}$ alkyl optionally substituted by 1, 2, 3 or more halogens; —$NR^{11}R^{12}$ or —$P(O)R^{11}R^{12}$ wherein $R^{11}$ and $R^{12}$, at each occurrence, are each independently a $C_{1-6}$ alkyl optionally substituted by 1, 2, 3 or more halogens.

8. The compound according to claim 1, or a pharmaceutically acceptable salt, stereoisomer, or N-oxide thereof, wherein $R^{13}$, at each occurrence, is independently selected from the group consisting of F, Cl, Br, I, amino, cyano, nitro; $C_{1-4}$ alkyl optionally further substituted by 1, 2 or 3 F or Cl; —$OR^1$ wherein $R^{11}$ is a $C_{1-3}$ alkyl optionally substituted by 1, 2 or 3 F or Cl; —$SR^{11}$ wherein $R^{11}$ is a $C_{1-3}$ alkyl optionally substituted by 1, 2 or 3 F or Cl; —$NR^{11}R^{12}$ or —$P(O)R^{11}R^{12}$ wherein $R^{11}$ and $R^{12}$, at each occurrence, are each independently a $C_{1-3}$ alkyl; $C_{3-7}$ cyclic hydrocarbyl group; phenyl, 5- to 6-membered heteroaryl, and 9- to 10-membered heteroaryl, each optionally further substituted by 1, 2, 3 or more substitutes independently selected from the group consisting of F, Cl, Br, I, and methyl.

9. The compound according to claim 8, or a pharmaceutically acceptable salt, stereoisomer, or N-oxide thereof, wherein the $C_{1-3}$ alkyl is methyl, ethyl, propyl or isopropyl.

10. The compound according to claim 1, or a pharmaceutically acceptable salt, stereoisomer, or N-oxide thereof, wherein:

$R^{1a}$ is selected from the group consisting of $C_{2-6}$ alkenyl, and $C_{2-6}$ alkynyl, each of which is substituted by one phenyl, or 5- to 10-membered heteroaryl; phenyl, —$C_{1-3}$ alkylene-$C_{3-7}$ cyclic hydrocarbyl group, —$C_{1-3}$ alkylene-(5- to 7-membered monocyclic heterocyclic group), —$C_{1-3}$ alkylene-(8- to 10-membered benzo-fused heterocyclic group), —$C_{1-3}$ alkylenephenyl and —$C_{1-3}$ alkylene-(5- to 10-membered heteroaryl); and $R^{1b}$ does not exist or is selected from the group consisting of H; $C_{1-6}$ alkyl; $C_{3-7}$ cyclic hydrocarbyl group; phenyl; —$C_{1-3}$ alkylene-$C_{3-7}$ cyclic hydrocarbyl group; and —$C_{1-3}$ alkylene-phenyl; and the above alkyl, alkylene, cyclic hydrocarbyl group, heterocyclic group, phenyl, and heteroaryl, at each occurrence, are each optionally substituted by 1, 2, 3 or more $R^{13}$ substituents according to claim 1.

11. A compound according to claim 10, or a pharmaceutically acceptable salt, stereoisomer, or N-oxide thereof, wherein $R^{1a}$ is selected from the group consisting of phenyl, —$C_{1-3}$alkylene-$C_{3-7}$ cyclic hydrocarbyl group, —$C_{1-3}$ alkylene-phenyl, —$C_{1-3}$ alkylene-(5- to 7-membered monocyclic heterocyclic group), —$C_{1-3}$ alkylene-(9- to 10-membered benzo-fused heterocyclic group), —$C_{1-3}$ alkylene-(5- to 6-membered heteroaryl) and —$C_{1-3}$ alkylene-(9- to 10-membered heteroaryl), each of which is optionally substituted by 1, 2, 3 or more $R^{13}$ substituents.

12. The compound according to claim 11, or a pharmaceutically acceptable salt, stereoisomer, or N-oxide thereof, wherein $R^{13}$ is selected from the group consisting of $C_{1-4}$ alkyl-O—; halogen; and $C_{1-4}$ alkyl optionally substituted by 1, 2 or 3 substituents independently selected from halogen.

13. The compound according to claim 11, or a pharmaceutically acceptable salt, stereoisomer, or N-oxide thereof, wherein $X^4$ is C(=O).

14. The compound according to claim 10, or a pharmaceutically acceptable salt, stereoisomer, or N-oxide thereof, wherein:

$R^{1a}$ is selected from the group consisting of $C_{2-6}$ alkenyl and $C_{2-6}$ alkynyl, each of which is substituted by one phenyl, 5- to 6-membered heteroaryl or 9- to 10-membered heteroaryl, each of the phenyl, 5- to 6-membered heteroaryl and 9- to 10-membered heteroaryl is optionally substituted by 1, 2 or 3 substituents independently selected from the group consisting of F, Cl, Br, I, and $C_{1-4}$ alkyl;

phenyl optionally substituted by 1, 2 or 3 substituents independently selected from the group consisting of F, Cl, Br, I, and $C_{1-4}$ alkyl; and —$C_{1-3}$ alkylene-phenyl, —$C_{1-3}$ alkylene-(5- to 6-membered heteroaryl), and —$C_{1-3}$ alkylene-(9- to 10-membered heteroaryl), wherein the alkylene, at each occurrence, is optionally substituted by one —$NR^{11}R^{12}$, and each of the phenyl, 5- to 6-membered heteroaryl and 9- to 10-membered heteroaryl is optionally substituted by 1, 2 or 3 substituents independently selected from the group consisting of F, Cl, Br, I, and $C_{1-4}$ alkyl;

$R^{1b}$ does not exist;

$X^1$ does not exist; and $X^4$ is C(=O) or —O—C(=O)—.

15. The compound according to claim 14, or a pharmaceutically acceptable salt, stereoisomer, or N-oxide thereof, wherein the $C_{1-6}$ alkyl is methyl, ethyl, or propyl, isopropyl or tert-butyl.

16. The compound according to claim 14, or a pharmaceutically acceptable salt, stereoisomer, or N-oxide thereof, wherein the $C_{2-6}$ alkenyl is vinyl, 1-propenyl or 2-propenyl.

17. The compound according to claim 14, or a pharmaceutically acceptable salt, stereoisomer, or N-oxide thereof, wherein the $C_{2-6}$ alkynyl is ethynyl, 1-propynyl or 2-propynyl.

18. The compound according to claim 14, or a pharmaceutically acceptable salt, stereoisomer, or N-oxide thereof, wherein $R^{13}$ is a phenyl, pyridyl, indolyl or furyl, which is optionally substituted by 1, 2 or 3 substituents independently selected from the group consisting of F, Cl, Br and methyl.

19. The compound according to claim 18, or a pharmaceutically acceptable salt, stereoisomer, or N-oxide thereof, wherein:

$R^{1a}$ is selected from the group consisting of

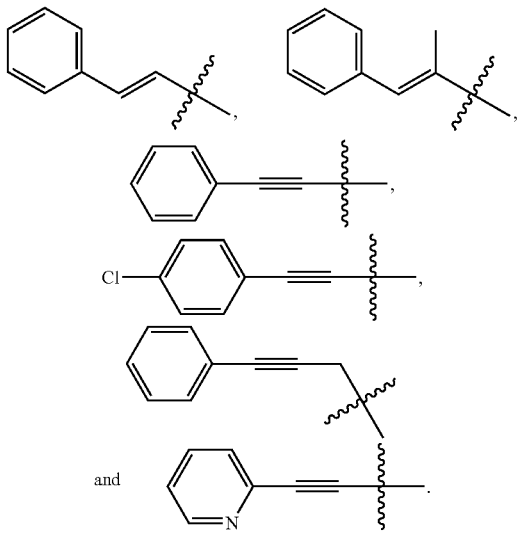

20. The compound according to claim 1, or a pharmaceutically acceptable salt, stereoisomer, or N-oxide thereof, wherein:

$R^{1a}$ is a group selected from the group consisting of an optionally substituted phenyl, -optionally substituted $C_{1-3}$ alkylene-(optionally substituted $C_{3-7}$ cyclic hydrocarbyl group), -optionally substituted $C_{1-3}$ alkylene-(optionally substituted 5- to 7-membered monocyclic heterocyclic group), -optionally substituted $C_{1-3}$ alkylene-(optionally substituted 8- to 10-membered benzo-fused heterocyclic group), -optionally substituted $C_{1-3}$ alkylene-optionally substituted phenyl, and -optionally substituted $C_{1-3}$ alkylene-(optionally substituted 5- to 10-membered heteroaryl);

$R^{1b}$ is selected from the group consisting of H, $C_{1-8}$ alkyl optionally substituted by 1, 2, 3 or more $R^{13}$; a saturated or partially unsaturated $C_{3-10}$ cyclic hydrocarbyl group; $C_{6-10}$ aryl; —$C_{1-6}$ alkylene-saturated or partially unsaturated $C_{3-10}$ cyclic hydrocarbyl group; and —$C_{1-6}$ alkylene-$C_{6-10}$ aryl;

$X^1$ is $CR^{10}$ or N;

$X^4$ is C(=O);

wherein the term "optionally substituted" means being substituted by 1, 2, 3 or more $R^{13}$; and $R^{13}$ is as defined in claim 1.

21. The compound according to claim 20, or a pharmaceutically acceptable salt, stereoisomer, or N-oxide thereof, wherein $R^{1b}$ is a group selected from the group consisting of H, an optionally substituted $C_{1-4}$ alkyl, an optionally substituted $C_{3-7}$ cyclic hydrocarbyl group, an optionally substituted phenyl, -optionally substituted $C_{1-3}$ alkylene-(optionally substituted $C_{3-7}$ cyclic hydrocarbyl group), and -optionally substituted $C_{1-3}$ alkylene-optionally substituted phenyl;

wherein the term "optionally substituted" means being substituted by 1, 2, 3 or more $R^{13}$.

22. The compound according to claim 1, or a pharmaceutically acceptable salt, stereoisomer, or N-oxide thereof, wherein:

$R^{2a}$ is an optionally substituted phenyl; and/or $R^{2b}$ is an optionally substituted phenyl;

wherein the term "optionally substituted" means being substituted by 1, 2, 3 or more $R^{13}$.

23. The compound according to claim 1, or a pharmaceutically acceptable salt, stereoisomer, or N-oxide thereof, wherein the compound has a structure of formula (II):

formula (II)

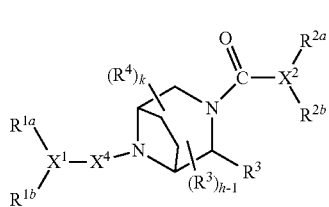

wherein R1a, R1b, X1, X4, R2a, R2b, X2 are as defined in claim 1.

24. The compound according to claim 1, or a pharmaceutically acceptable salt, stereoisomer, or N-oxide thereof, wherein

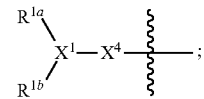

is:
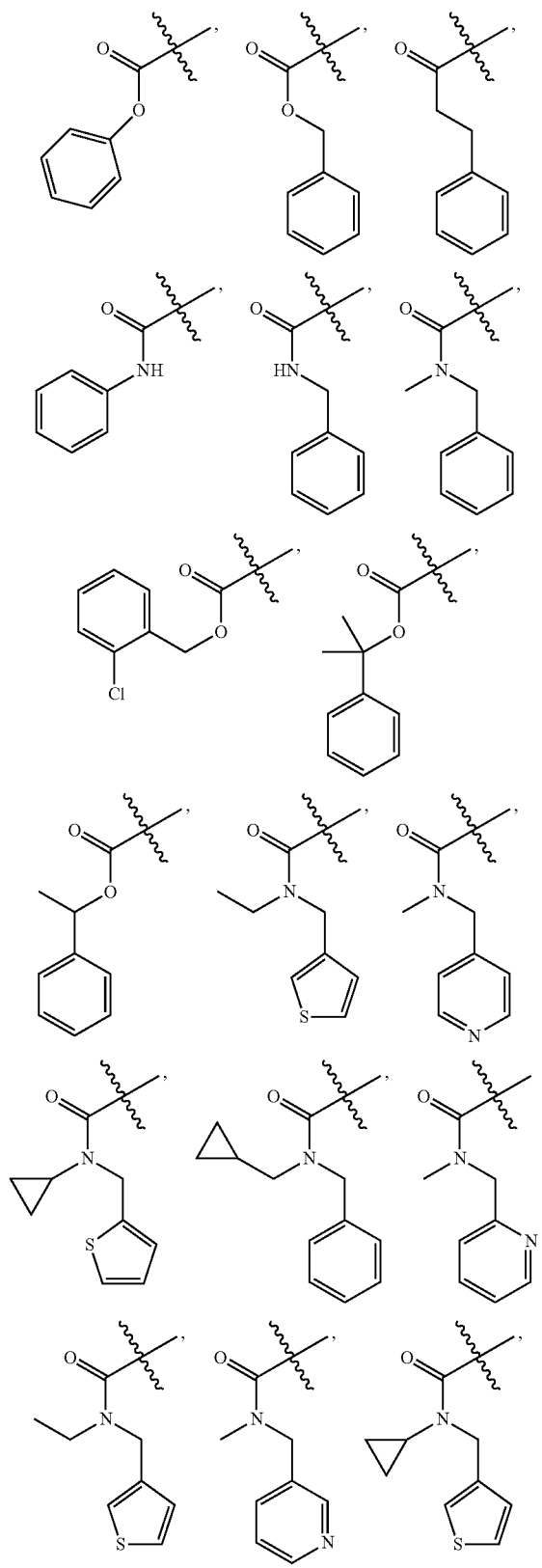
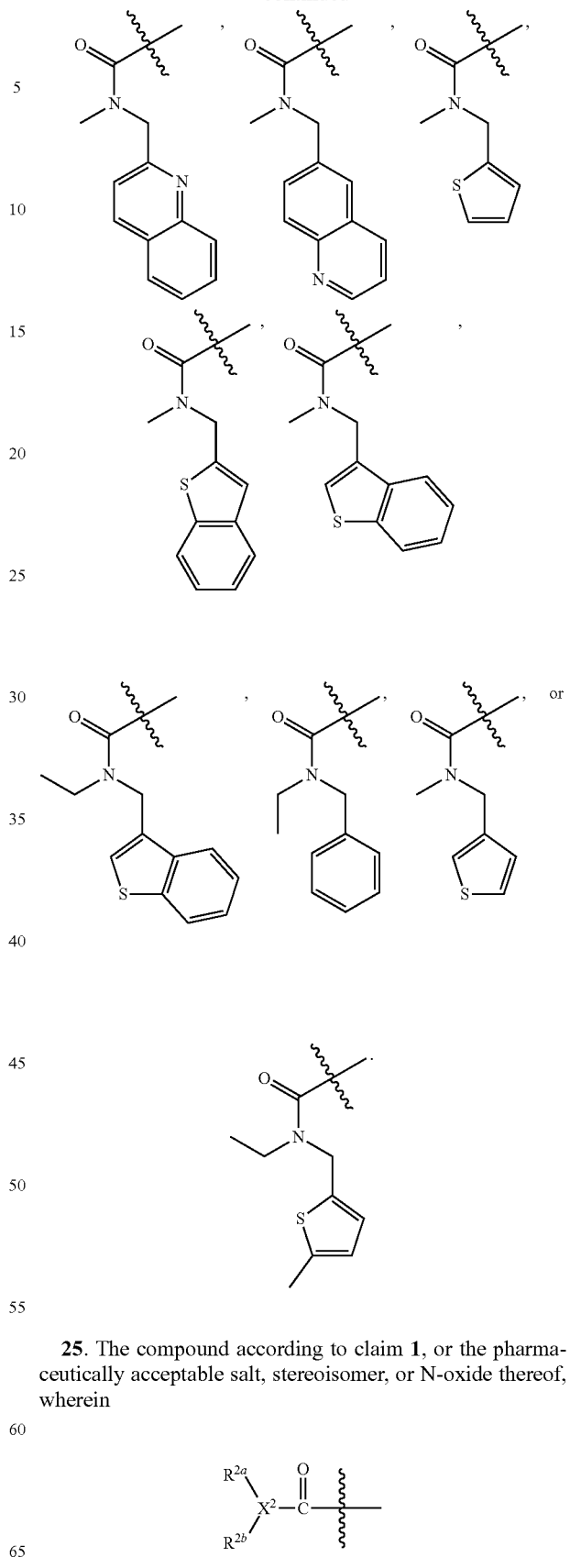
25. The compound according to claim 1, or the pharmaceutically acceptable salt, stereoisomer, or N-oxide thereof, wherein is:
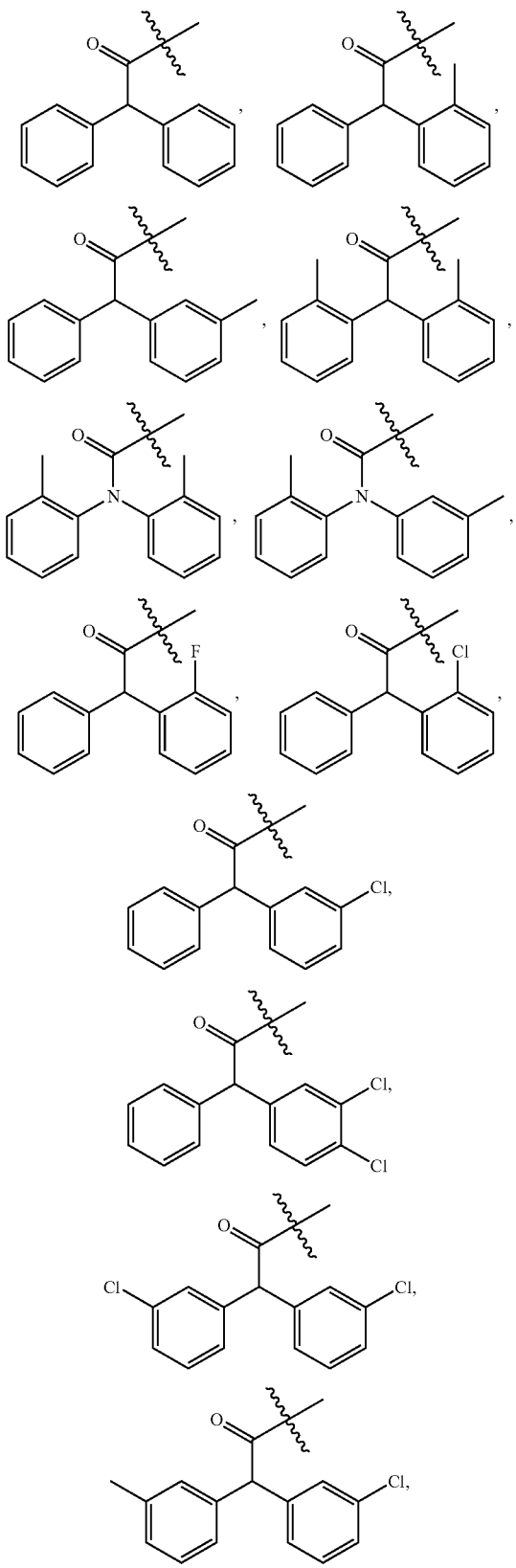
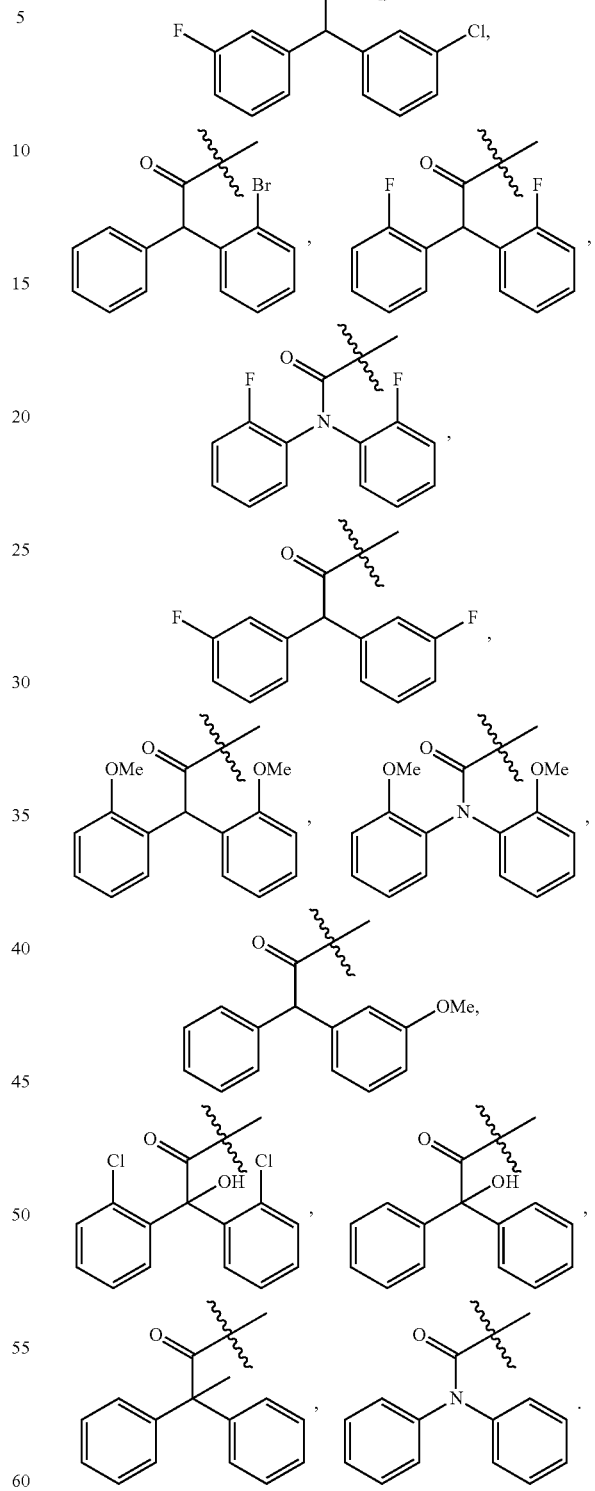
26. A pharmaceutical composition comprising a prophylactically or therapeutically effective amount of a compound according to claim 1 or a pharmaceutically acceptable salt, stereoisomer, or N-oxide thereof, and a pharmaceutically acceptable carrier.

27. A method for the prophylaxis or the treatment of an AT2 receptor-mediated disorder or a symptom associated therewith, comprising administering to a subject in need thereof an effective amount of the compound of claim 1 or a pharmaceutically acceptable salt, stereoisomer, or N-oxide thereof, or a pharmaceutical composition according to claim 26, wherein the AT2 receptor-mediated disorder is peripheral neuropathy, or neuralgia.

28. The compound according to claim 1, or a pharmaceutically acceptable salt, stereoisomer, or N-oxide thereof, wherein the compound has a structure selected from one of the following:

| No. | Structure |
|---|---|
| C34 | 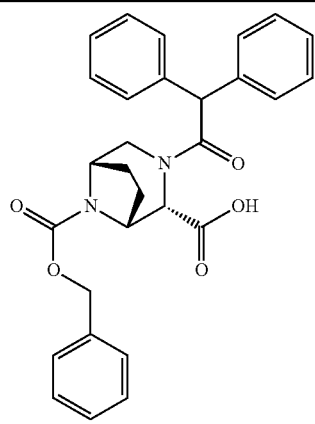 |
| C35 | 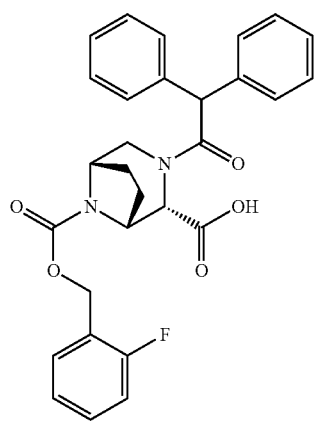 [SMILES: O=C(O)[C@@H]1[C@H]2CC[C@@H](CN1C(=O)C(c1ccccc1)c1ccccc1)N2C(=O)OCc1ccccc1F] |
| C36 | 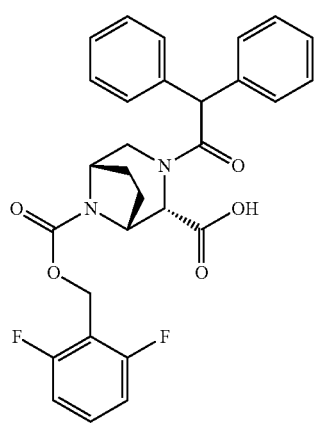 [SMILES: O=C(O)[C@@H]1[C@H]2CC[C@@H](CN1C(=O)C(c1ccccc1)c1ccccc1)N2C(=O)OCc1c(F)cccc1F] |

-continued

| No. | Structure |
|---|---|
| C37 | 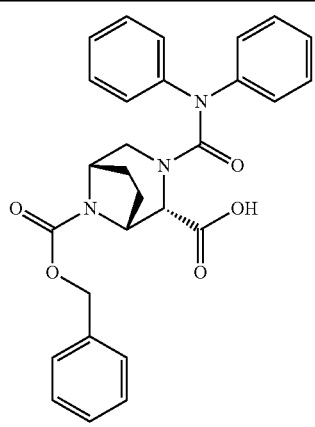 |
| C65 | 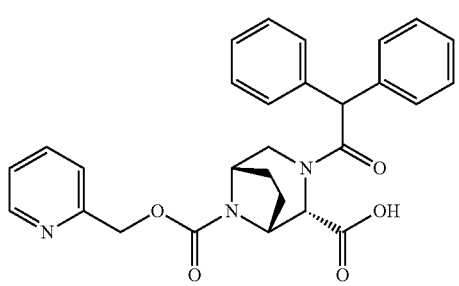 [SMILES: O=C(O)[C@@H]1[C@H]2CC[C@@H](CN1C(=O)C(c1ccccc1)c1ccccc1)N2C(=O)OCc1ccccn1] |
| C66 | 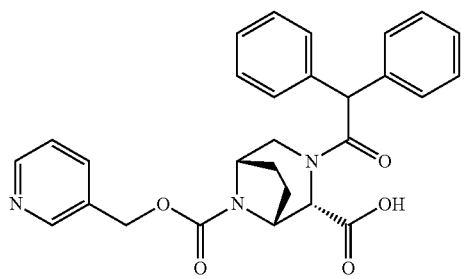 [SMILES: O=C(O)[C@@H]1[C@H]2CC[C@@H](CN1C(=O)C(c1ccccc1)c1ccccc1)N2C(=O)OCc1cccnc1] |
| C67 | 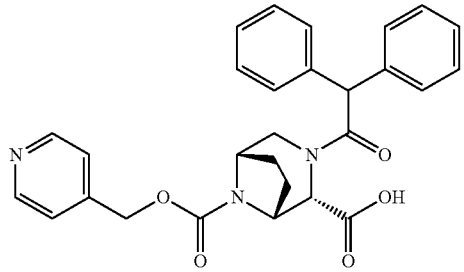 [SMILES: O=C(O)[C@@H]1[C@H]2CC[C@@H](CN1C(=O)C(c1ccccc1)c1ccccc1)N2C(=O)OCc1ccncc1] |
| C76 | 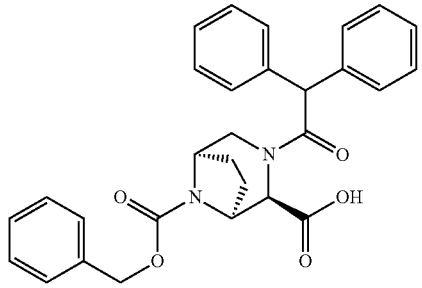 [SMILES: O=C(O)[C@H]1[C@@H]2CC[C@H](CN1C(=O)C(c1ccccc1)c1ccccc1)N2C(=O)OCc1ccccc1] |

| No. | Structure |
|---|---|
| C78 | 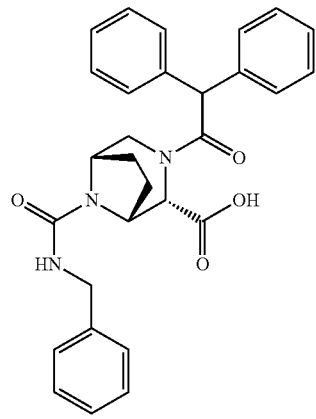 [SMILES: O=C(O)[C@@H]1[C@H]2CC[C@@H](CN1C(=O)C(c1ccccc1)c1ccccc1)N2C(=O)NCc1ccccc1] |
| C79 | 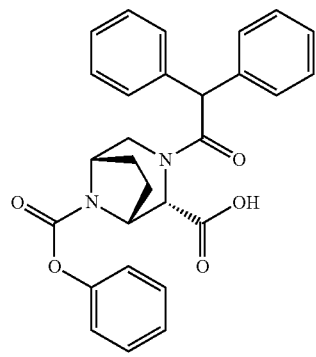 [SMILES: O=C(O)[C@@H]1[C@H]2CC[C@@H](CN1C(=O)C(c1ccccc1)c1ccccc1)N2C(=O)Oc1ccccc1] |
| C82 | 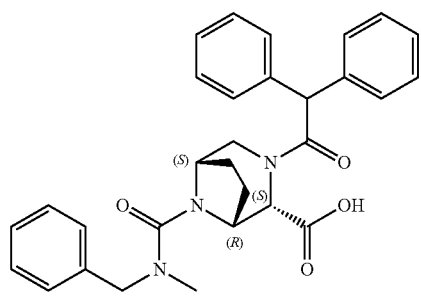 |
| C83 | 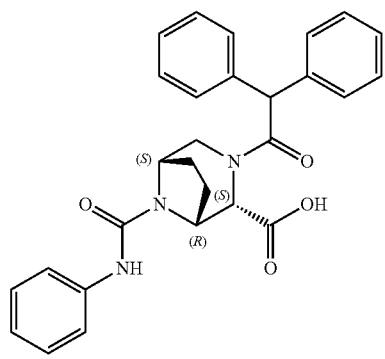 |
| No. | Structure |
|---|---|
| C84 | 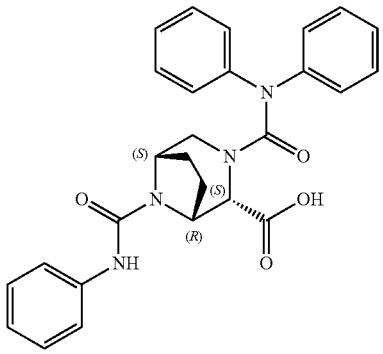 |
| C85 | 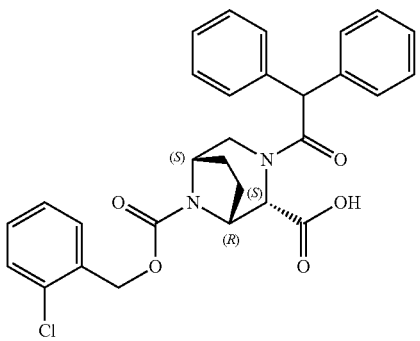 |
| C86 | 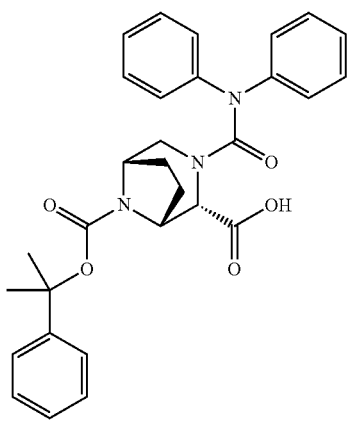 [SMILES: CC(C)(OC(=O)N1[C@H]2CC[C@@H]1[C@@H](C(=O)O)N(C(=O)N(c1ccccc1)c1ccccc1)C2)c1ccccc1] |
| C87 | 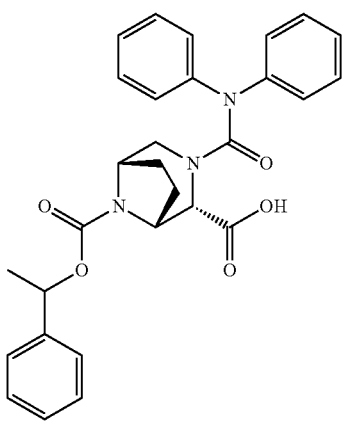 |

| No. | Structure |
|---|---|
| C111 | 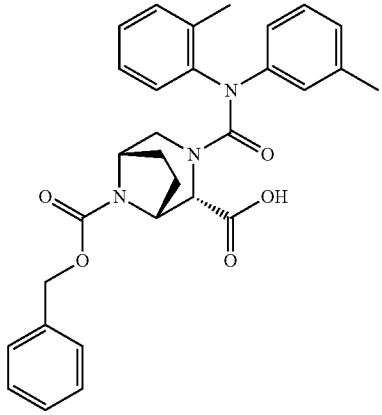 [SMILES: Cc1cccc(N(C(=O)N2C[C@@H]3CC[C@H]([C@H]2C(=O)O)N3C(=O)OCc2ccccc2)c2ccccc2C)c1] |
| C112 | 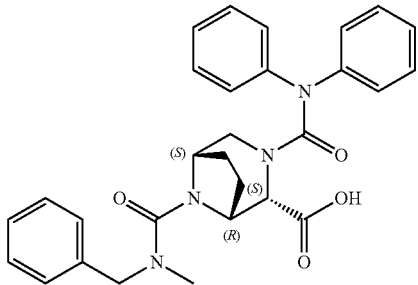 |
| C114 | 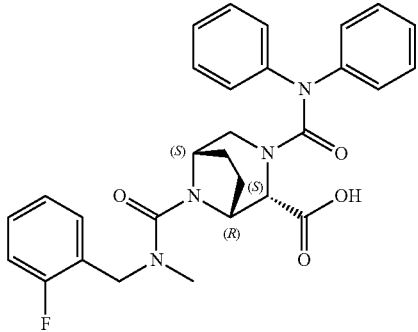 |
| C115 | 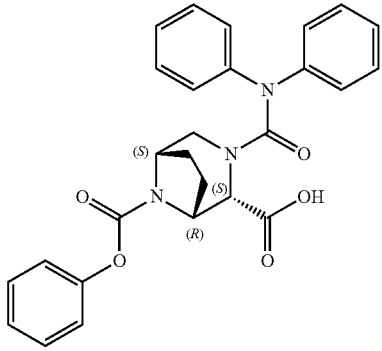 |
| No. | Structure |
|---|---|
| C117 | 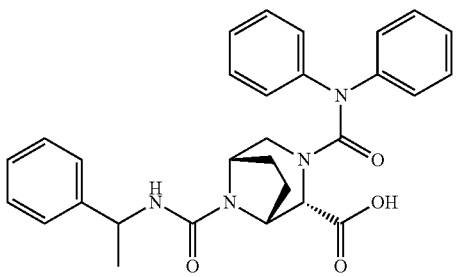 [SMILES: CC(NC(=O)N1[C@H]2CC[C@@H]1[C@@H](C(=O)O)N(C(=O)N(c1ccccc1)c1ccccc1)C2)c1ccccc1] |
| C118 | 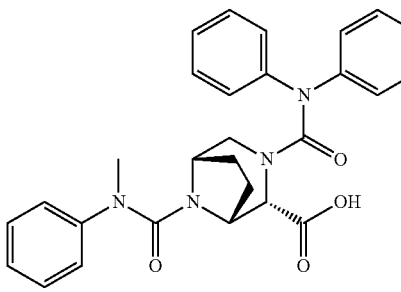 |
| C123 | 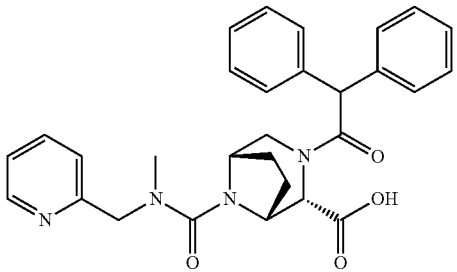 |
| C124 | 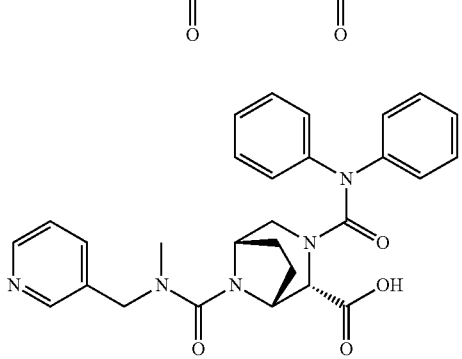 |
| C125 | 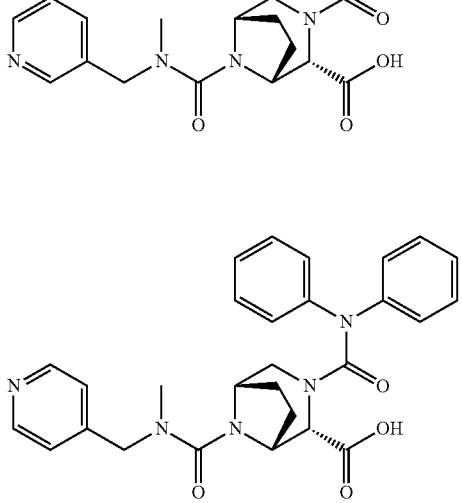 |

-continued
| No. | Structure |
|---|---|
| C126 | 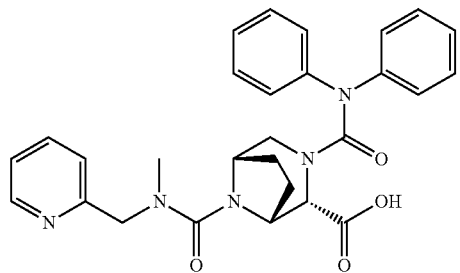 |
| C127 | 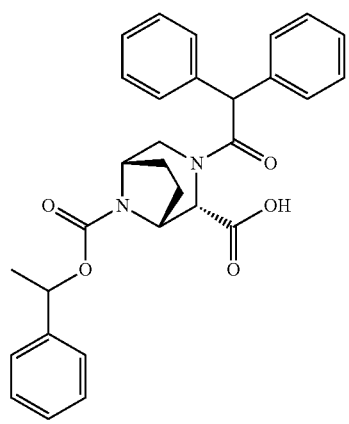 [SMILES: CC(OC(=O)N1[C@H]2CC[C@@H]1[C@@H](C(=O)O)N(C(=O)C(c1ccccc1)c1ccccc1)C2)c1ccccc1] |
| C128 | 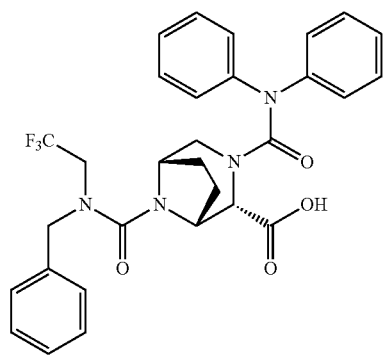 [SMILES: O=C(O)[C@@H]1[C@H]2CC[C@@H](CN1C(=O)N(c1ccccc1)c1ccccc1)N2C(=O)N(Cc1ccccc1)CC(F)(F)F] |
| C129 | 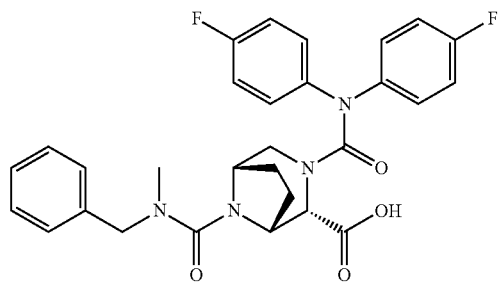 [SMILES: CN(Cc1ccccc1)C(=O)N1[C@H]2CC[C@@H]1[C@@H](C(=O)O)N(C(=O)N(c1ccc(F)cc1)c1ccc(F)cc1)C2] |
-continued
| No. | Structure |
|---|---|
| C133 | 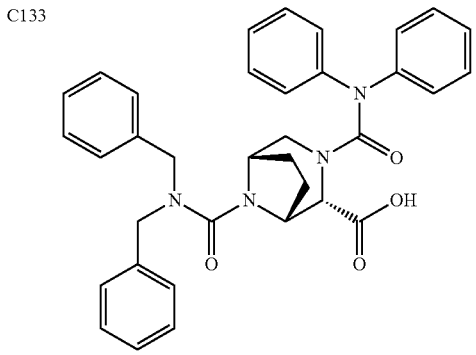 |
| C134 | 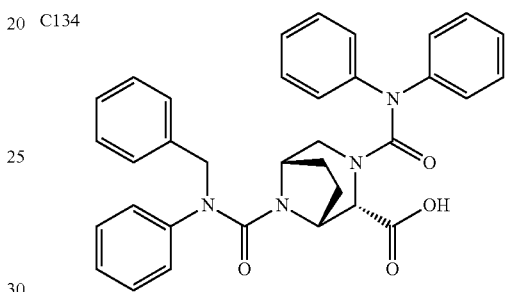 |
| C147 | 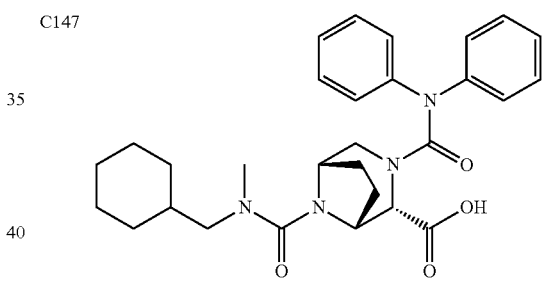 |
| C148 | 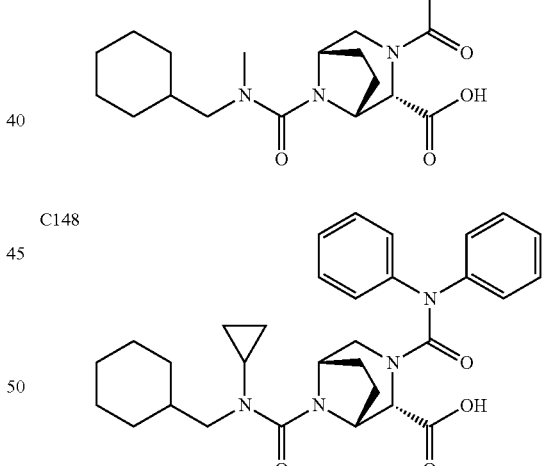 |
| C149 | 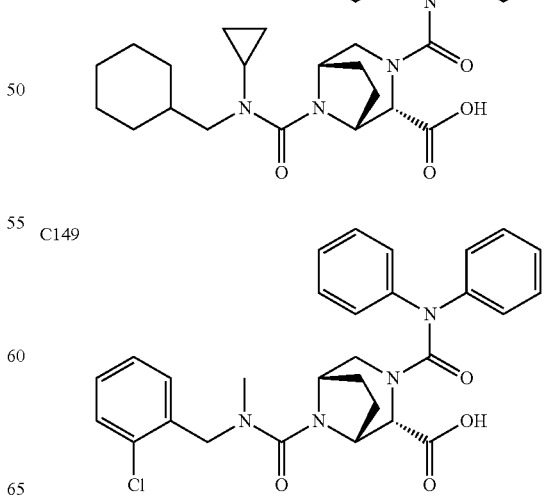 |

| No. | Structure |
|---|---|
| C150 | 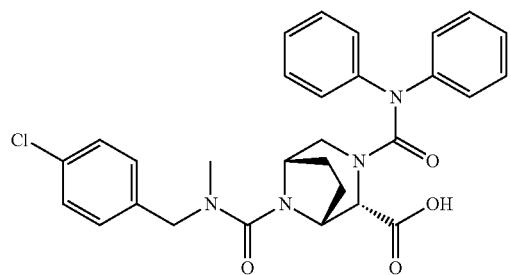 [SMILES: CN(Cc1ccc(Cl)cc1)C(=O)N1[C@H]2CC[C@@H]1[C@@H](C(=O)O)N(C(=O)N(c1ccccc1)c1ccccc1)C2] |
| C151 | 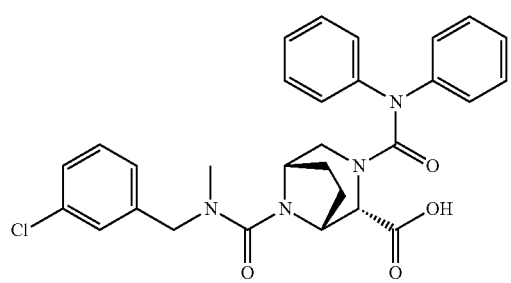 [SMILES: CN(Cc1cccc(Cl)c1)C(=O)N1[C@H]2CC[C@@H]1[C@@H](C(=O)O)N(C(=O)N(c1ccccc1)c1ccccc1)C2] |
| C152 | 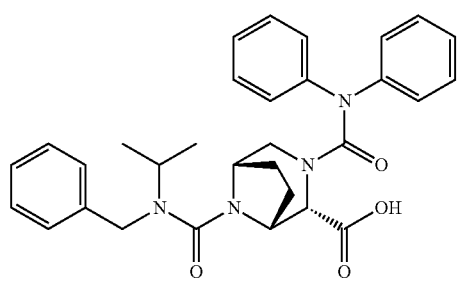 |
| C153 | 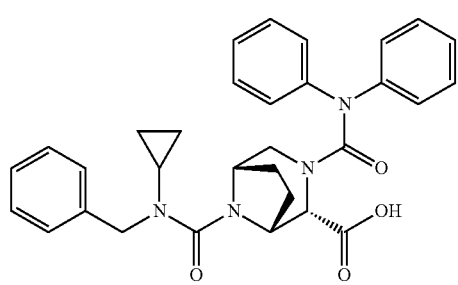 [SMILES: O=C(O)[C@@H]1[C@H]2CC[C@@H](CN1C(=O)N(c1ccccc1)c1ccccc1)N2C(=O)N(Cc1ccccc1)C1CC1] |
| C154 | 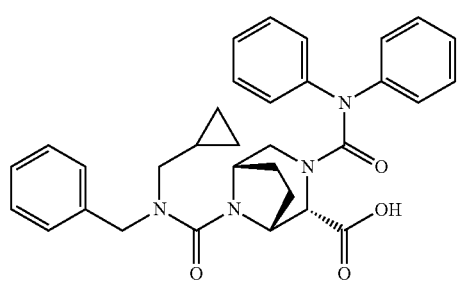 [SMILES: O=C(O)[C@@H]1[C@H]2CC[C@@H](CN1C(=O)N(c1ccccc1)c1ccccc1)N2C(=O)N(Cc1ccccc1)CC1CC1] |
| No. | Structure |
|---|---|
| C155 | 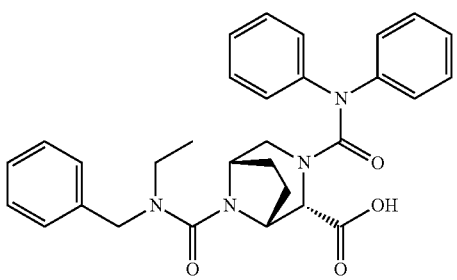 [SMILES: CCN(Cc1ccccc1)C(=O)N1[C@H]2CC[C@@H]1[C@@H](C(=O)O)N(C(=O)N(c1ccccc1)c1ccccc1)C2] |
| C156 | 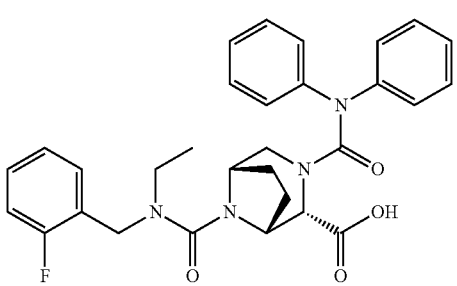 |
| C157 | 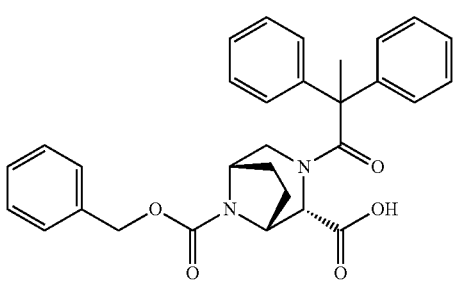 |
| C158 | 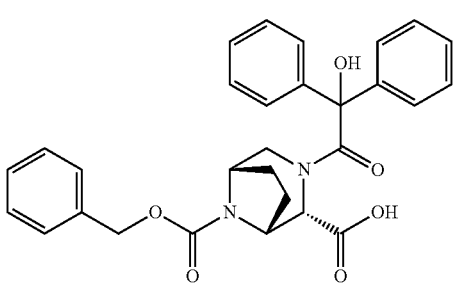 [SMILES: O=C(O)[C@@H]1[C@H]2CC[C@@H](CN1C(=O)C(O)(c1ccccc1)c1ccccc1)N2C(=O)OCc1ccccc1] |
| C159 | 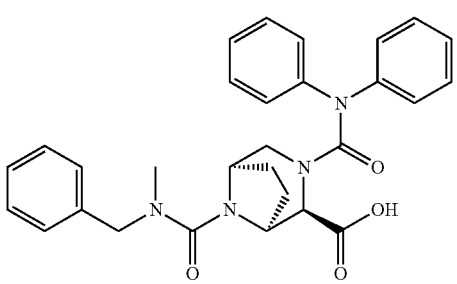 [SMILES: CN(Cc1ccccc1)C(=O)N1[C@@H]2CC[C@H]1[C@H](C(=O)O)N(C(=O)N(c1ccccc1)c1ccccc1)C2] |

-continued
| No. | Structure |
|---|---|
| C161 | 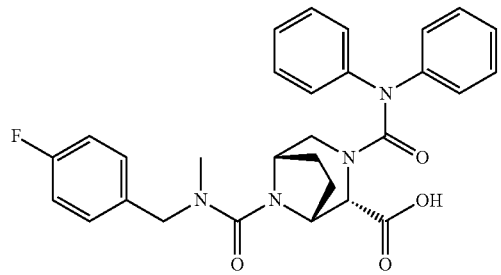 [SMILES: CN(Cc1ccc(F)cc1)C(=O)N1[C@H]2CC[C@@H]1[C@@H](C(=O)O)N(C(=O)N(c1ccccc1)c1ccccc1)C2] |
| C162 | 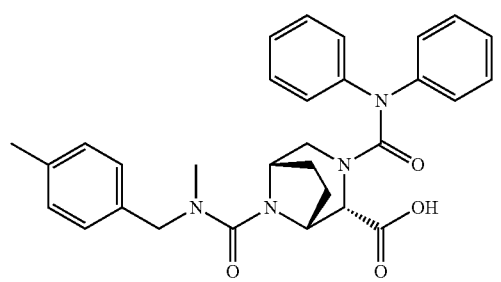 |
| C163 | 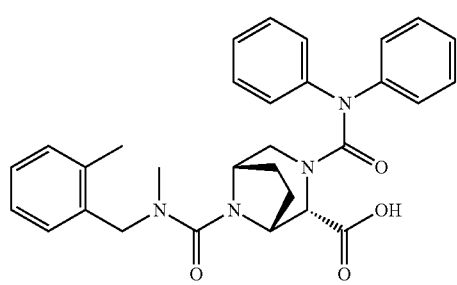 [SMILES: Cc1ccccc1CN(C)C(=O)N1[C@H]2CC[C@@H]1[C@@H](C(=O)O)N(C(=O)N(c1ccccc1)c1ccccc1)C2] |
| C164 | 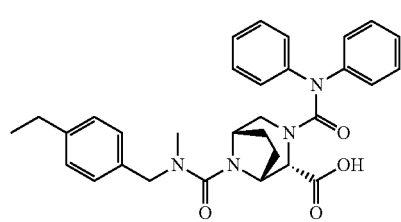 [SMILES: CCc1ccc(CN(C)C(=O)N2[C@H]3CC[C@@H]2[C@@H](C(=O)O)N(C(=O)N(c2ccccc2)c2ccccc2)C3)cc1] |
| C165 | 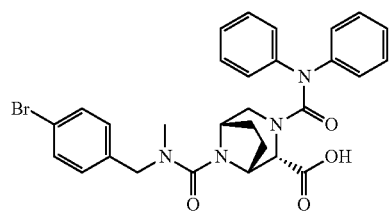 [SMILES: CN(Cc1ccc(Br)cc1)C(=O)N1[C@H]2CC[C@@H]1[C@@H](C(=O)O)N(C(=O)N(c1ccccc1)c1ccccc1)C2] |
| C166 | 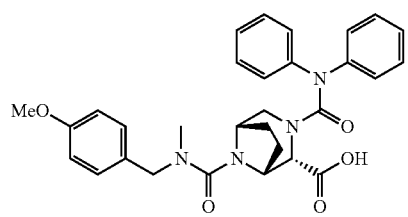 [SMILES: COc1ccc(CN(C)C(=O)N2[C@H]3CC[C@@H]2[C@@H](C(=O)O)N(C(=O)N(c2ccccc2)c2ccccc2)C3)cc1] |
-continued
| No. | Structure |
|---|---|
| C167 | 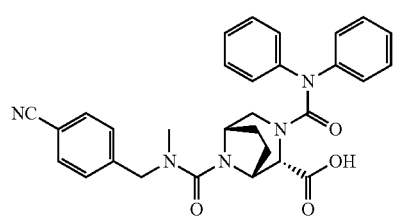 [SMILES: CN(Cc1ccc(C#N)cc1)C(=O)N1[C@H]2CC[C@@H]1[C@@H](C(=O)O)N(C(=O)N(c1ccccc1)c1ccccc1)C2] |
| C168 | 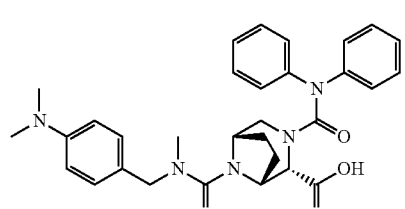 |
| C169 | 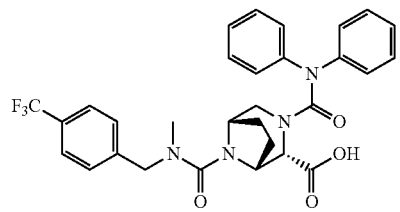 [SMILES: CN(Cc1ccc(C(F)(F)F)cc1)C(=O)N1[C@H]2CC[C@@H]1[C@@H](C(=O)O)N(C(=O)N(c1ccccc1)c1ccccc1)C2] |
| C170 | 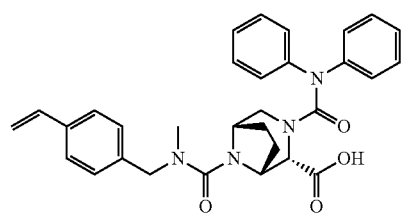 [SMILES: C=Cc1ccc(CN(C)C(=O)N2[C@H]3CC[C@@H]2[C@@H](C(=O)O)N(C(=O)N(c2ccccc2)c2ccccc2)C3)cc1] |
| C171 | 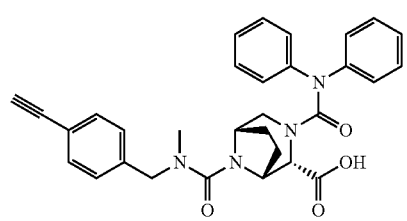 [SMILES: C#Cc1ccc(CN(C)C(=O)N2[C@H]3CC[C@@H]2[C@@H](C(=O)O)N(C(=O)N(c2ccccc2)c2ccccc2)C3)cc1] |
| C173 | 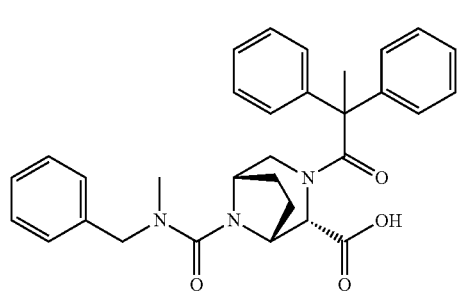 [SMILES: CN(Cc1ccccc1)C(=O)N1[C@H]2CC[C@@H]1[C@@H](C(=O)O)N(C(=O)C(C)(c1ccccc1)c1ccccc1)C2] |

| No. | Structure |
|---|---|
| C174 | 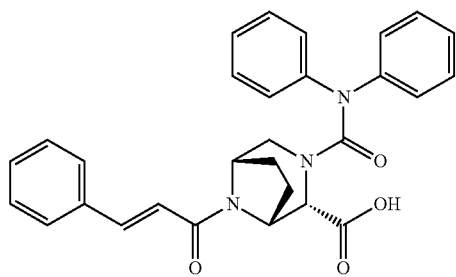 |
| C181 | 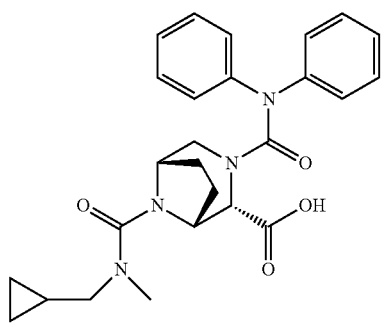 [SMILES: CN(CC1CC1)C(=O)N1[C@H]2CC[C@@H]1[C@@H](C(=O)O)N(C(=O)N(c1ccccc1)c1ccccc1)C2] |
| C183 | 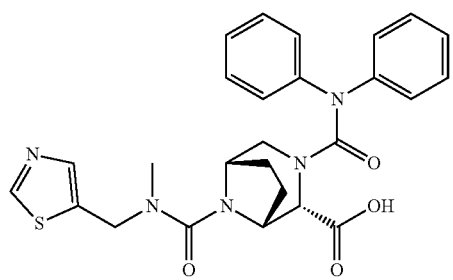 [SMILES: CN(Cc1cncs1)C(=O)N1[C@H]2CC[C@@H]1[C@@H](C(=O)O)N(C(=O)N(c1ccccc1)c1ccccc1)C2] |
| C184 | 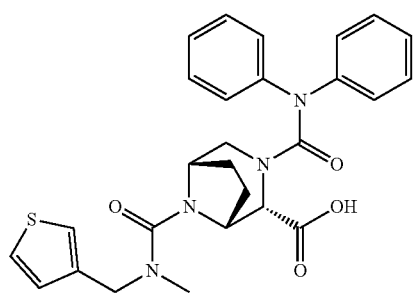 |
| C185 | 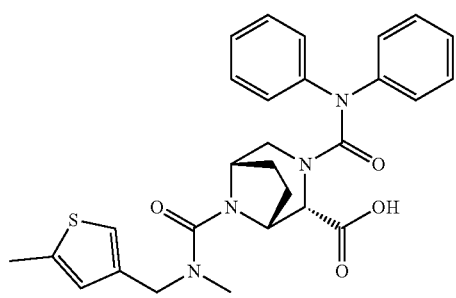 |
| No. | Structure |
|---|---|
| C186 | 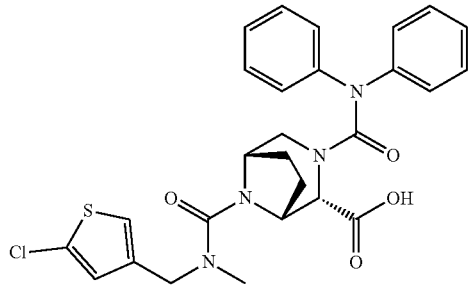 [SMILES: CN(Cc1csc(Cl)c1)C(=O)N1[C@H]2CC[C@@H]1[C@@H](C(=O)O)N(C(=O)N(c1ccccc1)c1ccccc1)C2] |
| C187 | 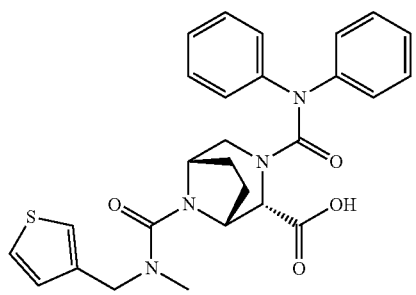 |
| C188 | 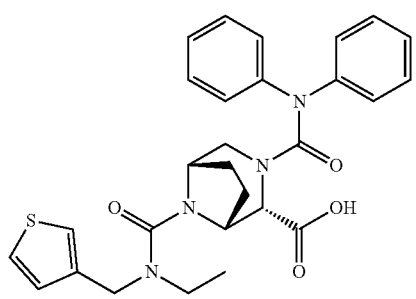 [SMILES: CCN(Cc1ccsc1)C(=O)N1[C@H]2CC[C@@H]1[C@@H](C(=O)O)N(C(=O)N(c1ccccc1)c1ccccc1)C2] |
| C189 | 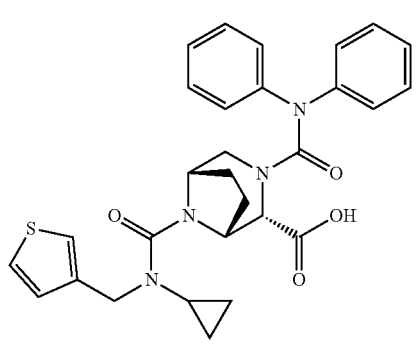 [SMILES: O=C(O)[C@@H]1[C@H]2CC[C@@H](CN1C(=O)N(c1ccccc1)c1ccccc1)N2C(=O)N(Cc1ccsc1)C1CC1] |
| C190 | 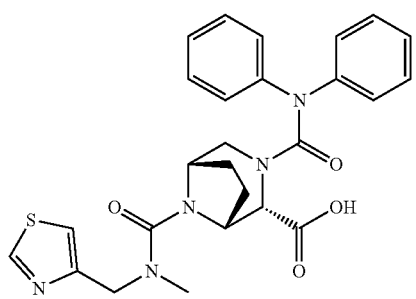 [SMILES: CN(Cc1cscn1)C(=O)N1[C@H]2CC[C@@H]1[C@@H](C(=O)O)N(C(=O)N(c1ccccc1)c1ccccc1)C2] |

| No. | Structure |
|---|---|
| C192 | 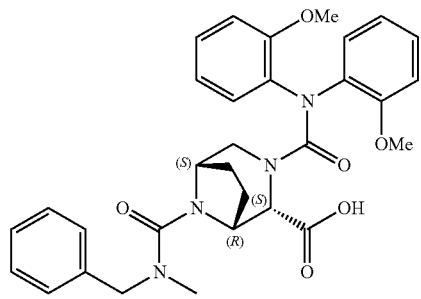 |
| C193 | 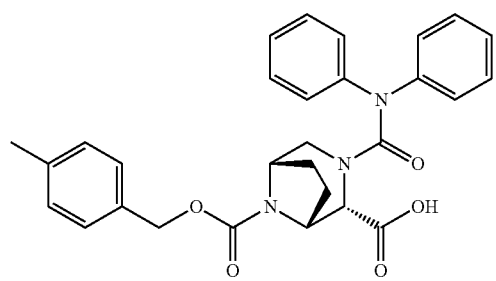 [SMILES: Cc1ccc(COC(=O)N2[C@H]3CC[C@@H]2[C@@H](C(=O)O)N(C(=O)N(c2ccccc2)c2ccccc2)C3)cc1] |
| C194 | 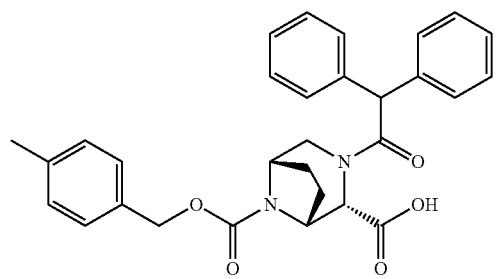 [SMILES: Cc1ccc(COC(=O)N2[C@H]3CC[C@@H]2[C@@H](C(=O)O)N(C(=O)C(c2ccccc2)c2ccccc2)C3)cc1] |
| C195 | 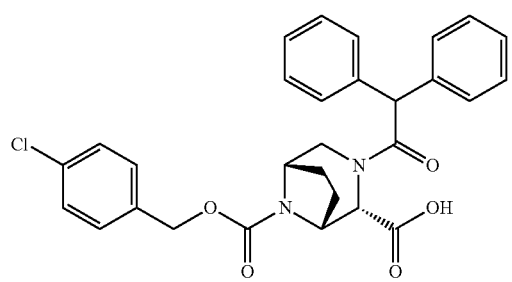 [SMILES: O=C(O)[C@@H]1[C@H]2CC[C@@H](CN1C(=O)C(c1ccccc1)c1ccccc1)N2C(=O)OCc1ccc(Cl)cc1] |
| C196 | 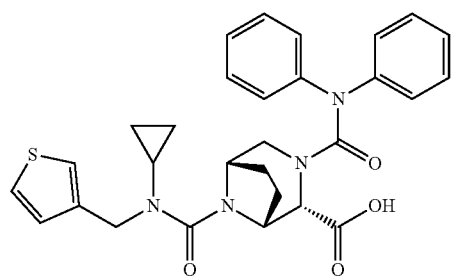 [SMILES: O=C(O)[C@@H]1[C@H]2CC[C@@H](CN1C(=O)N(c1ccccc1)c1ccccc1)N2C(=O)N(Cc1ccsc1)C1CC1] |
| No. | Structure |
|---|---|
| C197 | 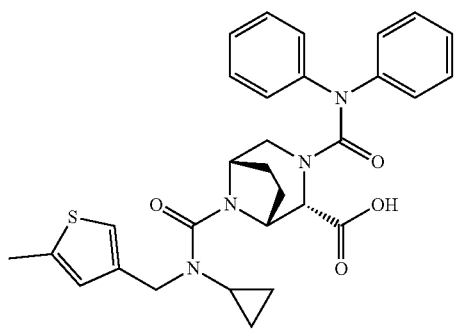 [SMILES: Cc1cc(CN(C(=O)N2[C@H]3CC[C@@H]2[C@@H](C(=O)O)N(C(=O)N(c2ccccc2)c2ccccc2)C3)C2CC2)cs1] |
| C198 | 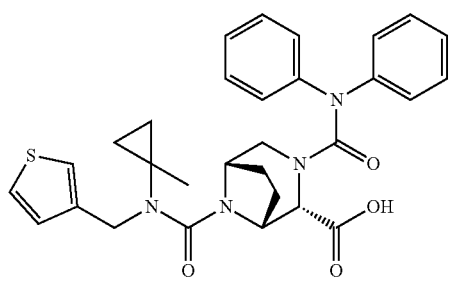 [SMILES: CC1(N(Cc2ccsc2)C(=O)N2[C@H]3CC[C@@H]2[C@@H](C(=O)O)N(C(=O)N(c2ccccc2)c2ccccc2)C3)CC1] |
| C199 | 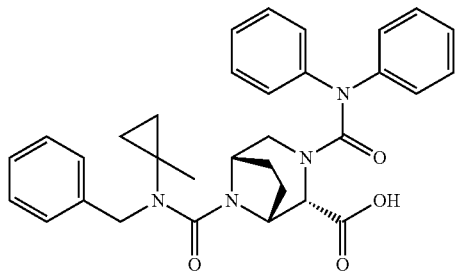 [SMILES: CC1(N(Cc2ccccc2)C(=O)N2[C@H]3CC[C@@H]2[C@@H](C(=O)O)N(C(=O)N(c2ccccc2)c2ccccc2)C3)CC1] |
| C200 | 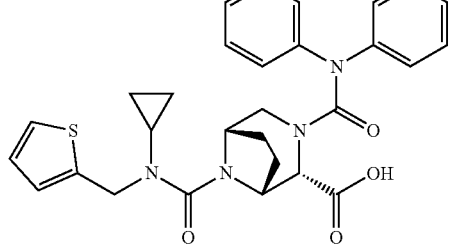 |
| C201 | 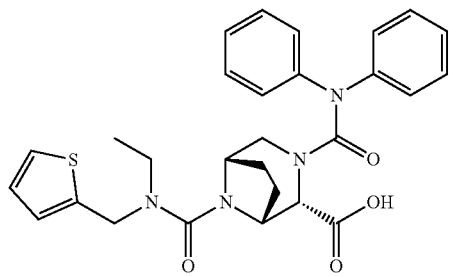 [SMILES: CCN(Cc1cccs1)C(=O)N1[C@H]2CC[C@@H]1[C@@H](C(=O)O)N(C(=O)N(c1ccccc1)c1ccccc1)C2] |

309
-continued
| No. | Structure |
|---|---|
| C202 | 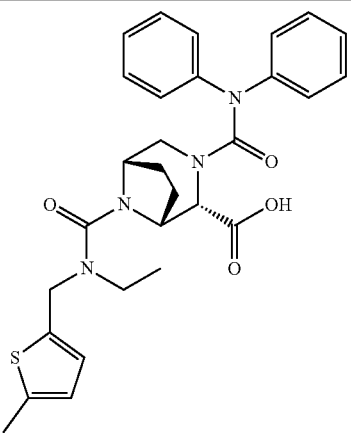 [SMILES: CCN(Cc1ccc(C)s1)C(=O)N1[C@H]2CC[C@@H]1[C@@H](C(=O)O)N(C(=O)N(c1ccccc1)c1ccccc1)C2] |
| C203 | 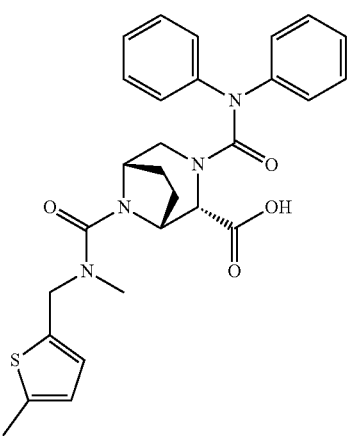 [SMILES: Cc1ccc(CN(C)C(=O)N2[C@H]3CC[C@@H]2[C@@H](C(=O)O)N(C(=O)N(c2ccccc2)c2ccccc2)C3)s1] |
| C204 | 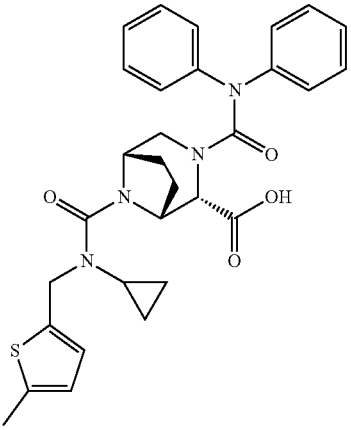 [SMILES: Cc1ccc(CN(C(=O)N2[C@H]3CC[C@@H]2[C@@H](C(=O)O)N(C(=O)N(c2ccccc2)c2ccccc2)C3)C2CC2)s1] |
| C205 | 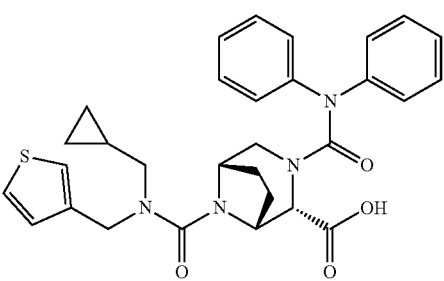 [SMILES: O=C(O)[C@@H]1[C@H]2CC[C@@H](CN1C(=O)N(c1ccccc1)c1ccccc1)N2C(=O)N(Cc1ccsc1)CC1CC1] |
310
-continued
| No. | Structure |
|---|---|
| C206 | 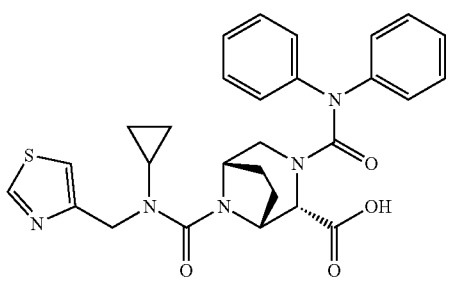 [SMILES: O=C(O)[C@@H]1[C@H]2CC[C@@H](CN1C(=O)N(c1ccccc1)c1ccccc1)N2C(=O)N(Cc1cscn1)C1CC1] |
| C207 | 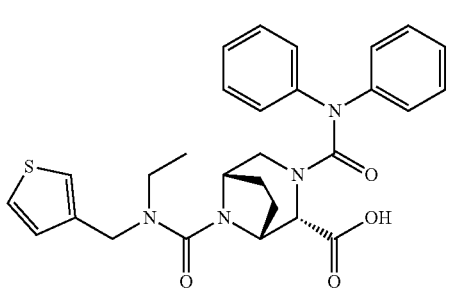 [SMILES: CCN(Cc1ccsc1)C(=O)N1[C@H]2CC[C@@H]1[C@@H](C(=O)O)N(C(=O)N(c1ccccc1)c1ccccc1)C2] |
| C208 | 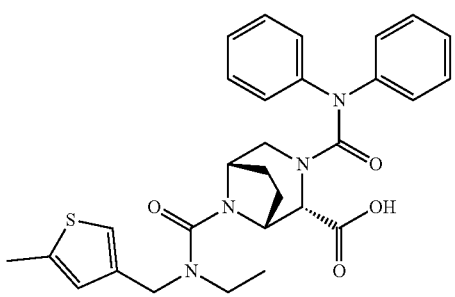 [SMILES: CCN(Cc1csc(C)c1)C(=O)N1[C@H]2CC[C@@H]1[C@@H](C(=O)O)N(C(=O)N(c1ccccc1)c1ccccc1)C2] |
| C209 | 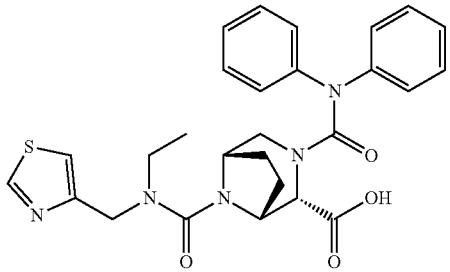 [SMILES: CCN(Cc1cscn1)C(=O)N1[C@H]2CC[C@@H]1[C@@H](C(=O)O)N(C(=O)N(c1ccccc1)c1ccccc1)C2] |
| C212 | 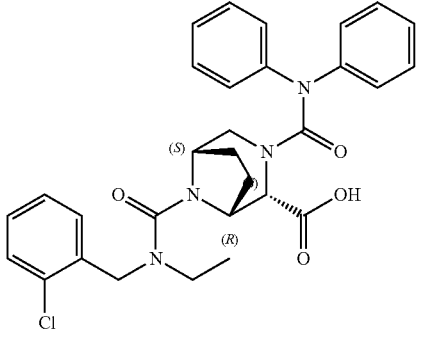 |

-continued
| No. | Structure |
|---|---|
| C213 | 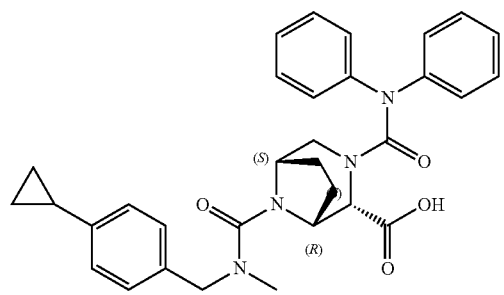 |
| C214 | 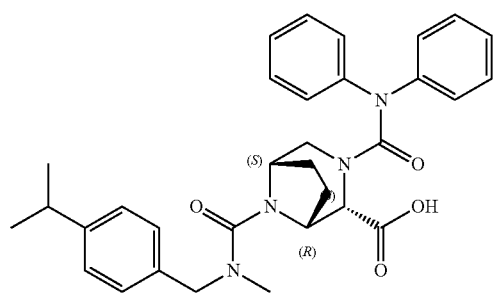 |
| C215 | 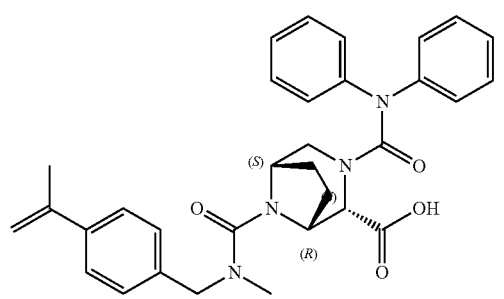 |
| C216 | 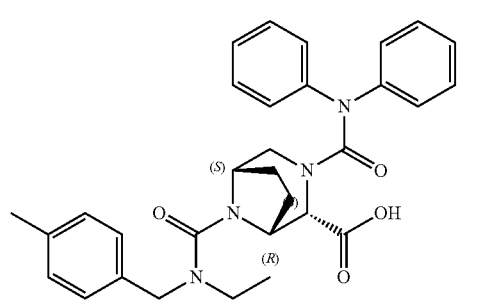 |
| C217 | 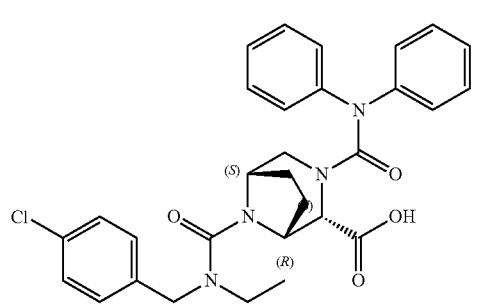 |
-continued
| No. | Structure |
|---|---|
| C218 | 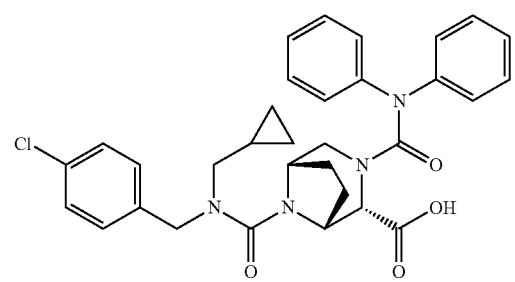 [SMILES: O=C(O)[C@@H]1[C@H]2CC[C@@H](CN1C(=O)N(c1ccccc1)c1ccccc1)N2C(=O)N(Cc1ccc(Cl)cc1)CC1CC1] |
| C219 | 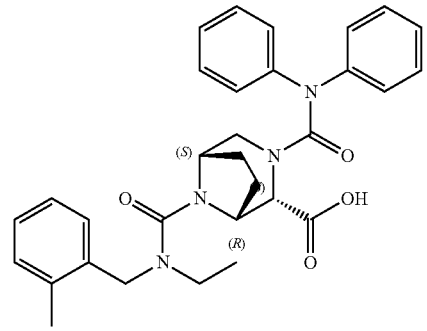 |
| C220 | 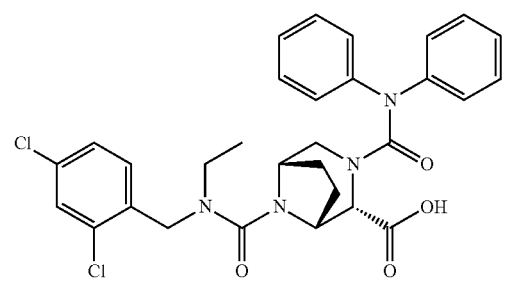 [SMILES: CCN(Cc1ccc(Cl)cc1Cl)C(=O)N1[C@H]2CC[C@@H]1[C@@H](C(=O)O)N(C(=O)N(c1ccccc1)c1ccccc1)C2] |
| C221 | 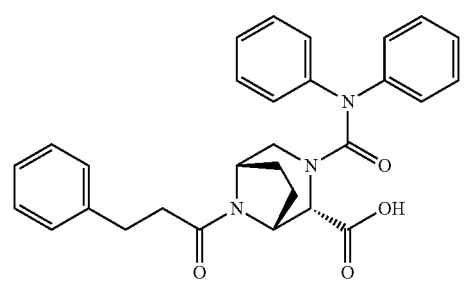 [SMILES: O=C(O)[C@@H]1[C@H]2CC[C@@H](CN1C(=O)N(c1ccccc1)c1ccccc1)N2C(=O)CCc1ccccc1] |
| C222 | 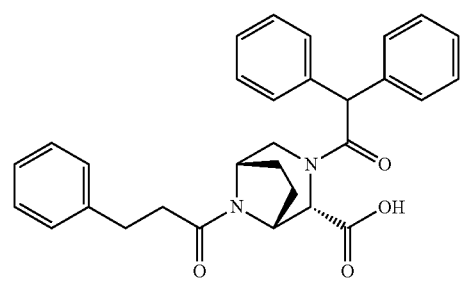 [SMILES: O=C(O)[C@@H]1[C@H]2CC[C@@H](CN1C(=O)C(c1ccccc1)c1ccccc1)N2C(=O)CCc1ccccc1] |

| No. | Structure |
|---|---|
| C223 | 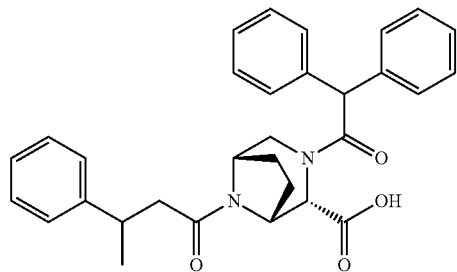 |
| C224 | 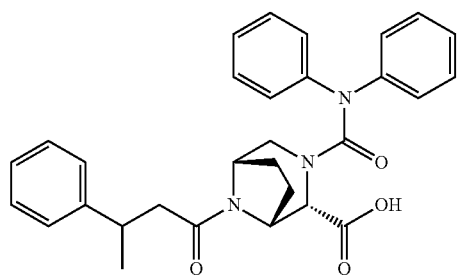 |
| C225 | 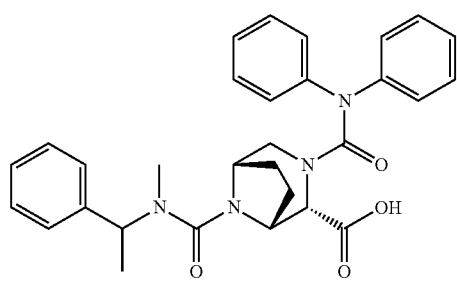 |
| C226 | 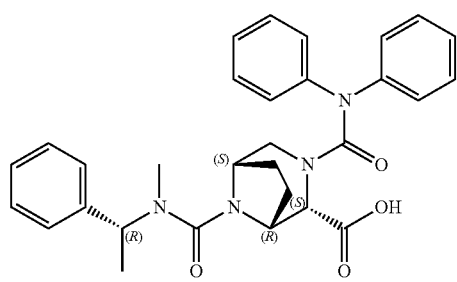 |
| C227 | 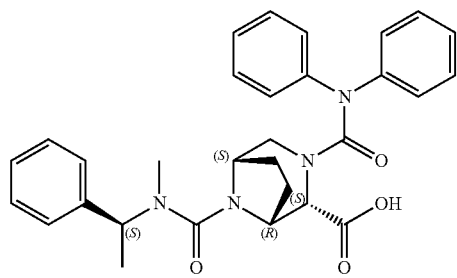 |
| No. | Structure |
|---|---|
| C228 | 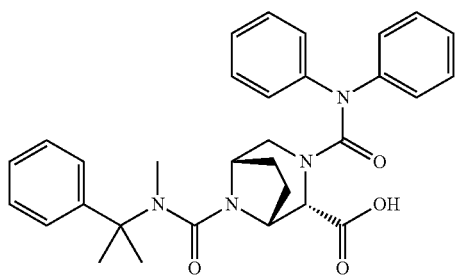 [SMILES: CN(C(=O)N1[C@H]2CC[C@@H]1[C@@H](C(=O)O)N(C(=O)N(c1ccccc1)c1ccccc1)C2)C(C)(C)c1ccccc1] |
| C229 | 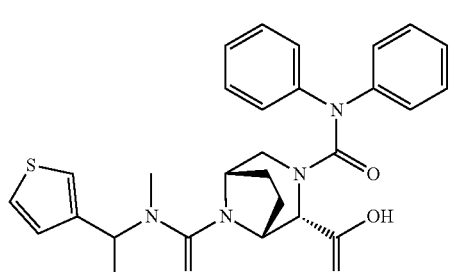 |
| C230 | 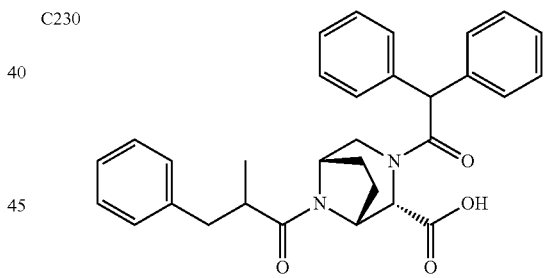 |
| C231 | 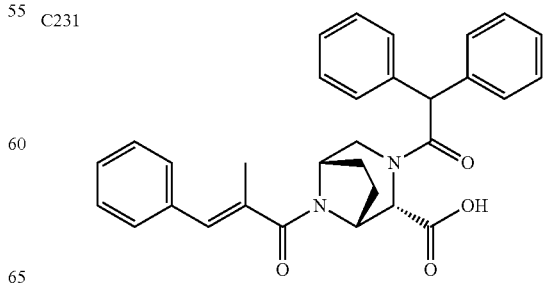 |

-continued
| No. | Structure |
|---|---|
| C234 | 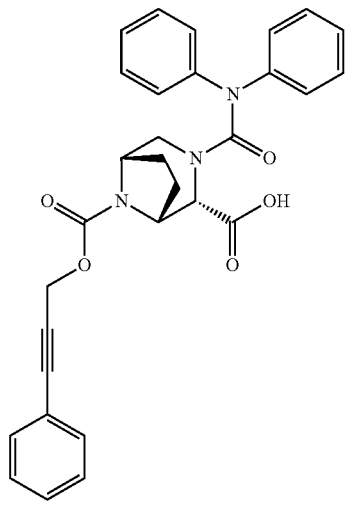 [SMILES: O=C(O)[C@@H]1[C@H]2CC[C@@H](CN1C(=O)N(c1ccccc1)c1ccccc1)N2C(=O)OCC#Cc1ccccc1] |
| C235 | 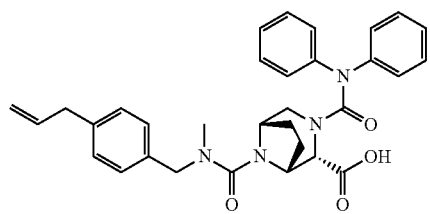 [SMILES: C=CCc1ccc(CN(C)C(=O)N2[C@H]3CC[C@@H]2[C@@H](C(=O)O)N(C(=O)N(c2ccccc2)c2ccccc2)C3)cc1] |
| C236 | 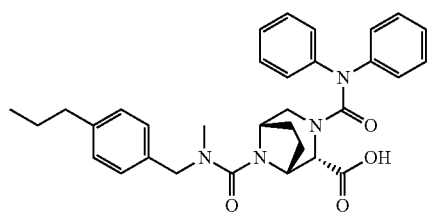 [SMILES: CCCc1ccc(CN(C)C(=O)N2[C@H]3CC[C@@H]2[C@@H](C(=O)O)N(C(=O)N(c2ccccc2)c2ccccc2)C3)cc1] |
| C237 | 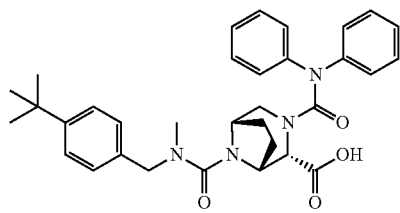 [SMILES: CN(Cc1ccc(C(C)(C)C)cc1)C(=O)N1[C@H]2CC[C@@H]1[C@@H](C(=O)O)N(C(=O)N(c1ccccc1)c1ccccc1)C2] |
| C244 | 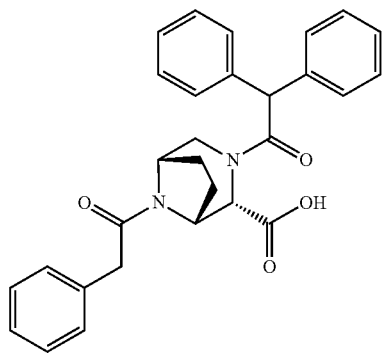 [SMILES: O=C(O)[C@@H]1[C@H]2CC[C@@H](CN1C(=O)C(c1ccccc1)c1ccccc1)N2C(=O)Cc1ccccc1] |
-continued
| No. | Structure |
|---|---|
| C245 | 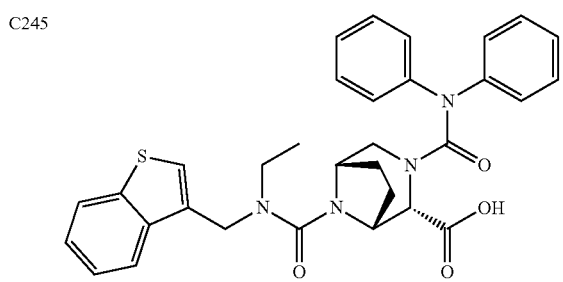 |
| C246 | 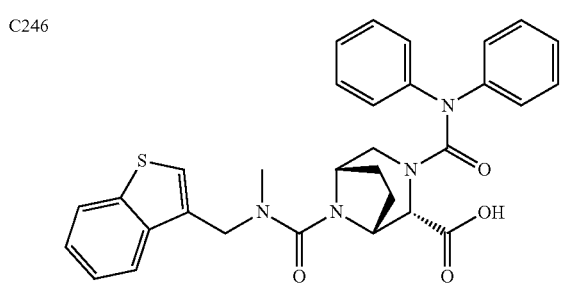 |
| C247 | 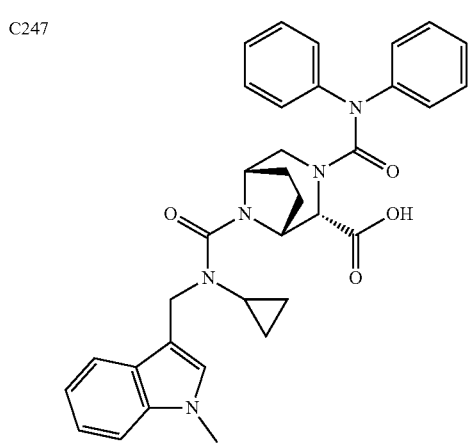 |
| C248 | 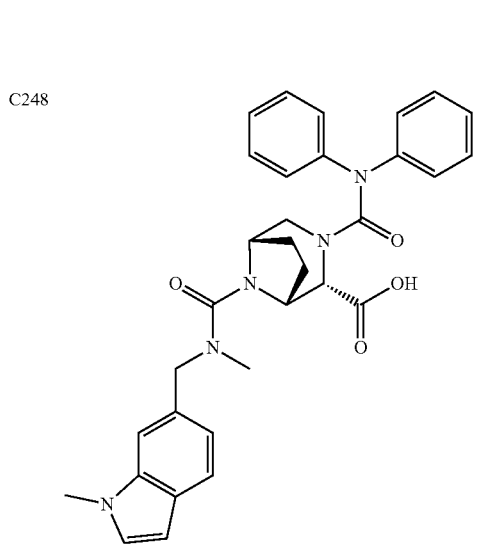 |

| No. | Structure |
|---|---|
| C249 | 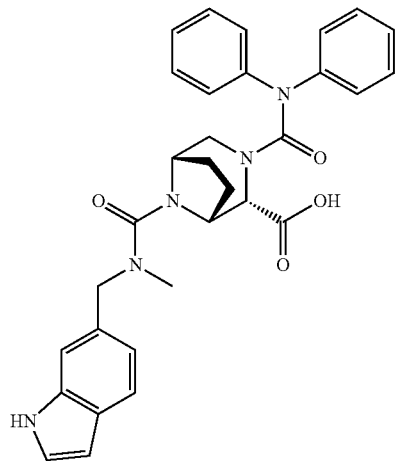 |
| C250 | 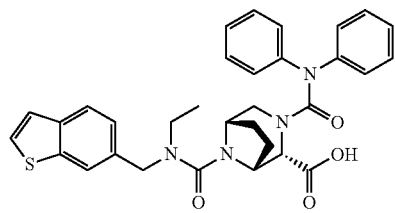 |
| C251 | 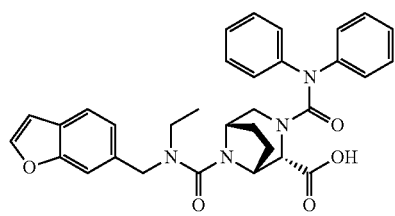 |
| C252 | 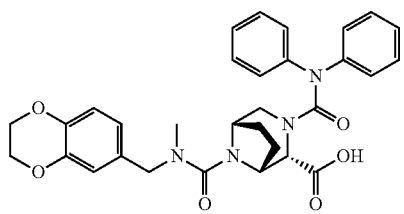 |
| C255 | 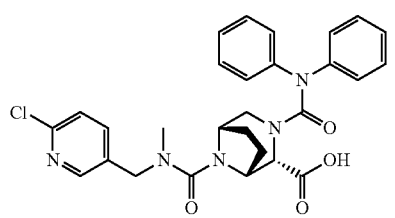 |
| No. | Structure |
|---|---|
| C256 | 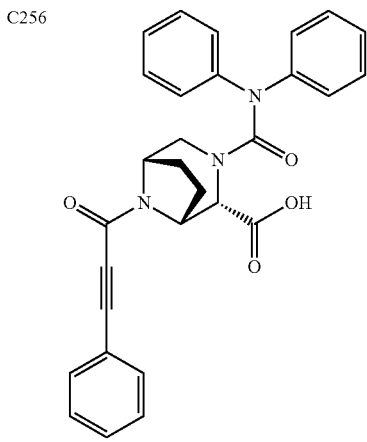 |
| C257 | 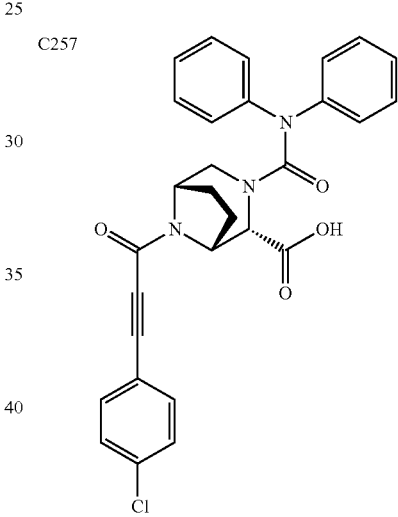 |
| C258 | 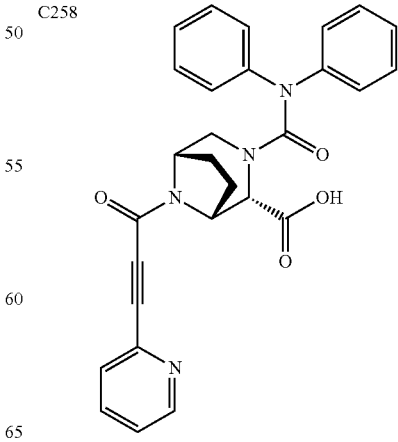 |

-continued
| No. | Structure |
|-----|-----------|
| C259 | 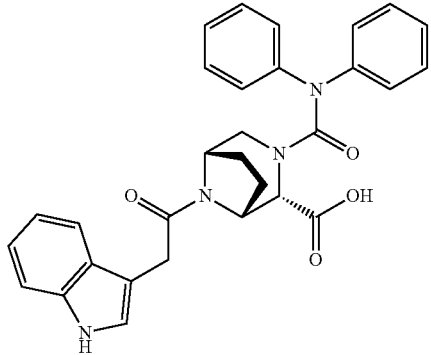 |
| C260 | 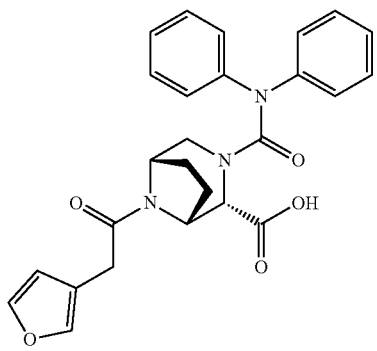 |
| C262 | 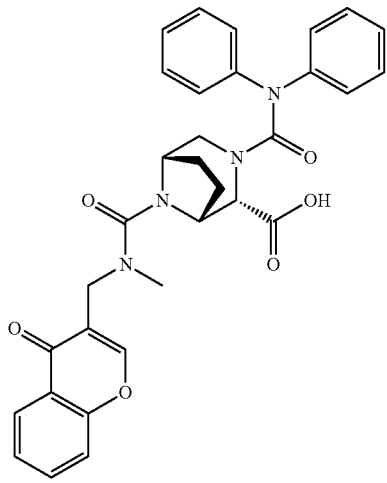 |
-continued
| No. | Structure |
|-----|-----------|
| C263 | 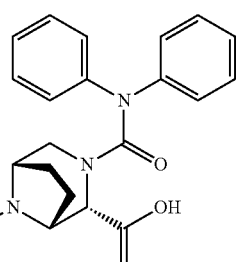 |
| C265 | 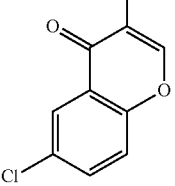 |
| C266 | 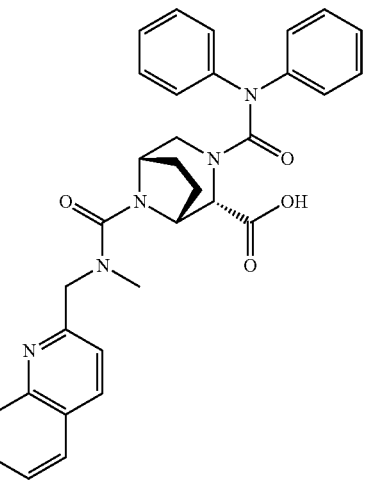 |

| No. | Structure |
|---|---|
| C269 | 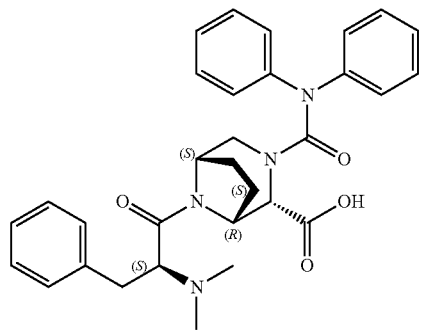 |
| C270 | 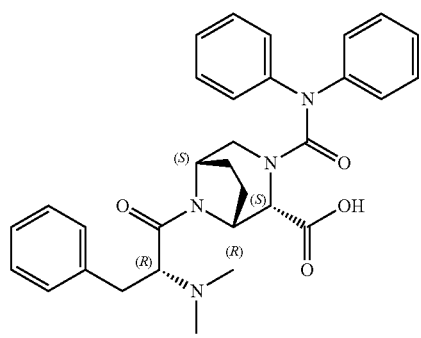 |
| C271 | 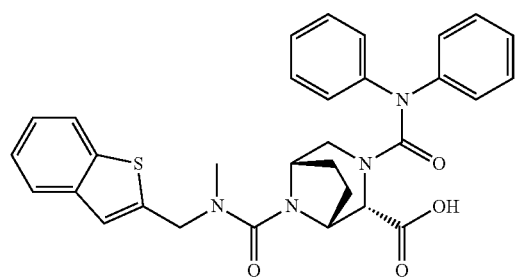 [SMILES: CN(Cc1cc2ccccc2s1)C(=O)N1[C@H]2CC[C@@H]1[C@@H](C(=O)O)N(C(=O)N(c1ccccc1)c1ccccc1)C2] |
| C272 | 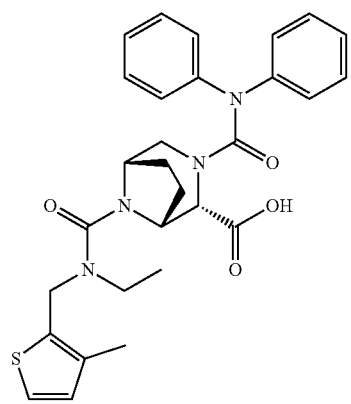 [SMILES: CCN(Cc1sccc1C)C(=O)N1[C@H]2CC[C@@H]1[C@@H](C(=O)O)N(C(=O)N(c1ccccc1)c1ccccc1)C2] |
| No. | Structure |
|---|---|
| C273 | 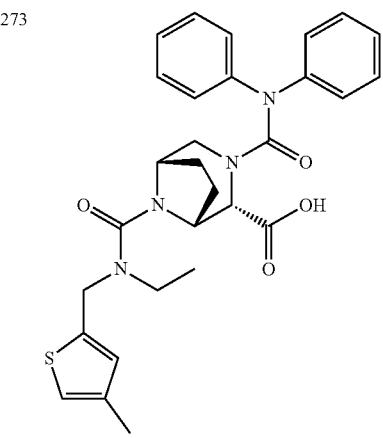 |
| C274 | 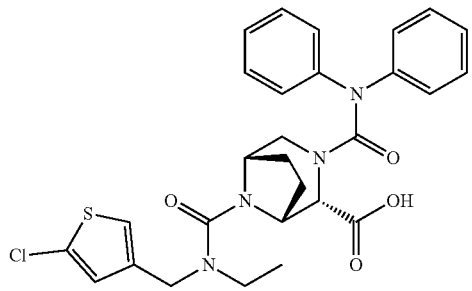 [SMILES: CCN(Cc1csc(Cl)c1)C(=O)N1[C@H]2CC[C@@H]1[C@@H](C(=O)O)N(C(=O)N(c1ccccc1)c1ccccc1)C2] |
| C277 | 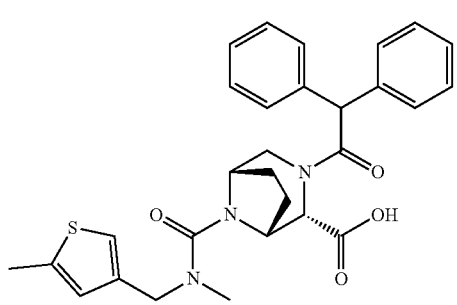 [SMILES: Cc1cc(CN(C)C(=O)N2[C@H]3CC[C@@H]2[C@@H](C(=O)O)N(C(=O)C(c2ccccc2)c2ccccc2)C3)cs1] |
| C278 | 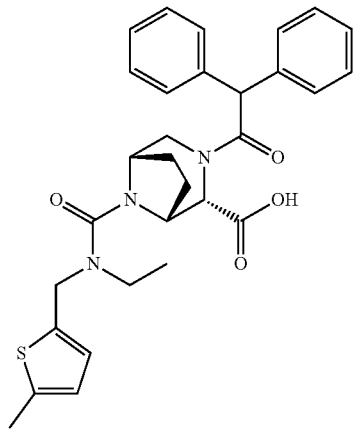 |

| No. | Structure |
|---|---|
| C279 | 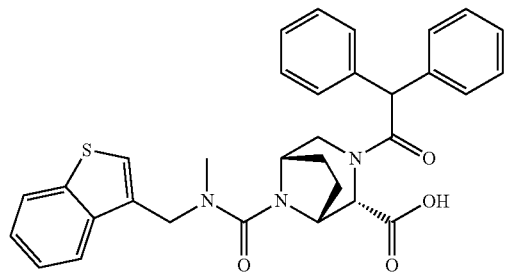 [SMILES: CN(Cc1csc2ccccc12)C(=O)N1[C@H]2CC[C@@H]1[C@@H](C(=O)O)N(C(=O)C(c1ccccc1)c1ccccc1)C2] |
| C281 | 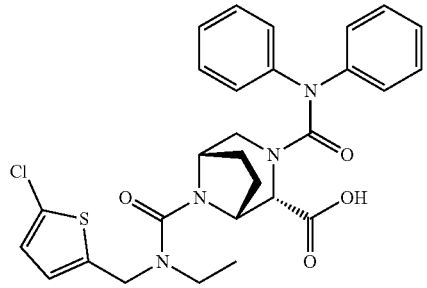 |
| C282 | 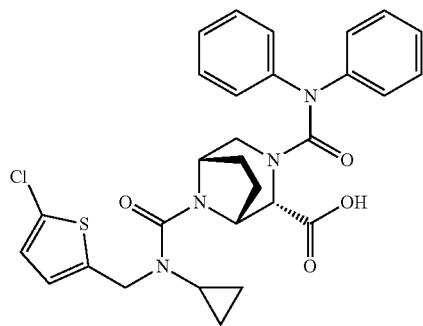 |
| C315 | 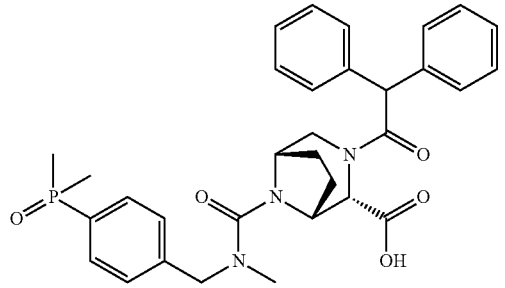 [SMILES: CN(Cc1ccc(P(C)(C)=O)cc1)C(=O)N1[C@H]2CC[C@@H]1[C@@H](C(=O)O)N(C(=O)C(c1ccccc1)c1ccccc1)C2] |
| C316 | 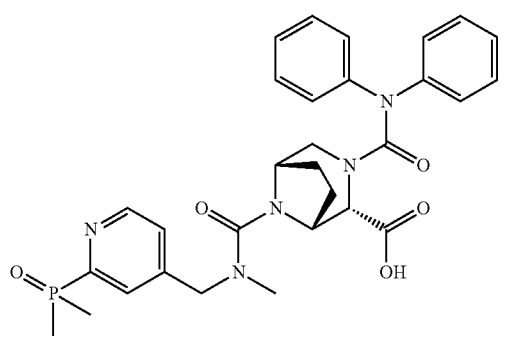 [SMILES: CN(Cc1ccnc(P(C)(C)=O)c1)C(=O)N1[C@H]2CC[C@@H]1[C@@H](C(=O)O)N(C(=O)N(c1ccccc1)c1ccccc1)C2] |
| No. | Structure |
|---|---|
| C317 | 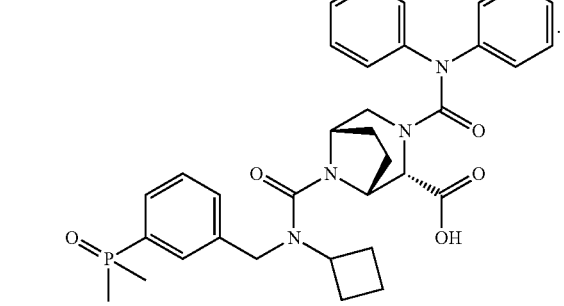 |
29. The compound according to claim 1, or a pharmaceutically acceptable salt, stereoisomer, or N-oxide thereof, wherein the compound has a structure selected from one of the following:
| No. | Structure |
|---|---|
| C35 | 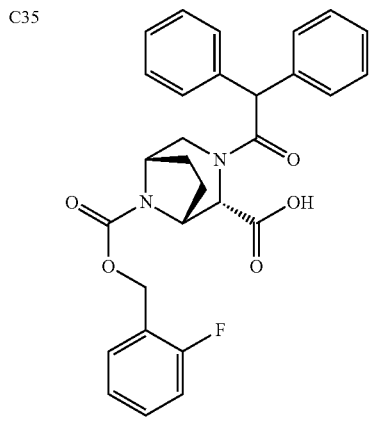 |
| C36 | 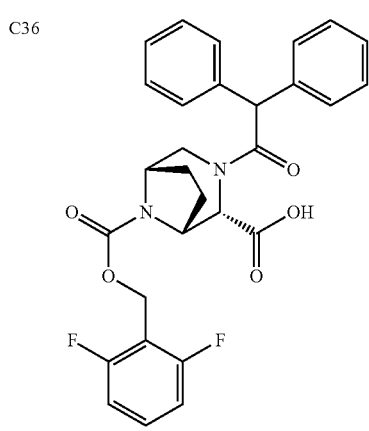 |

-continued
| No. | Structure |
|---|---|
| C37 | 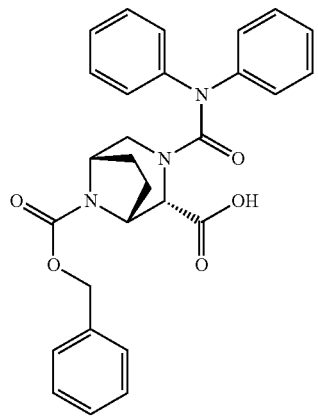 [SMILES: O=C(O)[C@@H]1[C@H]2CC[C@@H](CN1C(=O)N(c1ccccc1)c1ccccc1)N2C(=O)OCc1ccccc1] |
| C76 | 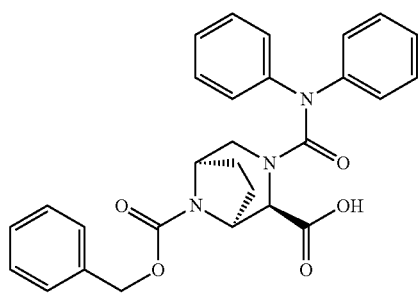 [SMILES: O=C(O)[C@H]1[C@@H]2CC[C@H](CN1C(=O)N(c1ccccc1)c1ccccc1)N2C(=O)OCc1ccccc1] |
| C78 | 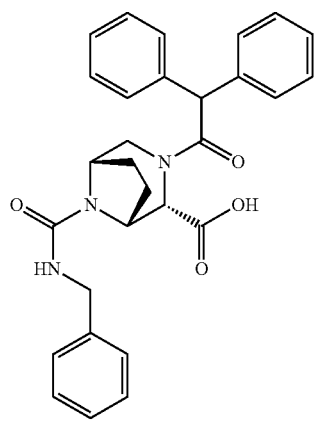 [SMILES: O=C(O)[C@@H]1[C@H]2CC[C@@H](CN1C(=O)C(c1ccccc1)c1ccccc1)N2C(=O)NCc1ccccc1] |
| C82 | 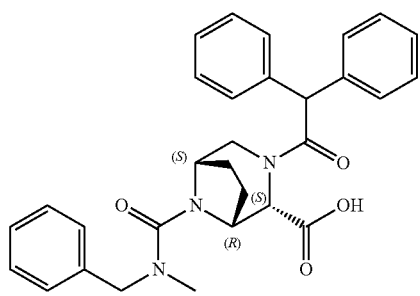 |
-continued
| No. | Structure |
|---|---|
| C83 | 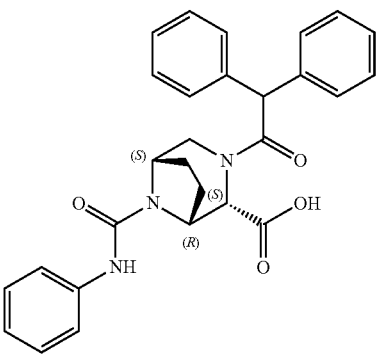 |
| C84 | 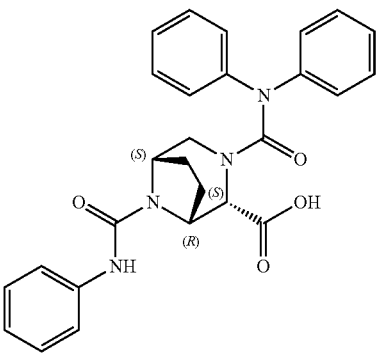 |
| C112 | 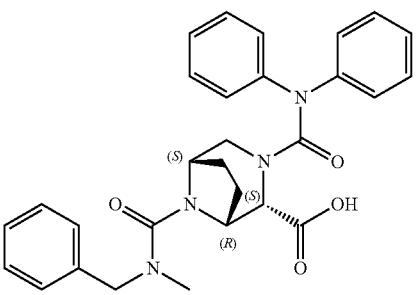 |
| C114 | 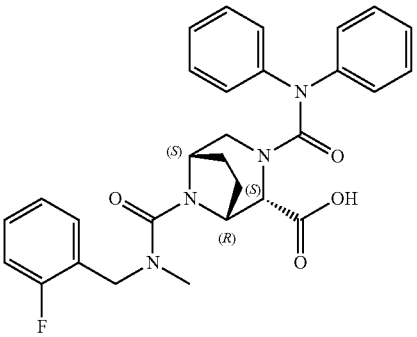 |

-continued
| No. | Structure |
|---|---|
| C115 | 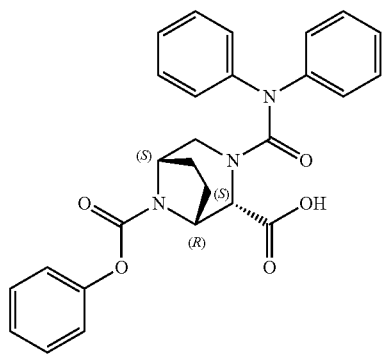 |
| C117 | 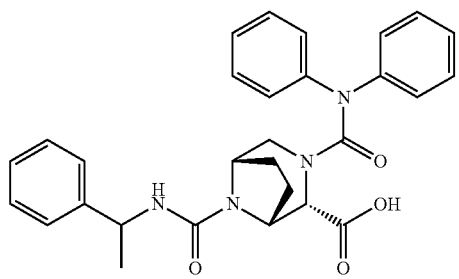 |
| C118 | 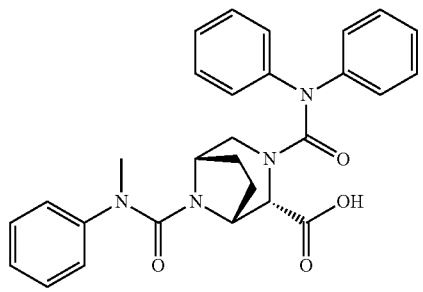 [SMILES: CN(C(=O)N1[C@H]2CC[C@@H]1[C@@H](C(=O)O)N(C(=O)N(c1ccccc1)c1ccccc1)C2)c1ccccc1] |
| C119 | 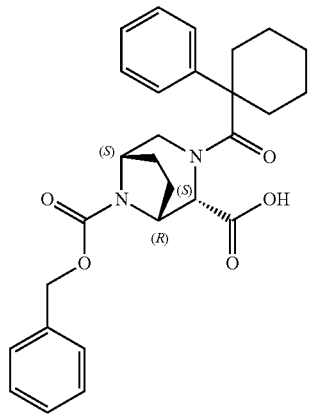 |
-continued
| No. | Structure |
|---|---|
| C123 | 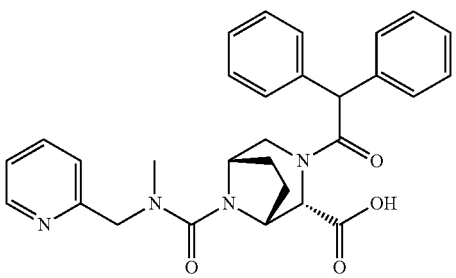 |
| C124 | 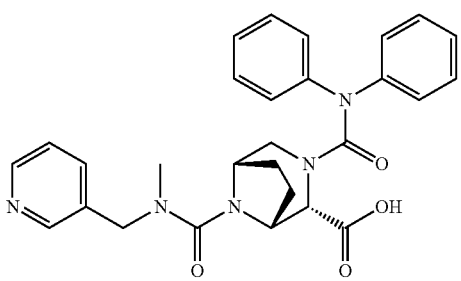 |
| C125 | 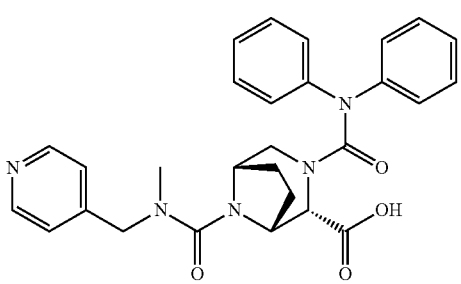 [SMILES: CN(Cc1ccncc1)C(=O)N1[C@H]2CC[C@@H]1[C@@H](C(=O)O)N(C(=O)N(c1ccccc1)c1ccccc1)C2] |
| C126 | 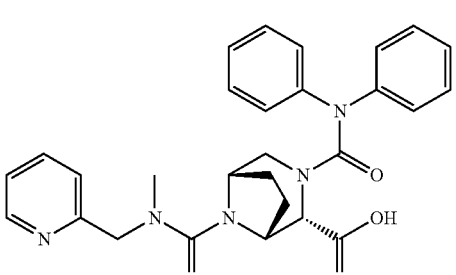 |
| C128 | 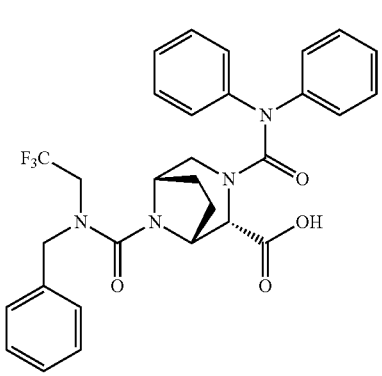 [SMILES: O=C(O)[C@@H]1[C@H]2CC[C@@H](CN1C(=O)N(c1ccccc1)c1ccccc1)N2C(=O)N(Cc1ccccc1)CC(F)(F)F] |

| No. | Structure |
|---|---|
| C129 | 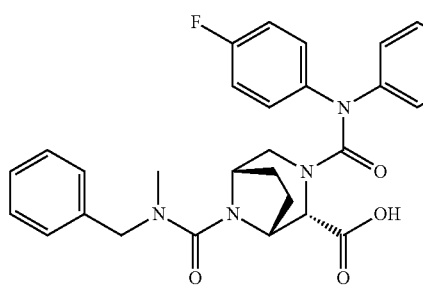 |
| C133 | 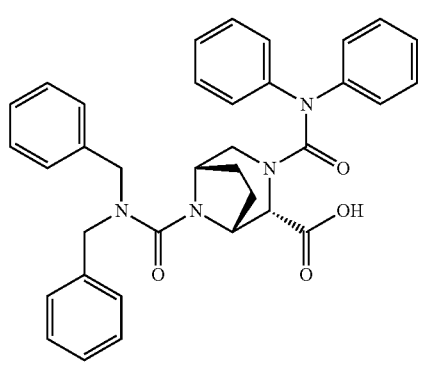 [SMILES: O=C(O)[C@@H]1[C@H]2CC[C@@H](CN1C(=O)N(c1ccccc1)c1ccccc1)N2C(=O)N(Cc1ccccc1)Cc1ccccc1] |
| C134 | 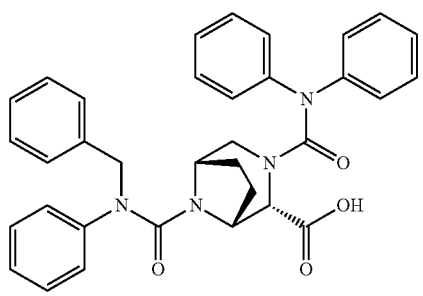 [SMILES: O=C(O)[C@@H]1[C@H]2CC[C@@H](CN1C(=O)N(c1ccccc1)c1ccccc1)N2C(=O)N(Cc1ccccc1)c1ccccc1] |
| C147 | 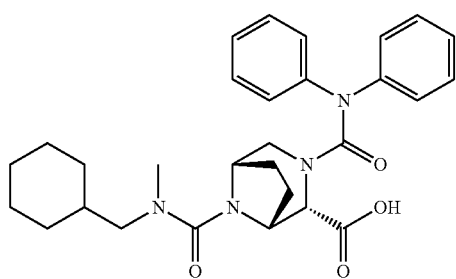 [SMILES: CN(CC1CCCCC1)C(=O)N1[C@H]2CC[C@@H]1[C@@H](C(=O)O)N(C(=O)N(c1ccccc1)c1ccccc1)C2] |
| C148 | 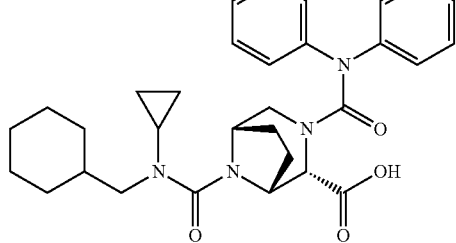 |
| No. | Structure |
|---|---|
| C149 | 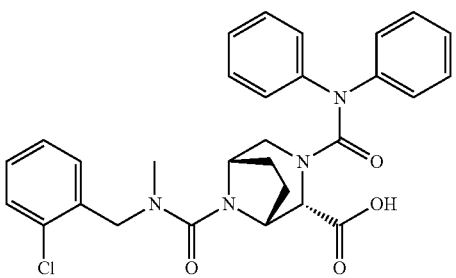 [SMILES: CN(Cc1ccccc1Cl)C(=O)N1[C@H]2CC[C@@H]1[C@@H](C(=O)O)N(C(=O)N(c1ccccc1)c1ccccc1)C2] |
| C150 | 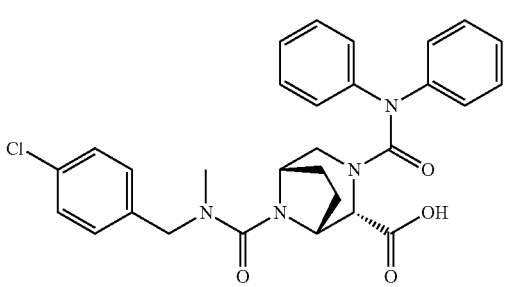 [SMILES: CN(Cc1ccc(Cl)cc1)C(=O)N1[C@H]2CC[C@@H]1[C@@H](C(=O)O)N(C(=O)N(c1ccccc1)c1ccccc1)C2] |
| C151 | 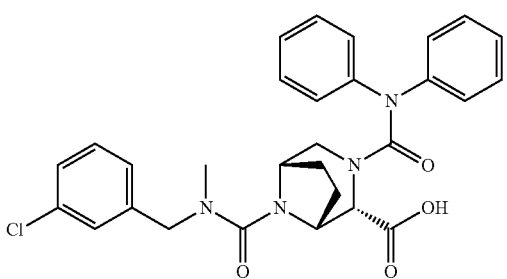 [SMILES: CN(Cc1cccc(Cl)c1)C(=O)N1[C@H]2CC[C@@H]1[C@@H](C(=O)O)N(C(=O)N(c1ccccc1)c1ccccc1)C2] |
| C152 | 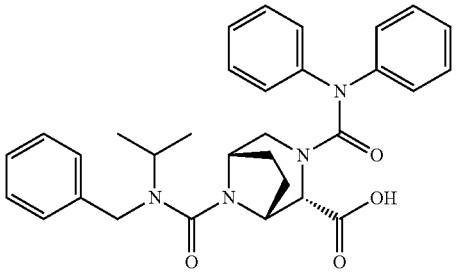 [SMILES: CC(C)N(Cc1ccccc1)C(=O)N1[C@H]2CC[C@@H]1[C@@H](C(=O)O)N(C(=O)N(c1ccccc1)c1ccccc1)C2] |
| C153 | 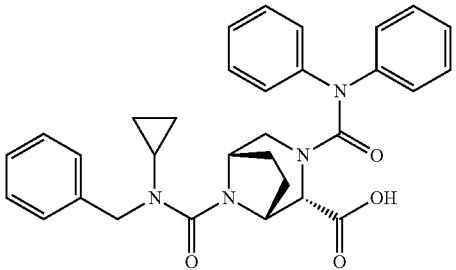 [SMILES: O=C(O)[C@@H]1[C@H]2CC[C@@H](CN1C(=O)N(c1ccccc1)c1ccccc1)N2C(=O)N(Cc1ccccc1)C1CC1] |

US 11,453,690 B2
331
-continued
| No. | Structure |
|---|---|
| C154 | 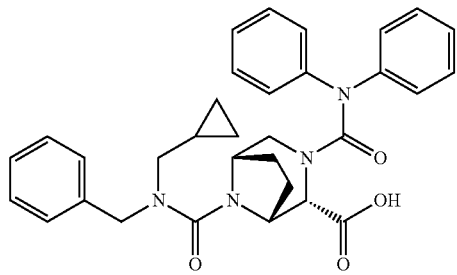 [SMILES: O=C(O)[C@@H]1[C@H]2CC[C@@H](CN1C(=O)N(c1ccccc1)c1ccccc1)N2C(=O)N(Cc1ccccc1)CC1CC1] |
| C155 | 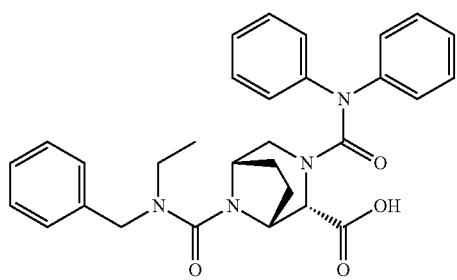 [SMILES: CCN(Cc1ccccc1)C(=O)N1[C@H]2CC[C@@H]1[C@@H](C(=O)O)N(C(=O)N(c1ccccc1)c1ccccc1)C2] |
| C156 | 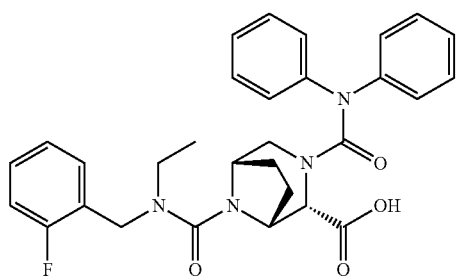 [SMILES: CCN(Cc1ccccc1F)C(=O)N1[C@H]2CC[C@@H]1[C@@H](C(=O)O)N(C(=O)N(c1ccccc1)c1ccccc1)C2] |
| C157 | 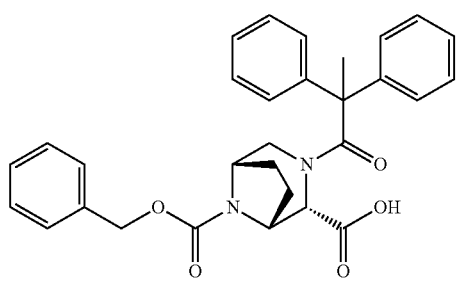 [SMILES: CC(C(=O)N1C[C@@H]2CC[C@H]([C@H]1C(=O)O)N2C(=O)OCc1ccccc1)(c1ccccc1)c1ccccc1] |
| C159 | 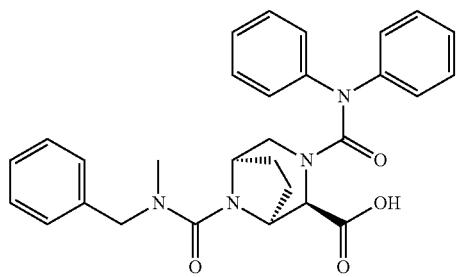 [SMILES: CN(Cc1ccccc1)C(=O)N1[C@@H]2CC[C@H]1[C@H](C(=O)O)N(C(=O)N(c1ccccc1)c1ccccc1)C2] |
332
-continued
| No. | Structure |
|---|---|
| C161 | 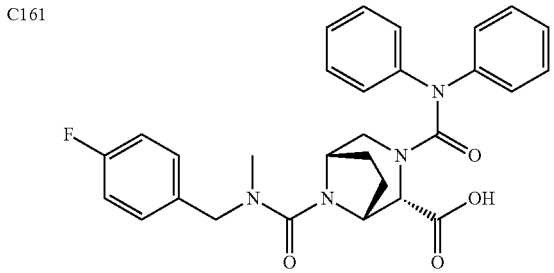 |
| C162 | 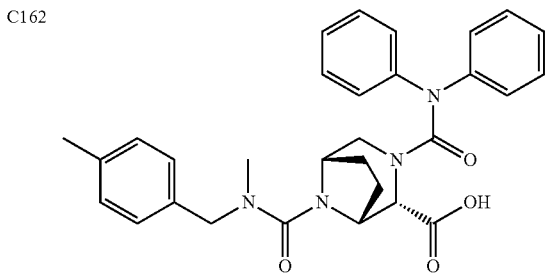 |
| C163 | 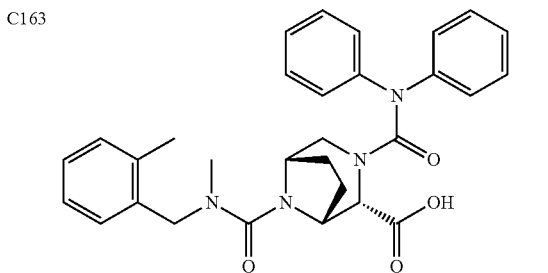 |
| C165 | 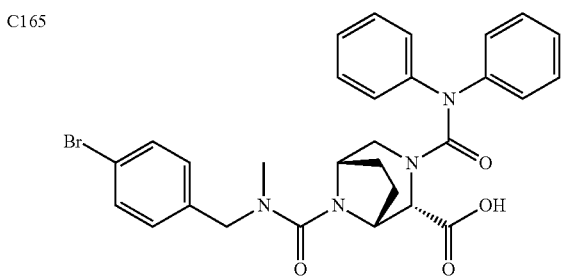 |
| C166 | 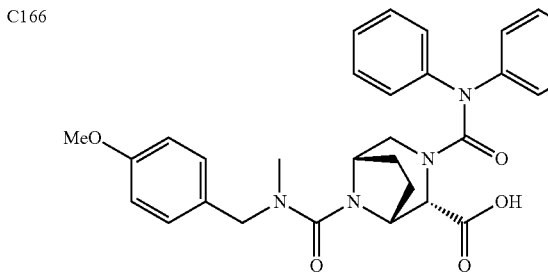 |

333
-continued

| No. | Structure |
|---|---|
| C167 | 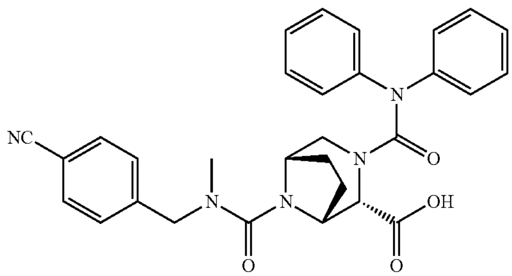 [SMILES: CN(Cc1ccc(C#N)cc1)C(=O)N1[C@H]2CC[C@@H]1[C@@H](C(=O)O)N(C(=O)N(c1ccccc1)c1ccccc1)C2] |
| C169 | 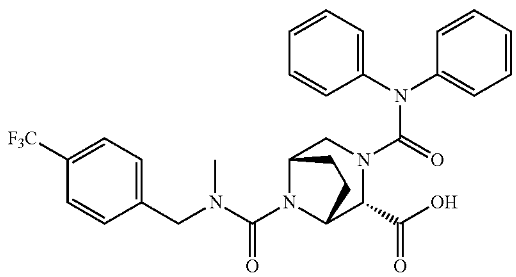 [SMILES: CN(Cc1ccc(C(F)(F)F)cc1)C(=O)N1[C@H]2CC[C@@H]1[C@@H](C(=O)O)N(C(=O)N(c1ccccc1)c1ccccc1)C2] |
| C171 | 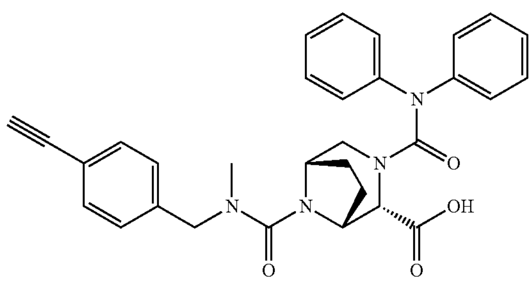 [SMILES: C#Cc1ccc(CN(C)C(=O)N2[C@H]3CC[C@@H]2[C@@H](C(=O)O)N(C(=O)N(c2ccccc2)c2ccccc2)C3)cc1] |
| C173 | 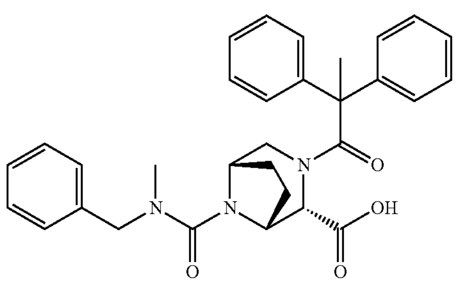 |
| C174 | 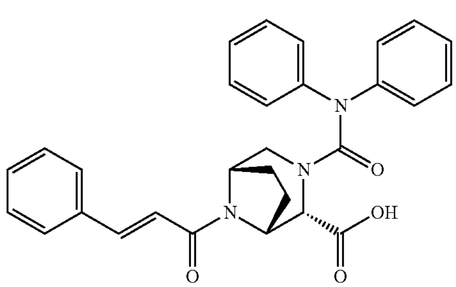 [SMILES: O=C(O)[C@@H]1[C@H]2CC[C@@H](CN1C(=O)N(c1ccccc1)c1ccccc1)N2C(=O)/C=C/c1ccccc1] |

334
-continued

| No. | Structure |
|---|---|
| C184 | 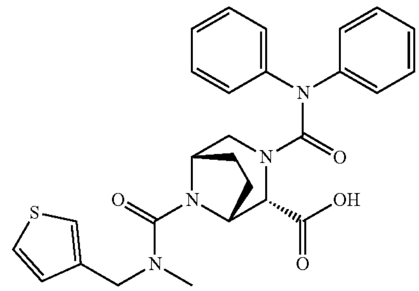 |
| C185 | 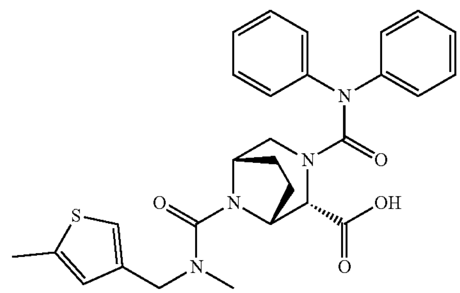 [SMILES: Cc1cc(CN(C)C(=O)N2[C@H]3CC[C@@H]2[C@@H](C(=O)O)N(C(=O)N(c2ccccc2)c2ccccc2)C3)cs1] |
| C186 | 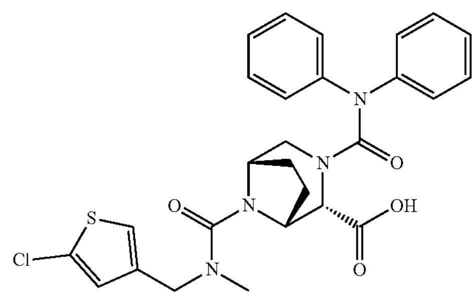 [SMILES: CN(Cc1csc(Cl)c1)C(=O)N1[C@H]2CC[C@@H]1[C@@H](C(=O)O)N(C(=O)N(c1ccccc1)c1ccccc1)C2] |
| C187 | 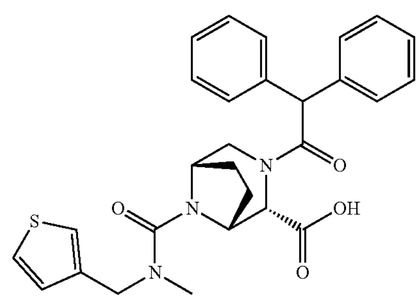 [SMILES: CN(Cc1ccsc1)C(=O)N1[C@H]2CC[C@@H]1[C@@H](C(=O)O)N(C(=O)C(c1ccccc1)c1ccccc1)C2] |
| C188 | 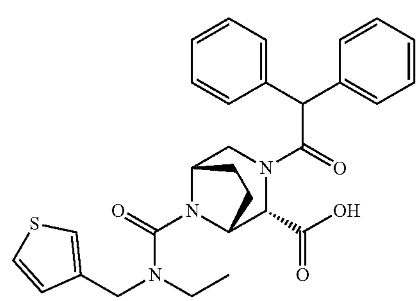 [SMILES: CCN(Cc1ccsc1)C(=O)N1[C@H]2CC[C@@H]1[C@@H](C(=O)O)N(C(=O)C(c1ccccc1)c1ccccc1)C2] |

335
-continued
| No. | Structure |
|---|---|
| C189 | 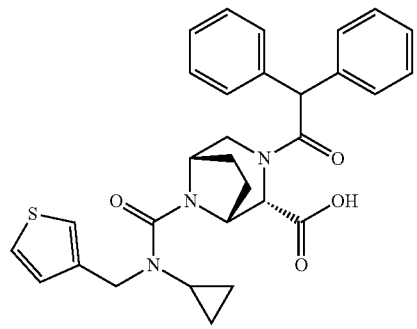 |
| C192 | 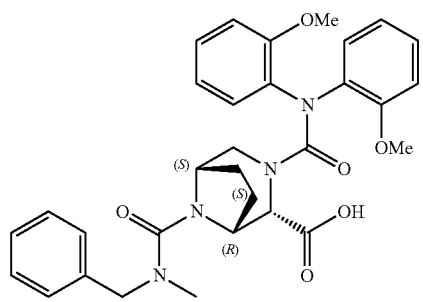 |
| C193 | 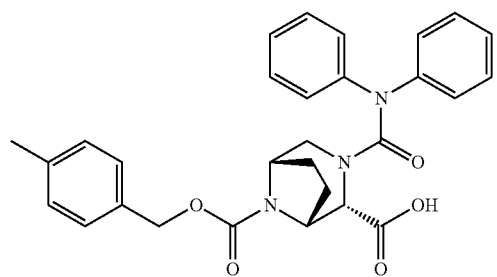 [SMILES: Cc1ccc(COC(=O)N2[C@H]3CC[C@@H]2[C@@H](C(=O)O)N(C(=O)N(c2ccccc2)c2ccccc2)C3)cc1] |
| C194 | 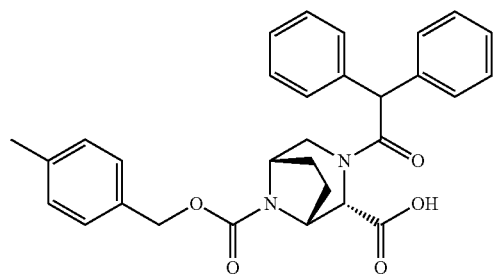 |
| C196 | 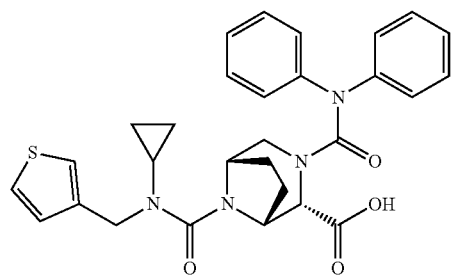 [SMILES: O=C(O)[C@@H]1[C@H]2CC[C@@H](CN1C(=O)N(c1ccccc1)c1ccccc1)N2C(=O)N(Cc1ccsc1)C1CC1] |
336
-continued
| No. | Structure |
|---|---|
| C197 | 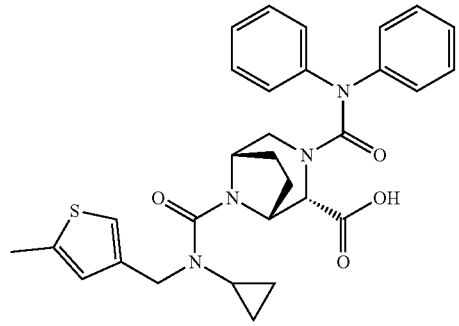 [SMILES: Cc1cc(CN(C(=O)N2[C@H]3CC[C@@H]2[C@@H](C(=O)O)N(C(=O)N(c2ccccc2)c2ccccc2)C3)C2CC2)cs1] |
| C198 | 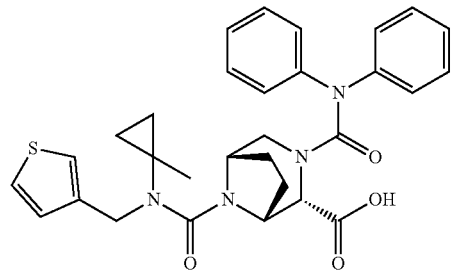 [SMILES: CC1(N(Cc2ccsc2)C(=O)N2[C@H]3CC[C@@H]2[C@@H](C(=O)O)N(C(=O)N(c2ccccc2)c2ccccc2)C3)CC1] |
| C200 | 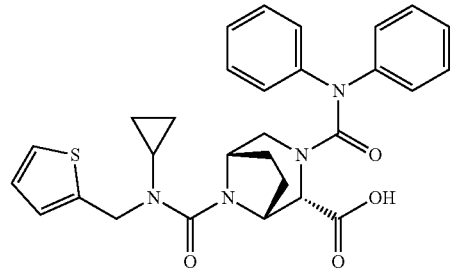 [SMILES: O=C(O)[C@@H]1[C@H]2CC[C@@H](CN1C(=O)N(c1ccccc1)c1ccccc1)N2C(=O)N(Cc1cccs1)C1CC1] |
| C201 | 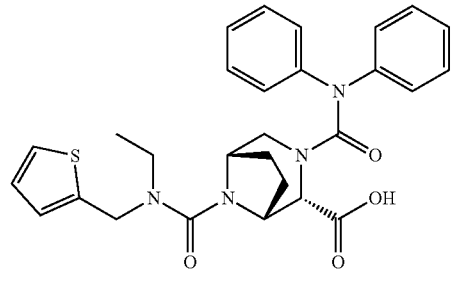 [SMILES: CCN(Cc1cccs1)C(=O)N1[C@H]2CC[C@@H]1[C@@H](C(=O)O)N(C(=O)N(c1ccccc1)c1ccccc1)C2] |
| C202 | 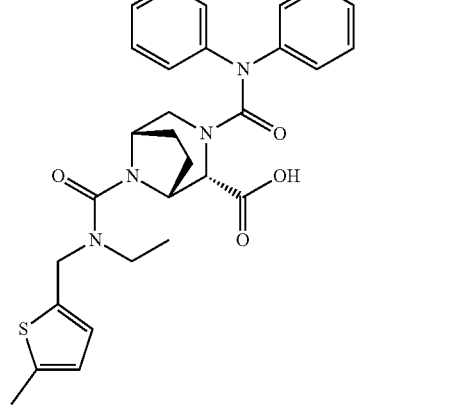 |

337
-continued
| No. | Structure |
|---|---|
| C203 | 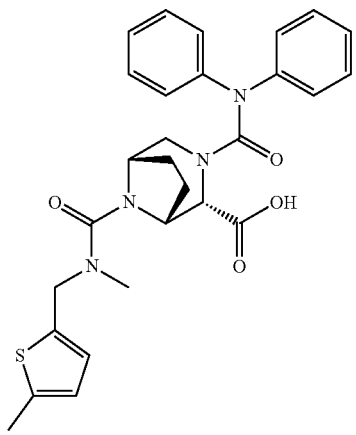 [SMILES: Cc1ccc(CN(C)C(=O)N2[C@H]3CC[C@@H]2[C@@H](C(=O)O)N(C(=O)N(c2ccccc2)c2ccccc2)C3)s1] |
| C204 | 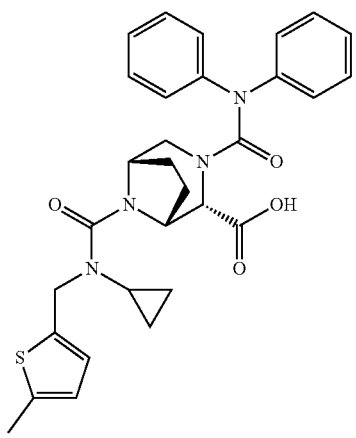 [SMILES: Cc1ccc(CN(C(=O)N2[C@H]3CC[C@@H]2[C@@H](C(=O)O)N(C(=O)N(c2ccccc2)c2ccccc2)C3)C2CC2)s1] |
| C205 lp;1p | 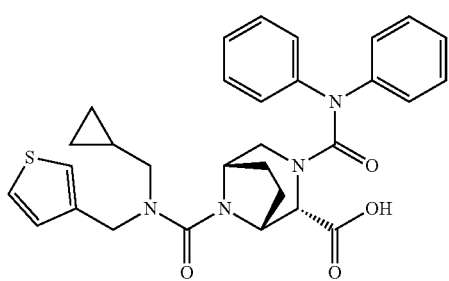 [SMILES: O=C(O)[C@@H]1[C@H]2CC[C@@H](CN1C(=O)N(c1ccccc1)c1ccccc1)N2C(=O)N(Cc1ccsc1)CC1CC1] |
| C206 | 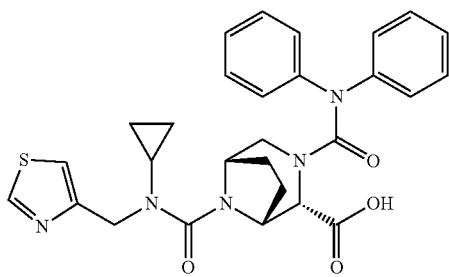 [SMILES: O=C(O)[C@@H]1[C@H]2CC[C@@H](CN1C(=O)N(c1ccccc1)c1ccccc1)N2C(=O)N(Cc1cscn1)C1CC1] |
338
-continued
| No. | Structure |
|---|---|
| C207 | 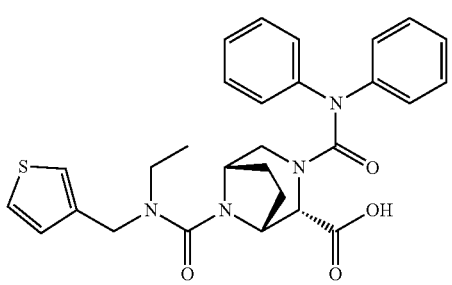 [SMILES: CCN(Cc1ccsc1)C(=O)N1[C@H]2CC[C@@H]1[C@@H](C(=O)O)N(C(=O)N(c1ccccc1)c1ccccc1)C2] |
| C208 | 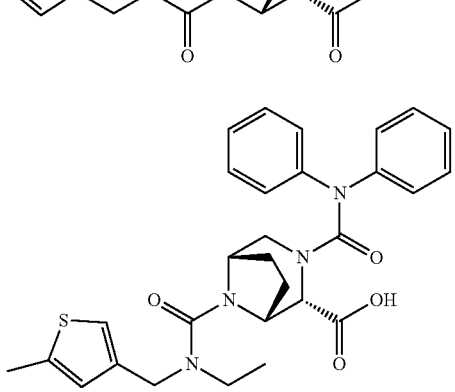 |
| C209 | 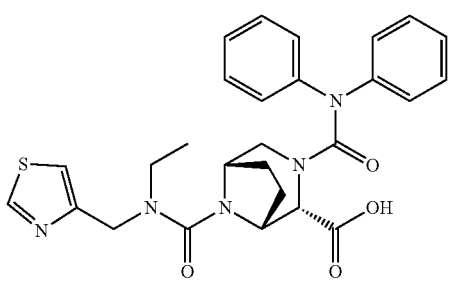 [SMILES: CCN(Cc1cscn1)C(=O)N1[C@H]2CC[C@@H]1[C@@H](C(=O)O)N(C(=O)N(c1ccccc1)c1ccccc1)C2] |
| C212 | 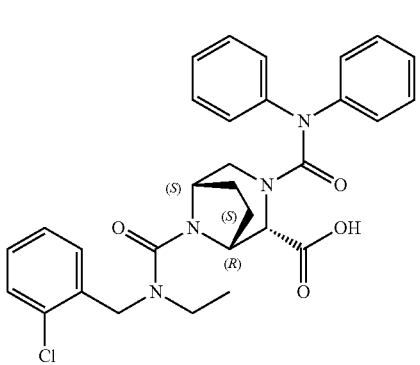 |
| C213 | 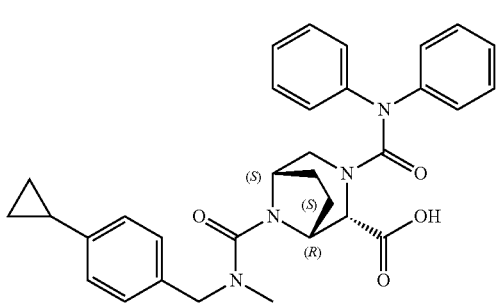 |

| No. | Structure | No. | Structure |
|---|---|---|---|
| C214 | 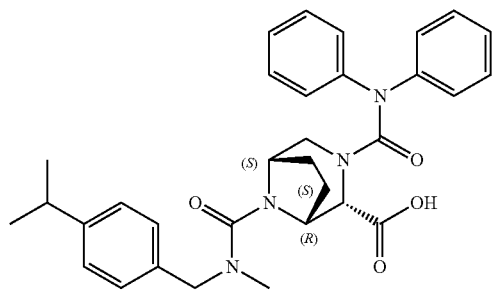 | C219 | 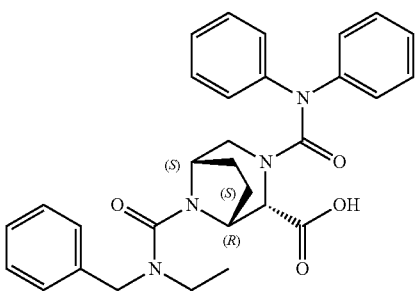 |
| C215 | 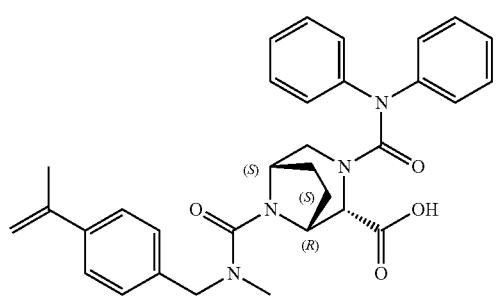 | C220 | 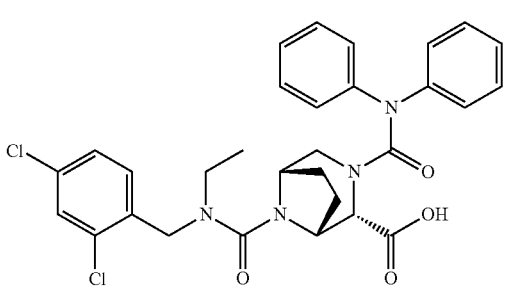 |
| C216 | 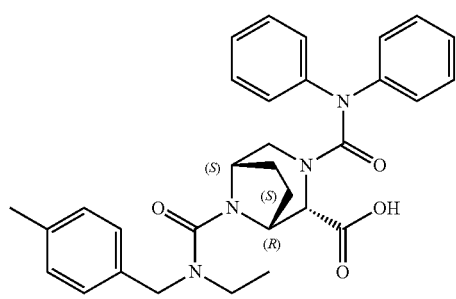 | C221 | 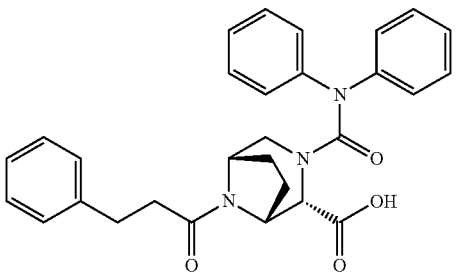 |
| C217 | 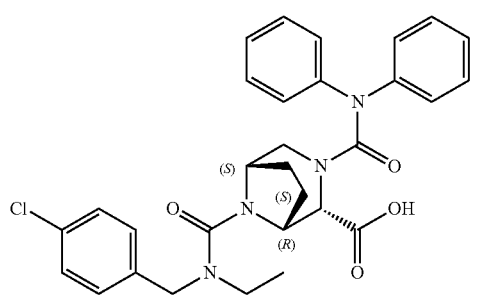 | C222 | 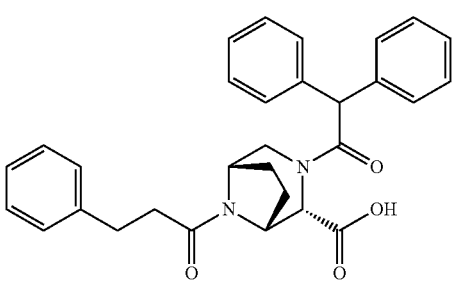 |
| C218 | 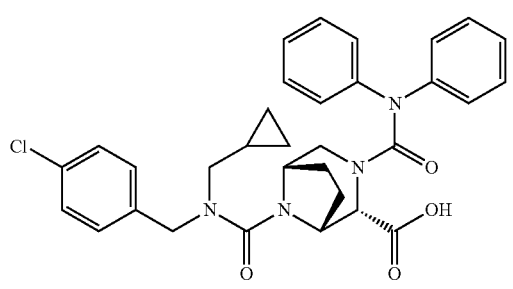 [SMILES: O=C(O)[C@@H]1[C@H]2CC[C@@H](CN1C(=O)N(c1ccccc1)c1ccccc1)N2C(=O)N(Cc1ccc(Cl)cc1)CC1CC1] | C223 | 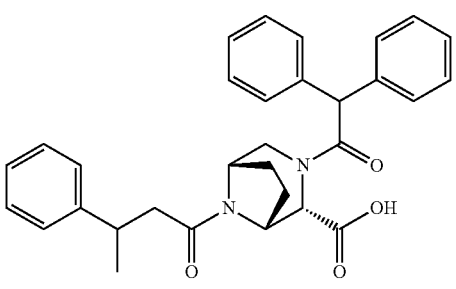 |

| No. | Structure |
|---|---|
| C224 | 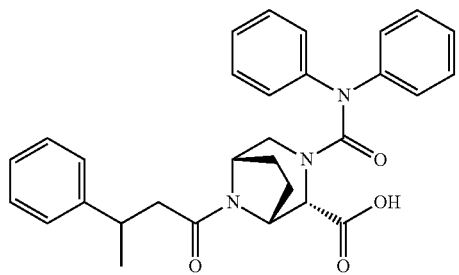 [SMILES: CC(CC(=O)N1[C@H]2CC[C@@H]1[C@@H](C(=O)O)N(C(=O)N(c1ccccc1)c1ccccc1)C2)c1ccccc1] |
| C225 | 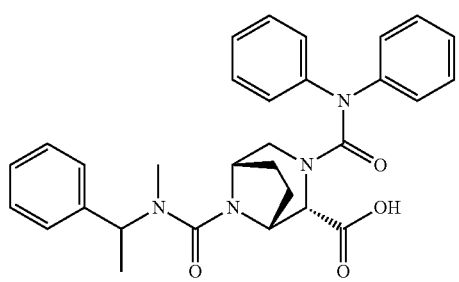 [SMILES: CC(c1ccccc1)N(C)C(=O)N1[C@H]2CC[C@@H]1[C@@H](C(=O)O)N(C(=O)N(c1ccccc1)c1ccccc1)C2] |
| C226 | 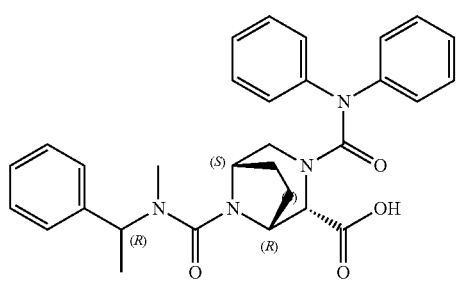 |
| C227 | 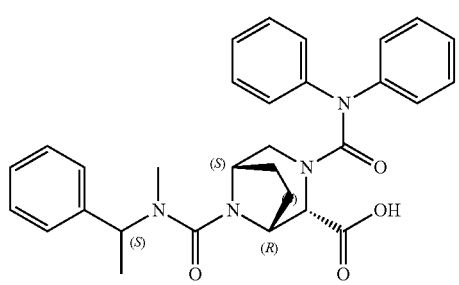 |
| C229 | 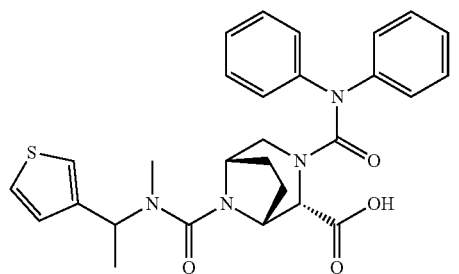 [SMILES: CC(c1ccsc1)N(C)C(=O)N1[C@H]2CC[C@@H]1[C@@H](C(=O)O)N(C(=O)N(c1ccccc1)c1ccccc1)C2] |
| No. | Structure |
|---|---|
| C230 | 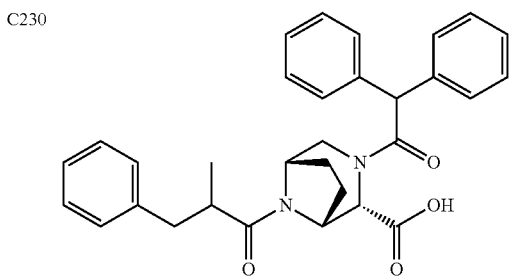 |
| C231 | 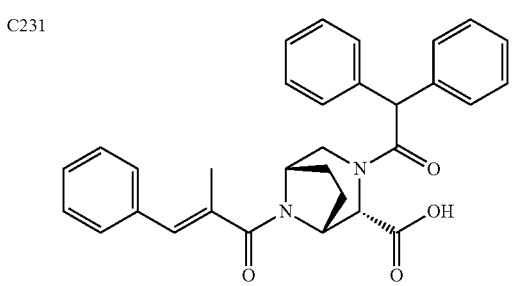 |
| C237 | 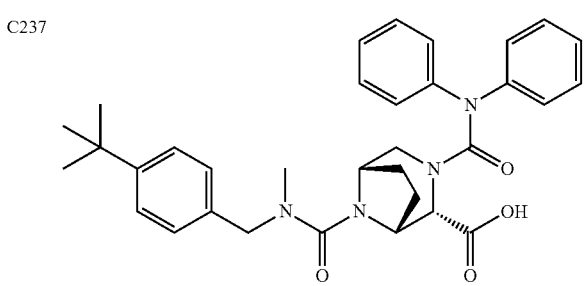 |
| C245 | 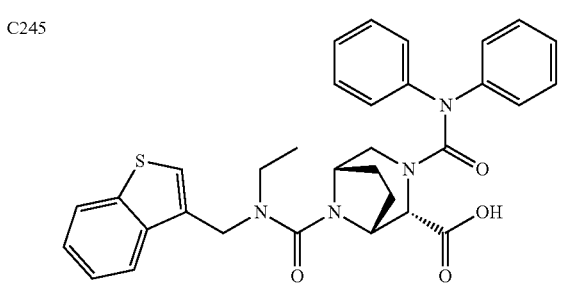 |
| C246 | 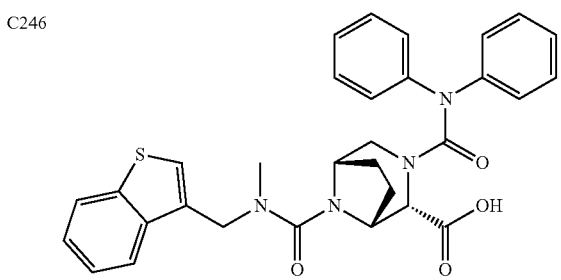 |

343
-continued
| No. | Structure |
|---|---|
| C249 | 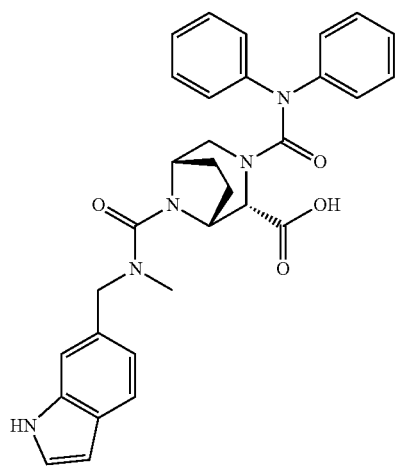 [SMILES: CN(Cc1ccc2cc[nH]c2c1)C(=O)N1[C@H]2CC[C@@H]1[C@@H](C(=O)O)N(C(=O)N(c1ccccc1)c1ccccc1)C2] |
| C252 | 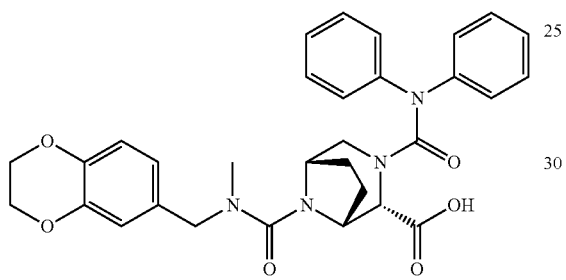 |
| C255 | 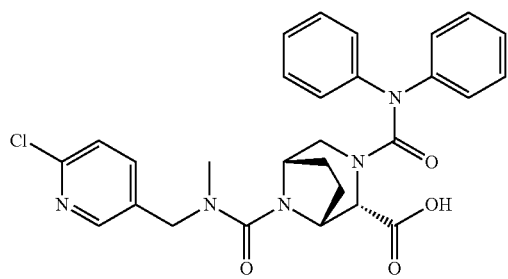 [SMILES: CN(Cc1ccc(Cl)nc1)C(=O)N1[C@H]2CC[C@@H]1[C@@H](C(=O)O)N(C(=O)N(c1ccccc1)c1ccccc1)C2] |
| C256 | 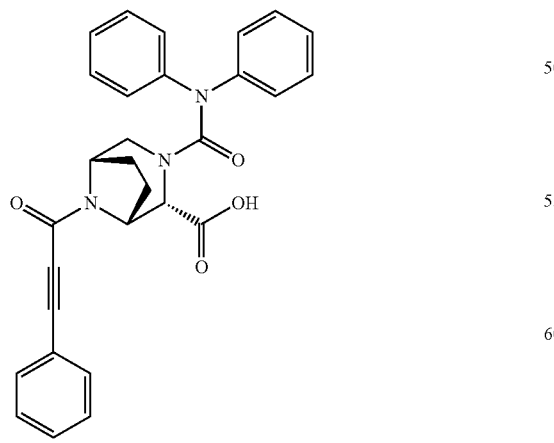 |
344
-continued
| No. | Structure |
|---|---|
| C257 | 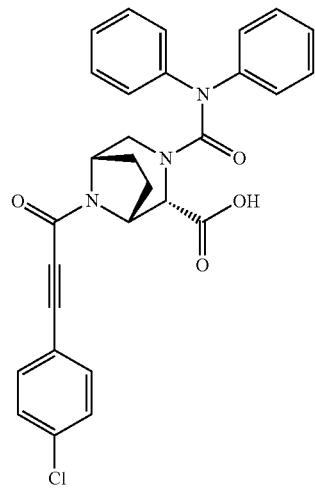 [SMILES: O=C(O)[C@@H]1[C@H]2CC[C@@H](CN1C(=O)N(c1ccccc1)c1ccccc1)N2C(=O)C#Cc1ccc(Cl)cc1] |
| C259 | 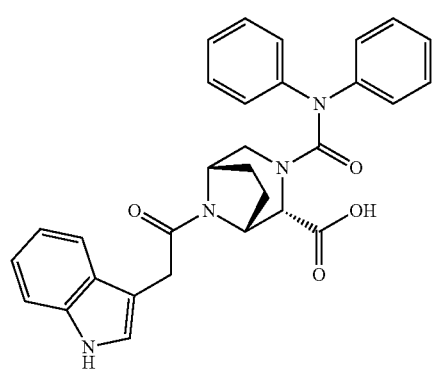 |
| C260 | 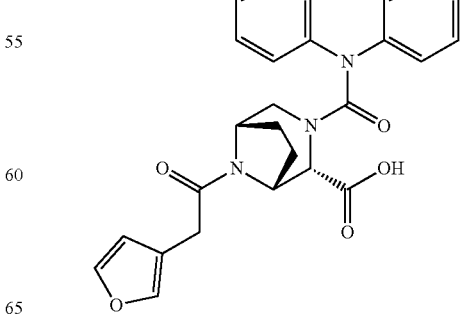 |

| No. | Structure |
|---|---|
| C265 | 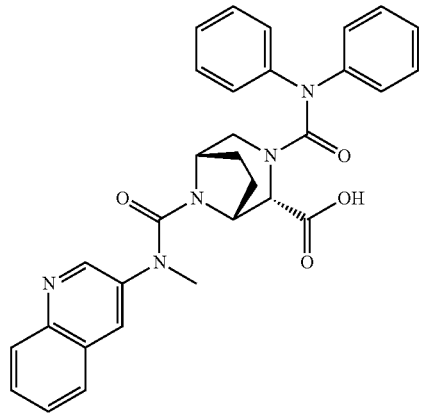 [SMILES: CN(C(=O)N1[C@H]2CC[C@@H]1[C@@H](C(=O)O)N(C(=O)N(c1ccccc1)c1ccccc1)C2)c1cnc2ccccc2c1] |
| C266 | 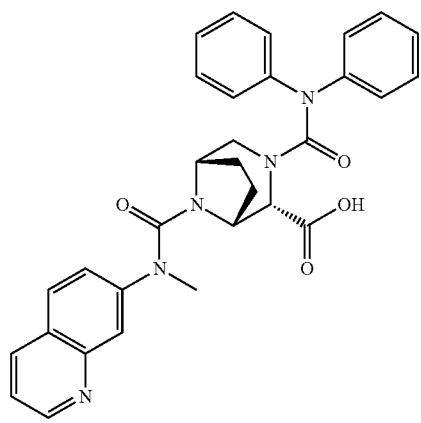 |
| C269 | 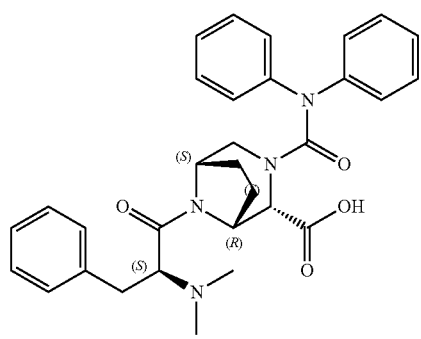 |
| C270 | 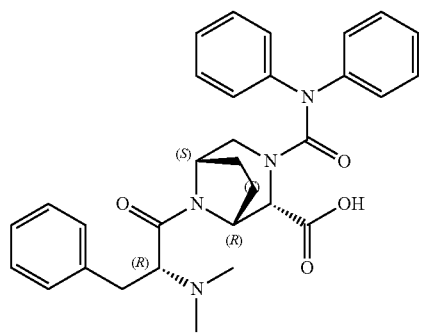 |
| No. | Structure |
|---|---|
| C271 | 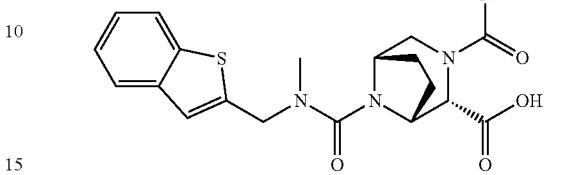 |
| C272 | 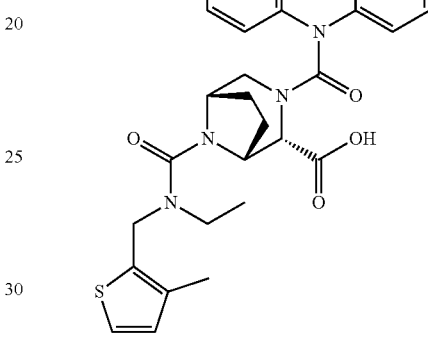 |
| C273 | 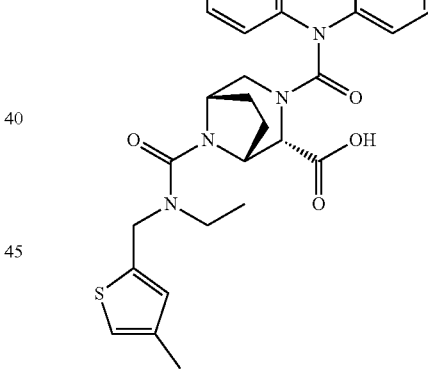 |
| C274 | 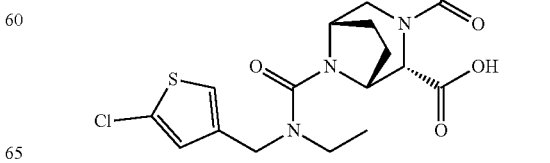 |

| No. | Structure |
|---|---|
| C277 | 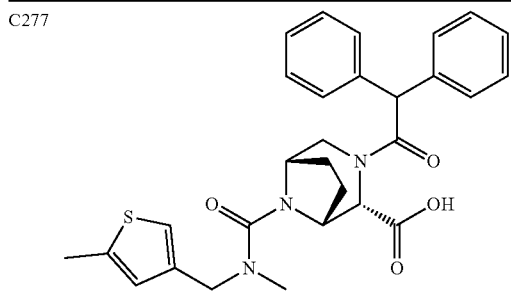 |
| C278 | 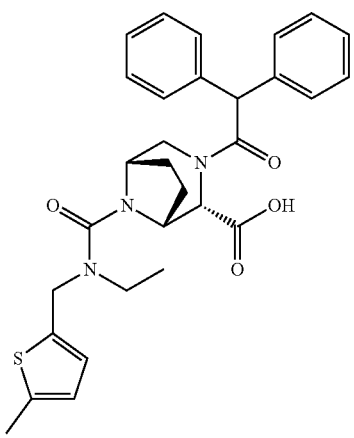 [SMILES: CCN(Cc1ccc(C)s1)C(=O)N1[C@H]2CC[C@@H]1[C@@H](C(=O)O)N(C(=O)C(c1ccccc1)c1ccccc1)C2] |
| C279 | 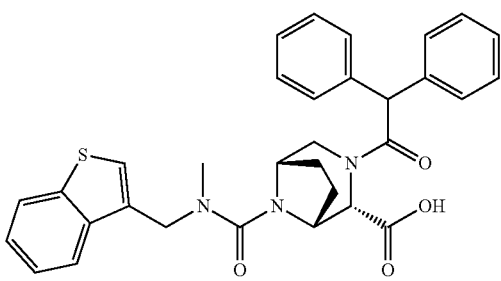 [SMILES: CN(Cc1csc2ccccc12)C(=O)N1[C@H]2CC[C@@H]1[C@@H](C(=O)O)N(C(=O)C(c1ccccc1)c1ccccc1)C2] |
| C281 | 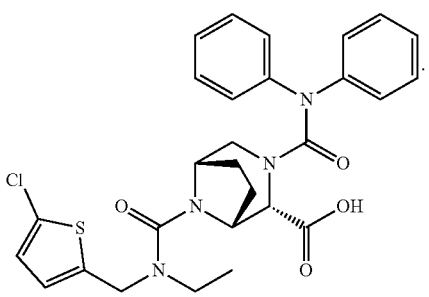 [SMILES: CCN(Cc1ccc(Cl)s1)C(=O)N1[C@H]2CC[C@@H]1[C@@H](C(=O)O)N(C(=O)N(c1ccccc1)c1ccccc1)C2] |

30. The compound according to claim 1, or a pharmaceutically acceptable salt, stereoisomer, or N-oxide thereof, wherein $R^{10}$ is H or methyl.

31. The compound according to claim 20, or a pharmaceutically acceptable salt, stereoisomer, or N-oxide thereof, wherein $R^{1a}$ is a group selected from the group consisting of an optionally substituted phenyl, —$C_{1-3}$ alkylene-(optionally substituted $C_{3-7}$ cyclic hydrocarbyl group), —$C_{1-3}$ alkylene-(optionally substituted 5- to 7-membered monocyclic heterocyclic group), —$C_{1-3}$alkylene-(optionally substituted 8- to 10-membered benzo-fused heterocyclic group), —$C_{1-3}$ alkylene-optionally substituted phenyl, and —$C_{1-3}$ alkylene-(optionally substituted 5- to 10-membered heteroaryl).

32. The compound according to claim 31, or a pharmaceutically acceptable salt, stereoisomer, or N-oxide thereof, wherein $R^{1a}$ is a group selected from the group consisting of an optionally substituted phenyl;

—$C_{1-3}$ alkylene-(optionally substituted $C_{3-7}$ cyclic hydrocarbyl group) wherein the cyclic hydrocarbyl group is cyclopropyl, cyclobutyl, cyclopentyl, or cyclohexyl;

—$C_{1-3}$ alkylene-(optionally substituted 8- to 10-membered benzo-fused heterocyclic group) wherein the heterocyclic group is

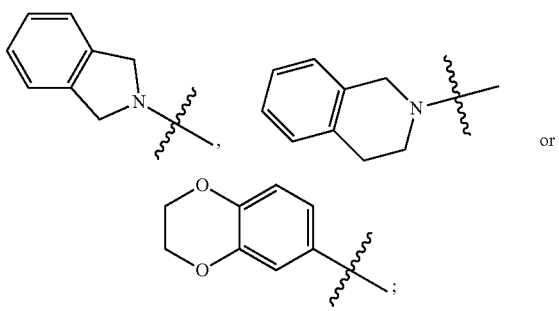

—$C_{1-3}$ alkylene-optionally substituted phenyl;

—$C_{1-3}$ alkylene-(optionally substituted 5- to 10-membered heteroaryl) wherein the heteroaryl

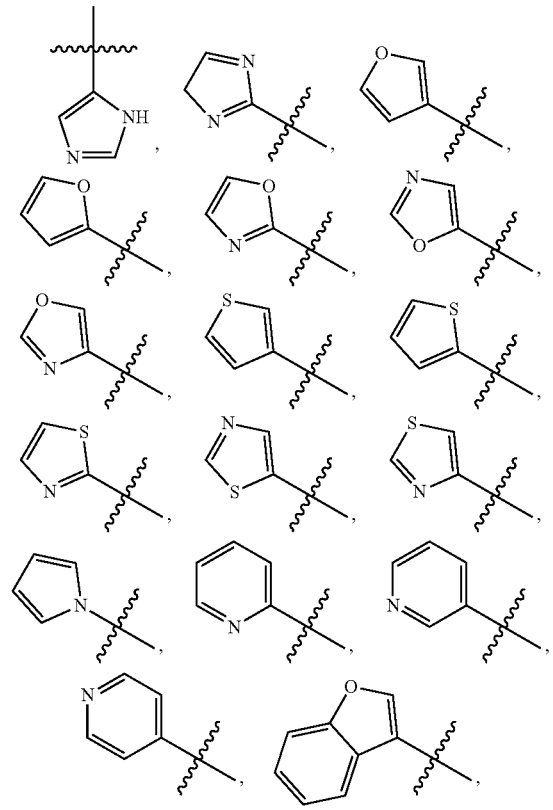

-continued

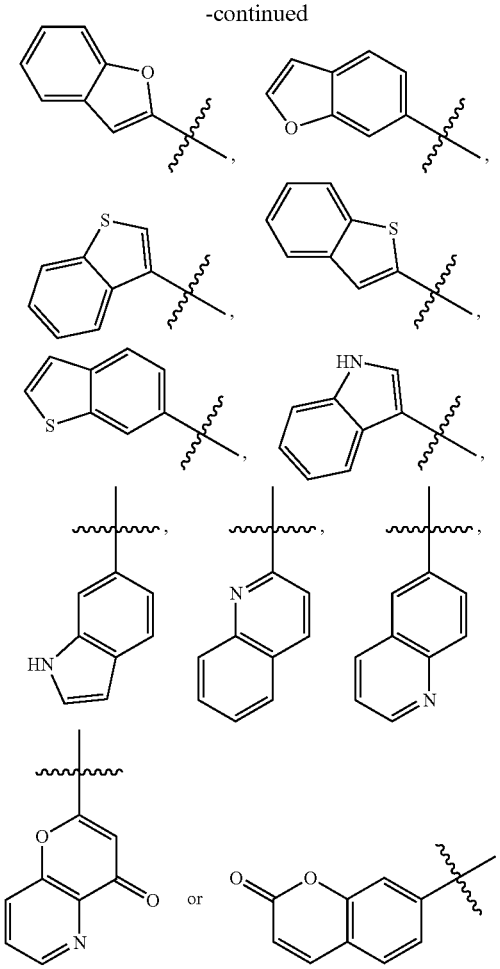

33. The compound according to claim 20, or a pharmaceutically acceptable salt, stereoisomer, or N-oxide thereof, wherein $R^{13}$ is selected from the group consisting of halogen; —$OR^{11}$ wherein $R^{11}$ is $C_{1-6}$ alkyl optionally substituted by 1, 2, 3 or more halogens; cyano; $C_{3-7}$ cyclic hydrocarbyl group; $C_{1-4}$ alkyl, $C_{2-4}$ alkenyl and $C_{2-4}$ alkynyl which are optionally substituted by 1, 2, 3 or more halogens; —$NR^{11}R^{12}$ wherein $R^{11}$ and $R^{12}$ are each independently selected from the group consisting of H and $C_{1-4}$ alkyl; and —$P(O)R^{11}R^{12}$ wherein $R^{11}$ and $R^{12}$ are each independently a $C_{1-6}$ alkyl optionally substituted by 1, 2, 3 or more halogens.

34. The compound according to claim 20, or a pharmaceutically acceptable salt, stereoisomer, or N-oxide thereof, wherein $R^{13}$ is selected from the group consisting of halogen; —$OR^{11}$ wherein $R^{11}$ is $C_{1-3}$ alkyl optionally substituted by 1, 2 or 3 F or Cl; cyano; $C_{3-7}$ cyclic hydrocarbyl group; and $C_{1-4}$ alkyl, $C_{2-4}$ alkenyl and $C_{2-4}$ alkynyl which are optionally substituted by 1, 2, 3 or more halogens; —$NR^{11}R^{12}$ wherein $R^{11}$ and $R^{12}$ are each independently selected from the group consisting of H and methyl; and —$P(O)R^{11}R^{12}$ wherein $R^{11}$ and $R^{12}$ are each independently a $C_{1-3}$ alkyl optionally substituted by 1, 2 or 3 F or Cl.

35. The compound according to claim 20, or a pharmaceutically acceptable salt, stereoisomer, or N-oxide thereof, wherein $R^{13}$ is selected from the group consisting of F, Cl, Br, OH, —$OC_{1-4}$ alkyl, —$N(C_{1-4}$ alkyl$)_2$, cyano, $C_{3-7}$ cyclic hydrocarbyl group, $C_{2-4}$ alkenyl and $C_{2-4}$ alkynyl; and $C_{1-4}$ alkyl optionally substituted by 1, 2, 3 or more F, Cl or Br; and —$P(O)R^{11}R^{12}$ wherein $R^{11}$ and $R^{12}$ are each independently methyl, ethyl, propyl or isopropyl.

36. The compound according to claim 20, or a pharmaceutically acceptable salt, stereoisomer, or N-oxide thereof, wherein $R^{13}$ is selected from the group consisting of F, Cl, Br, —$OCH_3$, —$N(CH_3)_2$, cyano, cyclopropyl, vinyl, 1-propenyl, 2-propenyl, ethynyl, 1-propenyl, 2-propynyl, methyl, ethyl, n-propyl, isopropyl, tert-butyl and $CF_3$; and —$P(O)R^{11}R^{12}$ wherein $R^{11}$ and $R^{12}$ are each independently methyl.

37. The compound according to claim 20, or a pharmaceutically acceptable salt, stereoisomer, or N-oxide thereof, wherein $R^{1a}$ is selected from the group consisting of

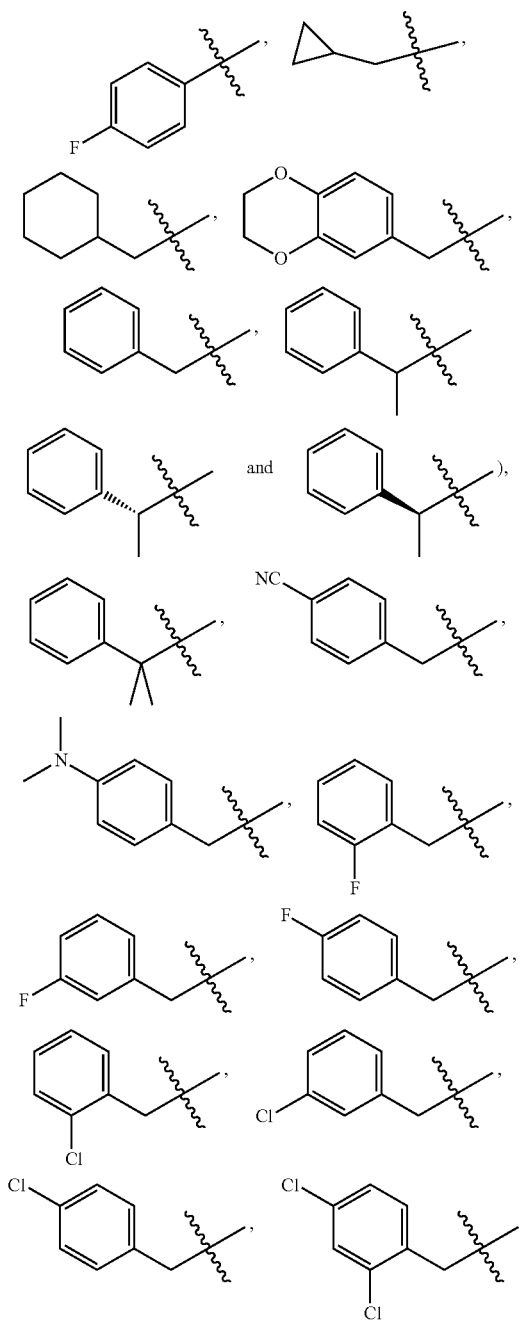

351
-continued
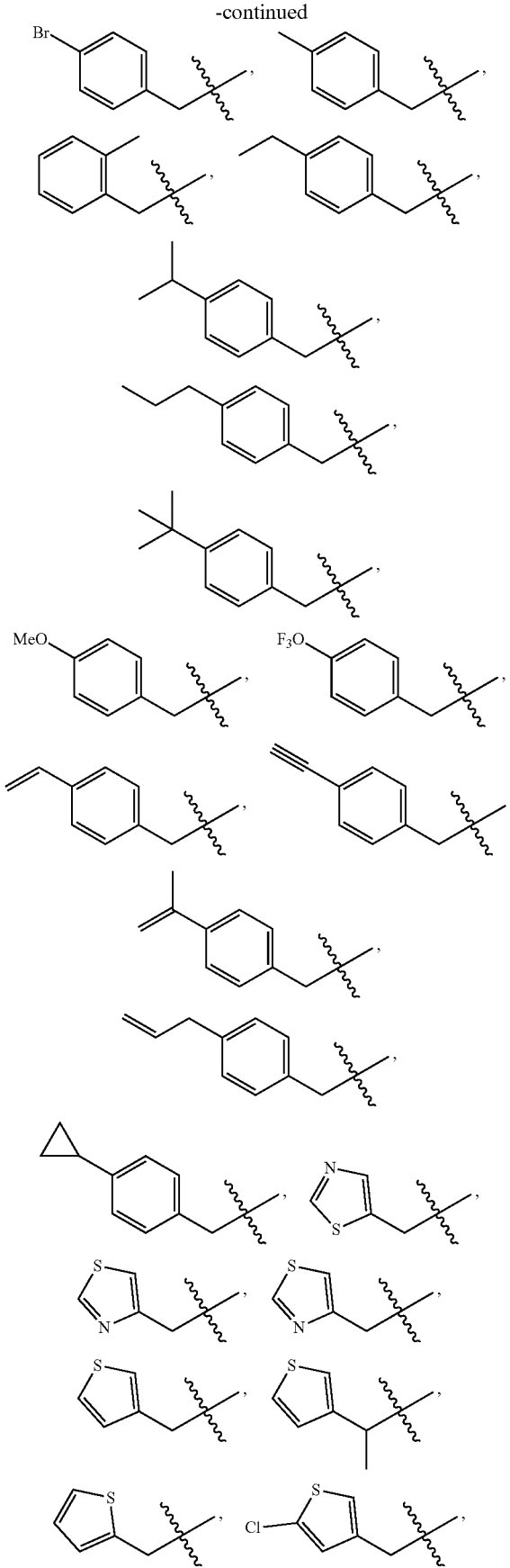
352
-continued
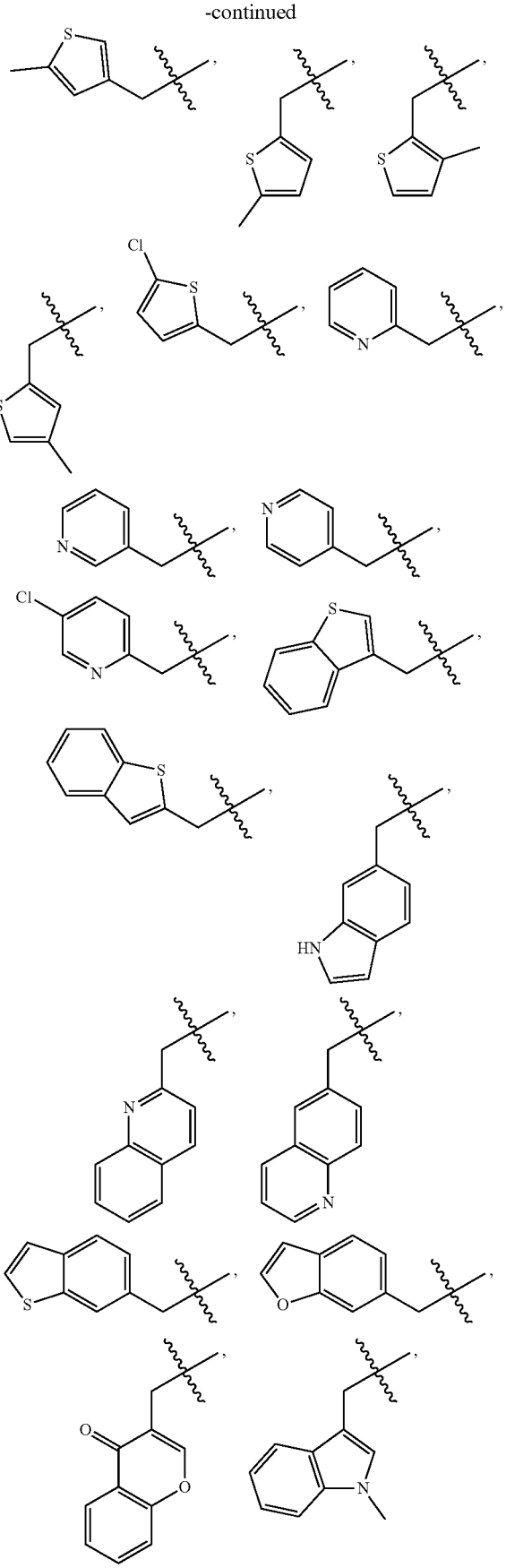

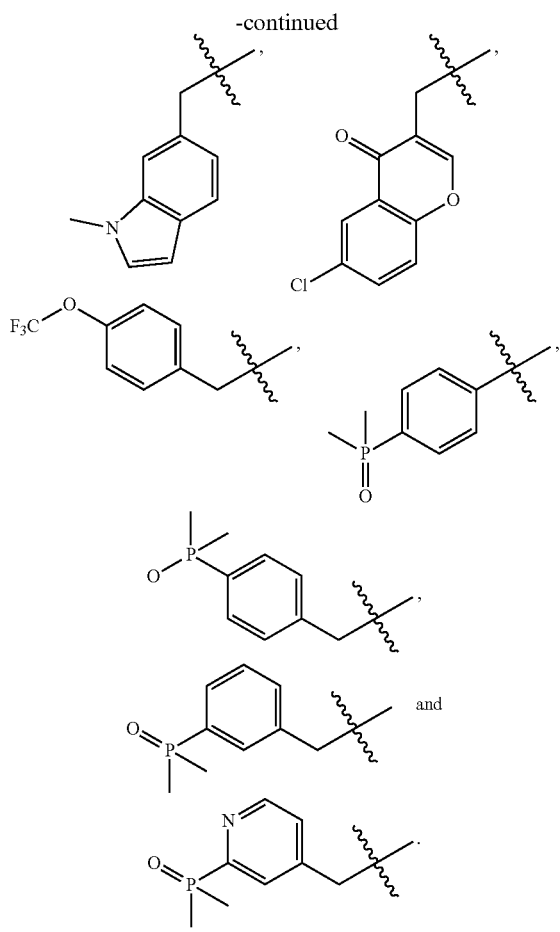

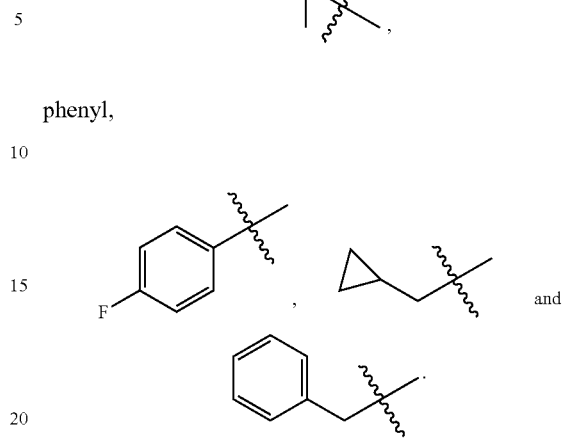

phenyl,

43. The compound according to claim 22, or a pharmaceutically acceptable salt, stereoisomer, or N-oxide thereof, wherein $R^{13}$ is selected from the group consisting of halogen and $-OR^{11}$, and wherein $R^{11}$ is selected from $C_{1-4}$ alkyl.

44. The compound according to claim 22, or a pharmaceutically acceptable salt, stereoisomer, or N-oxide thereof, wherein $R^{13}$ is selected from the group consisting of F, Cl, Br and $-OCH_3$.

45. The compound according to claim 22, or a pharmaceutically acceptable salt, stereoisomer, or N-oxide thereof, wherein each of $R^{2a}$ and $R^{2b}$ is selected from the group consisting of phenyl,

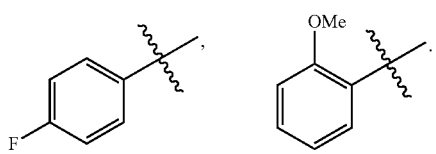 [SMILES: *c1ccc(F)cc1 ; *c1ccccc1OC]

38. The compound according to claim 21, or a pharmaceutically acceptable salt, stereoisomer, or N-oxide thereof, wherein $R^{1b}$ is a group selected from the group consisting of H, an optionally substituted $C_{1-4}$ alkyl, an optionally substituted $C_{3-7}$ cyclic hydrocarbyl group, an optionally substituted phenyl, $-C_{1-3}$ alkylene-(optionally substituted $C_{3-7}$ cyclic hydrocarbyl group), and $-C_{1-3}$ alkylene-optionally substituted phenyl.

39. The compound according to claim 21, or a pharmaceutically acceptable salt, stereoisomer, or N-oxide thereof, wherein $R^{1b}$ is a group selected from the group consisting of
H, phenyl;
an optionally substituted $C_{1-4}$ alkyl, wherein the alkyl is methyl, ethyl or isopropyl;
an optionally substituted $C_{3-7}$ cyclic hydrocarbyl group and $-C_{1-3}$ alkylene-($C_{3-7}$ cyclic hydrocarbyl group), wherein the cyclic hydrocarbyl group is cyclopropyl, cyclobutyl, cyclopentyl, or cyclohexyl; and
$-C_{1-3}$ alkylene-phenyl.

40. The compound according to claim 21, or a pharmaceutically acceptable salt, stereoisomer, or N-oxide thereof, wherein $R^{13}$ is selected from the group consisting of halogen and $C_{1-4}$ alkyl.

41. The compound according to claim 21, or a pharmaceutically acceptable salt, stereoisomer, or N-oxide thereof, wherein $R^{13}$ is selected from the group consisting of F, Cl, Br and methy.

42. The compound according to claim 21, or a pharmaceutically acceptable salt, stereoisomer, or N-oxide thereof, wherein $R^{1b}$ is selected from the group consisting of H, methyl, ethyl, isopropyl, $CF_3CH_2$, cyclopropyl,

46. The compound according to claim 25, or a pharmaceutically acceptable salt, stereoisomer, or N-oxide thereof, wherein

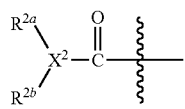

is

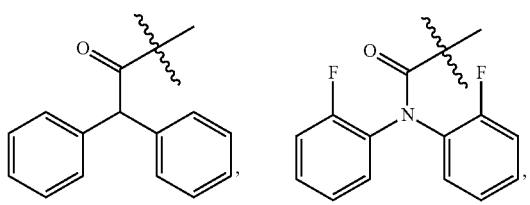

-continued

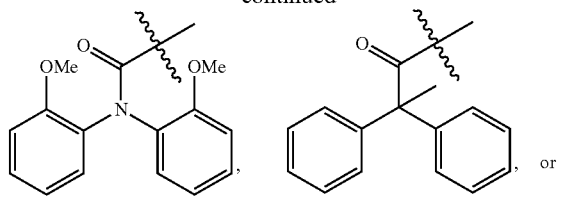, or

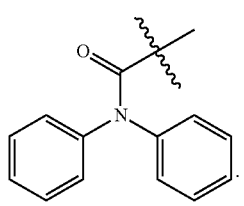.

47. The method according to claim 27, wherein the AT2 receptor-mediated disorder is peripheral neuropathy.

48. The method according to claim 27, wherein the AT2 receptor-mediated disorder is neuralgia.

49. The compound according to claim 1, or a pharmaceutically acceptable salt, stereoisomer, or N-oxide thereof, wherein the compound has the following structure:

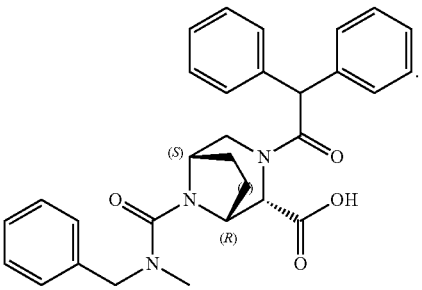

50. The compound according to claim 1, or a pharmaceutically acceptable salt, stereoisomer, or N-oxide thereof, wherein the compound has the following structure:

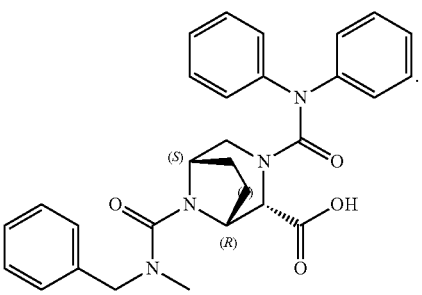

* * * * *

UNITED STATES PATENT AND TRADEMARK OFFICE
CERTIFICATE OF CORRECTION

PATENT NO. : 11,453,690 B2
APPLICATION NO. : 17/040569
DATED : September 27, 2022
INVENTOR(S) : Yanping Zhao et al.

It is certified that error appears in the above-identified patent and that said Letters Patent is hereby corrected as shown below:

In the Claims

In Claim 1 Column 285, Line 10, delete "$R^3$ is -C(=O)$R^{11}$;" and insert -- $R^3$ is -C(=O)O$R^{11}$; -- therefor.

Signed and Sealed this
Twenty-ninth Day of October, 2024

Katherine Kelly Vidal
*Director of the United States Patent and Trademark Office*